US009890387B2

(12) United States Patent
Spangenberg et al.

(10) Patent No.: US 9,890,387 B2
(45) Date of Patent: Feb. 13, 2018

(54) MODIFICATION OF FRUCTAN BIOSYNTHESIS, INCREASING PLANT BIOMASS, AND ENHANCING PRODUCTIVITY OF BIOCHEMICAL PATHWAYS IN A PLANT

(75) Inventors: German Spangenberg, Bundoora (AU); Aidyn Mouradov, Mill Park (AU); Megan Elizabeth Griffith, Templestowe (AU); Luciano Gaston Martelotto, Elwood (AU)

(73) Assignee: Agriculture Victoria Services PTY LTD, Attwood, Victoria (AU)

( * ) Notice: Subject to any disclaimer, the term of this patent is extended or adjusted under 35 U.S.C. 154(b) by 1398 days.

(21) Appl. No.: 13/063,992

(22) PCT Filed: Sep. 14, 2009

(86) PCT No.: PCT/AU2009/001211
§ 371 (c)(1), (2), (4) Date: Mar. 15, 2011

(87) PCT Pub. No.: WO2010/028456
PCT Pub. Date: Mar. 18, 2010

(65) Prior Publication Data

US 2011/0277187 A1 Nov. 10, 2011

Related U.S. Application Data

(60) Provisional application No. 61/097,008, filed on Sep. 15, 2008.

(30) Foreign Application Priority Data

May 18, 2009 (AU) ................................ 2009902230

(51) Int. Cl.
*C12N 15/82* (2006.01)
*C12N 9/10* (2006.01)

(52) U.S. Cl.
CPC ....... *C12N 15/8246* (2013.01); *C12N 9/1051* (2013.01); *C12N 15/8222* (2013.01); *C12N 15/8261* (2013.01)

(58) Field of Classification Search
None
See application file for complete search history.

(56) References Cited

U.S. PATENT DOCUMENTS

| | | | | |
|---|---|---|---|---|
| 6,664,444 | B1 * | 12/2003 | Koops et al. | 800/284 |
| 7,227,055 | B2 * | 6/2007 | Spangenberg et al. | 800/298 |
| 2002/0170086 | A1 | 11/2002 | Allen et al. | |

FOREIGN PATENT DOCUMENTS

| | | | |
|---|---|---|---|
| EP | 0952222 | A1 | 10/1999 |
| EP | 1914308 | A1 | 4/2008 |
| WO | 1994014970 | A1 | 7/1994 |
| WO | 9601904 | A1 | 1/1996 |
| WO | 9742326 | A2 | 11/1997 |
| WO | 1999046395 | A1 | 9/1999 |
| WO | 0006747 | A2 | 2/2000 |
| WO | 2001095691 | A2 | 12/2001 |
| WO | 2006111924 | A2 | 10/2006 |

OTHER PUBLICATIONS

Lammens et al, 2012, Plant J., 70:205-219.*
Pilon-Smits et al, 1999, Plant Physiol. Biochem., 37:313-317.*
Ebskamp et al, 1994, Nat. Biotech, 12:272-275.*
Shimizu-Sato et al, 2002, Nat. Biotech, 20:1041-1043.*
Tian et al, 2006, Planta, 224:496-507.*
Altenbach et al, 2007, Research Signpost, 37/661, "Everything You Always Wanted to Know About NK Cells but Were Afraid to Ask", ISBN: 81-7895-251-3.*
Lammens et al, 2012, The Plant J., 70:205-219.*
Garg, A. K. et al, Trehalose accumulation in rice plants confers high tolerance levels to different abiotic stresses, Proceeding of the National Academy of Sciences of USA, 2002, pp. 15898-15903, vol. 99, No. 25.
Miranda, J. A. et al., A bifunctional TPS-TPP enzyme from yeast confers tolerance to multiple and extreme abiotic-stress conditions in transgenic *Arabidopsis*, Planta, 2007, pp. 1411-1421, vol. 226, No. 6, XP002672407.
Kebeish, R. et al., Chloroplastic photorespiratory bypass increases photosynthesis and biomass production in *Arabidopsis thaliana*, Nature Biotechnology, 2007, pp. 593-599, vol. 25, No. 5, Publisher: Nature Publishing Group, New York, NY, US XP009110086.
Candian Examination Report dated Feb. 7, 2017 from corresponding Canadian Patent Application No. 2,737,059.
Chalmers, et al., Molecular genetics of fructan metabolism in perennial ryegrass, Plant Biotechnology Journal, 2005, pp. 459-474, vol. 3.

* cited by examiner

*Primary Examiner* — Jason Deveau Rosen
(74) *Attorney, Agent, or Firm* — Larson & Anderson, LLC

(57) ABSTRACT

The present invention relates to the modification of fructan biosynthesis in plants and, more particularly, to methods of manipulating fructan biosynthesis in photosynthetic cells, and to related nucleic acids and constructs. The present invention also relates to increasing plant biomass and, more particularly, to methods of enhancing biomass yield and/or yield stability, including shoot and/or root growth in a plant, and to related nucleic acids and constructs. The present invention also relates to methods of enhancing the productivity of biochemical pathways and, more particularly, to fusion proteins in plants, and to related nucleic acids and constructs.

12 Claims, 164 Drawing Sheets

FIGURE 4

Figure 1:
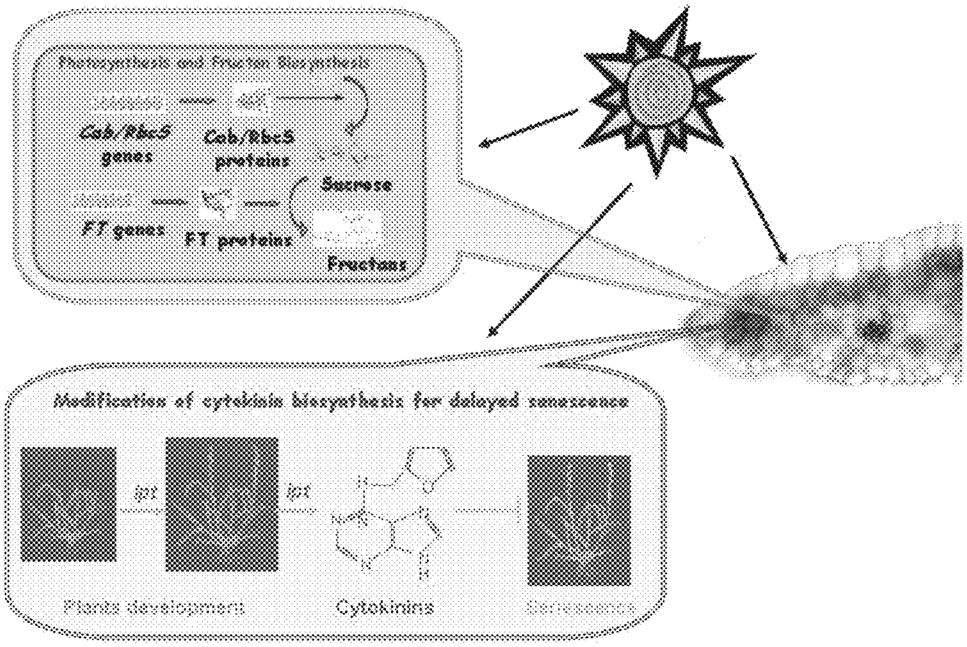

```
                  *        20         *        40         *        60
LpCABp : ATCACCCACATAGGACTACCAGCCTGGCCGACCACCTCCGACGAAGAAGAAGGCCGCCTC :  60

                  *        80         *       100         *       120
LpCABp : CACCGTCGAACCCGAGGCTGCTGCCCCAGGCGTCCTCGTACCGCGGGAGAATCCCAAGGT : 120

                  *       140         *       160         *       180
LpCABp : CACCCCCTCGCACCGGCGAGAAGCGGAGGGGATGGCGCCATCCCACCACCAGCCGCCACC : 180

                  *       200         *       220         *       240
LpCABp : GGTGTGCCGCCGCCGGGAGGCAGGGGAGGTCGCAGCACAGAGGCCACCGTCGCCCCTCCA : 240

                  *       260         *       280         *       300
LpCABp : TCCTCCGACCGCCGCCGCCCCGCCATCACACGGGAGGCCGGAAGTCCACCGCCGCCGCCC : 300

                  *       320         *       340         *       360
LpCABp : CCCCATCGGGAGGCAGGAAGCCGCCGCCGCTGCATCGAGGGGAGGACCCAGCCGCCGTCC : 360

                  *       380         *       400         *       420
LpCABp : CCGCCGCGCCATGAGGGAAGCCCACCGCCGCCGCGGTGGCGGGAGGAGCTAGGGTTTCTG : 420

                  *       440         *       460         *       480
LpCABp : GGGTGCGGGACGGGCGGGAGGAGCTAGGGTTTCTCTATGATTAAGTGCATGTATTGCGAA : 480

                  *       500         *       520         *       540
LpCABp : ATTAATGTTTCTACTTTTGTCATGGCCTTCTAGTCCGTCTAAAAAAAGCTGCCTTCTAGT : 540

                  *       560         *       580         *       600
LpCABp : GGGCGACATGGAACTCAGCGACATTCCTCCACCACACGCGCAGCGATCGTCCTGGCCGAT : 600

                  *       620         *       640         *       660
LpCABp : CCAGTTGAGCTCAACACCCCTGTGCCCTGTACAGGTGTCCGGCCCAGGGCTCGCCACACC : 660

                  *       680         *       700         *       720
LpCABp : AGCCGCCCCATCCAGGCACATCCACCCTCCGAGAACACGAGAGCCAATCGCAACGCAGAT : 720

                  *       740         *       760         *       780
LpCABp : CGTGATTTGTGAGATAAGGACGTGGCCCCCTCCCCTCGCGCGCACGGCATGGTATTTAAG : 780

                  *       800         *       820         *       840
LpCABp : CTCCATGCGCTGCTCCTCTCTTCCCCACGCAGCCACCGATCAATAGAAGCAGCAGCACAT : 840

                  *       860         *
LpCABp : CAGCAGCTTGCTCTATTCCGTCCAATAGCA : 870
```

FIGURE 5

```
                        *        20         *        40         *        60
LpRbcSp : ATCTGTTCATCTACCTTACTAGTCTGCATGATTAGTTTATTCGTTATTTTCGTAGTCATG :  60

                        *        80         *       100         *       120
LpRbcSp : ATTTATCAATTACTCGTACGGATTATTTCATATGGATATTTGCTTATATTTCCAACAATT : 120

                        *       140         *       160         *       180
LpRbcSp : TACACTGTCGAGTTTTGGCGCGGCTGCTGGAGTTACTCTTAGAGTAGTTGGACTTGAGAC : 180

                        *       200         *       220         *       240
LpRbcSp : AAAAGCTAGAATATCAATTATATATAGGAGTGAGGAGTTATTCTTTCGAAAGAACTTTAA : 240

                        *       260         *       280         *       300
LpRbcSp : ACGGTAGCTGCACTTAGTCGTCGCAATGAAATACTTGTCGTACTACCATGATAATTGGTA : 300

                        *       320         *       340         *       360
LpRbcSp : ATATGAGAGGGAATATTAATTCCTCAGTGATTTGAATTTTGTGTGCTCATGTGCAGTCAC : 360

                        *       380         *       400         *       420
LpRbcSp : CCACGCCATGCATCCGACGACGGGCGGCTATACCAACTCTTGCACTGATCCGGAGGGATA : 420

                        *       440         *       460         *       480
LpRbcSp : AGGCGCCATGCAACCAGGGAACGTCGTCCACCCCTTCCACATCCTGTATCAAATTAAGGA : 480

                        *       500         *       520         *       540
LpRbcSp : ACGGGCGCTGAGCCTATGCCGAGACATATATAATGCGGCGACTCGGACATGGAGGGGCCT : 540

                        *       560         *       580         *       600
LpRbcSp : CAGGCATAGCCCAGCTAGTTATCTCATTCTCTCCTTAGCAATAATACTTAGCACCATGGC : 600

                        *
LpRbcSp : CCCCGCGGTG : 610
```

FIGURE 7

```
                    *        20         *        40         *        60
Lp6GFFT : ATGGAGTCCAGCGCCGTCGTCGCCCAAGGCACCACGTCGCCGCTGCTCCCGTACGCCTAC :   60

                    *        80         *       100         *       120
Lp6GFFT : GCGCCGCTGCCGTCCTCTGCCGACGACGCCCGTGAAAACCAGAGTAGCGGCGGCGGTGTC :  120

                    *       140         *       160         *       180
Lp6GFFT : AGGTGGCGCGCGTGCGCGGCCTCGGCCCTGGTGGTGCTGCTGGTCGTCGTCGGCTTCTTC :  180

                    *       200         *       220         *       240
Lp6GFFT : GCGGGTGGCAGGGTGGATCTGGGTCAGGACGGCGAGGTGTCTGCGACTTCTTCGGTTCCT :  240

                    *       260         *       280         *       300
Lp6GFFT : GGGAGCAGCAGGGGCAAGGATTCCGGCGTGTCGGAGAAGGAGTCGCCCGCCGACGGCGGC :  300

                    *       320         *       340         *       360
Lp6GFFT : TTCCCGTGGAGCAACGCCATGCTGCAGTGGCAGCACACCGGGTTCCATTTCCAGCCACTC :  360

                    *       380         *       400         *       420
Lp6GFFT : AAGCACTACATGAACGATCCCAACGGTCCGGTCTACTATGGCGGATGGTACCACCTCTTC :  420

                    *       440         *       460         *       480
Lp6GFFT : TACCAGCACAACCCCTATGGCGACTCGTGGGGAAACGTATCTTGGGGACATGCCGTGTCC :  480

                    *       500         *       520         *       540
Lp6GFFT : AAGGACCTGGTGAACTGGCGCCACCTCCCGGTCGCCTTGGTGCCCGATCAGTGGTACGAC :  540

                    *       560         *       580         *       600
Lp6GFFT : ATCAACGGCGTCCTGACGGGCTCTATCACAGTGCTCCCAGACGGGCGTGTCATCCTGCTA :  600

                    *       620         *       640         *       660
Lp6GFFT : TATACGGGGAACACCGACACCTTTTCGCAGGTCCAGTGCCTCGCAGTGCCCGCCGACCCA :  660

                    *       680         *       700         *       720
Lp6GFFT : TCTGACCCGCTCCTCCGTAGCTGGATCAAGCACCCCGCCAACCCCATCCTCTTCCCGCCA :  720

                    *       740         *       760         *       780
Lp6GFFT : CCTGGGATCGGGCTCAAGGACTTCCGTGACCCGCTCACAGCCTGGTTCGAACATTCCGAC :  780

                    *       800         *       820         *       840
Lp6GFFT : AACACGTGGCGCACCATCATCGGATCCAAGGATGACGACGGCCACGCCGGCATCGTCCTT :  840

                    *       860         *       880         *       900
Lp6GFFT : AGCTACAAGACCACCGACTTTGTGAATTATGAGCTCATGCCAGGGAACATGCATCGTGGC :  900

                    *       920         *       940         *       960
Lp6GFFT : CCCGACGGCACCGGCATGTACGAGTGCCTTGACATCTACCCTGTGGGCGGCAACTCATCC :  960

                    *       980         *      1000         *      1020
Lp6GFFT : GAGATGTTGGGTGGCGACTCCTCACCTGAGGTGTTGTTCGTGCTCAAGGAGAGCGCCAAC : 1020

                    *      1040         *      1060         *      1080
Lp6GFFT : GACGAGTGGCACGACTACTACGCGCTTGGGTGGTTTGACGCTGCCGCCAACACGTGGACG : 1080

                    *      1100         *      1120         *      1140
Lp6GFFT : CCACAGGACCCCGAGGCGGACCTTGGGATCGGCCTCAGGTACGACTGGGGCAAGTACTAC : 1140
```

FIGURE 7 CONT

```
   *        1160          *        1180          *        1200
Lp6GFFT : GCGTCCAAGTCCTTCTACGACCCGATCAAGAACCGGCGTGTCGTTTGGGCTTTCGTCGGC : 1200

                *        1220          *        1240          *        1260
Lp6GFFT : GAGACCGACTCTGAGCAGGCCGACAAAGCCAAGGGATGGGCGTCCCTCATGTCGATTCCC : 1260

                *        1280          *        1300          *        1320
Lp6GFFT : AGGACGGTGGAGCTTGACAAGAAGACCCGGACGAACCTGATCCAATGGCCAGTGGAGGAG : 1320

                *        1340          *        1360          *        1380
Lp6GFFT : ATCGAGACCCTTCGCAGGAACGTCACAGACCTCGGTGGCATCACCGTTGAAGCCGGCTCC : 1380

                *        1400          *        1420          *        1440
Lp6GFFT : GTCATTCACCTTCCCCTCCAACAAGGCGGGCAGCTTGACATCGAGGCCTCCTTCCGTCTC : 1440

                *        1460          *        1480          *        1500
Lp6GFFT : AACTCTTCGGACATCGATGCACTCAACGAGGCCGACGTCGGCTTCAACTGCAGTAGCAGC : 1500

                *        1520          *        1540          *        1560
Lp6GFFT : GATGGGGCAGCCGTGCGTGGTGCGCTCGGCCCCTTTGGCCTCCTCGTCTTCGCCGACGGT : 1560

                *        1580          *        1600          *        1620
Lp6GFFT : CGCCACGAACAGACGGCGGCGTACTTCTACGTGTCCAAGGGCCTCGACGGCAGCCTCCTG : 1620

                *        1640          *        1660          *        1680
Lp6GFFT : ACGCACTACTGCCACGACGAGTCACGGTCGACGCGAGCAAAGGACGTCGTGAGCCGGGTG : 1680

                *        1700          *        1720          *        1740
Lp6GFFT : GTTGGCGGCACTGTGCCAGTGCTTGACGGTGAAACCTTTTCAGTGAGGGTGCTAGTGGAC : 1740

                *        1760          *        1780          *        1800
Lp6GFFT : CACTCCATCGTGCAGAGCTTCGTGATGGGTGGGAGGACCACGGTGACATCGCGGGCATAC : 1800

                *        1820          *        1840          *        1860
Lp6GFFT : CCGACGGAGGCCATCTACGCCGCGGCAGGGGTGTACCTGTTCAACAACGCAACGAGCGCC : 1860

                *        1880          *        1900          *        1920
Lp6GFFT : ACCATCACCGCCGAAGGGCTCGTCGTGTACGAGATGGCCTCGGCCGAGAGTCGGGCCTTC : 1920

                *
Lp6GFFT : TTGGCTGACGACATGTAG : 1938
```

FIGURE 8

```
                    *        20         *        40         *        60
Lp6GFFT : MESSAVVAQGTTSPLLPYAYAPLPSSADDARENQSSGGGVRWRACAASALVVLLVVVGFF :  60

                    *        80         *       100         *       120
Lp6GFFT : AGGRVDLGQDGEVSATSSVPGSSRGKDSGVSEKESPADGGFPWSNAMLQWQHTGFHFQPL : 120

                    *       140         *       160         *       180
Lp6GFFT : KHYMNDPNGPVYYGGWYHLFYQHNPYGDSWGNVSWGHAVSKDLVNWRHLPVALVPDQWYD : 180

                    *       200         *       220         *       240
Lp6GFFT : INGVLTGSITVLPDGRVILLYTGNTDTFSQVQCLAVPADPSDPLLRSWIKHPANPILFPP : 240

                    *       260         *       280         *       300
Lp6GFFT : PGIGLKDFRDPLTAWFEHSDNTWRTIIGSKDDDGHAGIVLSYKTTDFVNYELMPGNMHRG : 300

                    *       320         *       340         *       360
Lp6GFFT : PDGTGMYECLDIYPVGGNSSEMLGGDSSPEVLFVLKESANDEWHDYYALGWFDAAANTWT : 360

                    *       380         *       400         *       420
Lp6GFFT : PQDPEADLGIGLRYDWGKYYASKSFYDPIKNRRVVWAFVGETDSEQADKAKGWASLMSIP : 420

                    *       440         *       460         *       480
Lp6GFFT : RTVELDKKTRTNLIQWPVEEIETLRRNVTDLGGITVEAGSVIHLPLQQGGQLDIEASFRL : 480

                    *       500         *       520         *       540
Lp6GFFT : NSSDIDALNEADVGFNCSSSDGAAVRGALGPFGLLVFADGRHEQTAAYFYVSKGLDGSLL : 540

                    *       560         *       580         *       600
Lp6GFFT : THYCHDESRSTRAKDVVSRVVGGTVPVLDGETFSVRVLVDHSIVQSFVMGGRTTVTSRAY : 600

                    *       620         *       640
Lp6GFFT : PTEAIYAAAGVYLFNNATSATITAEGLVVYEMASAESRAFLADDM* : 645
```

FIGURE 9

```
                    *        20         *        40         *        60
Lp1-FFT : atggagtcccgggccattcccagcgcggcgtacgcgccacttctgccatccgccgcagac :   60

                    *        80         *       100         *       120
Lp1-FFT : gacgtcgccctggccaagcaggaccgcccccggcgtggggtggcgcgggttcttaaccgtg :  120

                    *       140         *       160         *       180
Lp1-FFT : ctggccgcctgcggcgtggtggtgctcctcgtcggtgccactttgctcgcggggtccagg :  180

                    *       200         *       220         *       240
Lp1-FFT : atgggtcaggccggagacggcgaaggcaacaccgacgaggacggggccggagggttcccg :  240

                    *       260         *       280         *       300
Lp1-FFT : tggagcaacgagatgctgcagtggcagcgcgccgggttccattaccagccggaggggcac :  300

                    *       320         *       340         *       360
Lp1-FFT : ttcatgagcgatccaaacggtccggtatactaccgtggatattaccacctcttctttcag :  360

                    *       380         *       400         *       420
Lp1-FFT : tacaaccgaagaggggtcgcgtgggatgactacatagagtggggccacgtggtgtcccag :  420

                    *       440         *       460         *       480
Lp1-FFT : gacctggtacactggcgccctctcccactggccatgcggcctgaccattggtacgacaag :  480

                    *       500         *       520         *       540
Lp1-FFT : aagggcgtcttgtcgggtaccatcacggtgctccacaatggcacgctcgtcctcctctac :  540

                    *       560         *       580         *       600
Lp1-FFT : acggggtcacagaagaccctatggccgagtcccagtgcatcgccgtcccgaccgacccc :  600

                    *       620         *       640         *       660
Lp1-FFT : aacgaccccctccttcgccattggaccaagcaccccgccaaccccgttctcgctcaccca :  660

                    *       680         *       700         *       720
Lp1-FFT : caggggtccagggcatggacttccgagaccccaccagcgcgtggtgggacaagtccgac :  720

                    *       740         *       760         *       780
Lp1-FFT : tccacgtggcgcattctcatcggttccaaggacgacgacaatggcagccatgctggcatc :  780

                    *       800         *       820         *       840
Lp1-FFT : gccttcatcttcaagaccaaggacttccttagcttcgagcgtgtcccaggtatcgtgcat :  840

                    *       860         *       880         *       900
Lp1-FFT : cgtgtcgagggtaccggcatgtgggagtgcatcgacttttaccccgttggaggtggccac :  900

                    *       920         *       940         *       960
Lp1-FFT : aactcttcgtcggaggagttgtacgtgataaaggcgagcatggacgacgaacgacacgac :  960

                    *       980         *      1000         *      1020
Lp1-FFT : tactactcattggggaggtatgacgcggcagcgaacacatggacgccattggacgccgag : 1020

                    *      1040         *      1060         *      1080
Lp1-FFT : ctagacttggggattgggctgaggtacgactggggcaagctctacgcttccacgtcgttc : 1080

                    *      1100         *      1120         *      1140
Lp1-FFT : tacgatccactgaagcagcggcgaattatgttggggtatgtaggcgaggtcgactctgcg : 1140
```

FIGURE 9 CONT

```
                      *        1160          *        1180          *        1200
Lpl-FFT : cgagccgacgttgccaagggatgggcctcacttcagtcgattccgaggacagtggcacta : 1200

                      *        1220          *        1240          *        1260
Lpl-FFT : gacgagaagacccggacgaacctcctcctatggccggtggaggaggtggaggccctccgc : 1260

                      *        1280          *        1300          *        1320
Lpl-FFT : tacaactccaccgacctcagcggcatcactgttgagaacggctccatcttccacctccct : 1320

                      *        1340          *        1360          *        1380
Lpl-FFT : ctccaccaagccactcagctggacatcgaggcttccttccgcctcgatgcttctgatgtt : 1380

                      *        1400          *        1420          *        1440
Lpl-FFT : gctgccatcaacgaggccgacgtcggctacaactgcagcagcagcggtggcgcggccgct : 1440

                      *        1460          *        1480          *        1500
Lpl-FFT : cgtggcgctctcgggcccttcggcctcctcgtccatgccgccggagacctccgtggcgag : 1500

                      *        1520          *        1540          *        1560
Lpl-FFT : cagacggcggtgtacttctacgtgtccagggccctcgacggtagcctccggaccagcttc : 1560

                      *        1580          *        1600          *        1620
Lpl-FFT : tgcaacgacgagacgcggtcgtcacgggcccgggacgtgacgaagcgggtggtgggcagc : 1620

                      *        1640          *        1660          *        1680
Lpl-FFT : acggtgccggtgctcgacggcgaggcgttgtcgatgagggtgctcgtggaccactccatc : 1680

                      *        1700          *        1720          *        1740
Lpl-FFT : gtgcagagcttcgcgatgggtgggagggtcacggcgacgtcgcgagtgtacccgacggag : 1740

                      *        1760          *        1780          *        1800
Lpl-FFT : gccatctacgccagggctggggtgtacctgttcaacaacgccaccggcgccagcgtgaca : 1800

                      *        1820          *        1840          *        1860
Lpl-FFT : gcggagaggctcatcgtgcacgagatggcgtcggcagtatacgacgagaccgtcatggtt : 1860

                      *
Lpl-FFT : aaggactcatag : 1872
```

FIGURE 10

```
                   *        20         *        40         *        60
Lp1-FFT : MESRAIPSAAYAPLLPSAADDVALAKQDRPGVGWRGFLTVLAACGVVVLLVGATLLAGSR :  60

                   *        80         *       100         *       120
Lp1-FFT : MGQAGDGEGNTDEDGAGGFPWSNEMLQWQRAGFHYQPEGHFMSDPNGPVYYRGYYHLFFQ : 120

                   *       140         *       160         *       180
Lp1-FFT : YNRRGVAWDDYIEWGHVVSQDLVHWRPLPLAMRPDHWYDKKGVLSGTITVLHNGTLVLLY : 180

                   *       200         *       220         *       240
Lp1-FFT : TGVTEDPMAESQCIAVPTDPNDPLLRHWTKHPANPVLAHPQGVQGMDFRDPTSAWWDKSD : 240

                   *       260         *       280         *       300
Lp1-FFT : STWRILIGSKDDDNGSHAGIAFIFKTKDFLSFERVPGIVHRVEGTGMWECIDFYPVGGGH : 300

                   *       320         *       340         *       360
Lp1-FFT : NSSSEELYVIKASMDDERHDYYSLGRYDAAANTWTPLDAELDLGIGLRYDWGKLYASTSF : 360

                   *       380         *       400         *       420
Lp1-FFT : YDPLKQRRIMLGYVGEVDSARADVAKGWASLQSIPRTVALDEKTRTNLLLWPVEEVEALR : 420

                   *       440         *       460         *       480
Lp1-FFT : YNSTDLSGITVENGSIFHLPLHQATQLDIEASFRLDASDVAAINEADVGYNCSSSGGAAA : 480

                   *       500         *       520         *       540
Lp1-FFT : RGALGPFGLLVHAAGDLRGEQTAVYFYVSRALDGSLRTSFCNDEIRSSRARDVTKRVVGS : 540

                   *       560         *       580         *       600
Lp1-FFT : IVPVLDGEALSMRVLVDHSIVQSFAMGGRVTATSRVYPTEAIYARAGVYLFNNATGASVI : 600

                   *       620
Lp1-FFT : AERLIVHEMASAVYDETVMVKDS* : 623
```

FIGURE 12

```
                          *        20         *        40         *        60
FT fusion 1 : ATGGAGTCCCCAAGCGCCGTCGTCCCSGGCACCACGGCGCCGCTGCTTCCTTATGCGTAC :   60

                         *        80         *       100         *       120
FT fusion 1: GCGCCGCTGCCGTCGTCCGCCGACGACGCCCGTCAAAACCGGAGTGGCGGGAGGTGGCGC :  120

                         *       140         *       160         *       180
FT fusion 1: GCGTGCGCCGCCGTGCTGGCCGCATCGGCGTTGTCGGTGGTCGTCGTGGTCGGGCTCCTC :  180

                         *       200         *       220         *       240
FT fusion 1: GCGGGCGGCAGGGTGGATCGGGTCCCGGCCGGCGGAGACGTGGCGTCGGCCACGGTGCCG :  240

                         *       260         *       280         *       300
FT fusion 1: GCCGTGCCGATGGAGTTCCCGAGGAGCCGGGGCAAGGACTTCGGCGTGTCGGAGAAGTCC :  300

                         *       320         *       340         *       360
FT fusion 1: TCCGGTGCCTACTCCACCGACGGCGGGTTCCCGTGGAGCAACGCCATGCTGCAGTGGCAG :  360

                         *       380         *       400         *       420
FT fusion 1: CGCACCGGGTTCCATTTCCAGCCGGAGCAGCACTACATGAACGATCCCAACGGCCCCGTG :  420

                         *       440         *       460         *       480
FT fusion 1: TACTACGGCGGATGGTACCACCTCTTCTACCAGCACAACCCCAAGGGCGACAGCTGGGGC :  480

                         *       500         *       520         *       540
FT fusion 1: AACATCGCGTGGGCCCACGCCGTCTCCAAGGACATGGTCAACTGGCGCCACCTCCCTCTC :  540

                         *       560         *       580         *       600
FT fusion 1: GCCATGGTTCCCGACCAGTGGTACGACAGCAACGGCGTCCTCACCGGCTCCATCACCGTG :  600

                         *       620         *       640         *       660
FT fusion 1: CTCCCCGACGGCCAGGTCATCCTGCTCTACACCGGCAACACCGACACCCTAGCCCAGGTC :  660

                         *       680         *       700         *       720
FT fusion 1: CAGTGCCTCGCCACGCCCGCCGACCCGTCCGACCCGCTCCTCCGCGAGTGGGTCAAGCAC :  720

                         *       740         *       760         *       780
FT fusion 1: CCCGCCAACCCCATCCTCTACCCTCCCCCGGCATCGGCCTCAAGGACTTCCGCGACCCC :  780

                       *       800         *       820         *       840
FT fusion 1: CTCACCGCCTGGTTCGACCACTCCGACCACACCTGGCGCACCGTCATCGGCTCCAAGGAC :  840

                         *       860         *       880         *       900
FT fusion 1: GACGACGGCCACGCCGGCATCATCCTCAGCTACAAGACCAAGGACTTCGTCAACTACGAG :  900

                         *       920         *       940         *       960
FT fusion 1: CTCATGCCGGGGAACATGCACCGCGGGCCCGACGGCACCGGAATGTACGAGTGCATCGAC :  960

                         *       980         *      1000         *      1020
FT fusion 1: CTCTACCCCGTCGGCGGCAACTCGTCCGAGATGCTCGGCGGCGACGACTCGCCCGGCGTG : 1020

                         *      1040         *      1060         *      1080
FT fusion 1: CTCTTCGTGCTCAAGGAGAGCAGCGACGACGAGCGCCACGACTACTACGCGCTCGGAAGG : 1080

                         *      1100         *      1120         *      1140
FT fusion 1: TTCGAYGCCGTCGCCAACGTTTGGACGCCCATCGACCGGGAGCTGGACCTTGGGATCGGG : 1140

                         *      1160         *      1180         *      1200
FT fusion 1: CTCAGATACGACTGGGGAAAGTACTACGCCTCCAAGTCCTTCTACGACCAGAAGAAGAAC : 1200
```

FIGURE 12 CONT

```
                     *      1220          *      1240          *      1260
FT fusion 1: CGCCGCATCGTATGGGCATACATCGGCGAGACCGACTCCGAGCAGGCCGACATCACCAAG : 1260

                     *      1280          *      1300          *      1320
FT fusion 1: GGATGGGCCAATCTCATGACGATTCCAAGAACGGTGGAGCTTGACAGGAAGACCCGCACA : 1320

                     *      1340          *      1360          *      1380
FT fusion 1: AACCTCATCCAATGGCCAGTGGAGGAGGTCGACACCCTCCGCAGGAACTCCACGGACCTC : 1380

                     *      1400          *      1420          *      1440
FT fusion 1: GGTCGCATCACCGTCAACGCCGGCTCCGTCATTCGCCTCCCCCTCCACCAGGGCGCTCAA : 1440

                     *      1460          *      1480          *      1500
FT fusion 1: CTCGACATCGAGGCCTCCTTCCAACTCAACTCTTCCGACGTGGATGCTATCAACGAGGCC : 1500

                     *      1520          *      1540          *      1560
FT fusion 1: GACGTCGGCTACAACTGCAGCACCAGTGGTGCCGCCGTACGGGGGGCGCTCGGCCCCTTT : 1560

                     *      1580          *      1600          *      1620
FT fusion 1: GGCCTCCTCGTCCTTGCCAACGGCCGCACCGAACAGACGGCTGTGTACTTCTACGTGTCC : 1620

                     *      1640          *      1660          *      1680
FT fusion 1: AAGGGCGTCGACGGTGCCCTCCAGACCCACTTCTGCCACGACGAGTCACGGTCAACGCGG : 1680

                     *      1700          *      1720          *      1740
FT fusion 1: GCAAAGGATGTCGTGAATAGGATGATTGGCAGCATCGTGCCGGTGCTTGACGGTGAGACC : 1740

                     *      1760          *      1780          *      1800
FT fusion 1: TTTTCGGTGAGGGTGCTAGTGGACCACTCCATCGTGCAGAGCTTCGCGATGGGCGGGAGG : 1800

                     *      1820          *      1840          *      1860
FT fusion 1: ATCACGGCGACGTCGCGGGCGTACCCGACGGAGGCCATCTACGCGGCCGCGGGGGTCTAC : 1860

                     *      1880          *      1900          *      1920
FT fusion 1: CTCTTCAACAACGCCACGGGCGCCACCGTCACCGCCGAGAGGCTCGTCGTGCACGAGATG : 1920

                     *      1940          *      1960          *      1980
FT fusion 1: GCCTCAGCTGACAACCATATCTTCACGAACGACGACTTGGGAGGAGGAAAGCTTGGAGGA : 1980

                     *      2000          *      2020          *      2040
FT fusion 1: GGAGAGTCCAGCGCCGTCGTCGCCCAAGGCACCACGTCGCCGCTGCTCCCGTACGCCTAC : 2040

                     *      2060          *      2080          *      2100
FT fusion 1: GCGCCGCTGCCGTCCTCTGCCGACGACGCCCGTGAAAACCAGAGTAGCGGCGGCGGTGTC : 2100

                     *      2120          *      2140          *      2160
FT fusion 1: AGGTGGCGCGCGTGCGCGGCCTCGGCCCTGGTGGTGCTGCTGGTCGTCGTCGGCTTCTTC : 2160

                     *      2180          *      2200          *      2220
FT fusion 1: GCGGGTGGCAGGGTGGATCTGGGTCAGGACGGCGAGGTGTCTGCGACTTCTTCGGTTCCT : 2220

                     *      2240          *      2260          *      2280
FT fusion 1: GGGAGCAGCAGGGGCAAGGATTCCGGCGTGTCGGAGAAGGAGTCGCCCGCCGACGGCGGC : 2280

                     *      2300          *      2320          *      2340
FT fusion 1: TTCCCGTGGAGCAACGCCATGCTGCAGTGGCAGCACACCGGGTTCCATTTCCAGCCACTC : 2340

                     *      2360          *      2380          *      2400
FT fusion 1: AAGCACTACATGAACGATCCCAACGGTCCGGTCTACTATGGCGGATGGTACCACCTCTTC : 2400

                     *      2420          *      2440          *      2460
FT fusion 1: TACCAGCACAACCCCTATGGCGACTCGTGGGGAAACGTATCTTGGGGACATGCCGTGTCC : 2460
```

FIGURE 12 CONT

```
                          *        2480          *        2500          *        2520
FT fusion 1: AAGGACCTGGTGAACTGGCGCCACCTCCCGGTCGCCTTGGTGCCCGATCAGTGGTACGAC : 2520

                          *        2540          *        2560          *        2580
FT fusion 1: ATCAACGGCGTCCTGACGGGCTCTATCACAGTGCTCCCAGACGGGCGTGTCATCCTGCTA : 2580

                          *        2600          *        2620          *        2640
FT fusion 1: TATACGGGGAACACCGACACCTTTTCGCAGGTCCAGTGCCTCGCAGTGCCCGCCGACCCA : 2640

                          *        2660          *        2680          *        2700
FT fusion 1: TCTGACCCGCTCCTCCGTAGCTGGATCAAGCACCCCGCCAACCCCATCCTCTTCCCGCCA : 2700

                          *        2720          *        2740          *        2760
FT fusion 1: CCTGGGATCGGGCTCAAGGACTTCCGTGACCCGCTCACAGCCTGGTTCGAACATTCCGAC : 2760

                          *        2780          *        2800          *        2820
FT fusion 1: AACACGTGGCGCACCATCATCGGATCCAAGGATGACGACGGCCACGCCGGCATCGTCCTT : 2820

                          *        2840          *        2860          *        2880
FT fusion 1: AGCTACAAGACCACCGACTTTGTGAATTATGAGCTCATGCCAGGGAACATGCATCGTGGC : 2880

                          *        2900          *        2920          *        2940
FT fusion 1: CCCGACGGCACCGGCATGTACGAGTGCCTTGACATCTACCCTGTGGGCGGCAACTCATCC : 2940

                          *        2960          *        2980          *        3000
FT fusion 1: GAGATGTTGGGTGGCGACTCCTCACATGAGGTGTTGTTCGTGCTCAAGGAGAGCGCCAAC : 3000

                          *        3020          *        3040          *        3060
FT fusion 1: GACGAGTGGCACGACTACTACGCGCTTGGGTGGTTTGACGCTGCCGCCAACACGTGGACG : 3060

                          *        3080          *        3100          *        3120
FT fusion 1: CCACAGGACCCCGAGGCGGACCTTGGGATCGGCCTCAGGTACGACTGGGGCAAGTACTAC : 3120

                          *        3140          *        3160          *        3180
FT fusion 1: GCGTCCAAGTCCTTCTACGACCCGATCAAGAACCGGCGTGTCGTTTGGGCTTTCGTCGGC : 3180

                          *        3200          *        3220          *        3240
FT fusion 1: GAGACCGACTCTGAGCAGGCCGACAAAGCCAAGGGATGGGCGTCCCTCATGTCGATTCCC : 3240

                          *        3260          *        3280          *        3300
FT fusion 1: AGGACGGTGGAGCTTGACAAGAAGACCCGGACGAACCTGATCCAATGGCCAGTGGAGGAG : 3300

                          *        3320          *        3340          *        3360
FT fusion 1: ATCGAGACCCTTCGCAGGAACGTCACAGACCTCGGTGGCATCACCGTTGAAGCCGGCTCC : 3360

                          *        3380          *        3400          *        3420
FT fusion 1: GTCATTCACCTTCCCCTCCAACAAGGCGGGCAGCTTGACATCGAGGCCTCCTTCCGTCTC : 3420

                          *        3440          *        3460          *        3480
FT fusion 1: AACTCTTCGGACATCGATGCACTCAACGAGGCCGACGTCGGCTTCAACTGCAGTAGCAGC : 3480

                          *        3500          *        3520          *        3540
FT fusion 1: GATGGGGTAGCCGTGCGTGGTGCGCTCGGCCCCTTTGGCCTCCTCGTCTTCGCCGACGGT : 3540

                          *        3560          *        3580          *        3600
FT fusion 1: CGCCACGAACAGACGGCGGCGTACTTCTACGTGTCCAAGGGCCTCGACGGCAGCCTCCTG : 3600

                          *        3620          *        3640          *        3660
FT fusion 1: ACGCACTACTGCCACGACGAGTCACGGTCGACGCGAGCAAAGGACGTCGTGAGCCGGGTG : 3660
```

FIGURE 12 CONT

```
                        *        3680            *        3700            *        3720

FT fusion 1: GTTGGCGGCACTGTGCCAGTGCTTGACGGTGAAACCTTTTCAGTGAGGGTGCTAGTGGAC : 3720

                        *        3740            *        3760            *        3780
FT fusion 1: CACTCCATCGTGCAGAGCTTCGTGATGGGTGGGAGGACCACGGTGACATCGCGGGCATAC : 3780

                        *        3800            *        3820            *        3840
FT fusion 1: CCGACGGAGGCCATCTACGCCGCGGCAGGGGTGTACCTGTTCAACAACGCAACGAGCGCC : 3840

                        *        3860            *        3880            *        3900
FT fusion 1: ACCATCACCGCCGAAGGGCTCGTCGTGTACGAGATGGCCTCGGCCGAGAGTCGGGCCTTC : 3900

                        *
FT fusion 1: TTGGCTGACGACATGTAG : 3918
```

FIGURE 13

```
Fusion 1: MESPSAVVPGTTAPLLPYAYAPLPSSADDARQNRSGGRWRACAAVLAASALSVVVVVGLL :   60

                    *        80         *       100         *       120
Fusion 1: AGGRVDRVPAGGDVASATVPAVPMEFPRSRGKDFGVSEKSSGAYSTDGGFPWSNAMLQWQ :  120

                    *       140         *       160         *       180
Fusion 1: RTGFHFQPEQHYMNDPNGPVYYGGWYHLFYQHNPKGDSWGNIAWAHAVSKDMVNWRHLPL :  180

                    *       200         *       220         *       240
Fusion 1: AMVPDQWYDSNGVLTGSITVLPDGQVILLYTGNTDTLAQVQCLATPADPSDPLLREWVKH :  240

                    *       260         *       280         *       300
Fusion 1: PANPILYPPPGIGLKDFRDPLTAWFDHSDHTWRTVIGSKDDDGHAGIILSYKTKDFVNYE :  300

                    *       320         *       340         *       360
Fusion 1: LMPGNMHRGPDGTGMYECIDLYPVGGNSSEMLGGDDSPGVLFVLKESSDDERHDYYALGR :  360

                    *       380         *       400         *       420
Fusion 1: FDAVANVWTPIDRELDLGIGLRYDWGKYYASKSFYDQKKNRRIVWAYIGETDSEQADITK :  420

                    *       440         *       460         *       480
Fusion 1: GWANLMTIPRTVELDRKTRTNLIQWPVEEVDTLRRNSTDLGRITVNAGSVIRLPLHQGAQ :  480

                    *       500         *       520         *       540
Fusion 1: LDIEASFQLNSSDVDAINEADVGYNCSTSGAAVRGALGPFGLLVLANGRTEQTAVYFYVS :  540

                    *       560         *       580         *       600
Fusion 1: KGVDGALQTHFCHDESRSTRAKDVVNRMIGSIVPVLDGETFSVRVLVDHSIVQSFAMGGR :  600

                    *       620         *       640         *       660
Fusion 1: ITATSRAYPTEAIYAAAGVYLFNNATGATVTAERLVVHEMASADNHIFTNDDLGGGKLGG :  660

                    *       680         *       700         *       720
Fusion 1: GESSAVVAQGTTSPLLPYAYAPLPSSADDARENQSSGGGVRWRACAASALVVLLVVVGFF :  720

                    *       740         *       760         *       780
Fusion 1: AGGRVDLGQDGEVSATSSVPGSSRGKDSGVSEKESPADGGFPWSNAMLQWQHTGFHFQPL :  780

                    *       800         *       820         *       840
Fusion 1: KHYMNDPNGPVYYGGWYHLFYQHNPYGDSWGNVSWGHAVSKDLVNWRHLPVALVPDQWYD :  840

                    *       860         *       880         *       900
Fusion 1: INGVLTGSITVLPDGRVILLYTGNTDTFSQVQCLAVPADPSDPLLRSWIKHPANPILFPP :  900

                    *       920         *       940         *       960
Fusion 1: PGIGLKDFRDPLTAWFEHSDNTWRTIIGSKDDDGHAGIVLSYKTTDFVNYELMPGNMHRG :  960

                    *       980         *      1000         *      1020
Fusion 1: PDGTGMYECLDIYPVGGNSSEMLGGDSSHEVLFVLKESANDEWHDYYALGWFDAAANTWT : 1020

                    *      1040         *      1060         *      1080
Fusion 1: PQDPEADLGIGLRYDWGKYYASKSFYDPIKNRRVVWAFVGETDSEQADKAKGWASLMSIP : 1080

                    *      1100         *      1120         *      1140
Fusion 1: RTVELDKKTRTNLIQWPVEEIETLRRNVTDLGGITVEAGSVIHLPLQQGGQLDIEASFRL : 1140

                  *      1160         *      1180         *      1200
Fusion 1: NSSDIDALNEADVGFNCSSSDGVAVRGALGPFGLLVFADGRHEQTAAYFYVSKGLDGSLL : 1200
```

FIGURE 13 CONT

```
                   *        1220          *        1240          *        1260
Fusion 1: THYCHDESRSTRAKDVVSRVVGGIVPVLDGETFSVRVLVDHSIVQSFVMGGRTTVISRAY : 1260

                   *        1280          *        1300
Fusion 1: PTEAIYAAAGVYLFNNATSATITAEGLVVYEMASAESRAFLADDM* : 1305
```

FIGURE 14

```
                        *        20         *        40         *        60
FT fusion 3: ATGGAGTCCCCAAGCGCCGTCGTCCCCGGCACCACGGCGCCGCTGCTTCCTTATGCGTAC :   60

                        *        80         *       100         *       120
FT fusion 3: GCGCCGCTGCCGTCGTCCGCCGACGACGCCCGTCAAAACCGGAGTGGCGGGAGGTGGCGC :  120

                        *       140         *       160         *       180
FT fusion 3: GCGTGCGCCGCCGTGCTGGCCGCATCGGCGTTGGCGGTGGTCGTCGTGGTCGGGCTCCTC :  180

                        *       200         *       220         *       240
FT fusion 3: GCGGGCGGCAGGGTGGATCGGGTCCCAGCCGGCGGAGACGTGGCGTCGGCCACGGTGCCG :  240

                        *       260         *       280         *       300
FT fusion 3: GCCGTGCCGATGGAGTTCCCGAGGAGCCGGGGCAAGGACTTCGGCGTGTCGGAGAAGTCC :  300

                        *       320         *       340         *       360
FT fusion 3: TCCGGTGCCTACTCCACCGACGGCGGGTTCCCGTGGAGCAACGCCATGCTGCAGTGGCAG :  360

                        *       380         *       400         *       420
FT fusion 3: CGCACCGGGTTCCATTTCCAGCCGGAGCAGCACTACATGAACGATCCCAACGGCCCCGTG :  420

                        *       440         *       460         *       480
FT fusion 3: TACTACGGCGGATGGTACCACCTCTTCTACCAGCACAACCCCAAGGGCGACAGCTGGGGC :  480

                        *       500         *       520         *       540
FT fusion 3: AACATCGCGTGGGCCCACGCCGTCTCCAAGGACATGGTCAACTGGCGCCACCTCCCTCTC :  540

                        *       560         *       580         *       600
FT fusion 3: GCCATGGTTCCCGACCAGTGGTACGACAGCAACGGCGTCCTCACCGGCTCCATCACCGTG :  600

                        *       620         *       640         *       660
FT fusion 3: CTCCCCGACGGCCAGGTCATCCTGCTCTACACCGGCAACACCGACACCCTAGCCCAGGTC :  660

                        *       680         *       700         *       720
FT fusion 3: CAGTGCCTCGCCACGCCCGCCGACCCGTCCGACCCGCTCCTCCGCGAGTGGGTCAAGCAC :  720

                        *       740         *       760         *       780
FT fusion 3: CCCGCCAACCCCATCCTCTACCCTCCCCCCGGCATCGGCCTCAAGGACTTCCGCGACCCC :  780

                        *       800         *       820         *       840
FT fusion 3: CTCACCGCCTGGTTCGACCACTCCGACCACACCTGGCGCACCGTCATCGGCTCCAAGGAC :  840

                        *       860         *       880         *       900
FT fusion 3: GACGACGGCCACGCCGGCATCATCCTCAGCTACAAGACCAAGGACTTCGTCAACTACGAG :  900

                        *       920         *       940         *       960
FT fusion 3: CTCATGCCGGGGAACATGCACCGCGGGCCCGACGGCACCGGAATGTACGAGTGCATCGAC :  960

                        *       980         *      1000         *      1020
FT fusion 3: CTCTACCCCGTCGGCGGCAACTCGTCCGAGATGCTCGGCGGCGACGACTCGCCCGGCGTG : 1020

                        *      1040         *      1060         *      1080
FT fusion 3: CTCTTCGTGCTCAAGGAGAGCAGCGACGACGAGCGCCACGACTACTACGCGCTCGGAAGG : 1080

                        *      1100         *      1120         *      1140
FT fusion 3: TTCGACGCCGTCGCCAACGTTTGGACGCCCATCGACCGGGAGCTGGACCTTGGGATCGGG : 1140

                        *      1160         *      1180         *      1200
FT fusion 3: CTCAGATACGACTGGGGAAAGTACTACGCCTCCAAGTCCTTCTACGACCAGAAGAAGAAC : 1200
```

FIGURE 14 CONT

```
                    *      1220         *      1240         *      1260
FT fusion 3: CGCCGCATCGTATGGGCATACATCGGCGAGACCGACTCCGAGCAGGCCGACATCACCAAG : 1260

                    *      1280         *      1300         *      1320
FT fusion 3: GGATGGGCCAATCTCATGACGATTCCAAGAACGGTGGAGCTTGACAGGAAGACCCGCACA : 1320

                    *      1340         *      1360         *      1380
FT fusion 3: AACCTCATCCAATGGCCAGTGGAGGAGGTCGACACCCTCCGCAGGAACTCCACGGACCTC : 1380

                    *      1400         *      1420         *      1440
FT fusion 3: GGTCGCATCACCGTCAACGCCGGCTCCGTCATTCGCCTCCCCCTCCACCAGGGCGCTCAA : 1440

                    *      1460         *      1480         *      1500
FT fusion 3: CTCGACATCGAGGCCTCCTTCCAACTCAACTCTTCCGACGTGGATGCTATCAACGAGGCC : 1500

                    *      1520         *      1540         *      1560
FT fusion 3: GACGTCGGCTACAACTGCAGCACCAGTGGTGCCGCCGTACGGGGGCGCTCGGCCCCTTT : 1560

                    *      1580         *      1600         *      1620
FT fusion 3: GGCCTCCTCGTCCTTGCCAACGGCCGCACCGAACAGACGGCTGTGTACTTCTACGTGTCC : 1620

                    *      1640         *      1660         *      1680
FT fusion 3: AAGGGCGTCGACGGTGCCCTCCAGACCCACTTCTGCCACGACGAGTCACGGTCAACGCGG : 1680

                    *      1700         *      1720         *      1740
FT fusion 3: GCAAAGGATGTCGTGAATAGGATGATTGGCAGCATCGTGCCGGTGCTTGACGGTGAGACC : 1740

                    *      1760         *      1780         *      1800
FT fusion 3: TTTTCGGTGAGGGTGCTAGTGGACCACTCCATCGTGCAGAGCTTCGCGATGGGCGGGAGG : 1800

                    *      1820         *      1840         *      1860
FT fusion 3: ATCACGGCGACGTCGCGGGCGTACCCGACGGAGGCCATCTACGCGGCCGCGGGGGTCTAC : 1860

                    *      1880         *      1900         *      1920
FT fusion 3: CTCTTCAACAACGCCACGGGCGCCACCGTCACCGCCGAGAGGCTCGTCGTGCACGAGATG : 1920

                    *      1940         *      1960         *      1980
FT fusion 3: GCCTCAGCTGACAACCATATCTTCACGAACGACGACTTGGGAGGAGGAAAGCTTAAGCTT : 1980

                    *      2000         *      2020         *      2040
FT fusion 3: GGAGGAGGAGAGTCCAGCGCCGTCGTCGCCCAAGGCACCACGTCGCCGCTGCTCCCGTAC : 2040

                    *      2060         *      2080         *      2100
FT fusion 3: GCCTACGCGCCGCTGCCGTCCTCTGCCGACGACGCCCGTGAAAACCAGAGTAGCGGCGGC : 2100

                    *      2120         *      2140         *      2160
FT fusion 3: GGTGTCAGGTGGCGCGCGTGCGCGGCCTCGGCCCTGGTGGTGCTGCTGGTCGTCGTCGGC : 2160

                    *      2180         *      2200         *      2220
FT fusion 3: TTCTTCGCGGGTGGCAGGGTGGATCTGGGTCAGGACGGCGAGGTGTCTGCGACTTCTTCG : 2220

                    *      2240         *      2260         *      2280
FT fusion 3: GTTCCTGGGAGCAGCAGGGGCAAGGATTCCGGCGTGTCGGAGAAGGAGTCGCCCGCCGAC : 2280

                    *      2300         *      2320         *      2340
FT fusion 3: GGCGGCTTCCCGTGGAGCAACGCCATGCTGCAGTGGCAGCACACCGGGTTCCATTTCCAG : 2340

                    *      2360         *      2380         *      2400
FT fusion 3: CCACTCAAGCACTACATGAACGATCCCAACGGTCCGGTCTACTATGGCGGATGGTACCAC : 2400

                    *      2420         *      2440         *      2460
FT fusion 3: CTCTTCTACCAGCACAACCCCTATGGCGACTCGTGGGGAAACGTATCTTGGGGACATGCC : 2460
```

FIGURE 14 CONT

```
                    *        2480          *        2500          *        2520
FT fusion 3: GTGTCCAAGGACCTGGTGAACTGGCGCCACCTCCCGGTCGCCTTGGTGCCCGATCAGTGG : 2520

                    *        2540          *        2560          *        2580
FT fusion 3: TACGACATCAACGGCGTCCTGACGGGCTCTATCACAGTGCTCCCAGACGGGCGTGTCATC : 2580

                    *        2600          *        2620          *        2640
FT fusion 3: CTGCTATATACGGGGAACACCGACACCTTTTCGCAGGTCCAGTGCCTCGCAGTGCCCGCC : 2640

                    *        2660          *        2680          *        2700
FT fusion 3: GACCCATCTGACCCGCTCCTCCGTAGCTGGATCAAGCACCCCGCCAACCCCATCCTCTTC : 2700

                    *        2720          *        2740          *        2760
FT fusion 3: CCGCCACCTGGGATCGGGCTCAAGGACTTCCGTGACCCGCTCACAGCCTGGTTCGAACAT : 2760

                    *        2780          *        2800          *        2820
FT fusion 3: TCCGACAACACGTGGCGCACCATCATCGGATCCAAGGATGACGACGGCCACGCCGGCATC : 2820

                    *        2840          *        2860          *        2880
FT fusion 3: GTCCTTAGCTACAAGACCACCGACTTTGTGAATTATGAGCTCATGCCAGGGAACATGCAT : 2880

                    *        2900          *        2920          *        2940
FT fusion 3: CGTGGCCCCGACGGCACCGGCATGTACGAGTGCCTTGACATCTACCCTGTGGGCGGCAAC : 2940

                    *        2960          *        2980          *        3000
FT fusion 3: TCATCCGAGATGTTGGGTGGCGACTCCTCACCTGAGGTGTTGTTCGTGCTCAAGGAGAGC : 3000

                    *        3020          *        3040          *        3060
FT fusion 3: GCCAACGACGAGTGGCACGACTACTACGCGCTTGGGTGGTTTGACGCTGCCGCCAACACG : 3060

                    *        3080          *        3100          *        3120
FT fusion 3: TGGACGCCACAGGACCCCGAGGCGGACCTTGGGATCGGCCTCAGGTACGACTGGGGCAAG : 3120

                    *        3140          *        3160          *        3180
FT fusion 3: TACTACGCGTCCAAGTCCTTCTACGACCCGATCAAGAACCGGCGTGTCGTTTGGGCTTTC : 3180

                    *        3200          *        3220          *        3240
FT fusion 3: GTCGGCGAGACCGACTCTGAGCAGGCCGACAAAGCCAAGGGATGGGCGTCCCTCATGTCG : 3240

                    *        3260          *        3280          *        3300
FT fusion 3: ATTCCCAGGACGGTGGAGCTTGACAAGAAGACCCGGACGAACCTGATCCAATGGCCAGTG : 3300

                    *        3320          *        3340          *        3360
FT fusion 3: GAGGAGATCGAGACCCTTCGCAGGAACGTCACAGACCTCGGTGGCATCACCGTTGAAGCC : 3360

                    *        3380          *        3400          *        3420
FT fusion 3: GGCTCCGTCATTCACCTTCCCCTCCAACAAGGCGGGCAGCTTGACATCGAGGCCTCCTTC : 3420

                    *        3440          *        3460          *        3480
FT fusion 3: CGTCTCAACTCTTCGGACATCGATGCACTCAACGAGGCCGACGTCGGCTTCAACTGCAGT : 3480

                    *        3500          *        3520          *        3540
FT fusion 3: AGCAGCGATGGGGCAGCCGTGCGTGGTGCGCTCGGCCCCTTTGGCCTCCTCGTCTTCGCC : 3540

                    *        3560          *        3580          *        3600
FT fusion 3: GACGGTCGCCACGAACAGACGGCGGCGTACTTCTACGTGTCCAAGGGCCTCGACGGCAGC : 3600

                    *        3620          *        3640          *        3660
FT fusion 3: CTCCTGACGCACTACTGCCACGACGAGTCACGGTCGACGCGAGCAAAGGACGTCGTGAGC : 3660

                    *        3680          *        3700          *        3720
FT fusion 3: CGGGTGGTTGGCGGCACTGTGCCAGTGCTTGACGGTGAAACCTTTTCAGTGAGGGTGCTA : 3720
```

FIGURE 14 CONT

```
                    *       3740          *       3760          *       3780
FT fusion 3: GTGGACCACTCCATCGTGCAGAGCTTCGTGATGGGTGGGAGGACCACGGTGACATCGCGG : 3780

                    *       3800          *       3820          *       3840
FT fusion 3: GCATACCCGACGGAGGCCATCTACGCCGCGGCAGGGGTGTACCTGTTCAACAACGCAACG : 3840

                    *       3860          *       3880          *       3900
FT fusion 3: AGCGCCACCATCACCGCCGAAGGGCTCGTCGTGTACGAGATGGCCTCGGCCGAGAGTCGG : 3900

                    *       3920
FT fusion 3: GCCTTCTTGGCTGACGACATGTAG : 3924
```

FIGURE 15

```
                    *        20         *        40         *        60
FT fusion 3: MESPSAVVPGTTAPLLPYAYAPLPSSADDARQNRSGGRWRACAAVLAASALAVVVVVGLL :   60

                    *        80         *       100         *       120
FT fusion 3: AGGRVDRVPAGGDVASATVPAVPMEFPRSRGKDFGVSEKSSGAYSTDGGFPWSNAMLQWQ :  120

                    *       140         *       160         *       180
FT fusion 3: RTGFHFQPEQHYMNDPNGPVYYGGWYHLFYQHNPKGDSWGNIAWAHAVSKDMVNWRHLPL :  180

                    *       200         *       220         *       240
FT fusion 3: AMVPDQWYDSNGVLTGSITVLPDGQVILLYTGNTDTLAQVQCLATPADPSDPLLREWVKH :  240

                    *       260         *       280         *       300
FT fusion 3: PANPILYPPPGIGLKDFRDPLTAWFDHSDHTWRTVIGSKDDDGHAGIILSYKTKDFVNYE :  300

                    *       320         *       340         *       360
FT fusion 3: LMPGNMHRGPDGTGMYECIDLYPVGGNSSEMLGGDDSPGVLFVLKESSDDERHDYYALGR :  360

                    *       380         *       400         *       420
FT fusion 3: FDAVANVWTPIDRELDLGIGLRYDWGKYYASKSFYDQKKNRRIVWAYIGETDSEQADITK :  420

                    *       440         *       460         *       480
FT fusion 3: GWANLMTIPRTVELDRKTRTNLIQWPVEEVDTLRRNSTDLGRITVNAGSVIRLPLHQGAQ :  480

                    *       500         *       520         *       540
FT fusion 3: LDIEASFQLNSSDVDAINEADVGYNCSTSGAAVRGALGPFGLLVLANGRTEQTAVYFYVS :  540

                    *       560         *       580         *       600
FT fusion 3: KGVDGALQTHFCHDESRSTRAKDVVNRMIGSIVPVLDGETFSVRVLVDHSIVQSFAMGGR :  600

                    *       620         *       640         *       660
FT fusion 3: ITATSRAYPTEAIYAAAGVYLFNNATGATVTAERLVVHEMASADNHIFTNDDLGGGKLKL :  660

                    *       680         *       700         *       720
FT fusion 3: GGGESSAVVAQGTTSPLLPYAYAPLPSSADDARENQSSGGGVRWRACAASALVVLLVVVG :  720

                    *       740         *       760         *       780
FT fusion 3: FFAGGRVDLGQDGEVSATSSVPGSSRGKDSGVSEKESPADGGFPWSNAMLQWQHTGFHFQ :  780

                    *       800         *       820         *       840
FT fusion 3: PLKHYMNDPNGPVYYGGWYHLFYQHNPYGDSWGNVSWGHAVSKDLVNWRHLPVALVPDQW :  840

                    *       860         *       880         *       900
FT fusion 3: YDINGVLTGSITVLPDGRVILLYTGNTDTFSQVQCLAVPADPSDPLLRSWIKHPANPILF :  900

                    *       920         *       940         *       960
FT fusion 3: PPPGIGLKDFRDPLTAWFEHSDNTWRTIIGSKDDDGHAGIVLSYKTTDFVNYELMPGNMH :  960

                    *       980         *      1000         *      1020
FT fusion 3: RGPDGTGMYECLDIYPVGGNSSEMLGGDSSPEVLFVLKESANDEWHDYYALGWFDAAANT : 1020

                    *      1040         *      1060         *      1080
FT fusion 3: WTPQDPEADLGIGLRYDWGKYYASKSFYDPIKNRRVVWAFVGETDSEQADKAKGWASLMS : 1080

                    *      1100         *      1120         *      1140
FT fusion 3: IPRTVELDKKTRTNLIQWPVEEIETLRRNVTDLGGITVEAGSVIHLPLQQGGQLDIEASF : 1140

                    *      1160         *      1180         *      1200
FT fusion 3: RLNSSDIDALNEADVGFNCSSSDGAAVRGALGPFGLLVFADGRHEQTAAYFYVSKGLDGS : 1200
```

FIGURE 15 CONT

```
                      *      1220         *      1240         *      1260
FT fusion 3: LLTHYCHDESRSTRAKDVVSRVVGGTVPVLDGETFSVRVLVDHSIVQSFVMGGRTTVTSR : 1260

                      *      1280         *      1300
FT fusion 3: AYPTEAIYAAAGVYLFNNATSATITAEGLVVYEMASAESRAFLADDM* : 1307
```

A

B

FIGURE 23
A
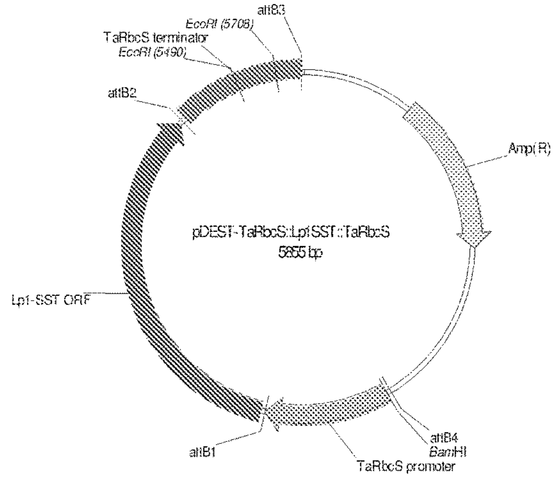
B
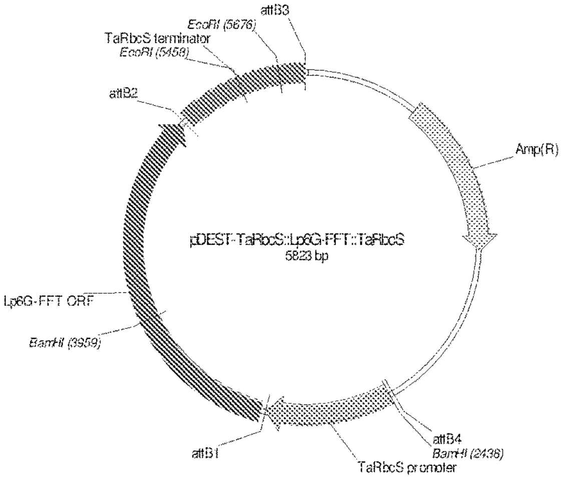
C
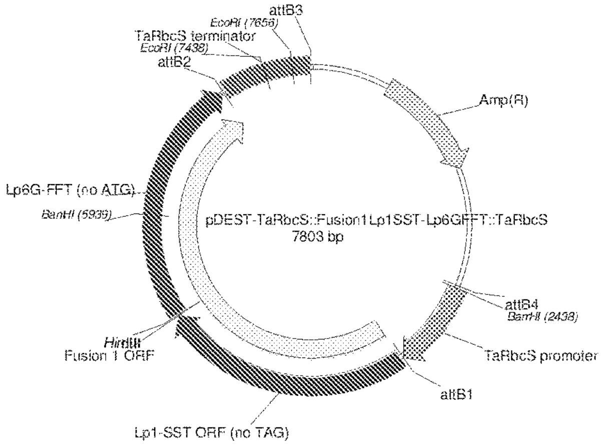

FIGURE 23 CONTINUED
D
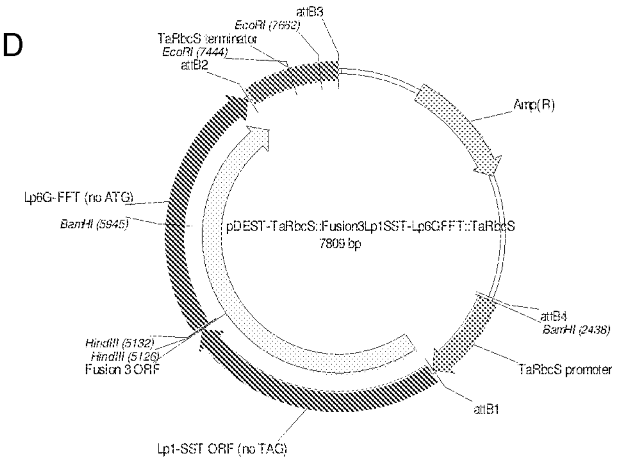
E
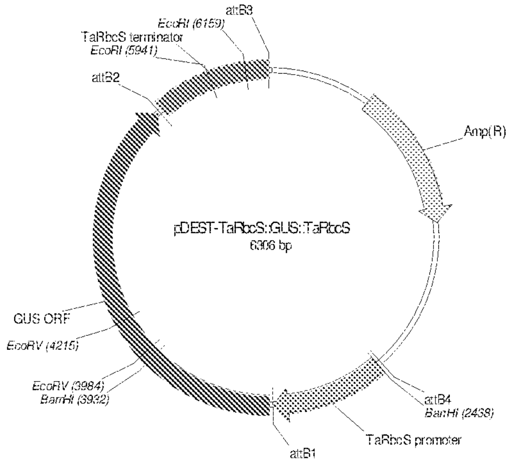

FIGURE 24

```
          *        20         *        40         *        60
: GATCCGGTGACTCAAAAAAGAAGAGCCGCCATCTGTCCAAGCGCCACTCCTACGAGAACT :   60

          *        80         *       100         *       120
: AAAATCCTATTCCCTCCGTAAATAAATATAAGAGTGTTTAGATCACTACTTCTTTACAGA :  120

          *       140         *       160         *       180
: GAATTTCCTTCCCTCCAAGGGGAGGCGAATCCATAGGCACATCGACGGATATGGAGGGGG :  180

          *       200         *       220         *       240
: GAAACATATATTTTACTATGCTAGTTCAGTTAATTCTACCAAGAAAACATATATTTTATT :  240

          *       260         *       280         *       300
: TTGACAAACATTGTATAAATGTAGACATTCACATACACGTATGTACACCACCCTCTATGA :  300

          *       320         *       340         *       360
: TTGCACACCCGCACACTATATGCCTATGAGCATACTTTCAAGAGTGAGCCAGCAAATTTT :  360

          *       380         *       400         *       420
: ATGATAAAATGAAATATTTTGCCCAGCCAACTCAGTCGCATCCTCGGACAATTTGTTATC :  420

          *       440         *       460         *       480
: AAGGAACTCACCCAAAAACAAGCAAAGCTAGAAAAAGGTTGTGTGGCAGCCACCTAATGA :  480

          *       500         *       520         *       540
: CATGAAGGACTGAAATTTCCAGCACACACAATGTATCCGACGGCAATGCTTCTTCCACTG :  540

          *       560         *       580         *       600
: ATCCGGAGAAGATAAGGAAACGAGGCAACCAGCGAACGTGAGCCATCCCAACCACATCTG :  600

          *       620         *       640         *       660
: TACCAAAGAAACGGGGCTATATATACCGTGGTGACCCGGCAATGGGGTCCTCAACTGTAG :  660

          *       680         *       700         *       720
: CCGGCATCCTCCTCTCCTCCGATAATACAAATACCCAAGTTTGTACAAAAAAGCAGGCTT :  720

          *       740         *       760         *       780
: CATGGAGTCCCCAAGCGCCGTCGTCCCCGGCACCACGGCGCCGCTGCTTCCTTATGCGTA :  780

          *       800         *       820         *       840
: CGCGCCGCTGCCGTCGTCCGCCGACGACGCCCGTCAAAACCGGAGTGGCGGGAGGTGGCG :  840

          *       860         *       880         *       900
: CGCGTGCGCCGCCGTGCTGGCCGCATCGGCGTTGGCGGTGGTCGTCGTGGTCGGGCTCCT :  900

          *       920         *       940         *       960
: CGCGGGCGGCAGGGTGGATCGGGTCCCGGCCGGCGGAGACGTGGCGTCGGCCACGGTGCC :  960

          *       980         *      1000         *      1020
: GGCCGTGCCGATGGAGTTCCCGAGGAGCCGGGGCAAGGACTTCGGCGTGTCGGAGAAGTC : 1020

          *      1040         *      1060         *      1080
: CTCCGGTGCCTACTCCACCGACGGCGGGTTCCCGTGGAGCAACGCCATGCTGCAGTGGCA : 1080

          *      1100         *      1120         *      1140
: GCGCACCGGGTTCCATTTCCAGCCGGAGCAGCACTACATGAACGATCCCAACGGCCCCGT : 1140

          *      1160         *      1180         *      1200
: GTACTACGGCGGATGGTACCACCTCTTCTACCAGCACAACCCCAAGGGCGACAGCTGGGG : 1200
```

FIGURE 24 CONT

```
          *        1220         *        1240         *        1260
: CAACATCGCGTGGGCCCACGCCGTCTCCAAGGACATGGTCAACTGGCGCCACCTCCCTCT : 1260

          *        1280         *        1300         *        1320
: CGCCATGGTTCCCGACCAGTGGTACGACAGCAACGGCGTCCTCACCGGCTCCATCACCGT : 1320

          *        1340         *        1360         *        1380
: GCTCCCCGACGGCCAGGTCATCCTGCTCTACACCGGCAACACCGACACCCTAGCCCAGGT : 1380

          *        1400         *        1420         *        1440
: CCAGTGCCTCGCCACGCCCGCCGACCCGTCCGACCCGCTCCTCCGCGAGTGGGTCAAGCA : 1440

          *        1460         *        1480         *        1500
: CCCCGCCAACCCCATCCTCTACCCTCCCCCCGGCATCGGCCTCAAGGACTTCCGCGACCC : 1500

          *        1520         *        1540         *        1560
: CCTCACCGCCTGGTTCGACCACTCCGACCACACCTGGCGCACCGTCATCGGCTCCAAGGA : 1560

          *        1580         *        1600         *        1620
: CGACGACGGCCACGCCGGCATCATCCTCAGCTACAAGACCAAGGACTTCGTCAACTACGA : 1620

          *        1640         *        1660         *        1680
: GCTCATGCCGGGGAACATGCACCGCGGGCCCGACGGCACCGGAATGTACGAGTGCATCGA : 1680

          *        1700         *        1720         *        1740
: CCTCTACCCCGTCGGCGGCAACTCGTCCGAGATGCTCGGCGGCGACGACTCGCCCGGCGT : 1740

          *        1760         *        1780         *        1800
: GCTCTTCGTGCTCAAGGAGAGCAGCGACGACGAGCGCCACGACTACTACGCGCTCGGAAG : 1800

          *        1820         *        1840         *        1860
: GTTCGACGCCGTCGCCAACGTTTGGACGCCCATCGACCGGGAGCTGGACCTTGGGATCGG : 1860

          *        1880         *        1900         *        1920
: GCTCAGATACGACTGGGGAAAGTACTACGCCTCCAAGTCCTTCTACGACCAGAAGAAGAA : 1920

          *        1940         *        1960         *        1980
: CCGCCGCATCGTATGGGCATACATCGGCGAGACCGACTCCGAGCAGGCCGACATCACCAA : 1980

          *        2000         *        2020         *        2040
: GGGATGGGCCAATCTCATGACGATTCCAAGAACGGTGGAGCTTGACAGGAAGACCCGCAC : 2040

          *        2060         *        2080         *        2100
: AAACCTCATCCAATGGCCAGTGGAGGAGGTCGACACCCTCCGCAGGAACTCCACGGACCT : 2100

          *        2120         *        2140         *        2160
: CGGTCGCATCACCGTCAACGCCGGCTCCGTCATTCGCCTCCCCCTCCACCAGGGCGCTCA : 2160

          *        2180         *        2200         *        2220
: ACTCGACATCGAGGCCTCCTTCCAACTCAACTCTTCCGACGTGGATGCTATCAACGAGGC : 2220

          *        2240         *        2260         *        2280
: CGACGTCGGCTACAACTGCAGCACCAGTGGTGCCGCCGTACGGGGGGCGCTCGGCCCCTT : 2280

          *        2300         *        2320         *        2340
: TGGCCTCCTCGTCCTTGCCAACGGCCGCACCGAACAGACGGCTGTGTACTTCTACGTGTC : 2340

          *        2360         *        2380         *        2400
: CAAGGGCGTCGACGGTGCCCTCCAGACCCACTTCTGCCACGACGAGTCACGGTCAACGCG : 2400
```

FIGURE 24 CONT

```
                    *        2420          *        2440          *        2460
 : GGCAAAGGATGTCGTGAATAGGATGATTGGCAGCATCGTGCCGGTGCTTGACGGTGAGAC : 2460

                    *        2480          *        2500          *        2520
 : CTTTTCGGTGAGGGTGCTAGTGGACCACTCCATCGTGCAGAGCTTCGCGATGGGCGGGAG : 2520

                    *        2540          *        2560          *        2580
 : GATCACGGCGACGTCGCGGGCGTACCCGACGGAGGCCATCTACGCGGCCGCGGGGGTCTA : 2580

                    *        2600          *        2620          *        2640
 : CCTCTTCAACAACGCCACGGGCGCCACCGTCACCGCCGAGAGGCTCGTCGTGCACGAGAT : 2640

                    *        2660          *        2680          *        2700
 : GGCCTCAGCTGACAACCATATCTTCACGAACGACGACTTGTAGGACCCAGCTTTCTTGTA : 2700

                    *        2720          *        2740          *        2760
 : CAAAGTGGACTATGAGTTGAAACAATGGCCTATCTCATATGAAGATCTTTTGTGAATTTC : 2760

                    *        2780          *        2800          *        2820
 : ACTTTTGTCCACGACCTCTGTTGCACGACTCTGCTTTCCGACCGGAGCATACCTTTTGTT : 2820

                    *        2840          *        2860          *        2880
 : CTATATGATTTGTGTATGTATGTAGGAACCTATGTTCTCGAGCATGCATACATAATTCCT : 2880

                    *        2900          *        2920          *        2940
 : CATAGGTCTATATACACCGGCTATCCATATGCAAAACCTGTGTAATATTTGTTATATACA : 2940

                    *        2960          *        2980          *        3000
 : ACACGCGGACCATTGTCTTGCTGTTATTAATTCTTTTTTCCCGCAAAAAAGGAAAAGTTT : 3000

                    *        3020          *        3040          *        3060
 : CTTTATTTGGCACTGCAATGGATATGCCTCACAGCTAGTGGGTGGAGAATTCAGTATTTG : 3060

                    *        3080          *        3100          *        3120
 : ACATTAAGATTCCCTGATTTGCAATTGCAAATTTCAGTTTCTTTACTTATATCACTACAA : 3120

                    *        3140          *        3160          *        3180
 : AAGTCTTATTGTTTCTTTTCCACGTCATTACCATCTGCTCCATTGGTTTTTGCTAGTAGA : 3180

                    *        3200          *        3220          *        3240
 : ATAGGATGAAGCATGGACACAGATTAACTGAGCTCGAGCTCATATGAGCTCGGGTGAACA : 3240

                    *        3260          *        3280          *        3300
 : ATAAAATCTGAAAATACTTAGAAAGAATTCAAAATTTTCTGTTTTTTGTGGCAAAATTTG : 3300

                    *        3320          *        3340          *        3360
 : ACAAATGTTATAAATGCTTGCAAAGTTTCATCATAGAACGACATTCGTGGATGTCATGGC : 3360

                    *        3380          *        3400
 : AAAAAACAAATTCAGCACTCTGAAAATAACTTTTTTGAAGTATCG : 3405
```

FIGURE 25

```
            *        20         *        40         *        60
: GATCCGGTGACTCAAAAAAGAAGAGCCGCCATCTGTCCAAGCGCCACTCCTACGAGAACT :   60

            *        80         *       100         *       120
: AAAATCCTATTCCCTCCGTAAATAAATATAAGAGTGTTTAGATCACTACTTCTTTACAGA :  120

            *       140         *       160         *       180
: GAATTTCCTTCCCTCCAAGGGGAGGCGAATCCATAGGCACATCGACGGATATGGAGGGGG :  180

            *       200         *       220         *       240
: GAAACATATATTTTACTATGCTAGTTCAGTTAATTCTACCAAGAAAACATATATTTTATT :  240

            *       260         *       280         *       300
: TTGACAAACATTGTATAAATGTAGACATTCACATACACGTATGTACACCACCCTCTATGA :  300

            *       320         *       340         *       360
: TTGCACACCCGCACACTATATGCCTATGAGCATACTTTCAAGAGTGAGCCAGCAAATTTT :  360

            *       380         *       400         *       420
: ATGATAAAATGAAATATTTTGCCCAGCCAACTCAGTCGCATCCTCGGACAATTTGTTATC :  420

            *       440         *       460         *       480
: AAGGAACTCACCCAAAAACAAGCAAAGCTAGAAAAAGGTTGTGTGGCAGCCACCTAATGA :  480

            *       500         *       520         *       540
: CATGAAGGACTGAAATTTCCAGCACACACAATGTATCCGACGGCAATGCTTCTTCCACTG :  540

            *       560         *       580         *       600
: ATCCGGAGAAGATAAGGAAACGAGGCAACCAGCGAACGTGAGCCATCCCAACCACATCTG :  600

            *       620         *       640         *       660
: TACCAAAGAAACGGGGCTATATATACCGTGGTGACCCGGCAATGGGGTCCTCAACTGTAG :  660

            *       680         *       700         *       720
: CCGGCATCCTCCTCTCCTCCGATAATACAAATACCCAAGTTTGTACAAAAAAGCAGGCTT :  720

            *       740         *       760         *       780
: CATGGAGTCCAGCGCCGTCGTCGCCCAAGGCACCACGTCGCCGCTGCTCCCGTACGCCTA :  780

            *       800         *       820         *       840
: CGCGCCGCTGCCGTCCTCTGCCGACGACGCCCGTGAAAACCAGAGTAGCGGCGGCGGTGT :  840

            *       860         *       880         *       900
: CAGGTGGCGCGCGTGCGCGGCCTCGGCCCTGGTGGTGCTGCTGGTCGTCGTCGGCTTCTT :  900

            *       920         *       940         *       960
: CGCGGGTGGCAGGGTGGATCTGGGTCAGGACGGCGAGGTGTCTGCGACTTCTTCGGTTCC :  960

            *       980         *      1000         *      1020
: TGGGAGCAGCAGGGGCAAGGATTCCGGCGTGTCGGAGAAGGAGTCGCCCGCCGACGGCGG : 1020

            *      1040         *      1060         *      1080
: CTTCCCGTGGAGCAACGCCATGCTGCAGTGGCAGCACACCGGGTTCCATTTCCAGCCACT : 1080

            *      1100         *      1120         *      1140
: CAAGCACTACATGAACGATCCCAACGGTCCGGTCTACTATGGCGGATGGTACCACCTCTT : 1140

            *      1160         *      1180         *      1200
: CTACCAGCACAACCCCTATGGCGACTCGTGGGGAAACGTATCTTGGGGACATGCCGTGTC : 1200

            *      1220         *      1240         *      1260
: CAAGGACCTGGTGAACTGGCGCCACCTCCCGGTCGCCTTGGTGCCCGATCAGTGGTACGA : 1260
```

FIGURE 25 CONT

```
              *        1280         *        1300         *        1320
    : CATCAACGGCGTCCTGACGGGCTCTATCACAGTGCTCCCAGACGGGCGTGTCATCCTGCT : 1320
              *        1340         *        1360         *        1380
    : ATATACGGGGAACACCGACACCTTTTCGCAGGTCCAGTGCCTCGCAGTGCCCGCCGACCC : 1380
              *        1400         *        1420         *        1440
    : ATCTGACCCGCTCCTCCGTAGCTGGATCAAGCACCCCGCCAACCCCATCCTCTTCCCGCC : 1440
              *        1460         *        1480         *        1500
    : ACCTGGGATCGGGCTCAAGGACTTCCGTGACCCGCTCACAGCCTGGTTCGAACATTCCGA : 1500
              *        1520         *        1540         *        1560
    : CAACACGTGGCGCACCATCATCGGATCCAAGGATGACGACGGCCACGCCGGCATCGTCCT : 1560
              *        1580         *        1600         *        1620
    : TAGCTACAAGACCACCGACTTTGTGAATTATGAGCTCATGCCAGGGAACATGCATCGTGG : 1620
              *        1640         *        1660         *        1680
    : CCCCGACGGCACCGGCATGTACGAGTGCCTTGACATCTACCCTGTGGGCGGCAACTCATC : 1680
              *        1700         *        1720         *        1740
    : CGAGATGTTGGGTGGCGACTCCTCACCTGAGGTGTTGTTCGTGCTCAAGGAGAGCGCCAA : 1740
              *        1760         *        1780         *        1800
    : CGACGAGTGGCACGACTACTACGCGCTTGGGTGGTTTGACGCTGCCGCCAACACGTGGAC : 1800
              *        1820         *        1840         *        1860
    : GCCACAGGACCCCGAGGCGGACCTTGGGATCGGCCTCAGGTACGACTGGGGCAAGTACTA : 1860
              *        1880         *        1900         *        1920
    : CGCGTCCAAGTCCTTCTACGACCCGATCAAGAACCGGCGTGTCGTTTGGGCTTTCGTCGG : 1920
              *        1940         *        1960         *        1980
    : CGAGACCGACTCTGAGCAGGCCGACAAAGCCAAGGGATGGGCGTCCCTCATGTCGATTCC : 1980
              *        2000         *        2020         *        2040
    : CAGGACGGTGGAGCTTGACAAGAAGACCCGGACGAACCTGATCCAATGGCCAGTGGAGGA : 2040
              *        2060         *        2080         *        2100
    : GATCGAGACCCTTCGCAGGAACGTCACAGACCTCGGTGGCATCACCGTTGAAGCCGGCTC : 2100
              *        2120         *        2140         *        2160
    : CGTCATTCACCTTCCCCTCCAACAAGGCGGGCAGCTTGACATCGAGGCCTCCTTCCGTCT : 2160
              *        2180         *        2200         *        2220
    : CAACTCTTCGGACATCGATGCACTCAACGAGGCCGACGTCGGCTTCAACTGCAGTAGCAG : 2220
              *        2240         *        2260         *        2280
    : CGATGGGGCAGCCGTGCGTGGTGCGCTCGGCCCCTTTGGCCTCCTCGTCTTCGCCGACGG : 2280
              *        2300         *        2320         *        2340
    : TCGCCACGAACAGACGGCGGCGTACTTCTACGTGTCCAAGGGCCTCGACGGCAGCCTCCT : 2340
              *        2360         *        2380         *        2400
    : GACGCACTACTGCCACGACGAGTCACGGTCGACGCGAGCAAAGGACGTCGTGAGCCGGGT : 2400
              *        2420         *        2440         *        2460
    : GGTTGGCGGCACTGTGCCAGTGCTTGACGGTGAAACCTTTTCAGTGAGGGTGCTAGTGGA : 2460
              *        2480         *        2500         *        2520
    : CCACTCCATCGTGCAGAGCTTCGTGATGGGTGGGAGGACCACGGTGACATCGCGGGCATA : 2520
```

FIGURE 25 CONT

```
              *      2540          *      2560          *      2580
 : CCCGACGGAGGCCATCTACGCCGCGGCAGGGGTGTACCTGTTCAACAACGCAACGAGCGC : 2580

              *      2600          *      2620          *      2640
 : CACCATCACCGCCGAAGGGCTCGTCGTGTACGAGATGGCCTCGGCCGAGAGTCGGGCCTT : 2640

              *      2660          *      2680          *      2700
 : CTTGGCTGACGACCATGTAGACCCAGCTTTCTTGTACAAAGTGGACTATGAGTTGAAACA : 2700

              *      2720          *      2740          *      2760
 : ATGGCCTATCTCATATGAAGATCTTTTGTGAATTTCACTTTTGTCCACGACCTCTGTTGC : 2760

              *      2780          *      2800          *      2820
 : ACGACTCTGCTTTCCGACCGGAGCATACCTTTTGTTCTATATGATTTGTGTATGTATGTA : 2820

              *      2840          *      2860          *      2880
 : GGAACCTATGTTCTCGAGCATGCATACATAATTCCTCATAGGTCTATATACACCGGCTAT : 2880

              *      2900          *      2920          *      2940
 : CCATATGCAAAACCTGTGTAATATTTGTTATATACAACACGCGGACCATTGTCTTGCTGT : 2940

              *      2960          *      2980          *      3000
 : TATTAATTCTTTTTTCCCGCAAAAAAGGAAAAGTTTCTTTATTTGGCACTGCAATGGATA : 3000

              *      3020          *      3040          *      3060
 : TGCCTCACAGCTAGTGGGTGGAGAATTCAGTATTTGACATTAAGATTCCCTGATTTGCAA : 3060

              *      3080          *      3100          *      3120
 : TTGCAAATTTCAGTTTCTTTACTTATATCACTACAAAAGTCTTATTGTTTCTTTTCCACG : 3120

              *      3140          *      3160          *      3180
 : TCATTACCATCTGCTCCATTGGTTTTTGCTAGTAGAATAGGATGAAGCATGGACACAGAT : 3180

              *      3200          *      3220          *      3240
 : TAACTGAGCTCGAGCTCATATGAGCTCGGGTGAACAATAAAATCTGAAAATACTTAGAAA : 3240

              *      3260          *      3280          *      3300
 : GAATTCAAAATTTTCTGTTTTTTGTGGCAAAATTTGACAAATGTTATAAATGCTTGCAAA : 3300

              *      3320          *      3340          *      3360
 : GTTTCATCATAGAACGACATTCGTGGATGTCATGGCAAAAAACAAATTCAGCACTCTGAA : 3360

              *      3380
 : AATAACTTTTTTGAAGTATCG : 3381
```

FIGURE 26

```
              *        20         *        40         *        60
 : GATCCGGTGACTCAAAAAAGAAGAGCCGCCATCTGTCCAAGCGCCACTCCTACGAGAACT :   60

              *        80         *       100         *       120
 : AAAATCCTATTCCCTCCGTAAATAAATATAAGAGTGTTTAGATCACTACTTCTTTACAGA :  120

              *       140         *       160         *       180
 : GAATTTCCTTCCCTCCAAGGGGAGGCGAATCCATAGGCACATCGACGGATATGGAGGGGG :  180

              *       200         *       220         *       240
 : GAAACATATATTTTACTATGCTAGTTCAGTTAATTCTACCAAGAAAACATATATTTTATT :  240

              *       260         *       280         *       300
 : TTGACAAACATTGTATAAATGTAGACATTCACATACACGTATGTACACCACCCTCTATGA :  300

              *       320         *       340         *       360
 : TTGCACACCCGCACACTATATGCCTATGAGCATACTTTCAAGAGTGAGCCAGCAAATTTT :  360

              *       380         *       400         *       420
 : ATGATAAAATGAAATATTTTGCCCAGCCAACTCAGTCGCATCCTCGGACAATTTGTTATC :  420

              *       440         *       460         *       480
 : AAGGAACTCACCCAAAAACAAGCAAAGCTAGAAAAAGGTTGTGTGGCAGCCACCTAATGA :  480

              *       500         *       520         *       540
 : CATGAAGGACTGAAATTTCCAGCACACACAATGTATCCGACGGCAATGCTTCTTCCACTG :  540

              *       560         *       580         *       600
 : ATCCGGAGAAGATAAGGAAACGAGGCAACCAGCGAACGTGAGCCATCCCAACCACATCTG :  600

              *       620         *       640         *       660
 : TACCAAAGAAACGGGGCTATATATACCGTGGTGACCCGGCAATGGGGTCCTCAACTGTAG :  660

              *       680         *       700         *       720
 : CCGGCATCCTCCTCTCCTCCGATAATACAAATACCCAAGTTTGTACAAAAAAGCAGGCTT :  720

              *       740         *       760         *       780
 : CATGGAGTCCCCAAGCGCCGTCGTCCCGGGCACCACGGCGCCGCTGCTTCCTTATGCGTA :  780

              *       800         *       820         *       840
 : CGCGCCGCTGCCGTCGTCCGCCGACGACGCCCGTCAAAACCGGAGTGGCGGGAGGTGGCG :  840

              *       860         *       880         *       900
 : CGCGTGCGCCGCCGTGCTGGCCGCATCGGCGTTGTCGGTGGTCGTCGTGGTCGGGCTCCT :  900

              *       920         *       940         *       960
 : CGCGGGCGGCAGGGTGGATCGGGTCCCGGCCGGCGGAGACGTGGCGTCGGCCACGGTGCC :  960

              *       980         *      1000         *      1020
 : GGCCGTGCCGATGGAGTTCCCGAGGAGCCGGGGCAAGGACTTCGGCGTGTCGGAGAAGTC : 1020

              *      1040         *      1060         *      1080
 : CTCCGGTGCCTACTCCACCGACGGCGGGTTCCCGTGGAGCAACGCCATGCTGCAGTGGCA : 1080

              *      1100         *      1120         *      1140
 : GCGCACCGGGTTCCATTTCCAGCCGGAGCAGCACTACATGAACGATCCCAACGGCCCCGT : 1140
```

FIGURE 26 CONT

```
          *        1160          *        1180          *        1200
: GTACTACGGCGGATGGTACCACCTCTTCTACCAGCACAACCCCAAGGGCGACAGCTGGGG : 1200

          *        1220          *        1240          *        1260
: CAACATCGCGTGGGCCCACGCCGTCTCCAAGGACATGGTCAACTGGCGCCACCTCCCTCT : 1260

          *        1280          *        1300          *        1320
: CGCCATGGTTCCCGACCAGTGGTACGACAGCAACGGCGTCCTCACCGGCTCCATCACCGT : 1320

          *        1340          *        1360          *        1380
: GCTCCCCGACGGCCAGGTCATCCTGCTCTACACCGGCAACACCGACACCCTAGCCCAGGT : 1380

          *        1400          *        1420          *        1440
: CCAGTGCCTCGCCACGCCCGCCGACCCGTCCGACCCGCTCCTCCGCGAGTGGGTCAAGCA : 1440

          *        1460          *        1480          *        1500
: CCCCGCCAACCCCATCCTCTACCCTCCCCCCGGCATCGGCCTCAAGGACTTCCGCGACCC : 1500

          *        1520          *        1540          *        1560
: CCTCACCGCCTGGTTCGACCACTCCGACCACACCTGGCGCACCGTCATCGGCTCCAAGGA : 1560

          *        1580          *        1600          *        1620
: CGACGACGGCCACGCCGGCATCATCCTCAGCTACAAGACCAAGGACTTCGTCAACTACGA : 1620

          *        1640          *        1660          *        1680
: GCTCATGCCGGGGAACATGCACCGCGGGCCCGACGGCACCGGAATGTACGAGTGCATCGA : 1680

          *        1700          *        1720          *        1740
: CCTCTACCCCGTCGGCGGCAACTCGTCCGAGATGCTCGGCGGCGACGACTCGCCCGGCGT : 1740

          *        1760          *        1780          *        1800
: GCTCTTCGTGCTCAAGGAGAGCAGCGACGACGAGCGCCACGACTACTACGCGCTCGGAAG : 1800

          *        1820          *        1840          *        1860
: GTTCGATGCCGTCGCCAACGTTTGGACGCCCATCGACCGGGAGCTGGACCTTGGGATCGG : 1860

          *        1880          *        1900          *        1920
: GCTCAGATACGACTGGGGAAAGTACTACGCCTCCAAGTCCTTCTACGACCAGAAGAAGAA : 1920

          *        1940          *        1960          *        1980
: CCGCCGCATCGTATGGGCATACATCGGCGAGACCGACTCCGAGCAGGCCGACATCACCAA : 1980

          *        2000          *        2020          *        2040
: GGGATGGGCCAATCTCATGACGATTCCAAGAACGGTGGAGCTTGACAGGAAGACCCGCAC : 2040

          *        2060          *        2080          *        2100
: AAACCTCATCCAATGGCCAGTGGAGGAGGTCGACACCCTCCGCAGGAACTCCACGGACCT : 2100

          *        2120          *        2140          *        2160
: CGGTCGCATCACCGTCAACGCCGGCTCCGTCATTCGCCTCCCCCTCCACCAGGGCGCTCA : 2160

          *        2180          *        2200          *        2220
: ACTCGACATCGAGGCCTCCTTCCAACTCAACTCTTCCGACGTGGATGCTATCAACGAGGC : 2220

          *        2240          *        2260          *        2280
: CGACGTCGGCTACAACTGCAGCACCAGTGGTGCCGCCGTACGGGGGGCGCTCGGCCCCTT : 2280

          *        2300          *        2320          *        2340
: TGGCCTCCTCGTCCTTGCCAACGGCCGCACCGAACAGACGGCTGTGTACTTCTACGTGTC : 2340

          *        2360          *        2380          *        2400
```

FIGURE 26 CONT

```
: CAAGGGCGTCGACGGTGCCCTCCAGACCCACTTCTGCCACGACGAGTCACGGTCAACGCG : 2400

         *       2420        *       2440        *       2460
: GGCAAAGGATGTCGTGAATAGGATGATTGGCAGCATCGTGCCGGTGCTTGACGGTGAGAC : 2460

         *       2480        *       2500        *       2520
: CTTTTCGGTGAGGGTGCTAGTGGACCACTCCATCGTGCAGAGCTTCGCGATGGGCGGGAG : 2520

         *       2540        *       2560        *       2580
: GATCACGGCGACGTCGCGGGCGTACCCGACGGAGGCCATCTACGCGGCCGCGGGGGTCTA : 2580

         *       2600        *       2620        *       2640
: CCTCTTCAACAACGCCACGGGCGCCACCGTCACCGCCGAGAGGCTCGTCGTGCACGAGAT : 2640

         *       2660        *       2680        *       2700
: GGCCTCAGCTGACAACCATATCTTCACGAACGACGACTTGGGAGGAGGAAAGCTTGGAGG : 2700

         *       2720        *       2740        *       2760
: AGGAGAGTCCAGCGCCGTCGTCGCCCAAGGCACCACGTCGCCGCTGCTCCCGTACGCCTA : 2760

         *       2780        *       2800        *       2820
: CGCGCCGCTGCCGTCCTCTGCCGACGACGCCCGTGAAAACCAGAGTAGCGGCGGCGGTGT : 2820

         *       2840        *       2860        *       2880
: CAGGTGGCGCGCGTGCGCGGCCTCGGCCCTGGTGGTGCTGCTGGTCGTCGTCGGCTTCTT : 2880

         *       2900        *       2920        *       2940
: CGCGGGTGGCAGGGTGGATCTGGGTCAGGACGGCGAGGTGTCTGCGACTTCTTCGGTTCC : 2940

         *       2960        *       2980        *       3000
: TGGGAGCAGCAGGGGCAAGGATTCCGGCGTGTCGGAGAAGGAGTCGCCCGCCGACGGCGG : 3000

         *       3020        *       3040        *       3060
: CTTCCCGTGGAGCAACGCCATGCTGCAGTGGCAGCACACCGGGTTCCATTTCCAGCCACT : 3060

         *       3080        *       3100        *       3120
: CAAGCACTACATGAACGATCCCAACGGTCCGGTCTACTATGGCGGATGGTACCACCTCTT : 3120

         *       3140        *       3160        *       3180
: CTACCAGCACAACCCCTATGGCGACTCGTGGGGAAACGTATCTTGGGGACATGCCGTGTC : 3180

         *       3200        *       3220        *       3240
: CAAGGACCTGGTGAACTGGCGCCACCTCCCGGTCGCCTTGGTGCCCGATCAGTGGTACGA : 3240

         *       3260        *       3280        *       3300
: CATCAACGGCGTCCTGACGGGCTCTATCACAGTGCTCCCAGACGGGCGTGTCATCCTGCT : 3300

         *       3320        *       3340        *       3360
: ATATACGGGGAACACCGACACCTTTTCGCAGGTCCAGTGCCTCGCAGTGCCCGCCGACCC : 3360

         *       3380        *       3400        *       3420
: ATCTGACCCGCTCCTCCGTAGCTGGATCAAGCACCCCGCCAACCCCATCCTCTTCCCGCC : 3420

         *       3440        *       3460        *       3480
: ACCTGGGATCGGGCTCAAGGACTTCCGTGACCCGCTCACAGCCTGGTTCGAACATTCCGA : 3480

         *       3500        *       3520        *       3540
: CAACACGTGGCGCACCATCATCGGATCCAAGGATGACGACGGCCACGCCGGCATCGTCCT : 3540

         *       3560        *       3580        *       3600
```

FIGURE 26 CONT

: TAGCTACAAGACCACCGACTTTGTGAATTATGAGCTCATGCCAGGGAACATGCATCGTGG : 3600

* 3620 * 3640 * 3660
: CCCCGACGGCACCGGCATGTACGAGTGCCTTGACATCTACCCTGTGGGCGGCAACTCATC : 3660

* 3680 * 3700 * 3720
: CGAGATGTTGGGTGGCGACTCCTCACATGAGGTGTTGTTCGTGCTCAAGGAGAGCGCCAA : 3720

* 3740 * 3760 * 3780
: CGACGAGTGGCACGACTACTACGCGCTTGGGTGGTTTGACGCTGCCGCCAACACGTGGAC : 3780

* 3800 * 3820 * 3840
: GCCACAGGACCCCGAGGCGGACCTTGGGATCGGCCTCAGGTACGACTGGGGCAAGTACTA : 3840

* 3860 * 3880 * 3900
: CGCGTCCAAGTCCTTCTACGACCCGATCAAGAACCGGCGTGTCGTTTGGGCTTTCGTCGG : 3900

* 3920 * 3940 * 3960
: CGAGACCGACTCTGAGCAGGCCGACAAAGCCAAGGGATGGGCGTCCCTCATGTCGATTCC : 3960

* 3980 * 4000 * 4020
: CAGGACGGTGGAGCTTGACAAGAAGACCCGGACGAACCTGATCCAATGGCCAGTGGAGGA : 4020

* 4040 * 4060 * 4080
: GATCGAGACCCTTCGCAGGAACGTCACAGACCTCGGTGGCATCACCGTTGAAGCCGGCTC : 4080

* 4100 * 4120 * 4140
: CGTCATTCACCTTCCCCTCCAACAAGGCGGGCAGCTTGACATCGAGGCCTCCTTCCGTCT : 4140

* 4160 * 4180 * 4200
: CAACTCTTCGGACATCGATGCACTCAACGAGGCCGACGTCGGCTTCAACTGCAGTAGCAG : 4200

* 4220 * 4240 * 4260
: CGATGGGGTAGCCGTGCGTGGTGCGCTCGGCCCCTTTGGCCTCCTCGTCTTCGCCGACGG : 4260

* 4280 * 4300 * 4320
: TCGCCACGAACAGACGGCGGCGTACTTCTACGTGTCCAAGGGCCTCGACGGCAGCCTCCT : 4320

* 4340 * 4360 * 4380
: GACGCACTACTGCCACGACGAGTCACGGTCGACGCGAGCAAAGGACGTCGTGAGCCGGGT : 4380

* 4400 * 4420 * 4440
: GGTTGGCGGCACTGTGCCAGTGCTTGACGGTGAAACCTTTTCAGTGAGGGTGCTAGTGGA : 4440

* 4460 * 4480 * 4500
: CCACTCCATCGTGCAGAGCTTCGTGATGGGTGGGAGGACCACGGTGACATCGCGGGCATA : 4500

* 4520 * 4540 * 4560
: CCCGACGGAGGCCATCTACGCCGCGGCAGGGGTGTACCTGTTCAACAACGCAACGAGCGC : 4560

* 4580 * 4600 * 4620
: CACCATCACCGCCGAAGGGCTCGTCGTGTACGAGATGGCCTCGGCCGAGAGTCGGGCCTT : 4620

* 4640 * 4660 * 4680
: CTTGGCTGACGACATG[illegible]*GACCCAGCTTTCTTGTACAAAGTGGACTATGAGTTGAAACA* : 4680

* 4700 * 4720 * 4740
: *ATGGCCTATCTCATATGAAGATCTTTTGTGAATTTCACTTTTGTCCACGACCTCTGTTGC* : 4740

* 4760 * 4780 * 4800
: *ACGACTCTGCTTTCCGACCGGAGCATACCTTTTGTTCTATATGATTTGTGTATGTATGTA* : 4800

FIGURE 26 CONT

```
              *        4820          *        4840          *        4860
: GGAACCTATGTTCTCGAGCATGCATACATAATTCCTCATAGGTCTATATACACCGGCTAT : 4860

              *        4880          *        4900          *        4920
: CCATATGCAAAACCTGTGTAATATTTGTTATATACAACACGCGGACCATTGTCTTGCTGT : 4920

              *        4940          *        4960          *        4980
: TATTAATTCTTTTTTCCCGCAAAAAAGGAAAAGTTTCTTTATTTGGCACTGCAATGGATA : 4980

              *        5000          *        5020          *        5040
: TGCCTCACAGCTAGTGGGTGGAGAATTCAGTATTTGACATTAAGATTCCCTGATTTGCAA : 5040

              *        5060          *        5080          *        5100
: TTGCAAATTTCAGTTTCTTTACTTATATCACTACAAAAGTCTTATTGTTTCTTTTCCACG : 5100

              *        5120          *        5140          *        5160
: TCATTACCATCTGCTCCATTGGTTTTTGCTAGTAGAATAGGATGAAGCATGGACACAGAT : 5160

              *        5180          *        5200          *        5220
: TAACTGAGCTCGAGCTCATATGAGCTCGGGTGAACAATAAAATCTGAAAATACTTAGAAA : 5220

              *        5240          *        5260          *        5280
: GAATTCAAAATTTTCTGTTTTTTGTGGCAAAATTTGACAAATGTTATAAATGCTTGCAAA : 5280

              *        5300          *        5320          *        5340
: GTTTCATCATAGAACGACATTCGTGGATGTCATGGCAAAAAACAAATTCAGCACTCTGAA : 5340

              *        5360
: AATAACTTTTTTGAAGTATCG : 5361
```

FIGURE 27

```
          *        20         *        40         *        60
: GATCCGGTGACTCAAAAAAGAAGAGCCGCCATCTGTCCAAGCGCCACTCCTACGAGAACT :   60

          *        80         *       100         *       120
: AAAATCCTATTCCCTCCGTAAATAAATATAAGAGTGTTTAGATCACTACTTCTTTACAGA :  120

          *       140         *       160         *       180
: GAATTTCCTTCCCTCCAAGGGGAGGCGAATCCATAGGCACATCGACGGATATGGAGGGGG :  180

          *       200         *       220         *       240
: GAAACATATATTTTACTATGCTAGTTCAGTTAATTCTACCAAGAAAACATATATTTTATT :  240

          *       260         *       280         *       300
: TTGACAAACATTGTATAAATGTAGACATTCACATACACGTATGTACACCACCCTCTATGA :  300

          *       320         *       340         *       360
: TTGCACACCCGCACACTATATGCCTATGAGCATACTTTCAAGAGTGAGCCAGCAAATTTT :  360

          *       380         *       400         *       420
: ATGATAAAATGAAATATTTTGCCCAGCCAACTCAGTCGCATCCTCGGACAATTTGTTATC :  420

          *       440         *       460         *       480
: AAGGAACTCACCCAAAAACAAGCAAAGCTAGAAAAAGGTTGTGTGGCAGCCACCTAATGA :  480

          *       500         *       520         *       540
: CATGAAGGACTGAAATTTCCAGCACACACAATGTATCCGACGGCAATGCTTCTTCCACTG :  540

          *       560         *       580         *       600
: ATCCGGAGAAGATAAGGAAACGAGGCAACCAGCGAACGTGAGCCATCCCAACCACATCTG :  600

          *       620         *       640         *       660
: TACCAAAGAAACGGGGCTATATATACCGTGGTGACCCGGCAATGGGGTCCTCAACTGTAG :  660

          *       680         *       700         *       720
: CCGGCATCCTCCTCTCCTCCGATAATACAAATACCCAAGTTTGTACAAAAAAGCAGGCTT :  720

          *       740         *       760         *       780
: CATGGAGTCCCCAAGCGCCGTCGTCCCCGGCACCACGGCGCCGCTGCTTCCTTATGCGTA :  780

          *       800         *       820         *       840
: CGCGCCGCTGCCGTCGTCCGCCGACGACGCCCGTCAAAACCGGAGTGGCGGGAGGTGGCG :  840

          *       860         *       880         *       900
: CGCGTGCGCCGCCGTGCTGGCCGCATCGGCGTTGGCGGTGGTCGTCGTGGTCGGGCTCCT :  900

          *       920         *       940         *       960
: CGCGGGCGGCAGGGTGGATCGGGTCCCAGCCGGCGGAGACGTGGCGTCGGCCACGGTGCC :  960

          *       980         *      1000         *      1020
: GGCCGTGCCGATGGAGTTCCCGAGGAGCCGGGGCAAGGACTTCGGCGTGTCGGAGAAGTC : 1020

          *      1040         *      1060         *      1080
: CTCCGGTGCCTACTCCACCGACGGCGGGTTCCCGTGGAGCAACGCCATGCTGCAGTGGCA : 1080

          *      1100         *      1120         *      1140
: GCGCACCGGGTTCCATTTCCAGCCGGAGCAGCACTACATGAACGATCCCAACGGCCCCGT : 1140

          *      1160         *      1180         *      1200
```

FIGURE 27 CONT

```
: GTACTACGGCGGATGGTACCACCTCTTCTACCAGCACAACCCCAAGGGCGACAGCTGGGG : 1200

          *        1220         *        1240         *        1260
: CAACATCGCGTGGGCCCACGCCGTCTCCAAGGACATGGTCAACTGGCGCCACCTCCCTCT : 1260

          *        1280         *        1300         *        1320
: CGCCATGGTTCCCGACCAGTGGTACGACAGCAACGGCGTCCTCACCGGCTCCATCACCGT : 1320

          *        1340         *        1360         *        1380
: GCTCCCCGACGGCCAGGTCATCCTGCTCTACACCGGCAACACCGACACCCTAGCCCAGGT : 1380

          *        1400         *        1420         *        1440
: CCAGTGCCTCGCCACGCCCGCCGACCCGTCCGACCCGCTCCTCCGCGAGTGGGTCAAGCA : 1440

          *        1460         *        1480         *        1500
: CCCCGCCAACCCCATCCTCTACCCTCCCCCCGGCATCGGCCTCAAGGACTTCCGCGACCC : 1500

          *        1520         *        1540         *        1560
: CCTCACCGCCTGGTTCGACCACTCCGACCACACCTGGCGCACCGTCATCGGCTCCAAGGA : 1560

          *        1580         *        1600         *        1620
: CGACGACGGCCACGCCGGCATCATCCTCAGCTACAAGACCAAGGACTTCGTCAACTACGA : 1620

          *        1640         *        1660         *        1680
: GCTCATGCCGGGGAACATGCACCGCGGGCCCGACGGCACCGGAATGTACGAGTGCATCGA : 1680

          *        1700         *        1720         *        1740
: CCTCTACCCCGTCGGCGGCAACTCGTCCGAGATGCTCGGCGGCGACGACTCGCCCGGCGT : 1740

          *        1760         *        1780         *        1800
: GCTCTTCGTGCTCAAGGAGAGCAGCGACGACGAGCGCCACGACTACTACGCGCTCGGAAG : 1800

          *        1820         *        1840         *        1860
: GTTCGACGCCGTCGCCAACGTTTGGACGCCCATCGACCGGGAGCTGGACCTTGGGATCGG : 1860

          *        1880         *        1900         *        1920
: GCTCAGATACGACTGGGGAAAGTACTACGCCTCCAAGTCCTTCTACGACCAGAAGAAGAA : 1920

          *        1940         *        1960         *        1980
: CCGCCGCATCGTATGGGCATACATCGGCGAGACCGACTCCGAGCAGGCCGACATCACCAA : 1980

          *        2000         *        2020         *        2040
: GGGATGGGCCAATCTCATGACGATTCCAAGAACGGTGGAGCTTGACAGGAAGACCCGCAC : 2040

          *        2060         *        2080         *        2100
: AAACCTCATCCAATGGCCAGTGGAGGAGGTCGACACCCTCCGCAGGAACTCCACGGACCT : 2100

          *        2120         *        2140         *        2160
: CGGTCGCATCACCGTCAACGCCGGCTCCGTCATTCGCCTCCCCCTCCACCAGGGCGCTCA : 2160

          *        2180         *        2200         *        2220
: ACTCGACATCGAGGCCTCCTTCCAACTCAACTCTTCCGACGTGGATGCTATCAACGAGGC : 2220

          *        2240         *        2260         *        2280
: CGACGTCGGCTACAACTGCAGCACCAGTGGTGCCGCCGTACGGGGGGCGCTCGGCCCCTT : 2280

          *        2300         *        2320         *        2340
: TGGCCTCCTCGTCCTTGCCAACGGCCGCACCGAACAGACGGCTGTGTACTTCTACGTGTC : 2340

          *        2360         *        2380         *        2400
: CAAGGGCGTCGACGGTGCCCTCCAGACCCACTTCTGCCACGACGAGTCACGGTCAACGCG : 2400
```

FIGURE 27 CONT

```
        *        2420          *        2440          *        2460
: GGCAAAGGATGTCGTGAATAGGATGATTGGCAGCATCGTGCCGGTGCTTGACGGTGAGAC : 2460

          *        2480          *        2500          *        2520
: CTTTTCGGTGAGGGTGCTAGTGGACCACTCCATCGTGCAGAGCTTCGCGATGGGCGGGAG : 2520

          *        2540          *        2560          *        2580
: GATCACGGCGACGTCGCGGGCGTACCCGACGGAGGCCATCTACGCGGCCGCGGGGGTCTA : 2580

          *        2600          *        2620          *        2640
: CCTCTTCAACAACGCCACGGGCGCCACCGTCACCGCCGAGAGGCTCGTCGTGCACGAGAT : 2640

          *        2660          *        2680          *        2700
: GGCCTCAGCTGACAACCATATCTTCACGAACGACGACTTGGGAGGAGGAAAGCTTAAGCT : 2700

          *        2720          *        2740          *        2760
: TGGAGGAGGAGAGTCCAGCGCCGTCGTCGCCCAAGGCACCACGTCGCCGCTGCTCCCGTA : 2760

          *        2780          *        2800          *        2820
: CGCCTACGCGCCGCTGCCGTCCTCTGCCGACGACGCCCGTGAAAACCAGAGTAGCGGCGG : 2820

          *        2840          *        2860          *        2880
: CGGTGTCAGGTGGCGCGCGTGCGCGGCCTCGGCCCTGGTGGTGCTGCTGGTCGTCGTCGG : 2880

          *        2900          *        2920          *        2940
: CTTCTTCGCGGGTGGCAGGGTGGATCTGGGTCAGGACGGCGAGGTGTCTGCGACTTCTTC : 2940

          *        2960          *        2980          *        3000
: GGTTCCTGGGAGCAGCAGGGGCAAGGATTCCGGCGTGTCGGAGAAGGAGTCGCCCGCCGA : 3000

          *        3020          *        3040          *        3060
: CGGCGGCTTCCCGTGGAGCAACGCCATGCTGCAGTGGCAGCACACCGGGTTCCATTTCCA : 3060

          *        3080          *        3100          *        3120
: GCCACTCAAGCACTACATGAACGATCCCAACGGTCCGGTCTACTATGGCGGATGGTACCA : 3120

          *        3140          *        3160          *        3180
: CCTCTTCTACCAGCACAACCCCTATGGCGACTCGTGGGGAAACGTATCTTGGGGACATGC : 3180

          *        3200          *        3220          *        3240
: CGTGTCCAAGGACCTGGTGAACTGGCGCCACCTCCCGGTCGCCTTGGTGCCCGATCAGTG : 3240

          *        3260          *        3280          *        3300
: GTACGACATCAACGGCGTCCTGACGGGCTCTATCACAGTGCTCCCAGACGGGCGTGTCAT : 3300

          *        3320          *        3340          *        3360
: CCTGCTATATACGGGGAACACCGACACCTTTTCGCAGGTCCAGTGCCTCGCAGTGCCCGC : 3360

          *        3380          *        3400          *        3420
: CGACCCATCTGACCCGCTCCTCCGTAGCTGGATCAAGCACCCCGCCAACCCCATCCTCTT : 3420

          *        3440          *        3460          *        3480
: CCCGCCACCTGGGATCGGGCTCAAGGACTTCCGTGACCCGCTCACAGCCTGGTTCGAACA : 3480

          *        3500          *        3520          *        3540
: TTCCGACAACACGTGGCGCACCATCATCGGATCCAAGGATGACGACGGCCACGCCGGCAT : 3540

          *        3560          *        3580          *        3600
: CGTCCTTAGCTACAAGACCACCGACTTTGTGAATTATGAGCTCATGCCAGGGAACATGCA : 3600
```

FIGURE 27 CONT

```
              *        3620         *        3640         *        3660
: TCGTGGCCCCGACGGCACCGGCATGTACGAGTGCCTTGACATCTACCCTGTGGGCGGCAA : 3660

              *        3680         *        3700         *        3720
: CTCATCCGAGATGTTGGGTGGCGACTCCTCACCTGAGGTGTTGTTCGTGCTCAAGGAGAG : 3720

              *        3740         *        3760         *        3780
: CGCCAACGACGAGTGGCACGACTACTACGCGCTTGGGTGGTTTGACGCTGCCGCCAACAC : 3780

              *        3800         *        3820         *        3840
: GTGGACGCCACAGGACCCCGAGGCGGACCTTGGGATCGGCCTCAGGTACGACTGGGGCAA : 3840

              *        3860         *        3880         *        3900
: GTACTACGCGTCCAAGTCCTTCTACGACCCGATCAAGAACCGGCGTGTCGTTTGGGCTTT : 3900

              *        3920         *        3940         *        3960
: CGTCGGCGAGACCGACTCTGAGCAGGCCGACAAAGCCAAGGGATGGGCGTCCCTCATGTC : 3960

              *        3980         *        4000         *        4020
: GATTCCCAGGACGGTGGAGCTTGACAAGAAGACCCGGACGAACCTGATCCAATGGCCAGT : 4020

              *        4040         *        4060         *        4080
: GGAGGAGATCGAGACCCTTCGCAGGAACGTCACAGACCTCGGTGGCATCACCGTTGAAGC : 4080

              *        4100         *        4120         *        4140
: CGGCTCCGTCATTCACCTTCCCCTCCAACAAGGCGGGCAGCTTGACATCGAGGCCTCCTT : 4140

              *        4160         *        4180         *        4200
: CCGTCTCAACTCTTCGGACATCGATGCACTCAACGAGGCCGACGTCGGCTTCAACTGCAG : 4200

              *        4220         *        4240         *        4260
: TAGCAGCGATGGGGCAGCCGTGCGTGGTGCGCTCGGCCCCTTTGGCCTCCTCGTCTTCGC : 4260

              *        4280         *        4300         *        4320
: CGACGGTCGCCACGAACAGACGGCGGCGTACTTCTACGTGTCCAAGGGCCTCGACGGCAG : 4320

              *        4340         *        4360         *        4380
: CCTCCTGACGCACTACTGCCACGACGAGTCACGGTCGACGCGAGCAAAGGACGTCGTGAG : 4380

              *        4400         *        4420         *        4440
: CCGGGTGGTTGGCGGCACTGTGCCAGTGCTTGACGGTGAAACCTTTTCAGTGAGGGTGCT : 4440

              *        4460         *        4480         *        4500
: AGTGGACCACTCCATCGTGCAGAGCTTCGTGATGGGTGGGAGGACCACGGTGACATCGCG : 4500

              *        4520         *        4540         *        4560
: GGCATACCCGACGGAGGCCATCTACGCCGCGGCAGGGGTGTACCTGTTCAACAACGCAAC : 4560

              *        4580         *        4600         *        4620
: GAGCGCCACCATCACCGCCGAAGGGCTCGTCGTGTACGAGATGGCCTCGGCCGAGAGTCG : 4620

              *        4640         *        4660         *        4680
: GGCCTTCTTGGCTGACGACATGTAGGACCCAGCTTTCTTGTACAAAGTGGACTATGAGTT : 4680

              *        4700         *        4720         *        4740
: GAAACAATGGCCTATCTCATATGAAGATCTTTTGTGAATTTCACTTTTGTCCACGACCTC : 4740

              *        4760         *        4780         *        4800
: TGTTGCACGACTCTGCTTTCCGACCGGAGCATACCTTTTGTTCTATATGATTTGTGTATG : 4800
```

FIGURE 27 CONT

```
              *        4820          *        4840          *        4860
: TATGTAGGAACCTATGTTCTCGAGCATGCATACATAATTCCTCATAGGTCTATATACACC : 4860

              *        4880          *        4900          *        4920
: GGCTATCCATATGCAAAACCTGTGTAATATTTGTTATATACAACACGCGGACCATTGTCT : 4920

              *        4940          *        4960          *        4980
: TGCTGTTATTAATTCTTTTTTCCCGCAAAAAAGGAAAAGTTTCTTTATTTGGCACTGCAA : 4980

              *        5000          *        5020          *        5040
: TGGATATGCCTCACAGCTAGTGGGTGGAGAATTCAGTATTTGACATTAAGATTCCCTGAT : 5040

              *        5060          *        5080          *        5100
: TTGCAATTGCAAATTTCAGTTTCTTTACTTATATCACTACAAAAGTCTTATTGTTTCTTT : 5100

              *        5120          *        5140          *        5160
: TCCACGTCATTACCATCTGCTCCATTGGTTTTTGCTAGTAGAATAGGATGAAGCATGGAC : 5160

              *        5180          *        5200          *        5220
: ACAGATTAACTGAGCTCGAGCTCATATGAGCTCGGGTGAACAATAAAATCTGAAAATACT : 5220

              *        5240          *        5260          *        5280
: TAGAAAGAATTCAAAATTTTCTGTTTTTTGTGGCAAAATTTGACAAATGTTATAAATGCT : 5280

              *        5300          *        5320          *        5340
: TGCAAAGTTTCATCATAGAACGACATTCGTGGATGTCATGGCAAAAAACAAATTCAGCAC : 5340

              *        5360
: TCTGAAAATAACTTTTTTGAAGTATCG : 5367
```

FIGURE 29
A
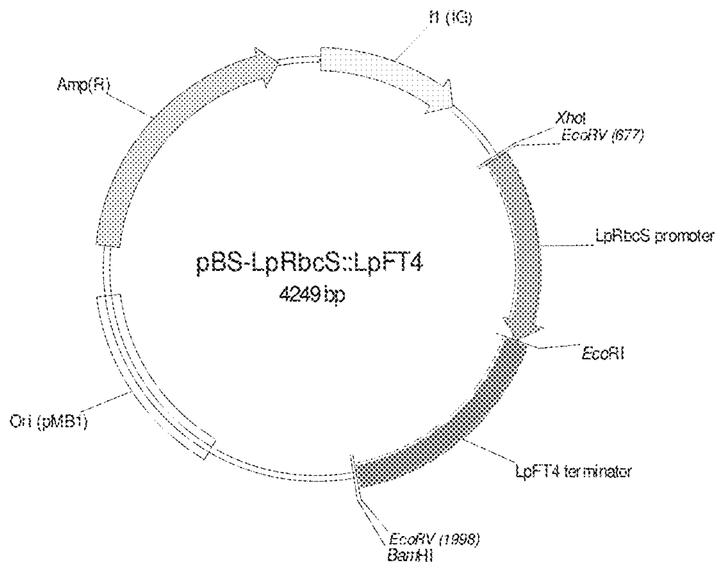
B
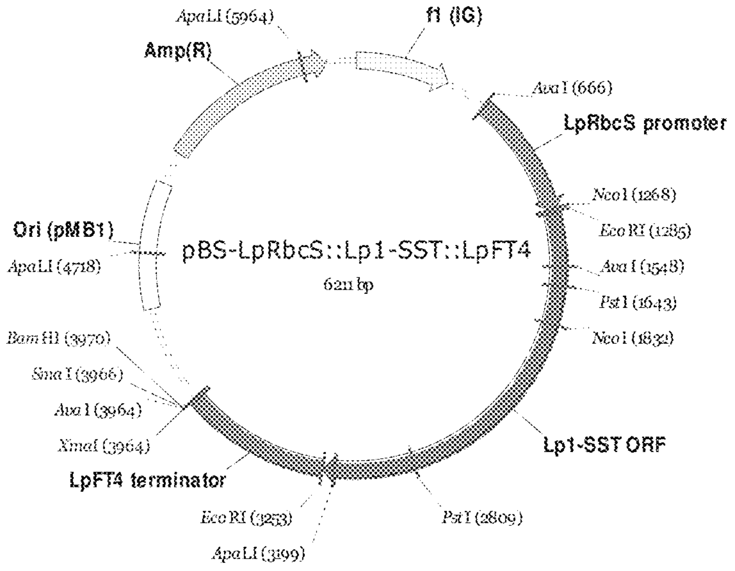

FIGURE 30
A
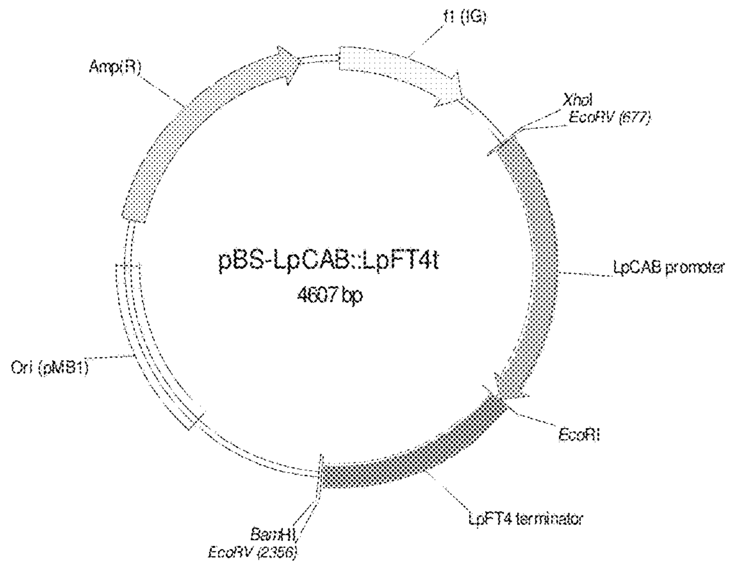
B
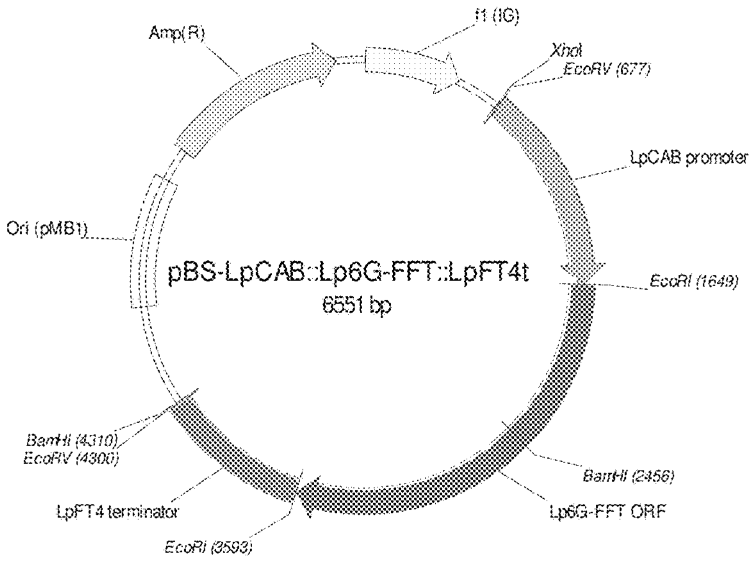

FIGURE 31

```
                *         20          *         40          *         60
 : ATCTGTTCATCTACCTTACTAGTCTGCATGATTAGTTTATTCGTTATTTTCGTAGTCATG :   60

                *         80          *        100          *        120
 : ATTTATCAATTACTCGTACGGATTATTTCATATGGATATTTGCTTATATTTCCAACAATT :  120

                *        140          *        160          *        180
 : TACACTGTCGAGTTTTGGCGCGGCTGCTGGAGTTACTCTTAGAGTAGTTGGACTTGAGAC :  180

                *        200          *        220          *        240
 : AAAAGCTAGAATATCAATTATATATAGGAGTGAGGAGTTATTCTTTCGAAAGAACTTTAA :  240

                *        260          *        280          *        300
 : ACGGTAGCTGCACTTAGTCGTCGCAATGAAATACTTGTCGTACTACCATGATAATTGGTA :  300

                *        320          *        340          *        360
 : ATATGAGAGGGAATATTAATTCCTCAGTGATTTGAATTTTGTGTGCTCATGTGCAGTCAC :  360

                *        380          *        400          *        420
 : CCACGCCATGCATCCGACGACGGGCGGCTATACCAACTCTTGCACTGATCCGGAGGGATA :  420

                *        440          *        460          *        480
 : AGGCGCCATGCAACCAGGGAACGTCGTCCACCCCTTCCACATCCTGTATCAAATTAAGGA :  480

                *        500          *        520          *        540
 : ACGGGCGCTGAGCCTATGCCGAGACATATATAATGCGGCGACTCGGACATGGAGGGGCCT :  540

                *        560          *        580          *        600
 : CAGGCATAGCCCAGCTAGTTATCTCATTCTCTCCTTAGCAATAATACTTAGCACCATGGC :  600

                *        620          *        640          *        660
 : CCCCGCGGTGGAATTCATGGAGTCCCCAAGCGCCGTCGTCCCCGGCACCACGGCGCCGCT :  660

                *        680          *        700          *        720
 : GCTTCCTTATGCGTACGCGCCGCTGCCGTCGTCCGCCGACGACGCCCGTCAAAACCGGAG :  720

                *        740          *        760          *        780
 : TGGCGGGAGGTGGCGCGCGTGCGCCGCCGTGCTGGCCGCATCGGCGTTGGCGGTGGTCGT :  780

                *        800          *        820          *        840
 : CGTGGTCGGGCTCCTCGCGGGCGGCAGGGTGGATCGGGTCCCGGCCGGCGGAGACGTGGC :  840

                *        860          *        880          *        900
 : GTCGGCCACGGTGCCGGCCGTGCCGATGGAGTTCCCGAGGAGCCGGGGCAAGGACTTCGG :  900

                *        920          *        940          *        960
 : CGTGTCGGAGAAGTCCTCCGGTGCCTACTCCACCGACGGCGGGTTCCCGTGGAGCAACGC :  960

                *        980          *       1000          *       1020
 : CATGCTGCAGTGGCAGCGCACCGGGTTCCATTTCCAGCCGGAGCAGCACTACATGAACGA : 1020

                *       1040          *       1060          *       1080
 : TCCCAACGGCCCCGTGTACTACGGCGGATGGTACCACCTCTTCTACCAGCACAACCCCAA : 1080

                *       1100          *       1120          *       1140
 : GGGCGACAGCTGGGGCAACATCGCGTGGGCCCACGCCGTCTCCAAGGACATGGTCAACTG : 1140
```

FIGURE 31 CONT

```
         *        1160         *        1180         *        1200
: GCGCCACCTCCCTCTCGCCATGGTTCCCGACCAGTGGTACGACAGCAACGGCGTCCTCAC : 1200

         *        1220         *        1240         *        1260
: CGGCTCCATCACCGTGCTCCCCGACGGCCAGGTCATCCTGCTCTACACCGGCAACACCGA : 1260

         *        1280         *        1300         *        1320
: CACCCTAGCCCAGGTCCAGTGCCTCGCCACGCCCGCCGACCCGTCCGACCCGCTCCTCCG : 1320

         *        1340         *        1360         *        1380
: CGAGTGGGTCAAGCACCCCGCCAACCCCATCCTCTACCCTCCCCCCGGCATCGGCCTCAA : 1380

         *        1400         *        1420         *        1440
: GGACTTCCGCGACCCCCTCACCGCCTGGTTCGACCACTCCGACCACACCTGGCGCACCGT : 1440

         *        1460         *        1480         *        1500
: CATCGGCTCCAAGGACGACGACGGCCACGCCGGCATCATCCTCAGCTACAAGACCAAGGA : 1500

         *        1520         *        1540         *        1560
: CTTCGTCAACTACGAGCTCATGCCGGGGAACATGCACCGCGGGCCCGACGGCACCGGAAT : 1560

         *        1580         *        1600         *        1620
: GTACGAGTGCATCGACCTCTACCCCGTCGGCGGCAACTCGTCCGAGATGCTCGGCGGCGA : 1620

         *        1640         *        1660         *        1680
: CGACTCGCCCGGCGTGCTCTTCGTGCTCAAGGAGAGCAGCGACGACGAGCGCCACGACTA : 1680

         *        1700         *        1720         *        1740
: CTACGCGCTCGGAAGGTTCGACGCCGTCGCCAACGTTTGGACGCCCATCGACCGGGAGCT : 1740

         *        1760         *        1780         *        1800
: GGACCTTGGGATCGGGCTCAGATACGACTGGGGAAAGTACTACGCCTCCAAGTCCTTCTA : 1800

         *        1820         *        1840         *        1860
: CGACCAGAAGAAGAACCGCCGCATCGTATGGGCATACATCGGCGAGACCGACTCCGAGCA : 1860

         *        1880         *        1900         *        1920
: GGCCGACATCACCAAGGGATGGGCCAATCTCATGACGATTCCAAGAACGGTGGAGCTTGA : 1920

         *        1940         *        1960         *        1980
: CAGGAAGACCCGCACAAACCTCATCCAATGGCCAGTGGAGGAGGTCGACACCCTCCGCAG : 1980

         *        2000         *        2020         *        2040
: GAACTCCACGGACCTCGGTCGCATCACCGTCAACGCCGGCTCCGTCATTCGCCTCCCCCT : 2040

         *        2060         *        2080         *        2100
: CCACCAGGGCGCTCAACTCGACATCGAGGCCTCCTTCCAACTCAACTCTTCCGACGTGGA : 2100

         *        2120         *        2140         *        2160
: TGCTATCAACGAGGCCGACGTCGGCTACAACTGCAGCACCAGTGGTGCCGCCGTACGGGG : 2160

         *        2180         *        2200         *        2220
: GGCGCTCGGCCCCTTTGGCCTCCTCGTCCTTGCCAACGGCCGCACCGAACAGACGGCTGT : 2220

         *        2240         *        2260         *        2280
: GTACTTCTACGTGTCCAAGGGCGTCGACGGTGCCCTCCAGACCCACTTCTGCCACGACGA : 2280

         *        2300         *        2320         *        2340
: GTCACGGTCAACGCGGGCAAAGGATGTCGTGAATAGGATGATTGGCAGCATCGTGCCGGT : 2340

         *        2360         *        2380         *        2400
```

FIGURE 31 CONT

```
: GCTTGACGGTGAGACCTTTTCGGTGAGGGTGCTAGTGGACCACTCCATCGTGCAGAGCTT : 2400

                *         2420         *         2440         *         2460
: CGCGATGGGCGGGAGGATCACGGCGACGTCGCGGGCGTACCCGACGGAGGCCATCTACGC : 2460

                *         2480         *         2500         *         2520
: GGCCGCGGGGGTCTACCTCTTCAACAACGCCACGGGCGCCACCGTCACCGCCGAGAGGCT : 2520

                *         2540         *         2560         *         2580
: CGTCGTGCACGAGATGGCCTCAGCTGACAACCATATCTTCACGAACGACGACTTGTAGGA : 2580

                *         2600         *         2620         *         2640
: ATTCAACAATAATTTTCTGAGCCTAGTATCCATGATCATGATATAGTAAGGGAAAAATCA : 2640

                *         2660         *         2680         *         2700
: TATCTATAAGTTTCCGAACTTAGTGAAAAAAAACCTGTAAAAGATATGCAGTCATATACA : 2700

                *         2720         *         2740         *         2760
: CATGTGAAATTAGGTAGGAAAATATGATAATCTCGTAGATGAGGAAAAAATATTGTACAC : 2760

                *         2780         *         2800         *         2820
: CAAACTATTGTAAGTTACAGTAATGTAATGTAAAAAAAGTTTTTAAGTTACAGAAGGTAC : 2820

                *         2840         *         2860         *         2880
: ATACCGCAAATAATCATATTATTTTACCAAGATATTTTTTTCTGGAGTATTCCTTTCAAG : 2880

                *         2900         *         2920         *         2940
: TATCTTTTATCTCTAGAATCTTCTCCAATCATGAGTGGCAACCGAAATGGAGCTCCTGTG : 2940

                *         2960         *         2980         *         3000
: TTGCTCCCCGTGTCTCACCCCTTTCGGCCCCACTGTCATTGGGTGGACCTATTCTCACGG : 3000

                *         3020         *         3040         *         3060
: CGGCTGTCCTGAGAAACAAAAATAGCAGCTGAAATGAAGACACGGCGACACGCAAGCCAG : 3060

                *         3080         *         3100         *         3120
: CATCTCTCATTGAACCTGCGGAGTGAGATAGCTCTCGTGGCGCTGCTCTACTTGACGCGT : 3120

                *         3140         *         3160         *         3180
: TTGTCTCATACAACAGCGCATGGCTCCTTCATGTCAGGTCCATGATCCACAGATGGTATG : 3180

                *         3200         *         3220         *         3240
: ATTGGGTTTGGAACATTTTTTTGGGTTTGTGATATGTCGTAGATACAAAGGGAAATGTCTG : 3240

                *         3260         *         3280
: AAGCATGCATGGATGGGTTCCCTGCTCATGTACTCAATGT : 3280
```

FIGURE 32

```
         *        20         *        40         *        60
: ACCCACATAGGACTACCAGCCTGGCCGACCACCTCCGACGAAGAAGAAGGCCGCCTCCAC :   60

         *        80         *       100         *       120
: CGTCGAACCCGAGGCTGCTGCCCCAGGCGTCCTCGTACCGCGGGAGAATCCCAAGGTCAC :  120

         *       140         *       160         *       180
: CCCCTCGCACCGGCGAGAAGCGGAGGGGATGGCGCCATCCCACCACCAGCCGCCACCGGT :  180

         *       200         *       220         *       240
: GTGCCGCCGCCGGGAGGCAGGGGAGGTCGCAGCACAGAGGCCACCGTCGCCCCTCCATCC :  240

         *       260         *       280         *       300
: TCCGACCGCCGCCGCCCCGCCATCACACGGGAGGCCGGAAGTCCACCGCCGCCGCCCCCC :  300

         *       320         *       340         *       360
: CATCGGGAGGCAGGAAGCCGCCGCCGCTGCATCGAGGGGAGGACCCAGCCGCCGTCCCCG :  360

         *       380         *       400         *       420
: CCGCGCCATGAGGGAAGCCCACCGCCGCCGCGGTGGCGGGAGGAGCTAGGGTTTCTGGGG :  420

         *       440         *       460         *       480
: TGCGGGACGGGCGGGAGGAGCTAGGGTTTCTCTATGATTAAGTGCATGTATTGCGAAATT :  480

         *       500         *       520         *       540
: AATGTTTCTACTTTTGTCATGGCCTTCTAGTCCGTCTAAAAAAAGCTGCCTTCTAGTGGG :  540

         *       560         *       580         *       600
: CGACATGGAACTCAGCGACATTCCTCCACCACACGCGCAGCGATCGTCCTGGCCGATCCA :  600

         *       620         *       640         *       660
: GTTGAGCTCAACACCCCTGTGCCCTGTACAGGTGTCCGGCCCAGGGCTCGCCACACCAGC :  660

         *       680         *       700         *       720
: CGCCCCATCCAGGCACATCCACCCTCCGAGAACACGAGAGCCAATCGCAACGCAGATCGT :  720

         *       740         *       760         *       780
: GATTTGTGAGATAAGGACGTGGCCCCCTCCCCTCGCGCGCACGGCATGGTATTTAAGCTC :  780

         *       800         *       820         *       840
: CATGCGCTGCTCCTCTCTTCCCCACGCAGCCACCGATCAATAGAAGCAGCAGCACATCAG :  840

         *       860         *       880         *       900
: CAGCTTGCTCTATTCCGTCCAATAGCAGAATTCGATTATGGAGTCCAGCGCCGTCGTCGC :  900

         *       920         *       940         *       960
: CCAAGGCACCACGTCGCCGCTGCTCCCGTACGCCTACGCGCCGCTGCCGTCCTCTGCCGA :  960

         *       980         *      1000         *      1020
: CGACGCCCGTGAAAACCAGAGTAGCGGCGGCGGTGTCAGGTGGCGCGCGTGCGCGGCCTC : 1020

         *      1040         *      1060         *      1080
: GGCCCTGGTGGTGCTGCTGGTCGTCGTCGGCTTCTTCGCGGGTGGCAGGGTGGATCTGGG : 1080

         *      1100         *      1120         *      1140
: TCAGGACGGCGAGGTGTCTGCGACTTCTTCGGTTCCTGGGAGCAGCAGGGGCAAGGATTC : 1140

         *      1160         *      1180         *      1200
: CGGCGTGTCGGAGAAGGAGTCGCCCGCCGACGGCGGCTTCCCGTGGAGCAACGCCATGCT : 1200

         *      1220         *      1240         *      1260
: GCAGTGGCAGCACACCGGGTTCCATTTCCAGCCACTCAAGCACTACATGAACGATCCCAA : 1260
```

FIGURE 32 CONT

```
          *        1280          *        1300          *        1320
: CGGTCCGGTCTACTATGGCGGATGGTACCACCTCTTCTACCAGCACAACCCCTATGGCGA : 1320

          *        1340          *        1360          *        1380
: CTCGTGGGGAAACGTATCTTGGGGACATGCCGTGTCCAAGGACCTGGTGAACTGGCGCCA : 1380

          *        1400          *        1420          *        1440
: CCTCCCGGTCGCCTTGGTGCCCGATCAGTGGTACGACATCAACGGCGTCCTGACGGGCTC : 1440

          *        1460          *        1480          *        1500
: TATCACAGTGCTCCCAGACGGGCGTGTCATCCTGCTATATACGGGGAACACCGACACCTT : 1500

          *        1520          *        1540          *        1560
: TTCGCAGGTCCAGTGCCTCGCAGTGCCCGCCGACCCATCTGACCCGCTCCTCCGTAGCTG : 1560

          *        1580          *        1600          *        1620
: GATCAAGCACCCCGCCAACCCCATCCTCTTCCCGCCACCTGGGATCGGGCTCAAGGACTT : 1620

          *        1640          *        1660          *        1680
: CCGTGACCCGCTCACAGCCTGGTTCGAACATTCCGACAACACGTGGCGCACCATCATCGG : 1680

          *        1700          *        1720          *        1740
: ATCCAAGGATGACGACGGCCACGCCGGCATCGTCCTTAGCTACAAGACCACCGACTTTGT : 1740

          *        1760          *        1780          *        1800
: GAATTATGAGCTCATGCCAGGGAACATGCATCGTGGCCCCGACGGCACCGGCATGTACGA : 1800

          *        1820          *        1840          *        1860
: GTGCCTTGACATCTACCCTGTGGGCGGCAACTCATCCGAGATGTTGGGTGGCGACTCCTC : 1860

          *        1880          *        1900          *        1920
: ACCTGAGGTGTTGTTCGTGCTCAAGGAGAGCGCCAACGACGAGTGGCACGACTACTACGC : 1920

          *        1940          *        1960          *        1980
: GCTTGGGTGGTTTGACGCTGCCGCCAACACGTGGACGCCACAGGACCCCGAGGCGGACCT : 1980

          *        2000          *        2020          *        2040
: TGGGATCGGCCTCAGGTACGACTGGGGCAAGTACTACGCGTCCAAGTCCTTCTACGACCC : 2040

          *        2060          *        2080          *        2100
: GATCAAGAACCGGCGTGTCGTTTGGGCTTTCGTCGGCGAGACCGACTCTGAGCAGGCCGA : 2100

          *        2120          *        2140          *        2160
: CAAAGCCAAGGGATGGGCGTCCCTCATGTCGATTCCCAGGACGGTGGAGCTTGACAAGAA : 2160

          *        2180          *        2200          *        2220
: GACCCGGACGAACCTGATCCAATGGCCAGTGGAGGAGATCGAGACCCTTCGCAGGAACGT : 2220

          *        2240          *        2260          *        2280
: CACAGACCTCGGTGGCATCACCGTTGAAGCCGGCTCCGTCATTCACCTTCCCCTCCAACA : 2280

          *        2300          *        2320          *        2340
: AGGCGGGCAGCTTGACATCGAGGCCTCCTTCCGTCTCAACTCTTCGGACATCGATGCACT : 2340

          *        2360          *        2380          *        2400
: CAACGAGGCCGACGTCGGCTTCAACTGCAGTAGCAGCGATGGGGCAGCCGTGCGTGGTGC : 2400

          *        2420          *        2440          *        2460
: GCTCGGCCCCTTTGGCCTCCTCGTCTTCGCCGACGGTCGCCACGAACAGACGGCGGCGTA : 2460

          *        2480          *        2500          *        2520
: CTTCTACGTGTCCAAGGGCCTCGACGGCAGCCTCCTGACGCACTACTGCCACGACGAGTC : 2520
```

FIGURE 32 CONT

```
          *        2540          *        2560          *        2580
: ACGGTCGACGCGAGCAAAGGACGTCGTGAGCCGGGTGGTTGGCGGCACTGTGCCAGTGCT : 2580

          *        2600          *        2620          *        2640
: TGACGGTGAAACCTTTTCAGTGAGGGTGCTAGTGGACCACTCCATCGTGCAGAGCTTCGT : 2640

          *        2660          *        2680          *        2700
: GATGGGTGGGAGGACCACGGTGACATCGCGGGCATACCCGACGGAGGCCATCTACGCCGC : 2700

          *        2720          *        2740          *        2760
: GGCAGGGGTGTACCTGTTCAACAACGCAACGAGCGCCACCATCACCGCCGAAGGGCTCGT : 2760

          *        2780          *        2800          *        2820
: CGTGTACGAGATGGCCTCGGCCGAGAGTCGGGCCTTCTTGGCTGACGACATGTAGATGAA : 2820

          *        2840          *        2860          *        2880
: AACTAGTCAAGAACATGTCAATGGCGATCGTCAAGCTTGCTGGATGGGGATCGTGGTCAC : 2880

          *        2900          *        2920          *        2940
: AGAGATCTTCATTCGCAAGTTCGCGGGTATGTTGTAGCTAGGGTGGTGCCAAATCACTAG : 2940

          *        2960          *        2980          *        3000
: TGAATTCAACAATAATTTTCTGAGCCTAGTATCCATGATCATGATATAGTAAGGGAAAAA : 3000

          *        3020          *        3040          *        3060
: TCATATCTATAAGTTTCCGAACTTAGTGAAAAAAAACCTGTAAAAGATATGCAGTCATAT : 3060

          *        3080          *        3100          *        3120
: ACACATGTGAAATTAGGTAGGAAAATATGATAATCTCGTAGATGAGGAAAAAATATTGTA : 3120

          *        3140          *        3160          *        3180
: CACCAAACTATTGTAAGTTACAGTAATGTAATGTAAAAAAAGTTTTTAAGTTACAGAAGG : 3180

          *        3200          *        3220          *        3240
: TACATACCGCAAATAATCATATTATTTTACCAAGATATTTTTTTCTGGAGTATTCCTTTC : 3240

          *        3260          *        3280          *        3300
: AAGTATCTTTTATCTCTAGAATCTTCTCCAATCATGAGTGGCAACCGAAATGGAGCTCCT : 3300

          *        3320          *        3340          *        3360
: GTGTTGCTCCCCGTGTCTCACCCCTTTCGGCCCCACTGTCATTGGGTGGACCTATTCTCA : 3360

          *        3380          *        3400          *        3420
: CGGCGGCTGTCCTGAGAAACAAAAATAGCAGCTGAAATGAAGACACGGCGACACGCAAGC : 3420

          *        3440          *        3460          *        3480
: CAGCATCTCTCATTGAACCTGCGGAGTGAGATAGCTCTCGTGGCGCTGCTCTACTTGACG : 3480

          *        3500          *        3520          *        3540
: CGTTTGTCTCATACAACAGCGCATGGCTCCTTCATGTCAGGTCCATGATCCACAGATGGT : 3540

          *        3560          *        3580          *        3600
: ATGATTGGGTTTGGAACATTTTTTGGGTTTGTGATATGTCGTAGATACAAAGGGAAATGT : 3600

          *        3620          *        3640
: CTGAAGCATGCATGGATGGGTTCCCTGCTCATGTACTCAAT : 3641
```

FIGURE 34
A.
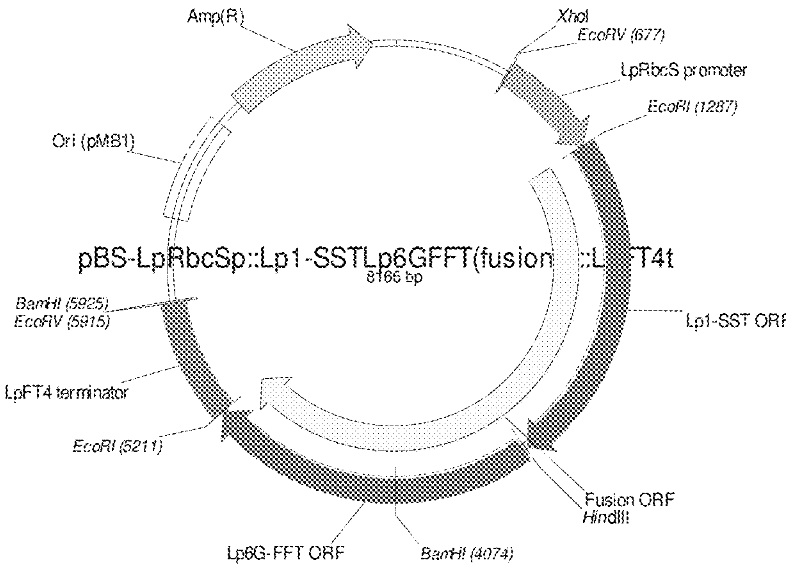
B.
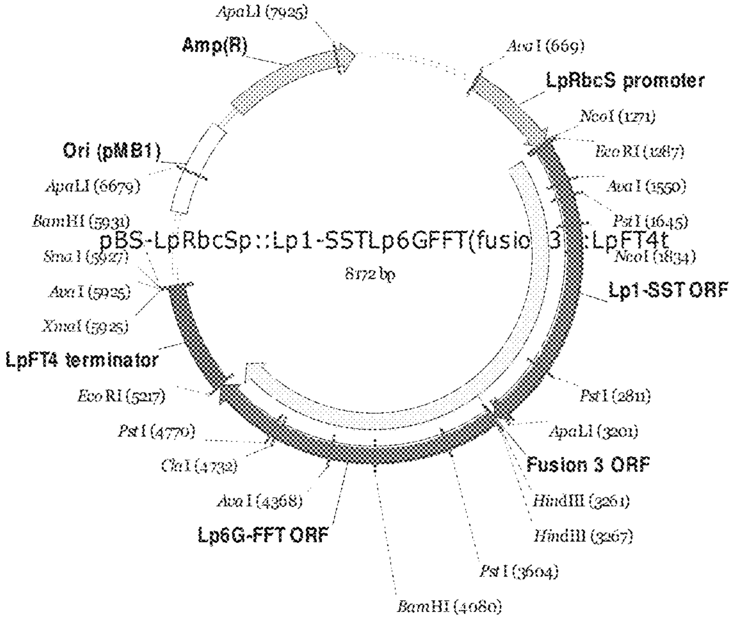

FIGURE 35

```
          *        20         *        40         *        60
: TGTTCATCTACCTTACTAGTCTGCATGATTAGTTTATTCGTTATTTTCGTAGTCATGATT :   60

          *        80         *       100         *       120
: TATCAATTACTCGTACGGATTATTTCATATGGATATTTGCTTATATTTCCAACAATTTAC :  120

          *       140         *       160         *       180
: ACTGTCGAGTTTTGGCGCGGCTGCTGGAGTTACTCTTAGAGTAGTTGGACTTGAGACAAA :  180

          *       200         *       220         *       240
: AGCTAGAATATCAATTATATATAGGAGTGAGGAGTTATTCTTTCGAAAGAACTTTAAACG :  240

          *       260         *       280         *       300
: GTAGCTGCACTTAGTCGTCGCAATGAAATACTTGTCGTACTACCATGATAATTGGTAATA :  300

          *       320         *       340         *       360
: TGAGAGGGAATATTAATTCCTCAGTGATTTGAATTTTGTGTGCTCATGTGCAGTCACCCA :  360

          *       380         *       400         *       420
: CGCCATGCATCCGACGACGGGCGGCTATACCAACTCTTGCACTGATCCGGAGGGATAAGG :  420

          *       440         *       460         *       480
: CGCCATGCAACCAGGGAACGTCGTCCACCCCTTCCACATCCTGTATCAAATTAAGGAACG :  480

          *       500         *       520         *       540
: GGCGCTGAGCCTATGCCGAGACATATATAATGCGGCGACTCGGACATGGAGGGGCCTCAG :  540

          *       560         *       580         *       600
: GCATAGCCCAGCTAGTTATCTCATTCTCTCCTTAGCAATAATACTTAGCACCATGGCCCC :  600

          *       620         *       640         *       660
: CGCGGTGAATTCATGGAGTCCCCAAGCGCCGTCGTCCCGGGCACCACGGCGCCGCTGCTT :  660

          *       680         *       700         *       720
: CCTTATGCGTACGCGCCGCTGCCGTCGTCCGCCGACGACGCCCGTCAAAACCGGAGTGGC :  720

          *       740         *       760         *       780
: GGGAGGTGGCGCGCGTGCGCCGCCGTGCTGGCCGCATCGGCGTTGTCGGTGGTCGTCGTG :  780

          *       800         *       820         *       840
: GTCGGGCTCCTCGCGGGCGGCAGGGTGGATCGGGTCCCGGCCGGCGGAGACGTGGCGTCG :  840

          *       860         *       880         *       900
: GCCACGGTGCCGGCCGTGCCGATGGAGTTCCCGAGGAGCCGGGGCAAGGACTTCGGCGTG :  900

          *       920         *       940         *       960
: TCGGAGAAGTCCTCCGGTGCCTACTCCACCGACGGCGGGTTCCCGTGGAGCAACGCCATG :  960

          *       980         *      1000         *      1020
: CTGCAGTGGCAGCGCACCGGGTTCCATTTCCAGCCGGAGCAGCACTACATGAACGATCCC : 1020

          *      1040         *      1060         *      1080
: AACGGCCCCGTGTACTACGGCGGATGGTACCACCTCTTCTACCAGCACAACCCCAAGGGC : 1080

          *      1100         *      1120         *      1140
: GACAGCTGGGGCAACATCGCGTGGGCCCACGCCGTCTCCAAGGACATGGTCAACTGGCGC : 1140
```

FIGURE 35 CONT

```
           *       1160          *       1180          *       1200
: CACCTCCCTCTCGCCATGGTTCCCGACCAGTGGTACGACAGCAACGGCGTCCTCACCGGC : 1200

           *       1220          *       1240          *       1260
: TCCATCACCGTGCTCCCCGACGGCCAGGTCATCCTGCTCTACACCGGCAACACCGACACC : 1260

           *       1280          *       1300          *       1320
: CTAGCCCAGGTCCAGTGCCTCGCCACGCCCGCCGACCCGTCCGACCCGCTCCTCCGCGAG : 1320

           *       1340          *       1360          *       1380
: TGGGTCAAGCACCCCGCCAACCCCATCCTCTACCCTCCCCCCGGCATCGGCCTCAAGGAC : 1380

           *       1400          *       1420          *       1440
: TTCCGCGACCCCCTCACCGCCTGGTTCGACCACTCCGACCACACCTGGCGCACCGTCATC : 1440

           *       1460          *       1480          *       1500
: GGCTCCAAGGACGACGACGGCCACGCCGGCATCATCCTCAGCTACAAGACCAAGGACTTC : 1500

           *       1520          *       1540          *       1560
: GTCAACTACGAGCTCATGCCGGGGAACATGCACCGCGGGCCCGACGGCACCGGAATGTAC : 1560

           *       1580          *       1600          *       1620
: GAGTGCATCGACCTCTACCCCGTCGGCGGCAACTCGTCCGAGATGCTCGGCGGCGACGAC : 1620

           *       1640          *       1660          *       1680
: TCGCCCGGCGTGCTCTTCGTGCTCAAGGAGAGCAGCGACGACGAGCGCCACGACTACTAC : 1680

           *       1700          *       1720          *       1740
: GCGCTCGGAAGGTTCGATGCCGTCGCCAACGTTTGGACGCCCATCGACCGGGAGCTGGAC : 1740

           *       1760          *       1780          *       1800
: CTTGGGATCGGGCTCAGATACGACTGGGGAAAGTACTACGCCTCCAAGTCCTTCTACGAC : 1800

           *       1820          *       1840          *       1860
: CAGAAGAAGAACCGCCGCATCGTATGGGCATACATCGGCGAGACCGACTCCGAGCAGGCC : 1860

           *       1880          *       1900          *       1920
: GACATCACCAAGGGATGGGCCAATCTCATGACGATTCCAAGAACGGTGGAGCTTGACAGG : 1920

           *       1940          *       1960          *       1980
: AAGACCCGCACAAACCTCATCCAATGGCCAGTGGAGGAGGTCGACACCCTCCGCAGGAAC : 1980

           *       2000          *       2020          *       2040
: TCCACGGACCTCGGTCGCATCACCGTCAACGCCGGCTCCGTCATTCGCCTCCCCCTCCAC : 2040

           *       2060          *       2080          *       2100
: CAGGGCGCTCAACTCGACATCGAGGCCTCCTTCCAACTCAACTCTTCCGACGTGGATGCT : 2100

           *       2120          *       2140          *       2160
: ATCAACGAGGCCGACGTCGGCTACAACTGCAGCACCAGTGGTGCCGCCGTACGGGGGGCG : 2160

           *       2180          *       2200          *       2220
: CTCGGCCCCTTTGGCCTCCTCGTCCTTGCCAACGGCCGCACCGAACAGACGGCTGTGTAC : 2220

           *       2240          *       2260          *       2280
: TTCTACGTGTCCAAGGGCGTCGACGGTGCCCTCCAGACCCACTTCTGCCACGACGAGTCA : 2280

           *       2300          *       2320          *       2340
: CGGTCAACGCGGGCAAAGGATGTCGTGAATAGGATGATTGGCAGCATCGTGCCGGTGCTT : 2340

           *       2360          *       2380          *       2400
```

FIGURE 35 CONT

```
: GACGGTGAGACCTTTTCGGTGAGGGTGCTAGTGGACCACTCCATCGTGCAGAGCTTCGCG : 2400

            *        2420         *        2440         *        2460
: ATGGGCGGGAGGATCACGGCGACGTCGCGGGCGTACCCGACGGAGGCCATCTACGCGGCC : 2460

            *        2480         *        2500         *        2520
: GCGGGGGTCTACCTCTTCAACAACGCCACGGGCGCCACCGTCACCGCCGAGAGGCTCGTC : 2520

            *        2540         *        2560         *        2580
: GTGCACGAGATGGCCTCAGCTGACAACCATATCTTCACGAACGACGACTTGGGAGGAGGA : 2580

            *        2600         *        2620         *        2640
: AAGCTTGGAGGAGGAGAGTCCAGCGCCGTCGTCGCCCAAGGCACCACGTCGCCGCTGCTC : 2640

            *        2660         *        2680         *        2700
: CCGTACGCCTACGCGCCGCTGCCGTCCTCTGCCGACGACGCCCGTGAAAACCAGAGTAGC : 2700

            *        2720         *        2740         *        2760
: GGCGGCGGTGTCAGGTGGCGCGCGTGCGCGGCCTCGGCCCTGGTGGTGCTGCTGGTCGTC : 2760

            *        2780         *        2800         *        2820
: GTCGGCTTCTTCGCGGGTGGCAGGGTGGATCTGGGTCAGGACGGCGAGGTGTCTGCGACT : 2820

            *        2840         *        2860         *        2880
: TCTTCGGTTCCTGGGAGCAGCAGGGGCAAGGATTCCGGCGTGTCGGAGAAGGAGTCGCCC : 2880

            *        2900         *        2920         *        2940
: GCCGACGGCGGCTTCCCGTGGAGCAACGCCATGCTGCAGTGGCAGCACACCGGGTTCCAT : 2940

            *        2960         *        2980         *        3000
: TTCCAGCCACTCAAGCACTACATGAACGATCCCAACGGTCCGGTCTACTATGGCGGATGG : 3000

            *        3020         *        3040         *        3060
: TACCACCTCTTCTACCAGCACAACCCCTATGGCGACTCGTGGGGAAACGTATCTTGGGGA : 3060

            *        3080         *        3100         *        3120
: CATGCCGTGTCCAAGGACCTGGTGAACTGGCGCCACCTCCCGGTCGCCTTGGTGCCCGAT : 3120

            *        3140         *        3160         *        3180
: CAGTGGTACGACATCAACGGCGTCCTGACGGGCTCTATCACAGTGCTCCCAGACGGGCGT : 3180

            *        3200         *        3220         *        3240
: GTCATCCTGCTATATACGGGGAACACCGACACCTTTTCGCAGGTCCAGTGCCTCGCAGTG : 3240

            *        3260         *        3280         *        3300
: CCCGCCGACCCATCTGACCCGCTCCTCCGTAGCTGGATCAAGCACCCCGCCAACCCCATC : 3300

            *        3320         *        3340         *        3360
: CTCTTCCCGCCACCTGGGATCGGGCTCAAGGACTTCCGTGACCCGCTCACAGCCTGGTTC : 3360

            *        3380         *        3400         *        3420
: GAACATTCCGACAACACGTGGCGCACCATCATCGGATCCAAGGATGACGACGGCCACGCC : 3420

            *        3440         *        3460         *        3480
: GGCATCGTCCTTAGCTACAAGACCACCGACTTTGTGAATTATGAGCTCATGCCAGGGAAC : 3480

            *        3500         *        3520         *        3540
: ATGCATCGTGGCCCCGACGGCACCGGCATGTACGAGTGCCTTGACATCTACCCTGTGGGC : 3540

          *        3560         *        3580         *        3600
```

FIGURE 35 CONT

```
: GGCAACTCATCCGAGATGTTGGGTGGCGACTCCTCACATGAGGTGTTGTTCGTGCTCAAG : 3600

           *        3620         *        3640         *        3660
: GAGAGCGCCAACGACGAGTGGCACGACTACTACGCGCTTGGGTGGTTTGACGCTGCCGCC : 3660

           *        3680         *        3700         *        3720
: AACACGTGGACGCCACAGGACCCCGAGGCGGACCTTGGGATCGGCCTCAGGTACGACTGG : 3720

           *        3740         *        3760         *        3780
: GGCAAGTACTACGCGTCCAAGTCCTTCTACGACCCGATCAAGAACCGGCGTGTCGTTTGG : 3780

           *        3800         *        3820         *        3840
: GCTTTCGTCGGCGAGACCGACTCTGAGCAGGCCGACAAAGCCAAGGGATGGGCGTCCCTC : 3840

           *        3860         *        3880         *        3900
: ATGTCGATTCCCAGGACGGTGGAGCTTGACAAGAAGACCCGGACGAACCTGATCCAATGG : 3900

           *        3920         *        3940         *        3960
: CCAGTGGAGGAGATCGAGACCCTTCGCAGGAACGTCACAGACCTCGGTGGCATCACCGTT : 3960

           *        3980         *        4000         *        4020
: GAAGCCGGCTCCGTCATTCACCTTCCCCTCCAACAAGGCGGGCAGCTTGACATCGAGGCC : 4020

           *        4040         *        4060         *        4080
: TCCTTCCGTCTCAACTCTTCGGACATCGATGCACTCAACGAGGCCGACGTCGGCTTCAAC : 4080

           *        4100         *        4120         *        4140
: TGCAGTAGCAGCGATGGGGTAGCCGTGCGTGGTGCGCTCGGCCCCTTTGGCCTCCTCGTC : 4140

           *        4160         *        4180         *        4200
: TTCGCCGACGGTCGCCACGAACAGACGGCGGCGTACTTCTACGTGTCCAAGGGCCTCGAC : 4200

           *        4220         *        4240         *        4260
: GGCAGCCTCCTGACGCACTACTGCCACGACGAGTCACGGTCGACGCGAGCAAAGGACGTC : 4260

           *        4280         *        4300         *        4320
: GTGAGCCGGGTGGTTGGCGGCACTGTGCCAGTGCTTGACGGTGAAACCTTTTCAGTGAGG : 4320

           *        4340         *        4360         *        4380
: GTGCTAGTGGACCACTCCATCGTGCAGAGCTTCGTGATGGGTGGGAGGACCACGGTGACA : 4380

           *        4400         *        4420         *        4440
: TCGCGGGCATACCCGACGGAGGCCATCTACGCCGCGGCAGGGGTGTACCTGTTCAACAAC : 4440

           *        4460         *        4480         *        4500
: GCAACGAGCGCCACCATCACCGCCGAAGGGCTCGTCGTGTACGAGATGGCCTCGGCCGAG : 4500

           *        4520         *        4540         *        4560
: AGTCGGGCCTTCTTGGCTGACGACATGTAAGAATTCAACAATAATTTTCTGAGCCTAGTA : 4560

           *        4580         *        4600         *        4620
: TCCATGATCATGATATAGTAAGGGAAAAATCATATCTATAAGTTTCCGAACTTAGTGAAA : 4620

           *        4640         *        4660         *        4680
: AAAAACCTGTAAAAGATATGCAGTCATATACACATGTGAAATTAGGTAGGAAAATATGAT : 4680

           *        4700         *        4720         *        4740
: AATCTCGTAGATGAGGAAAAAATATTGTACACCAAACTATTGTAAGTTACAGTAATGTAA : 4740

           *        4760         *        4780         *        4800
: TGTAAAAAAAGTTTTTAAGTTACAGAAGGTACATACCGCAAATAATCATATTATTTTACC : 4800
```

FIGURE 35 CONT

```
          *        4820          *        4840          *        4860
: AAGATATTTTTTTCTGGAGTATTCCTTTCAAGTATCTTTTATCTCTAGAATCTTCTCCAA : 4860

          *        4880          *        4900          *        4920
: TCATGAGTGGCAACCGAAATGGAGCTCCTGTGTTGCTCCCCGTGTCTCACCCCTTTCGGC : 4920

          *        4940          *        4960          *        4980
: CCCACTGTCATTGGGTGGACCTATTCTCACGGCGGCTGTCCTGAGAAACAAAAATAGCAG : 4980

          *        5000          *        5020          *        5040
: CTGAAATGAAGACACGGCGACACGCAAGCCAGCATCTCTCATTGAACCTGCGGAGTGAGA : 5040

          *        5060          *        5080          *        5100
: TAGCTCTCGTGGCGCTGCTCTACTTGACGCGTTTGTCTCATACAACAGCGCATGGCTCCT : 5100

          *        5120          *        5140          *        5160
: TCATGTCAGGTCCATGATCCACAGATGGTATGATTGGGTTTGGAACATTTTTTGGGTTTG : 5160

          *        5180          *        5200          *        5220
: TGATATGTCGTAGATACAAAGGGAAATGTCTGAAGCATGCATGGATGGGTTCCCTGCTCA : 5220

          *
: TGTACTCAATGT : 5232
```

FIGURE 36

```
           *        20         *        40         *        60
: TGTTCATCTACCTTACTAGTCTGCATGATTAGTTTATTCGTTATTTTCGTAGTCATGATT :  60

           *        80         *       100         *       120
: TATCAATTACTCGTACGGATTATTTCATATGGATATTTGCTTATATTTCCAACAATTTAC : 120

           *       140         *       160         *       180
: ACTGTCGAGTTTTGGCGCGGCTGCTGGAGTTACTCTTAGAGTAGTTGGACTTGAGACAAA : 180

           *       200         *       220         *       240
: AGCTAGAATATCAATTATATATAGGAGTGAGGAGTTATTCTTTCGAAAGAACTTTAAACG : 240

           *       260         *       280         *       300
: GTAGCTGCACTTAGTCGTCGCAATGAAATACTTGTCGTACTACCATGATAATTGGTAATA : 300

           *       320         *       340         *       360
: TGAGAGGGAATATTAATTCCTCAGTGATTTGAATTTTGTGTGCTCATGTGCAGTCACCCA : 360

           *       380         *       400         *       420
: CGCCATGCATCCGACGACGGGCGGCTATACCAACTCTTGCACTGATCCGGAGGGATAAGG : 420

           *       440         *       460         *       480
: CGCCATGCAACCAGGGAACGTCGTCCACCCCTTCCACATCCTGTATCAAATTAAGGAACG : 480

           *       500         *       520         *       540
: GGCGCTGAGCCTATGCCGAGACATATATAATGCGGCGACTCGGACATGGAGGGGCCTCAG : 540

           *       560         *       580         *       600
: GCATAGCCCAGCTAGTTATCTCATTCTCTCCTTAGCAATAATACTTAGCACCATGGCCCC : 600

           *       620         *       640         *       660
: CGCGGTATGGAGTCCCCAAGCGCCGTCGTCCCCGGCACCACGGCGCCGCTGCTTCCTTAT : 660
        M  E  S  P  S  A  V  V  P  G  T  T  A  P  L  L  P  Y

           *       680         *       700         *       720
: GCGTACGCGCCGCTGCCGTCGTCCGCCGACGACGCCCGTCAAAACCGGAGTGGCGGGAGG : 720
  A  Y  A  P  L  P  S  S  A  D  D  A  R  Q  N  R  S  G  G  R

           *       740         *       760         *       780
: TGGCGCGCGTGCGCCGCCGTGCTGGCCGCATCGGCGTTGGCGGTGGTCGTCGTGGTCGGG : 780
    W  R  A  C  A  A  V  L  A  A  S  A  L  A  V  V  V  V  V  G
```

FIGURE 36 CONT

```
         *       800         *       820         *       840
: CTCCTCGCGGGCGGCAGGGTGGATCGGGTCCCAGCCGGCGGAGACGTGGCGTCGGCCACG :  840

  L  L  A  G  G  R  V  D  R  V  P  A  G  G  D  V  A  S  A  T

         *       860         *       880         *       900
: GTGCCGGCCGTGCCGATGGAGTTCCCGAGGAGCCGGGGCAAGGACTTCGGCGTGTCGGAG :  900

  V  P  A  V  P  M  E  F  P  R  S  R  G  K  D  F  G  V  S  E

         *       920         *       940         *       960
: AAGTCCTCCGGTGCCTACTCCACCGACGGCGGGTTCCCGTGGAGCAACGCCATGCTGCAG :  960

  K  S  S  G  A  Y  S  T  D  G  G  F  P  W  S  N  A  M  L  Q

         *       980         *      1000         *      1020
: TGGCAGCGCACCGGGTTCCATTTCCAGCCGGAGCAGCACTACATGAACGATCCCAACGGC : 1020

  W  Q  R  T  G  F  H  F  Q  P  E  Q  H  Y  M  N  D  P  N  G

         *      1040         *      1060         *      1080
: CCCGTGTACTACGGCGGATGGTACCACCTCTTCTACCAGCACAACCCCAAGGGCGACAGC : 1080

  P  V  Y  Y  G  G  W  Y  H  L  F  Y  Q  H  N  P  K  G  D  S

         *      1100         *      1120         *      1140
: TGGGGCAACATCGCGTGGGCCCACGCCGTCTCCAAGGACATGGTCAACTGGCGCCACCTC : 1140

  W  G  N  I  A  W  A  H  A  V  S  K  D  M  V  N  W  R  H  L

         *      1160         *      1180         *      1200
: CCTCTCGCCATGGTTCCCGACCAGTGGTACGACAGCAACGGCGTCCTCACCGGCTCCATC : 1200

  P  L  A  M  V  P  D  Q  W  Y  D  S  N  G  V  L  T  G  S  I

         *      1220         *      1240         *      1260
: ACCGTGCTCCCCGACGGCCAGGTCATCCTGCTCTACACCGGCAACACCGACACCCTAGCC : 1260

  T  V  L  P  D  G  Q  V  I  L  L  Y  T  G  N  T  D  T  L  A

         *      1280         *      1300         *      1320
: CAGGTCCAGTGCCTCGCCACGCCCGCCGACCCGTCCGACCCGCTCCTCCGCGAGTGGGTC : 1320

  Q  V  Q  C  L  A  T  P  A  D  P  S  D  P  L  L  R  E  W  V

         *      1340         *      1360         *      1380
: AAGCACCCCGCCAACCCCATCCTCTACCCTCCCCCCGGCATCGGCCTCAAGGACTTCCGC : 1380

  K  H  P  A  N  P  I  L  Y  P  P  P  G  I  G  L  K  D  F  R

         *      1400         *      1420         *      1440
: GACCCCCTCACCGCCTGGTTCGACCACTCCGACCACACCTGGCGCACCGTCATCGGCTCC : 1440
```

FIGURE 36 CONT

```
D P L T A W F D H S D H T W R T V I G S

             *         1460          *         1480          *         1500
: AAGGACGACGACGGCCACGCCGGCATCATCCTCAGCTACAAGACCAAGGACTTCGTCAAC : 1500

K D D D G H A G I I L S Y K T K D F V N

             *         1520          *         1540          *         1560
: TACGAGCTCATGCCGGGGAACATGCACCGCGGGCCCGACGGCACCGGAATGTACGAGTGC : 1560

Y E L M P G N M H R G P D G T G M Y E C

             *         1580          *         1600          *         1620
: ATCGACCTCTACCCCGTCGGCGGCAACTCGTCCGAGATGCTCGGCGGCGACGACTCGCCC : 1620

I D L Y P V G G N S S E M L G G D D S P

             *         1640          *         1660          *         1680
: GGCGTGCTCTTCGTGCTCAAGGAGAGCAGCGACGACGAGCGCCACGACTACTACGCGCTC : 1680

G V L F V L K E S S D D E R H D Y Y A L

             *         1700          *         1720          *         1740
: GGAAGGTTCGACGCCGTCGCCAACGTTTGGACGCCCATCGACCGGGAGCTGGACCTTGGG : 1740

G R F D A V A N V W T P I D R E L D L G

             *         1760          *         1780          *         1800
: ATCGGGCTCAGATACGACTGGGGAAAGTACTACGCCTCCAAGTCCTTCTACGACCAGAAG : 1800

I G L R Y D W G K Y Y A S K S F Y D Q K

             *         1820          *         1840          *         1860
: AAGAACCGCCGCATCGTATGGGCATACATCGGCGAGACCGACTCCGAGCAGGCCGACATC : 1860

K N R R I V W A Y I G E T D S E Q A D I

             *         1880          *         1900          *         1920
: ACCAAGGGATGGGCCAATCTCATGACGATTCCAAGAACGGTGGAGCTTGACAGGAAGACC : 1920

T K G W A N L M T I P R T V E L D R K T

             *         1940          *         1960          *         1980
: CGCACAAACCTCATCCAATGGCCAGTGGAGGAGGTCGACACCCTCCGCAGGAACTCCACG : 1980

R T N L I Q W P V E E V D T L R R N S T

             *         2000          *         2020          *         2040
: GACCTCGGTCGCATCACCGTCAACGCCGGCTCCGTCATTCGCCTCCCCCTCCACCAGGGC : 2040

D L G R I T V N A G S V I R L P L H Q G
```

FIGURE 36 CONT

```
          *       2060         *       2080         *       2100
: GCTCAACTCGACATCGAGGCCTCCTTCCAACTCAACTCTTCCGACGTGGATGCTATCAAC : 2100
  A  Q  L  D  I  E  A  S  F  Q  L  N  S  S  D  V  D  A  I  N

          *       2120         *       2140         *       2160
: GAGGCCGACGTCGGCTACAACTGCAGCACCAGTGGTGCCGCCGTACGGGGGGCGCTCGGC : 2160
  E  A  D  V  G  Y  N  C  S  T  S  G  A  A  V  R  G  A  L  G

          *       2180         *       2200         *       2220
: CCCTTTGGCCTCCTCGTCCTTGCCAACGGCCGCACCGAACAGACGGCTGTGTACTTCTAC : 2220
  P  F  G  L  L  V  L  A  N  G  R  T  E  Q  T  A  V  Y  F  Y

          *       2240         *       2260         *       2280
: GTGTCCAAGGGCGTCGACGGTGCCCTCCAGACCCACTTCTGCCACGACGAGTCACGGTCA : 2280
  V  S  K  G  V  D  G  A  L  Q  T  H  F  C  H  D  E  S  R  S

          *       2300         *       2320         *       2340
: ACGCGGGCAAAGGATGTCGTGAATAGGATGATTGGCAGCATCGTGCCGGTGCTTGACGGT : 2340
  T  R  A  K  D  V  V  N  R  M  I  G  S  I  V  P  V  L  D  G

          *       2360         *       2380         *       2400
: GAGACCTTTTCGGTGAGGGTGCTAGTGGACCACTCCATCGTGCAGAGCTTCGCGATGGGC : 2400
  E  T  F  S  V  R  V  L  V  D  H  S  I  V  Q  S  F  A  M  G

          *       2420         *       2440         *       2460
: GGGAGGATCACGGCGACGTCGCGGGCGTACCCGACGGAGGCCATCTACGCGGCCGCGGGG : 2460
  G  R  I  T  A  T  S  R  A  Y  P  T  E  A  I  Y  A  A  A  G

          *       2480         *       2500         *       2520
: GTCTACCTCTTCAACAACGCCACGGGCGCCACCGTCACCGCCGAGAGGCTCGTCGTGCAC : 2520
  V  Y  L  F  N  N  A  T  G  A  T  V  T  A  E  R  L  V  V  H

          *       2540         *       2560         *       2580
: GAGATGGCCTCAGCTGACAACCATATCTTCACGAACGACGACTTGGGAGGAGGAAAGCTT : 2580
  E  M  A  S  A  D  N  H  I  F  T  N  D  D  L  G  G  G  K  L

          *       2600         *       2620         *       2640
: AAGCTTGGAGGAGGAGAGTCCAGCGCCGTCGTCGCCCAAGGCACCACGTCGCCGCTGCTC : 2640
  K  L  G  G  G  E  S  S  A  V  V  A  Q  G  T  T  S  P  L  L

          *       2660         *       2680         *       2700
: CCGTACGCCTACGCGCCGCTGCCGTCCTCTGCCGACGACGCCCGTGAAAACCAGAGTAGC : 2700
```

FIGURE 36 CONT

```
 P   Y   A   Y   A   P   L   P   S   S   A   D   D   A   R   E   N   Q   S   S

             *        2720          *        2740          *        2760
: GGCGGCGGTGTCAGGTGGCGCGCGTGCGCGGCCTCGGCCCTGGTGGTGCTGCTGGTCGTC : 2760
 G   G   G   V   R   W   R   A   C   A   A   S   A   L   V   V   L   L   V   V

             *        2780          *        2800          *        2820
: GTCGGCTTCTTCGCGGGTGGCAGGGTGGATCTGGGTCAGGACGGCGAGGTGTCTGCGACT : 2820
 V   G   F   F   A   G   G   R   V   D   L   G   Q   D   G   E   V   S   A   T

             *        2840          *        2860          *        2880
: TCTTCGGTTCCTGGGAGCAGCAGGGGCAAGGATTCCGGCGTGTCGGAGAAGGAGTCGCCC : 2880
 S   S   V   P   G   S   S   R   G   K   D   S   G   V   S   E   K   E   S   P

             *        2900          *        2920          *        2940
: GCCGACGGCGGCTTCCCGTGGAGCAACGCCATGCTGCAGTGGCAGCACACCGGGTTCCAT : 2940
 A   D   G   G   F   P   W   S   N   A   M   L   Q   W   Q   H   T   G   F   H

             *        2960          *        2980          *        3000
: TTCCAGCCACTCAAGCACTACATGAACGATCCCAACGGTCCGGTCTACTATGGCGGATGG : 3000
 F   Q   P   L   K   H   Y   M   N   D   P   N   G   P   V   Y   Y   G   G   W

             *        3020          *        3040          *        3060
: TACCACCTCTTCTACCAGCACAACCCCTATGGCGACTCGTGGGGAAACGTATCTTGGGGA : 3060
 Y   H   L   F   Y   Q   H   N   P   Y   G   D   S   W   G   N   V   S   W   G

             *        3080          *        3100          *        3120
: CATGCCGTGTCCAAGGACCTGGTGAACTGGCGCCACCTCCCGGTCGCCTTGGTGCCCGAT : 3120
 H   A   V   S   K   D   L   V   N   W   R   H   L   P   V   A   L   V   P   D

             *        3140          *        3160          *        3180
: CAGTGGTACGACATCAACGGCGTCCTGACGGGCTCTATCACAGTGCTCCCAGACGGGCGT : 3180
 Q   W   Y   D   I   N   G   V   L   T   G   S   I   T   V   L   P   D   G   R

             *        3200          *        3220          *        3240
: GTCATCCTGCTATATACGGGGAACACCGACACCTTTTCGCAGGTCCAGTGCCTCGCAGTG : 3240
 V   I   L   L   Y   T   G   N   T   D   T   F   S   Q   V   Q   C   L   A   V

             *        3260          *        3280          *        3300
: CCCGCCGACCCATCTGACCCGCTCCTCCGTAGCTGGATCAAGCACCCCGCCAACCCCATC : 3300
 P   A   D   P   S   D   P   L   L   R   S   W   I   K   H   P   A   N   P   I
```

FIGURE 36 CONT

```
             *        3320          *        3340          *        3360
: CTCTTCCCGCCACCTGGGATCGGGCTCAAGGACTTCCGTGACCCGCTCACAGCCTGGTTC : 3360
  L  F  P  P  P  G  I  G  L  K  D  F  R  D  P  L  T  A  W  F

             *        3380          *        3400          *        3420
: GAACATTCCGACAACACGTGGCGCACCATCATCGGATCCAAGGATGACGACGGCCACGCC : 3420
  E  H  S  D  N  T  W  R  T  I  I  G  S  K  D  D  D  G  H  A

             *        3440          *        3460          *        3480
: GGCATCGTCCTTAGCTACAAGACCACCGACTTTGTGAATTATGAGCTCATGCCAGGGAAC : 3480
  G  I  V  L  S  Y  K  T  T  D  F  V  N  Y  E  L  M  P  G  N

             *        3500          *        3520          *        3540
: ATGCATCGTGGCCCCGACGGCACCGGCATGTACGAGTGCCTTGACATCTACCCTGTGGGC : 3540
  M  H  R  G  P  D  G  T  G  M  Y  E  C  L  D  I  Y  P  V  G

             *        3560          *        3580          *        3600
: GGCAACTCATCCGAGATGTTGGGTGGCGACTCCTCACCTGAGGTGTTGTTCGTGCTCAAG : 3600
  G  N  S  S  E  M  L  G  G  D  S  S  P  E  V  L  F  V  L  K

             *        3620          *        3640          *        3660
: GAGAGCGCCAACGACGAGTGGCACGACTACTACGCGCTTGGGTGGTTTGACGCTGCCGCC : 3660
  E  S  A  N  D  E  W  H  D  Y  Y  A  L  G  W  F  D  A  A  A

             *        3680          *        3700          *        3720
: AACACGTGGACGCCACAGGACCCCGAGGCGGACCTTGGGATCGGCCTCAGGTACGACTGG : 3720
  N  T  W  T  P  Q  D  P  E  A  D  L  G  I  G  L  R  Y  D  W

             *        3740          *        3760          *        3780
: GGCAAGTACTACGCGTCCAAGTCCTTCTACGACCCGATCAAGAACCGGCGTGTCGTTTGG : 3780
  G  K  Y  Y  A  S  K  S  F  Y  D  P  I  K  N  R  R  V  V  W

             *        3800          *        3820          *        3840
: GCTTTCGTCGGCGAGACCGACTCTGAGCAGGCCGACAAAGCCAAGGGATGGGCGTCCCTC : 3840
  A  F  V  G  E  T  D  S  E  Q  A  D  K  A  K  G  W  A  S  L

             *        3860          *        3880          *        3900
: ATGTCGATTCCCAGGACGGTGGAGCTTGACAAGAAGACCCGGACGAACCTGATCCAATGG : 3900
  M  S  I  P  R  T  V  E  L  D  K  K  T  R  T  N  L  I  Q  W
```

FIGURE 36 CONT

```
         *        3920          *        3940          *        3960
: CCAGTGGAGGAGATCGAGACCCTTCGCAGGAACGTCACAGACCTCGGTGGCATCACCGTT : 3960
  P  V  E  E  I  E  T  L  R  R  N  V  T  D  L  G  G  I  T  V

          *        3980          *        4000          *        4020
: GAAGCCGGCTCCGTCATTCACCTTCCCCTCCAACAAGGCGGGCAGCTTGACATCGAGGCC : 4020
  E  A  G  S  V  I  H  L  P  L  Q  Q  G  G  Q  L  D  I  E  A

          *        4040          *        4060          *        4080
: TCCTTCCGTCTCAACTCTTCGGACATCGATGCACTCAACGAGGCCGACGTCGGCTTCAAC : 4080
  S  F  R  L  N  S  S  D  I  D  A  L  N  E  A  D  V  G  F  N

          *        4100          *        4120          *        4140
: TGCAGTAGCAGCGATGGGGCAGCCGTGCGTGGTGCGCTCGGCCCCTTTGGCCTCCTCGTC : 4140
  C  S  S  S  D  G  A  A  V  R  G  A  L  G  P  F  G  L  L  V

          *        4160          *        4180          *        4200
: TTCGCCGACGGTCGCCACGAACAGACGGCGGCGTACTTCTACGTGTCCAAGGGCCTCGAC : 4200
  F  A  D  G  R  H  E  Q  T  A  A  Y  F  Y  V  S  K  G  L  D

          *        4220          *        4240          *        4260
: GGCAGCCTCCTGACGCACTACTGCCACGACGAGTCACGGTCGACGCGAGCAAAGGACGTC : 4260
  G  S  L  L  T  H  Y  C  H  D  E  S  R  S  T  R  A  K  D  V

          *        4280          *        4300          *        4320
: GTGAGCCGGGTGGTTGGCGGCACTGTGCCAGTGCTTGACGGTGAAACCTTTTCAGTGAGG : 4320
  V  S  R  V  V  G  G  T  V  P  V  L  D  G  E  T  F  S  V  R

          *        4340          *        4360          *        4380
: GTGCTAGTGGACCACTCCATCGTGCAGAGCTTCGTGATGGGTGGGAGGACCACGGTGACA : 4380
  V  L  V  D  H  S  I  V  Q  S  F  V  M  G  G  R  T  T  V  T

          *        4400          *        4420          *        4440
: TCGCGGGCATACCCGACGGAGGCCATCTACGCCGCGGCAGGGGTGTACCTGTTCAACAAC : 4440
  S  R  A  Y  P  T  E  A  I  Y  A  A  A  G  V  Y  L  F  N  N

          *        4460          *        4480          *        4500
: GCAACGAGCGCCACCATCACCGCCGAAGGGCTCGTCGTGTACGAGATGGCCTCGGCCGAG : 4500
  A  T  S  A  T  I  T  A  E  G  L  V  V  Y  E  M  A  S  A  E

          *        4520          *        4540          *        4560
: AGTCGGGCCTTCTTGGCTGACGACATGTAGAACAATAATTTTCTGAGCCTAGTATCCATG : 4560
```

FIGURE 36 CONT

```
S  R  A  F  L  A  D  D  M  *

                *      4580          *      4600          *      4620
 : ATCATGATATAGTAAGGGAAAAATCATATCTATAAGTTTCCGAACTTAGTGAAAAAAAAC : 4620

                *      4640          *      4660          *      4680
 : CTGTAAAAGATATGCAGTCATATACACATGTGAAATTAGGTAGGAAAATATGATAATCTC : 4680

                *      4700          *      4720          *      4740
 : GTAGATGAGGAAAAAATATTGTACACCAAACTATTGTAAGTTACAGTAATGTAATGTAAA : 4740

                *      4760          *      4780          *      4800
 : AAAAGTTTTTAAGTTACAGAAGGTACATACCGCAAATAATCATATTATTTTACCAAGATA : 4800

                *      4820          *      4840          *      4860
 : TTTTTTTCTGGAGTATTCCTTTCAAGTATCTTTTATCTCTAGAATCTTCTCCAATCATGA : 4860

                *      4880          *      4900          *      4920
 : GTGGCAACCGAAATGGAGCTCCTGTGTTGCTCCCCGTGTCTCACCCCTTTCGGCCCCACT : 4920

                *      4940          *      4960          *      4980
 : GTCATTGGGTGGACCTATTCTCACGGCGGCTGTCCTGAGAAACAAAAATAGCAGCTGAAA : 4980

                *      5000          *      5020          *      5040
 : TGAAGACACGGCGACACGCAAGCCAGCATCTCTCATTGAACCTGCGGAGTGAGATAGCTC : 5040

                *      5060          *      5080          *      5100
 : TCGTGGCGCTGCTCTACTTGACGCGTTTGTCTCATACAACAGCGCATGGCTCCTTCATGT : 5100

                *      5120          *      5140          *      5160
 : CAGGTCCATGATCCACAGATGGTATGATTGGGTTTGGAACATTTTTTGGGTTTGTGATAT : 5160

                *      5180          *      5200          *      5220
 : GTCGTAGATACAAAGGGAAATGTCTGAAGCATGCATGGATGGGTTCCCTGCTCATGTACT : 5220

 : CAATGT : 5226
```

FIGURE 38

```
                 *        20         *        40         *        60
 : CGTGGTCGAGATTGTGTATTATTCTTTAGTTATTACAAGACTTTTAGCTAAAATTTGAAA :   60

                 *        80         *       100         *       120
 : GAATTTACTTTAAGAAAATCTTAACATCTGAGATAATTTCAGCAATAGATTATATTTTTC :  120

                 *       140         *       160         *       180
 : ATTACTCTAGCAGTATTTTTGCAGATCAATCGCAACATATATGGTTGTTAGAAAAAATGC :  180

                 *       200         *       220         *       240
 : ACTATATATATATATATTATTTTTTCAATTAAAAGTGCATGATATATAATATATATATAT :  240

                 *       260         *       280         *       300
 : ATATATATATGTGTGTGTGTATATGGTCAAAGAAATTCTTATACAAATATACACGAACAC :  300

                 *       320         *       340         *       360
 : ATATATTTGACAAAATCAAAGTATTACACTAAACAATGAGTTGGTGCATGGCCAAAACAA :  360

                 *       380         *       400         *       420
 : ATATGTAGATTAAAAATTCCAGCCTCCAAAAAAAAATCCAAGTGTTGTAAAGCATTATAT :  420

                 *       440         *       460         *       480
 : ATATATAGTAGATCCCAAATTTTTGTACAATTCCACACTGATCGAATTTTTAAAGTTGAA :  480

                 *       500         *       520         *       540
 : TATCTGACGTAGGATTTTTTTAATGTCTTACCTGACCATTTACTAATAACATTCATACGT :  540

                 *       560         *       580         *       600
 : TTTCATTTGAAATATCCTCTATAATTATATTGAATTTGGCACATAATAAGAAACCTAATT :  600

                 *       620         *       640         *       660
 : GGTGATTTATTTTACTAGTAAATTTCTGGTGATGGGCTTTCTACTAGAAAGCTCTCGGAA :  660

                 *       680         *       700         *       720
 : AATCTTGGACCAAATCCATATTCCATGACTTCGATTGTTAACCCTATTAGTTTTCACAAA :  720

                 *       740         *       760         *       780
 : CATACTATCAATATCATTGCAACGGAAAAGGTACAAGTAAAACATTCAATCCGATAGGGA :  780

                 *       800         *       820         *       840
 : AGTGATGTAGGAGGTTGGGAAGACAGGCCCAGAAAGAGATTTATCTGACTTGTTTTGTGT :  840

                 *       860         *       880         *       900
 : ATAGTTTTCAATGTTCATAAAGGAAGATGGAGACTTGAGAAGTTTTTTTTGGACTTTGTT :  900

                 *       920         *       940         *       960
 : TAGCTTTGTTGGGCGTTTTTTTTTTTTGATCAATAACTTTGTTGGGCTTATGATTTGTAA :  960

                 *       980         *      1000         *      1020
 : TATTTTCGTGGACTCTTTAGTTTATTTAGACGTGCTAACTTTGTTGGGCTTATGACTTGT : 1020

                 *      1040         *      1060         *      1080
 : TGTAACATATTGTAACAGATGACTTGATGTGCGACTAATCTTTACACATTAAACATAGTT : 1080

                 *      1100         *      1120         *      1140
 : CTGTTTTTTGAAAGTTCTTATTTTCATTTTTATTTGAATGTTATATATTTTTCTATATTT : 1140
```

FIGURE 38 CONT

```
        *      1160          *      1180          *      1200
: ATAATTCTAGTAAAAGGCAAATTTTGCTTTTAAATGAAAAAAATATATATTCCACAGTTT : 1200

        *      1220          *      1240          *      1260
: CACCTAATCTTATGCATTTAGCAGTACAAATTCAAAAATTTCCCATTTTTATTCATGAAT : 1260

        *      1280          *      1300          *      1320
: CATACCATTATATATTAACTAAATCCAAGGTAAAAAAAAGGTATGAAAGCTCTATAGTAA : 1320

        *      1340          *      1360          *      1380
: GTAAAATATAAATTCCCCATAAGGAAAGGGCCAAGTCCACCAGGCAAGTAAAATGAGCAA : 1380

        *      1400          *      1420          *      1440
: GCACCACTCCACCATCACACAATTTCACTCATAGATAACGATAAGATTCATGGAATTATC : 1440

        *      1460          *      1480          *      1500
: TTCCACGTGGCATTATTCCAGCGGTTCAAGCCGATAAGGGTCTCAACACCTCTCCTTAGG : 1500

        *      1520          *      1540          *      1560
: CCCTTGTGGCCGTTACCAAGTAAAATTAACCTCACACATATCCACACTCAAAATCCAACG : 1560

        *      1580          *      1600          *      1620
: GTGTAGATCCTAGTCCACTTGAATCTCATGTATCCTAGACCCTCCGATCACTCCAAAGCT : 1620

        *      1640          *      1660          *      1680
: TGTTCTCATTGTTGTTATCATTATATATAGATGACCAAAGCACTAGACCAAACCTCAGTC : 1680

        *      1700          *      1720          *      1740
: ACACAAAGAGTAAAGAAGAACATAAGTTTGTACAAAAAAGCAGGCTTCATGGAGTCCCCA : 1740

        *      1760          *      1780          *      1800
: AGCGCCGTCGTCCCCGGCACCACGGCGCCGCTGCTTCCTTATGCGTACGCGCCGCTGCCG : 1800

        *      1820          *      1840          *      1860
: TCGTCCGCCGACGACGCCCGTCAAAACCGGAGTGGCGGGAGGTGGCGCGCGTGCGCCGCC : 1860

        *      1880          *      1900          *      1920
: GTGCTGGCCGCATCGGCGTTGGCGGTGGTCGTCGTGGTCGGGCTCCTCGCGGGCGGCAGG : 1920

        *      1940          *      1960          *      1980
: GTGGATCGGGTCCCAGCCGGCGGAGACGTGGCGTCGGCCACGGTGCCGGCCGTGCCGATG : 1980

        *      2000          *      2020          *      2040
: GAGTTCCCGAGGAGCCGGGGCAAGGACTTCGGCGTGTCGGAGAAGTCCTCCGGTGCCTAC : 2040

        *      2060          *      2080          *      2100
: TCCACCGACGGCGGGTTCCCGTGGAGCAACGCCATGCTGCAGTGGCAGCGCACCGGGTTC : 2100

        *      2120          *      2140          *      2160
: CATTTCCAGCCGGAGCAGCACTACATGAACGATCCCAACGGCCCCGTGTACTACGGCGGA : 2160

        *      2180          *      2200          *      2220
: TGGTACCACCTCTTCTACCAGCACAACCCCAAGGGCGACAGCTGGGGCAACATCGCGTGG : 2220

        *      2240          *      2260          *      2280
: GCCCACGCCGTCTCCAAGGACATGGTCAACTGGCGCCACCTCCCTCTCGCCATGGTTCCC : 2280

        *      2300          *      2320          *      2340
: GACCAGTGGTACGACAGCAACGGCGTCCTCACCGGCTCCATCACCGTGCTCCCCGACGGC : 2340

        *      2360          *      2380          *      2400
```

FIGURE 38 CONT

```
: CAGGTCATCCTGCTCTACACCGGCAACACCGACACCCTAGCCCAGGTCCAGTGCCTCGCC : 2400

           *       2420         *       2440         *       2460
: ACGCCCGCCGACCCGTCCGACCCGCTCCTCCGCGAGTGGGTCAAGCACCCCGCCAACCCC : 2460

           *       2480         *       2500         *       2520
: ATCCTCTACCCTCCCCCCGGCATCGGCCTCAAGGACTTCCGCGACCCCCTCACCGCCTGG : 2520

           *       2540         *       2560         *       2580
: TTCGACCACTCCGACCACACCTGGCGCACCGTCATCGGCTCCAAGGACGACGACGGCCAC : 2580

           *       2600         *       2620         *       2640
: GCCGGCATCATCCTCAGCTACAAGACCAAGGACTTCGTCAACTACGAGCTCATGCCGGGG : 2640

           *       2660         *       2680         *       2700
: AACATGCACCGCGGGCCCGACGGCACCGGAATGTACGAGTGCATCGACCTCTACCCCGTC : 2700

           *       2720         *       2740         *       2760
: GGCGGCAACTCGTCCGAGATGCTCGGCGGCGACGACTCGCCCGGCGTGCTCTTCGTGCTC : 2760

           *       2780         *       2800         *       2820
: AAGGAGAGCAGCGACGACGAGCGCCACGACTACTACGCGCTCGGAAGGTTCGACGCCGTC : 2820

           *       2840         *       2860         *       2880
: GCCAACGTTTGGACGCCCATCGACCGGGAGCTGGACCTTGGGATCGGGCTCAGATACGAC : 2880

           *       2900         *       2920         *       2940
: TGGGGAAAGTACTACGCCTCCAAGTCCTTCTACGACCAGAAGAAGAACCGCCGCATCGTA : 2940

           *       2960         *       2980         *       3000
: TGGGCATACATCGGCGAGACCGACTCCGAGCAGGCCGACATCACCAAGGGATGGGCCAAT : 3000

           *       3020         *       3040         *       3060
: CTCATGACGATTCCAAGAACGGTGGAGCTTGACAGGAAGACCCGCACAAACCTCATCCAA : 3060

           *       3080         *       3100         *       3120
: TGGCCAGTGGAGGAGGTCGACACCCTCCGCAGGAACTCCACGGACCTCGGTCGCATCACC : 3120

           *       3140         *       3160         *       3180
: GTCAACGCCGGCTCCGTCATTCGCCTCCCCCTCCACCAGGGCGCTCAACTCGACATCGAG : 3180

           *       3200         *       3220         *       3240
: GCCTCCTTCCAACTCAACTCTTCCGACGTGGATGCTATCAACGAGGCCGACGTCGGCTAC : 3240

           *       3260         *       3280         *       3300
: AACTGCAGCACCAGTGGTGCCGCCGTACGGGGGGCGCTCGGCCCCTTTGGCCTCCTCGTC : 3300

           *       3320         *       3340         *       3360
: CTTGCCAACGGCCGCACCGAACAGACGGCTGTGTACTTCTACGTGTCCAAGGGCGTCGAC : 3360

           *       3380         *       3400         *       3420
: GGTGCCCTCCAGACCCACTTCTGCCACGACGAGTCACGGTCAACGCGGGCAAAGGATGTC : 3420

           *       3440         *       3460         *       3480
: GTGAATAGGATGATTGGCAGCATCGTGCCGGTGCTTGACGGTGAGACCTTTTCGGTGAGG : 3480

           *       3500         *       3520         *       3540
: GTGCTAGTGGACCACTCCATCGTGCAGAGCTTCGCGATGGGCGGGAGGATCACGGCGACG : 3540

           *       3560         *       3580         *       3600
: TCGCGGGCGTACCCGACGGAGGCCATCTACGCGGCCGCGGGGGTCTACCTCTTCAACAAC : 3600
```

FIGURE 38 CONT

```
         *       3620          *       3640          *       3660
: GCCACGGGCGCCACCGTCACCGCCGAGAGGCTCGTCGTGCACGAGATGGCCTCAGCTGAC : 3660

         *       3680          *       3700          *       3720
: AACCATATCTTCACGAACGACGACTTGGGAGGAGGAAAGCTTAAGCTTGGAGGAGGAGAG : 3720

         *       3740          *       3760          *       3780
: TCCAGCGCCGTCGTCGCCCAAGGCACCACGTCGCCGCTGCTCCCGTACGCCTACGCGCCG : 3780

         *       3800          *       3820          *       3840
: CTGCCGTCCTCTGCCGACGACGCCCGTGAAAACCAGAGTAGCGGCGGCGGTGTCAGGTGG : 3840

         *       3860          *       3880          *       3900
: CGCGCGTGCGCGGCCTCGGCCCTGGTGGTGCTGCTGGTCGTCGTCGGCTTCTTCGCGGGT : 3900

         *       3920          *       3940          *       3960
: GGCAGGGTGGATCTGGGTCAGGACGGCGAGGTGTCTGCGACTTCTTCGGTTCCTGGGAGC : 3960

         *       3980          *       4000          *       4020
: AGCAGGGGCAAGGATTCCGGCGTGTCGGAGAAGGAGTCGCCCGCCGACGGCGGCTTCCCG : 4020

         *       4040          *       4060          *       4080
: TGGAGCAACGCCATGCTGCAGTGGCAGCACACCGGGTTCCATTTCCAGCCACTCAAGCAC : 4080

         *       4100          *       4120          *       4140
: TACATGAACGATCCCAACGGTCCGGTCTACTATGGCGGATGGTACCACCTCTTCTACCAG : 4140

         *       4160          *       4180          *       4200
: CACAACCCCTATGGCGACTCGTGGGGAAACGTATCTTGGGGACATGCCGTGTCCAAGGAC : 4200

         *       4220          *       4240          *       4260
: CTGGTGAACTGGCGCCACCTCCCGGTCGCCTTGGTGCCCGATCAGTGGTACGACATCAAC : 4260

         *       4280          *       4300          *       4320
: GGCGTCCTGACGGGCTCTATCACAGTGCTCCCAGACGGGCGTGTCATCCTGCTATATACG : 4320

         *       4340          *       4360          *       4380
: GGGAACACCGACACCTTTTCGCAGGTCCAGTGCCTCGCAGTGCCCGCCGACCCATCTGAC : 4380

         *       4400          *       4420          *       4440
: CCGCTCCTCCGTAGCTGGATCAAGCACCCCGCCAACCCCATCCTCTTCCCGCCACCTGGG : 4440

         *       4460          *       4480          *       4500
: ATCGGGCTCAAGGACTTCCGTGACCCGCTCACAGCCTGGTTCGAACATTCCGACAACACG : 4500

         *       4520          *       4540          *       4560
: TGGCGCACCATCATCGGATCCAAGGATGACGACGGCCACGCCGGCATCGTCCTTAGCTAC : 4560

         *       4580          *       4600          *       4620
: AAGACCACCGACTTTGTGAATTATGAGCTCATGCCAGGGAACATGCATCGTGGCCCCGAC : 4620

         *       4640          *       4660          *       4680
: GGCACCGGCATGTACGAGTGCCTTGACATCTACCCTGTGGGCGGCAACTCATCCGAGATG : 4680

         *       4700          *       4720          *       4740
: TTGGGTGGCGACTCCTCACATGAGGTGTTGTTCGTGCTCAAGGAGAGCGCCAACGACGAG : 4740

         *       4760          *       4780          *       4800
: TGGCACGACTACTACGCGCTTGGGTGGTTTGACGCTGCCGCCAACACGTGGACGCCACAG : 4800
```

FIGURE 38 CONT

```
           *        4820         *        4840         *        4860
: GACCCCGAGGCGGACCTTGGGATCGGCCTCAGGTACGACTGGGGCAAGTACTACGCGTCC : 4860

           *        4880         *        4900         *        4920
: AAGTCCTTCTACGACCCGATCAAGAACCGGCGTGTCGTTTGGGCTTTCGTCGGCGAGACC : 4920

           *        4940         *        4960         *        4980
: GACTCTGAGCAGGCCGACAAAGCCAAGGGATGGGCGTCCCTCATGTCGATTCCCAGGACG : 4980

           *        5000         *        5020         *        5040
: GTGGAGCTTGACAAGAAGACCCGGACGAACCTGATCCAATGGCCAGTGGAGGAGATCGAG : 5040

           *        5060         *        5080         *        5100
: ACCCTTCGCAGGAACGTCACAGACCTCGGTGGCATCACCGTTGAAGCCGGCTCCGTCATT : 5100

           *        5120         *        5140         *        5160
: CACCTTCCCCTCCAACAAGGCGGGCAGCTTGACATCGAGGCCTCCTTCCGTCTCAACTCT : 5160

           *        5180         *        5200         *        5220
: TCGGACATCGATGCACTCAACGAGGCCGACGTCGGCTTCAACTGCAGTAGCAGCGATGGG : 5220

           *        5240         *        5260         *        5280
: GTAGCCGTGCGTGGTGCGCTCGGCCCCTTTGGCCTCCTCGTCTTCGCCGACGGTCGCCAC : 5280

           *        5300         *        5320         *        5340
: GAACAGACGGCGGCGTACTTCTACGTGTCCAAGGGCCTCGACGGCAGCCTCCTGACGCAC : 5340

           *        5360         *        5380         *        5400
: TACTGCCACGACGAGTCACGGTCGACGCGAGCAAAGGACGTCGTGAGCCGGGTGGTTGGC : 5400

           *        5420         *        5440         *        5460
: GGCACTGTGCCAGTGCTTGACGGTGAAACCTTTTCAGTGAGGGTGCTAGTGGACCACTCC : 5460

           *        5480         *        5500         *        5520
: ATCGTGCAGAGCTTCGTGATGGGTGGGAGGACCACGGTGACATCGCGGGCATACCCGACG : 5520

           *        5540         *        5560         *        5580
: GAGGCCATCTACGCCGCGGCAGGGGTGTACCTGTTCAACAACGCAACGAGCGCCACCATC : 5580

           *        5600         *        5620         *        5640
: ACCGCCGAAGGGCTCGTCGTGTACGAGATGGCCTCGGCCGAGAGTCGGGCCTTCTTGGCT : 5640

           *        5660         *        5680         *        5700
: GACGACATGTAGACCCAGCTTTCTTGTACAAAGTGGGATCTAGTAACATAGATGACACCG : 5700

           *        5720         *        5740         *        5760
: CGCGCGATAATTTATCCTAGTTTGCGCGCTATATTTTGTTTTCTATCGCGTATTAAATGT : 5760

           *        5780         *        5800         *        5820
: ATAATTGCGGGACTCTAATCATAAAAACCCATCTCATAAATAACGTCATGCATTACATGT : 5820

           *        5840         *        5860         *        5880
: TAATTATTACATGCTTAACGTAATTCAACAGAAATTATATGATAATCATCGCAAGACCGG : 5880

           *        5900         *        5920
: CAACAGGATTCAATCTTAAGAAACTTTATTGCCAAATGTTTGAACGATC : 5929
```

FIGURE 41

```
             *        20         *        40         *        60
: CCTGCAGAAGTAACACCAAACAACAGGGTGAGCATCGACAAAAGAAACAGTACCAAGCAA :   60

             *        80         *       100         *       120
: ATAAATAGCGTATGAAGGCAGGGCTAAAAAAATCCACATATAGCTGCTGCATATGCCATC :  120

             *       140         *       160         *       180
: ATCCAAGTATATCAAGATCAAAATAATTATAAAACATACTTGTTTATTATAATAGATAGG :  180

             *       200         *       220         *       240
: TACTCAAGGTTAGAGCATATGAATAGATGCTGCATATGCCATCATGTATATGCATCAGTA :  240

             *       260         *       280         *       300
: AAACCCACATCAACATGTATACCTATCCTAGATCGATATTTCCATCCATCTTAAACTCGT :  300

             *       320         *       340         *       360
: AACTATGAAGATGTATGACACACACATACAGTTCCAAAATTAATAAATACACCAGGTAGT :  360

             *       380         *       400         *       420
: TTGAAACAGTATTCTACTCCGATCTAGAACGAATGAACGACCGCCCAACCACACCACATC :  420

             *       440         *       460         *       480
: ATCACAACCAAGCGAACAAAAAGCATCTCTGTATATGCATCAGTAAAACCCGCATCAACA :  480

             *       500         *       520         *       540
: TGTATACCTATCCTAGATCGATATTTCCATCCATCATTTTCAATTCGTAACTATGAATAT :  540

             *       560         *       580         *       600
: GTATGGCACACACATACAGATCCAAAATTAATAAATCCACCAGGTAGTTTGAAACAGAAT :  600

             *       620         *       640         *       660
: TCTACTCCGATCTAGAACGACCGCCCAACCAGACCACATCATCACAACCAAGACAAAAAA :  660

             *       680         *       700         *       720
: AAGCATGAAAAGATGACCCGACAAACAAGTGCACGGCATATATTGAAATAAAGGAAAAGG :  720

             *       740         *       760         *       780
: GCAAACCAAACCCTATGCAACGAAACAAAAAAAATCATGAAATCGATCCCGTCTGCGGAA :  780

             *       800         *       820         *       840
: CGGCTAGAGCCATCCCAGGATTCCCCAAAGAGAAACACTGGCAAGTTAGCAATCAGAACG :  840

             *       860         *       880         *       900
: TGTCTGACGTACAGGTCGCATCCGTGTACGAACGCTAGCAGCACGGATCTAACACAAACA :  900

             *       920         *       940         *       960
: CGGATCTAACACAAACATGAACAGAAGTAGAACTACCGGGCCCTAACCATGGACCGGAAC :  960

             *       980         *      1000         *      1020
: GCCGATCTAGAGAAGGTAGAGAGGGGGGGGGGGGGAGGACGAGCGGCGTACCTTGAAGCG : 1020

             *      1040         *      1060         *      1080
: GAGGTGCCGACGGGTGGATTTGGGGGAGATCTGGTTGTGTGTGTGTGCGCTCCGAACAAC : 1080

             *      1100         *      1120         *      1140
: ACGAGGTTGGGGAAAGAGGGTGTGGAGGGGGTGTCTATTTATTACGGCGGGCGAGGAAGG : 1140
```

FIGURE 41 CONT

```
                 *        1160         *        1180         *        1200
: GAAAGCGAAGGAGCGGTGGGAAAGGAATCCCCCGTAGCTGCCGGTGCCGTGAGAGGAGGA : 1200

                 *        1220         *        1240         *        1260
: GGAGGCCGCCTGCCGTGCCGGCTCACGTCTGCCGCTCCGCCACGCAATTTCTGGATGCCG : 1260

                 *        1280         *        1300         *        1320
: ACAGCGGAGCAAGTCCAACGGTGGAGCGGAACTCTCGAGAGGGGTCCAGAGGCAGCGACA : 1320

                 *        1340         *        1360         *        1380
: GAGATGCCGTGCCGTCTGCTTCGCTTGGCCCGACGCGACGCTGCTGGTTCGCTGGTTGGT : 1380

                 *        1400         *        1420         *        1440
: GTCCGTTAGACTCGTCGACGGCGTTTAACAGGCTGGCATTATCTACTCGAAACAAGAAAA : 1440

                 *        1460         *        1480         *        1500
: ATGTTTCCTTAGTTTTTTTAATTTCTTAAAGGGTATTTGTTTAATTTTTAGTCACTTTAT : 1500

                 *        1520         *        1540         *        1560
: TTTATTCTATTTTATATCTAAATTATTAAATAAAAAAACTAAAATAGAGTTTTAGTTTTC : 1560

                 *        1580         *        1600         *        1620
: TTAATTTAGAGGCTAAAATAGAATAAAATAGATGTACTAAAAAAATTAGTCTATAAAAAC : 1620

                 *        1640         *        1660         *        1680
: CATTAACCCTAAACCCTAAATGGATGTACTAATAAAATGGATGAAGTATTATATAGGTGA : 1680

                 *        1700         *        1720         *        1740
: AGCTATTTGCAAAAAAAAAGGAGAACACATGCACACTAAAAAGATAAAACTGTAGAGTCC : 1740

                 *        1760         *        1780         *        1800
: TGTTGTCAAAATACTCAATTGTCCTTTAGACCATGTCTAACTGTTCATTTATATGATTCT : 1800

                 *        1820         *        1840         *        1860
: CTAAAACACTGATATTATTGTAGTACTATAGATTATATTATTCGTAGAGTAAAGTTTAAA : 1860

                 *        1880         *        1900         *        1920
: TATATGTATAAAGATAGATAAACTGCACTTCAAACAAGTGTGACAAAAAAATATGTGGT : 1920

                 *        1940         *        1960         *        1980
: AATTTTTTATAACTTAGACATGCAATGCTCATTATCTCTAGAGAGGGGCACGACCGGGTC : 1980

                 *        2000         *        2020         *        2040
: ACGCTGCACTGCAGATGGAGTCCCCAAGCGCCGTCGTCCCCGGCACCACGGCGCCGCTGC : 2040

                 *        2060         *        2080         *        2100
: TTCCTTATGCGTACGCGCCGCTGCCGTCGTCCGCCGACGACGCCCGTCAAAACCGGAGTG : 2100

                 *        2120         *        2140         *        2160
: GCGGGAGGTGGCGCGCGTGCGCCGCCGTGCTGGCCGCATCGGCGTTGGCGGTGGTCGTCG : 2160

                 *        2180         *        2200         *        2220
: TGGTCGGGCTCCTCGCGGGCGGCAGGGTGGATCGGGTCCCAGCCGGCGGAGACGTGGCGT : 2220

                 *        2240         *        2260         *        2280
: CGGCCACGGTGCCGGCCGTGCCGATGGAGTTCCCGAGGAGCCGGGGCAAGGACTTCGGCG : 2280

                 *        2300         *        2320         *        2340
: TGTCGGAGAAGTCCTCCGGTGCCTACTCCACCGACGGCGGGTTCCCGTGGAGCAACGCCA : 2340

                 *        2360         *        2380         *        2400
```

FIGURE 41 CONT

```
: TGCTGCAGTGGCAGCGCACCGGGTTCCATTTCCAGCCGGAGCAGCACTACATGAACGATC : 2400

           *        2420         *        2440         *        2460
: CCAACGGCCCCGTGTACTACGGCGGATGGTACCACCTCTTCTACCAGCACAACCCCAAGG : 2460

           *        2480         *        2500         *        2520
: GCGACAGCTGGGGCAACATCGCGTGGGCCCACGCCGTCTCCAAGGACATGGTCAACTGGC : 2520

           *        2540         *        2560         *        2580
: GCCACCTCCCTCTCGCCATGGTTCCCGACCAGTGGTACGACAGCAACGGCGTCCTCACCG : 2580

           *        2600         *        2620         *        2640
: GCTCCATCACCGTGCTCCCCGACGGCCAGGTCATCCTGCTCTACACCGGCAACACCGACA : 2640

           *        2660         *        2680         *        2700
: CCCTAGCCCAGGTCCAGTGCCTCGCCACGCCCGCCGACCCGTCCGACCCGCTCCTCCGCG : 2700

           *        2720         *        2740         *        2760
: AGTGGGTCAAGCACCCCGCCAACCCCATCCTCTACCCTCCCCCCGGCATCGGCCTCAAGG : 2760

           *        2780         *        2800         *        2820
: ACTTCCGCGACCCCCTCACCGCCTGGTTCGACCACTCCGACCACACCTGGCGCACCGTCA : 2820

           *        2840         *        2860         *        2880
: TCGGCTCCAAGGACGACGACGGCCACGCCGGCATCATCCTCAGCTACAAGACCAAGGACT : 2880

           *        2900         *        2920         *        2940
: TCGTCAACTACGAGCTCATGCCGGGGAACATGCACCGCGGGCCCGACGGCACCGGAATGT : 2940

           *        2960         *        2980         *        3000
: ACGAGTGCATCGACCTCTACCCCGTCGGCGGCAACTCGTCCGAGATGCTCGGCGGCGACG : 3000

           *        3020         *        3040         *        3060
: ACTCGCCCGGCGTGCTCTTCGTGCTCAAGGAGAGCAGCGACGACGAGCGCCACGACTACT : 3060

           *        3080         *        3100         *        3120
: ACGCGCTCGGAAGGTTCGACGCCGTCGCCAACGTTTGGACGCCCATCGACCGGGAGCTGG : 3120

           *        3140         *        3160         *        3180
: ACCTTGGGATCGGGCTCAGATACGACTGGGGAAAGTACTACGCCTCCAAGTCCTTCTACG : 3180

           *        3200         *        3220         *        3240
: ACCAGAAGAAGAACCGCCGCATCGTATGGGCATACATCGGCGAGACCGACTCCGAGCAGG : 3240

           *        3260         *        3280         *        3300
: CCGACATCACCAAGGGATGGGCCAATCTCATGACGATTCCAAGAACGGTGGAGCTTGACA : 3300

           *        3320         *        3340         *        3360
: GGAAGACCCGCACAAACCTCATCCAATGGCCAGTGGAGGAGGTCGACACCCTCCGCAGGA : 3360

           *        3380         *        3400         *        3420
: ACTCCACGGACCTCGGTCGCATCACCGTCAACGCCGGCTCCGTCATTCGCCTCCCCCTCC : 3420

           *        3440         *        3460         *        3480
: ACCAGGGCGCTCAACTCGACATCGAGGCCTCCTTCCAACTCAACTCTTCCGACGTGGATG : 3480

           *        3500         *        3520         *        3540
: CTATCAACGAGGCCGACGTCGGCTACAACTGCAGCACCAGTGGTGCCGCCGTACGGGGGG : 3540

           *        3560         *        3580         *        3600
: CGCTCGGCCCCTTTGGCCTCCTCGTCCTTGCCAACGGCCGCACCGAACAGACGGCTGTGT : 3600
```

FIGURE 41 CONT

```
          *        3620          *        3640          *        3660
: ACTTCTACGTGTCCAAGGGCGTCGACGGTGCCCTCCAGACCCACTTCTGCCACGACGAGT : 3660

          *        3680          *        3700          *        3720
: CACGGTCAACGCGGGCAAAGGATGTCGTGAATAGGATGATTGGCAGCATCGTGCCGGTGC : 3720

          *        3740          *        3760          *        3780
: TTGACGGTGAGACCTTTTCGGTGAGGGTGCTAGTGGACCACTCCATCGTGCAGAGCTTCG : 3780

          *        3800          *        3820          *        3840
: CGATGGGCGGGAGGATCACGGCGACGTCGCGGGCGTACCCGACGGAGGCCATCTACGCGG : 3840

          *        3860          *        3880          *        3900
: CCGCGGGGGTCTACCTCTTCAACAACGCCACGGGCGCCACCGTCACCGCCGAGAGGCTCG : 3900

          *        3920          *        3940          *        3960
: TCGTGCACGAGATGGCCTCAGCTGACAACCATATCTTCACGAACGACGACTTGGGAGGAG : 3960

          *        3980          *        4000          *        4020
: GAAAGCTTAAGCTTGGAGGAGGAGAGTCCAGCGCCGTCGTCGCCCAAGGCACCACGTCGC : 4020

          *        4040          *        4060          *        4080
: CGCTGCTCCCGTACGCCTACGCGCCGCTGCCGTCCTCTGCCGACGACGCCCGTGAAAACC : 4080

          *        4100          *        4120          *        4140
: AGAGTAGCGGCGGCGGTGTCAGGTGGCGCGCGTGCGCGGCCTCGGCCCTGGTGGTGCTGC : 4140

          *        4160          *        4180          *        4200
: TGGTCGTCGTCGGCTTCTTCGCGGGTGGCAGGGTGGATCTGGGTCAGGACGGCGAGGTGT : 4200

          *        4220          *        4240          *        4260
: CTGCGACTTCTTCGGTTCCTGGGAGCAGCAGGGGCAAGGATTCCGGCGTGTCGGAGAAGG : 4260

          *        4280          *        4300          *        4320
: AGTCGCCCGCCGACGGCGGCTTCCCGTGGAGCAACGCCATGCTGCAGTGGCAGCACACCG : 4320

          *        4340          *        4360          *        4380
: GGTTCCATTTCCAGCCACTCAAGCACTACATGAACGATCCCAACGGTCCGGTCTACTATG : 4380

          *        4400          *        4420          *        4440
: GCGGATGGTACCACCTCTTCTACCAGCACAACCCCTATGGCGACTCGTGGGGAAACGTAT : 4440

          *        4460          *        4480          *        4500
: CTTGGGGACATGCCGTGTCCAAGGACCTGGTGAACTGGCGCCACCTCCCGGTCGCCTTGG : 4500

          *        4520          *        4540          *        4560
: TGCCCGATCAGTGGTACGACATCAACGGCGTCCTGACGGGCTCTATCACAGTGCTCCCAG : 4560

          *        4580          *        4600          *        4620
: ACGGGCGTGTCATCCTGCTATATACGGGGAACACCGACACCTTTTCGCAGGTCCAGTGCC : 4620

          *        4640          *        4660          *        4680
: TCGCAGTGCCCGCCGACCCATCTGACCCGCTCCTCCGTAGCTGGATCAAGCACCCCGCCA : 4680

          *        4700          *        4720          *        4740
: ACCCCATCCTCTTCCCGCCACCTGGGATCGGGCTCAAGGACTTCCGTGACCCGCTCACAG : 4740

          *        4760          *        4780          *        4800
: CCTGGTTCGAACATTCCGACAACACGTGGCGCACCATCATCGGATCCAAGGATGACGACG : 4800
```

FIGURE 41 CONT

```
         *        4820          *        4840          *        4860
: GCCACGCCGGCATCGTCCTTAGCTACAAGACCACCGACTTTGTGAATTATGAGCTCATGC : 4860

         *        4880          *        4900          *        4920
: CAGGGAACATGCATCGTGGCCCCGACGGCACCGGCATGTACGAGTGCCTTGACATCTACC : 4920

         *        4940          *        4960          *        4980
: CTGTGGGCGGCAACTCATCCGAGATGTTGGGTGGCGACTCCTCACCTGAGGTGTTGTTCG : 4980

         *        5000          *        5020          *        5040
: TGCTCAAGGAGAGCGCCAACGACGAGTGGCACGACTACTACGCGCTTGGGTGGTTTGACG : 5040

         *        5060          *        5080          *        5100
: CTGCCGCCAACACGTGGACGCCACAGGACCCCGAGGCGGACCTTGGGATCGGCCTCAGGT : 5100

         *        5120          *        5140          *        5160
: ACGACTGGGGCAAGTACTACGCGTCCAAGTCCTTCTACGACCCGATCAAGAACCGGCGTG : 5160

         *        5180          *        5200          *        5220
: TCGTTTGGGCTTTCGTCGGCGAGACCGACTCTGAGCAGGCCGACAAAGCCAAGGGATGGG : 5220

         *        5240          *        5260          *        5280
: CGTCCCTCATGTCGATTCCCAGGACGGTGGAGCTTGACAAGAAGACCCGGACGAACCTGA : 5280

         *        5300          *        5320          *        5340
: TCCAATGGCCAGTGGAGGAGATCGAGACCCTTCGCAGGAACGTCACAGACCTCGGTGGCA : 5340

         *        5360          *        5380          *        5400
: TCACCGTTGAAGCCGGCTCCGTCATTCACCTTCCCCTCCAACAAGGCGGGCAGCTTGACA : 5400

         *        5420          *        5440          *        5460
: TCGAGGCCTCCTTCCGTCTCAACTCTTCGGACATCGATGCACTCAACGAGGCCGACGTCG : 5460

         *        5480          *        5500          *        5520
: GCTTCAACTGCAGTAGCAGCGATGGGGCAGCCGTGCGTGGTGCGCTCGGCCCCTTTGGCC : 5520

         *        5540          *        5560          *        5580
: TCCTCGTCTTCGCCGACGGTCGCCACGAACAGACGGCGGCGTACTTCTACGTGTCCAAGG : 5580

         *        5600          *        5620          *        5640
: GCCTCGACGGCAGCCTCCTGACGCACTACTGCCACGACGAGTCACGGTCGACGCGAGCAA : 5640

         *        5660          *        5680          *        5700
: AGGACGTCGTGAGCCGGGTGGTTGGCGGCACTGTGCCAGTGCTTGACGGTGAAACCTTTT : 5700

         *        5720          *        5740          *        5760
: CAGTGAGGGTGCTAGTGGACCACTCCATCGTGCAGAGCTTCGTGATGGGTGGGAGGACCA : 5760

         *        5780          *        5800          *        5820
: CGGTGACATCGCGGGCATACCCGACGGAGGCCATCTACGCCGCGGCAGGGGTGTACCTGT : 5820

         *        5840          *        5860          *        5880
: TCAACAACGCAACGAGCGCCACCATCACCGCCGAAGGGCTCGTCGTGTACGAGATGGCCT : 5880

         *        5900          *        5920          *        5940
: CGGCCGAGAGTCGGGCCTTCTTGGCTGACGACATGTAGAACAATAATTTTCTGAGCCTAG : 5940

         *        5960          *        5980          *        6000
: TATCCATGATCATGATATAGTAAGGGAAAAATCATATCTATAAGTTTCCGAACTTAGTGA : 6000
```

FIGURE 41 CONT

```
              *        6020          *        6040          *        6060
: AAAAAAACCTGTAAAAGATATGCAGTCATATACACATGTGAAATTAGGTAGGAAAATATG : 6060

              *        6080          *        6100          *        6120
: ATAATCTCGTAGATGAGGAAAAAATATTGTACACCAAACTATTGTAAGTTACAGTAATGT : 6120

              *        6140          *        6160          *        6180
: AATGTAAAAAAAGTTTTTAAGTTACAGAAGGTACATACCGCAAATAATCATATTATTTTA : 6180

              *        6200          *        6220          *        6240
: CCAAGATATTTTTTTCTGGAGTATTCCTTTCAAGTATCTTTTATCTCTAGAATCTTCTCC : 6240

              *        6260          *        6280          *        6300
: AATCATGAGTGGCAACCGAAATGGAGCTCCTGTGTTGCTCCCCGTGTCTCACCCCTTTCG : 6300

              *        6320          *        6340          *        6360
: GCCCCACTGTCATTGGGTGGACCTATTCTCACGGCGGCTGTCCTGAGAAACAAAAATAGC : 6360

              *        6380          *        6400          *        6420
: AGCTGAAATGAAGACACGGCGACACGCAAGCCAGCATCTCTCATTGAACCTGCGGAGTGA : 6420

              *        6440          *        6460          *        6480
: GATAGCTCTCGTGGCGCTGCTCTACTTGACGCGTTTGTCTCATACAACAGCGCATGGCTC : 6480

              *        6500          *        6520          *        6540
: CTTCATGTCAGGTCCATGATCCACAGATGGTATGATTGGGTTTGGAACATTTTTTGGGTT : 6540

              *        6560          *        6580          *        6600
: TGTGATATGTCGTAGATACAAAGGGAAATGTCTGAAGCATGCATGGATGGGTTCCCTGCT : 6600

              *
: CATGTACTCAATGT : 6614
```

FIGURE 42

```
             *        20         *        40         *        60
: GATCTCCTTTGCCCCAGAGATCACAATGGACGACTTCCTCTATCTCTACGATCTAGTCAG :   60

             *        80         *       100         *       120
: GAAGTTCGACGGAGAAGGTGACGATACCATGTTCACCACTGATAATGAGAAGATTAGCCT :  120

             *       140         *       160         *       180
: TTTCAATTTCAGAAAGAATGCTAACCCACAGATGGTTAGAGAGGCTTACGCAGCAGGTCT :  180

             *       200         *       220         *       240
: CATCAAGACGATCTACCCGAGCAATAATCTCCAGGAGATCAAATACCTTCCCAAGAAGGT :  240

             *       260         *       280         *       300
: TAAAGATGCAGTCAAAAGATTCAGGACTAACTGCATCAAGAACACAGAGAAAGATATATT :  300

             *       320         *       340         *       360
: TCTCAAGATCAGAAGTACTATTCCAGTATGGACGATTCAAGGCTTGCTTCACAAACCAAG :  360

             *       380         *       400         *       420
: GCAAGTAATAGAGATTGGAGTCTCTAAAAAGGTAGTTCCCACTGAATCAAAGGCCATGGA :  420

             *       440         *       460         *       480
: GTCAAAGATTCAAATAGAGGACCTAACAGAACTCGCCGTAAAGACTGGCGAACAGTTCAT :  480

             *       500         *       520         *       540
: ACAGAGTCTCTTACGACTCAATGACAAGAAGAAAATCTTCGTCAACATGGTGGAGCACGA :  540

             *       560         *       580         *       600
: CACACTTGTCTACTCCAAAAATATCAAAGATACAGTCTCAGAAGACCAAAGGGCAATTGA :  600

             *       620         *       640         *       660
: GACTTTTCAACAAAGGGTAATATCCGGAAACCTCCTCGGATTCCATTGCCCAGCTATCTG :  660

             *       680         *       700         *       720
: TCACTTTATTGTGAAGATAGTGGAAAAGGAAGGTGGCTCCTACAAATGCCATCATTGCGA :  720

             *       740         *       760         *       780
: TAAAGGAAAGGCCATCGTTGAAGATGCCTCTGCCGACAGTGGTCCCAAAGATGGACCCCC :  780

             *       800         *       820         *       840
: ACCCACGAGGAGCATCGTGGAAAAAGAAGACGTTCCAACCACGTCTTCAAAGCAAGTGGA :  840

             *       860         *       880         *       900
: TTGATGTGATAACATGGTGGAGCACGACACACTTGTCTACTCCAAAAATATCAAAGATAC :  900

             *       920         *       940         *       960
: AGTCTCAGAAGACCAAAGGGCAATTGAGACTTTTCAACAAAGGGTAATATCCGGAAACCT :  960

             *       980         *      1000         *      1020
: CCTCGGATTCCATTGCCCAGCTATCTGTCACTTTATTGTGAAGATAGTGGAAAAGGAAGG : 1020

             *      1040         *      1060         *      1080
: TGGCTCCTACAAATGCCATCATTGCGATAAAGGAAAGGCCATCGTTGAAGATGCCTCTGC : 1080

             *      1100         *      1120         *      1140
: CGACAGTGGTCCCAAAGATGGACCCCCACCCACGAGGAGCATCGTGGAAAAAGAAGACGT : 1140
```

FIGURE 42 CONT

```
                *        1160         *        1180         *        1200
: TCCAACCACGTCTTCAAAGCAAGTGGATTGATGTGATATCTCCACTGACGTAAGGGATGA : 1200

                *        1220         *        1240         *        1260
: CGCACAATCCCACTATCCTTCGCAAGACCCTTCCTCTATATAAGGAAGTTCATTTCATTT : 1260

                *        1280         *        1300         *        1320
: GGAGAGGACACGCTGAAATCACCAGTCTATGGAGTCCCCAAGCGCCGTCGTCCCCGGCAC : 1320

                *        1340         *        1360         *        1380
: CACGGCGCCGCTGCTTCCTTATGCGTACGCGCCGCTGCCGTCGTCCGCCGACGACGCCCG : 1380

                *        1400         *        1420         *        1440
: TCAAAACCGGAGTGGCGGGAGGTGGCGCGCGTGCGCCGCCGTGCTGGCCGCATCGGCGTT : 1440

                *        1460         *        1480         *        1500
: GGCGGTGGTCGTCGTGGTCGGGCTCCTCGCGGGCGGCAGGGTGGATCGGGTCCCAGCCGG : 1500

                *        1520         *        1540         *        1560
: CGGAGACGTGGCGTCGGCCACGGTGCCGGCCGTGCCGATGGAGTTCCCGAGGAGCCGGGG : 1560

                *        1580         *        1600         *        1620
: CAAGGACTTCGGCGTGTCGGAGAAGTCCTCCGGTGCCTACTCCACCGACGGCGGGTTCCC : 1620

                *        1640         *        1660         *        1680
: GTGGAGCAACGCCATGCTGCAGTGGCAGCGCACCGGGTTCCATTTCCAGCCGGAGCAGCA : 1680

                *        1700         *        1720         *        1740
: CTACATGAACGATCCCAACGGCCCCGTGTACTACGGCGGATGGTACCACCTCTTCTACCA : 1740

                *        1760         *        1780         *        1800
: GCACAACCCCAAGGGCGACAGCTGGGGCAACATCGCGTGGGCCCACGCCGTCTCCAAGGA : 1800

                *        1820         *        1840         *        1860
: CATGGTCAACTGGCGCCACCTCCCTCTCGCCATGGTTCCCGACCAGTGGTACGACAGCAA : 1860

                *        1880         *        1900         *        1920
: CGGCGTCCTCACCGGCTCCATCACCGTGCTCCCCGACGGCCAGGTCATCCTGCTCTACAC : 1920

                *        1940         *        1960         *        1980
: CGGCAACACCGACACCCTAGCCCAGGTCCAGTGCCTCGCCACGCCCGCCGACCCGTCCGA : 1980

                *        2000         *        2020         *        2040
: CCCGCTCCTCCGCGAGTGGGTCAAGCACCCCGCCAACCCCATCCTCTACCCTCCCCCCGG : 2040

                *        2060         *        2080         *        2100
: CATCGGCCTCAAGGACTTCCGCGACCCCCTCACCGCCTGGTTCGACCACTCCGACCACAC : 2100

                *        2120         *        2140         *        2160
: CTGGCGCACCGTCATCGGCTCCAAGGACGACGACGGCCACGCCGGCATCATCCTCAGCTA : 2160

                *        2180         *        2200         *        2220
: CAAGACCAAGGACTTCGTCAACTACGAGCTCATGCCGGGGAACATGCACCGCGGGCCCGA : 2220

                *        2240         *        2260         *        2280
: CGGCACCGGAATGTACGAGTGCATCGACCTCTACCCCGTCGGCGGCAACTCGTCCGAGAT : 2280

                *        2300         *        2320         *        2340
: GCTCGGCGGCGACGACTCGCCCGGCGTGCTCTTCGTGCTCAAGGAGAGCAGCGACGACGA : 2340

                *        2360         *        2380         *        2400
```

FIGURE 42 CONT

```
: GCGCCACGACTACTACGCGCTCGGAAGGTTCGACGCCGTCGCCAACGTTTGGACGCCCAT : 2400

           *        2420          *        2440          *        2460
: CGACCGGGAGCTGGACCTTGGGATCGGGCTCAGATACGACTGGGGAAAGTACTACGCCTC : 2460

           *        2480          *        2500          *        2520
: CAAGTCCTTCTACGACCAGAAGAAGAACCGCCGCATCGTATGGGCATACATCGGCGAGAC : 2520

           *        2540          *        2560          *        2580
: CGACTCCGAGCAGGCCGACATCACCAAGGGATGGGCCAATCTCATGACGATTCCAAGAAC : 2580

           *        2600          *        2620          *        2640
: GGTGGAGCTTGACAGGAAGACCCGCACAAACCTCATCCAATGGCCAGTGGAGGAGGTCGA : 2640

           *        2660          *        2680          *        2700
: CACCCTCCGCAGGAACTCCACGGACCTCGGTCGCATCACCGTCAACGCCGGCTCCGTCAT : 2700

           *        2720          *        2740          *        2760
: TCGCCTCCCCCTCCACCAGGGCGCTCAACTCGACATCGAGGCCTCCTTCCAACTCAACTC : 2760

           *        2780          *        2800          *        2820
: TTCCGACGTGGATGCTATCAACGAGGCCGACGTCGGCTACAACTGCAGCACCAGTGGTGC : 2820

           *        2840          *        2860          *        2880
: CGCCGTACGGGGGGCGCTCGGCCCCTTTGGCCTCCTCGTCCTTGCCAACGGCCGCACCGA : 2880

           *        2900          *        2920          *        2940
: ACAGACGGCTGTGTACTTCTACGTGTCCAAGGGCGTCGACGGTGCCCTCCAGACCCACTT : 2940

           *        2960          *        2980          *        3000
: CTGCCACGACGAGTCACGGTCAACGCGGGCAAAGGATGTCGTGAATAGGATGATTGGCAG : 3000

           *        3020          *        3040          *        3060
: CATCGTGCCGGTGCTTGACGGTGAGACCTTTTCGGTGAGGGTGCTAGTGGACCACTCCAT : 3060

           *        3080          *        3100          *        3120
: CGTGCAGAGCTTCGCGATGGGCGGGAGGATCACGGCGACGTCGCGGGCGTACCCGACGGA : 3120

           *        3140          *        3160          *        3180
: GGCCATCTACGCGGCCGCGGGGGTCTACCTCTTCAACAACGCCACGGGCGCCACCGTCAC : 3180

           *        3200          *        3220          *        3240
: CGCCGAGAGGCTCGTCGTGCACGAGATGGCCTCAGCTGACAACCATATCTTCACGAACGA : 3240

           *        3260          *        3280          *        3300
: CGACTTGGGAGGAGGAAAGCTTAAGCTTGGAGGAGGAGAGTCCAGCGCCGTCGTCGCCCA : 3300

           *        3320          *        3340          *        3360
: AGGCACCACGTCGCCGCTGCTCCCGTACGCCTACGCGCCGCTGCCGTCCTCTGCCGACGA : 3360

           *        3380          *        3400          *        3420
: CGCCCGTGAAAACCAGAGTAGCGGCGGCGGTGTCAGGTGGCGCGCGTGCGCGGCCTCGGC : 3420

           *        3440          *        3460          *        3480
: CCTGGTGGTGCTGCTGGTCGTCGTCGGCTTCTTCGCGGGTGGCAGGGTGGATCTGGGTCA : 3480

           *        3500          *        3520          *        3540
: GGACGGCGAGGTGTCTGCGACTTCTTCGGTTCCTGGGAGCAGCAGGGGCAAGGATTCCGG : 3540

           *        3560          *        3580          *        3600
: CGTGTCGGAGAAGGAGTCGCCCGCCGACGGCGGCTTCCCGTGGAGCAACGCCATGCTGCA : 3600
```

FIGURE 42 CONT

```
          *       3620          *       3640          *       3660
: GTGGCAGCACACCGGGTTCCATTTCCAGCCACTCAAGCACTACATGAACGATCCCAACGG : 3660

          *       3680          *       3700          *       3720
: TCCGGTCTACTATGGCGGATGGTACCACCTCTTCTACCAGCACAACCCCTATGGCGACTC : 3720

          *       3740          *       3760          *       3780
: GTGGGGAAACGTATCTTGGGGACATGCCGTGTCCAAGGACCTGGTGAACTGGCGCCACCT : 3780

          *       3800          *       3820          *       3840
: CCCGGTCGCCTTGGTGCCCGATCAGTGGTACGACATCAACGGCGTCCTGACGGGCTCTAT : 3840

          *       3860          *       3880          *       3900
: CACAGTGCTCCCAGACGGGCGTGTCATCCTGCTATATACGGGGAACACCGACACCTTTTC : 3900

          *       3920          *       3940          *       3960
: GCAGGTCCAGTGCCTCGCAGTGCCCGCCGACCCATCTGACCCGCTCCTCCGTAGCTGGAT : 3960

          *       3980          *       4000          *       4020
: CAAGCACCCCGCCAACCCCATCCTCTTCCCGCCACCTGGGATCGGGCTCAAGGACTTCCG : 4020

          *       4040          *       4060          *       4080
: TGACCCGCTCACAGCCTGGTTCGAACATTCCGACAACACGTGGCGCACCATCATCGGATC : 4080

          *       4100          *       4120          *       4140
: CAAGGATGACGACGGCCACGCCGGCATCGTCCTTAGCTACAAGACCACCGACTTTGTGAA : 4140

          *       4160          *       4180          *       4200
: TTATGAGCTCATGCCAGGGAACATGCATCGTGGCCCCGACGGCACCGGCATGTACGAGTG : 4200

          *       4220          *       4240          *       4260
: CCTTGACATCTACCCTGTGGGCGGCAACTCATCCGAGATGTTGGGTGGCGACTCCTCACC : 4260

          *       4280          *       4300          *       4320
: TGAGGTGTTGTTCGTGCTCAAGGAGAGCGCCAACGACGAGTGGCACGACTACTACGCGCT : 4320

          *       4340          *       4360          *       4380
: TGGGTGGTTTGACGCTGCCGCCAACACGTGGACGCCACAGGACCCCGAGGCGGACCTTGG : 4380

          *       4400          *       4420          *       4440
: GATCGGCCTCAGGTACGACTGGGGCAAGTACTACGCGTCCAAGTCCTTCTACGACCCGAT : 4440

          *       4460          *       4480          *       4500
: CAAGAACCGGCGTGTCGTTTGGGCTTTCGTCGGCGAGACCGACTCTGAGCAGGCCGACAA : 4500

          *       4520          *       4540          *       4560
: AGCCAAGGGATGGGCGTCCCTCATGTCGATTCCCAGGACGGTGGAGCTTGACAAGAAGAC : 4560

          *       4580          *       4600          *       4620
: CCGGACGAACCTGATCCAATGGCCAGTGGAGGAGATCGAGACCCTTCGCAGGAACGTCAC : 4620

          *       4640          *       4660          *       4680
: AGACCTCGGTGGCATCACCGTTGAAGCCGGCTCCGTCATTCACCTTCCCCTCCAACAAGG : 4680

          *       4700          *       4720          *       4740
: CGGGCAGCTTGACATCGAGGCCTCCTTCCGTCTCAACTCTTCGGACATCGATGCACTCAA : 4740

          *       4760          *       4780          *       4800
: CGAGGCCGACGTCGGCTTCAACTGCAGTAGCAGCGATGGGGCAGCCGTGCGTGGTGCGCT : 4800
```

FIGURE 42 CONT

```
         *        4820          *        4840          *        4860
: CGGCCCCTTTGGCCTCCTCGTCTTCGCCGACGGTCGCCACGAACAGACGGCGGCGTACTT : 4860

         *        4880          *        4900          *        4920
: CTACGTGTCCAAGGGCCTCGACGGCAGCCTCCTGACGCACTACTGCCACGACGAGTCACG : 4920

         *        4940          *        4960          *        4980
: GTCGACGCGAGCAAAGGACGTCGTGAGCCGGGTGGTTGGCGGCACTGTGCCAGTGCTTGA : 4980

         *        5000          *        5020          *        5040
: CGGTGAAACCTTTTCAGTGAGGGTGCTAGTGGACCACTCCATCGTGCAGAGCTTCGTGAT : 5040

         *        5060          *        5080          *        5100
: GGGTGGGAGGACCACGGTGACATCGCGGGCATACCCGACGGAGGCCATCTACGCCGCGGC : 5100

         *        5120          *        5140          *        5160
: AGGGGTGTACCTGTTCAACAACGCAACGAGCGCCACCATCACCGCCGAAGGGCTCGTCGT : 5160

         *        5180          *        5200          *        5220
: GTACGAGATGGCCTCGGCCGAGAGTCGGGCCTTCTTGGCTGACGACATGTAGAACAATAA : 5220

         *        5240          *        5260          *        5280
: TTTTCTGAGCCTAGTATCCATGATCATGATATAGTAAGGGAAAAATCATATCTATAAGTT : 5280

         *        5300          *        5320          *        5340
: TCCGAACTTAGTGAAAAAAAACCTGTAAAAGATATGCAGTCATATACACATGTGAAATTA : 5340

         *        5360          *        5380          *        5400
: GGTAGGAAAATATGATAATCTCGTAGATGAGGAAAAAATATTGTACACCAAACTATTGTA : 5400

         *        5420          *        5440          *        5460
: AGTTACAGTAATGTAATGTAAAAAAAGTTTTTAAGTTACAGAAGGTACATACCGCAAATA : 5460

         *        5480          *        5500          *        5520
: ATCATATTATTTTACCAAGATATTTTTTTCTGGAGTATTCCTTTCAAGTATCTTTTATCT : 5520

         *        5540          *        5560          *        5580
: CTAGAATCTTCTCCAATCATGAGTGGCAACCGAAATGGAGCTCCTGTGTTGCTCCCCGTG : 5580

         *        5600          *        5620          *        5640
: TCTCACCCCTTTCGGCCCCACTGTCATTGGGTGGACCTATTCTCACGGCGGCTGTCCTGA : 5640

         *        5660          *        5680          *        5700
: GAAACAAAAATAGCAGCTGAAATGAAGACACGGCGACACGCAAGCCAGCATCTCTCATTG : 5700

         *        5720          *        5740          *        5760
: AACCTGCGGAGTGAGATAGCTCTCGTGGCGCTGCTCTACTTGACGCGTTTGTCTCATACA : 5760

         *        5780          *        5800          *        5820
: ACAGCGCATGGCTCCTTCATGTCAGGTCCATGATCCACAGATGGTATGATTGGGTTTGGA : 5820

         *        5840          *        5860          *        5880
: ACATTTTTTGGGTTTGTGATATGTCGTAGATACAAAGGGAAATGTCTGAAGCATGCATGG : 5880

         *        5900
: ATGGGTTCCCTGCTCATGTACTCAATGT : 5908
```

FIGURE 43

```
            *        20         *        40         *        60
: ACGGANGGTAAACAAATTCGGGTCAAGGCGGAAGCCAGCGCGCCACCCCACGTCAGCAAA :   60

            *        80         *       100         *       120
: TACGGAGGCGCGGGGTTGACGGCGTCACCCGGTCCTAACGGCGACCAACAAACCAGCCAG :  120

            *       140         *       160         *       180
: AAGAAATTACAGTAAAAAAAAAGTAAATTGCACTTTGATCCACCTTTTATTACCTAAGTC :  180

            *       200         *       220         *       240
: TCAATTTGGATCACCCTTAAACCTATCTTTTCAATTTGGGCCGGGTTGTGGTTTGGACTA :  240

            *       260         *       280         *       300
: CCATGAACAACTTTTCGTCATGTCTAACTTCCCTTTCAGCAAACATATGAACCATATATA :  300

            *       320         *       340         *       360
: GAGGAGATCGGCCGTATACTAGAGCTGATGTGTTTAAGGTCGTTGATTGCACGAGAAAAA :  360

            *       380         *       400         *       420
: AAAATCCAAATCGCAACAATAGCAAATTTATCTGGTTCAAAGTGAAAAGATATGTTTAAA :  420

            *       440         *       460         *       480
: GGTAGTCCAAAGTAAAACTTATAGATAATAAAATGTGGTCCAAAGCGTAATTCACTCAAA :  480

            *       500         *       520         *       540
: AAAAATCAACGAGACGTGTACCAAACGGAGACAAACGGCATCTTCTCGAAATTTCCAACC :  540

            *       560         *       580         *       600
: GTCGCTCGCCGCCTCGTCTTCCCGGAACCGCGGTGGTTTAAGCGTGGCGGATTCTTCAAG :  600

            *       620         *       640         *       660
: CAGACGGAGACGTATGGAGTCCCCAAGCGCCGTCGTCCCCGGCACCACGGCGCCGCTGCT :  660

            *       680         *       700         *       720
: TCCTTATGCGTACGCGCCGCTGCCGTCGTCCGCCGACGACGCCCGTCAAAACCGGAGTGG :  720

            *       740         *       760         *       780
: CGGGAGGTGGCGCGCGTGCGCCGCCGTGCTGGCCGCATCGGCGTTGGCGGTGGTCGTCGT :  780

            *       800         *       820         *       840
: GGTCGGGCTCCTCGCGGGCGGCAGGGTGGATCGGGTCCCAGCCGGCGGAGACGTGGCGTC :  840

            *       860         *       880         *       900
: GGCCACGGTGCCGGCCGTGCCGATGGAGTTCCCGAGGAGCCGGGGCAAGGACTTCGGCGT :  900

            *       920         *       940         *       960
: GTCGGAGAAGTCCTCCGGTGCCTACTCCACCGACGGCGGGTTCCCGTGGAGCAACGCCAT :  960

            *       980         *      1000         *      1020
: GCTGCAGTGGCAGCGCACCGGGTTCCATTTCCAGCCGGAGCAGCACTACATGAACGATCC : 1020

            *      1040         *      1060         *      1080
: CAACGGCCCCGTGTACTACGGCGGATGGTACCACCTCTTCTACCAGCACAACCCCAAGGG : 1080

            *      1100         *      1120         *      1140
: CGACAGCTGGGGCAACATCGCGTGGGCCCACGCCGTCTCCAAGGACATGGTCAACTGGCG : 1140
```

FIGURE 43 CONT

```
          *        1160          *        1180          *        1200
: CCACCTCCCTCTCGCCATGGTTCCCGACCAGTGGTACGACAGCAACGGCGTCCTCACCGG : 1200

          *        1220          *        1240          *        1260
: CTCCATCACCGTGCTCCCCGACGGCCAGGTCATCCTGCTCTACACCGGCAACACCGACAC : 1260

          *        1280          *        1300          *        1320
: CCTAGCCCAGGTCCAGTGCCTCGCCACGCCCGCCGACCCGTCCGACCCGCTCCTCCGCGA : 1320

          *        1340          *        1360          *        1380
: GTGGGTCAAGCACCCCGCCAACCCCATCCTCTACCCTCCCCCCGGCATCGGCCTCAAGGA : 1380

          *        1400          *        1420          *        1440
: CTTCCGCGACCCCCTCACCGCCTGGTTCGACCACTCCGACCACACCTGGCGCACCGTCAT : 1440

          *        1460          *        1480          *        1500
: CGGCTCCAAGGACGACGACGGCCACGCCGGCATCATCCTCAGCTACAAGACCAAGGACTT : 1500

          *        1520          *        1540          *        1560
: CGTCAACTACGAGCTCATGCCGGGGAACATGCACCGCGGGCCCGACGGCACCGGAATGTA : 1560

          *        1580          *        1600          *        1620
: CGAGTGCATCGACCTCTACCCCGTCGGCGGCAACTCGTCCGAGATGCTCGGCGGCGACGA : 1620

          *        1640          *        1660          *        1680
: CTCGCCCGGCGTGCTCTTCGTGCTCAAGGAGAGCAGCGACGACGAGCGCCACGACTACTA : 1680

          *        1700          *        1720          *        1740
: CGCGCTCGGAAGGTTCGACGCCGTCGCCAACGTTTGGACGCCCATCGACCGGGAGCTGGA : 1740

          *        1760          *        1780          *        1800
: CCTTGGGATCGGGCTCAGATACGACTGGGGAAAGTACTACGCCTCCAAGTCCTTCTACGA : 1800

          *        1820          *        1840          *        1860
: CCAGAAGAAGAACCGCCGCATCGTATGGGCATACATCGGCGAGACCGACTCCGAGCAGGC : 1860

          *        1880          *        1900          *        1920
: CGACATCACCAAGGGATGGGCCAATCTCATGACGATTCCAAGAACGGTGGAGCTTGACAG : 1920

          *        1940          *        1960          *        1980
: GAAGACCCGCACAAACCTCATCCAATGGCCAGTGGAGGAGGTCGACACCCTCCGCAGGAA : 1980

          *        2000          *        2020          *        2040
: CTCCACGGACCTCGGTCGCATCACCGTCAACGCCGGCTCCGTCATTCGCCTCCCCCTCCA : 2040

          *        2060          *        2080          *        2100
: CCAGGGCGCTCAACTCGACATCGAGGCCTCCTTCCAACTCAACTCTTCCGACGTGGATGC : 2100

          *        2120          *        2140          *        2160
: TATCAACGAGGCCGACGTCGGCTACAACTGCAGCACCAGTGGTGCCGCCGTACGGGGGGC : 2160

          *        2180          *        2200          *        2220
: GCTCGGCCCCTTTGGCCTCCTCGTCCTTGCCAACGGCCGCACCGAACAGACGGCTGTGTA : 2220

          *        2240          *        2260          *        2280
: CTTCTACGTGTCCAAGGGCGTCGACGGTGCCCTCCAGACCCACTTCTGCCACGACGAGTC : 2280

          *        2300          *        2320          *        2340
: ACGGTCAACGCGGGCAAAGGATGTCGTGAATAGGATGATTGGCAGCATCGTGCCGGTGCT : 2340
```

FIGURE 43 CONT

```
              *        2360          *        2380          *        2400
: TGACGGTGAGACCTTTTCGGTGAGGGTGCTAGTGGACCACTCCATCGTGCAGAGCTTCGC : 2400

              *        2420          *        2440          *        2460
: GATGGGCGGGAGGATCACGGCGACGTCGCGGGCGTACCCGACGGAGGCCATCTACGCGGC : 2460

              *        2480          *        2500          *        2520
: CGCGGGGGTCTACCTCTTCAACAACGCCACGGGCGCCACCGTCACCGCCGAGAGGCTCGT : 2520

              *        2540          *        2560          *        2580
: CGTGCACGAGATGGCCTCAGCTGACAACCATATCTTCACGAACGACGACTTGGGAGGAGG : 2580

              *        2600          *        2620          *        2640
: AAAGCTTAAGCTTGGAGGAGGAGAGTCCAGCGCCGTCGTCGCCCAAGGCACCACGTCGCC : 2640

              *        2660          *        2680          *        2700
: GCTGCTCCCGTACGCCTACGCGCCGCTGCCGTCCTCTGCCGACGACGCCCGTGAAAACCA : 2700

              *        2720          *        2740          *        2760
: GAGTAGCGGCGGCGGTGTCAGGTGGCGCGCGTGCGCGGCCTCGGCCCTGGTGGTGCTGCT : 2760

              *        2780          *        2800          *        2820
: GGTCGTCGTCGGCTTCTTCGCGGGTGGCAGGGTGGATCTGGGTCAGGACGGCGAGGTGTC : 2820

              *        2840          *        2860          *        2880
: TGCGACTTCTTCGGTTCCTGGGAGCAGCAGGGGCAAGGATTCCGGCGTGTCGGAGAAGGA : 2880

              *        2900          *        2920          *        2940
: GTCGCCCGCCGACGGCGGCTTCCCGTGGAGCAACGCCATGCTGCAGTGGCAGCACACCGG : 2940

              *        2960          *        2980          *        3000
: GTTCCATTTCCAGCCACTCAAGCACTACATGAACGATCCCAACGGTCCGGTCTACTATGG : 3000

              *        3020          *        3040          *        3060
: CGGATGGTACCACCTCTTCTACCAGCACAACCCCTATGGCGACTCGTGGGGAAACGTATC : 3060

              *        3080          *        3100          *        3120
: TTGGGGACATGCCGTGTCCAAGGACCTGGTGAACTGGCGCCACCTCCCGGTCGCCTTGGT : 3120

              *        3140          *        3160          *        3180
: GCCCGATCAGTGGTACGACATCAACGGCGTCCTGACGGGCTCTATCACAGTGCTCCCAGA : 3180

              *        3200          *        3220          *        3240
: CGGGCGTGTCATCCTGCTATATACGGGGAACACCGACACCTTTTCGCAGGTCCAGTGCCT : 3240

              *        3260          *        3280          *        3300
: CGCAGTGCCCGCCGACCCATCTGACCCGCTCCTCCGTAGCTGGATCAAGCACCCCGCCAA : 3300

              *        3320          *        3340          *        3360
: CCCCATCCTCTTCCCGCCACCTGGGATCGGGCTCAAGGACTTCCGTGACCCGCTCACAGC : 3360

              *        3380          *        3400          *        3420
: CTGGTTCGAACATTCCGACAACACGTGGCGCACCATCATCGGATCCAAGGATGACGACGG : 3420

              *        3440          *        3460          *        3480
: CCACGCCGGCATCGTCCTTAGCTACAAGACCACCGACTTTGTGAATTATGAGCTCATGCC : 3480

              *        3500          *        3520          *        3540
: AGGGAACATGCATCGTGGCCCCGACGGCACCGGCATGTACGAGTGCCTTGACATCTACCC : 3540

              *        3560          *        3580          *        3600
```

FIGURE 43 CONT

```
: TGTGGGCGGCAACTCATCCGAGATGTTGGGTGGCGACTCCTCACCTGAGGTGTTGTTCGT : 3600

           *       3620          *       3640          *       3660
: GCTCAAGGAGAGCGCCAACGACGAGTGGCACGACTACTACGCGCTTGGGTGGTTTGACGC : 3660

           *       3680          *       3700          *       3720
: TGCCGCCAACACGTGGACGCCACAGGACCCCGAGGCGGACCTTGGGATCGGCCTCAGGTA : 3720

           *       3740          *       3760          *       3780
: CGACTGGGGCAAGTACTACGCGTCCAAGTCCTTCTACGACCCGATCAAGAACCGGCGTGT : 3780

           *       3800          *       3820          *       3840
: CGTTTGGGCTTTCGTCGGCGAGACCGACTCTGAGCAGGCCGACAAAGCCAAGGGATGGGC : 3840

           *       3860          *       3880          *       3900
: GTCCCTCATGTCGATTCCCAGGACGGTGGAGCTTGACAAGAAGACCCGGACGAACCTGAT : 3900

           *       3920          *       3940          *       3960
: CCAATGGCCAGTGGAGGAGATCGAGACCCTTCGCAGGAACGTCACAGACCTCGGTGGCAT : 3960

           *       3980          *       4000          *       4020
: CACCGTTGAAGCCGGCTCCGTCATTCACCTTCCCCTCCAACAAGGCGGGCAGCTTGACAT : 4020

           *       4040          *       4060          *       4080
: CGAGGCCTCCTTCCGTCTCAACTCTTCGGACATCGATGCACTCAACGAGGCCGACGTCGG : 4080

           *       4100          *       4120          *       4140
: CTTCAACTGCAGTAGCAGCGATGGGGCAGCCGTGCGTGGTGCGCTCGGCCCCTTTGGCCT : 4140

           *       4160          *       4180          *       4200
: CCTCGTCTTCGCCGACGGTCGCCACGAACAGACGGCGGCGTACTTCTACGTGTCCAAGGG : 4200

           *       4220          *       4240          *       4260
: CCTCGACGGCAGCCTCCTGACGCACTACTGCCACGACGAGTCACGGTCGACGCGAGCAAA : 4260

           *       4280          *       4300          *       4320
: GGACGTCGTGAGCCGGGTGGTTGGCGGCACTGTGCCAGTGCTTGACGGTGAAACCTTTTC : 4320

           *       4340          *       4360          *       4380
: AGTGAGGGTGCTAGTGGACCACTCCATCGTGCAGAGCTTCGTGATGGGTGGAGGACCAC : 4380

           *       4400          *       4420          *       4440
: GGTGACATCGCGGGCATACCCGACGGAGGCCATCTACGCCGCGGCAGGGGTGTACCTGTT : 4440

           *       4460          *       4480          *       4500
: CAACAACGCAACGAGCGCCACCATCACCGCCGAAGGGCTCGTCGTGTACGAGATGGCCTC : 4500

           *       4520          *       4540          *       4560
: GGCCGAGAGTCGGGCCTTCTTGGCTGACGACATGTAGAACAATAATTTTCTGAGCCTAGT : 4560

           *       4580          *       4600          *       4620
: ATCCATGATCATGATATAGTAAGGGAAAAATCATATCTATAAGTTTCCGAACTTAGTGAA : 4620

           *       4640          *       4660          *       4680
: AAAAAACCTGTAAAAGATATGCAGTCATATACACATGTGAAATTAGGTAGGAAAATATGA : 4680

           *       4700          *       4720          *       4740
: TAATCTCGTAGATGAGGAAAAAATATTGTACACCAAACTATTGTAAGTTACAGTAATGTA : 4740

           *       4760          *       4780          *       4800
```

FIGURE 43 CONT

```
: ATGTAAAAAAAGTTTTTAAGTTACAGAAGGTACATACCGCAAATAATCATATTATTTTAC : 4800

          *       4820         *       4840         *       4860
: CAAGATATTTTTTTCTGGAGTATTCCTTTCAAGTATCTTTTATCTCTAGAATCTTCTCCA : 4860

          *       4880         *       4900         *       4920
: ATCATGAGTGGCAACCGAAATGGAGCTCCTGTGTTGCTCCCCGTGTCTCACCCCTTTCGG : 4920

          *       4940         *       4960         *       4980
: CCCCACTGTCATTGGGTGGACCTATTCTCACGGCGGCTGTCCTGAGAAACAAAAATAGCA : 4980

          *       5000         *       5020         *       5040
: GCTGAAATGAAGACACGGCGACACGCAAGCCAGCATCTCTCATTGAACCTGCGGAGTGAG : 5040

          *       5060         *       5080         *       5100
: ATAGCTCTCGTGGCGCTGCTCTACTTGACGCGTTTGTCTCATACAACAGCGCATGGCTCC : 5100

          *       5120         *       5140         *       5160
: TTCATGTCAGGTCCATGATCCACAGATGGTATGATTGGGTTTGGAACATTTTTTGGGTTT : 5160

          *       5180         *       5200         *       5220
: GTGATATGTCGTAGATACAAAGGGAAATGTCTGAAGCATGCATGGATGGGTTCCCTGCTC : 5220

          *
: ATGTACTCAATGT : 5233
```

FIGURE 44

```
          *        20          *        40          *        60
: CTAGCATACTCGAGGTCATTCATATGCTTGAGAAGAGAGTCGGGATAGTCCAAAATAAAA :    60

          *        80          *       100          *       120
: CAAAGGTAAGATTACCTGGTCAAAAGTGAAAACATCAGTTAAAAGGTGGTATAAAGTAAA :   120

          *       140          *       160          *       180
: ATATCGGTAATAAAAGGTGGCCCAAAGTGAAATTTACTCTTTTCTACTATTATAAAAATT :   180

          *       200          *       220          *       240
: GAGGATGTTTTTGTCGGTACTTTGATACGTCATTTTTGTATGAATTGGTTTTTAAGTTTA :   240

          *       260          *       280          *       300
: TTCGCTTTTGGAAATGCATATCTGTATTTGAGTCGGGTTTTAAGTTCGTTTGCTTTTGTA :   300

          *       320          *       340          *       360
: AATACAGAGGGATTTGTATAAGAAATATCTTTAAAAAAACCCATATGCTAATTTGACATA :   360

          *       380          *       400          *       420
: ATTTTTGAGAAAAATATATATTCAGGCGAATTCTCACAATGAACAATAATAAGATTAAAA :   420

          *       440          *       460          *       480
: TAGCTTTCCCCCGTTGCAGCGCATGGGTATTTTTTCTAGTAAAAATAAAAGATAAACTTA :   480

          *       500          *       520          *       540
: GACTCAAAACATTTACAAAAACAACCCCTAAAGTTCCTAAAGCCCAAAGTGCTATCCACG :   540

          *       560          *       580          *       600
: ATCCATAGCAAGCCCAGCCCAACCCAACCCAACCCAACCCACCCCAGTCCAGCCAACTGG :   600

          *       620          *       640          *       660
: ACAATAGTCTCCACACCCCCCCACTATCACCGTGAGTTGTCCGCACGCACCGCACGTCTC :   660

          *       680          *       700          *       720
: GCAGCCAAAAAAAAAAAAAAGAAAGAAAAAAAAGAAAAAGAAAAAACAGCAGGTGGGTCC :   720

          *       740          *       760          *       780
: GGGTCGTGGGGGCCGGAAACGCGAGGAGGATCGCGAGCCAGCGACGAGGCCGGCCCTCCC :   780

          *       800          *       820          *       840
: TCCGCTTCCAAAGAAACGCCCCCCATCGCCACTATATACATACCCCCCCCTCTCCTCCCA :   840

          *       860          *       880          *       900
: TCCCCCCAACCCTACCACCACCACCACCACCACCTCCACCTCCTCCCCCCTCGCTGCCGG :   900

          *       920          *       940          *       960
: ACGACGAGCTCCTCCCCCCTCCCCCTCCGCCGCCGCCGCGCCGGTAACCACCCCGCCCCT :   960

          *       980          *      1000          *      1020
: CTCCTCTTTCTTTCTCCGTTTTTTTTTCCGTCTCGGTCTCGATCTTTGGCCTTGGTAGTT :  1020

          *      1040          *      1060          *      1080
: TGGGTGGGCGAGAGGCGGCTTCGTGCGCGCCCAGATCGGTGCGCGGGAGGGGCGGGATCT :  1080

          *      1100          *      1120          *      1140
: CGCGGCTGGGGCTCTCGCCGGCGTGGATCCGGCCCGGATCTCGCGGGGAATGGGGCTCTC :  1140

          *      1160          *      1180          *      1200
: GGATGTAGATCTGCGATCCGCCGTTGTTGGGGGAGATGATGGGGGGTTTAAAATTTCCGC :  1200

          *      1220          *      1240          *      1260
```

FIGURE 44 CONT

: *CATGCTAAACAAGATCAGGAAGAGGGGAAAAGGGCACTATGGTTTATATTTTTATATATT* : 1260

* 1280 * 1300 * 1320
: *TCTGCTGCTTCGTCAGGCTTAGATGTGCTAGATCTTTCTTTCTTCTTTTTGTGGGTAGAA* : 1320

* 1340 * 1360 * 1380
: *TTTGAATCCCTCAGCATTGTTCATCGGTAGTTTTTCTTTTCATGATTTGTGACAAATGCA* : 1380

* 1400 * 1420 * 1440
: *GCCTCGTGCGGAGCTTTTTTGTAG*ATGGAGTCCCCAAGCGCCGTCGTCCCCGGCACCACG : 1440

* 1460 * 1480 * 1500
: GCGCCGCTGCTTCCTTATGCGTACGCGCCGCTGCCGTCGTCCGCCGACGACGCCCGTCAA : 1500

* 1520 * 1540 * 1560
: AACCGGAGTGGCGGGAGGTGGCGCGCGTGCGCCGCCGTGCTGGCCGCATCGGCGTTGGCG : 1560

* 1580 * 1600 * 1620
: GTGGTCGTCGTGGTCGGGCTCCTCGCGGGCGGCAGGGTGGATCGGGTCCCAGCCGGCGGA : 1620

* 1640 * 1660 * 1680
: GACGTGGCGTCGGCCACGGTGCCGGCCGTGCCGATGGAGTTCCCGAGGAGCCGGGGCAAG : 1680

* 1700 * 1720 * 1740
: GACTTCGGCGTGTCGGAGAAGTCCTCCGGTGCCTACTCCACCGACGGCGGGTTCCCGTGG : 1740

* 1760 * 1780 * 1800
: AGCAACGCCATGCTGCAGTGGCAGCGCACCGGGTTCCATTTCCAGCCGGAGCAGCACTAC : 1800

* 1820 * 1840 * 1860
: ATGAACGATCCCAACGGCCCCGTGTACTACGGCGGATGGTACCACCTCTTCTACCAGCAC : 1860

* 1880 * 1900 * 1920
: AACCCCAAGGGCGACAGCTGGGGCAACATCGCGTGGGCCCACGCCGTCTCCAAGGACATG : 1920

* 1940 * 1960 * 1980
: GTCAACTGGCGCCACCTCCCTCTCGCCATGGTTCCCGACCAGTGGTACGACAGCAACGGC : 1980

* 2000 * 2020 * 2040
: GTCCTCACCGGCTCCATCACCGTGCTCCCCGACGGCCAGGTCATCCTGCTCTACACCGGC : 2040

* 2060 * 2080 * 2100
: AACACCGACACCCTAGCCCAGGTCCAGTGCCTCGCCACGCCCGCCGACCCGTCCGACCCG : 2100

* 2120 * 2140 * 2160
: CTCCTCCGCGAGTGGGTCAAGCACCCCGCCAACCCCATCCTCTACCCTCCCCCCGGCATC : 2160

* 2180 * 2200 * 2220
: GGCCTCAAGGACTTCCGCGACCCCCTCACCGCCTGGTTCGACCACTCCGACCACACCTGG : 2220

* 2240 * 2260 * 2280
: CGCACCGTCATCGGCTCCAAGGACGACGACGGCCACGCCGGCATCATCCTCAGCTACAAG : 2280

* 2300 * 2320 * 2340
: ACCAAGGACTTCGTCAACTACGAGCTCATGCCGGGGAACATGCACCGCGGGCCCGACGGC : 2340

* 2360 * 2380 * 2400
: ACCGGAATGTACGAGTGCATCGACCTCTACCCCGTCGGCGGCAACTCGTCCGAGATGCTC : 2400

* 2420 * 2440 * 2460
: GGCGGCGACGACTCGCCCGGCGTGCTCTTCGTGCTCAAGGAGAGCAGCGACGACGAGCGC : 2460

* 2480 * 2500 * 2520
: CACGACTACTACGCGCTCGGAAGGTTCGACGCCGTCGCCAACGTTTGGACGCCCATCGAC : 2520

FIGURE 44 CONT

```
           *        2540         *        2560         *        2580
: CGGGAGCTGGACCTTGGGATCGGGCTCAGATACGACTGGGGAAAGTACTACGCCTCCAAG : 2580

           *        2600         *        2620         *        2640
: TCCTTCTACGACCAGAAGAAGAACCGCCGCATCGTATGGGCATACATCGGCGAGACCGAC : 2640

           *        2660         *        2680         *        2700
: TCCGAGCAGGCCGACATCACCAAGGGATGGGCCAATCTCATGACGATTCCAAGAACGGTG : 2700

           *        2720         *        2740         *        2760
: GAGCTTGACAGGAAGACCCGCACAAACCTCATCCAATGGCCAGTGGAGGAGGTCGACACC : 2760

           *        2780         *        2800         *        2820
: CTCCGCAGGAACTCCACGGACCTCGGTCGCATCACCGTCAACGCCGGCTCCGTCATTCGC : 2820

           *        2840         *        2860         *        2880
: CTCCCCCTCCACCAGGGCGCTCAACTCGACATCGAGGCCTCCTTCCAACTCAACTCTTCC : 2880

           *        2900         *        2920         *        2940
: GACGTGGATGCTATCAACGAGGCCGACGTCGGCTACAACTGCAGCACCAGTGGTGCCGCC : 2940

           *        2960         *        2980         *        3000
: GTACGGGGGGCGCTCGGCCCCTTTGGCCTCCTCGTCCTTGCCAACGGCCGCACCGAACAG : 3000

           *        3020         *        3040         *        3060
: ACGGCTGTGTACTTCTACGTGTCCAAGGGCGTCGACGGTGCCCTCCAGACCCACTTCTGC : 3060

           *        3080         *        3100         *        3120
: CACGACGAGTCACGGTCAACGCGGGCAAAGGATGTCGTGAATAGGATGATTGGCAGCATC : 3120

           *        3140         *        3160         *        3180
: GTGCCGGTGCTTGACGGTGAGACCTTTTCGGTGAGGGTGCTAGTGGACCACTCCATCGTG : 3180

           *        3200         *        3220         *        3240
: CAGAGCTTCGCGATGGGCGGGAGGATCACGGCGACGTCGCGGGCGTACCCGACGGAGGCC : 3240

           *        3260         *        3280         *        3300
: ATCTACGCGGCCGCGGGGGTCTACCTCTTCAACAACGCCACGGGCGCCACCGTCACCGCC : 3300

           *        3320         *        3340         *        3360
: GAGAGGCTCGTCGTGCACGAGATGGCCTCAGCTGACAACCATATCTTCACGAACGACGAC : 3360

           *        3380         *        3400         *        3420
: TTGGGAGGAGGAAAGCTTAAGCTTGGAGGAGGAGAGTCCAGCGCCGTCGTCGCCCAAGGC : 3420

           *        3440         *        3460         *        3480
: ACCACGTCGCCGCTGCTCCCGTACGCCTACGCGCCGCTGCCGTCCTCTGCCGACGACGCC : 3480

           *        3500         *        3520         *        3540
: CGTGAAAACCAGAGTAGCGGCGGCGGTGTCAGGTGGCGCGCGTGCGCGGCCTCGGCCCTG : 3540

           *        3560         *        3580         *        3600
: GTGGTGCTGCTGGTCGTCGTCGGCTTCTTCGCGGGTGGCAGGGTGGATCTGGGTCAGGAC : 3600

           *        3620         *        3640         *        3660
: GGCGAGGTGTCTGCGACTTCTTCGGTTCCTGGGAGCAGCAGGGGCAAGGATTCCGGCGTG : 3660

           *        3680         *        3700         *        3720
: TCGGAGAAGGAGTCGCCCGCCGACGGCGGCTTCCCGTGGAGCAACGCCATGCTGCAGTGG : 3720

           *        3740         *        3760         *        3780
: CAGCACACCGGGTTCCATTTCCAGCCACTCAAGCACTACATGAACGATCCCAACGGTCCG : 3780
```

FIGURE 44 CONT

```
          *        3800          *        3820          *        3840
: GTCTACTATGGCGGATGGTACCACCTCTTCTACCAGCACAACCCCTATGGCGACTCGTGG : 3840

          *        3860          *        3880          *        3900
: GGAAACGTATCTTGGGGACATGCCGTGTCCAAGGACCTGGTGAACTGGCGCCACCTCCCG : 3900

          *        3920          *        3940          *        3960
: GTCGCCTTGGTGCCCGATCAGTGGTACGACATCAACGGCGTCCTGACGGGCTCTATCACA : 3960

          *        3980          *        4000          *        4020
: GTGCTCCCAGACGGGCGTGTCATCCTGCTATATACGGGGAACACCGACACCTTTTCGCAG : 4020

          *        4040          *        4060          *        4080
: GTCCAGTGCCTCGCAGTGCCCGCCGACCCATCTGACCCGCTCCTCCGTAGCTGGATCAAG : 4080

          *        4100          *        4120          *        4140
: CACCCCGCCAACCCCATCCTCTTCCCGCCACCTGGGATCGGGCTCAAGGACTTCCGTGAC : 4140

          *        4160          *        4180          *        4200
: CCGCTCACAGCCTGGTTCGAACATTCCGACAACACGTGGCGCACCATCATCGGATCCAAG : 4200

          *        4220          *        4240          *        4260
: GATGACGACGGCCACGCCGGCATCGTCCTTAGCTACAAGACCACCGACTTTGTGAATTAT : 4260

          *        4280          *        4300          *        4320
: GAGCTCATGCCAGGGAACATGCATCGTGGCCCCGACGGCACCGGCATGTACGAGTGCCTT : 4320

          *        4340          *        4360          *        4380
: GACATCTACCCTGTGGGCGGCAACTCATCCGAGATGTTGGGTGGCGACTCCTCACCTGAG : 4380

          *        4400          *        4420          *        4440
: GTGTTGTTCGTGCTCAAGGAGAGCGCCAACGACGAGTGGCACGACTACTACGCGCTTGGG : 4440

          *        4460          *        4480          *        4500
: TGGTTTGACGCTGCCGCCAACACGTGGACGCCACAGGACCCCGAGGCGGACCTTGGGATC : 4500

          *        4520          *        4540          *        4560
: GGCCTCAGGTACGACTGGGGCAAGTACTACGCGTCCAAGTCCTTCTACGACCCGATCAAG : 4560

          *        4580          *        4600          *        4620
: AACCGGCGTGTCGTTTGGGCTTTCGTCGGCGAGACCGACTCTGAGCAGGCCGACAAAGCC : 4620

          *        4640          *        4660          *        4680
: AAGGGATGGGCGTCCCTCATGTCGATTCCCAGGACGGTGGAGCTTGACAAGAAGACCCGG : 4680

          *        4700          *        4720          *        4740
: ACGAACCTGATCCAATGGCCAGTGGAGGAGATCGAGACCCTTCGCAGGAACGTCACAGAC : 4740

          *        4760          *        4780          *        4800
: CTCGGTGGCATCACCGTTGAAGCCGGCTCCGTCATTCACCTTCCCCTCCAACAAGGCGGG : 4800

          *        4820          *        4840          *        4860
: CAGCTTGACATCGAGGCCTCCTTCCGTCTCAACTCTTCGGACATCGATGCACTCAACGAG : 4860

          *        4880          *        4900          *        4920
: GCCGACGTCGGCTTCAACTGCAGTAGCAGCGATGGGGCAGCCGTGCGTGGTGCGCTCGGC : 4920

          *        4940          *        4960          *        4980
: CCCTTTGGCCTCCTCGTCTTCGCCGACGGTCGCCACGAACAGACGGCGGCGTACTTCTAC : 4980

          *        5000          *        5020          *        5040
: GTGTCCAAGGGCCTCGACGGCAGCCTCCTGACGCACTACTGCCACGACGAGTCACGGTCG : 5040
```

FIGURE 44 CONT

```
      *      5060        *      5080        *      5100
: ACGCGAGCAAAGGACGTCGTGAGCCGGGTGGTTGGCGGCACTGTGCCAGTGCTTGACGGT : 5100

          *      5120        *      5140        *      5160
: GAAACCTTTTCAGTGAGGGTGCTAGTGGACCACTCCATCGTGCAGAGCTTCGTGATGGGT : 5160

          *      5180        *      5200        *      5220
: GGGAGGACCACGGTGACATCGCGGGCATACCCGACGGAGGCCATCTACGCCGCGGCAGGG : 5220

          *      5240        *      5260        *      5280
: GTGTACCTGTTCAACAACGCAACGAGCGCCACCATCACCGCCGAAGGGCTCGTCGTGTAC : 5280

          *      5300        *      5320        *      5340
: GAGATGGCCTCGGCCGAGAGTCGGGCCTTCTTGGCTGACGACATGTAAAACAATAATTTT : 5340

          *      5360        *      5380        *      5400
: CTGAGCCTAGTATCCATGATCATGATATAGTAAGGGAAAAATCATATCTATAAGTTTCCG : 5400

          *      5420        *      5440        *      5460
: AACTTAGTGAAAAAAAACCTGTAAAAGATATGCAGTCATATACACATGTGAAATTAGGTA : 5460

          *      5480        *      5500        *      5520
: GGAAAATATGATAATCTCGTAGATGAGGAAAAAATATTGTACACCAAACTATTGTAAGTT : 5520

          *      5540        *      5560        *      5580
: ACAGTAATGTAATGTAAAAAAAGTTTTTAAGTTACAGAAGGTACATACCGCAAATAATCA : 5580

          *      5600        *      5620        *      5640
: TATTATTTTACCAAGATATTTTTTTCTGGAGTATTCCTTTCAAGTATCTTTTATCTCTAG : 5640

          *      5660        *      5680        *      5700
: AATCTTCTCCAATCATGAGTGGCAACCGAAATGGAGCTCCTGTGTTGCTCCCCGTGTCTC : 5700

          *      5720        *      5740        *      5760
: ACCCCTTTCGGCCCCACTGTCATTGGGTGGACCTATTCTCACGGCGGCTGTCCTGAGAAA : 5760

          *      5780        *      5800        *      5820
: CAAAAATAGCAGCTGAAATGAAGACACGGCGACACGCAAGCCAGCATCTCTCATTGAACC : 5820

          *      5840        *      5860        *      5880
: TGCGGAGTGAGATAGCTCTCGTGGCGCTGCTCTACTTGACGCGTTTGTCTCATACAACAG : 5880

          *      5900        *      5920        *      5940
: CGCATGGCTCCTTCATGTCAGGTCCATGATCCACAGATGGTATGATTGGGTTTGGAACAT : 5940

          *      5960        *      5980        *      6000
: TTTTTGGGTTTGTGATATGTCGTAGATACAAAGGGAAATGTCTGAAGCATGCATGGATGG : 6000

          *      6020
: GTTCCCTGCTCATGTACTCAATGT : 6024
```

FIGURE 45

* 20 * 40 * 60
: TTTAGCGACACACATTTAGTGACGACTGATTGACAAATTATTTTTCGTCTCACAAAAATT : 60

* 80 * 100 * 120
: TTAGTGACGAAATATGATTTATAAATGACGAAATTATTTGTCCCTGATAATTGAATTTGT : 120

* 140 * 160 * 180
: TGTAGTGAGCCTTAGGAGTTACATATGTTACAAGGTATAATGGAGGAATAATGAATGAAA : 180

* 200 * 220 * 240
: ATAAAGGGACACTTAAGCCACCAATGGCTTGGGAGTTGCTGCATGCACCAAGAAAATTGT : 240

* 260 * 280 * 300
: AACATATACACCAACTCCATTTGGAGTAATGCAGCAATAATTGTTTTCAACGGCAACAAT : 300

* 320 * 340 * 360
: CAACTGCCAAGTCATCCATCATTATGTAACATATATGAGAAGTGCACCAACGGCCATAAA : 360

* 380 * 400 * 420
: TCAACATCTATGTGGCCATGCAAAAAATGTGAATTCTTAAATTATTAAAATGCCACACTA : 420

* 440 * 460 * 480
: ACACCATAAGAACAAATTTCATCTCTGTCATAAACATAGCATATCAGCAAAAAATTACAG : 480

* 500 * 520 * 540
: AACCTAAATATTGTTTCTTTCCTCTCTACTTTTAGAATATAATGTTGAATACATTTTATT : 540

* 560 * 580 * 600
: AGAGTAATTAGTCATAATTATCAGAGTTATAACTGTTGCTTATTTATTCTACTAAGAAGA : 600

* 620 * 640 * 660
: ATCTATTGAATTCTAGAGATTAAATACATATTTATCAATAAAATATCTTTAAAGATAATG : 660

* 680 * 700 * 720
: TTCTTAACACTCCTCAAAGCTGGATAACATTATAATTATTAAAAGAAGAAGAAATTATGA : 720

* 740 * 760 * 780
: AATGGGAAAAAGTTATTTTCATAGATTTTTTATTTGGGAGATCTTGGAGAGAATGGTGTA : 780

* 800 * 820 * 840
: TTTTTGGGGAAGGGGATTTTTTTTATTTTAAAAAACTATTTTAATTAATTTTCGGATATT : 840

* 860 * 880 * 900
: TGCCATCCACAAATATGCTACCAATAAAGAAAGAAAGAAGTACAGAACTCTCATGAGGTG : 900

* 920 * 940 * 960
: GTTTCTTTAAGTAGATTTAGATTGCACTAGTTATTGGACAAGATATTTCTTTTTATAAAG : 960

* 980 * 1000 * 1020
: AAAAAGTCAAAAAAATATATGATTCAAAACGAGCCTTATAAATTGTTGGGTAAAGTTTGA : 1020

* 1040 * 1060 * 1080
: GAGGTAAAATTATTTATCTTTAAGATAATTTTTTTTGAAAGAAAAGGAGGTGAGTTGAAAG : 1080

* 1100 * 1120 * 1140
: AAATCAAACTTAAAAGGGAGATTTATGTAATTATTGCTGTATTTTTTTTAATCTCTTTTC : 1140

* 1160 * 1180 * 1200

FIGURE 45 CONT

```
: TTCTAGCATATTCTAACTTGGTAGGTAAACTCTGTGACTTGACGGATTTTATTGATAAAA : 1200

                 *        1220          *         1240          *         1260
: GAAAACATATTTCATCGGGTCCAATCTGAGGAACAGTTTGTCGGATTTTGAGAGTCAAAT : 1260

                 *        1280          *         1300          *         1320
: AATTTAACTTTGACAGTAAATTTAGACATGAAATTTTATTTTATTTTAAAAATAAAATAT : 1320

                 *        1340          *         1360          *         1380
: ACATATTTAAACACCATATAAAAAGTACATTTAAGTCACAATAATTAATAATTCAAGATA : 1380

                 *        1400          *         1420          *         1440
: TATGAAAAAGTTTGCGATAAAAAATATACTTATTTGAATTCTGGAATTGCCACAAAGAAA : 1440

                 *        1460          *         1480          *         1500
: ATAAATATTTTTTGGTAAAGATTTAGAGTATTATAATTGAATGAGTAGCTACTCGGACCA : 1500

                 *        1520          *         1540          *         1560
: CTACATGTTTAAAACATGGCAAGGAATATGAGTGTGTTATCACTCTATAAATAGAAGGCT : 1560

                 *        1580          *         1600          *         1620
: TCATTAGTCTAGAGAACTAGTCACAAGCAATCAAATGGAGTCCCCAAGCGCCGTCGTCCC : 1620

                 *        1640          *         1660          *         1680
: CGGCACCACGGCGCCGCTGCTTCCTTATGCGTACGCGCCGCTGCCGTCGTCCGCCGACGA : 1680

                 *        1700          *         1720          *         1740
: CGCCCGTCAAAACCGGAGTGGCGGGAGGTGGCGCGCGTGCGCCGCCGTGCTGGCCGCATC : 1740

                 *        1760          *         1780          *         1800
: GGCGTTGGCGGTGGTCGTCGTGGTCGGGCTCCTCGCGGGCGGCAGGGTGGATCGGGTCCC : 1800

                 *        1820          *         1840          *         1860
: AGCCGGCGGAGACGTGGCGTCGGCCACGGTGCCGGCCGTGCCGATGGAGTTCCCGAGGAG : 1860

                 *        1880          *         1900          *         1920
: CCGGGGCAAGGACTTCGGCGTGTCGGAGAAGTCCTCCGGTGCCTACTCCACCGACGGCGG : 1920

                 *        1940          *         1960          *         1980
: GTTCCCGTGGAGCAACGCCATGCTGCAGTGGCAGCGCACCGGGTTCCATTTCCAGCCGGA : 1980

                 *        2000          *         2020          *         2040
: GCAGCACTACATGAACGATCCCAACGGCCCCGTGTACTACGGCGGATGGTACCACCTCTT : 2040

                 *        2060          *         2080          *         2100
: CTACCAGCACAACCCCAAGGGCGACAGCTGGGGCAACATCGCGTGGGCCCACGCCGTCTC : 2100

                 *        2120          *         2140          *         2160
: CAAGGACATGGTCAACTGGCGCCACCTCCCTCTCGCCATGGTTCCCGACCAGTGGTACGA : 2160

                 *        2180          *         2200          *         2220
: CAGCAACGGCGTCCTCACCGGCTCCATCACCGTGCTCCCCGACGGCCAGGTCATCCTGCT : 2220

                 *        2240          *         2260          *         2280
: CTACACCGGCAACACCGACACCCTAGCCCAGGTCCAGTGCCTCGCCACGCCCGCCGACCC : 2280

                 *        2300          *         2320          *         2340
: GTCCGACCCGCTCCTCCGCGAGTGGGTCAAGCACCCCGCCAACCCCATCCTCTACCCTCC : 2340

                 *        2360          *         2380          *         2400
```

FIGURE 45 CONT

```
: CCCCGGCATCGGCCTCAAGGACTTCCGCGACCCCCTCACCGCCTGGTTCGACCACTCCGA : 2400

         *        2420         *        2440         *        2460
: CCACACCTGGCGCACCGTCATCGGCTCCAAGGACGACGACGGCCACGCCGGCATCATCCT : 2460

         *        2480         *        2500         *        2520
: CAGCTACAAGACCAAGGACTTCGTCAACTACGAGCTCATGCCGGGGAACATGCACCGCGG : 2520

         *        2540         *        2560         *        2580
: GCCCGACGGCACCGGAATGTACGAGTGCATCGACCTCTACCCCGTCGGCGGCAACTCGTC : 2580

         *        2600         *        2620         *        2640
: CGAGATGCTCGGCGGCGACGACTCGCCCGGCGTGCTCTTCGTGCTCAAGGAGAGCAGCGA : 2640

         *        2660         *        2680         *        2700
: CGACGAGCGCCACGACTACTACGCGCTCGGAAGGTTCGACGCCGTCGCCAACGTTTGGAC : 2700

         *        2720         *        2740         *        2760
: GCCCATCGACCGGGAGCTGGACCTTGGGATCGGGCTCAGATACGACTGGGGAAAGTACTA : 2760

         *        2780         *        2800         *        2820
: CGCCTCCAAGTCCTTCTACGACCAGAAGAAGAACCGCCGCATCGTATGGGCATACATCGG : 2820

         *        2840         *        2860         *        2880
: CGAGACCGACTCCGAGCAGGCCGACATCACCAAGGGATGGGCCAATCTCATGACGATTCC : 2880

         *        2900         *        2920         *        2940
: AAGAACGGTGGAGCTTGACAGGAAGACCCGCACAAACCTCATCCAATGGCCAGTGGAGGA : 2940

         *        2960         *        2980         *        3000
: GGTCGACACCCTCCGCAGGAACTCCACGGACCTCGGTCGCATCACCGTCAACGCCGGCTC : 3000

         *        3020         *        3040         *        3060
: CGTCATTCGCCTCCCCCTCCACCAGGGCGCTCAACTCGACATCGAGGCCTCCTTCCAACT : 3060

         *        3080         *        3100         *        3120
: CAACTCTTCCGACGTGGATGCTATCAACGAGGCCGACGTCGGCTACAACTGCAGCACCAG : 3120

         *        3140         *        3160         *        3180
: TGGTGCCGCCGTACGGGGGGCGCTCGGCCCCTTTGGCCTCCTCGTCCTTGCCAACGGCCG : 3180

         *        3200         *        3220         *        3240
: CACCGAACAGACGGCTGTGTACTTCTACGTGTCCAAGGGCGTCGACGGTGCCCTCCAGAC : 3240

         *        3260         *        3280         *        3300
: CCACTTCTGCCACGACGAGTCACGGTCAACGCGGGCAAAGGATGTCGTGAATAGGATGAT : 3300

         *        3320         *        3340         *        3360
: TGGCAGCATCGTGCCGGTGCTTGACGGTGAGACCTTTTCGGTGAGGGTGCTAGTGGACCA : 3360

         *        3380         *        3400         *        3420
: CTCCATCGTGCAGAGCTTCGCGATGGGCGGGAGGATCACGGCGACGTCGCGGGCGTACCC : 3420

         *        3440         *        3460         *        3480
: GACGGAGGCCATCTACGCGGCCGCGGGGGTCTACCTCTTCAACAACGCCACGGGCGCCAC : 3480

         *        3500         *        3520         *        3540
: CGTCACCGCCGAGAGGCTCGTCGTGCACGAGATGGCCTCAGCTGACAACCATATCTTCAC : 3540

         *        3560         *        3580         *        3600
: GAACGACGACTTGGGAGGAGGAAAGCTTAAGCTTGGAGGAGGAGAGTCCAGCGCCGTCGT : 3600
```

FIGURE 45 CONT

```
                 *        3620          *        3640          *        3660
: CGCCCAAGGCACCACGTCGCCGCTGCTCCCGTACGCCTACGCGCCGCTGCCGTCCTCTGC : 3660

                 *        3680          *        3700          *        3720
: CGACGACGCCCGTGAAAACCAGAGTAGCGGCGGCGGTGTCAGGTGGCGCGCGTGCGCGGC : 3720

                 *        3740          *        3760          *        3780
: CTCGGCCCTGGTGGTGCTGCTGGTCGTCGTCGGCTTCTTCGCGGGTGGCAGGGTGGATCT : 3780

                 *        3800          *        3820          *        3840
: GGGTCAGGACGGCGAGGTGTCTGCGACTTCTTCGGTTCCTGGGAGCAGCAGGGGCAAGGA : 3840

                 *        3860          *        3880          *        3900
: TTCCGGCGTGTCGGAGAAGGAGTCGCCCGCCGACGGCGGCTTCCCGTGGAGCAACGCCAT : 3900

                 *        3920          *        3940          *        3960
: GCTGCAGTGGCAGCACACCGGGTTCCATTTCCAGCCACTCAAGCACTACATGAACGATCC : 3960

                 *        3980          *        4000          *        4020
: CAACGGTCCGGTCTACTATGGCGGATGGTACCACCTCTTCTACCAGCACAACCCCTATGG : 4020

                 *        4040          *        4060          *        4080
: CGACTCGTGGGGAAACGTATCTTGGGGACATGCCGTGTCCAAGGACCTGGTGAACTGGCG : 4080

                 *        4100          *        4120          *        4140
: CCACCTCCCGGTCGCCTTGGTGCCCGATCAGTGGTACGACATCAACGGCGTCCTGACGGG : 4140

                 *        4160          *        4180          *        4200
: CTCTATCACAGTGCTCCCAGACGGGCGTGTCATCCTGCTATATACGGGGAACACCGACAC : 4200

                 *        4220          *        4240          *        4260
: CTTTTCGCAGGTCCAGTGCCTCGCAGTGCCCGCCGACCCATCTGACCCGCTCCTCCGTAG : 4260

                 *        4280          *        4300          *        4320
: CTGGATCAAGCACCCCGCCAACCCCATCCTCTTCCCGCCACCTGGGATCGGGCTCAAGGA : 4320

                 *        4340          *        4360          *        4380
: CTTCCGTGACCCGCTCACAGCCTGGTTCGAACATTCCGACAACACGTGGCGCACCATCAT : 4380

                 *        4400          *        4420          *        4440
: CGGATCCAAGGATGACGACGGCCACGCCGGCATCGTCCTTAGCTACAAGACCACCGACTT : 4440

                 *        4460          *        4480          *        4500
: TGTGAATTATGAGCTCATGCCAGGGAACATGCATCGTGGCCCCGACGGCACCGGCATGTA : 4500

                 *        4520          *        4540          *        4560
: CGAGTGCCTTGACATCTACCCTGTGGGCGGCAACTCATCCGAGATGTTGGGTGGCGACTC : 4560

                 *        4580          *        4600          *        4620
: CTCACCTGAGGTGTTGTTCGTGCTCAAGGAGAGCGCCAACGACGAGTGGCACGACTACTA : 4620

                 *        4640          *        4660          *        4680
: CGCGCTTGGGTGGTTTGACGCTGCCGCCAACACGTGGACGCCACAGGACCCCGAGGCGGA : 4680

                 *        4700          *        4720          *        4740
: CCTTGGGATCGGCCTCAGGTACGACTGGGGCAAGTACTACGCGTCCAAGTCCTTCTACGA : 4740

                 *        4760          *        4780          *        4800
: CCCGATCAAGAACCGGCGTGTCGTTTGGGCTTTCGTCGGCGAGACCGACTCTGAGCAGGC : 4800
```

FIGURE 45 CONT

```
             *        4820          *        4840          *        4860
: CGACAAAGCCAAGGGATGGGCGTCCCTCATGTCGATTCCCAGGACGGTGGAGCTTGACAA : 4860

             *        4880          *        4900          *        4920
: GAAGACCCGGACGAACCTGATCCAATGGCCAGTGGAGGAGATCGAGACCCTTCGCAGGAA : 4920

             *        4940          *        4960          *        4980
: CGTCACAGACCTCGGTGGCATCACCGTTGAAGCCGGCTCCGTCATTCACCTTCCCCTCCA : 4980

             *        5000          *        5020          *        5040
: ACAAGGCGGGCAGCTTGACATCGAGGCCTCCTTCCGTCTCAACTCTTCGGACATCGATGC : 5040

             *        5060          *        5080          *        5100
: ACTCAACGAGGCCGACGTCGGCTTCAACTGCAGTAGCAGCGATGGGGCAGCCGTGCGTGG : 5100

             *        5120          *        5140          *        5160
: TGCGCTCGGCCCCTTTGGCCTCCTCGTCTTCGCCGACGGTCGCCACGAACAGACGGCGGC : 5160

             *        5180          *        5200          *        5220
: GTACTTCTACGTGTCCAAGGGCCTCGACGGCAGCCTCCTGACGCACTACTGCCACGACGA : 5220

             *        5240          *        5260          *        5280
: GTCACGGTCGACGCGAGCAAAGGACGTCGTGAGCCGGGTGGTTGGCGGCACTGTGCCAGT : 5280

             *        5300          *        5320          *        5340
: GCTTGACGGTGAAACCTTTTCAGTGAGGGTGCTAGTGGACCACTCCATCGTGCAGAGCTT : 5340

             *        5360          *        5380          *        5400
: CGTGATGGGTGGGAGGACCACGGTGACATCGCGGGCATACCCGACGGAGGCCATCTACGC : 5400

             *        5420          *        5440          *        5460
: CGCGGCAGGGGTGTACCTGTTCAACAACGCAACGAGCGCCACCATCACCGCCGAAGGGCT : 5460

             *        5480          *        5500          *        5520
: CGTCGTGTACGAGATGGCCTCGGCCGAGAGTCGGGCCTTCTTGGCTGACGACATGTAGAA : 5520

             *        5540          *        5560          *        5580
: CAATAATTTTCTGAGCCTAGTATCCATGATCATGATATAGTAAGGGAAAAATCATATCTA : 5580

             *        5600          *        5620          *        5640
: TAAGTTTCCGAACTTAGTGAAAAAAAACCTGTAAAAGATATGCAGTCATATACACATGTG : 5640

             *        5660          *        5680          *        5700
: AAATTAGGTAGGAAAATATGATAATCTCGTAGATGAGGAAAAAATATTGTACACCAAACT : 5700

             *        5720          *        5740          *        5760
: ATTGTAAGTTACAGTAATGTAATGTAAAAAAAGTTTTTAAGTTACAGAAGGTACATACCG : 5760

             *        5780          *        5800          *        5820
: CAAATAATCATATTATTTTACCAAGATATTTTTTTCTGGAGTATTCCTTTCAAGTATCTT : 5820

             *        5840          *        5860          *        5880
: TTATCTCTAGAATCTTCTCCAATCATGAGTGGCAACCGAAATGGAGCTCCTGTGTTGCTC : 5880

             *        5900          *        5920          *        5940
: CCCGTGTCTCACCCCTTTCGGCCCCACTGTCATTGGGTGGACCTATTCTCACGGCGGCTG : 5940

             *        5960          *        5980          *        6000
: TCCTGAGAAACAAAAATAGCAGCTGAAATGAAGACACGGCGACACGCAAGCCAGCATCTC : 6000
```

FIGURE 45 CONT

```
            *        6020          *        6040          *        6060
:  TCATTGAACCTGCGGAGTGAGATAGCTCTCGTGGCGCTGCTCTACTTGACGCGTTTGTCT  :  6060

            *        6080          *        6100          *        6120
:  CATACAACAGCGCATGGCTCCTTCATGTCAGGTCCATGATCCACAGATGGTATGATTGGG  :  6120

            *        6140          *        6160          *        6180
:  TTTGGAACATTTTTTGGGTTTGTGATATGTCGTAGATACAAAGGGAAATGTCTGAAGCAT  :  6180

            *        6200          *
:  GCATGGATGGGTTCCCTGCTCATGTACTCAATGT  :  6214
```

FIGURE 46

```
        *       20         *       40         *       60
: AAGAATCTCAAACACGGAGATCACAAAGTTTGAAAGAAAATTTATTTCTTCGACTCAAAA :   60

        *       80         *      100         *      120
: CAAACTTACGAAATTTAGGTAGAACTTATATACATTATATTGTAATTTTTTGTAACAAAA :  120

        *      140         *      160         *      180
: TGTTTTTATTATTATTATAGAATTTTACTGGTTAAATTAAAAATGAATAGAAAAGGTGAA :  180

        *      200         *      220         *      240
: TTAAGAGGAGAGAGGAGGTAAACATTTTCTTCTATTTTTTCATATTTTCAGGATAAATTA :  240

        *      260         *      280         *      300
: TTGTAAAAGTTTACAAGATTTCCATTTGACTAGTGTAAATGAGGAATATTCTCTAGTAAG :  300

        *      320         *      340         *      360
: ATCATTATTTCATCTACTTCTTTTATCTTCTACCAGTAGAGGAATAAACAATATTTAGCT :  360

        *      380         *      400         *      420
: CCTTTGTAAATACAAATTAATTTTCGTTCTTGACATCATTCAATTTTAATTTTACGTATA :  420

        *      440         *      460         *      480
: AAATAAAAGATCATACCTATTAGAACGATTAAGGAGAAATACAATTCGAATGAGAAGGAT :  480

        *      500         *      520         *      540
: GTGCCGCTTGTTATAATAAACAGCCACACGACGTAAACGTAAAATGACCACATGATGGGC :  540

        *      560         *      580         *      600
: CAATAGACATGGACCGACTACTAATAATAGTAAGTTACATTTTAGGATGGAATAAATATC :  600

        *      620         *      640         *      660
: ATACCGACATCAGTTTGAAAGAAAAGGGAAAAAAAGAAAAAATAAATAAAAGATATACTA :  660

        *      680         *      700         *      720
: CCGACATGAGTTCCAAAAAGCAAAAAAAAAGATCAAGCCGACACAGACACGCGTAGAGAG :  720

        *      740         *      760         *      780
: CAAAATGACTTTGACGTCACACCACGAAAACAGACGCTTCATACGTGTCCCTTTATCTCT :  780

        *      800         *      820         *      840
: CTCAGTCTCTCTATAAACTTAGTGAGACCCTCCTCTGTTTTACTCACAAATTTAAATGGA :  840

        *      860         *      880         *      900
: GTCCCCAAGCGCCGTCGTCCCCGGCACCACGGCGCCGCTGCTTCCTTATGCGTACGCGCC :  900

        *      920         *      940         *      960
: GCTGCCGTCGTCCGCCGACGACGCCCGTCAAAACCGGAGTGGCGGGAGGTGGCGCGCGTG :  960

        *      980         *     1000         *     1020
: CGCCGCCGTGCTGGCCGCATCGGCGTTGGCGGTGGTCGTCGTGGTCGGGCTCCTCGCGGG : 1020

        *     1040         *     1060         *     1080
: CGGCAGGGTGGATCGGGTCCCAGCCGGCGGAGACGTGGCGTCGGCCACGGTGCCGGCCGT : 1080

        *     1100         *     1120         *     1140
: GCCGATGGAGTTCCCGAGGAGCCGGGGCAAGGACTTCGGCGTGTCGGAGAAGTCCTCCGG : 1140
```

FIGURE 46 CONT

```
                *       1160        *       1180        *       1200
: TGCCTACTCCACCGACGGCGGGTTCCCGTGGAGCAACGCCATGCTGCAGTGGCAGCGCAC : 1200

                *       1220        *       1240        *       1260
: CGGGTTCCATTTCCAGCCGGAGCAGCACTACATGAACGATCCCAACGGCCCCGTGTACTA : 1260

                *       1280        *       1300        *       1320
: CGGCGGATGGTACCACCTCTTCTACCAGCACAACCCCAAGGGCGACAGCTGGGGCAACAT : 1320

                *       1340        *       1360        *       1380
: CGCGTGGGCCCACGCCGTCTCCAAGGACATGGTCAACTGGCGCCACCTCCCTCTCGCCAT : 1380

                *       1400        *       1420        *       1440
: GGTTCCCGACCAGTGGTACGACAGCAACGGCGTCCTCACCGGCTCCATCACCGTGCTCCC : 1440

                *       1460        *       1480        *       1500
: CGACGGCCAGGTCATCCTGCTCTACACCGGCAACACCGACACCCTAGCCCAGGTCCAGTG : 1500

                *       1520        *       1540        *       1560
: CCTCGCCACGCCCGCCGACCCGTCCGACCCGCTCCTCCGCGAGTGGGTCAAGCACCCCGC : 1560

                *       1580        *       1600        *       1620
: CAACCCCATCCTCTACCCTCCCCCCGGCATCGGCCTCAAGGACTTCCGCGACCCCCTCAC : 1620

                *       1640        *       1660        *       1680
: CGCCTGGTTCGACCACTCCGACCACACCTGGCGCACCGTCATCGGCTCCAAGGACGACGA : 1680

                *       1700        *       1720        *       1740
: CGGCCACGCCGGCATCATCCTCAGCTACAAGACCAAGGACTTCGTCAACTACGAGCTCAT : 1740

                *       1760        *       1780        *       1800
: GCCGGGGAACATGCACCGCGGGCCCGACGGCACCGGAATGTACGAGTGCATCGACCTCTA : 1800

                *       1820        *       1840        *       1860
: CCCCGTCGGCGGCAACTCGTCCGAGATGCTCGGCGGCGACGACTCGCCCGGCGTGCTCTT : 1860

                *       1880        *       1900        *       1920
: CGTGCTCAAGGAGAGCAGCGACGACGAGCGCCACGACTACTACGCGCTCGGAAGGTTCGA : 1920

                *       1940        *       1960        *       1980
: CGCCGTCGCCAACGTTTGGACGCCCATCGACCGGGAGCTGGACCTTGGGATCGGGCTCAG : 1980

                *       2000        *       2020        *       2040
: ATACGACTGGGGAAAGTACTACGCCTCCAAGTCCTTCTACGACCAGAAGAAGAACCGCCG : 2040

                *       2060        *       2080        *       2100
: CATCGTATGGGCATACATCGGCGAGACCGACTCCGAGCAGGCCGACATCACCAAGGGATG : 2100

                *       2120        *       2140        *       2160
: GGCCAATCTCATGACGATTCCAAGAACGGTGGAGCTTGACAGGAAGACCCGCACAAACCT : 2160

                *       2180        *       2200        *       2220
: CATCCAATGGCCAGTGGAGGAGGTCGACACCCTCCGCAGGAACTCCACGGACCTCGGTCG : 2220

                *       2240        *       2260        *       2280
: CATCACCGTCAACGCCGGCTCCGTCATTCGCCTCCCCCTCCACCAGGGCGCTCAACTCGA : 2280

                *       2300        *       2320        *       2340
: CATCGAGGCCTCCTTCCAACTCAACTCTTCCGACGTGGATGCTATCAACGAGGCCGACGT : 2340

                *       2360        *       2380        *       2400
```

FIGURE 46 CONT

```
: CGGCTACAACTGCAGCACCAGTGGTGCCGCCGTACGGGGGGCGCTCGGCCCCTTTGGCCT : 2400

         *        2420          *        2440          *        2460
: CCTCGTCCTTGCCAACGGCCGCACCGAACAGACGGCTGTGTACTTCTACGTGTCCAAGGG : 2460

         *        2480          *        2500          *        2520
: CGTCGACGGTGCCCTCCAGACCCACTTCTGCCACGACGAGTCACGGTCAACGCGGGCAAA : 2520

         *        2540          *        2560          *        2580
: GGATGTCGTGAATAGGATGATTGGCAGCATCGTGCCGGTGCTTGACGGTGAGACCTTTTC : 2580

         *        2600          *        2620          *        2640
: GGTGAGGGTGCTAGTGGACCACTCCATCGTGCAGAGCTTCGCGATGGGCGGGAGGATCAC : 2640

         *        2660          *        2680          *        2700
: GGCGACGTCGCGGGCGTACCCGACGGAGGCCATCTACGCGGCCGCGGGGGTCTACCTCTT : 2700

         *        2720          *        2740          *        2760
: CAACAACGCCACGGGCGCCACCGTCACCGCCGAGAGGCTCGTCGTGCACGAGATGGCCTC : 2760

         *        2780          *        2800          *        2820
: AGCTGACAACCATATCTTCACGAACGACGACTTGGGAGGAGGAAAGCTTAAGCTTGGAGG : 2820

         *        2840          *        2860          *        2880
: AGGAGAGTCCAGCGCCGTCGTCGCCCAAGGCACCACGTCGCCGCTGCTCCCGTACGCCTA : 2880

         *        2900          *        2920          *        2940
: CGCGCCGCTGCCGTCCTCTGCCGACGACGCCCGTGAAAACCAGAGTAGCGGCGGCGGTGT : 2940

         *        2960          *        2980          *        3000
: CAGGTGGCGCGCGTGCGCGGCCTCGGCCCTGGTGGTGCTGCTGGTCGTCGTCGGCTTCTT : 3000

         *        3020          *        3040          *        3060
: CGCGGGTGGCAGGGTGGATCTGGGTCAGGACGGCGAGGTGTCTGCGACTTCTTCGGTTCC : 3060

         *        3080          *        3100          *        3120
: TGGGAGCAGCAGGGGCAAGGATTCCGGCGTGTCGGAGAAGGAGTCGCCCGCCGACGGCGG : 3120

         *        3140          *        3160          *        3180
: CTTCCCGTGGAGCAACGCCATGCTGCAGTGGCAGCACACCGGGTTCCATTTCCAGCCACT : 3180

         *        3200          *        3220          *        3240
: CAAGCACTACATGAACGATCCCAACGGTCCGGTCTACTATGGCGGATGGTACCACCTCTT : 3240

         *        3260          *        3280          *        3300
: CTACCAGCACAACCCCTATGGCGACTCGTGGGGAAACGTATCTTGGGGACATGCCGTGTC : 3300

         *        3320          *        3340          *        3360
: CAAGGACCTGGTGAACTGGCGCCACCTCCCGGTCGCCTTGGTGCCCGATCAGTGGTACGA : 3360

         *        3380          *        3400          *        3420
: CATCAACGGCGTCCTGACGGGCTCTATCACAGTGCTCCCAGACGGGCGTGTCATCCTGCT : 3420

         *        3440          *        3460          *        3480
: ATATACGGGGAACACCGACACCTTTTCGCAGGTCCAGTGCCTCGCAGTGCCCGCCGACCC : 3480

         *        3500          *        3520          *        3540
: ATCTGACCCGCTCCTCCGTAGCTGGATCAAGCACCCCGCCAACCCCATCCTCTTCCCGCC : 3540

         *        3560          *        3580          *        3600
: ACCTGGGATCGGGCTCAAGGACTTCCGTGACCCGCTCACAGCCTGGTTCGAACATTCCGA : 3600
```

FIGURE 46 CONT

```
               *      3620          *      3640          *      3660
: CAACACGTGGCGCACCATCATCGGATCCAAGGATGACGACGGCCACGCCGGCATCGTCCT : 3660

               *      3680          *      3700          *      3720
: TAGCTACAAGACCACCGACTTTGTGAATTATGAGCTCATGCCAGGGAACATGCATCGTGG : 3720

               *      3740          *      3760          *      3780
: CCCCGACGGCACCGGCATGTACGAGTGCCTTGACATCTACCCTGTGGGCGGCAACTCATC : 3780

               *      3800          *      3820          *      3840
: CGAGATGTTGGGTGGCGACTCCTCACCTGAGGTGTTGTTCGTGCTCAAGGAGAGCGCCAA : 3840

               *      3860          *      3880          *      3900
: CGACGAGTGGCACGACTACTACGCGCTTGGGTGGTTTGACGCTGCCGCCAACACGTGGAC : 3900

               *      3920          *      3940          *      3960
: GCCACAGGACCCCGAGGCGGACCTTGGGATCGGCCTCAGGTACGACTGGGGCAAGTACTA : 3960

               *      3980          *      4000          *      4020
: CGCGTCCAAGTCCTTCTACGACCCGATCAAGAACCGGCGTGTCGTTTGGGCTTTCGTCGG : 4020

               *      4040          *      4060          *      4080
: CGAGACCGACTCTGAGCAGGCCGACAAAGCCAAGGGATGGGCGTCCCTCATGTCGATTCC : 4080

               *      4100          *      4120          *      4140
: CAGGACGGTGGAGCTTGACAAGAAGACCCGGACGAACCTGATCCAATGGCCAGTGGAGGA : 4140

               *      4160          *      4180          *      4200
: GATCGAGACCCTTCGCAGGAACGTCACAGACCTCGGTGGCATCACCGTTGAAGCCGGCTC : 4200

               *      4220          *      4240          *      4260
: CGTCATTCACCTTCCCCTCCAACAAGGCGGGCAGCTTGACATCGAGGCCTCCTTCCGTCT : 4260

               *      4280          *      4300          *      4320
: CAACTCTTCGGACATCGATGCACTCAACGAGGCCGACGTCGGCTTCAACTGCAGTAGCAG : 4320

               *      4340          *      4360          *      4380
: CGATGGGGCAGCCGTGCGTGGTGCGCTCGGCCCCTTTGGCCTCCTCGTCTTCGCCGACGG : 4380

               *      4400          *      4420          *      4440
: TCGCCACGAACAGACGGCGGCGTACTTCTACGTGTCCAAGGGCCTCGACGGCAGCCTCCT : 4440

               *      4460          *      4480          *      4500
: GACGCACTACTGCCACGACGAGTCACGGTCGACGCGAGCAAAGGACGTCGTGAGCCGGGT : 4500

               *      4520          *      4540          *      4560
: GGTTGGCGGCACTGTGCCAGTGCTTGACGGTGAAACCTTTTCAGTGAGGGTGCTAGTGGA : 4560

               *      4580          *      4600          *      4620
: CCACTCCATCGTGCAGAGCTTCGTGATGGGTGGGAGGACCACGGTGACATCGCGGGCATA : 4620

               *      4640          *      4660          *      4680
: CCCGACGGAGGCCATCTACGCCGCGGCAGGGGTGTACCTGTTCAACAACGCAACGAGCGC : 4680

               *      4700          *      4720          *      4740
: CACCATCACCGCCGAAGGGCTCGTCGTGTACGAGATGGCCTCGGCCGAGAGTCGGGCCTT : 4740

               *      4760          *      4780          *      4800
: CTTGGCTGACGACATGTAAAACAATAATTTTCTGAGCCTAGTATCCATGATCATGATATA : 4800
```

FIGURE 46 CONT

```
         *        4820          *        4840          *        4860
: GTAAGGGAAAAATCATATCTATAAGTTTCCGAACTTAGTGAAAAAAAACCTGTAAAAGAT : 4860

         *        4880          *        4900          *        4920
: ATGCAGTCATATACACATGTGAAATTAGGTAGGAAAATATGATAATCTCGTAGATGAGGA : 4920

         *        4940          *        4960          *        4980
: AAAAATATTGTACACCAAACTATTGTAAGTTACAGTAATGTAATGTAAAAAAAGTTTTTA : 4980

         *        5000          *        5020          *        5040
: AGTTACAGAAGGTACATACCGCAAATAATCATATTATTTTACCAAGATATTTTTTTCTGG : 5040

         *        5060          *        5080          *        5100
: AGTATTCCTTTCAAGTATCTTTTATCTCTAGAATCTTCTCCAATCATGAGTGGCAACCGA : 5100

         *        5120          *        5140          *        5160
: AATGGAGCTCCTGTGTTGCTCCCCGTGTCTCACCCCTTTCGGCCCCACTGTCATTGGGTG : 5160

         *        5180          *        5200          *        5220
: GACCTATTCTCACGGCGGCTGTCCTGAGAAACAAAAATAGCAGCTGAAATGAAGACACGG : 5220

         *        5240          *        5260          *        5280
: CGACACGCAAGCCAGCATCTCTCATTGAACCTGCGGAGTGAGATAGCTCTCGTGGCGCTG : 5280

         *        5300          *        5320          *        5340
: CTCTACTTGACGCGTTTGTCTCATACAACAGCGCATGGCTCCTTCATGTCAGGTCCATGA : 5340

         *        5360          *        5380          *        5400
: TCCACAGATGGTATGATTGGGTTTGGAACATTTTTTGGGTTTGTGATATGTCGTAGATAC : 5400

         *        5420          *        5440          *
: AAAGGGAAATGTCTGAAGCATGCATGGATGGGTTCCCTGCTCATGTACTCAATGT : 5455
```

FIGURE 47

```
         *        20         *        40         *        60
: AATTGTTGTCTAATCTTGGTAGTAGTAATCACTACATTGGTGCTTCACATACCAGAGACC :   60

         *        80         *       100         *       120
: TGGATTCTCAAGGCAGAGCCATAGTTTGATATTTTGGCGTCTCCGATAAGCATAGATTGA :  120

         *       140         *       160         *       180
: CTTTGGTCTAGCGGTAAGAGCACCTCAAGTGAGGATCTCATGAGTCGTCTTTCTAGTTCC :  180

         *       200         *       220         *       240
: AGCACATGGTAGCGTTTTGCACCAATGGTATTTGCAAATTTGTTCTTATAACAATGTCAT :  240

         *       260         *       280         *       300
: AATGAAATTTTTTGAATAGGCCCCCCATCAAGAAACTAGGGATTGAAAGAGAGAATTGGA :  300

         *       320         *       340         *       360
: TCTCTATTTTTACACATAAGAGATTTGGAAAGGTCTATTGGTTTTTTCTATTCAATTTGT :  360

         *       380         *       400         *       420
: AAATGATCGTACATATTGTAACGATTAAAACAATTGAAGCATAGTTTAAAGACTTGCCAA :  420

         *       440         *       460         *       480
: AAGTTGTTTCTCCTCGAGACACCATTTAGAAAATGACAATTGTTGTCCATCAAATATGAA :  480

         *       500         *       520         *       540
: TTAAGTTTGCTTATGAAGCGATTTTTGGGATACTTTAATGTAGTGTGCTTTGTCTCTGCT :  540

         *       560         *       580         *       600
: AAAATTTGTACCAGAGACCTCATGATTTTCAATTGTTTCACTGAACACATTACAATTGGA :  600

         *       620         *       640         *       660
: ACTTATGCTTGATAGGCAATAAATAACTGAGGTCAAAATTTGAAGACCACTTTTTATATG :  660

         *       680         *       700         *       720
: CAATTTCTTAGTTATTTCACGTTGATGTCATCTAGTTCAAATATTTTTCTCCCGCGACTC :  720

         *       740         *       760         *       780
: TCTTAATCTTTGTATTCAACAAATGAACATTTGGACATAGTCTTACGGGGAGAAGGGTGG :  780

         *       800         *       820         *       840
: AGAGAGATTGTTTTCGAAAAGAAAAAAAAAATTCATACGGAAGGAGCAATAATTAAAGGA :  840

         *       860         *       880         *       900
: AAAAGAAAAGTAGTTTGAAAAGTGCAAAGAAATTGCTGTGTCTTATTGGACCACTACTAG :  900

         *       920         *       940         *       960
: GCCCACCTAAATAACCAATCTATAAAGGAAACAGCCCACTACCCATTTCGCACGCACAAA :  960

         *       980         *      1000         *      1020
: AATCAAATTGTAGGAGAAAGGAAGAGAATTCTAAAAACCGCTCTCACTTTCTCTCTCTAG : 1020

         *      1040         *      1060         *      1080
: AAAAACAAAAATCTCTCTCTCTCTTTCTCTCTCTAACATCAATGGAGTCCCCAAGCGCCG : 1080

         *      1100         *      1120         *      1140
: TCGTCCCCGGCACCACGGCGCCGCTGCTTCCTTATGCGTACGCGCCGCTGCCGTCGTCCG : 1140


         *      1160         *      1180         *      1200
```

FIGURE 47 CONT

```
: CCGACGACGCCCGTCAAAACCGGAGTGGCGGGAGGTGGCGCGCGTGCGCCGCCGTGCTGG : 1200

           *        1220         *        1240         *        1260
: CCGCATCGGCGTTGGCGGTGGTCGTCGTGGTCGGGCTCCTCGCGGGCGGCAGGGTGGATC : 1260

           *        1280         *        1300         *        1320
: GGGTCCCAGCCGGCGGAGACGTGGCGTCGGCCACGGTGCCGGCCGTGCCGATGGAGTTCC : 1320

           *        1340         *        1360         *        1380
: CGAGGAGCCGGGGCAAGGACTTCGGCGTGTCGGAGAAGTCCTCCGGTGCCTACTCCACCG : 1380

           *        1400         *        1420         *        1440
: ACGGCGGGTTCCCGTGGAGCAACGCCATGCTGCAGTGGCAGCGCACCGGGTTCCATTTCC : 1440

           *        1460         *        1480         *        1500
: AGCCGGAGCAGCACTACATGAACGATCCCAACGGCCCCGTGTACTACGGCGGATGGTACC : 1500

           *        1520         *        1540         *        1560
: ACCTCTTCTACCAGCACAACCCCAAGGGCGACAGCTGGGGCAACATCGCGTGGGCCCACG : 1560

           *        1580         *        1600         *        1620
: CCGTCTCCAAGGACATGGTCAACTGGCGCCACCTCCCTCTCGCCATGGTTCCCGACCAGT : 1620

           *        1640         *        1660         *        1680
: GGTACGACAGCAACGGCGTCCTCACCGGCTCCATCACCGTGCTCCCCGACGGCCAGGTCA : 1680

           *        1700         *        1720         *        1740
: TCCTGCTCTACACCGGCAACACCGACACCCTAGCCCAGGTCCAGTGCCTCGCCACGCCCG : 1740

           *        1760         *        1780         *        1800
: CCGACCCGTCCGACCCGCTCCTCCGCGAGTGGGTCAAGCACCCCGCCAACCCCATCCTCT : 1800

           *        1820         *        1840         *        1860
: ACCCTCCCCCCGGCATCGGCCTCAAGGACTTCCGCGACCCCCTCACCGCCTGGTTCGACC : 1860

           *        1880         *        1900         *        1920
: ACTCCGACCACACCTGGCGCACCGTCATCGGCTCCAAGGACGACGACGGCCACGCCGGCA : 1920

           *        1940         *        1960         *        1980
: TCATCCTCAGCTACAAGACCAAGGACTTCGTCAACTACGAGCTCATGCCGGGGAACATGC : 1980

           *        2000         *        2020         *        2040
: ACCGCGGGCCCGACGGCACCGGAATGTACGAGTGCATCGACCTCTACCCCGTCGGCGGCA : 2040

           *        2060         *        2080         *        2100
: ACTCGTCCGAGATGCTCGGCGGCGACGACTCGCCCGGCGTGCTCTTCGTGCTCAAGGAGA : 2100

           *        2120         *        2140         *        2160
: GCAGCGACGACGAGCGCCACGACTACTACGCGCTCGGAAGGTTCGACGCCGTCGCCAACG : 2160

           *        2180         *        2200         *        2220
: TTTGGACGCCCATCGACCGGGAGCTGGACCTTGGGATCGGGCTCAGATACGACTGGGGAA : 2220

           *        2240         *        2260         *        2280
: AGTACTACGCCTCCAAGTCCTTCTACGACCAGAAGAAGAACCGCCGCATCGTATGGGCAT : 2280

           *        2300         *        2320         *        2340
: ACATCGGCGAGACCGACTCCGAGCAGGCCGACATCACCAAGGGATGGGCCAATCTCATGA : 2340

           *        2360         *        2380         *        2400
: CGATTCCAAGAACGGTGGAGCTTGACAGGAAGACCCGCACAAACCTCATCCAATGGCCAG : 2400
```

FIGURE 47 CONT

```
          *       2420          *       2440          *       2460
: TGGAGGAGGTCGACACCCTCCGCAGGAACTCCACGGACCTCGGTCGCATCACCGTCAACG : 2460

          *       2480          *       2500          *       2520
: CCGGCTCCGTCATTCGCCTCCCCCTCCACCAGGGCGCTCAACTCGACATCGAGGCCTCCT : 2520

          *       2540          *       2560          *       2580
: TCCAACTCAACTCTTCCGACGTGGATGCTATCAACGAGGCCGACGTCGGCTACAACTGCA : 2580

          *       2600          *       2620          *       2640
: GCACCAGTGGTGCCGCCGTACGGGGGGCGCTCGGCCCCTTTGGCCTCCTCGTCCTTGCCA : 2640

          *       2660          *       2680          *       2700
: ACGGCCGCACCGAACAGACGGCTGTGTACTTCTACGTGTCCAAGGGCGTCGACGGTGCCC : 2700

          *       2720          *       2740          *       2760
: TCCAGACCCACTTCTGCCACGACGAGTCACGGTCAACGCGGGCAAAGGATGTCGTGAATA : 2760

          *       2780          *       2800          *       2820
: GGATGATTGGCAGCATCGTGCCGGTGCTTGACGGTGAGACCTTTTCGGTGAGGGTGCTAG : 2820

          *       2840          *       2860          *       2880
: TGGACCACTCCATCGTGCAGAGCTTCGCGATGGGCGGGAGGATCACGGCGACGTCGCGGG : 2880

          *       2900          *       2920          *       2940
: CGTACCCGACGGAGGCCATCTACGCGGCCGCGGGGGTCTACCTCTTCAACAACGCCACGG : 2940

          *       2960          *       2980          *       3000
: GCGCCACCGTCACCGCCGAGAGGCTCGTCGTGCACGAGATGGCCTCAGCTGACAACCATA : 3000

          *       3020          *       3040          *       3060
: TCTTCACGAACGACGACTTGGGAGGAGGAAAGCTTAAGCTTGGAGGAGGAGAGTCCAGCG : 3060

          *       3080          *       3100          *       3120
: CCGTCGTCGCCCAAGGCACCACGTCGCCGCTGCTCCCGTACGCCTACGCGCCGCTGCCGT : 3120

          *       3140          *       3160          *       3180
: CCTCTGCCGACGACGCCCGTGAAAACCAGAGTAGCGGCGGCGGTGTCAGGTGGCGCGCGT : 3180

          *       3200          *       3220          *       3240
: GCGCGGCCTCGGCCCTGGTGGTGCTGCTGGTCGTCGTCGGCTTCTTCGCGGGTGGCAGGG : 3240

          *       3260          *       3280          *       3300
: TGGATCTGGGTCAGGACGGCGAGGTGTCTGCGACTTCTTCGGTTCCTGGGAGCAGCAGGG : 3300

          *       3320          *       3340          *       3360
: GCAAGGATTCCGGCGTGTCGGAGAAGGAGTCGCCCGCCGACGGCGGCTTCCCGTGGAGCA : 3360

          *       3380          *       3400          *       3420
: ACGCCATGCTGCAGTGGCAGCACACCGGGTTCCATTTCCAGCCACTCAAGCACTACATGA : 3420

          *       3440          *       3460          *       3480
: ACGATCCCAACGGTCCGGTCTACTATGGCGGATGGTACCACCTCTTCTACCAGCACAACC : 3480

          *       3500          *       3520          *       3540
: CCTATGGCGACTCGTGGGGAAACGTATCTTGGGGACATGCCGTGTCCAAGGACCTGGTGA : 3540

          *       3560          *       3580          *       3600
: ACTGGCGCCACCTCCCGGTCGCCTTGGTGCCCGATCAGTGGTACGACATCAACGGCGTCC : 3600
```

FIGURE 47 CONT

```
           *        3620          *        3640          *        3660
: TGACGGGCTCTATCACAGTGCTCCCAGACGGGCGTGTCATCCTGCTATATACGGGGAACA : 3660

           *        3680          *        3700          *        3720
: CCGACACCTTTTCGCAGGTCCAGTGCCTCGCAGTGCCCGCCGACCCATCTGACCCGCTCC : 3720

           *        3740          *        3760          *        3780
: TCCGTAGCTGGATCAAGCACCCCGCCAACCCCATCCTCTTCCCGCCACCTGGGATCGGGC : 3780

           *        3800          *        3820          *        3840
: TCAAGGACTTCCGTGACCCGCTCACAGCCTGGTTCGAACATTCCGACAACACGTGGCGCA : 3840

           *        3860          *        3880          *        3900
: CCATCATCGGATCCAAGGATGACGACGGCCACGCCGGCATCGTCCTTAGCTACAAGACCA : 3900

           *        3920          *        3940          *        3960
: CCGACTTTGTGAATTATGAGCTCATGCCAGGGAACATGCATCGTGGCCCCGACGGCACCG : 3960

           *        3980          *        4000          *        4020
: GCATGTACGAGTGCCTTGACATCTACCCTGTGGGCGGCAACTCATCCGAGATGTTGGGTG : 4020

           *        4040          *        4060          *        4080
: GCGACTCCTCACCTGAGGTGTTGTTCGTGCTCAAGGAGAGCGCCAACGACGAGTGGCACG : 4080

           *        4100          *        4120          *        4140
: ACTACTACGCGCTTGGGTGGTTTGACGCTGCCGCCAACACGTGGACGCCACAGGACCCCG : 4140

           *        4160          *        4180          *        4200
: AGGCGGACCTTGGGATCGGCCTCAGGTACGACTGGGGCAAGTACTACGCGTCCAAGTCCT : 4200

           *        4220          *        4240          *        4260
: TCTACGACCCGATCAAGAACCGGCGTGTCGTTTGGGCTTTCGTCGGCGAGACCGACTCTG : 4260

           *        4280          *        4300          *        4320
: AGCAGGCCGACAAAGCCAAGGGATGGGCGTCCCTCATGTCGATTCCCAGGACGGTGGAGC : 4320

           *        4340          *        4360          *        4380
: TTGACAAGAAGACCCGGACGAACCTGATCCAATGGCCAGTGGAGGAGATCGAGACCCTTC : 4380

           *        4400          *        4420          *        4440
: GCAGGAACGTCACAGACCTCGGTGGCATCACCGTTGAAGCCGGCTCCGTCATTCACCTTC : 4440

           *        4460          *        4480          *        4500
: CCCTCCAACAAGGCGGGCAGCTTGACATCGAGGCCTCCTTCCGTCTCAACTCTTCGGACA : 4500

           *        4520          *        4540          *        4560
: TCGATGCACTCAACGAGGCCGACGTCGGCTTCAACTGCAGTAGCAGCGATGGGGCAGCCG : 4560

           *        4580          *        4600          *        4620
: TGCGTGGTGCGCTCGGCCCCTTTGGCCTCCTCGTCTTCGCCGACGGTCGCCACGAACAGA : 4620

           *        4640          *        4660          *        4680
: CGGCGGCGTACTTCTACGTGTCCAAGGGCCTCGACGGCAGCCTCCTGACGCACTACTGCC : 4680

           *        4700          *        4720          *        4740
: ACGACGAGTCACGGTCGACGCGAGCAAAGGACGTCGTGAGCCGGGTGGTTGGCGGCACTG : 4740

           *        4760          *        4780          *        4800
: TGCCAGTGCTTGACGGTGAAACCTTTTCAGTGAGGGTGCTAGTGGACCACTCCATCGTGC : 4800
```

FIGURE 47 CONT

```
           *        4820          *        4840          *        4860
: AGAGCTTCGTGATGGGTGGGAGGACCACGGTGACATCGCGGGCATACCCGACGGAGGCCA : 4860

           *        4880          *        4900          *        4920
: TCTACGCCGCGGCAGGGGTGTACCTGTTCAACAACGCAACGAGCGCCACCATCACCGCCG : 4920

           *        4940          *        4960          *        4980
: AAGGGCTCGTCGTGTACGAGATGGCCTCGGCCGAGAGTCGGGCCTTCTTGGCTGACGACA : 4980

           *        5000          *        5020          *        5040
: TGTAGAACAATAATTTTCTGAGCCTAGTATCCATGATCATGATATAGTAAGGGAAAAATC : 5040

           *        5060          *        5080          *        5100
: ATATCTATAAGTTTCCGAACTTAGTGAAAAAAAACCTGTAAAAGATATGCAGTCATATAC : 5100

           *        5120          *        5140          *        5160
: ACATGTGAAATTAGGTAGGAAAATATGATAATCTCGTAGATGAGGAAAAAATATTGTACA : 5160

           *        5180          *        5200          *        5220
: CCAAACTATTGTAAGTTACAGTAATGTAATGTAAAAAAAGTTTTTAAGTTACAGAAGGTA : 5220

           *        5240          *        5260          *        5280
: CATACCGCAAATAATCATATTATTTTACCAAGATATTTTTTTCTGGAGTATTCCTTTCAA : 5280

           *        5300          *        5320          *        5340
: GTATCTTTTATCTCTAGAATCTTCTCCAATCATGAGTGGCAACCGAAATGGAGCTCCTGT : 5340

           *        5360          *        5380          *        5400
: GTTGCTCCCCGTGTCTCACCCCTTTCGGCCCCACTGTCATTGGGTGGACCTATTCTCACG : 5400

           *        5420          *        5440          *        5460
: GCGGCTGTCCTGAGAAACAAAAATAGCAGCTGAAATGAAGACACGGCGACACGCAAGCCA : 5460

           *        5480          *        5500          *        5520
: GCATCTCTCATTGAACCTGCGGAGTGAGATAGCTCTCGTGGCGCTGCTCTACTTGACGCG : 5520

           *        5540          *        5560          *        5580
: TTTGTCTCATACAACAGCGCATGGCTCCTTCATGTCAGGTCCATGATCCACAGATGGTAT : 5580

           *        5600          *        5620          *        5640
: GATTGGGTTTGGAACATTTTTTGGGTTTGTGATATGTCGTAGATACAAAGGGAAATGTCT : 5640

           *        5660          *        5680
: GAAGCATGCATGGATGGGTTCCCTGCTCATGTACTCAATGT : 5681
```

FIGURE 49
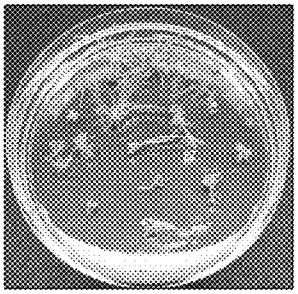
*LpRbcS::Lp1-SST::LpFT4*
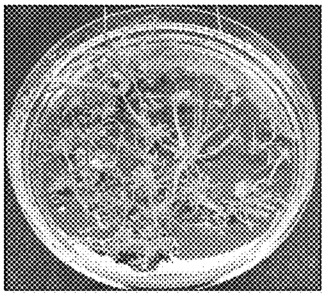
*LpRbcS:: FT fusion1::LpFT4*
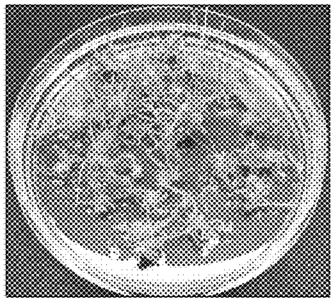
*LpRbcS:: FT fusion3::LpFT4*
*LpRbcS::Lp1-SST::LpFT4*
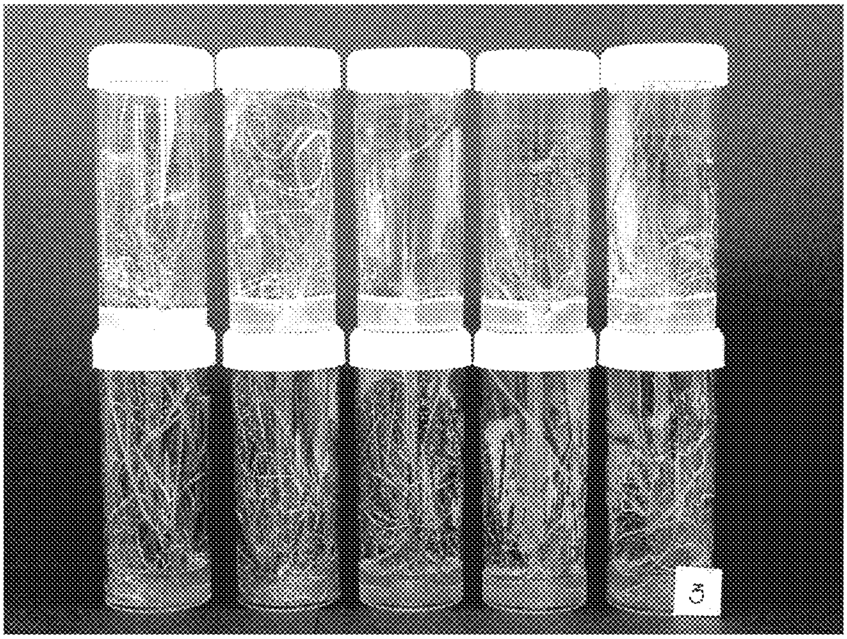
*LpRbcS::Lp1-SST-6G-FFT FT fusion3::LpFT4*

*LpRbcS::FT fusion 1* *Control*

A

B

C

D

A

B

C

D

FIGURE 66
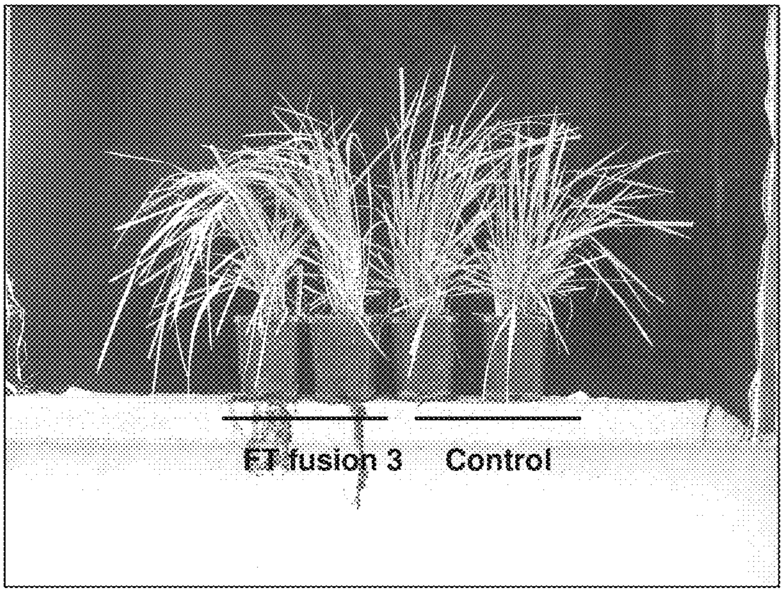
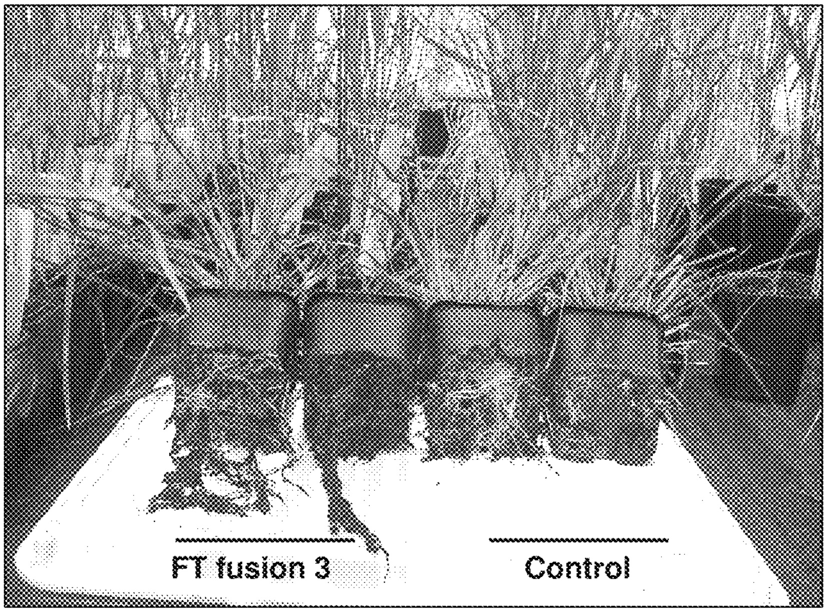

FIGURE 70
A
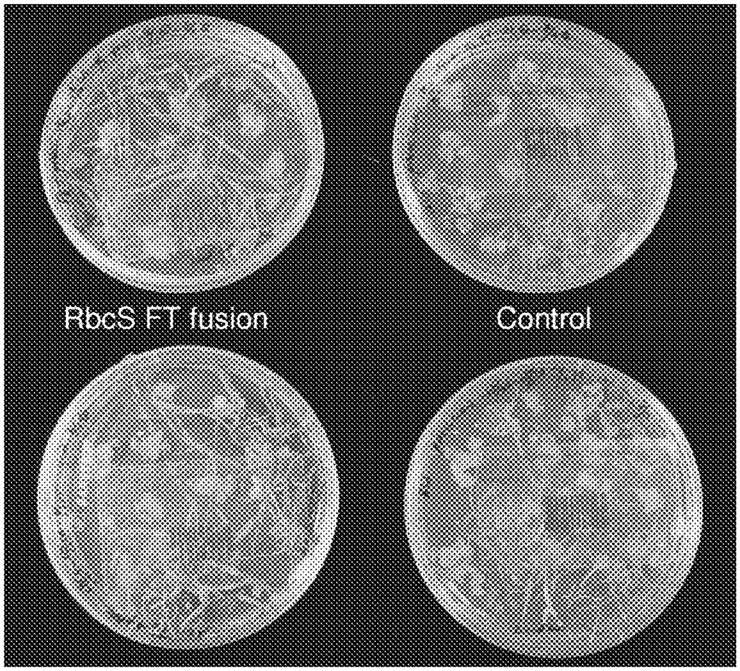
B
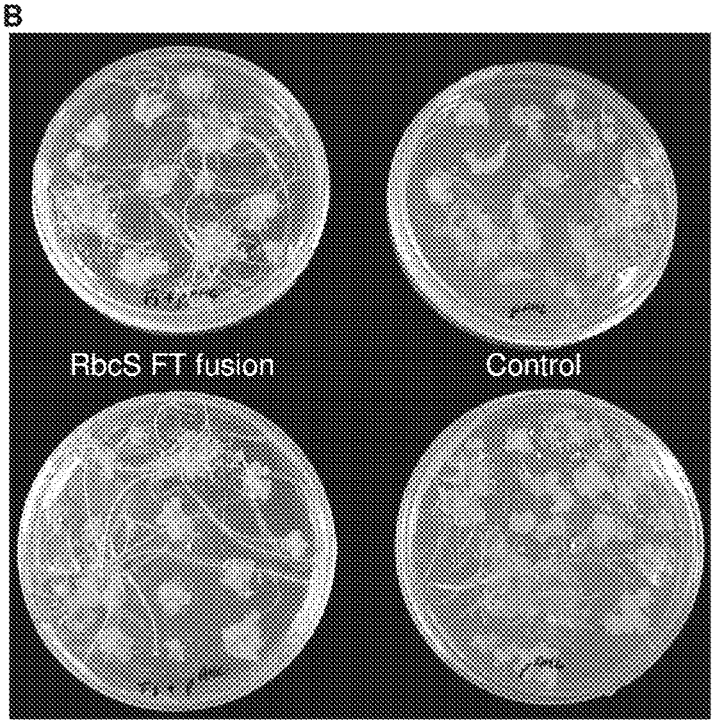

A

FIGURE 72
Control TaRbcs::FT fusion3
control LpRbcS::Fusion3

LXR LXR Control LXR+ FT fusion 1 FT fusion 1

FT fusion 1+ LXR

FIGURE 86
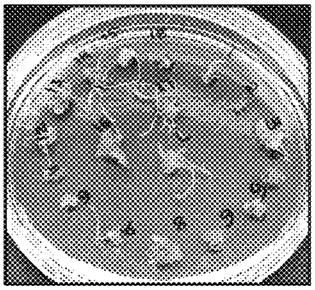
TaRbcS FT fusion 3
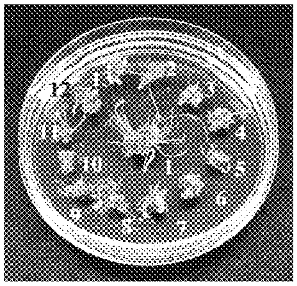
TaRbcS FT fusion 1
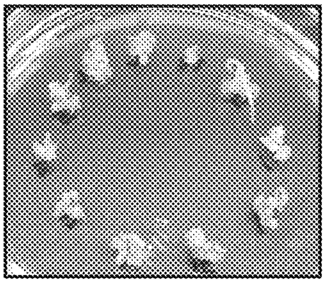
Control
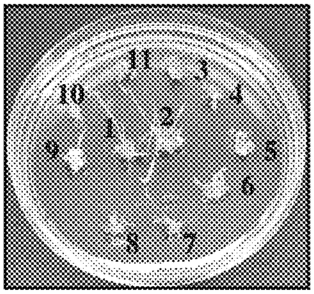
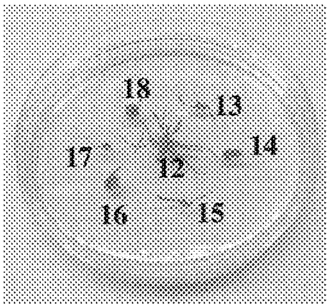
TaRbcS FT fusion plus LXR

SEQUENCE LISTING

```
<160> NUMBER OF SEQ ID NOS: 61

<210> SEQ ID NO 1
<211> LENGTH: 870
<212> TYPE: DNA
<213> ORGANISM: Lolium perenne

<400> SEQUENCE: 1

atcacccaca taggactacc agcctggccg accacctccg acgaagaaga aggccgcctc      60

caccgtcgaa cccgaggctg ctgccccagg cgtcctcgta ccgcgggaga atcccaaggt     120

caccccctcg caccggcgag aagcggaggg gatggcgcca tcccaccacc agccgccacc     180

ggtgtgccgc cgccgggagg caggggaggt cgcagcacag aggccaccgt cgcccctcca     240

tcctccgacc gccgccgccc cgccatcaca cgggaggccg gaagtccacc gccgccgccc     300

ccccatcggg aggcaggaag ccgccgccgc tgcatcgagg ggaggaccca gccgccgtcc     360

ccgccgcgcc atgagggaag cccaccgccg ccgcggtggc gggaggagct agggtttctg     420

gggtgcggga cgggcgggag gagctagggt ttctctatga ttaagtgcat gtattgcgaa     480

attaatgttt ctacttttgt catggccttc tagtccgtct aaaaaaagct gccttctagt     540

gggcgacatg gaactcagcg acattcctcc accacacgcg cagcgatcgt cctggccgat     600

ccagttgagc tcaacacccc tgtgccctgt acaggtgtcc ggcccagggc tcgccacacc     660

agccgcccca tccaggcaca tccaccctcc gagaacacga gagccaatcg caacgcagat     720

cgtgatttgt gagataagga cgtggccccc tcccctcgcg cgcacggcat ggtatttaag     780
```

ctccatgcgc tgctcctctc ttccccacgc agccaccgat caatagaagc agcagcacat 840
cagcagcttg ctctattccg tccaatagca 870

<210> SEQ ID NO 2
<211> LENGTH: 610
<212> TYPE: DNA
<213> ORGANISM: Lolium perenne

<400> SEQUENCE: 2
atctgttcat ctaccttact agtctgcatg attagtttat tcgttatttt cgtagtcatg 60
atttatcaat tactcgtacg gattatttca tatggatatt tgcttatatt tccaacaatt 120
tacactgtcg agttttggcg cggctgctgg agttactctt agagtagttg gacttgagac 180
aaaagctaga atatcaatta tatataggag tgaggagtta ttctttcgaa agaactttaa 240
acggtagctg cacttagtcg tcgcaatgaa atacttgtcg tactaccatg ataattggta 300
atatgagagg gaatattaat tcctcagtga tttgaatttt gtgtgctcat gtgcagtcac 360
ccacgccatg catccgacga cgggcggcta taccaactct tgcactgatc cggagggata 420
aggcgccatg caaccaggga acgtcgtcca ccccttccac atcctgtatc aaattaagga 480
acgggcgctg agcctatgcc gagacatata taatgcggcg actcggacat ggaggggcct 540
caggcatagc ccagctagtt atctcattct ctccttagca ataatactta gcaccatggc 600
ccccgcggtg 610

<210> SEQ ID NO 3
<211> LENGTH: 1938
<212> TYPE: DNA
<213> ORGANISM: Lolium perenne

<400> SEQUENCE: 3
atggagtcca gcgccgtcgt cgcccaaggc accacgtcgc cgctgctccc gtacgcctac 60
gcgccgctgc cgtcctctgc cgacgacgcc cgtgaaaacc agagtagcgg cggcggtgtc 120
aggtggcgcg cgtgcgcggc ctcggccctg gtggtgctgc tggtcgtcgt cggcttcttc 180
gcgggtggca gggtggatct gggtcaggac ggcgaggtgt ctgcgacttc ttcggttcct 240
gggagcagca ggggcaagga ttccggcgtg tcggagaagg agtcgcccgc cgacggcggc 300
ttcccgtgga gcaacgccat gctgcagtgg cagcacaccg ggttccattt ccagccactc 360
aagcactaca tgaacgatcc caacggtccg gtctactatg gcggatggta ccacctcttc 420
taccagcaca accccctatgg cgactcgtgg ggaaacgtat cttggggaca tgccgtgtcc 480
aaggacctgg tgaactggcg ccacctcccg gtcgccttgg tgcccgatca gtggtacgac 540
atcaacggcg tcctgacggg ctctatcaca gtgctcccag acgggcgtgt catcctgcta 600
tatacgggga acaccgacac cttttcgcag gtccagtgcc tcgcagtgcc cgccgaccca 660
tctgacccgc tcctccgtag ctggatcaag caccccgcca accccatcct cttcccgcca 720
cctgggatcg ggctcaagga cttccgtgac ccgctcacag cctggttcga acattccgac 780
aacacgtggc gcaccatcat cggatccaag gatgacgacg gccacgccgg catcgtcctt 840
agctacaaga ccaccgactt tgtgaattat gagctcatgc cagggaacat gcatcgtggc 900
cccgacggca ccggcatgta cgagtgcctt gacatctacc ctgtgggcgg caactcatcc 960
gagatgttgg gtggcgactc ctcacctgag gtgttgttcg tgctcaagga gagcgccaac 1020
gacgagtggc acgactacta cgcgcttggg tggtttgacg ctgccgccaa cacgtggacg 1080
ccacaggacc ccgaggcgga ccttgggatc ggcctcaggt acgactgggg caagtactac 1140

```
gcgtccaagt ccttctacga cccgatcaag aaccggcgtg tcgtttgggc tttcgtcggc   1200

gagaccgact ctgagcaggc cgacaaagcc aagggatggg cgtccctcat gtcgattccc   1260

aggacggtgg agcttgacaa gaagacccgg acgaacctga tccaatggcc agtggaggag   1320

atcgagaccc ttcgcaggaa cgtcacagac ctcggtggca tcaccgttga agccggctcc   1380

gtcattcacc ttcccctcca acaaggcggg cagcttgaca tcgaggcctc cttccgtctc   1440

aactcttcgg acatcgatgc actcaacgag gccgacgtcg gcttcaactg cagtagcagc   1500

gatggggcag ccgtgcgtgg tgcgctcggc ccctttggcc tcctcgtctt cgccgacggt   1560

cgccacgaac agacggcggc gtacttctac gtgtccaagg gcctcgacgg cagcctcctg   1620

acgcactact gccacgacga gtcacggtcg acgcgagcaa aggacgtcgt gagccgggtg   1680

gttggcggca ctgtgccagt gcttgacggt gaaacctttt cagtgagggt gctagtggac   1740

cactccatcg tgcagagctt cgtgatgggt gggaggacca cggtgacatc gcgggcatac   1800

ccgacggagg ccatctacgc cgcggcaggg gtgtacctgt tcaacaacgc aacgagcgcc   1860

accatcaccg ccgaagggct cgtcgtgtac gagatggcct cggccgagag tcgggccttc   1920

ttggctgacg acatgtag                                                 1938
```

<210> SEQ ID NO 4
<211> LENGTH: 645
<212> TYPE: PRT
<213> ORGANISM: Lolium perenne

<400> SEQUENCE: 4

```
Met Glu Ser Ser Ala Val Val Ala Gln Gly Thr Thr Ser Pro Leu Leu
1               5                   10                  15

Pro Tyr Ala Tyr Ala Pro Leu Pro Ser Ser Ala Asp Asp Ala Arg Glu
            20                  25                  30

Asn Gln Ser Ser Gly Gly Gly Val Arg Trp Arg Ala Cys Ala Ala Ser
        35                  40                  45

Ala Leu Val Val Leu Leu Val Val Val Gly Phe Phe Ala Gly Gly Arg
    50                  55                  60

Val Asp Leu Gly Gln Asp Gly Glu Val Ser Ala Thr Ser Ser Val Pro
65                  70                  75                  80

Gly Ser Ser Arg Gly Lys Asp Ser Gly Val Ser Glu Lys Glu Ser Pro
                85                  90                  95

Ala Asp Gly Gly Phe Pro Trp Ser Asn Ala Met Leu Gln Trp Gln His
            100                 105                 110

Thr Gly Phe His Phe Gln Pro Leu Lys His Tyr Met Asn Asp Pro Asn
        115                 120                 125

Gly Pro Val Tyr Tyr Gly Gly Trp Tyr His Leu Phe Tyr Gln His Asn
    130                 135                 140

Pro Tyr Gly Asp Ser Trp Gly Asn Val Ser Trp Gly His Ala Val Ser
145                 150                 155                 160

Lys Asp Leu Val Asn Trp Arg His Leu Pro Val Ala Leu Val Pro Asp
                165                 170                 175

Gln Trp Tyr Asp Ile Asn Gly Val Leu Thr Gly Ser Ile Thr Val Leu
            180                 185                 190

Pro Asp Gly Arg Val Ile Leu Leu Tyr Thr Gly Asn Thr Asp Thr Phe
        195                 200                 205

Ser Gln Val Gln Cys Leu Ala Val Pro Ala Asp Pro Ser Asp Pro Leu
    210                 215                 220
```

-continued

```
Leu Arg Ser Trp Ile Lys His Pro Ala Asn Pro Ile Leu Phe Pro Pro
225                 230                 235                 240

Pro Gly Ile Gly Leu Lys Asp Phe Arg Asp Pro Leu Thr Ala Trp Phe
                245                 250                 255

Glu His Ser Asp Asn Thr Trp Arg Thr Ile Ile Gly Ser Lys Asp Asp
            260                 265                 270

Asp Gly His Ala Gly Ile Val Leu Ser Tyr Lys Thr Thr Asp Phe Val
        275                 280                 285

Asn Tyr Glu Leu Met Pro Gly Asn Met His Arg Gly Pro Asp Gly Thr
    290                 295                 300

Gly Met Tyr Glu Cys Leu Asp Ile Tyr Pro Val Gly Gly Asn Ser Ser
305                 310                 315                 320

Glu Met Leu Gly Gly Asp Ser Ser Pro Glu Val Leu Phe Val Leu Lys
                325                 330                 335

Glu Ser Ala Asn Asp Glu Trp His Asp Tyr Tyr Ala Leu Gly Trp Phe
            340                 345                 350

Asp Ala Ala Ala Asn Thr Trp Thr Pro Gln Asp Pro Glu Ala Asp Leu
        355                 360                 365

Gly Ile Gly Leu Arg Tyr Asp Trp Gly Lys Tyr Tyr Ala Ser Lys Ser
    370                 375                 380

Phe Tyr Asp Pro Ile Lys Asn Arg Arg Val Val Trp Ala Phe Val Gly
385                 390                 395                 400

Glu Thr Asp Ser Glu Gln Ala Asp Lys Ala Lys Gly Trp Ala Ser Leu
                405                 410                 415

Met Ser Ile Pro Arg Thr Val Glu Leu Asp Lys Lys Thr Arg Thr Asn
            420                 425                 430

Leu Ile Gln Trp Pro Val Glu Glu Ile Glu Thr Leu Arg Arg Asn Val
        435                 440                 445

Thr Asp Leu Gly Gly Ile Thr Val Glu Ala Gly Ser Val Ile His Leu
    450                 455                 460

Pro Leu Gln Gln Gly Gly Gln Leu Asp Ile Glu Ala Ser Phe Arg Leu
465                 470                 475                 480

Asn Ser Ser Asp Ile Asp Ala Leu Asn Glu Ala Asp Val Gly Phe Asn
                485                 490                 495

Cys Ser Ser Ser Asp Gly Ala Ala Val Arg Gly Ala Leu Gly Pro Phe
            500                 505                 510

Gly Leu Leu Val Phe Ala Asp Gly Arg His Glu Gln Thr Ala Ala Tyr
        515                 520                 525

Phe Tyr Val Ser Lys Gly Leu Asp Gly Ser Leu Leu Thr His Tyr Cys
    530                 535                 540

His Asp Glu Ser Arg Ser Thr Arg Ala Lys Asp Val Val Ser Arg Val
545                 550                 555                 560

Val Gly Gly Thr Val Pro Val Leu Asp Gly Glu Thr Phe Ser Val Arg
                565                 570                 575

Val Leu Val Asp His Ser Ile Val Gln Ser Phe Val Met Gly Gly Arg
            580                 585                 590

Thr Thr Val Thr Ser Arg Ala Tyr Pro Thr Glu Ala Ile Tyr Ala Ala
        595                 600                 605

Ala Gly Val Tyr Leu Phe Asn Asn Ala Thr Ser Ala Thr Ile Thr Ala
    610                 615                 620

Glu Gly Leu Val Val Tyr Glu Met Ala Ser Ala Glu Ser Arg Ala Phe
625                 630                 635                 640

Leu Ala Asp Asp Met
```

-continued

645

<210> SEQ ID NO 5
<211> LENGTH: 1872
<212> TYPE: DNA
<213> ORGANISM: Lolium perenne

<400> SEQUENCE: 5

```
atggagtccc gggccattcc cagcgcggcg tacgcgccac ttctgccatc cgccgcagac     60

gacgtcgccc tggccaagca ggaccgcccc ggcgtggggt ggcgcgggtt cttaaccgtg    120

ctggccgcct gcggcgtggt ggtgctcctc gtcggtgcca ctttgctcgc ggggtccagg    180

atgggtcagg ccggagacgg cgaaggcaac accgacgagg acggggccgg agggttcccg    240

tggagcaacg agatgctgca gtggcagcgc gccgggttcc attaccagcc ggaggggcac    300

ttcatgagcg atccaaacgg tccggtatac taccgtggat attaccacct cttctttcag    360

tacaaccgaa gaggggtcgc gtgggatgac tacatagagt ggggccacgt ggtgtcccag    420

gacctggtac actggcgccc tctcccactg gccatgcggc ctgaccattg gtacgacaag    480

aagggcgtct tgtcgggtac catcacggtg ctccacaatg gcacgctcgt cctcctctac    540

acgggggtca cagaagaccc tatggccgag tcccagtgca tcgccgtccc gaccgacccc    600

aacgaccccc tccttcgcca ttggaccaag caccccgcca accccgttct cgctcaccca    660

cagggggtcc agggcatgga cttccgagac ccccaccagcg cgtggtggga caagtccgac    720

tccacgtggc gcattctcat cggttccaag gacgacgaca atggcagcca tgctggcatc    780

gccttcatct tcaagaccaa ggacttcctt agcttcgagc gtgtcccagg tatcgtgcat    840

cgtgtcgagg gtaccggcat gtgggagtgc atcgactttt accccgttgg aggtggccac    900

aactcttcgt cggaggagtt gtacgtgata aaggcgagca tggacgacga acgacacgac    960

tactactcat tggggaggta tgacgcggca gcgaacacat ggacgccatt ggacgccgag   1020

ctagacttgg ggattgggct gaggtacgac tggggcaagc tctacgcttc cacgtcgttc   1080

tacgatccac tgaagcagcg gcgaattatg ttggggtatg taggcgaggt cgactctgcg   1140

cgagccgacg ttgccaaggg atgggcctca cttcagtcga ttccgaggac agtggcacta   1200

gacgagaaga cccggacgaa cctcctccta tggccggtgg aggaggtgga ggccctccgc   1260

tacaactcca ccgacctcag cggcatcact gttgagaacg gctccatctt ccacctccct   1320

ctccaccaag ccactcagct ggacatcgag gcttccttcc gcctcgatgc ttctgatgtt   1380

gctgccatca acgaggccga cgtcggctac aactgcagca gcagcggtgg cgcggccgct   1440

cgtggcgctc tcgggccctt cggcctcctc gtccatgccg ccggagacct ccgtggcgag   1500

cagacggcgg tgtacttcta cgtgtccagg gccctcgacg gtagcctccg gaccagcttc   1560

tgcaacgacg agacgcggtc gtcacgggcc cgggacgtga cgaagcgggt ggtgggcagc   1620

acggtgccgg tgctcgacgg cgaggcgttg tcgatgaggg tgctcgtgga ccactccatc   1680

gtgcagagct tcgcgatggg tgggagggtc acggcgacgt cgcgagtgta cccgacggag   1740

gccatctacg ccagggctgg ggtgtacctg ttcaacaacg ccaccggcgc cagcgtgaca   1800

gcggagaggc tcatcgtgca cgagatggcg tcggcagtat acgacgagac cgtcatggtt   1860

aaggactcat ag                                                        1872
```

<210> SEQ ID NO 6
<211> LENGTH: 623
<212> TYPE: PRT
<213> ORGANISM: Lolium perenne

<400> SEQUENCE: 6

```
Met Glu Ser Arg Ala Ile Pro Ser Ala Ala Tyr Ala Pro Leu Leu Pro
1               5                   10                  15

Ser Ala Ala Asp Asp Val Ala Leu Ala Lys Gln Asp Arg Pro Gly Val
            20                  25                  30

Gly Trp Arg Gly Phe Leu Thr Val Leu Ala Ala Cys Gly Val Val Val
        35                  40                  45

Leu Leu Val Gly Ala Thr Leu Leu Ala Gly Ser Arg Met Gly Gln Ala
    50                  55                  60

Gly Asp Gly Glu Gly Asn Thr Asp Glu Asp Gly Ala Gly Gly Phe Pro
65                  70                  75                  80

Trp Ser Asn Glu Met Leu Gln Trp Gln Arg Ala Gly Phe His Tyr Gln
                85                  90                  95

Pro Glu Gly His Phe Met Ser Asp Pro Asn Gly Pro Val Tyr Tyr Arg
            100                 105                 110

Gly Tyr Tyr His Leu Phe Phe Gln Tyr Asn Arg Arg Gly Val Ala Trp
        115                 120                 125

Asp Asp Tyr Ile Glu Trp Gly His Val Val Ser Gln Asp Leu Val His
    130                 135                 140

Trp Arg Pro Leu Pro Leu Ala Met Arg Pro Asp His Trp Tyr Asp Lys
145                 150                 155                 160

Lys Gly Val Leu Ser Gly Thr Ile Thr Val Leu His Asn Gly Thr Leu
                165                 170                 175

Val Leu Leu Tyr Thr Gly Val Thr Glu Asp Pro Met Ala Glu Ser Gln
            180                 185                 190

Cys Ile Ala Val Pro Thr Asp Pro Asn Asp Pro Leu Leu Arg His Trp
        195                 200                 205

Thr Lys His Pro Ala Asn Pro Val Leu Ala His Pro Gln Gly Val Gln
    210                 215                 220

Gly Met Asp Phe Arg Asp Pro Thr Ser Ala Trp Trp Asp Lys Ser Asp
225                 230                 235                 240

Ser Thr Trp Arg Ile Leu Ile Gly Ser Lys Asp Asp Asp Asn Gly Ser
                245                 250                 255

His Ala Gly Ile Ala Phe Ile Phe Lys Thr Lys Asp Phe Leu Ser Phe
            260                 265                 270

Glu Arg Val Pro Gly Ile Val His Arg Val Glu Gly Thr Gly Met Trp
        275                 280                 285

Glu Cys Ile Asp Phe Tyr Pro Val Gly Gly Gly His Asn Ser Ser Ser
    290                 295                 300

Glu Glu Leu Tyr Val Ile Lys Ala Ser Met Asp Asp Glu Arg His Asp
305                 310                 315                 320

Tyr Tyr Ser Leu Gly Arg Tyr Asp Ala Ala Ala Asn Thr Trp Thr Pro
                325                 330                 335

Leu Asp Ala Glu Leu Asp Leu Gly Ile Gly Leu Arg Tyr Asp Trp Gly
            340                 345                 350

Lys Leu Tyr Ala Ser Thr Ser Phe Tyr Asp Pro Leu Lys Gln Arg Arg
        355                 360                 365

Ile Met Leu Gly Tyr Val Gly Glu Val Asp Ser Ala Arg Ala Asp Val
    370                 375                 380

Ala Lys Gly Trp Ala Ser Leu Gln Ser Ile Pro Arg Thr Val Ala Leu
385                 390                 395                 400

Asp Glu Lys Thr Arg Thr Asn Leu Leu Leu Trp Pro Val Glu Glu Val
```

```
                405                 410                 415

Glu Ala Leu Arg Tyr Asn Ser Thr Asp Leu Ser Gly Ile Thr Val Glu
            420                 425                 430

Asn Gly Ser Ile Phe His Leu Pro Leu His Gln Ala Thr Gln Leu Asp
        435                 440                 445

Ile Glu Ala Ser Phe Arg Leu Asp Ala Ser Asp Val Ala Ala Ile Asn
    450                 455                 460

Glu Ala Asp Val Gly Tyr Asn Cys Ser Ser Ser Gly Gly Ala Ala Ala
465                 470                 475                 480

Arg Gly Ala Leu Gly Pro Phe Gly Leu Leu Val His Ala Ala Gly Asp
                485                 490                 495

Leu Arg Gly Glu Gln Thr Ala Val Tyr Phe Tyr Val Ser Arg Ala Leu
            500                 505                 510

Asp Gly Ser Leu Arg Thr Ser Phe Cys Asn Asp Glu Thr Arg Ser Ser
        515                 520                 525

Arg Ala Arg Asp Val Thr Lys Arg Val Val Gly Ser Thr Val Pro Val
    530                 535                 540

Leu Asp Gly Glu Ala Leu Ser Met Arg Val Leu Val Asp His Ser Ile
545                 550                 555                 560

Val Gln Ser Phe Ala Met Gly Gly Arg Val Thr Ala Thr Ser Arg Val
                565                 570                 575

Tyr Pro Thr Glu Ala Ile Tyr Ala Arg Ala Gly Val Tyr Leu Phe Asn
            580                 585                 590

Asn Ala Thr Gly Ala Ser Val Thr Ala Glu Arg Leu Ile Val His Glu
        595                 600                 605

Met Ala Ser Ala Val Tyr Asp Glu Thr Val Met Val Lys Asp Ser
    610                 615                 620
```

<210> SEQ ID NO 7
<211> LENGTH: 3918
<212> TYPE: DNA
<213> ORGANISM: Artificial Sequence
<220> FEATURE:
<223> OTHER INFORMATION: Fusion construct

<400> SEQUENCE: 7

```
atggagtccc caagcgccgt cgtcccsggc accacggcgc cgctgcttcc ttatgcgtac     60

gcgccgctgc cgtcgtccgc cgacgacgcc cgtcaaaacc ggagtggcgg gaggtggcgc    120

gcgtgcgccg ccgtgctggc cgcatcggcg ttgtcggtgg tcgtcgtggt cgggctcctc    180

gcgggcggca gggtggatcg ggtcccggcc ggcggagacg tggcgtcggc cacggtgccg    240

gccgtgccga tggagttccc gaggagccgg ggcaaggact tcggcgtgtc ggagaagtcc    300

tccggtgcct actccaccga cggcgggttc ccgtggagca acgccatgct gcagtggcag    360

cgcaccgggt tccatttcca gccggagcag cactacatga acgatcccaa cggccccgtg    420

tactacggcg gatggtacca cctcttctac cagcacaacc ccaagggcga cagctggggc    480

aacatcgcgt gggcccacgc cgtctccaag gacatggtca actggcgcca cctccctctc    540

gccatggttc ccgaccagtg gtacgacagc aacggcgtcc tcaccggctc catcaccgtg    600

ctccccgacg gccaggtcat cctgctctac accggcaaca ccgacaccct agcccaggtc    660

cagtgcctcg ccacgcccgc cgacccgtcc gacccgctcc tccgcgagtg ggtcaagcac    720

cccgccaacc ccatcctcta ccctcccccc ggcatcggcc tcaaggactt ccgcgacccc    780

ctcaccgcct ggttcgacca ctccgaccac acctggcgca ccgtcatcgg ctccaaggac    840
```

-continued gacgacggcc acgccggcat catcctcagc tacaagacca aggacttcgt caactacgag 900
ctcatgccgg ggaacatgca ccgcgggccc gacggcaccg gaatgtacga gtgcatcgac 960
ctctaccccg tcggcggcaa ctcgtccgag atgctcggcg gcgacgactc gcccggcgtg 1020
ctcttcgtgc tcaaggagag cagcgacgac gagcgccacg actactacgc gctcggaagg 1080
ttcgaygccg tcgccaacgt ttggacgccc atcgaccggg agctggacct tgggatcggg 1140
ctcagatacg actggggaaa gtactacgcc tccaagtcct tctacgacca gaagaagaac 1200
cgccgcatcg tatgggcata catcggcgag accgactccg agcaggccga catcaccaag 1260
ggatgggcca atctcatgac gattccaaga acggtggagc ttgacaggaa gacccgcaca 1320
aacctcatcc aatggccagt ggaggaggtc gacaccctcc gcaggaactc cacggacctc 1380
ggtcgcatca ccgtcaacgc cggctccgtc attcgcctcc ccctccacca gggcgctcaa 1440
ctcgacatcg aggcctcctt ccaactcaac tcttccgacg tggatgctat caacgaggcc 1500
gacgtcggct acaactgcag caccagtggt gccgccgtac ggggggcgct cggccccttt 1560
ggcctcctcg tccttgccaa cggccgcacc gaacagacgg ctgtgtactt ctacgtgtcc 1620
aagggcgtcg acggtgccct ccagacccac ttctgccacg acgagtcacg gtcaacgcgg 1680
gcaaaggatg tcgtgaatag gatgattggc agcatcgtgc cggtgcttga cggtgagacc 1740
ttttcggtga gggtgctagt ggaccactcc atcgtgcaga gcttcgcgat gggcgggagg 1800
atcacggcga cgtcgcgggc gtacccgacg gaggccatct acgcggccgc gggggtctac 1860
ctcttcaaca acgccacggg cgccaccgtc accgccgaga ggctcgtcgt gcacgagatg 1920
gcctcagctg acaaccatat cttcacgaac gacgacttgg gaggaggaaa gcttggagga 1980
ggagagtcca gcgccgtcgt cgcccaaggc accacgtcgc cgctgctccc gtacgcctac 2040
gcgccgctgc cgtcctctgc cgacgacgcc cgtgaaaacc agagtagcgg cggcggtgtc 2100
aggtggcgcg cgtgcgcggc ctcggccctg gtggtgctgc tggtcgtcgt cggcttcttc 2160
gcgggtggca gggtggatct gggtcaggac ggcgaggtgt ctgcgacttc ttcggttcct 2220
gggagcagca ggggcaagga ttccggcgtg tcggagaagg agtcgcccgc cgacggcggc 2280
ttcccgtgga gcaacgccat gctgcagtgg cagcacaccg ggttccattt ccagccactc 2340
aagcactaca tgaacgatcc caacggtccg gtctactatg gcggatggta ccacctcttc 2400
taccagcaca accccctatgg cgactcgtgg ggaaacgtat cttggggaca tgccgtgtcc 2460
aaggacctgg tgaactggcg ccacctcccg gtcgccttgg tgcccgatca gtggtacgac 2520
atcaacggcg tcctgacggg ctctatcaca gtgctcccag acgggcgtgt catcctgcta 2580
tatacgggga acaccgacac cttttcgcag gtccagtgcc tcgcagtgcc cgccgaccca 2640
tctgacccgc tcctccgtag ctggatcaag caccccgcca accccatcct cttcccgcca 2700
cctgggatcg ggctcaagga cttccgtgac ccgctcacag cctggttcga acattccgac 2760
aacacgtggc gcaccatcat cggatccaag gatgacgacg gccacgccgg catcgtcctt 2820
agctacaaga ccaccgactt tgtgaattat gagctcatgc cagggaacat gcatcgtggc 2880
cccgacggca ccggcatgta cgagtgcctt gacatctacc ctgtgggcgg caactcatcc 2940
gagatgttgg gtggcgactc ctcacatgag gtgttgttcg tgctcaagga gagcgccaac 3000
gacgagtggc acgactacta cgcgcttggg tggtttgacg ctgccgccaa cacgtggacg 3060
ccacaggacc ccgaggcgga ccttgggatc ggcctcaggt acgactgggg caagtactac 3120
gcgtccaagt ccttctacga cccgatcaag aaccggcgtg tcgtttgggc tttcgtcggc 3180
gagaccgact ctgagcaggc cgacaaagcc aagggatggg cgtccctcat gtcgattccc 3240

-continued

```
aggacggtgg agcttgacaa gaagacccgg acgaacctga tccaatggcc agtggaggag   3300

atcgagaccc ttcgcaggaa cgtcacagac ctcggtggca tcaccgttga agccggctcc   3360

gtcattcacc ttcccctcca acaaggcggg cagcttgaca tcgaggcctc cttccgtctc   3420

aactcttcgg acatcgatgc actcaacgag gccgacgtcg gcttcaactg cagtagcagc   3480

gatggggtag ccgtgcgtgg tgcgctcggc ccctttggcc tcctcgtctt cgccgacggt   3540

cgccacgaac agacggcggc gtacttctac gtgtccaagg gcctcgacgg cagcctcctg   3600

acgcactact gccacgacga gtcacggtcg acgcgagcaa aggacgtcgt gagccgggtg   3660

gttggcggca ctgtgccagt gcttgacggt gaaacctttt cagtgagggt gctagtggac   3720

cactccatcg tgcagagctt cgtgatgggt gggaggacca cggtgacatc gcgggcatac   3780

ccgacggagg ccatctacgc cgcggcaggg gtgtacctgt tcaacaacgc aacgagcgcc   3840

accatcaccg ccgaagggct cgtcgtgtac gagatggcct cggccgagag tcgggccttc   3900

ttggctgacg acatgtag                                                 3918
```

```
<210> SEQ ID NO 8
<211> LENGTH: 1305
<212> TYPE: PRT
<213> ORGANISM: Artificial Sequence
<220> FEATURE:
<223> OTHER INFORMATION: Fusion construct

<400> SEQUENCE: 8

Met Glu Ser Pro Ser Ala Val Val Pro Gly Thr Thr Ala Pro Leu Leu
1               5                   10                  15

Pro Tyr Ala Tyr Ala Pro Leu Pro Ser Ser Ala Asp Asp Ala Arg Gln
            20                  25                  30

Asn Arg Ser Gly Gly Arg Trp Arg Ala Cys Ala Ala Val Leu Ala Ala
        35                  40                  45

Ser Ala Leu Ser Val Val Val Val Val Gly Leu Leu Ala Gly Gly Arg
    50                  55                  60

Val Asp Arg Val Pro Ala Gly Gly Asp Val Ala Ser Ala Thr Val Pro
65                  70                  75                  80

Ala Val Pro Met Glu Phe Pro Arg Ser Arg Gly Lys Asp Phe Gly Val
                85                  90                  95

Ser Glu Lys Ser Ser Gly Ala Tyr Ser Thr Asp Gly Gly Phe Pro Trp
            100                 105                 110

Ser Asn Ala Met Leu Gln Trp Gln Arg Thr Gly Phe His Phe Gln Pro
        115                 120                 125

Glu Gln His Tyr Met Asn Asp Pro Asn Gly Pro Val Tyr Tyr Gly Gly
    130                 135                 140

Trp Tyr His Leu Phe Tyr Gln His Asn Pro Lys Gly Asp Ser Trp Gly
145                 150                 155                 160

Asn Ile Ala Trp Ala His Ala Val Ser Lys Asp Met Val Asn Trp Arg
                165                 170                 175

His Leu Pro Leu Ala Met Val Pro Asp Gln Trp Tyr Asp Ser Asn Gly
            180                 185                 190

Val Leu Thr Gly Ser Ile Thr Val Leu Pro Asp Gly Gln Val Ile Leu
        195                 200                 205

Leu Tyr Thr Gly Asn Thr Asp Thr Leu Ala Gln Val Gln Cys Leu Ala
    210                 215                 220

Thr Pro Ala Asp Pro Ser Asp Pro Leu Leu Arg Glu Trp Val Lys His
225                 230                 235                 240
```

```
Pro Ala Asn Pro Ile Leu Tyr Pro Pro Pro Gly Ile Gly Leu Lys Asp
                245                 250                 255

Phe Arg Asp Pro Leu Thr Ala Trp Phe Asp His Ser Asp His Thr Trp
            260                 265                 270

Arg Thr Val Ile Gly Ser Lys Asp Asp Asp Gly His Ala Gly Ile Ile
        275                 280                 285

Leu Ser Tyr Lys Thr Lys Asp Phe Val Asn Tyr Glu Leu Met Pro Gly
    290                 295                 300

Asn Met His Arg Gly Pro Asp Gly Thr Gly Met Tyr Glu Cys Ile Asp
305                 310                 315                 320

Leu Tyr Pro Val Gly Gly Asn Ser Ser Glu Met Leu Gly Gly Asp Asp
                325                 330                 335

Ser Pro Gly Val Leu Phe Val Leu Lys Glu Ser Ser Asp Asp Glu Arg
            340                 345                 350

His Asp Tyr Tyr Ala Leu Gly Arg Phe Asp Ala Val Ala Asn Val Trp
        355                 360                 365

Thr Pro Ile Asp Arg Glu Leu Asp Leu Gly Ile Gly Leu Arg Tyr Asp
    370                 375                 380

Trp Gly Lys Tyr Tyr Ala Ser Lys Ser Phe Tyr Asp Gln Lys Lys Asn
385                 390                 395                 400

Arg Arg Ile Val Trp Ala Tyr Ile Gly Glu Thr Asp Ser Glu Gln Ala
                405                 410                 415

Asp Ile Thr Lys Gly Trp Ala Asn Leu Met Thr Ile Pro Arg Thr Val
            420                 425                 430

Glu Leu Asp Arg Lys Thr Arg Thr Asn Leu Ile Gln Trp Pro Val Glu
        435                 440                 445

Glu Val Asp Thr Leu Arg Arg Asn Ser Thr Asp Leu Gly Arg Ile Thr
    450                 455                 460

Val Asn Ala Gly Ser Val Ile Arg Leu Pro Leu His Gln Gly Ala Gln
465                 470                 475                 480

Leu Asp Ile Glu Ala Ser Phe Gln Leu Asn Ser Ser Asp Val Asp Ala
                485                 490                 495

Ile Asn Glu Ala Asp Val Gly Tyr Asn Cys Ser Thr Ser Gly Ala Ala
            500                 505                 510

Val Arg Gly Ala Leu Gly Pro Phe Gly Leu Leu Val Leu Ala Asn Gly
        515                 520                 525

Arg Thr Glu Gln Thr Ala Val Tyr Phe Tyr Val Ser Lys Gly Val Asp
    530                 535                 540

Gly Ala Leu Gln Thr His Phe Cys His Asp Glu Ser Arg Ser Thr Arg
545                 550                 555                 560

Ala Lys Asp Val Val Asn Arg Met Ile Gly Ser Ile Val Pro Val Leu
                565                 570                 575

Asp Gly Glu Thr Phe Ser Val Arg Val Leu Val Asp His Ser Ile Val
            580                 585                 590

Gln Ser Phe Ala Met Gly Gly Arg Ile Thr Ala Thr Ser Arg Ala Tyr
        595                 600                 605

Pro Thr Glu Ala Ile Tyr Ala Ala Ala Gly Val Tyr Leu Phe Asn Asn
    610                 615                 620

Ala Thr Gly Ala Thr Val Thr Ala Glu Arg Leu Val Val His Glu Met
625                 630                 635                 640

Ala Ser Ala Asp Asn His Ile Phe Thr Asn Asp Asp Leu Gly Gly Gly
                645                 650                 655
```

-continued

```
Lys Leu Gly Gly Gly Glu Ser Ser Ala Val Val Ala Gln Gly Thr Thr
            660                 665                 670

Ser Pro Leu Leu Pro Tyr Ala Tyr Ala Pro Leu Pro Ser Ser Ala Asp
        675                 680                 685

Asp Ala Arg Glu Asn Gln Ser Ser Gly Gly Gly Val Arg Trp Arg Ala
    690                 695                 700

Cys Ala Ala Ser Ala Leu Val Val Leu Leu Val Val Val Gly Phe Phe
705                 710                 715                 720

Ala Gly Gly Arg Val Asp Leu Gly Gln Asp Gly Glu Val Ser Ala Thr
                725                 730                 735

Ser Ser Val Pro Gly Ser Ser Arg Gly Lys Asp Ser Gly Val Ser Glu
            740                 745                 750

Lys Glu Ser Pro Ala Asp Gly Gly Phe Pro Trp Ser Asn Ala Met Leu
        755                 760                 765

Gln Trp Gln His Thr Gly Phe His Phe Gln Pro Leu Lys His Tyr Met
    770                 775                 780

Asn Asp Pro Asn Gly Pro Val Tyr Tyr Gly Gly Trp Tyr His Leu Phe
785                 790                 795                 800

Tyr Gln His Asn Pro Tyr Gly Asp Ser Trp Gly Asn Val Ser Trp Gly
                805                 810                 815

His Ala Val Ser Lys Asp Leu Val Asn Trp Arg His Leu Pro Val Ala
            820                 825                 830

Leu Val Pro Asp Gln Trp Tyr Asp Ile Asn Gly Val Leu Thr Gly Ser
        835                 840                 845

Ile Thr Val Leu Pro Asp Gly Arg Val Ile Leu Leu Tyr Thr Gly Asn
    850                 855                 860

Thr Asp Thr Phe Ser Gln Val Gln Cys Leu Ala Val Pro Ala Asp Pro
865                 870                 875                 880

Ser Asp Pro Leu Leu Arg Ser Trp Ile Lys His Pro Ala Asn Pro Ile
                885                 890                 895

Leu Phe Pro Pro Pro Gly Ile Gly Leu Lys Asp Phe Arg Asp Pro Leu
            900                 905                 910

Thr Ala Trp Phe Glu His Ser Asp Asn Thr Trp Arg Thr Ile Ile Gly
        915                 920                 925

Ser Lys Asp Asp Asp Gly His Ala Gly Ile Val Leu Ser Tyr Lys Thr
    930                 935                 940

Thr Asp Phe Val Asn Tyr Glu Leu Met Pro Gly Asn Met His Arg Gly
945                 950                 955                 960

Pro Asp Gly Thr Gly Met Tyr Glu Cys Leu Asp Ile Tyr Pro Val Gly
                965                 970                 975

Gly Asn Ser Ser Glu Met Leu Gly Gly Asp Ser Ser His Glu Val Leu
            980                 985                 990

Phe Val Leu Lys Glu Ser Ala Asn  Asp Glu Trp His Asp  Tyr Tyr Ala
        995                 1000                 1005

Leu Gly  Trp Phe Asp Ala Ala  Ala Asn Thr Trp Thr  Pro Gln Asp
    1010                 1015                 1020

Pro Glu  Ala Asp Leu Gly Ile  Gly Leu Arg Tyr Asp  Trp Gly Lys
    1025                 1030                 1035

Tyr Tyr  Ala Ser Lys Ser Phe  Tyr Asp Pro Ile Lys  Asn Arg Arg
    1040                 1045                 1050

Val Val  Trp Ala Phe Val Gly  Glu Thr Asp Ser Glu  Gln Ala Asp
    1055                 1060                 1065

Lys Ala  Lys Gly Trp Ala Ser  Leu Met Ser Ile Pro  Arg Thr Val
```

1070 1075 1080

Glu Leu Asp Lys Lys Thr Arg Thr Asn Leu Ile Gln Trp Pro Val
1085 1090 1095

Glu Glu Ile Glu Thr Leu Arg Arg Asn Val Thr Asp Leu Gly Gly
1100 1105 1110

Ile Thr Val Glu Ala Gly Ser Val Ile His Leu Pro Leu Gln Gln
1115 1120 1125

Gly Gly Gln Leu Asp Ile Glu Ala Ser Phe Arg Leu Asn Ser Ser
1130 1135 1140

Asp Ile Asp Ala Leu Asn Glu Ala Asp Val Gly Phe Asn Cys Ser
1145 1150 1155

Ser Ser Asp Gly Val Ala Val Arg Gly Ala Leu Gly Pro Phe Gly
1160 1165 1170

Leu Leu Val Phe Ala Asp Gly Arg His Glu Gln Thr Ala Ala Tyr
1175 1180 1185

Phe Tyr Val Ser Lys Gly Leu Asp Gly Ser Leu Leu Thr His Tyr
1190 1195 1200

Cys His Asp Glu Ser Arg Ser Thr Arg Ala Lys Asp Val Val Ser
1205 1210 1215

Arg Val Val Gly Gly Thr Val Pro Val Leu Asp Gly Glu Thr Phe
1220 1225 1230

Ser Val Arg Val Leu Val Asp His Ser Ile Val Gln Ser Phe Val
1235 1240 1245

Met Gly Gly Arg Thr Thr Val Thr Ser Arg Ala Tyr Pro Thr Glu
1250 1255 1260

Ala Ile Tyr Ala Ala Ala Gly Val Tyr Leu Phe Asn Asn Ala Thr
1265 1270 1275

Ser Ala Thr Ile Thr Ala Glu Gly Leu Val Val Tyr Glu Met Ala
1280 1285 1290

Ser Ala Glu Ser Arg Ala Phe Leu Ala Asp Asp Met
1295 1300 1305

<210> SEQ ID NO 9
<211> LENGTH: 3924
<212> TYPE: DNA
<213> ORGANISM: Artificial Sequence
<220> FEATURE:
<223> OTHER INFORMATION: Fusion construct

<400> SEQUENCE: 9
atggagtccc caagcgccgt cgtccccggc accacggcgc cgctgcttcc ttatgcgtac 60
gcgccgctgc cgtcgtccgc cgacgacgcc cgtcaaaacc ggagtggcgg gaggtggcgc 120
gcgtgcgccg ccgtgctggc cgcatcggcg ttggcggtgg tcgtcgtggt cgggctcctc 180
gcgggcggca gggtggatcg ggtcccagcc ggcggagacg tggcgtcggc cacggtgccg 240
gccgtgccga tggagttccc gaggagccgg ggcaaggact tcggcgtgtc ggagaagtcc 300
tccggtgcct actccaccga cggcgggttc ccgtggagca acgccatgct gcagtggcag 360
cgcaccgggt tccatttcca gccggagcag cactacatga acgatcccaa cggccccgtg 420
tactacggcg gatggtacca cctcttctac cagcacaacc ccaagggcga cagctggggc 480
aacatcgcgt gggcccacgc cgtctccaag gacatggtca actggcgcca cctccctctc 540
gccatggttc ccgaccagtg gtacgacagc aacggcgtcc tcaccggctc catcaccgtg 600
ctccccgacg gccaggtcat cctgctctac accggcaaca ccgacaccct agcccaggtc 660

-continued

```
cagtgcctcg ccacgcccgc cgacccgtcc gacccgctcc tccgcgagtg ggtcaagcac    720
cccgccaacc ccatcctcta ccctcccccc ggcatcggcc tcaaggactt ccgcgacccc    780
ctcaccgcct ggttcgacca ctccgaccac acctggcgca ccgtcatcgg ctccaaggac    840
gacgacggcc acgccggcat catcctcagc tacaagacca aggacttcgt caactacgag    900
ctcatgccgg ggaacatgca ccgcgggccc gacggcaccg gaatgtacga gtgcatcgac    960
ctctaccccg tcggcggcaa ctcgtccgag atgctcggcg gcgacgactc gcccggcgtg   1020
ctcttcgtgc tcaaggagag cagcgacgac gagcgccacg actactacgc gctcggaagg   1080
ttcgacgccg tcgccaacgt ttggacgccc atcgaccggg agctggacct tgggatcggg   1140
ctcagatacg actggggaaa gtactacgcc tccaagtcct tctacgacca gaagaagaac   1200
cgccgcatcg tatgggcata catcggcgag accgactccg agcaggccga catcaccaag   1260
ggatgggcca atctcatgac gattccaaga acggtggagc ttgacaggaa gacccgcaca   1320
aacctcatcc aatggccagt ggaggaggtc gacaccctcc gcaggaactc cacggacctc   1380
ggtcgcatca ccgtcaacgc cggctccgtc attcgcctcc ccctccacca gggcgctcaa   1440
ctcgacatcg aggcctcctt ccaactcaac tcttccgacg tggatgctat caacgaggcc   1500
gacgtcggct acaactgcag caccagtggt gccgccgtac ggggggcgct cggccccttt   1560
ggcctcctcg tccttgccaa cggccgcacc gaacagacgg ctgtgtactt ctacgtgtcc   1620
aagggcgtcg acggtgccct ccagacccac ttctgccacg acgagtcacg gtcaacgcgg   1680
gcaaaggatg tcgtgaatag gatgattggc agcatcgtgc cggtgcttga cggtgagacc   1740
ttttcggtga gggtgctagt ggaccactcc atcgtgcaga gcttcgcgat gggcgggagg   1800
atcacggcga cgtcgcgggc gtacccgacg gaggccatct acgcggccgc gggggtctac   1860
ctcttcaaca acgccacggg cgccaccgtc accgccgaga ggctcgtcgt gcacgagatg   1920
gcctcagctg acaaccatat cttcacgaac gacgacttgg gaggaggaaa gcttaagctt   1980
ggaggaggag agtccagcgc cgtcgtcgcc caaggcacca cgtcgccgct gctcccgtac   2040
gcctacgcgc cgctgccgtc ctctgccgac gacgcccgtg aaaaccagag tagcggcggc   2100
ggtgtcaggt ggcgcgcgtg cgcggcctcg gccctggtgg tgctgctggt cgtcgtcggc   2160
ttcttcgcgg gtggcagggt ggatctgggt caggacggcg aggtgtctgc gacttcttcg   2220
gttcctggga gcagcagggg caaggattcc ggcgtgtcgg agaaggagtc gcccgccgac   2280
ggcggcttcc cgtggagcaa cgccatgctg cagtggcagc acaccgggtt ccatttccag   2340
ccactcaagc actacatgaa cgatcccaac ggtccggtct actatggcgg atggtaccac   2400
ctcttctacc agcacaaccc ctatggcgac tcgtggggaa acgtatcttg gggacatgcc   2460
gtgtccaagg acctggtgaa ctggcgccac ctcccggtcg ccttggtgcc cgatcagtgg   2520
tacgacatca acggcgtcct gacgggctct atcacagtgc tcccagacgg gcgtgtcatc   2580
ctgctatata cggggaacac cgacaccttt tcgcaggtcc agtgcctcgc agtgcccgcc   2640
gacccatctg acccgctcct ccgtagctgg atcaagcacc ccgccaaccc catcctcttc   2700
ccgccacctg ggatcgggct caaggacttc cgtgacccgc tcacagcctg gttcgaacat   2760
tccgacaaca cgtggcgcac catcatcgga tccaaggatg acgacggcca cgccggcatc   2820
gtccttagct acaagaccac cgactttgtg aattatgagc tcatgccagg gaacatgcat   2880
cgtggccccg acggcaccgg catgtacgag tgccttgaca tctaccctgt gggcggcaac   2940
tcatccgaga tgttgggtgg cgactcctca cctgaggtgt tgttcgtgct caaggagagc   3000
gccaacgacg agtggcacga ctactacgcg cttgggtggt ttgacgctgc cgccaacacg   3060
```

-continued tggacgccac aggaccccga ggcggacctt gggatcggcc tcaggtacga ctggggcaag 3120
tactacgcgt ccaagtcctt ctacgacccg atcaagaacc ggcgtgtcgt ttgggctttc 3180
gtcggcgaga ccgactctga gcaggccgac aaagccaagg gatgggcgtc cctcatgtcg 3240
attcccagga cggtggagct tgacaagaag acccggacga acctgatcca atggccagtg 3300
gaggagatcg agacccttcg caggaacgtc acagacctcg gtggcatcac cgttgaagcc 3360
ggctccgtca ttcaccttcc cctccaacaa ggcgggcagc ttgacatcga ggcctccttc 3420
cgtctcaact cttcggacat cgatgcactc aacgaggccg acgtcggctt caactgcagt 3480
agcagcgatg gggcagccgt gcgtggtgcg ctcggcccct ttggcctcct cgtcttcgcc 3540
gacggtcgcc acgaacagac ggcggcgtac ttctacgtgt ccaagggcct cgacggcagc 3600
ctcctgacgc actactgcca cgacgagtca cggtcgacgc gagcaaagga cgtcgtgagc 3660
cgggtggttg gcggcactgt gccagtgctt gacggtgaaa ccttttcagt gagggtgcta 3720
gtggaccact ccatcgtgca gagcttcgtg atgggtggga ggaccacggt gacatcgcgg 3780
gcatacccga cggaggccat ctacgccgcg gcaggggtgt acctgttcaa caacgcaacg 3840
agcgccacca tcaccgccga agggctcgtc gtgtacgaga tggcctcggc cgagagtcgg 3900
gccttcttgg ctgacgacat gtag 3924

<210> SEQ ID NO 10
<211> LENGTH: 1307
<212> TYPE: PRT
<213> ORGANISM: Artificial Sequence
<220> FEATURE:
<223> OTHER INFORMATION: Fusion construct

<400> SEQUENCE: 10

Met Glu Ser Pro Ser Ala Val Val Pro Gly Thr Thr Ala Pro Leu Leu
1 5 10 15

Pro Tyr Ala Tyr Ala Pro Leu Pro Ser Ser Ala Asp Asp Ala Arg Gln
20 25 30

Asn Arg Ser Gly Gly Arg Trp Arg Ala Cys Ala Ala Val Leu Ala Ala
35 40 45

Ser Ala Leu Ala Val Val Val Val Val Gly Leu Leu Ala Gly Gly Arg
50 55 60

Val Asp Arg Val Pro Ala Gly Gly Asp Val Ala Ser Ala Thr Val Pro
65 70 75 80

Ala Val Pro Met Glu Phe Pro Arg Ser Arg Gly Lys Asp Phe Gly Val
85 90 95

Ser Glu Lys Ser Ser Gly Ala Tyr Ser Thr Asp Gly Gly Phe Pro Trp
100 105 110

Ser Asn Ala Met Leu Gln Trp Gln Arg Thr Gly Phe His Phe Gln Pro
115 120 125

Glu Gln His Tyr Met Asn Asp Pro Asn Gly Pro Val Tyr Tyr Gly Gly
130 135 140

Trp Tyr His Leu Phe Tyr Gln His Asn Pro Lys Gly Asp Ser Trp Gly
145 150 155 160

Asn Ile Ala Trp Ala His Ala Val Ser Lys Asp Met Val Asn Trp Arg
165 170 175

His Leu Pro Leu Ala Met Val Pro Asp Gln Trp Tyr Asp Ser Asn Gly
180 185 190

Val Leu Thr Gly Ser Ile Thr Val Leu Pro Asp Gly Gln Val Ile Leu
195 200 205

-continued

```
Leu Tyr Thr Gly Asn Thr Asp Thr Leu Ala Gln Val Gln Cys Leu Ala
    210                 215                 220

Thr Pro Ala Asp Pro Ser Asp Pro Leu Leu Arg Glu Trp Val Lys His
225                 230                 235                 240

Pro Ala Asn Pro Ile Leu Tyr Pro Pro Pro Gly Ile Gly Leu Lys Asp
                245                 250                 255

Phe Arg Asp Pro Leu Thr Ala Trp Phe Asp His Ser Asp His Thr Trp
            260                 265                 270

Arg Thr Val Ile Gly Ser Lys Asp Asp Asp Gly His Ala Gly Ile Ile
        275                 280                 285

Leu Ser Tyr Lys Thr Lys Asp Phe Val Asn Tyr Glu Leu Met Pro Gly
    290                 295                 300

Asn Met His Arg Gly Pro Asp Gly Thr Gly Met Tyr Glu Cys Ile Asp
305                 310                 315                 320

Leu Tyr Pro Val Gly Gly Asn Ser Ser Glu Met Leu Gly Gly Asp Asp
                325                 330                 335

Ser Pro Gly Val Leu Phe Val Leu Lys Glu Ser Ser Asp Asp Glu Arg
            340                 345                 350

His Asp Tyr Tyr Ala Leu Gly Arg Phe Asp Ala Val Ala Asn Val Trp
        355                 360                 365

Thr Pro Ile Asp Arg Glu Leu Asp Leu Gly Ile Gly Leu Arg Tyr Asp
    370                 375                 380

Trp Gly Lys Tyr Tyr Ala Ser Lys Ser Phe Tyr Asp Gln Lys Lys Asn
385                 390                 395                 400

Arg Arg Ile Val Trp Ala Tyr Ile Gly Glu Thr Asp Ser Glu Gln Ala
                405                 410                 415

Asp Ile Thr Lys Gly Trp Ala Asn Leu Met Thr Ile Pro Arg Thr Val
            420                 425                 430

Glu Leu Asp Arg Lys Thr Arg Thr Asn Leu Ile Gln Trp Pro Val Glu
        435                 440                 445

Glu Val Asp Thr Leu Arg Arg Asn Ser Thr Asp Leu Gly Arg Ile Thr
    450                 455                 460

Val Asn Ala Gly Ser Val Ile Arg Leu Pro Leu His Gln Gly Ala Gln
465                 470                 475                 480

Leu Asp Ile Glu Ala Ser Phe Gln Leu Asn Ser Ser Asp Val Asp Ala
                485                 490                 495

Ile Asn Glu Ala Asp Val Gly Tyr Asn Cys Ser Thr Ser Gly Ala Ala
            500                 505                 510

Val Arg Gly Ala Leu Gly Pro Phe Gly Leu Leu Val Leu Ala Asn Gly
        515                 520                 525

Arg Thr Glu Gln Thr Ala Val Tyr Phe Tyr Val Ser Lys Gly Val Asp
    530                 535                 540

Gly Ala Leu Gln Thr His Phe Cys His Asp Glu Ser Arg Ser Thr Arg
545                 550                 555                 560

Ala Lys Asp Val Val Asn Arg Met Ile Gly Ser Ile Val Pro Val Leu
                565                 570                 575

Asp Gly Glu Thr Phe Ser Val Arg Val Leu Val Asp His Ser Ile Val
            580                 585                 590

Gln Ser Phe Ala Met Gly Gly Arg Ile Thr Ala Thr Ser Arg Ala Tyr
        595                 600                 605

Pro Thr Glu Ala Ile Tyr Ala Ala Ala Gly Val Tyr Leu Phe Asn Asn
    610                 615                 620
```

-continued

```
Ala Thr Gly Ala Thr Val Thr Ala Glu Arg Leu Val Val His Glu Met
625                 630                 635                 640

Ala Ser Ala Asp Asn His Ile Phe Thr Asn Asp Asp Leu Gly Gly Gly
                645                 650                 655

Lys Leu Lys Leu Gly Gly Gly Glu Ser Ser Ala Val Val Ala Gln Gly
            660                 665                 670

Thr Thr Ser Pro Leu Leu Pro Tyr Ala Tyr Ala Pro Leu Pro Ser Ser
        675                 680                 685

Ala Asp Asp Ala Arg Glu Asn Gln Ser Ser Gly Gly Gly Val Arg Trp
    690                 695                 700

Arg Ala Cys Ala Ala Ser Ala Leu Val Val Leu Leu Val Val Val Gly
705                 710                 715                 720

Phe Phe Ala Gly Gly Arg Val Asp Leu Gly Gln Asp Gly Glu Val Ser
                725                 730                 735

Ala Thr Ser Ser Val Pro Gly Ser Ser Arg Gly Lys Asp Ser Gly Val
            740                 745                 750

Ser Glu Lys Glu Ser Pro Ala Asp Gly Gly Phe Pro Trp Ser Asn Ala
        755                 760                 765

Met Leu Gln Trp Gln His Thr Gly Phe His Phe Gln Pro Leu Lys His
    770                 775                 780

Tyr Met Asn Asp Pro Asn Gly Pro Val Tyr Tyr Gly Gly Trp Tyr His
785                 790                 795                 800

Leu Phe Tyr Gln His Asn Pro Tyr Gly Asp Ser Trp Gly Asn Val Ser
                805                 810                 815

Trp Gly His Ala Val Ser Lys Asp Leu Val Asn Trp Arg His Leu Pro
            820                 825                 830

Val Ala Leu Val Pro Asp Gln Trp Tyr Asp Ile Asn Gly Val Leu Thr
        835                 840                 845

Gly Ser Ile Thr Val Leu Pro Asp Gly Arg Val Ile Leu Leu Tyr Thr
    850                 855                 860

Gly Asn Thr Asp Thr Phe Ser Gln Val Gln Cys Leu Ala Val Pro Ala
865                 870                 875                 880

Asp Pro Ser Asp Pro Leu Leu Arg Ser Trp Ile Lys His Pro Ala Asn
                885                 890                 895

Pro Ile Leu Phe Pro Pro Pro Gly Ile Gly Leu Lys Asp Phe Arg Asp
            900                 905                 910

Pro Leu Thr Ala Trp Phe Glu His Ser Asp Asn Thr Trp Arg Thr Ile
        915                 920                 925

Ile Gly Ser Lys Asp Asp Asp Gly His Ala Gly Ile Val Leu Ser Tyr
    930                 935                 940

Lys Thr Thr Asp Phe Val Asn Tyr Glu Leu Met Pro Gly Asn Met His
945                 950                 955                 960

Arg Gly Pro Asp Gly Thr Gly Met Tyr Glu Cys Leu Asp Ile Tyr Pro
                965                 970                 975

Val Gly Gly Asn Ser Ser Glu Met Leu Gly Gly Asp Ser Ser Pro Glu
            980                 985                 990

Val Leu Phe Val Leu Lys Glu Ser  Ala Asn Asp Glu Trp  His Asp Tyr
        995                 1000                 1005

Tyr Ala  Leu Gly Trp Phe Asp  Ala Ala Ala Asn Thr  Trp Thr Pro
    1010                 1015                 1020

Gln Asp  Pro Glu Ala Asp Leu  Gly Ile Gly Leu Arg  Tyr Asp Trp
    1025                 1030                 1035

Gly Lys  Tyr Tyr Ala Ser Lys  Ser Phe Tyr Asp Pro  Ile Lys Asn
```

1040 1045 1050

Arg Arg Val Val Trp Ala Phe Val Gly Glu Thr Asp Ser Glu Gln
1055 1060 1065

Ala Asp Lys Ala Lys Gly Trp Ala Ser Leu Met Ser Ile Pro Arg
1070 1075 1080

Thr Val Glu Leu Asp Lys Lys Thr Arg Thr Asn Leu Ile Gln Trp
1085 1090 1095

Pro Val Glu Glu Ile Glu Thr Leu Arg Arg Asn Val Thr Asp Leu
1100 1105 1110

Gly Gly Ile Thr Val Glu Ala Gly Ser Val Ile His Leu Pro Leu
1115 1120 1125

Gln Gln Gly Gly Gln Leu Asp Ile Glu Ala Ser Phe Arg Leu Asn
1130 1135 1140

Ser Ser Asp Ile Asp Ala Leu Asn Glu Ala Asp Val Gly Phe Asn
1145 1150 1155

Cys Ser Ser Ser Asp Gly Ala Ala Val Arg Gly Ala Leu Gly Pro
1160 1165 1170

Phe Gly Leu Leu Val Phe Ala Asp Gly Arg His Glu Gln Thr Ala
1175 1180 1185

Ala Tyr Phe Tyr Val Ser Lys Gly Leu Asp Gly Ser Leu Leu Thr
1190 1195 1200

His Tyr Cys His Asp Glu Ser Arg Ser Thr Arg Ala Lys Asp Val
1205 1210 1215

Val Ser Arg Val Val Gly Gly Thr Val Pro Val Leu Asp Gly Glu
1220 1225 1230

Thr Phe Ser Val Arg Val Leu Val Asp His Ser Ile Val Gln Ser
1235 1240 1245

Phe Val Met Gly Gly Arg Thr Thr Val Thr Ser Arg Ala Tyr Pro
1250 1255 1260

Thr Glu Ala Ile Tyr Ala Ala Ala Gly Val Tyr Leu Phe Asn Asn
1265 1270 1275

Ala Thr Ser Ala Thr Ile Thr Ala Glu Gly Leu Val Val Tyr Glu
1280 1285 1290

Met Ala Ser Ala Glu Ser Arg Ala Phe Leu Ala Asp Asp Met
1295 1300 1305

<210> SEQ ID NO 11
<211> LENGTH: 648
<212> TYPE: PRT
<213> ORGANISM: Lolium perenne

<400> SEQUENCE: 11

Met Asp Ser Ser Arg Val Ile Leu Ile Pro Gly Thr Pro Pro Leu Pro
1 5 10 15

Tyr Ala Tyr Glu Gln Leu Pro Ser Ser Ser Ala Asp Ala Lys Gly Ile
20 25 30

Glu Glu Glu Arg Ala Gly Gly Gly Gly Leu Arg Trp Arg Ala Cys Ala
35 40 45

Ala Val Leu Ala Ala Ser Ala Val Val Ala Leu Val Val Ala Ala Ala
50 55 60

Val Phe Gly Ala Ser Gly Ala Gly Trp Asp Ala Val Ala Ala Ser Val
65 70 75 80

Pro Ala Thr Pro Ala Thr Glu Phe Pro Arg Ser Arg Gly Lys Glu His
85 90 95

-continued

```
Gly Val Ser Glu Lys Thr Ser Gly Ala Tyr Ser Ala Asn Ala Phe Pro
            100                 105                 110

Trp Ser Asn Ala Met Leu Gln Trp Gln Arg Thr Gly Tyr His Phe Gln
        115                 120                 125

Pro Asp Lys Tyr Tyr Gln Asn Asp Pro Asn Gly Pro Val Tyr Tyr Gly
    130                 135                 140

Gly Trp Tyr His Phe Phe Tyr Gln Tyr Asn Pro Ser Gly Ser Val Trp
145                 150                 155                 160

Glu Pro Gln Ile Val Trp Gly His Ala Val Ser Lys Asp Leu Ile His
                165                 170                 175

Trp Arg His Leu Pro Pro Ala Leu Val Pro Asp Gln Trp Tyr Asp Ile
            180                 185                 190

Lys Gly Val Leu Thr Gly Ser Ile Thr Val Leu Pro Asp Gly Lys Val
        195                 200                 205

Ile Leu Leu Tyr Thr Gly Asn Thr Glu Thr Phe Ala Gln Val Thr Cys
    210                 215                 220

Leu Ala Glu Pro Ala Asp Pro Ser Asp Pro Leu Leu Arg Glu Trp Val
225                 230                 235                 240

Lys His Pro Ala Asn Pro Val Val Phe Pro Pro Pro Gly Ile Gly Met
                245                 250                 255

Lys Asp Phe Arg Asp Pro Thr Thr Ala Trp Phe Asp Glu Ser Asp Gly
            260                 265                 270

Thr Trp Arg Thr Ile Ile Gly Ser Lys Asn Asp Ser Asp His Ser Gly
        275                 280                 285

Ile Val Phe Ser Tyr Lys Thr Lys Asp Phe Leu Ser Tyr Glu Leu Met
    290                 295                 300

Pro Gly Tyr Met Tyr Arg Gly Pro Lys Gly Thr Gly Glu Tyr Glu Cys
305                 310                 315                 320

Ile Asp Leu Tyr Ala Val Gly Gly Gly Arg Lys Ala Ser Asp Met Tyr
                325                 330                 335

Asn Ser Thr Ala Glu Asp Val Leu Tyr Val Leu Lys Glu Ser Ser Asp
            340                 345                 350

Asp Asp Arg His Asp Trp Tyr Ser Leu Gly Arg Phe Asp Ala Ala Ala
        355                 360                 365

Asn Lys Trp Thr Pro Ile Asp Glu Glu Leu Glu Leu Gly Val Gly Leu
    370                 375                 380

Arg Tyr Asp Trp Gly Lys Tyr Tyr Ala Ser Lys Ser Phe Tyr Asp Pro
385                 390                 395                 400

Val Lys Lys Arg Arg Val Val Trp Ala Tyr Val Gly Glu Thr Asp Ser
                405                 410                 415

Glu Arg Ala Asp Ile Thr Lys Gly Trp Ala Asn Leu Gln Ser Ile Pro
            420                 425                 430

Arg Thr Val Glu Leu Asp Glu Lys Thr Arg Thr Asn Leu Val Gln Trp
        435                 440                 445

Pro Val Glu Glu Leu Asp Ala Leu Arg Ile Asn Thr Thr Asp Leu Ser
    450                 455                 460

Gly Ile Thr Val Gly Ala Gly Ser Val Ala Phe Leu Pro Leu His Gln
465                 470                 475                 480

Thr Ala Gln Leu Asp Ile Glu Ala Thr Phe Arg Ile Asp Ala Ser Ala
                485                 490                 495

Ile Glu Ala Leu Asn Glu Ala Asp Val Ser Tyr Asn Cys Thr Thr Ser
            500                 505                 510

Ser Gly Ala Ala Thr Arg Gly Ala Leu Gly Pro Phe Gly Leu Leu Val
```

```
        515                 520                 525

Leu Ala Asn Arg Ala Leu Thr Glu Gln Thr Gly Val Tyr Phe Tyr Val
    530                 535                 540

Ser Lys Gly Leu Asp Gly Gly Leu Arg Thr His Phe Cys His Asp Glu
545                 550                 555                 560

Leu Arg Ser Ser His Ala Ser Asp Val Val Lys Arg Val Val Gly Ser
                565                 570                 575

Thr Val Pro Val Leu Asp Gly Glu Asp Phe Ser Val Arg Val Leu Val
            580                 585                 590

Asp His Ser Ile Val Gln Ser Phe Ala Met Gly Gly Arg Leu Thr Ala
        595                 600                 605

Thr Ser Arg Ala Tyr Pro Thr Glu Ala Ile Tyr Ala Ala Ala Gly Val
    610                 615                 620

Tyr Met Phe Asn Asn Ala Thr Gly Thr Ser Val Thr Ala Glu Lys Leu
625                 630                 635                 640

Val Val His Asp Met Asp Ser Ser
                645


<210> SEQ ID NO 12
<211> LENGTH: 638
<212> TYPE: PRT
<213> ORGANISM: Lolium perenne

<400> SEQUENCE: 12

Met Glu Ser Ser Ala Val Val Pro Gly Thr Thr Ala Arg Leu Leu Pro
1               5                   10                  15

Tyr Ala Tyr Ala Pro Leu Pro Ser Ser Ala Asp Asp Ala Arg Glu Asn
            20                  25                  30

Gln Gly Ser Asp Gly Val Arg Trp Arg Ala Cys Ala Ala Val Leu Ala
        35                  40                  45

Ala Ser Ala Leu Ala Val Leu Val Val Val Gly Leu Leu Ala Gly Gly
    50                  55                  60

Arg Val Asp Arg Pro Gly Pro Ala Ala Val Pro Ala Val Pro Thr Glu
65                  70                  75                  80

Ile Pro Arg Ser Arg Gly Lys Asp Phe Gly Val Ser Glu Lys Ser Ser
                85                  90                  95

Gly Ala Tyr Ser Ala Asp Gly Gly Phe Pro Trp Ser Asn Ala Met Leu
            100                 105                 110

Gln Trp Gln Arg Thr Gly Phe His Phe Gln Pro Glu Gln His Tyr Met
        115                 120                 125

Asn Asp Pro Asn Gly Pro Val Tyr Tyr Gly Gly Trp Tyr His Leu Phe
    130                 135                 140

Tyr Gln Tyr Asn Pro Lys Gly Asp Ser Trp Gly Asn Ile Ala Trp Ala
145                 150                 155                 160

His Ala Val Ser Lys Asp Met Val Asn Trp Arg His Leu Pro Leu Ala
                165                 170                 175

Met Val Pro Asp Gln Trp Tyr Asp Ser Asn Gly Val Leu Thr Gly Ser
            180                 185                 190

Ile Thr Val Leu Pro Asp Gly Arg Val Ile Leu Leu Tyr Thr Gly Asn
        195                 200                 205

Thr Asp Thr Leu Ala Gln Val Gln Cys Leu Ala Glu Pro Ala Asp Pro
    210                 215                 220

Ser Asp Pro Leu Leu Arg Glu Trp Ile Lys His Pro Ala Asn Pro Ile
225                 230                 235                 240
```

-continued

```
Leu Phe Pro Pro Pro Gly Ile Gly Leu Lys Asp Phe Arg Asp Pro Leu
                245                 250                 255

Thr Asp Trp Phe Asp His Ser Asp Asp Thr Trp Arg Thr Val Ile Gly
            260                 265                 270

Ser Lys Asp Asp Asp Gly His Ala Gly Ile Ile Leu Ser Tyr Lys Thr
        275                 280                 285

Lys Asp Phe Val Asn Tyr Glu Leu Met Pro Gly Asn Met His Arg Gly
    290                 295                 300

Pro Asp Gly Thr Gly Met Tyr Glu Cys Ile Asp Leu Tyr Pro Val Gly
305                 310                 315                 320

Gly Asn Ser Ser Glu Met Leu Gly Gly Asp Asp Ser Pro Asp Val Leu
                325                 330                 335

Phe Val Leu Lys Glu Ser Ser Asp Asp Glu Arg His Asp Tyr Tyr Ala
            340                 345                 350

Leu Gly Arg Phe Asp Ala Ala Ala Asn Ile Trp Thr Pro Ile Asp Gln
        355                 360                 365

Glu Leu Asp Leu Gly Ile Gly Leu Arg Tyr Asp Trp Gly Lys Tyr Tyr
    370                 375                 380

Ala Ser Lys Ser Phe Tyr Asp Gln Arg Lys Asn Arg Arg Val Val Trp
385                 390                 395                 400

Ala Tyr Ile Gly Glu Thr Asp Ser Glu Gln Ala Asp Ile Thr Lys Gly
                405                 410                 415

Trp Ala Asn Leu Met Thr Ile Pro Arg Thr Val Glu Leu Asp Lys Lys
            420                 425                 430

Thr Arg Thr Asn Leu Ile Gln Trp Pro Val Glu Glu Val Asp Thr Leu
        435                 440                 445

Arg Arg Asn Ser Thr Asp Leu Gly Arg Ile Thr Val Asn Ala Gly Ser
    450                 455                 460

Val Ile Arg Leu Pro Leu His Gln Gly Ala Gln Leu Asp Ile Glu Ala
465                 470                 475                 480

Ser Phe Gln Leu Asn Ser Ser Asp Val Asp Ala Leu Asn Glu Ala Asp
                485                 490                 495

Val Gly Tyr Asn Cys Ser Thr Ser Gly Ala Ala Val Arg Gly Ala Leu
            500                 505                 510

Gly Pro Phe Gly Leu Leu Val Leu Ala Asn Gly Arg Thr Glu Gln Thr
        515                 520                 525

Ala Val Tyr Phe Tyr Val Ser Lys Gly Val Asp Gly Ala Leu Gln Thr
    530                 535                 540

His Phe Cys His Asp Glu Ser Arg Ser Thr Arg Ala Lys Asp Val Val
545                 550                 555                 560

Asn Arg Met Ile Gly Ser Ile Val Pro Val Leu Asp Gly Glu Thr Phe
                565                 570                 575

Ser Val Arg Val Leu Leu Asp His Ser Ile Val Gln Ser Phe Ala Met
            580                 585                 590

Gly Gly Arg Ile Thr Ala Thr Ser Arg Ala Tyr Pro Thr Glu Ala Ile
        595                 600                 605

Tyr Ala Ala Ala Gly Val Tyr Val Phe Asn Asn Ala Thr Gly Ala Thr
    610                 615                 620

Val Thr Ala Glu Arg Leu Val Val Tyr Glu Met Ala Ser Ala
625                 630                 635
```

<210> SEQ ID NO 13
<211> LENGTH: 608
<212> TYPE: PRT

<213> ORGANISM: Lolium perenne

<400> SEQUENCE: 13

```
Met Glu Ser Arg Ala Phe Pro Asn Ala Ala Tyr Ala Pro Leu Leu Pro
1               5                   10                  15

Pro Thr Ala Asp Asp Ala Thr Leu Gly Lys Gln Asp Arg Pro Gly Val
            20                  25                  30

Gly Trp Arg Gly Phe Leu Thr Val Leu Ala Ala Ser Gly Val Val Val
        35                  40                  45

Leu Leu Val Ala Ala Thr Met Leu Ala Gly Ser Arg Met Gly Gln Ala
    50                  55                  60

Gly Asp Thr Asp Glu Asp Gly Ala Gly Gly Phe Pro Trp Ser Asn Glu
65                  70                  75                  80

Met Leu Gln Trp Gln Arg Ala Gly Phe His Tyr Gln Pro Glu Gly His
                85                  90                  95

Phe Met Ser Asp Pro Asp Gly Pro Val Tyr Tyr Arg Gly Tyr Tyr His
            100                 105                 110

Leu Phe Phe Gln Tyr Asn Arg Arg Gly Val Ala Trp Asp Asp Tyr Ile
        115                 120                 125

Glu Trp Gly His Val Val Ser Gln Asp Leu Val His Trp Arg Pro Leu
    130                 135                 140

Pro Leu Ala Leu Arg Pro Asp His Trp Tyr Asp Lys Lys Gly Val Leu
145                 150                 155                 160

Ser Gly Thr Ile Thr Val Leu His Asn Gly Thr Leu Val Leu Leu Tyr
                165                 170                 175

Thr Gly Val Thr Glu Asp Pro Met Ala Glu Ser Gln Cys Ile Ala Val
            180                 185                 190

Pro Thr Asp Pro Asn Asp Pro Leu Leu Arg His Trp Thr Lys His Pro
        195                 200                 205

Ala Asn Pro Val Leu Ala His Pro Gln Gly Val Gln Gly Met Asp Phe
    210                 215                 220

Arg Asp Pro Thr Ser Ala Trp Phe Asp Lys Ser Asp Ala Thr Trp Arg
225                 230                 235                 240

Ile Leu Ile Gly Ser Lys Asp Asp Asp Asn Gly Ser His Ala Gly Ile
                245                 250                 255

Ala Phe Ile Phe Lys Thr Lys Asp Phe Leu Ser Phe Glu Arg Val Pro
            260                 265                 270

Gly Ile Val His Arg Val Glu Gly Thr Gly Met Trp Glu Cys Ile Asp
        275                 280                 285

Phe Tyr Pro Val Gly Gly Gly His Asn Ser Ser Ser Glu Glu Leu Tyr
    290                 295                 300

Val Ile Lys Ala Ser Met Asp Asp Glu Arg His Asp Tyr Tyr Ser Leu
305                 310                 315                 320

Gly Arg Tyr Asp Ala Ala Ala Asn Thr Trp Thr Pro Leu Asp Ala Glu
                325                 330                 335

Leu Asp Leu Gly Ile Gly Leu Arg Tyr Asp Trp Gly Lys Leu Tyr Ala
            340                 345                 350

Ala Thr Ser Phe Tyr Asp Pro Leu Lys Gln Arg Arg Ile Met Leu Gly
        355                 360                 365

Tyr Val Gly Glu Thr Asp Ser Ala Arg Ala Asp Val Ala Lys Gly Trp
    370                 375                 380

Ala Ser Leu Gln Ser Ile Pro Arg Thr Val Thr Leu Asp Glu Lys Thr
385                 390                 395                 400
```

-continued

```
Arg Thr Asn Leu Leu Leu Trp Pro Val Glu Glu Val Glu Ala Leu Arg
                405                 410                 415

Tyr Asn Ser Thr Asp Leu Ser Gly Ile Thr Val Asp Asn Gly Ser Val
            420                 425                 430

Phe His Leu Pro Leu His Gln Ala Thr Gln Leu Asp Ile Glu Ala Ser
        435                 440                 445

Phe Arg Leu Asp Ala Ser Asp Val Ala Ala Ile Asn Glu Ala Asp Val
    450                 455                 460

Gly Tyr Asn Cys Ser Ser Ser Gly Gly Ala Ala Ala Arg Gly Ala Ile
465                 470                 475                 480

Gly Pro Phe Gly Leu Leu Val His Ala Ala Gly Asp Leu Arg Gly Glu
                485                 490                 495

Gln Thr Ala Val Tyr Phe Tyr Val Ser Arg Ala Leu Asp Gly Thr Leu
            500                 505                 510

Arg Thr Ser Phe Cys Asn Asp Glu Thr Arg Ser Ser Arg Ala Arg Asp
        515                 520                 525

Val Thr Lys Arg Val Val Gly Ser Thr Val Pro Val Leu His Gly Glu
    530                 535                 540

Ala Leu Ser Met Arg Val Leu Val Asp His Ser Ile Val Gln Ser Phe
545                 550                 555                 560

Ala Met Gly Gly Arg Val Thr Ala Thr Ser Arg Val Tyr Pro Thr Glu
                565                 570                 575

Ala Ile Tyr Ala Arg Ala Gly Val Tyr Leu Phe Asn Asn Ala Thr Gly
            580                 585                 590

Ala Ser Val Thr Ala Glu Arg Leu Ile Val His Glu Met Ala Ser Ala
        595                 600                 605


<210> SEQ ID NO 14
<211> LENGTH: 612
<212> TYPE: PRT
<213> ORGANISM: Lolium perenne

<400> SEQUENCE: 14

Met Glu Ser Arg Ala Phe Pro Ser Ala Ala Tyr Ala Pro Leu Leu Pro
1               5                   10                  15

Pro Thr Ala Asp Asp Ala Thr Leu Gly Lys Gln Asp Arg Pro Gly Val
            20                  25                  30

Gly Trp Arg Gly Phe Leu Thr Val Leu Ala Ala Ser Gly Val Val Val
        35                  40                  45

Leu Leu Val Ala Ala Ser Leu Leu Ala Gly Ser Arg Met Gly Gln Ala
    50                  55                  60

Gly Asp Gly Glu Gly Asn Thr Asp Glu Asp Gly Ala Gly Gly Phe Pro
65                  70                  75                  80

Trp Ser Asn Glu Met Leu Gln Trp Gln Arg Ala Gly Phe His Tyr Gln
                85                  90                  95

Pro Glu Gly His Phe Met Ser Asp Pro Asp Gly Pro Val Tyr Tyr Arg
            100                 105                 110

Gly Tyr Tyr His Leu Phe Phe Gln Tyr Asn Arg Arg Gly Val Ala Trp
        115                 120                 125

Asp Asp Tyr Ile Glu Trp Gly His Val Val Ser Gln Asp Leu Val His
    130                 135                 140

Trp Arg Pro Leu Pro Val Ala Met Arg Pro Asp His Trp Tyr Asp Lys
145                 150                 155                 160

Lys Gly Val Leu Ser Gly Thr Ile Thr Val Leu His Asn Gly Thr Leu
                165                 170                 175
```

-continued

```
Val Leu Leu Tyr Thr Gly Val Thr Glu Asp Pro Met Ala Glu Ser Gln
            180                 185                 190

Cys Ile Ala Val Pro Thr Asp Pro Asn Asn Pro Leu Leu Arg His Trp
        195                 200                 205

Thr Lys His Pro Ala Asn Pro Val Leu Ala His Pro Gln Gly Val Gln
    210                 215                 220

Gly Met Asp Phe Arg Asp Pro Thr Ser Ala Trp Phe Asp Lys Ser Asp
225                 230                 235                 240

Ala Thr Trp Arg Ile Leu Ile Gly Ser Lys Asp Asp Asp Asn Gly Ser
                245                 250                 255

His Ala Gly Ile Ala Phe Ile Phe Lys Thr Lys Asp Phe Leu Ser Phe
            260                 265                 270

Glu Arg Val Pro Gly Ile Val His Arg Val Glu Gly Thr Gly Met Trp
        275                 280                 285

Glu Cys Ile Asp Phe Tyr Pro Val Gly Gly Gly His Asn Ser Ser Ser
    290                 295                 300

Glu Glu Leu Tyr Val Ile Lys Ala Ser Met Asp Asp Glu Arg His Asp
305                 310                 315                 320

Tyr Tyr Ser Leu Gly Arg Tyr Asp Ala Ala Ala Asn Thr Trp Thr Pro
                325                 330                 335

Leu Asp Ala Glu Leu Asp Leu Gly Ile Gly Leu Arg Tyr Asp Trp Gly
            340                 345                 350

Lys Leu Tyr Ala Ala Thr Ser Phe Tyr Asp Pro Leu Lys Gln Arg Arg
        355                 360                 365

Ile Met Leu Gly Tyr Val Gly Glu Thr Asp Ser Ala Arg Ala Asp Val
    370                 375                 380

Ala Lys Gly Trp Ala Ser Leu Gln Ser Ile Pro Arg Thr Val Thr Leu
385                 390                 395                 400

Asp Glu Lys Thr Arg Thr Asn Leu Leu Leu Trp Pro Val Glu Glu Val
                405                 410                 415

Glu Ala Leu Arg Tyr Asn Ser Thr Asp Leu Ser Gly Ile Thr Ile Asp
            420                 425                 430

Asn Gly Ser Val Phe His Leu Pro Leu His Gln Ala Thr Gln Leu Asp
        435                 440                 445

Ile Glu Ala Ser Phe Arg Leu Asp Ala Ser Asp Val Ala Ala Ile Asn
    450                 455                 460

Glu Ala Asp Val Gly Tyr Asn Cys Ser Ser Ser Gly Gly Ala Ala Ala
465                 470                 475                 480

Arg Gly Ala Ile Gly Pro Phe Gly Leu Leu Val His Ala Ala Gly Asp
                485                 490                 495

Leu Arg Gly Glu Gln Thr Ala Val Tyr Phe Tyr Val Ser Arg Ala Leu
            500                 505                 510

Asp Gly Thr Leu Arg Thr Ser Phe Cys Asn Asp Glu Thr Arg Ser Ser
        515                 520                 525

Arg Ala Arg Asp Val Thr Lys Arg Val Val Gly Ser Thr Val Pro Val
    530                 535                 540

Leu Asp Gly Glu Ala Leu Ser Met Arg Val Leu Val Asp His Ser Ile
545                 550                 555                 560

Val Gln Ser Phe Ala Met Gly Gly Arg Val Thr Ala Thr Ser Arg Val
                565                 570                 575

Tyr Pro Thr Glu Ala Ile Tyr Ala Arg Ala Gly Val Tyr Leu Phe Asn
            580                 585                 590
```

```
Asn Ala Thr Gly Ala Ser Val Thr Ala Glu Arg Leu Ile Val His Glu
        595                 600                 605

Met Ala Ser Ala
    610


<210> SEQ ID NO 15
<211> LENGTH: 644
<212> TYPE: PRT
<213> ORGANISM: Lolium perenne

<400> SEQUENCE: 15

Met Glu Ser Ser Ala Val Val Pro Gly Thr Thr Ala Pro Leu Leu Pro
1               5                   10                  15

Tyr Ala Tyr Ala Pro Leu Pro Ser Ser Ser Asp Asp Ala Arg Glu Asn
            20                  25                  30

Arg Ser Ser Gly Gly Val Arg Trp Arg Ala Cys Ala Ala Val Leu Ala
        35                  40                  45

Ala Ser Ala Leu Ala Val Val Val Val Val Gly Leu Leu Ala Gly Gly
    50                  55                  60

Arg Val Asp Arg Val Pro Ala Gly Ala Asp Val Ala Ser Ala Thr Val
65                  70                  75                  80

Pro Ala Val Pro Met Glu Phe Pro Arg Ser Arg Gly Lys Asp Leu Gly
                85                  90                  95

Val Ser Glu Lys Ser Ser Gly Ala Tyr Ser Ala Asp Gly Gly Phe Pro
            100                 105                 110

Trp Ser Asn Ala Met Leu Gln Trp Gln Arg Thr Gly Phe His Phe Gln
        115                 120                 125

Pro Glu Gln His Tyr Met Asn Asp Pro Asn Gly Pro Val Tyr Tyr Gly
    130                 135                 140

Gly Trp Tyr His Leu Phe Tyr Gln His Asn Pro Lys Gly Asp Ser Trp
145                 150                 155                 160

Gly Asn Ile Ala Trp Ala His Ala Val Ser Lys Asp Met Val Asn Trp
                165                 170                 175

Arg His Leu Pro Leu Ala Met Val Pro Asp Gln Trp Tyr Asp Ser Asn
            180                 185                 190

Gly Val Leu Thr Gly Ser Ile Thr Val Leu Pro Asp Gly Gln Val Ile
        195                 200                 205

Leu Leu Tyr Thr Gly Asn Thr Asp Thr Leu Ala Gln Val Gln Cys Leu
    210                 215                 220

Ala Thr Pro Ala Asp Pro Ser Asp Pro Leu Leu Arg Glu Trp Ile Lys
225                 230                 235                 240

His Pro Ala Asn Pro Ile Leu Phe Pro Pro Pro Gly Ile Gly Leu Lys
                245                 250                 255

Asp Phe Arg Asp Pro Leu Thr Ala Trp Phe Asp His Ser Asp His Thr
            260                 265                 270

Trp Arg Thr Val Ile Gly Ser Lys Asp Asp Asp Gly His Ala Gly Ile
        275                 280                 285

Ile Leu Ser Tyr Lys Thr Lys Asp Phe Val Asn Tyr Glu Leu Met Pro
    290                 295                 300

Gly Asn Met His Arg Gly Pro Asp Gly Thr Gly Met Tyr Glu Cys Ile
305                 310                 315                 320

Asp Leu Tyr Pro Val Gly Gly Asn Ser Ser Glu Met Leu Gly Gly Asp
                325                 330                 335

Asp Ser Pro Asp Val Leu Phe Val Leu Lys Glu Ser Ser Asp Asp Glu
            340                 345                 350
```

Arg His Asp Tyr Tyr Ala Leu Gly Arg Phe Asp Ala Val Ala Asn Val
355 360 365

Trp Thr Pro Ile Asp Arg Asp Leu Asp Leu Gly Ile Gly Leu Arg Tyr
370 375 380

Asp Trp Gly Lys Tyr Tyr Ala Ser Lys Ser Phe Tyr Asp Gln Lys Lys
385 390 395 400

Asn Arg Arg Ile Val Trp Ala Tyr Ile Gly Glu Thr Asp Ser Glu Gln
405 410 415

Ala Asp Ile Thr Lys Gly Trp Ala Asn Leu Met Thr Ile Pro Arg Thr
420 425 430

Val Glu Leu Asp Arg Lys Thr Arg Thr Asn Leu Ile Gln Trp Pro Val
435 440 445

Glu Glu Val Asp Thr Leu Arg Arg Asn Ser Thr Asp Leu Gly Arg Ile
450 455 460

Thr Val Asn Ala Gly Ser Val Ile Arg Leu Pro Leu His Gln Gly Ala
465 470 475 480

Gln Leu Asp Ile Glu Ala Ser Phe Gln Leu Asn Ser Ser Asp Val Asp
485 490 495

Ala Ile Asn Glu Ala Asp Val Gly Tyr Asn Cys Ser Thr Ser Gly Ala
500 505 510

Ala Val Arg Gly Ala Leu Gly Pro Phe Gly Leu Leu Val Leu Ala Asn
515 520 525

Gly Arg Thr Glu Gln Thr Ala Val Tyr Phe Tyr Val Ser Lys Gly Val
530 535 540

Asp Gly Gly Leu Gln Thr His Phe Cys His Asp Glu Ser Arg Ser Thr
545 550 555 560

Arg Ala Lys Asp Val Val Asn Arg Met Ile Gly Ser Ile Val Pro Val
565 570 575

Leu Asp Gly Glu Thr Phe Ser Val Arg Val Leu Val Asp His Ser Ile
580 585 590

Val Gln Ser Phe Ala Met Gly Gly Arg Ile Thr Ala Thr Ser Arg Ala
595 600 605

Tyr Pro Thr Glu Ala Ile Tyr Ala Ala Ala Gly Val Tyr Leu Phe Asn
610 615 620

Asn Ala Thr Gly Ala Thr Val Thr Ala Glu Arg Leu Val Val His Glu
625 630 635 640

Met Ala Ser Ala

<210> SEQ ID NO 16
<211> LENGTH: 612
<212> TYPE: PRT
<213> ORGANISM: Lolium perenne

<400> SEQUENCE: 16

Met Glu Ser Arg Ala Phe Pro Ser Ala Ala Tyr Ala Pro Leu Leu Pro
1 5 10 15

Ser Ala Ala Asp Asp Val Ala Leu Ala Lys Gln Asp Arg Pro Gly Val
20 25 30

Gly Trp Arg Gly Phe Leu Thr Val Leu Ala Ala Cys Gly Val Val Val
35 40 45

Leu Leu Val Gly Ala Thr Leu Leu Ala Gly Ser Arg Met Gly Gln Ala
50 55 60

Gly Asp Gly Glu Gly Asn Thr Asp Glu Asp Gly Ala Gly Gly Phe Pro
65 70 75 80

-continued

```
Trp Ser Asn Glu Met Leu Gln Trp Gln Arg Ala Gly Phe His Tyr Gln
                85                  90                  95

Pro Glu Gly His Phe Met Ser Asp Pro Asn Gly Pro Val Tyr Tyr Arg
            100                 105                 110

Gly Tyr Tyr His Leu Phe Phe Gln Tyr Asn Arg Arg Gly Val Ala Trp
        115                 120                 125

Asp Asp Tyr Ile Glu Trp Gly His Val Val Ser Gln Asp Leu Val His
    130                 135                 140

Trp Arg Pro Leu Pro Leu Ala Met Arg Pro Asp His Trp Tyr Asp Lys
145                 150                 155                 160

Lys Gly Val Leu Ser Gly Thr Ile Thr Val Leu His Asn Gly Thr Leu
                165                 170                 175

Val Leu Leu Tyr Thr Gly Val Thr Glu Asp Pro Met Ala Glu Ser Gln
            180                 185                 190

Cys Ile Ala Val Pro Thr Asp Pro Asn Asp Pro Leu Leu Arg His Trp
        195                 200                 205

Thr Lys His Pro Ala Asn Pro Val Leu Ala His Pro Gln Gly Val Gln
    210                 215                 220

Gly Met Asp Phe Arg Asp Pro Thr Ser Ala Trp Trp Asp Lys Ser Asp
225                 230                 235                 240

Ala Thr Trp Arg Ile Leu Ile Gly Ser Lys Asp Asp Asp Asn Gly Ser
                245                 250                 255

His Ala Gly Ile Ala Phe Ile Phe Lys Thr Lys Asp Phe Leu Ser Phe
            260                 265                 270

Glu Arg Val Pro Gly Ile Val His Arg Val Glu Gly Thr Gly Met Trp
        275                 280                 285

Glu Cys Ile Asp Phe Tyr Pro Val Gly Gly Gly His Asn Ser Ser Ser
    290                 295                 300

Glu Glu Leu Tyr Val Ile Lys Ala Ser Met Asp Asp Glu Arg His Asp
305                 310                 315                 320

Tyr Tyr Ser Leu Gly Arg Tyr Asp Ala Ala Ala Asn Thr Trp Thr Pro
                325                 330                 335

Leu Asp Ala Glu Leu Asp Leu Gly Ile Gly Leu Arg Tyr Asp Trp Gly
            340                 345                 350

Lys Leu Tyr Ala Ser Thr Ser Phe Tyr Asp Pro Val Lys Gln Arg Arg
        355                 360                 365

Ile Met Leu Gly Tyr Val Gly Glu Val Asp Ser Ala Arg Ala Asp Val
    370                 375                 380

Ala Lys Gly Trp Ala Ser Leu Gln Ser Ile Pro Arg Thr Val Ala Leu
385                 390                 395                 400

Asp Glu Lys Thr Arg Thr Asn Leu Leu Leu Trp Pro Val Glu Glu Val
                405                 410                 415

Glu Ala Leu Arg Tyr Asn Ser Thr Asp Leu Ser Gly Ile Thr Ile Asp
            420                 425                 430

Asn Gly Ser Val Phe His Leu Pro Leu His Gln Thr Thr Gln Leu Asp
        435                 440                 445

Ile Glu Ala Ser Phe Arg Leu Asp Ala Ser Asp Val Ala Ala Ile Asn
    450                 455                 460

Glu Ala Asp Val Gly Tyr Asn Cys Ser Ser Ser Gly Gly Ala Ala Ala
465                 470                 475                 480

Arg Gly Ala Leu Gly Pro Phe Gly Leu Leu Val His Ala Ala Gly Asp
                485                 490                 495
```

```
Leu Arg Gly Glu Gln Thr Ala Val Tyr Phe Tyr Val Ser Arg Ala Leu
            500                 505                 510

Asp Gly Thr Leu Arg Thr Ser Phe Cys Asn Asp Glu Thr Arg Ser Ser
        515                 520                 525

Arg Ala Arg Asp Val Thr Lys Arg Val Val Gly Ser Thr Val Pro Val
    530                 535                 540

Leu Asp Gly Glu Ala Leu Ser Met Arg Val Leu Val Asp His Ser Ile
545                 550                 555                 560

Val Gln Ser Phe Ala Met Gly Gly Arg Thr Thr Ala Thr Ser Arg Val
                565                 570                 575

Tyr Pro Thr Glu Ala Ile Tyr Ala Arg Ala Gly Val Tyr Leu Phe Asn
            580                 585                 590

Asn Ala Thr Gly Ala Gly Val Thr Ala Glu Arg Leu Ile Val His Glu
        595                 600                 605

Met Ala Ser Ala
    610


<210> SEQ ID NO 17
<211> LENGTH: 608
<212> TYPE: PRT
<213> ORGANISM: Lolium perenne

<400> SEQUENCE: 17

Met Glu Ser Arg Asp Phe Pro Ser Ala Ala Tyr Ala Pro Leu Leu Pro
1               5                   10                  15

Ser Ala Ala Asp Asp Val Ala Leu Ala Lys Gln Asp Arg Pro Gly Val
            20                  25                  30

Gly Trp Arg Gly Phe Leu Thr Val Leu Ala Ala Cys Gly Val Val Val
        35                  40                  45

Leu Leu Val Ala Ala Ser Leu Leu Ala Gly Ser Arg Met Gly Gln Ala
    50                  55                  60

Gly Asp Thr Asp Glu Asp Gly Ala Gly Gly Phe Pro Trp Ser Asn Glu
65                  70                  75                  80

Met Leu Gln Trp Gln Arg Ala Gly Phe His Tyr Gln Pro Glu Gly His
                85                  90                  95

Phe Met Ser Asp Pro Asp Gly Pro Val Tyr Tyr Arg Gly Tyr Tyr His
            100                 105                 110

Leu Phe Phe Gln Tyr Asn Arg Arg Gly Val Ala Trp Asp Asp Tyr Ile
        115                 120                 125

Glu Trp Gly His Val Val Ser Gln Asp Leu Val His Trp Arg Pro Leu
    130                 135                 140

Pro Leu Ala Met Arg Pro Asp His Trp Tyr Asp Lys Lys Gly Val Leu
145                 150                 155                 160

Ser Gly Thr Ile Thr Val Leu His Asn Gly Thr Leu Val Leu Leu Tyr
                165                 170                 175

Thr Gly Val Thr Glu Asp Pro Met Ala Glu Ser Gln Cys Ile Ala Val
            180                 185                 190

Pro Thr Asp Pro Asn Asp Pro Leu Leu Arg His Trp Thr Lys His Pro
        195                 200                 205

Ala Asn Pro Val Leu Ala His Pro Gln Gly Val Gln Gly Met Asp Phe
    210                 215                 220

Arg Asp Pro Thr Ser Ala Trp Trp Asp Lys Ser Asp Ser Thr Trp Arg
225                 230                 235                 240

Ile Leu Ile Gly Ser Lys Asp Asp Asp Asn Gly Ser His Ala Gly Ile
                245                 250                 255
```

```
Ala Phe Ile Phe Lys Thr Lys Asp Phe Leu Ser Phe Glu Arg Val Pro
            260                 265                 270

Gly Ile Val His Arg Val Glu Gly Thr Gly Met Trp Glu Cys Ile Asp
        275                 280                 285

Phe Tyr Pro Val Gly Gly Gly His Asn Ser Ser Ser Glu Glu Leu Tyr
    290                 295                 300

Val Ile Lys Ala Ser Met Asp Asp Glu Arg His Asp Tyr Tyr Ser Leu
305                 310                 315                 320

Gly Arg Tyr Asp Ala Ala Ala Asn Thr Trp Thr Pro Leu Asp Ala Glu
                325                 330                 335

Leu Asp Leu Gly Ile Gly Leu Arg Tyr Asp Trp Gly Lys Leu Tyr Ala
            340                 345                 350

Ser Thr Ser Phe Tyr Asp Pro Leu Lys Gln Arg Arg Ile Met Leu Gly
        355                 360                 365

Tyr Val Gly Glu Val Asp Ser Ala Arg Ala Asp Val Ala Lys Gly Trp
    370                 375                 380

Ala Ser Leu Gln Ser Ile Pro Arg Thr Val Ala Leu Asp Glu Lys Thr
385                 390                 395                 400

Arg Thr Asn Leu Leu Leu Trp Pro Val Glu Glu Val Glu Ala Leu Arg
                405                 410                 415

Tyr Asn Ser Thr Asp Leu Ser Gly Ile Thr Val Glu Asn Gly Ser Ile
            420                 425                 430

Phe His Leu Pro Leu His Gln Ala Thr Gln Leu Asp Ile Glu Ala Ser
        435                 440                 445

Phe Arg Leu Asp Ala Ser Asp Val Ala Ala Ile Asn Glu Ala Asp Val
    450                 455                 460

Gly Tyr Asn Cys Ser Ser Ser Gly Gly Ala Ala Ala Arg Gly Ala Leu
465                 470                 475                 480

Gly Pro Phe Gly Leu Leu Val His Ala Ala Gly Asp Leu Arg Gly Glu
                485                 490                 495

Gln Thr Ala Val Tyr Phe Tyr Val Ser Arg Ala Leu Asp Gly Ser Leu
            500                 505                 510

Arg Thr Ser Phe Cys Asn Asp Glu Thr Arg Ser Ser Arg Ala Arg Asp
        515                 520                 525

Val Thr Lys Arg Val Val Gly Ser Thr Val Pro Val Leu Asp Gly Glu
    530                 535                 540

Val Leu Ala Met Arg Val Leu Val Asp His Ser Ile Val Gln Ser Phe
545                 550                 555                 560

Ala Met Gly Gly Arg Val Thr Ala Thr Ser Arg Val Tyr Pro Thr Glu
                565                 570                 575

Ala Ile Tyr Ala Arg Ala Gly Val Tyr Leu Phe Asn Asn Ala Thr Gly
            580                 585                 590

Ala Ser Val Thr Ala Glu Arg Leu Ile Val His Glu Met Ala Ser Ala
        595                 600                 605
```

<210> SEQ ID NO 18
<211> LENGTH: 659
<212> TYPE: PRT
<213> ORGANISM: Lolium perenne

<400> SEQUENCE: 18

```
Met Pro Met Glu Ala Arg Asp Gly Val Ser Met Pro Tyr Ser Tyr Ala
1               5                   10                  15

Ala Leu Pro Glu Asp Ala Glu Ala Ala Val Val Gly Arg Gly Arg Arg
```

-continued

```
            20                  25                  30

Thr Gly Pro Leu Phe Ala Ala Leu Leu Leu Thr Leu Val Ala Ala Leu
        35                  40                  45

Leu Ala Val Ala Ala Leu Ala Gly Val Arg Leu Val Gly Glu Leu Pro
    50                  55                  60

Ala Gly Gly Val Val Met Pro Asn His Pro Met Glu Val Met Asp Val
65                  70                  75                  80

Ser Gly Ser Arg Gly Pro Glu Ser Gly Val Ser Glu Lys Thr Ser Gly
                85                  90                  95

Ala Ala Ser Glu Ser Gly Gly Met Leu Gly Ala Asp Ala Gly Ser Asn
            100                 105                 110

Ala Phe Pro Trp Ser Asn Ala Met Leu Gln Trp Gln Arg Thr Gly Phe
        115                 120                 125

His Phe Gln Pro Glu Lys Asn Trp Met Asn Asp Pro Asn Gly Pro Val
    130                 135                 140

Tyr Tyr Lys Gly Trp Tyr His Leu Phe Tyr Gln Tyr Asn Pro Glu Gly
145                 150                 155                 160

Ala Ile Trp Gly Asn Lys Ile Ala Trp Gly His Ala Val Ser Arg Asp
                165                 170                 175

Met Leu Arg Trp Arg His Leu Pro Ile Ala Met Phe Pro Asp Gln Trp
            180                 185                 190

Tyr Asp Ile Asn Gly Ala Trp Ser Gly Ser Ala Thr Val Leu Pro Asp
        195                 200                 205

Gly Arg Ile Val Met Leu Tyr Thr Gly Ser Thr Asn Ala Ser Val Gln
    210                 215                 220

Val Gln Cys Leu Ala Phe Pro Ser Asp Pro Ser Asp Pro Leu Leu Thr
225                 230                 235                 240

Asn Trp Thr Lys Tyr Glu Gly Asn Pro Val Leu Tyr Pro Pro Pro His
                245                 250                 255

Val Gly Glu Lys Asp Phe Arg Asp Pro Thr Thr Ala Trp Tyr Asp Gly
            260                 265                 270

Ser Asp Gly Met Trp Arg Ile Val Ile Gly Ser Lys Asp Asn Arg Arg
        275                 280                 285

Ala Gly Met Ala Leu Thr Tyr Lys Thr Lys Asn Phe His Asp Phe Glu
    290                 295                 300

Leu Val Pro Gly Val Leu His Arg Val Pro Ala Thr Gly Met Trp Glu
305                 310                 315                 320

Cys Ile Asp Leu Tyr Pro Val Gly Gly Ala Arg Gly Ile Asp Met Thr
                325                 330                 335

Glu Ala Val Ala Ala Ala Ser Asn Ser Gly Gly Gly Glu Val Leu His
            340                 345                 350

Val Met Lys Glu Ser Ser Asp Asp Asp Arg His Asp Tyr Tyr Ala Leu
        355                 360                 365

Gly Arg Tyr Asp Ala Ala Thr Asn Lys Trp Thr Pro Leu Asp Ala Asp
    370                 375                 380

Ala Asp Val Gly Ile Gly Leu Arg Tyr Asp Trp Gly Lys Phe Tyr Ala
385                 390                 395                 400

Ser Lys Thr Phe Tyr Asp Pro Ala Lys Lys Arg Arg Val Leu Trp Gly
                405                 410                 415

Trp Val Gly Glu Thr Asp Ser Glu Arg Ala Asp Val Ala Lys Gly Trp
            420                 425                 430

Ala Ser Leu Gln Ser Ile Pro Arg Thr Val Val Leu Asp Thr Lys Thr
        435                 440                 445
```

```
Gly Ser Asn Leu Ile Gln Trp Pro Val Val Glu Val Glu Thr Leu Arg
    450                 455                 460

Thr Asn Ser Thr Asn Leu Gly Ser Ile Ile Val Glu His Gly Ser Val
465                 470                 475                 480

Phe Pro Leu Ser Leu His Arg Ala Thr Gln Leu Asp Ile Glu Ala Ser
                485                 490                 495

Phe Arg Leu Asp Pro Leu Asp Val Ala Ala Ala Lys Glu Ala Asp Val
            500                 505                 510

Gly Tyr Asn Cys Ser Thr Ser Gly Gly Ala Ala Gly Arg Gly Ala Leu
        515                 520                 525

Gly Pro Phe Gly Leu Leu Val Leu Ala Asp Ala Arg Arg His Gly Gly
    530                 535                 540

Asp Thr Glu Gln Thr Ala Val Tyr Phe Tyr Val Ala Arg Gly Leu Asp
545                 550                 555                 560

Gly Asn Leu Arg Thr His Phe Cys His Asp Glu Ser Arg Ser Ser Arg
                565                 570                 575

Ala Asn Asp Ile Val Lys Arg Val Val Gly Asn Ile Val Pro Val Leu
            580                 585                 590

Asp Gly Glu Ala Leu Ser Val Arg Val Leu Val Asp His Ser Ile Val
        595                 600                 605

Glu Ser Phe Ala Gln Gly Gly Arg Ser Val Val Thr Ser Arg Val Tyr
    610                 615                 620

Pro Thr Glu Ala Ile Tyr Ala Asn Ala Gly Val Tyr Leu Phe Asn Asn
625                 630                 635                 640

Ala Thr Gly Ala Arg Val Thr Ala Thr Ser Leu Val Val His Glu Met
                645                 650                 655

Asp Pro Ser


<210> SEQ ID NO 19
<211> LENGTH: 504
<212> TYPE: PRT
<213> ORGANISM: Lolium perenne

<400> SEQUENCE: 19

Met His Ala Asp Pro Asn Gly Pro Val Tyr Tyr Arg Gly Trp Tyr His
1               5                   10                  15

Leu Phe Tyr Gln Tyr Asn Pro Glu Gly Ala Val Trp Gly Asn Ile Ala
            20                  25                  30

Trp Gly His Ala Val Ser Arg Asp Leu Val His Trp Arg His Leu Pro
        35                  40                  45

Leu Ala Met Val Pro Asp Gln Trp Tyr Asp Ile Asn Gly Val Trp Thr
    50                  55                  60

Gly Ser Ala Thr Val Phe Pro Asp Gly Thr Leu Asn Met Leu Tyr Thr
65                  70                  75                  80

Gly Ser Thr Asn Ala Ser Val Gln Ala Gln Cys Leu Ala Val Pro Glu
                85                  90                  95

Asp Pro Asn Asp Ser Leu Leu Arg Asn Trp Thr Lys His Glu Ala Asn
            100                 105                 110

Pro Val Leu Leu Pro Pro Pro Gly Ile Gly Asp Lys Asp Phe Arg Asp
        115                 120                 125

Pro Thr Thr Ala Trp Phe Asp Glu Ser Asp Gln Thr Trp Arg Thr Val
    130                 135                 140

Ile Gly Ser Lys Asp Asn Asn Gly His Ala Gly Ile Ala Met Val Tyr
145                 150                 155                 160
```

-continued

```
Lys Thr Lys Asp Phe Leu Asn Tyr Glu Leu Ile Pro Gly Tyr Leu His
                165                 170                 175

Arg Val Asp Gly Thr Gly Met Trp Glu Cys Ile Asp Phe Tyr Pro Val
            180                 185                 190

Gly Gly Lys Asn Gly Ser Glu Glu Leu Tyr Val Ile Lys Glu Ser Ser
        195                 200                 205

Asp Asp Asp Arg His Asp Trp Tyr Thr Leu Gly Lys Tyr Asp Ala Ala
    210                 215                 220

Ala Asn Thr Phe Thr Ala Ala Asp Pro Glu Asn Asp Leu Gly Ile Gly
225                 230                 235                 240

Leu Arg Tyr Asp Trp Gly Lys Phe Tyr Ala Ser Lys Thr Phe Tyr Asp
                245                 250                 255

Pro Ala Lys Lys Arg Arg Val Leu Trp Gly Trp Ile Gly Glu Thr Asp
            260                 265                 270

Ser Glu Arg Ala Asp Val Ala Lys Gly Trp Ala Ser Leu Met Ser Ile
        275                 280                 285

Pro Arg Thr Val Glu Leu Asp Glu Lys Thr Trp Thr Asn Leu Ile Gln
    290                 295                 300

Trp Pro Val Glu Glu Ile Glu Thr Leu Arg Ile Lys Ser Thr Asp Leu
305                 310                 315                 320

Gly Gly Ile Thr Ile Asp His Gly Ser Val Tyr Pro Leu Pro Leu His
                325                 330                 335

Arg Ala Thr Gln Leu Asp Ile Glu Ala Ser Phe Arg Leu Asp Ala Ala
            340                 345                 350

Thr Val Ala Ala Leu Asn Glu Ala Asp Val Gly Tyr Asn Cys Ser Thr
        355                 360                 365

Ser Gly Gly Ser Thr His Arg Gly Ala Leu Gly Pro Phe Gly Ile Leu
    370                 375                 380

Val Leu Ala Asp Gly Lys Ala Glu Gln Thr Ala Val Tyr Phe Tyr Val
385                 390                 395                 400

Ser Lys Gly Leu Asp Gly Ala Leu Glu Thr His Phe Cys His Asp Glu
                405                 410                 415

Ser Arg Ser Thr Leu Ala Lys Asp Val Val Lys Arg Val Val Gly Tyr
            420                 425                 430

Thr Val Pro Val Leu Asp Gly Glu Ala Phe Ser Val Arg Val Leu Val
        435                 440                 445

Asp His Ser Ile Val Glu Ser Phe Ala Met Gly Gly Arg Ser Thr Ala
    450                 455                 460

Thr Ser Arg Val Tyr Pro Thr Glu Ser Ile Tyr Gly Ala Ala Gly Ala
465                 470                 475                 480

Tyr Leu Phe Asn Asn Ala Thr Gly Gly Ser Val Thr Val Glu Lys Leu
                485                 490                 495

Val Val His Glu Met Asp Ser Ser
            500


<210> SEQ ID NO 20
<211> LENGTH: 627
<212> TYPE: PRT
<213> ORGANISM: Lolium perenne

<400> SEQUENCE: 20

Met Glu Ser Ser Ala Val Val Val Pro Gly Thr Thr Ala Pro Leu Leu
1               5                   10                  15

Pro Tyr Asp Ser Arg Glu Asn Gln Ser Ser Gly Gly Gly Val Trp Trp
```

-continued

```
            20                  25                  30

Arg Ala Cys Ala Ala Ser Ala Val Val Leu Leu Val Val Gly Phe
        35                  40                  45

Phe Ala Gly Gly Arg Val Asp Leu Gly Gln Ala Gly Glu Val Ser Ala
    50                  55                  60

Thr Ser Ser Val Pro Ala Ala Met Met Glu Ile Pro Arg Ser Arg Gly
65                  70                  75                  80

Lys Asn Phe Gly Val Ser Glu Lys Ala Asp Gly Gly Phe Pro Trp Ser
                85                  90                  95

Asn Ala Met Leu Gln Trp Gln His Thr Gly Phe His Phe Gln Pro Leu
            100                 105                 110

Lys His Tyr Met Asn Asp Pro Asn Gly Pro Val Tyr Tyr Gly Gly Trp
        115                 120                 125

Tyr His Leu Phe Tyr Gln His Asn Pro Tyr Gly Asp Ser Trp Gly Asn
    130                 135                 140

Val Ser Trp Gly His Ala Val Ser Lys Asp Leu Val Asn Trp Arg His
145                 150                 155                 160

Leu Pro Val Ala Leu Val Pro Asp Gln Trp Tyr Asp Ile Asn Gly Val
                165                 170                 175

Leu Thr Gly Ser Ile Thr Val Leu Pro Asp Gly Arg Val Ile Leu Leu
            180                 185                 190

Tyr Thr Gly Asn Thr Asp Thr Phe Ser Gln Val Gln Cys Leu Ala Val
        195                 200                 205

Pro Ala Asp Pro Ser Asp Pro Leu Leu Arg Ser Trp Ile Lys His Pro
    210                 215                 220

Ala Asn Pro Ile Leu Phe Pro Pro Pro Gly Ile Gly Leu Lys Asp Phe
225                 230                 235                 240

Arg Asp Pro Leu Thr Ala Trp Phe Glu His Ser Asp Asn Thr Trp Arg
                245                 250                 255

Thr Ile Ile Gly Ser Lys Asp Asp Asp Gly His Ala Gly Ile Val Leu
            260                 265                 270

Ser Tyr Lys Thr Thr Asp Phe Val Asn Tyr Glu Leu Met Pro Gly Asn
        275                 280                 285

Met His Arg Gly Pro Asp Gly Thr Gly Met Tyr Glu Cys Leu Asp Ile
    290                 295                 300

Tyr Pro Val Gly Gly Asn Ser Ser Glu Met Leu Gly Gly Asp Ser Ser
305                 310                 315                 320

Pro Glu Val Leu Phe Val Leu Lys Glu Ser Ala Asn Asp Glu Trp His
                325                 330                 335

Asp Tyr Tyr Ala Leu Gly Trp Phe Asp Ala Thr Ala Asn Thr Trp Thr
            340                 345                 350

Pro Gln Asp Pro Glu Ala Asp Leu Gly Ile Gly Leu Arg Tyr Asp Trp
        355                 360                 365

Gly Lys Tyr Tyr Ala Ser Lys Ser Phe Tyr Asp Pro Ile Lys Asn Arg
    370                 375                 380

Arg Val Val Trp Ala Phe Val Gly Glu Thr Asp Ser Glu Gln Ala Asp
385                 390                 395                 400

Lys Ala Lys Gly Trp Ala Ser Leu Met Ser Ile Pro Arg Met Val Glu
                405                 410                 415

Leu Asp Lys Lys Thr Arg Thr Asn Leu Ile Gln Trp Pro Val Glu Glu
            420                 425                 430

Ile Glu Thr Leu Arg Arg Asn Val Thr Asp Leu Gly Gly Ile Thr Val
        435                 440                 445
```

```
Glu Ala Gly Ser Val Ile His Leu Pro Leu Gln Gln Gly Gly Gln Leu
    450                 455                 460

Asp Ile Glu Ala Ser Phe Arg Leu Asn Ser Ser Asp Ile Asp Ala Leu
465                 470                 475                 480

Asn Glu Ala Asp Val Gly Phe Asn Cys Ser Ser Ser Ala Gly Ala Ala
                485                 490                 495

Val Arg Gly Ala Leu Gly Pro Phe Gly Leu Leu Val Phe Ala Asp Gly
            500                 505                 510

Arg His Glu Gln Thr Ala Ala Tyr Phe Tyr Val Ser Lys Gly Leu Asp
        515                 520                 525

Gly Ser Leu Leu Thr His Tyr Cys His Asp Glu Ser Arg Ser Thr Arg
    530                 535                 540

Ala Lys Asp Val Val Ser Arg Val Val Gly Gly Thr Val Pro Val Leu
545                 550                 555                 560

Asp Gly Glu Thr Phe Ser Val Arg Val Leu Val Asp His Ser Ile Val
                565                 570                 575

Gln Ser Phe Val Met Gly Gly Arg Thr Thr Val Thr Ser Arg Ala Tyr
            580                 585                 590

Pro Thr Glu Ala Ile Tyr Ala Ala Ala Gly Val Tyr Leu Phe Asn Asn
        595                 600                 605

Ala Thr Ser Ala Thr Ile Thr Ala Glu Gly Leu Val Val Tyr Glu Met
    610                 615                 620

Ala Ser Ala
625


<210> SEQ ID NO 21
<211> LENGTH: 602
<212> TYPE: PRT
<213> ORGANISM: Lolium perenne

<400> SEQUENCE: 21

Met Gly Ser His Gly Lys Pro Pro Leu Pro Tyr Ala Tyr Lys Pro Leu
1               5                   10                  15

Pro Ser Asp Ala Asp Gly Glu Arg Ala Gly Cys Thr Arg Trp Arg Val
            20                  25                  30

Cys Ala Val Ala Leu Thr Ala Ser Ala Met Val Val Val Val Val Gly
        35                  40                  45

Ala Thr Leu Leu Ala Gly Phe Arg Val Asp Gln Ala Val Asp Glu Glu
    50                  55                  60

Ala Ala Gly Gly Phe Pro Trp Ser Asn Glu Met Leu Gln Trp Gln Arg
65                  70                  75                  80

Ser Gly Tyr His Phe Gln Thr Ala Lys Asn Tyr Met Ser Asp Pro Asn
                85                  90                  95

Gly Leu Met Tyr Tyr Arg Gly Trp Tyr His Met Phe Phe Gln Tyr Asn
            100                 105                 110

Pro Val Gly Thr Asp Trp Asp Asp Gly Met Glu Trp Gly His Ala Val
        115                 120                 125

Ser Arg Asn Leu Val Gln Trp Arg Thr Leu Pro Ile Ala Met Val Ala
    130                 135                 140

Asp Gln Trp Tyr Asp Ile Leu Gly Val Leu Ser Gly Ser Met Thr Val
145                 150                 155                 160

Leu Pro Asn Gly Thr Val Ile Met Ile Tyr Thr Gly Ala Thr Asn Ala
                165                 170                 175

Ser Ala Val Glu Val Gln Cys Ile Ala Thr Pro Ala Asp Pro Thr Asp
```

```
        180                 185                 190

Pro Leu Leu Arg Arg Trp Thr Lys His Pro Ala Asn Pro Val Ile Trp
        195                 200                 205

Ser Pro Pro Gly Val Gly Thr Lys Asp Phe Arg Asp Pro Met Thr Ala
    210                 215                 220

Trp Tyr Asp Glu Ser Asp Asp Thr Trp Arg Thr Leu Leu Gly Lys Ser
225                 230                 235                 240

Asp Asp Asn Asn Gly His His Asp Gly Ile Ala Met Met Tyr Lys Thr
                245                 250                 255

Lys Asp Phe Leu Asn Tyr Glu Leu Ile Pro Gly Ile Leu His Arg Val
            260                 265                 270

Glu Arg Thr Gly Glu Trp Glu Cys Ile Asp Phe Tyr Pro Val Gly Arg
        275                 280                 285

Arg Thr Ser Asp Asn Ser Ser Glu Met Leu His Val Leu Lys Ala Ser
    290                 295                 300

Met Asp Asp Glu Arg His Asp Tyr Tyr Ser Leu Gly Thr Tyr Asp Ser
305                 310                 315                 320

Ala Ala Asn Arg Trp Thr Pro Ile Asp Pro Glu Leu Asp Leu Gly Ile
                325                 330                 335

Gly Leu Arg Tyr Asp Trp Gly Lys Phe Tyr Ala Ser Thr Ser Phe Tyr
            340                 345                 350

Asp Pro Ala Lys Lys Arg Arg Val Leu Met Gly Tyr Val Gly Glu Val
        355                 360                 365

Asp Ser Lys Arg Ala Asp Val Val Lys Gly Trp Ala Ser Ile Gln Ser
    370                 375                 380

Val Pro Arg Thr Ile Ala Leu Asp Glu Lys Thr Arg Thr Asn Leu Leu
385                 390                 395                 400

Leu Trp Pro Val Glu Glu Ile Glu Thr Leu Arg Leu Asn Ala Thr Glu
                405                 410                 415

Leu Ser Asp Val Thr Leu Asn Thr Gly Ser Val Ile His Ile Pro Leu
            420                 425                 430

Arg Gln Gly Thr Gln Leu Asp Ile Glu Ala Thr Phe His Leu Asp Ala
        435                 440                 445

Ser Ala Val Ala Ala Leu Asn Glu Ala Asp Val Gly Tyr Asn Cys Ser
    450                 455                 460

Ser Ser Gly Gly Ala Val Asn Arg Gly Ala Leu Gly Pro Phe Gly Leu
465                 470                 475                 480

Leu Val Leu Ala Ala Gly Asp Arg Arg Gly Glu Gln Thr Ala Val Tyr
                485                 490                 495

Phe Tyr Val Ser Arg Gly Leu Asp Gly Gly Leu His Thr Ser Phe Cys
            500                 505                 510

Gln Asp Glu Leu Arg Ser Ser Arg Ala Lys Asp Val Thr Lys Arg Val
        515                 520                 525

Ile Gly Ser Thr Val Pro Val Leu Asp Gly Glu Ala Phe Ser Met Arg
    530                 535                 540

Val Leu Val Asp His Ser Ile Val Gln Gly Phe Ala Met Gly Gly Arg
545                 550                 555                 560

Thr Thr Met Thr Ser Arg Val Tyr Pro Met Glu Ala Tyr Gln Glu Ala
                565                 570                 575

Lys Val Tyr Leu Phe Asn Asn Ala Thr Gly Ala Ser Val Thr Ala Glu
            580                 585                 590

Arg Leu Val Val His Glu Met Asp Ser Ala
        595                 600
```

<210> SEQ ID NO 22
<211> LENGTH: 578
<212> TYPE: PRT
<213> ORGANISM: Lolium perenne

<400> SEQUENCE: 22

```
Met Gly Asn Pro Lys Trp Val Leu Ala Pro Trp Ala Val Leu Leu Leu
1               5                   10                  15

Leu Gln Leu Ala Ser Ala Ser His His Ala Arg Leu Ser Leu Glu Thr
            20                  25                  30

Glu Ala Ala Ser Pro Ser Val Pro Ala Ser Ile Val Ser Pro Leu Leu
        35                  40                  45

Arg Thr Gly Tyr His Phe Gln Pro Pro Met Asn Trp Ile Asn Asp Pro
    50                  55                  60

Asn Gly Pro Leu Tyr Tyr Lys Gly Trp Tyr His Leu Phe Tyr Gln Tyr
65                  70                  75                  80

Asn Pro Lys Gly Ala Val Trp Gly Asn Ile Ile Trp Ala His Ser Val
                85                  90                  95

Ser Arg Asp Leu Ile Asn Trp Ile Ala Leu Glu Pro Ala Ile Ser Pro
            100                 105                 110

Thr Ile Pro Thr Asp Gln Tyr Gly Val Trp Ser Gly Ser Thr Thr Ile
        115                 120                 125

Leu His Asp Gly Thr Pro Ala Ile Leu Tyr Thr Gly Ile Asp Arg Pro
    130                 135                 140

Ser Val Asn Tyr Gln Ile Gln Asn Ile Ala Leu Pro Lys Asn Ala Ser
145                 150                 155                 160

Asp Pro Leu Leu Arg Glu Trp Tyr Lys Pro Gly Tyr Asn Pro Ile Ala
                165                 170                 175

Val Pro Val Glu Gly Ile Asn Ala Thr Gln Phe Arg Asp Pro Thr Thr
            180                 185                 190

Ala Trp Phe Ala Gly Arg His Trp Arg Met Leu Val Gly Gly Leu Arg
        195                 200                 205

Pro Gly Thr Leu Arg Gly Glu Ala Ile Leu Tyr Arg Ser Arg Asp Phe
    210                 215                 220

Lys His Trp Val Arg Ala Lys His Pro Leu His Ser Ala Leu Thr Gly
225                 230                 235                 240

Met Trp Glu Cys Pro Asp Phe Phe Pro Val Gly Lys Ala Gly Val Glu
                245                 250                 255

Lys Gly Leu Asp Thr Ser Glu Tyr Gly Ala Ala Ala Gly Val Glu Lys
            260                 265                 270

His Val Leu Lys Asn Ser Leu Asp Leu Thr Arg Tyr Asp Tyr Tyr Thr
        275                 280                 285

Ile Gly Thr Tyr Asp Asn Val Lys Glu Arg Tyr Val Pro Asp Asn Pro
    290                 295                 300

Thr Gly Asp Val Tyr Gln Arg Leu Gln Tyr Asp Tyr Gly Asn Phe Tyr
305                 310                 315                 320

Ala Ser Lys Thr Phe Phe Asp Pro Val Lys Gln Arg Arg Ile Leu Leu
                325                 330                 335

Gly Trp Ala Asn Glu Ser Asp Ser Val Ala His Asp Lys Ala Lys Gly
            340                 345                 350

Trp Ala Gly Ile Gln Ala Ile Pro Arg Lys Ile Trp Leu Asp Pro Ser
        355                 360                 365

Gly Lys Gln Leu Val Gln Trp Pro Val Glu Glu Leu Glu Lys Leu Arg
```

```
    370                 375                 380

Gly Lys Pro Val Asn Val Gly Asp Lys Val Val Lys Pro Gly Gln His
385                 390                 395                 400

Phe Glu Val Thr Gly Leu Gln Ser Tyr Gln Ser Asp Val Glu Val Ser
                405                 410                 415

Phe Glu Val Ser Ser Leu Asp Lys Ala Glu Pro Phe Asp Pro Ala Tyr
            420                 425                 430

Ser Asn Asp Ala Gln Lys Leu Cys Gly Ile Lys Gly Ala Asp Val Lys
        435                 440                 445

Gly Gly Val Gly Pro Phe Gly Leu Trp Val Leu Ser Ser Ala Asp Leu
    450                 455                 460

Ala Glu Lys Thr Ala Val Phe Phe Arg Val Phe Lys Asp Gly Tyr Gly
465                 470                 475                 480

Lys Pro Ile Val Leu Met Cys Ser Asp Pro Thr Lys Ser Ser Leu Thr
                485                 490                 495

Pro Asp Leu Tyr Lys Pro Thr Phe Ala Gly Phe Val Asp Thr Asp Ile
            500                 505                 510

Ser Ser Gly Lys Ile Ser Leu Arg Ser Leu Ile Asp Arg Ser Val Val
        515                 520                 525

Glu Ser Phe Gly Ala Gly Gly Lys Thr Cys Ile Leu Ser Arg Val Tyr
    530                 535                 540

Pro Ser Met Ala Leu Gly Lys Asp Ala His Leu His Val Phe Asn Asn
545                 550                 555                 560

Gly Glu Thr Asp Ile Lys Val Ser Lys Leu Thr Ala Trp Glu Met Lys
                565                 570                 575

Arg Pro
```

<210> SEQ ID NO 23
<211> LENGTH: 612
<212> TYPE: PRT
<213> ORGANISM: Lolium perenne

<400> SEQUENCE: 23

```
Met Glu Ser Arg Ala Ile Pro Ser Ala Ala Tyr Ala Pro Leu Leu Pro
1               5                   10                  15

Ser Ala Ala Asp Asp Val Ala Leu Ala Lys Gln Asp Arg Pro Gly Val
            20                  25                  30

Gly Trp Arg Gly Phe Leu Thr Val Leu Ala Ala Cys Gly Val Val Val
        35                  40                  45

Leu Leu Val Gly Ala Thr Leu Leu Ala Gly Ser Arg Met Gly Gln Ala
    50                  55                  60

Gly Asp Gly Glu Gly Asn Thr Asp Glu Asp Gly Ala Gly Gly Phe Pro
65                  70                  75                  80

Trp Ser Asn Glu Met Leu Gln Trp Gln Arg Ala Gly Phe His Tyr Gln
                85                  90                  95

Pro Glu Gly His Phe Met Ser Asp Pro Asn Gly Pro Val Tyr Tyr Arg
            100                 105                 110

Gly Tyr Tyr His Leu Phe Phe Gln Tyr Asn Arg Arg Gly Val Ala Trp
        115                 120                 125

Asp Asp Tyr Ile Glu Trp Gly His Val Val Ser Gln Asp Leu Val His
    130                 135                 140

Trp Arg Pro Leu Pro Leu Ala Met Arg Pro Asp His Trp Tyr Asp Lys
145                 150                 155                 160

Lys Gly Val Leu Ser Gly Thr Ile Thr Val Leu His Asn Gly Thr Leu
```

-continued

```
                165                 170                 175

Val Leu Leu Tyr Thr Gly Val Thr Glu Asp Pro Met Ala Glu Ser Gln
            180                 185                 190

Cys Ile Ala Val Pro Thr Asp Pro Asn Asp Pro Leu Leu Arg His Trp
        195                 200                 205

Thr Lys His Pro Ala Asn Pro Val Leu Ala His Pro Gln Gly Val Gln
    210                 215                 220

Gly Met Asp Phe Arg Asp Pro Thr Ser Ala Trp Trp Asp Lys Ser Asp
225                 230                 235                 240

Ser Thr Trp Arg Ile Leu Ile Gly Ser Lys Asp Asp Asp Asn Gly Ser
                245                 250                 255

His Ala Gly Ile Ala Phe Ile Phe Lys Thr Lys Asp Phe Leu Ser Phe
            260                 265                 270

Glu Arg Val Pro Gly Ile Val His Arg Val Glu Gly Thr Gly Met Trp
        275                 280                 285

Glu Cys Ile Asp Phe Tyr Pro Val Gly Gly Gly His Asn Ser Ser Ser
    290                 295                 300

Glu Glu Leu Tyr Val Ile Lys Ala Ser Met Asp Asp Glu Arg His Asp
305                 310                 315                 320

Tyr Tyr Ser Leu Gly Arg Tyr Asp Ala Ala Ala Asn Thr Trp Thr Pro
                325                 330                 335

Leu Asp Ala Glu Leu Asp Leu Gly Ile Gly Leu Arg Tyr Asp Trp Gly
            340                 345                 350

Lys Leu Tyr Ala Ser Thr Ser Phe Tyr Asp Pro Leu Lys Gln Arg Arg
        355                 360                 365

Ile Met Leu Gly Tyr Val Gly Glu Val Asp Ser Ala Arg Ala Asp Val
    370                 375                 380

Ala Lys Gly Trp Ala Ser Leu Gln Ser Ile Pro Arg Thr Val Ala Leu
385                 390                 395                 400

Asp Glu Lys Thr Arg Thr Asn Leu Leu Leu Trp Pro Val Glu Glu Val
                405                 410                 415

Glu Ala Leu Arg Tyr Asn Ser Thr Asp Leu Ser Gly Ile Thr Val Glu
            420                 425                 430

Asn Gly Ser Ile Phe His Leu Pro Leu His Gln Ala Thr Gln Leu Asp
        435                 440                 445

Ile Glu Ala Ser Phe Arg Leu Asp Ala Ser Asp Val Ala Ala Ile Asn
    450                 455                 460

Glu Ala Asp Val Gly Tyr Asn Cys Ser Ser Ser Gly Gly Ala Ala Ala
465                 470                 475                 480

Arg Gly Ala Leu Gly Pro Phe Gly Leu Leu Val His Ala Ala Gly Asp
                485                 490                 495

Leu Arg Gly Glu Gln Thr Ala Val Tyr Phe Tyr Val Ser Arg Ala Leu
            500                 505                 510

Asp Gly Ser Leu Arg Thr Ser Phe Cys Asn Asp Glu Thr Arg Ser Ser
        515                 520                 525

Arg Ala Arg Asp Val Thr Lys Arg Val Val Gly Ser Thr Val Pro Val
    530                 535                 540

Leu Asp Gly Glu Ala Leu Ser Met Arg Val Leu Val Asp His Ser Ile
545                 550                 555                 560

Val Gln Ser Phe Ala Met Gly Gly Arg Val Thr Ala Thr Ser Arg Val
                565                 570                 575

Tyr Pro Thr Glu Ala Ile Tyr Ala Arg Ala Gly Val Tyr Leu Phe Asn
            580                 585                 590
```

```
Asn Ala Thr Gly Ala Ser Val Thr Ala Glu Arg Leu Ile Val His Glu
        595                 600                 605

Met Ala Ser Ala
    610


<210> SEQ ID NO 24
<211> LENGTH: 643
<212> TYPE: PRT
<213> ORGANISM: Lolium perenne
<220> FEATURE:
<221> NAME/KEY: misc_feature
<222> LOCATION: (493)..(493)
<223> OTHER INFORMATION: Xaa can be any naturally occurring amino acid
<220> FEATURE:
<221> NAME/KEY: misc_feature
<222> LOCATION: (579)..(579)
<223> OTHER INFORMATION: Xaa can be any naturally occurring amino acid
<220> FEATURE:
<221> NAME/KEY: misc_feature
<222> LOCATION: (633)..(633)
<223> OTHER INFORMATION: Xaa can be any naturally occurring amino acid
<220> FEATURE:
<221> NAME/KEY: misc_feature
<222> LOCATION: (639)..(639)
<223> OTHER INFORMATION: Xaa can be any naturally occurring amino acid

<400> SEQUENCE: 24

Met Glu Ser Pro Ser Ala Val Val Pro Gly Thr Thr Ala Pro Leu Leu
1               5                   10                  15

Pro Tyr Ala Tyr Ala Pro Leu Pro Ser Ser Ala Asp Asp Ala Arg Gln
            20                  25                  30

Asn Arg Ser Gly Gly Arg Trp Arg Ala Cys Ala Ala Val Leu Ala Ala
        35                  40                  45

Ser Ala Leu Ala Val Val Val Val Val Gly Leu Leu Ala Gly Gly Arg
    50                  55                  60

Val Asp Arg Val Pro Ala Gly Gly Asp Val Ala Ser Ala Thr Val Pro
65                  70                  75                  80

Ala Val Pro Met Glu Phe Pro Arg Ser Arg Gly Lys Asp Phe Gly Val
                85                  90                  95

Ser Glu Lys Ser Ser Gly Ala Tyr Ser Thr Asp Gly Gly Phe Pro Trp
            100                 105                 110

Ser Asn Ala Met Leu Gln Trp Gln Arg Thr Gly Phe His Phe Gln Pro
        115                 120                 125

Glu Gln His Tyr Met Asn Asp Pro Asn Gly Pro Val Tyr Tyr Gly Gly
    130                 135                 140

Trp Tyr His Leu Phe Tyr Gln His Asn Pro Lys Gly Asp Ser Trp Gly
145                 150                 155                 160

Asn Ile Ala Trp Ala His Ala Val Ser Lys Asp Met Val Asn Trp Arg
                165                 170                 175

His Leu Pro Leu Ala Met Val Pro Asp Gln Trp Tyr Asp Ser Asn Gly
            180                 185                 190

Val Leu Thr Gly Ser Ile Thr Val Leu Pro Asp Gly Gln Val Ile Leu
        195                 200                 205

Leu Tyr Thr Gly Asn Thr Asp Thr Leu Ala Gln Val Gln Cys Leu Ala
    210                 215                 220

Thr Pro Ala Asp Pro Ser Asp Pro Leu Leu Arg Glu Trp Val Lys His
225                 230                 235                 240

Pro Ala Asn Pro Ile Leu Tyr Pro Pro Pro Gly Ile Gly Leu Lys Asp
                245                 250                 255
```

```
Phe Arg Asp Pro Leu Thr Ala Trp Phe Asp His Ser Asp His Thr Trp
            260                 265                 270

Arg Thr Val Ile Gly Ser Lys Asp Asp Asp Gly His Ala Gly Ile Ile
        275                 280                 285

Leu Ser Tyr Lys Thr Lys Asp Phe Val Asn Tyr Glu Leu Met Pro Gly
    290                 295                 300

Asn Met His Arg Gly Pro Asp Gly Thr Gly Met Tyr Glu Cys Ile Asp
305                 310                 315                 320

Leu Tyr Pro Val Gly Gly Asn Ser Ser Glu Met Leu Gly Gly Asp Asp
                325                 330                 335

Ser Pro Gly Val Leu Phe Val Leu Lys Glu Ser Ser Asp Asp Glu Arg
            340                 345                 350

His Asp Tyr Tyr Ala Leu Gly Arg Phe Asp Ala Val Ala Asn Val Trp
        355                 360                 365

Thr Pro Ile Asp Arg Glu Leu Asp Leu Gly Ile Gly Leu Arg Tyr Asp
    370                 375                 380

Trp Gly Lys Tyr Tyr Ala Ser Lys Ser Phe Tyr Asp Gln Lys Lys Asn
385                 390                 395                 400

Arg Arg Ile Val Trp Ala Tyr Ile Gly Glu Thr Asp Ser Glu Gln Ala
                405                 410                 415

Asp Ile Thr Lys Gly Trp Ala Asn Leu Met Thr Ile Pro Arg Thr Val
            420                 425                 430

Glu Leu Asp Arg Lys Thr Arg Thr Asn Leu Ile Gln Trp Pro Val Glu
        435                 440                 445

Glu Val Asp Thr Leu Arg Arg Asn Ser Thr Asp Leu Gly Arg Ile Thr
    450                 455                 460

Val Asn Ala Gly Ser Val Ile Arg Leu Pro Leu His Gln Gly Ala Gln
465                 470                 475                 480

Leu Asp Ile Glu Ala Ser Phe Gln Leu Asn Ser Ser Xaa Val Asp Ala
                485                 490                 495

Ile Asn Glu Ala Asp Val Gly Tyr Asn Cys Ser Thr Ser Gly Ala Ala
            500                 505                 510

Val Arg Gly Ala Leu Gly Pro Phe Gly Leu Leu Val Leu Ala Asn Gly
        515                 520                 525

Arg Thr Glu Gln Thr Ala Val Tyr Phe Tyr Val Ser Lys Gly Val Asp
    530                 535                 540

Gly Ala Leu Gln Thr His Phe Cys His Asp Glu Ser Arg Ser Thr Arg
545                 550                 555                 560

Ala Lys Asp Val Val Asn Arg Met Ile Gly Ser Ile Val Pro Val Leu
                565                 570                 575

Asp Gly Xaa Thr Phe Ser Val Arg Val Leu Val Asp His Ser Ile Val
            580                 585                 590

Gln Ser Phe Ala Met Gly Gly Arg Ile Thr Ala Thr Ser Arg Ala Tyr
        595                 600                 605

Pro Thr Glu Ala Ile Tyr Ala Ala Ala Gly Val Tyr Leu Phe Asn Asn
    610                 615                 620

Ala Thr Gly Ala Thr Val Thr Ala Xaa Arg Leu Val Val His Xaa Met
625                 630                 635                 640

Ala Ser Ala
```

<210> SEQ ID NO 25
<211> LENGTH: 635
<212> TYPE: PRT
<213> ORGANISM: Lolium perenne

<400> SEQUENCE: 25

```
Met Glu Ser Ser Ala Val Val Ala Gln Gly Thr Thr Ser Pro Leu Leu
1               5                   10                  15

Pro Tyr Ala Tyr Ala Pro Leu Pro Ser Ser Ala Asp Asp Ala Arg Glu
            20                  25                  30

Asn Gln Ser Ser Gly Gly Gly Val Arg Trp Arg Ala Cys Ala Ala Ser
        35                  40                  45

Ala Leu Val Val Leu Leu Val Val Val Gly Phe Phe Ala Gly Gly Arg
    50                  55                  60

Val Asp Leu Gly Gln Asp Gly Glu Val Ser Ala Thr Ser Ser Val Pro
65                  70                  75                  80

Gly Ser Ser Arg Gly Lys Asp Ser Gly Val Ser Glu Lys Glu Ser Pro
                85                  90                  95

Ala Asp Gly Gly Phe Pro Trp Ser Asn Ala Met Leu Gln Trp Gln His
            100                 105                 110

Thr Gly Phe His Phe Gln Pro Leu Lys His Tyr Met Asn Asp Pro Asn
        115                 120                 125

Gly Pro Val Tyr Tyr Gly Gly Trp Tyr His Leu Phe Tyr Gln His Asn
    130                 135                 140

Pro Tyr Gly Asp Ser Trp Gly Asn Val Ser Trp Gly His Ala Val Ser
145                 150                 155                 160

Lys Asp Leu Val Asn Trp Arg His Leu Pro Val Ala Leu Val Pro Asp
                165                 170                 175

Gln Trp Tyr Asp Ile Asn Gly Val Leu Thr Gly Ser Ile Thr Val Leu
            180                 185                 190

Pro Asp Gly Arg Val Ile Leu Leu Tyr Thr Gly Asn Thr Asp Thr Phe
        195                 200                 205

Ser Gln Val Gln Cys Leu Ala Val Pro Ala Asp Pro Phe Asp Pro Leu
    210                 215                 220

Leu Arg Ser Trp Ile Lys His Pro Ala Asn Pro Ile Leu Phe Pro Pro
225                 230                 235                 240

Pro Gly Ile Gly Leu Lys Asp Phe Arg Asp Pro Leu Thr Ala Trp Phe
                245                 250                 255

Glu His Ser Asp Asn Thr Trp Arg Thr Ile Ile Gly Ser Lys Asp Asp
            260                 265                 270

Asp Gly His Ala Gly Ile Val Leu Ser Tyr Lys Thr Thr Asp Phe Val
        275                 280                 285

Asn Tyr Glu Leu Met Pro Gly Asn Met His Arg Gly Pro Asp Gly Thr
    290                 295                 300

Gly Met Tyr Glu Cys Leu Asp Ile Phe Pro Val Gly Gly Asn Ser Ser
305                 310                 315                 320

Glu Met Leu Gly Gly Asp Ser Ser Pro Glu Val Leu Phe Val Leu Lys
                325                 330                 335

Glu Ser Ala Asn Asp Glu Trp His Asp Tyr Tyr Ala Leu Gly Trp Phe
            340                 345                 350

Asp Ala Ala Ala Asn Thr Trp Thr Pro Gln Asp Pro Glu Ala Asp Leu
        355                 360                 365

Gly Ile Gly Leu Arg Tyr Asp Trp Gly Lys Tyr Tyr Ala Ser Lys Ser
    370                 375                 380

Phe Tyr Asp Pro Ile Lys Asn Arg Arg Val Val Trp Ala Phe Val Gly
385                 390                 395                 400

Glu Thr Asp Ser Glu Gln Ala Asp Lys Ala Lys Gly Trp Ala Ser Leu
```

-continued

```
                405                 410                 415

Met Ser Ile Pro Arg Thr Val Glu Leu Asp Lys Lys Thr Arg Thr Asn
            420                 425                 430

Leu Ile Gln Trp Pro Val Glu Glu Ile Glu Thr Leu Arg Arg Asn Val
        435                 440                 445

Thr Asp Leu Gly Gly Ile Thr Val Glu Ala Gly Ser Val Ile His Leu
    450                 455                 460

Pro Leu Gln Gln Gly Gly Gln Leu Asp Ile Glu Ala Ser Phe Arg Leu
465                 470                 475                 480

Asn Ser Ser Asp Ile Asp Ala Leu Asn Glu Ala Asp Val Gly Phe Asn
                485                 490                 495

Cys Ser Ser Ser Asp Gly Ala Ala Val Arg Gly Ala Leu Gly Pro Phe
            500                 505                 510

Gly Leu Leu Val Phe Ala Asp Gly Arg His Glu Gln Thr Ala Ala Tyr
        515                 520                 525

Phe Tyr Val Ser Lys Gly Leu Asp Gly Ser Leu Leu Thr His Tyr Cys
    530                 535                 540

His Asp Glu Ser Arg Ser Thr Arg Ala Lys Asp Val Val Ser Arg Val
545                 550                 555                 560

Val Gly Gly Thr Val Pro Val Leu Asp Gly Glu Thr Phe Ser Val Arg
                565                 570                 575

Val Leu Val Asp His Ser Ile Val Gln Ser Phe Val Met Gly Gly Arg
            580                 585                 590

Thr Thr Val Thr Ser Arg Ala Tyr Pro Thr Glu Ala Ile Tyr Ala Ala
        595                 600                 605

Ala Gly Val Tyr Leu Phe Asn Asn Ala Thr Ser Ala Thr Ile Thr Ala
    610                 615                 620

Glu Gly Leu Val Val Tyr Glu Met Ala Ser Ala
625                 630                 635


<210> SEQ ID NO 26
<211> LENGTH: 568
<212> TYPE: PRT
<213> ORGANISM: Lolium perenne

<400> SEQUENCE: 26

Met Ala Gln Gly Trp Pro Phe Phe Leu Leu Val Leu Phe Ser Cys Val
1               5                   10                  15

Ser Asn His Leu Val Asn Gly Glu Arg Val Phe Leu Phe Pro Gln Ser
            20                  25                  30

His Lys Val Ser Ser Ile Val Ser Lys Arg Tyr Arg Thr Ala Tyr His
        35                  40                  45

Phe Gln Pro Pro Lys Asn Trp Ile Asn Asp Pro Asn Gly Pro Met Tyr
    50                  55                  60

Tyr Asn Gly Ile Tyr His Glu Phe Tyr Gln Tyr Asn Pro Asn Gly Ser
65                  70                  75                  80

Leu Trp Gly Asn Ile Ile Trp Gly His Ser Val Ser Thr Asp Leu Ile
                85                  90                  95

Asn Trp Ile Pro Val Glu Pro Ala Ile Glu Arg Asp Ile Pro Ser Asp
            100                 105                 110

Ile Ser Gly Cys Trp Thr Gly Ser Ala Thr Ile Ile Ser Gly Asp Gln
        115                 120                 125

Pro Ile Ile Ile Tyr Thr Gly Ala Asp Lys Glu Asn Arg Gln Leu Gln
    130                 135                 140
```

-continued

```
Asn Ile Val Leu Pro Lys Asn Lys Ser Asp Pro Tyr Leu Arg Glu Trp
145                 150                 155                 160

Thr Lys Ala Gly Asn Asn Pro Val Ile Gln Pro Val Gly Pro Gly Leu
                165                 170                 175

Asn Ala Ser Gln Phe Arg Asp Pro Thr Thr Gly Trp Ile Gly Pro Asp
            180                 185                 190

Gly Leu Trp Arg Ile Ala Val Gly Ala Glu Leu Asn Gly Tyr Gly Ala
        195                 200                 205

Ala Leu Leu Tyr Lys Ser Gln Asp Phe Leu Asn Trp Thr Arg Val Asp
    210                 215                 220

His Pro Leu Tyr Ser Ser Asn Ala Ser Ser Met Trp Glu Cys Pro Asp
225                 230                 235                 240

Phe Phe Ala Val Leu Pro Gly Asn Ser Gly Gly Leu Asp Leu Ser Ala
                245                 250                 255

Glu Ile Pro Asn Gly Ala Lys His Val Leu Lys Met Ser Leu Asp Ser
            260                 265                 270

Cys Asp Lys Tyr Met Ile Gly Val Tyr Asp Leu Lys Ser Asp Thr Phe
        275                 280                 285

Met Pro Asp Ser Val Leu Asp Asp Arg Arg Leu Trp Ser Arg Ile Asp
    290                 295                 300

His Gly Asn Phe Tyr Ala Ser Lys Ser Phe Phe Asp Ser Lys Lys Gly
305                 310                 315                 320

Arg Arg Ile Ile Trp Gly Trp Thr Asn Glu Thr Asp Ser Ser Ser Asp
                325                 330                 335

Asp Val Ala Lys Gly Trp Ala Gly Ile His Ala Ile Pro Arg Thr Ile
            340                 345                 350

Trp Leu Asp Ser Tyr Gly Lys Gln Leu Leu Gln Trp Pro Val Glu Glu
        355                 360                 365

Ile Glu Ser Leu Arg Arg Asn Glu Ile Ser Tyr Gln Gly Leu Glu Leu
    370                 375                 380

Lys Lys Gly Asp Leu Phe Glu Ile Lys Gly Thr Asp Thr Ser Gln Ala
385                 390                 395                 400

Asp Val Gln Val Asp Phe Glu Leu Thr Ser Ile Asp Asn Ala Asp Thr
                405                 410                 415

Phe Asp Pro Ser Trp Leu Leu Asp Val Glu Lys Gln Cys Arg Glu Ala
            420                 425                 430

Gly Ala Ser Val Gln Gly Gly Ile Gly Pro Phe Gly Leu Val Val Leu
        435                 440                 445

Ala Ser Asp Asn Met Glu Glu His Thr Ala Val His Phe Arg Val Tyr
    450                 455                 460

Lys Ser Gln Gln Ser Tyr Met Ile Leu Met Cys Ser Asp Pro Arg Arg
465                 470                 475                 480

Ser Ser Leu Arg Ser Gly Met Tyr Thr Pro Ala Tyr Gly Gly Phe Phe
                485                 490                 495

Glu Phe Asp Leu Gln Lys Glu Arg Lys Ile Ser Leu Arg Thr Leu Ile
            500                 505                 510

Asp Arg Ser Ala Val Glu Ser Phe Gly Gly Gly Gly Arg Val Cys Ile
        515                 520                 525

Met Ala Arg Val Tyr Pro Val Val Leu Val Asp Asp Gly Gly Ala His
    530                 535                 540

Met Tyr Ala Phe Asn Asn Gly Ser Thr Thr Val Arg Val Pro Gln Leu
545                 550                 555                 560

Arg Ala Trp Ser Met Ser Arg Ala
```

-continued

565

<210> SEQ ID NO 27
<211> LENGTH: 638
<212> TYPE: PRT
<213> ORGANISM: Lolium perenne

<400> SEQUENCE: 27

```
Met Glu Ser Arg Ser Ile Pro Gly Ala Tyr Ala Tyr Glu Pro Leu Pro
1               5                   10                  15

His Ser Ser Asp Asp Ala His Gly His Asp Asp Arg Arg Ser Ala Gly
            20                  25                  30

Gly Val Arg Trp Arg Ala Cys Ala Ala Val Leu Ala Ala Ser Ala Leu
        35                  40                  45

Val Val Phe Val Val Ala Ser Thr Leu Ala Gly Ser Arg Val Asp Arg
    50                  55                  60

Val Ala Val Asp Val Ala Ala Met Pro Ala Leu Ser Glu Thr Ala Arg
65                  70                  75                  80

Ser Arg Gly Lys Asp Ala Gly Val Ser Glu Lys Thr Ser Gly Ala Ala
                85                  90                  95

Asp Glu Met Gly Phe Leu Gly Ala Gly Ser Gly Ala Asp Ala Asp Gly
            100                 105                 110

Phe Pro Trp Ser Asn Ala Met Leu Gln Trp Gln Arg Thr Gly Phe His
        115                 120                 125

Phe Gln Pro Glu Met Asn Trp Met Asn Asp Pro Asn Gly Pro Val Tyr
    130                 135                 140

Tyr Arg Gly Trp Tyr His Leu Phe Tyr Gln Tyr Asn Pro Glu Gly Ala
145                 150                 155                 160

Val Trp Gly Asn Ile Ala Trp Gly His Ala Val Ser Arg Asp Leu Val
                165                 170                 175

His Trp Arg His Leu Pro Leu Ala Met Val Pro Asp Gln Trp Tyr Asp
            180                 185                 190

Ile Asn Gly Val Trp Thr Gly Ser Ala Thr Val Phe Pro Asp Gly Thr
        195                 200                 205

Leu Asn Met Leu Tyr Thr Gly Ser Thr Asn Ala Ser Val Gln Val Gln
    210                 215                 220

Cys Leu Ala Val Pro Glu Asp Pro Asn Asp Ser Leu Leu Arg Asn Trp
225                 230                 235                 240

Thr Lys His Glu Ala Asn Pro Val Leu Leu Pro Pro Pro Gly Ile Gly
                245                 250                 255

Asp Lys Asp Phe Arg Asp Pro Thr Thr Ala Trp Phe Asp Glu Ser Asp
            260                 265                 270

Gln Thr Trp Arg Thr Val Ile Gly Ser Lys Asp Asn Asn Gly His Ala
        275                 280                 285

Gly Ile Ala Met Val Tyr Lys Thr Lys Asp Phe Leu Asn Tyr Glu Leu
    290                 295                 300

Ile Pro Gly Tyr Leu His Arg Val Asp Gly Thr Gly Met Trp Glu Cys
305                 310                 315                 320

Ile Asp Phe Tyr Pro Val Gly Gly Lys Asn Gly Ser Glu Glu Leu Tyr
                325                 330                 335

Val Ile Lys Glu Ser Ser Asp Asp Asp Arg His Asp Trp Tyr Thr Leu
            340                 345                 350

Gly Lys Tyr Asp Ala Ala Ala Asn Thr Phe Thr Ala Ala Asp Pro Glu
        355                 360                 365
```

```
Asn Asp Leu Gly Ile Gly Leu Arg Tyr Asp Trp Gly Lys Phe Tyr Ala
    370                 375                 380

Thr Lys Thr Phe Tyr Asp Pro Ala Lys Asn Arg Arg Val Leu Trp Gly
385                 390                 395                 400

Trp Ile Gly Glu Thr Asp Ser Glu Arg Ala Asp Val Ala Lys Gly Trp
                405                 410                 415

Ala Ser Leu Met Ser Ile Pro Arg Thr Val Glu Leu Asp Glu Lys Thr
            420                 425                 430

Arg Thr Asn Leu Ile Gln Trp Pro Val Glu Glu Leu Glu Thr Leu Arg
        435                 440                 445

Ile Lys Ser Thr Asp Leu Gly Gly Val Thr Ile Asp His Gly Ser Val
    450                 455                 460

Tyr Pro Leu Pro Leu His Arg Ala Thr Gln Leu Asp Ile Glu Ala Ser
465                 470                 475                 480

Phe Arg Ile Asp Thr Ala Thr Val Ala Ala Leu Asn Glu Ala Asp Val
                485                 490                 495

Gly Tyr Asn Cys Ser Thr Ser Gly Gly Ser Ala Asn Arg Gly Ala Leu
            500                 505                 510

Gly Pro Phe Gly Leu Leu Val Leu Ala Asp Gly Lys Ala Glu Gln Thr
        515                 520                 525

Ala Val Tyr Phe Tyr Val Ala Lys Gly Leu Asp Gly Thr Leu Gln Thr
    530                 535                 540

His Phe Cys His Asp Glu Ser Arg Ser Thr Leu Ala Arg Asp Val Val
545                 550                 555                 560

Lys Arg Val Val Gly Tyr Thr Val Pro Val Leu Asp Gly Glu Ala Phe
                565                 570                 575

Ser Val Arg Val Leu Val Asp His Ser Ile Val Glu Ser Phe Ala Met
            580                 585                 590

Gly Gly Arg Ser Thr Ala Thr Ser Arg Val Tyr Pro Thr Glu Ala Ile
        595                 600                 605

Tyr Gly Ala Ala Gly Ala Tyr Leu Phe Asn Asn Ala Thr Gly Gly Ser
    610                 615                 620

Val Thr Val Glu Lys Leu Val Val His Glu Met Asp Ser Ser
625                 630                 635


<210> SEQ ID NO 28
<211> LENGTH: 660
<212> TYPE: PRT
<213> ORGANISM: Lolium perenne
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (451)..(451)
<223> OTHER INFORMATION: Xaa can be any naturally occurring amino acid
<220> FEATURE:
<221> NAME/KEY: misc_feature
<222> LOCATION: (605)..(605)
<223> OTHER INFORMATION: Xaa can be any naturally occurring amino acid
<220> FEATURE:
<221> NAME/KEY: misc_feature
<222> LOCATION: (620)..(620)
<223> OTHER INFORMATION: Xaa can be any naturally occurring amino acid

<400> SEQUENCE: 28

Met Pro Met Glu Ala Arg Asp Gly Val Ser Met Pro Tyr Ser Tyr Ala
1               5                   10                  15

Ala Leu Pro Glu Asp Ala Glu Ala Ala Val Val Gly Arg Gly Arg Arg
```

-continued

```
            20                  25                  30

Thr Gly Pro Leu Phe Ala Ala Leu Leu Leu Thr Leu Val Ala Ala Leu
        35                  40                  45

Leu Ala Val Ala Ala Leu Ala Gly Val Arg Leu Val Gly Glu Leu Pro
    50                  55                  60

Ala Gly Gly Val Xaa Met Pro Asn His Pro Met Glu Val Met Asp Val
65                  70                  75                  80

Ser Gly Ser Arg Gly Pro Glu Ser Gly Val Ser Glu Lys Thr Ser Gly
                85                  90                  95

Ala Ala Ser Glu Ser Gly Gly Met Leu Gly Ala Asp Ala Gly Ser Asn
            100                 105                 110

Ala Phe Pro Trp Ser Asn Ala Met Leu Gln Trp Gln Arg Thr Gly Phe
        115                 120                 125

His Phe Gln Pro Glu Lys Asn Trp Met Asn Asp Pro Asn Gly Pro Val
    130                 135                 140

Tyr Tyr Lys Gly Trp Tyr His Leu Phe Tyr Gln Tyr Asn Pro Glu Gly
145                 150                 155                 160

Ala Ile Trp Gly Asn Lys Ile Ala Trp Gly His Ala Val Ser Arg Asp
                165                 170                 175

Met Leu Arg Trp Arg His Leu Pro Ile Ala Met Phe Pro Asp Gln Trp
            180                 185                 190

Tyr Asp Ile Asn Gly Ala Trp Ser Gly Ser Ala Thr Val Leu Pro Asp
        195                 200                 205

Gly Arg Ile Val Met Leu Tyr Thr Gly Ser Thr Asn Ala Ser Val Gln
    210                 215                 220

Val Gln Cys Leu Ala Phe Pro Ser Asp Pro Ser Asp Pro Leu Leu Thr
225                 230                 235                 240

Asn Trp Thr Lys Tyr Glu Gly Asn Pro Val Leu Tyr Pro Pro Pro His
                245                 250                 255

Val Gly Glu Lys Asp Phe Arg Asp Pro Thr Thr Ala Trp Tyr Asp Gly
            260                 265                 270

Ser Asp Gly Met Trp Arg Ile Val Ile Gly Ser Lys Asp Asn Arg Arg
        275                 280                 285

Ala Gly Met Ala Leu Thr Tyr Lys Thr Lys Asn Phe His Asp Phe Glu
    290                 295                 300

Leu Val Pro Gly Val Leu His Arg Val Pro Ala Thr Gly Met Trp Glu
305                 310                 315                 320

Cys Ile Asp Leu Tyr Pro Val Gly Gly Ala Arg Gly Ile Asp Met Thr
                325                 330                 335

Glu Ala Val Ala Ala Ala Ser Asn Ser Gly Gly Gly Glu Val Leu His
            340                 345                 350

Val Met Lys Glu Ser Ser Asp Asp Asp Arg His Asp Tyr Tyr Ala Leu
        355                 360                 365

Gly Arg Tyr Asp Ala Ala Thr Asn Lys Trp Thr Pro Leu Asp Ala Asp
    370                 375                 380

Ala Asp Val Gly Ile Gly Leu Arg Tyr Asp Trp Gly Lys Phe Tyr Ala
385                 390                 395                 400

Ser Lys Thr Phe Tyr Asp Pro Ala Lys Lys Arg Arg Val Leu Trp Gly
                405                 410                 415

Trp Val Gly Glu Thr Asp Ser Glu Arg Ala Asp Val Ala Lys Gly Trp
            420                 425                 430

Ala Ser Leu Gln Ser Ile Pro Arg Thr Val Val Leu Asp Thr Lys Thr
        435                 440                 445
```

Gly Ser Xaa Leu Ile Gln Trp Pro Val Val Glu Val Glu Thr Leu Arg
    450                 455                 460

Thr Asn Ser Thr Asn Leu Gly Ser Ile Ile Val Glu His Gly Ser Val
465                 470                 475                 480

Phe Pro Leu Ser Leu His Arg Ala Thr Gln Leu Asp Ile Glu Ala Ser
                485                 490                 495

Phe Arg Leu Asp Pro Leu Asp Val Ala Ala Ala Lys Glu Ala Asp Val
            500                 505                 510

Gly Tyr Asn Cys Ser Thr Ser Gly Gly Ala Ala Gly Arg Gly Ala Leu
        515                 520                 525

Gly Pro Phe Gly Leu Leu Val Leu Ala Asp Ala Arg Arg His Gly Gly
    530                 535                 540

Asp Thr Glu Gln Thr Ala Val Tyr Phe Tyr Val Ala Arg Gly Leu Asp
545                 550                 555                 560

Gly Asn Leu Arg Thr His Phe Cys His Asp Glu Ser Arg Ser Ser Arg
                565                 570                 575

Ala Asn Asp Ile Val Lys Arg Val Val Gly Asn Ile Val Pro Val Leu
            580                 585                 590

Asp Gly Glu Ala Leu Ser Val Arg Val Leu Val Asp Xaa Ser Ile Val
        595                 600                 605

Glu Ser Phe Ala Gln Gly Gly Arg Ser Val Val Xaa Ser Thr Glu Phe
    610                 615                 620

Asn Pro Thr Glu Ala Ile Tyr Ala Asn Ala Gly Val Tyr Leu Phe Asn
625                 630                 635                 640

Asn Ala Thr Gly Ala Arg Val Thr Ala Thr Ser Leu Val Val His Glu
                645                 650                 655

Met Asp Pro Ser
            660

<210> SEQ ID NO 29
<211> LENGTH: 650
<212> TYPE: PRT
<213> ORGANISM: Lolium perenne

<400> SEQUENCE: 29

Met Val Ala Asp Ser Gln Ala Cys Ile Tyr Pro Val Leu Met Val His
1               5                   10                  15

Thr Glu Ala Gly Pro Thr Asn Gln Pro Arg His Arg Pro Thr Ile Asn
            20                  25                  30

His Ala Arg Ser Ser Arg Val Arg Ser Ser Ile His Gln Leu Ser Ser
        35                  40                  45

Ile Phe Ser Asn Thr Met Lys Ser Arg Ala Thr Pro Pro Arg Leu Ile
    50                  55                  60

Gln Cys Val Ser Leu His Leu His Arg Thr Ser Gly Gly Ala Thr Arg
65                  70                  75                  80

Trp Arg Ala Cys Thr Thr Thr Val Leu Ala Val Gly Val Leu Ala His
                85                  90                  95

Ala Leu Ala Gly Ala Gly Glu Ile Met Ala Trp Trp Leu Gly Ala Gly
            100                 105                 110

Lys Gly Ala Asp Gly Phe Pro Trp Thr Ser Ala Met Leu Gln Trp Gln
        115                 120                 125

Arg Thr Gly Phe His Phe Gln Pro Glu Lys Asn Phe Met Ser Asp Pro
    130                 135                 140

Ser Gly Pro Val Tyr Tyr Arg Gly Trp Tyr His Leu Phe Tyr Gln Tyr

-continued

```
145                 150                 155                 160

Asn Pro Glu Gly Thr Val Gly Ala Asn Ile Thr Trp Gly His Ala Val
                165                 170                 175

Ser Arg Asp Leu Val His Trp Arg His Leu Pro Leu Ala Met Leu Pro
            180                 185                 190

Asp Arg Trp Tyr Asp Ile Asn Gly Val Trp Thr Gly Ser Ala Thr Met
        195                 200                 205

Leu Pro Asn Gly Thr Leu Thr Met Leu Tyr Thr Gly Ser Thr Asn Ala
    210                 215                 220

Ser Thr Gln Val Gln Cys Leu Ala Val Pro Ala Asn Pro Asn Asp Ser
225                 230                 235                 240

Leu Leu Arg Asn Trp Thr Lys His Pro Ala Asn Pro Val Leu Leu Pro
                245                 250                 255

Pro Pro Gly Ile Gly Asp Lys Asp Phe Arg Asp Pro Thr Thr Ala Trp
            260                 265                 270

Phe His Lys Ser Asp Ser Thr Trp His Ile Ala Ile Gly Ser Lys Asp
        275                 280                 285

Asp His Gly His Ser Gly Ile Ala Ile Thr Tyr Lys Thr Lys Asp Phe
    290                 295                 300

Val Ser Tyr Glu Leu Ile Pro Gly Phe Leu His Arg Val Glu Ser Thr
305                 310                 315                 320

Gly Met Trp Glu Cys Val Asp Phe Tyr Pro Val Gly Ser Arg Asp Gln
                325                 330                 335

Asp Ala Glu Asn Ser Ser Glu Glu Leu Leu Tyr Val Met Lys Ala Ser
            340                 345                 350

Met Asp Asp His Arg His Asp Cys Tyr Ala Leu Gly Arg Tyr Asp Ala
        355                 360                 365

Glu Ala Asn Ile Trp Thr Pro Val Asp Pro Glu Ala Asp Val Gly Ile
    370                 375                 380

Gly Leu Arg Tyr Asp Trp Gly Arg Phe Phe Ala Ser Lys Thr Phe Tyr
385                 390                 395                 400

Asp Pro Ala Lys Arg Arg Arg Val Leu Leu Gly Tyr Val Ala Glu Ala
                405                 410                 415

Asp Ser Glu Leu Ala Asp Val Ala Lys Gly Trp Ala Cys Leu Ser Ile
            420                 425                 430

Pro Arg Thr Val Ala Leu Asp Glu Lys Thr Arg Met Asn Leu Leu Gln
        435                 440                 445

Trp Pro Val Glu Glu Ile Glu Thr Leu Arg Leu Asn Thr Ile Asp Leu
    450                 455                 460

Gly Asn Ile Thr Ile Gly Thr Gly Ser Ile Phe Pro Leu Pro Leu Arg
465                 470                 475                 480

Gln Ala Thr Gln Leu Asp Met Glu Ala Ser Phe Arg Leu Asp Ala Ser
                485                 490                 495

Ala Ile Ala Ala Phe Asn Glu Val Asp Val Ser Tyr Asn Cys Ser Thr
            500                 505                 510

Ser Gly Gly Ala Ala Ser Arg Gly Thr Leu Gly Pro Phe Gly Leu Leu
        515                 520                 525

Val Leu Thr Thr Ala Asp Ser Arg Ser Glu Gln Met Ala Val Tyr Phe
    530                 535                 540

Tyr Val Ser Lys Ser Ile Asp Gly Thr Leu Gln Thr Ser Phe Cys His
545                 550                 555                 560

Asp Glu Ser Arg Ser Ser Arg Ala Trp Asp Val Val Lys Arg Val Val
                565                 570                 575
```

```
Gly Ser Thr Val Pro Val Leu His Gly Glu Ala Leu Ser Val Arg Val
            580                 585                 590

Leu Val Asp His Ser Ile Val Glu Ser Phe Ala Met Gly Gly Arg Ser
        595                 600                 605

Thr Val Thr Ser Arg Val Tyr Pro Thr Glu Ala Ile Tyr Glu Ala Ala
    610                 615                 620

Arg Ala Tyr Val Phe Asn Asn Ala Thr Gly Ser Thr Val Thr Val Glu
625                 630                 635                 640

Arg Leu Val Val His Asp Met Asp Ser Ala
                645                 650


<210> SEQ ID NO 30
<211> LENGTH: 637
<212> TYPE: PRT
<213> ORGANISM: Lolium perenne

<400> SEQUENCE: 30

Met Glu Ser Pro Ser Ala Val Val Pro Gly Thr Thr Ala Pro Leu Leu
1               5                   10                  15

Pro Tyr Ala Tyr Ala Pro Leu Pro Ser Ser Ala Asp Asp Ala Arg Gln
            20                  25                  30

Asn Arg Ser Gly Gly Arg Trp Arg Ala Cys Ala Ala Val Leu Ala Ala
        35                  40                  45

Ser Ala Leu Ala Val Val Val Val Val Gly Leu Leu Ala Gly Gly Arg
    50                  55                  60

Val Asp Arg Val Pro Ala Gly Gly Asp Val Ala Ser Ala Thr Val Pro
65                  70                  75                  80

Ala Val Pro Met Glu Phe Pro Arg Ser Arg Gly Lys Asp Phe Gly Val
                85                  90                  95

Ser Glu Lys Ser Ser Gly Ala Tyr Ser Thr Asp Gly Gly Phe Pro Trp
            100                 105                 110

Ser Asn Ala Met Leu Gln Trp Gln Arg Thr Gly Phe His Phe Gln Pro
        115                 120                 125

Glu Gln His Tyr Met Asn Asp Pro Asn Gly Pro Val Tyr Tyr Gly Gly
    130                 135                 140

Trp Tyr His Leu Phe Tyr Gln His Asn Pro Lys Gly Asp Ser Trp Gly
145                 150                 155                 160

Asn Ile Ala Trp Ala His Ala Val Ser Lys Asp Met Val Asn Trp Arg
                165                 170                 175

His Leu Pro Leu Ala Met Val Pro Asp Gln Trp Tyr Asp Ser Asn Gly
            180                 185                 190

Val Leu Thr Gly Ser Ile Thr Val Leu Pro Asp Gly Gln Val Ile Leu
        195                 200                 205

Leu Tyr Thr Gly Asn Thr Asp Thr Leu Ala Gln Val Gln Cys Leu Ala
    210                 215                 220

Thr Pro Ala Asp Pro Ser Asp Pro Leu Leu Arg Glu Trp Val Lys His
225                 230                 235                 240

Pro Ala Asn Pro Ile Leu Tyr Pro Pro Pro Gly Ile Gly Leu Lys Asp
                245                 250                 255

Phe Arg Asp Pro Leu Thr Ala Trp Phe Asp His Ser Asp His Thr Trp
            260                 265                 270

Arg Thr Val Ile Gly Ser Lys Asp Asp Asp Gly His Ala Gly Ile Ile
        275                 280                 285

Leu Ser Tyr Lys Thr Lys Asp Phe Val Asn Tyr Glu Leu Met Pro Gly
```

```
    290                 295                 300

Asn Met His Arg Gly Pro Asp Gly Thr Gly Met Tyr Glu Cys Ile Asp
305                 310                 315                 320

Leu Tyr Pro Val Gly Gly Asn Ser Ser Glu Met Leu Gly Gly Asp Asp
                325                 330                 335

Ser Pro Gly Val Leu Phe Val Leu Lys Glu Ser Ser Asp Asp Glu Arg
            340                 345                 350

His Asp Tyr Tyr Ala Leu Gly Arg Phe Asp Ala Val Ala Asn Val Trp
        355                 360                 365

Thr Pro Ile Asp Arg Glu Leu Asp Leu Gly Ile Gly Leu Arg Tyr Asp
    370                 375                 380

Trp Gly Lys Tyr Tyr Ala Ser Lys Ser Phe Tyr Asp Gln Lys Lys Asn
385                 390                 395                 400

Arg Arg Ile Val Trp Ala Tyr Ile Gly Glu Thr Asp Ser Glu Gln Ala
                405                 410                 415

Asp Ile Leu Met Thr Ile Pro Arg Thr Val Glu Leu Asp Arg Lys Thr
            420                 425                 430

Arg Thr Asn Leu Ile Gln Trp Pro Val Glu Glu Val Asp Thr Leu Arg
        435                 440                 445

Arg Asn Ser Thr Asp Leu Gly Arg Ile Thr Val Asn Ala Gly Ser Val
    450                 455                 460

Ile Arg Leu Pro Leu His Gln Gly Ala Gln Leu Asp Ile Glu Ala Ser
465                 470                 475                 480

Phe Gln Leu Asn Ser Ser Asp Val Asp Ala Ile Asn Glu Ala Asp Val
                485                 490                 495

Gly Tyr Asn Cys Ser Thr Ser Gly Ala Ala Val Arg Gly Ala Leu Gly
            500                 505                 510

Pro Phe Gly Leu Leu Val Leu Ala Asn Gly Arg Thr Glu Gln Thr Ala
        515                 520                 525

Val Tyr Phe Tyr Val Ser Lys Gly Val Asp Gly Ala Leu Gln Thr His
    530                 535                 540

Phe Cys His Asp Glu Ser Arg Ser Thr Arg Ala Lys Asp Val Val Asn
545                 550                 555                 560

Arg Met Ile Gly Ser Ile Val Pro Val Leu Asp Gly Glu Thr Phe Ser
                565                 570                 575

Val Arg Val Leu Val Asp His Ser Ile Val Gln Ser Phe Ala Met Gly
            580                 585                 590

Gly Arg Ile Thr Ala Thr Ser Arg Ala Tyr Pro Thr Glu Ala Ile Tyr
        595                 600                 605

Ala Ala Ala Gly Val Tyr Leu Phe Asn Asn Ala Thr Gly Ala Thr Val
    610                 615                 620

Thr Ala Glu Arg Leu Val Val His Glu Met Ala Ser Ala
625                 630                 635


<210> SEQ ID NO 31
<211> LENGTH: 635
<212> TYPE: PRT
<213> ORGANISM: Lolium perenne

<400> SEQUENCE: 31

Met Glu Ser Ser Ala Val Val Val Gln Gly Thr Thr Ala Pro Leu Leu
1               5                   10                  15

Pro Tyr Ala Tyr Ala Pro Leu Pro Ser Ser Ala Asp Asp Ala Arg Glu
            20                  25                  30
```

-continued

```
Asn Gln Ser Ser Gly Gly Gly Val Arg Trp Arg Ala Cys Ala Ala Ser
        35                  40                  45

Ala Leu Val Val Leu Leu Val Val Val Gly Phe Phe Ala Gly Gly Arg
    50                  55                  60

Val Asp Leu Gly Gln Asp Gly Glu Val Ser Ala Thr Ser Ser Val Pro
65                  70                  75                  80

Gly Ser Ser Arg Gly Lys Asp Ser Gly Val Ser Glu Lys Glu Ser Pro
                85                  90                  95

Ala Asp Gly Gly Phe Pro Trp Ser Asn Ala Met Leu Gln Trp Gln His
            100                 105                 110

Thr Gly Phe His Phe Gln Pro Leu Lys His Tyr Met Asn Asp Pro Asn
        115                 120                 125

Gly Pro Val Tyr Tyr Gly Gly Trp Tyr His Leu Phe Tyr Gln His Asn
    130                 135                 140

Pro Tyr Gly Asp Ser Trp Gly Asn Val Ser Trp Gly His Ala Val Ser
145                 150                 155                 160

Lys Asp Leu Val Asn Trp Arg His Leu Pro Val Ala Leu Val Pro Asp
                165                 170                 175

Gln Trp Tyr Asp Ile Asn Gly Val Leu Thr Gly Ser Ile Thr Val Leu
            180                 185                 190

Pro Asp Gly Arg Val Ile Leu Leu Tyr Thr Gly Asn Thr Asp Thr Phe
        195                 200                 205

Ser Gln Val Gln Cys Leu Ala Val Pro Ala Asp Pro Ser Asp Pro Leu
    210                 215                 220

Leu Arg Ser Trp Ile Lys His Pro Ala Asn Pro Ile Leu Phe Pro Pro
225                 230                 235                 240

Pro Gly Ile Gly Leu Lys Asp Phe Arg Asp Pro Leu Thr Ala Trp Phe
                245                 250                 255

Glu His Ser Asp Asn Thr Trp Arg Thr Ile Ile Gly Ser Lys Asp Asp
            260                 265                 270

Asp Gly His Ala Gly Ile Val Leu Ser Tyr Lys Thr Thr Asp Phe Val
        275                 280                 285

Asn Tyr Glu Leu Met Pro Gly Asn Met His Arg Gly Pro Asp Gly Thr
    290                 295                 300

Gly Met Tyr Glu Cys Leu Asp Ile Tyr Pro Val Gly Gly Asn Ser Ser
305                 310                 315                 320

Glu Met Leu Gly Gly Asp Ser Ser Pro Glu Val Leu Phe Val Leu Lys
                325                 330                 335

Glu Ser Ala Asn Asp Glu Trp His Asp Tyr Tyr Ala Leu Gly Trp Phe
            340                 345                 350

Asp Ala Ala Ala Asn Thr Trp Thr Pro Gln Asp Pro Glu Ala Asp Leu
        355                 360                 365

Gly Ile Gly Leu Arg Tyr Asp Trp Gly Lys Tyr Tyr Ala Ser Lys Ser
    370                 375                 380

Phe Tyr Asp Pro Ile Lys Asn Arg Arg Val Val Trp Ala Phe Val Gly
385                 390                 395                 400

Glu Thr Asp Ser Glu Gln Ala Asp Lys Ala Lys Gly Trp Ala Ser Leu
                405                 410                 415

Met Ser Ile Pro Arg Thr Val Glu Leu Asp Lys Lys Thr Arg Thr Asn
            420                 425                 430

Leu Ile Gln Trp Pro Val Glu Glu Ile Glu Thr Leu Arg Arg Asn Val
        435                 440                 445

Thr Asp Leu Gly Gly Ile Thr Val Glu Ala Gly Ser Val Ile His Leu
```

```
    450                 455                 460

Pro Leu Gln Gln Gly Gly Gln Leu Asp Ile Glu Ala Ser Phe Arg Leu
465                 470                 475                 480

Asn Ser Ser Asp Ile Asp Ala Leu Asn Glu Ala Asp Val Gly Phe Asn
                485                 490                 495

Cys Ser Ser Ser Asp Gly Ala Ala Val Arg Gly Ala Leu Gly Pro Phe
            500                 505                 510

Gly Leu Leu Val Phe Ala Asp Gly Arg His Glu Gln Thr Ala Ala Tyr
        515                 520                 525

Phe Tyr Val Ser Lys Gly Leu Asp Gly Ser Leu Leu Thr His Tyr Cys
    530                 535                 540

His Asp Glu Ser Arg Ser Thr Arg Ala Lys Asp Val Val Ser Arg Val
545                 550                 555                 560

Val Gly Gly Thr Val Pro Val Leu Asp Gly Glu Thr Phe Ser Val Arg
                565                 570                 575

Val Leu Val Asp His Ser Ile Val Gln Ser Phe Val Met Gly Gly Arg
            580                 585                 590

Thr Thr Val Thr Ser Arg Ala Tyr Pro Thr Glu Ala Ile Tyr Ala Ala
        595                 600                 605

Ala Gly Val Tyr Leu Phe Asn Asn Ala Thr Ser Ala Thr Ile Thr Ala
    610                 615                 620

Glu Gly Leu Val Val Tyr Glu Met Ala Ser Ala
625                 630                 635


<210> SEQ ID NO 32
<211> LENGTH: 635
<212> TYPE: PRT
<213> ORGANISM: Lolium perenne

<400> SEQUENCE: 32

Met Glu Ser Ser Ala Val Val Ala Gln Gly Thr Thr Ser Pro Leu Leu
1               5                   10                  15

Pro Tyr Ala Tyr Ala Pro Leu Pro Ser Ser Ala Asp Asp Ala Arg Glu
            20                  25                  30

Asn Gln Ser Ser Gly Gly Gly Val Arg Trp Arg Ala Cys Ala Ala Ser
        35                  40                  45

Ala Leu Val Val Leu Leu Val Val Val Gly Phe Phe Ala Gly Gly Arg
    50                  55                  60

Val Asp Leu Gly Gln Asp Gly Glu Val Ser Ala Thr Ser Ser Val Pro
65                  70                  75                  80

Gly Ser Ser Arg Gly Lys Asp Ser Gly Val Ser Glu Lys Glu Ser Pro
                85                  90                  95

Ala Asp Gly Gly Phe Pro Trp Ser Asn Ala Met Leu Gln Trp Gln His
            100                 105                 110

Thr Gly Phe His Phe Gln Pro Leu Lys His Tyr Met Asn Asp Pro Asn
        115                 120                 125

Gly Pro Val Tyr Tyr Gly Gly Trp Tyr His Leu Phe Tyr Gln His Asn
    130                 135                 140

Pro Tyr Gly Asp Ser Trp Gly Asn Val Ser Trp Gly His Ala Val Ser
145                 150                 155                 160

Lys Asp Leu Val Asn Trp Arg His Leu Pro Val Ala Leu Val Pro Asp
                165                 170                 175

Gln Trp Tyr Asp Ile Asn Gly Val Leu Thr Gly Ser Ile Thr Val Leu
            180                 185                 190
```

```
Pro Asp Gly Arg Val Ile Leu Leu Tyr Thr Gly Asn Thr Asp Thr Phe
        195                 200                 205

Ser Gln Val Gln Cys Leu Ala Val Pro Ala Asp Pro Ser Asp Pro Leu
    210                 215                 220

Leu Arg Ser Trp Ile Lys His Pro Ala Asn Pro Ile Leu Phe Pro Pro
225                 230                 235                 240

Pro Gly Ile Gly Leu Lys Asp Phe Arg Asp Pro Leu Thr Ala Trp Phe
                245                 250                 255

Glu His Ser Asp Asn Thr Trp Arg Thr Ile Ile Gly Ser Lys Asp Asp
            260                 265                 270

Asp Gly His Ala Gly Ile Val Leu Ser Tyr Lys Thr Thr Asp Phe Val
        275                 280                 285

Asn Tyr Glu Leu Met Pro Gly Asn Met His Arg Gly Pro Asp Gly Thr
    290                 295                 300

Gly Met Tyr Glu Cys Leu Asp Ile Tyr Pro Val Gly Gly Asn Ser Ser
305                 310                 315                 320

Glu Met Leu Gly Gly Asp Ser Ser Pro Glu Val Leu Phe Val Leu Lys
                325                 330                 335

Glu Ser Ala Asn Asp Glu Trp His Asp Tyr Tyr Ala Leu Gly Trp Phe
            340                 345                 350

Asp Ala Ala Ala Asn Thr Trp Thr Pro Gln Asp Pro Glu Ala Asp Leu
        355                 360                 365

Gly Ile Gly Leu Arg Tyr Asp Trp Gly Lys Tyr Tyr Ala Ser Lys Ser
    370                 375                 380

Phe Tyr Asp Pro Ile Lys Asn Arg Arg Val Val Trp Ala Phe Val Gly
385                 390                 395                 400

Glu Thr Asp Ser Glu Gln Ala Asp Lys Ala Lys Gly Trp Ala Ser Leu
                405                 410                 415

Met Ser Ile Pro Arg Thr Val Glu Leu Asp Lys Lys Thr Arg Thr Asn
            420                 425                 430

Leu Ile Gln Trp Pro Val Glu Glu Ile Glu Thr Leu Arg Arg Asn Val
        435                 440                 445

Thr Asp Leu Gly Gly Ile Thr Val Glu Ala Gly Ser Val Ile His Leu
    450                 455                 460

Pro Leu Gln Gln Gly Gly Gln Leu Asp Ile Glu Ala Ser Phe Arg Leu
465                 470                 475                 480

Asn Ser Ser Asp Ile Asp Ala Leu Asn Glu Ala Asp Val Gly Phe Asn
                485                 490                 495

Cys Ser Ser Ser Asp Gly Ala Ala Val Arg Gly Ala Leu Gly Pro Phe
            500                 505                 510

Gly Leu Leu Val Phe Ala Asp Gly Arg His Glu Gln Thr Ala Ala Tyr
        515                 520                 525

Phe Tyr Val Ser Lys Gly Leu Asp Gly Ser Leu Leu Thr His Tyr Cys
    530                 535                 540

His Asp Glu Ser Arg Ser Thr Arg Ala Lys Asp Val Val Ser Arg Val
545                 550                 555                 560

Val Gly Gly Thr Val Pro Val Leu Asp Gly Glu Thr Phe Ser Val Arg
                565                 570                 575

Val Leu Val Asp His Ser Ile Val Gln Ser Phe Val Met Gly Gly Arg
            580                 585                 590

Thr Thr Val Thr Ser Arg Ala Tyr Pro Thr Glu Ala Ile Tyr Ala Ala
        595                 600                 605

Ala Gly Val Tyr Leu Phe Asn Asn Ala Thr Ser Ala Thr Ile Thr Ala
```

610 615 620

Glu Gly Leu Val Val Tyr Glu Met Ala Ser Ala
625 630 635

<210> SEQ ID NO 33
<211> LENGTH: 690
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
<222> LOCATION: (9)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (32)..(34)
<223> OTHER INFORMATION: Xaa can be any naturally occurring amino acid
<220> FEATURE:
<221> NAME/KEY: misc_feature
<222> LOCATION: (36)..(39)
<223> OTHER INFORMATION: Xaa can be any naturally occurring amino acid
<220> FEATURE:
<221> NAME/KEY: misc_feature
<222> LOCATION: (41)..(44)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (72)..(82)
<223> OTHER INFORMATION: Xaa can be any naturally occurring amino acid
<220> FEATURE:
<221> NAME/KEY: misc_feature
<222> LOCATION: (84)..(106)
<223> OTHER INFORMATION: Xaa can be any naturally occurring amino acid
<220> FEATURE:
<221> NAME/KEY: misc_feature
<222> LOCATION: (108)..(111)
<223> OTHER INFORMATION: Xaa can be any naturally occurring amino acid
<220> FEATURE:
<221> NAME/KEY: misc_feature
<222> LOCATION: (114)..(121)
<223> OTHER INFORMATION: Xaa can be any naturally occurring amino acid
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<222> LOCATION: (171)..(171)
<223> OTHER INFORMATION: Xaa can be any naturally occurring amino acid
<220> FEATURE:
<221> NAME/KEY: misc_feature
<222> LOCATION: (173)..(173)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (222)..(222)

<223> OTHER INFORMATION: Xaa can be any naturally occurring amino acid
<220> FEATURE:
<221> NAME/KEY: misc_feature
<222> LOCATION: (230)..(230)
<223> OTHER INFORMATION: Xaa can be any naturally occurring amino acid
<220> FEATURE:
<221> NAME/KEY: misc_feature
<222> LOCATION: (233)..(236)
<223> OTHER INFORMATION: Xaa can be any naturally occurring amino acid
<220> FEATURE:
<221> NAME/KEY: misc_feature
<222> LOCATION: (255)..(255)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid
<220> FEATURE:
<221> NAME/KEY: misc_feature
<222> LOCATION: (274)..(274)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid
<220> FEATURE:
<221> NAME/KEY: misc_feature
<222> LOCATION: (291)..(291)
<223> OTHER INFORMATION: Xaa can be any naturally occurring amino acid
<220> FEATURE:
<221> NAME/KEY: misc_feature
<222> LOCATION: (305)..(306)
<223> OTHER INFORMATION: Xaa can be any naturally occurring amino acid
<220> FEATURE:
<221> NAME/KEY: misc_feature
<222> LOCATION: (328)..(328)
<223> OTHER INFORMATION: Xaa can be any naturally occurring amino acid
<220> FEATURE:
<221> NAME/KEY: misc_feature
<222> LOCATION: (332)..(332)
<223> OTHER INFORMATION: Xaa can be any naturally occurring amino acid
<220> FEATURE:
<221> NAME/KEY: misc_feature
<222> LOCATION: (351)..(366)
<223> OTHER INFORMATION: Xaa can be any naturally occurring amino acid
<220> FEATURE:
<221> NAME/KEY: misc_feature
<222> LOCATION: (368)..(368)
<223> OTHER INFORMATION: Xaa can be any naturally occurring amino acid
<220> FEATURE:
<221> NAME/KEY: misc_feature
<222> LOCATION: (403)..(403)
<223> OTHER INFORMATION: Xaa can be any naturally occurring amino acid
<220> FEATURE:
<221> NAME/KEY: misc_feature
<222> LOCATION: (459)..(459)
<223> OTHER INFORMATION: Xaa can be any naturally occurring amino acid
<220> FEATURE:
<221> NAME/KEY: misc_feature
<222> LOCATION: (469)..(469)
<223> OTHER INFORMATION: Xaa can be any naturally occurring amino acid
<220> FEATURE:
<221> NAME/KEY: misc_feature
<222> LOCATION: (488)..(488)
<223> OTHER INFORMATION: Xaa can be any naturally occurring amino acid
<220> FEATURE:
<221> NAME/KEY: misc_feature
<222> LOCATION: (500)..(500)
<223> OTHER INFORMATION: Xaa can be any naturally occurring amino acid
<220> FEATURE:
<221> NAME/KEY: misc_feature
<222> LOCATION: (505)..(505)
<223> OTHER INFORMATION: Xaa can be any naturally occurring amino acid
<220> FEATURE:
<221> NAME/KEY: misc_feature
<222> LOCATION: (524)..(527)
<223> OTHER INFORMATION: Xaa can be any naturally occurring amino acid
<220> FEATURE:
<221> NAME/KEY: misc_feature
<222> LOCATION: (551)..(551)
<223> OTHER INFORMATION: Xaa can be any naturally occurring amino acid
<220> FEATURE:
<221> NAME/KEY: misc_feature
<222> LOCATION: (566)..(566)
<223> OTHER INFORMATION: Xaa can be any naturally occurring amino acid
<220> FEATURE:
<221> NAME/KEY: misc_feature
<222> LOCATION: (568)..(571)
<223> OTHER INFORMATION: Xaa can be any naturally occurring amino acid
<220> FEATURE:
<221> NAME/KEY: misc_feature
<222> LOCATION: (574)..(574)
<223> OTHER INFORMATION: Xaa can be any naturally occurring amino acid
<220> FEATURE:
<221> NAME/KEY: misc_feature
<222> LOCATION: (592)..(592)
<223> OTHER INFORMATION: Xaa can be any naturally occurring amino acid
<220> FEATURE:
<221> NAME/KEY: misc_feature
<222> LOCATION: (615)..(616)
<223> OTHER INFORMATION: Xaa can be any naturally occurring amino acid
<220> FEATURE:
<221> NAME/KEY: misc_feature
<222> LOCATION: (626)..(626)
<223> OTHER INFORMATION: Xaa can be any naturally occurring amino acid
<220> FEATURE:
<221> NAME/KEY: misc_feature
<222> LOCATION: (647)..(647)
<223> OTHER INFORMATION: Xaa can be any naturally occurring amino acid

<400> SEQUENCE: 33

```
Xaa Xaa Xaa Xaa Xaa Xaa Xaa Met Xaa Xaa Xaa Xaa Xaa Pro Xaa Leu
1               5                   10                  15

Pro Tyr Ala Tyr Xaa Xaa Leu Pro Ser Ser Ala Asp Asp Ala Arg Xaa
            20                  25                  30

Xaa Xaa Glu Xaa Xaa Xaa Xaa Gly Xaa Xaa Xaa Xaa Trp Arg Ala Cys
        35                  40                  45

Ala Ala Val Leu Ala Ala Ser Ala Val Val Val Leu Val Val Val Ala
    50                  55                  60

Xaa Leu Ala Gly Gly Arg Val Xaa Xaa Xaa Xaa Xaa Xaa Xaa Xaa Xaa
65                  70                  75                  80

Xaa Xaa Ala Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Gly Xaa Xaa Xaa Xaa Val
            100                 105                 110

Ser Xaa Xaa Xaa Xaa Xaa Xaa Xaa Xaa Ala Ala Gly Gly Phe Pro Trp
        115                 120                 125

Ser Asn Ala Met Leu Gln Trp Gln Arg Thr Gly Phe His Phe Gln Pro
    130                 135                 140

Glu Xaa His Tyr Met Asn Asp Pro Asn Gly Pro Val Tyr Tyr Arg Gly
145                 150                 155                 160

Tyr Tyr His Leu Phe Tyr Gln Tyr Asn Pro Xaa Gly Xaa Ser Trp Gly
                165                 170                 175

Xaa Asn Ile Ala Trp Gly His Ala Val Ser Lys Asp Leu Val Asn Trp
            180                 185                 190

Arg His Leu Pro Leu Ala Met Val Pro Asp Gln Tyr Asp Asp Ile Asn
        195                 200                 205

Gly Val Leu Thr Gly Ser Ile Val Thr Leu Pro Asp Gly Xaa Val Ile
    210                 215                 220

Leu Leu Tyr Thr Gly Xaa Thr Asp Xaa Xaa Xaa Xaa Ala Gln Val Gln
225                 230                 235                 240

Cys Leu Ala Val Pro Ala Asp Pro Ser Asp Pro Leu Leu Arg Xaa Trp
```

-continued

```
                245                 250                 255

Thr Lys His Pro Ala Asn Pro Val Leu Phe Pro Pro Xaa Pro Gly Ile
            260                 265                 270

Gly Xaa Lys Asp Asp Phe Arg Asp Pro Thr Thr Ala Trp Phe Asp Xaa
        275                 280                 285

Ser Asp Xaa Thr Trp Arg Thr Val Ile Gly Ser Lys Asp Asp Asp Gly
    290                 295                 300

Xaa Xaa His Ala Gly Ile Ala Leu Ser Tyr Lys Thr Lys Asp Phe Leu
305                 310                 315                 320

Asn Tyr Glu Leu Met Pro Gly Xaa Met His Arg Xaa Val Asp Gly Thr
                325                 330                 335

Gly Met Trp Glu Cys Ile Asp Phe Tyr Pro Val Gly Gly Asn Xaa Xaa
            340                 345                 350

Xaa Xaa Xaa Xaa Xaa Xaa Xaa Xaa Xaa Xaa Xaa Xaa Xaa Xaa Ser Xaa
        355                 360                 365

Glu Val Leu Tyr Val Leu Lys Glu Ser Ser Asp Asp Glu Arg His Asp
    370                 375                 380

Tyr Tyr Ala Leu Gly Arg Tyr Asp Ala Ala Ala Asn Thr Trp Thr Pro
385                 390                 395                 400

Leu Asp Xaa Glu Leu Asp Leu Gly Ile Gly Leu Arg Tyr Asp Arg Tyr
                405                 410                 415

Asp Trp Gly Lys Tyr Tyr Ala Ser Lys Ser Phe Tyr Asp Pro Ile Lys
            420                 425                 430

Asn Arg Arg Val Val Trp Gly Tyr Val Gly Glu Thr Asp Ser Glu Arg
        435                 440                 445

Ala Asp Val Ala Lys Gly Trp Ala Ser Leu Xaa Ser Ile Pro Arg Thr
    450                 455                 460

Val Glu Leu Asp Xaa Lys Thr Arg Thr Asn Leu Ile Gln Trp Pro Val
465                 470                 475                 480

Glu Glu Val Glu Thr Leu Arg Xaa Asn Ser Thr Asp Leu Gly Gly Ile
                485                 490                 495

Thr Val Glu Xaa Gly Ser Val Phe Xaa Leu Pro Leu His Gln Ala Thr
            500                 505                 510

Gln Leu Asp Ile Glu Ala Ser Phe Arg Leu Asp Xaa Xaa Xaa Xaa Ala
        515                 520                 525

Ser Asp Val Ala Ala Leu Asn Glu Ala Asp Val Gly Tyr Asn Cys Ser
    530                 535                 540

Ser Ser Gly Gly Ala Ala Xaa Arg Arg Gly Ala Leu Gly Pro Phe Gly
545                 550                 555                 560

Leu Leu Val Leu Ala Xaa Gly Xaa Xaa Xaa Xaa Gly Arg Xaa Glu Gln
                565                 570                 575

Thr Ala Val Tyr Phe Tyr Val Ser Lys Gly Leu Asp Gly Ser Leu Xaa
            580                 585                 590

Thr His Phe Cys His Asp Glu Ser Arg Ser Ser Arg Ala Lys Asp Val
        595                 600                 605

Val Lys Arg Val Val Gly Xaa Xaa Ser Thr Val Pro Val Leu Asp Gly
    610                 615                 620

Glu Xaa Phe Ser Val Arg Val Leu Val Asp His Ser Ile Val Gln Ser
625                 630                 635                 640

Phe Ala Met Gly Gly Arg Xaa Val Thr Ala Thr Ser Arg Val Tyr Pro
                645                 650                 655

Thr Glu Ala Ile Tyr Ala Ala Ala Gly Val Tyr Leu Phe Asn Asn Ala
            660                 665                 670
```

```
Thr Gly Thr Ala Val Thr Ala Glu Arg Leu Val Val His Glu Met Ala
        675                 680                 685

Ser Ala
    690


<210> SEQ ID NO 34
<211> LENGTH: 3405
<212> TYPE: DNA
<213> ORGANISM: Artificial Sequence
<220> FEATURE:
<223> OTHER INFORMATION: Expression construct

<400> SEQUENCE: 34

gatccggtga ctcaaaaaag aagagccgcc atctgtccaa gcgccactcc tacgagaact     60

aaaatcctat tccctccgta aataaatata agagtgttta gatcactact tctttacaga    120

gaatttcctt ccctccaagg ggaggcgaat ccataggcac atcgacggat atggaggggg    180

gaaacatata ttttactatg ctagttcagt taattctacc aagaaaacat atattttatt    240

ttgacaaaca ttgtataaat gtagacattc acatacacgt atgtacacca ccctctatga    300

ttgcacaccc gcacactata tgcctatgag catactttca agagtgagcc agcaaatttt    360

atgataaaat gaaatatttt gcccagccaa ctcagtcgca tcctcggaca atttgttatc    420

aaggaactca cccaaaaaca agcaaagcta gaaaaaggtt gtgtggcagc cacctaatga    480

catgaaggac tgaaatttcc agcacacaca atgtatccga cggcaatgct tcttccactg    540

atccggagaa gataaggaaa cgaggcaacc agcgaacgtg agccatccca accacatctg    600

taccaaagaa acggggctat atataccgtg gtgacccggc aatggggtcc tcaactgtag    660

ccggcatcct cctctcctcc gataatacaa atacccaagt ttgtacaaaa aagcaggctt    720

catggagtcc ccaagcgccg tcgtccccgg caccacggcg ccgctgcttc cttatgcgta    780

cgcgccgctg ccgtcgtccg ccgacgacgc ccgtcaaaac cggagtggcg ggaggtggcg    840

cgcgtgcgcc gccgtgctgg ccgcatcggc gttggcggtg gtcgtcgtgg tcgggctcct    900

cgcgggcggc agggtggatc gggtcccggc cggcggagac gtggcgtcgg ccacggtgcc    960

ggccgtgccg atggagttcc cgaggagccg gggcaaggac ttcggcgtgt cggagaagtc   1020

ctccggtgcc tactccaccg acggcgggtt cccgtggagc aacgccatgc tgcagtggca   1080

gcgcaccggg ttccatttcc agccggagca gcactacatg aacgatccca acggccccgt   1140

gtactacggc ggatggtacc acctcttcta ccagcacaac cccaagggcg acagctgggg   1200

caacatcgcg tgggcccacg ccgtctccaa ggacatggtc aactggcgcc acctccctct   1260

cgccatggtt cccgaccagt ggtacgacag caacggcgtc ctcaccggct ccatcaccgt   1320

gctccccgac ggccaggtca tcctgctcta caccggcaac accgacaccc tagcccaggt   1380

ccagtgcctc gccacgcccg ccgacccgtc cgacccgctc ctccgcgagt gggtcaagca   1440

ccccgccaac cccatcctct accctccccc cggcatcggc ctcaaggact tccgcgaccc   1500

cctcaccgcc tggttcgacc actccgacca cacctggcgc accgtcatcg gctccaagga   1560

cgacgacggc cacgccggca tcatcctcag ctacaagacc aaggacttcg tcaactacga   1620

gctcatgccg gggaacatgc accgcgggcc cgacggcacc ggaatgtacg agtgcatcga   1680

cctctacccc gtcggcggca actcgtccga gatgctcggc ggcgacgact cgcccggcgt   1740

gctcttcgtg ctcaaggaga gcagcgacga cgagcgccac gactactacg cgctcggaag   1800

gttcgacgcc gtcgccaacg tttggacgcc catcgaccgg gagctggacc ttgggatcgg   1860
```

```
gctcagatac gactggggaa agtactacgc ctccaagtcc ttctacgacc agaagaagaa   1920
ccgccgcatc gtatgggcat acatcggcga gaccgactcc gagcaggccg acatcaccaa   1980
gggatgggcc aatctcatga cgattccaag aacggtggag cttgacagga agacccgcac   2040
aaacctcatc caatggccag tggaggaggt cgacaccctc cgcaggaact ccacggacct   2100
cggtcgcatc accgtcaacg ccggctccgt cattcgcctc cccctccacc agggcgctca   2160
actcgacatc gaggcctcct tccaactcaa ctcttccgac gtggatgcta tcaacgaggc   2220
cgacgtcggc tacaactgca gcaccagtgg tgccgccgta cggggggcgc tcggcccctt   2280
tggcctcctc gtccttgcca acggccgcac cgaacagacg gctgtgtact tctacgtgtc   2340
caagggcgtc gacggtgccc tccagaccca cttctgccac gacgagtcac ggtcaacgcg   2400
ggcaaaggat gtcgtgaata ggatgattgg cagcatcgtg ccggtgcttg acggtgagac   2460
cttttcggtg agggtgctag tggaccactc catcgtgcag agcttcgcga tgggcgggag   2520
gatcacggcg acgtcgcggg cgtacccgac ggaggccatc tacgcggccg cgggggtcta   2580
cctcttcaac aacgccacgg gcgccaccgt caccgccgag aggctcgtcg tgcacgagat   2640
ggcctcagct gacaaccata tcttcacgaa cgacgacttg taggacccag ctttcttgta   2700
caaagtggac tatgagttga aacaatggcc tatctcatat gaagatcttt tgtgaatttc   2760
acttttgtcc acgacctctg ttgcacgact ctgctttccg accggagcat accttttgtt   2820
ctatatgatt tgtgtatgta tgtaggaacc tatgttctcg agcatgcata cataattcct   2880
cataggtcta tatacaccgg ctatccatat gcaaaacctg tgtaatattt gttatataca   2940
acacgcggac cattgtcttg ctgttattaa ttcttttttc ccgcaaaaaa ggaaaagttt   3000
ctttatttgg cactgcaatg gatatgcctc acagctagtg ggtggagaat tcagtatttg   3060
acattaagat tccctgattt gcaattgcaa atttcagttt ctttacttat atcactacaa   3120
aagtcttatt gtttcttttc cacgtcatta ccatctgctc cattggtttt tgctagtaga   3180
ataggatgaa gcatggacac agattaactg agctcgagct catatgagct cgggtgaaca   3240
ataaaatctg aaaatactta gaaagaattc aaaattttct gtttttgtg gcaaaatttg   3300
acaaatgtta taaatgcttg caaagtttca tcatagaacg acattcgtgg atgtcatggc   3360
aaaaaacaaa ttcagcactc tgaaaataac tttttgaag tatcg                    3405
```

<210> SEQ ID NO 35
<211> LENGTH: 3381
<212> TYPE: DNA
<213> ORGANISM: Artificial Sequence
<220> FEATURE:
<223> OTHER INFORMATION: Expression construct

<400> SEQUENCE: 35

```
gatccggtga ctcaaaaaag aagagccgcc atctgtccaa gcgccactcc tacgagaact     60
aaaatcctat tccctccgta aataaatata agagtgttta gatcactact tctttacaga    120
gaatttcctt ccctccaagg ggaggcgaat ccataggcac atcgacggat atggaggggg    180
gaaacatata ttttactatg ctagttcagt taattctacc aagaaaacat atattttatt    240
ttgacaaaca ttgtataaat gtagacattc acatacacgt atgtacacca ccctctatga    300
ttgcacaccc gcacactata tgcctatgag catactttca agagtgagcc agcaaatttt    360
atgataaaat gaaatatttt gcccagccaa ctcagtcgca tcctcggaca atttgttatc    420
aaggaactca cccaaaaaca agcaaagcta gaaaaaggtt gtgtggcagc cacctaatga    480
catgaaggac tgaaatttcc agcacacaca atgtatccga cggcaatgct tcttccactg    540
```

-continued

```
atccggagaa gataaggaaa cgaggcaacc agcgaacgtg agccatccca accacatctg    600
taccaaagaa acggggctat atataccgtg gtgacccggc aatggggtcc tcaactgtag    660
ccggcatcct cctctcctcc gataatacaa atacccaagt ttgtacaaaa aagcaggctt    720
catggagtcc agcgccgtcg tcgcccaagg caccacgtcg ccgctgctcc cgtacgccta    780
cgcgccgctg ccgtcctctg ccgacgacgc ccgtgaaaac cagagtagcg gcggcggtgt    840
caggtggcgc gcgtgcgcgg cctcggccct ggtggtgctg ctggtcgtcg tcggcttctt    900
cgcgggtggc agggtggatc tgggtcagga cggcgaggtg tctgcgactt cttcggttcc    960
tgggagcagc aggggcaagg attccggcgt gtcggagaag gagtcgcccg ccgacggcgg   1020
cttcccgtgg agcaacgcca tgctgcagtg gcagcacacc gggttccatt tccagccact   1080
caagcactac atgaacgatc ccaacggtcc ggtctactat ggcggatggt accacctctt   1140
ctaccagcac aacccctatg gcgactcgtg gggaaacgta tcttggggac atgccgtgtc   1200
caaggacctg gtgaactggc gccacctccc ggtcgccttg gtgcccgatc agtggtacga   1260
catcaacggc gtcctgacgg gctctatcac agtgctccca gacgggcgtg tcatcctgct   1320
atatacgggg aacaccgaca ccttttcgca ggtccagtgc ctcgcagtgc ccgccgaccc   1380
atctgacccg ctcctccgta gctggatcaa gcaccccgcc aaccccatcc tcttcccgcc   1440
acctgggatc gggctcaagg acttccgtga cccgctcaca gcctggttcg aacattccga   1500
caacacgtgg cgcaccatca tcggatccaa ggatgacgac ggccacgccg gcatcgtcct   1560
tagctacaag accaccgact ttgtgaatta tgagctcatg ccagggaaca tgcatcgtgg   1620
ccccgacggc accggcatgt acgagtgcct tgacatctac cctgtgggcg gcaactcatc   1680
cgagatgttg ggtggcgact cctcacctga ggtgttgttc gtgctcaagg agagcgccaa   1740
cgacgagtgg cacgactact acgcgcttgg gtggtttgac gctgccgcca acacgtggac   1800
gccacaggac cccgaggcgg accttgggat cggcctcagg tacgactggg gcaagtacta   1860
cgcgtccaag tccttctacg acccgatcaa gaaccggcgt gtcgtttggg ctttcgtcgg   1920
cgagaccgac tctgagcagg ccgacaaagc caagggatgg gcgtccctca tgtcgattcc   1980
caggacggtg gagcttgaca agaagacccg gacgaacctg atccaatggc cagtggagga   2040
gatcgagacc cttcgcagga acgtcacaga cctcggtggc atcaccgttg aagccggctc   2100
cgtcattcac cttcccctcc aacaaggcgg gcagcttgac atcgaggcct ccttccgtct   2160
caactcttcg gacatcgatg cactcaacga ggccgacgtc ggcttcaact gcagtagcag   2220
cgatggggca gccgtgcgtg gtgcgctcgg cccctttggc ctcctcgtct tcgccgacgg   2280
tcgccacgaa cagacggcgg cgtacttcta cgtgtccaag ggcctcgacg gcagcctcct   2340
gacgcactac tgccacgacg agtcacggtc gacgcgagca aaggacgtcg tgagccgggt   2400
ggttggcggc actgtgccag tgcttgacgg tgaaaccttt tcagtgaggg tgctagtgga   2460
ccactccatc gtgcagagct tcgtgatggg tgggaggacc acggtgacat cgcgggcata   2520
cccgacggag gccatctacg ccgcggcagg ggtgtacctg ttcaacaacg caacgagcgc   2580
caccatcacc gccgaagggc tcgtcgtgta cgagatggcc tcggccgaga gtcgggcctt   2640
cttggctgac gaccatgtag acccagcttt cttgtacaaa gtggactatg agttgaaaca   2700
atggcctatc tcatatgaag atcttttgtg aatttcactt ttgtccacga cctctgttgc   2760
acgactctgc tttccgaccg gagcatacct tttgttctat atgatttgtg tatgtatgta   2820
ggaacctatg ttctcgagca tgcatacata attcctcata ggtctatata caccggctat   2880
```

```
ccatatgcaa aacctgtgta atatttgtta tatacaacac gcggaccatt gtcttgctgt   2940
tattaattct tttttcccgc aaaaaaggaa aagtttcttt atttggcact gcaatggata   3000
tgcctcacag ctagtgggtg gagaattcag tatttgacat taagattccc tgatttgcaa   3060
ttgcaaattt cagtttcttt acttatatca ctacaaaagt cttattgttt cttttccacg   3120
tcattaccat ctgctccatt ggtttttgct agtagaatag gatgaagcat ggacacagat   3180
taactgagct cgagctcata tgagctcggg tgaacaataa aatctgaaaa tacttagaaa   3240
gaattcaaaa ttttctgttt tttgtggcaa aatttgacaa atgttataaa tgcttgcaaa   3300
gtttcatcat agaacgacat tcgtggatgt catggcaaaa aacaaattca gcactctgaa   3360
aataactttt ttgaagtatc g                                              3381
```

<210> SEQ ID NO 36
<211> LENGTH: 5361
<212> TYPE: DNA
<213> ORGANISM: Artificial Sequence
<220> FEATURE:
<223> OTHER INFORMATION: Expression construct

<400> SEQUENCE: 36

```
gatccggtga ctcaaaaaag aagagccgcc atctgtccaa gcgccactcc tacgagaact     60
aaaatcctat tccctccgta aataaatata agagtgttta gatcactact tctttacaga    120
gaatttcctt ccctccaagg ggaggcgaat ccataggcac atcgacggat atggaggggg    180
gaaacatata ttttactatg ctagttcagt taattctacc aagaaaacat atattttatt    240
ttgacaaaca ttgtataaat gtagacattc acatacacgt atgtacacca ccctctatga    300
ttgcacaccc gcacactata tgcctatgag catactttca agagtgagcc agcaaatttt    360
atgataaaat gaaatatttt gcccagccaa ctcagtcgca tcctcggaca atttgttatc    420
aaggaactca cccaaaaaca agcaaagcta gaaaaaggtt gtgtggcagc cacctaatga    480
catgaaggac tgaaatttcc agcacacaca atgtatccga cggcaatgct tcttccactg    540
atccggagaa gataaggaaa cgaggcaacc agcgaacgtg agccatccca accacatctg    600
taccaaagaa acggggctat atataccgtg gtgacccggc aatggggtcc tcaactgtag    660
ccggcatcct cctctcctcc gataatacaa atacccaagt ttgtacaaaa aagcaggctt    720
catggagtcc ccaagcgccg tcgtcccggg caccacggcg ccgctgcttc cttatgcgta    780
cgcgccgctg ccgtcgtccg ccgacgacgc ccgtcaaaac cggagtggcg ggaggtggcg    840
cgcgtgcgcc gccgtgctgg ccgcatcggc gttgtcggtg gtcgtcgtgg tcgggctcct    900
cgcgggcggc agggtggatc gggtcccggc cggcggagac gtggcgtcgg ccacggtgcc    960
ggccgtgccg atggagttcc cgaggagccg gggcaaggac ttcggcgtgt cggagaagtc   1020
ctccggtgcc tactccaccg acggcgggtt cccgtggagc aacgccatgc tgcagtggca   1080
gcgcaccggg ttccatttcc agccggagca gcactacatg aacgatccca acggccccgt   1140
gtactacggc ggatggtacc acctcttcta ccagcacaac cccaagggcg acagctgggg   1200
caacatcgcg tgggcccacg ccgtctccaa ggacatggtc aactggcgcc acctccctct   1260
cgccatggtt cccgaccagt ggtacgacag caacggcgtc ctcaccggct ccatcaccgt   1320
gctccccgac ggccaggtca tcctgctcta caccggcaac accgacaccc tagcccaggt   1380
ccagtgcctc gccacgcccg ccgacccgtc cgacccgctc ctccgcgagt gggtcaagca   1440
ccccgccaac cccatcctct accctccccc cggcatcggc ctcaaggact tccgcgaccc   1500
cctcaccgcc tggttcgacc actccgacca cacctggcgc accgtcatcg gctccaagga   1560
```

-continued

```
cgacgacggc cacgccggca tcatcctcag ctacaagacc aaggacttcg tcaactacga   1620
gctcatgccg gggaacatgc accgcgggcc cgacggcacc ggaatgtacg agtgcatcga   1680
cctctacccc gtcggcggca actcgtccga gatgctcggc ggcgacgact cgcccggcgt   1740
gctcttcgtg ctcaaggaga gcagcgacga cgagcgccac gactactacg cgctcggaag   1800
gttcgatgcc gtcgccaacg tttggacgcc catcgaccgg gagctggacc ttgggatcgg   1860
gctcagatac gactggggaa agtactacgc ctccaagtcc ttctacgacc agaagaagaa   1920
ccgccgcatc gtatgggcat acatcggcga gaccgactcc gagcaggccg acatcaccaa   1980
gggatgggcc aatctcatga cgattccaag aacggtggag cttgacagga agacccgcac   2040
aaacctcatc caatggccag tggaggaggt cgacaccctc cgcaggaact ccacggacct   2100
cggtcgcatc accgtcaacg ccggctccgt cattcgcctc cccctccacc agggcgctca   2160
actcgacatc gaggcctcct tccaactcaa ctcttccgac gtggatgcta tcaacgaggc   2220
cgacgtcggc tacaactgca gcaccagtgg tgccgccgta cggggggcgc tcggcccctt   2280
tggcctcctc gtccttgcca acggccgcac cgaacagacg gctgtgtact tctacgtgtc   2340
caagggcgtc gacggtgccc tccagaccca cttctgccac gacgagtcac ggtcaacgcg   2400
ggcaaaggat gtcgtgaata ggatgattgg cagcatcgtg ccggtgcttg acggtgagac   2460
cttttcggtg agggtgctag tggaccactc catcgtgcag agcttcgcga tgggcgggag   2520
gatcacggcg acgtcgcggg cgtacccgac ggaggccatc tacgcggccg cgggggtcta   2580
cctcttcaac aacgccacgg gcgccaccgt caccgccgag aggctcgtcg tgcacgagat   2640
ggcctcagct gacaaccata tcttcacgaa cgacgacttg ggaggaggaa agcttggagg   2700
aggagagtcc agcgccgtcg tcgcccaagg caccacgtcg ccgctgctcc cgtacgccta   2760
cgcgccgctg ccgtcctctg ccgacgacgc ccgtgaaaac cagagtagcg gcggcggtgt   2820
caggtggcgc gcgtgcgcgg cctcggccct ggtggtgctg ctggtcgtcg tcggcttctt   2880
cgcgggtggc agggtggatc tgggtcagga cggcgaggtg tctgcgactt cttcggttcc   2940
tgggagcagc aggggcaagg attccggcgt gtcggagaag gagtcgcccg ccgacggcgg   3000
cttcccgtgg agcaacgcca tgctgcagtg gcagcacacc gggttccatt tccagccact   3060
caagcactac atgaacgatc ccaacggtcc ggtctactat ggcggatggt accacctctt   3120
ctaccagcac aacccctatg gcgactcgtg gggaaacgta tcttggggac atgccgtgtc   3180
caaggacctg gtgaactggc gccacctccc ggtcgccttg gtgcccgatc agtggtacga   3240
catcaacggc gtcctgacgg gctctatcac agtgctccca gacgggcgtg tcatcctgct   3300
atatacgggg aacaccgaca ccttttcgca ggtccagtgc ctcgcagtgc ccgccgaccc   3360
atctgacccg ctcctccgta gctggatcaa gcaccccgcc aaccccatcc tcttcccgcc   3420
acctgggatc gggctcaagg acttccgtga cccgctcaca gcctggttcg aacattccga   3480
caacacgtgg cgcaccatca tcggatccaa ggatgacgac ggccacgccg gcatcgtcct   3540
tagctacaag accaccgact ttgtgaatta tgagctcatg ccagggaaca tgcatcgtgg   3600
ccccgacggc accggcatgt acgagtgcct tgacatctac cctgtgggcg gcaactcatc   3660
cgagatgttg ggtggcgact cctcacatga ggtgttgttc gtgctcaagg agagcgccaa   3720
cgacgagtgg cacgactact acgcgcttgg gtggtttgac gctgccgcca acacgtggac   3780
gccacaggac cccgaggcgg accttgggat cggcctcagg tacgactggg gcaagtacta   3840
cgcgtccaag tccttctacg acccgatcaa gaaccggcgt gtcgtttggg ctttcgtcgg   3900
```

cgagaccgac tctgagcagg ccgacaaagc caagggatgg gcgtccctca tgtcgattcc 3960
caggacggtg gagcttgaca agaagacccg gacgaacctg atccaatggc cagtggagga 4020
gatcgagacc cttcgcagga acgtcacaga cctcggtggc atcaccgttg aagccggctc 4080
cgtcattcac cttcccctcc aacaaggcgg gcagcttgac atcgaggcct ccttccgtct 4140
caactcttcg gacatcgatg cactcaacga ggccgacgtc ggcttcaact gcagtagcag 4200
cgatggggta gccgtgcgtg gtgcgctcgg cccctttggc ctcctcgtct tcgccgacgg 4260
tcgccacgaa cagacggcgg cgtacttcta cgtgtccaag ggcctcgacg gcagcctcct 4320
gacgcactac tgccacgacg agtcacggtc gacgcgagca aaggacgtcg tgagccgggt 4380
ggttggcggc actgtgccag tgcttgacgg tgaaaccttt tcagtgaggg tgctagtgga 4440
ccactccatc gtgcagagct tcgtgatggg tgggaggacc acggtgacat cgcgggcata 4500
cccgacggag gccatctacg ccgcggcagg ggtgtacctg ttcaacaacg caacgagcgc 4560
caccatcacc gccgaagggc tcgtcgtgta cgagatggcc tcggccgaga gtcgggcctt 4620
cttggctgac gacatgtagg acccagcttt cttgtacaaa gtggactatg agttgaaaca 4680
atggcctatc tcatatgaag atcttttgtg aatttcactt ttgtccacga cctctgttgc 4740
acgactctgc tttccgaccg gagcatacct tttgttctat atgatttgtg tatgtatgta 4800
ggaacctatg ttctcgagca tgcatacata attcctcata ggtctatata caccggctat 4860
ccatatgcaa aacctgtgta atatttgtta tatacaacac gcggaccatt gtcttgctgt 4920
tattaattct tttttcccgc aaaaaaggaa aagtttcttt atttggcact gcaatggata 4980
tgcctcacag ctagtgggtg gagaattcag tatttgacat taagattccc tgatttgcaa 5040
ttgcaaattt cagtttcttt acttatatca ctacaaaagt cttattgttt cttttccacg 5100
tcattaccat ctgctccatt ggtttttgct agtagaatag gatgaagcat ggacacagat 5160
taactgagct cgagctcata tgagctcggg tgaacaataa aatctgaaaa tacttagaaa 5220
gaattcaaaa ttttctgttt tttgtggcaa aatttgacaa atgttataaa tgcttgcaaa 5280
gtttcatcat agaacgacat tcgtggatgt catggcaaaa aacaaattca gcactctgaa 5340
aataactttt ttgaagtatc g 5361

<210> SEQ ID NO 37
<211> LENGTH: 5367
<212> TYPE: DNA
<213> ORGANISM: Artificial Sequence
<220> FEATURE:
<223> OTHER INFORMATION: Expression construct

<400> SEQUENCE: 37
gatccggtga ctcaaaaaag aagagccgcc atctgtccaa gcgccactcc tacgagaact 60
aaaatcctat tccctccgta aataaatata agagtgttta gatcactact tctttacaga 120
gaatttcctt ccctccaagg ggaggcgaat ccataggcac atcgacggat atggaggggg 180
gaaacatata ttttactatg ctagttcagt taattctacc aagaaaacat atattttatt 240
ttgacaaaca ttgtataaat gtagacattc acatacacgt atgtacacca ccctctatga 300
ttgcacaccc gcacactata tgcctatgag catactttca agagtgagcc agcaaatttt 360
atgataaaat gaaatatttt gcccagccaa ctcagtcgca tcctcggaca atttgttatc 420
aaggaactca cccaaaaaca agcaaagcta gaaaaaggtt gtgtggcagc cacctaatga 480
catgaaggac tgaaatttcc agcacacaca atgtatccga cggcaatgct tcttccactg 540
atccggagaa gataaggaaa cgaggcaacc agcgaacgtg agccatccca accacatctg 600

-continued

```
taccaaagaa acggggctat atataccgtg gtgacccggc aatggggtcc tcaactgtag    660
ccggcatcct cctctcctcc gataatacaa atacccaagt ttgtacaaaa aagcaggctt    720
catggagtcc ccaagcgccg tcgtccccgg caccacggcg ccgctgcttc cttatgcgta    780
cgcgccgctg ccgtcgtccg ccgacgacgc ccgtcaaaac cggagtggcg ggaggtggcg    840
cgcgtgcgcc gccgtgctgg ccgcatcggc gttggcggtg gtcgtcgtgg tcgggctcct    900
cgcgggcggc agggtggatc gggtcccagc cggcggagac gtggcgtcgg ccacggtgcc    960
ggccgtgccg atggagttcc cgaggagccg gggcaaggac ttcggcgtgt cggagaagtc   1020
ctccggtgcc tactccaccg acggcgggtt cccgtggagc aacgccatgc tgcagtggca   1080
gcgcaccggg ttccatttcc agccggagca gcactacatg aacgatccca acggccccgt   1140
gtactacggc ggatggtacc acctcttcta ccagcacaac cccaagggcg acagctgggg   1200
caacatcgcg tgggcccacg ccgtctccaa ggacatggtc aactggcgcc acctccctct   1260
cgccatggtt cccgaccagt ggtacgacag caacggcgtc ctcaccggct ccatcaccgt   1320
gctccccgac ggccaggtca tcctgctcta caccggcaac accgacaccc tagcccaggt   1380
ccagtgcctc gccacgcccg ccgacccgtc cgacccgctc ctccgcgagt gggtcaagca   1440
ccccgccaac cccatcctct accctccccc cggcatcggc ctcaaggact tccgcgaccc   1500
cctcaccgcc tggttcgacc actccgacca cacctggcgc accgtcatcg gctccaagga   1560
cgacgacggc cacgccggca tcatcctcag ctacaagacc aaggacttcg tcaactacga   1620
gctcatgccg gggaacatgc accgcgggcc cgacggcacc ggaatgtacg agtgcatcga   1680
cctctacccc gtcggcggca actcgtccga gatgctcggc ggcgacgact cgcccggcgt   1740
gctcttcgtg ctcaaggaga gcagcgacga cgagcgccac gactactacg cgctcggaag   1800
gttcgacgcc gtcgccaacg tttggacgcc catcgaccgg gagctggacc ttgggatcgg   1860
gctcagatac gactggggaa agtactacgc ctccaagtcc ttctacgacc agaagaagaa   1920
ccgccgcatc gtatgggcat acatcggcga gaccgactcc gagcaggccg acatcaccaa   1980
gggatgggcc aatctcatga cgattccaag aacggtggag cttgacagga agacccgcac   2040
aaacctcatc caatggccag tggaggaggt cgacaccctc cgcaggaact ccacggacct   2100
cggtcgcatc accgtcaacg ccggctccgt cattcgcctc cccctccacc agggcgctca   2160
actcgacatc gaggcctcct tccaactcaa ctcttccgac gtggatgcta tcaacgaggc   2220
cgacgtcggc tacaactgca gcaccagtgg tgccgccgta cggggggcgc tcggcccctt   2280
tggcctcctc gtccttgcca acggccgcac cgaacagacg gctgtgtact tctacgtgtc   2340
caagggcgtc gacggtgccc tccagaccca cttctgccac gacgagtcac ggtcaacgcg   2400
ggcaaaggat gtcgtgaata ggatgattgg cagcatcgtg ccggtgcttg acggtgagac   2460
cttttcggtg agggtgctag tggaccactc catcgtgcag agcttcgcga tgggcgggag   2520
gatcacggcg acgtcgcggg cgtacccgac ggaggccatc tacgcggccg cgggggtcta   2580
cctcttcaac aacgccacgg gcgccaccgt caccgccgag aggctcgtcg tgcacgagat   2640
ggcctcagct gacaaccata tcttcacgaa cgacgacttg ggaggaggaa agcttaagct   2700
tggaggagga gagtccagcg ccgtcgtcgc ccaaggcacc acgtcgccgc tgctcccgta   2760
cgcctacgcg ccgctgccgt cctctgccga cgacgcccgt gaaaaccaga gtagcggcgg   2820
cggtgtcagg tggcgcgcgt gcgcggcctc ggccctggtg gtgctgctgg tcgtcgtcgg   2880
cttcttcgcg ggtggcaggg tggatctggg tcaggacggc gaggtgtctg cgacttcttc   2940
```

-continued

```
ggttcctggg agcagcaggg gcaaggattc cggcgtgtcg gagaaggagt cgcccgccga   3000
cggcggcttc ccgtggagca acgccatgct gcagtggcag cacaccgggt tccatttcca   3060
gccactcaag cactacatga acgatcccaa cggtccggtc tactatggcg gatggtacca   3120
cctcttctac cagcacaacc cctatggcga ctcgtgggga aacgtatctt ggggacatgc   3180
cgtgtccaag gacctggtga actggcgcca cctcccggtc gccttggtgc ccgatcagtg   3240
gtacgacatc aacggcgtcc tgacgggctc tatcacagtg ctcccagacg ggcgtgtcat   3300
cctgctatat acggggaaca ccgacacctt ttcgcaggtc cagtgcctcg cagtgcccgc   3360
cgacccatct gacccgctcc tccgtagctg gatcaagcac cccgccaacc ccatcctctt   3420
cccgccacct gggatcgggc tcaaggactt ccgtgacccg ctcacagcct ggttcgaaca   3480
ttccgacaac acgtggcgca ccatcatcgg atccaaggat gacgacggcc acgccggcat   3540
cgtccttagc tacaagacca ccgactttgt gaattatgag ctcatgccag ggaacatgca   3600
tcgtggcccc gacggcaccg gcatgtacga gtgccttgac atctaccctg tgggcggcaa   3660
ctcatccgag atgttgggtg gcgactcctc acctgaggtg ttgttcgtgc tcaaggagag   3720
cgccaacgac gagtggcacg actactacgc gcttgggtgg tttgacgctg ccgccaacac   3780
gtggacgcca caggaccccg aggcggacct tgggatcggc ctcaggtacg actggggcaa   3840
gtactacgcg tccaagtcct tctacgaccc gatcaagaac cggcgtgtcg tttgggcttt   3900
cgtcggcgag accgactctg agcaggccga caaagccaag ggatgggcgt ccctcatgtc   3960
gattcccagg acggtggagc ttgacaagaa gacccggacg aacctgatcc aatggccagt   4020
ggaggagatc gagacccttc gcaggaacgt cacagacctc ggtggcatca ccgttgaagc   4080
cggctccgtc attcaccttc ccctccaaca aggcgggcag cttgacatcg aggcctcctt   4140
ccgtctcaac tcttcggaca tcgatgcact caacgaggcc gacgtcggct tcaactgcag   4200
tagcagcgat ggggcagccg tgcgtggtgc gctcggcccc tttggcctcc tcgtcttcgc   4260
cgacggtcgc cacgaacaga cggcggcgta cttctacgtg tccaagggcc tcgacggcag   4320
cctcctgacg cactactgcc acgacgagtc acggtcgacg cgagcaaagg acgtcgtgag   4380
ccgggtggtt ggcggcactg tgccagtgct tgacggtgaa accttttcag tgagggtgct   4440
agtggaccac tccatcgtgc agagcttcgt gatgggtggg aggaccacgg tgacatcgcg   4500
ggcatacccg acggaggcca tctacgccgc ggcaggggtg tacctgttca acaacgcaac   4560
gagcgccacc atcaccgccg aagggctcgt cgtgtacgag atggcctcgg ccgagagtcg   4620
ggccttcttg gctgacgaca tgtaggaccc agctttcttg tacaaagtgg actatgagtt   4680
gaaacaatgg cctatctcat atgaagatct tttgtgaatt tcacttttgt ccacgacctc   4740
tgttgcacga ctctgctttc cgaccggagc ataccttttg ttctatatga tttgtgtatg   4800
tatgtaggaa cctatgttct cgagcatgca tacataattc ctcataggtc tatatacacc   4860
ggctatccat atgcaaaacc tgtgtaatat ttgttatata caacacgcgg accattgtct   4920
tgctgttatt aattcttttt tcccgcaaaa aaggaaaagt ttctttattt ggcactgcaa   4980
tggatatgcc tcacagctag tgggtggaga attcagtatt tgacattaag attccctgat   5040
ttgcaattgc aaatttcagt ttctttactt atatcactac aaaagtctta ttgtttcttt   5100
tccacgtcat taccatctgc tccattggtt tttgctagta gaataggatg aagcatggac   5160
acagattaac tgagctcgag ctcatatgag ctcgggtgaa caataaaatc tgaaaatact   5220
tagaaagaat tcaaaatttt ctgttttttg tggcaaaatt tgacaaatgt tataaatgct   5280
tgcaaagttt catcatagaa cgacattcgt ggatgtcatg gcaaaaaaca aattcagcac   5340
```

tctgaaaata actttttga agtatcg 5367

<210> SEQ ID NO 38
<211> LENGTH: 3280
<212> TYPE: DNA
<213> ORGANISM: Artificial Sequence
<220> FEATURE:
<223> OTHER INFORMATION: Expression construct

<400> SEQUENCE: 38
atctgttcat ctaccttact agtctgcatg attagtttat tcgttatttt cgtagtcatg 60
atttatcaat tactcgtacg gattatttca tatggatatt tgcttatatt tccaacaatt 120
tacactgtcg agttttggcg cggctgctgg agttactctt agagtagttg gacttgagac 180
aaaagctaga atatcaatta tatataggag tgaggagtta ttctttcgaa agaactttaa 240
acggtagctg cacttagtcg tcgcaatgaa atacttgtcg tactaccatg ataattggta 300
atatgagagg gaatattaat tcctcagtga tttgaatttt gtgtgctcat gtgcagtcac 360
ccacgccatg catccgacga cgggcggcta taccaactct tgcactgatc cggagggata 420
aggcgccatg caaccaggga acgtcgtcca ccccttccac atcctgtatc aaattaagga 480
acgggcgctg agcctatgcc gagacatata taatgcggcg actcggacat ggaggggcct 540
caggcatagc ccagctagtt atctcattct ctccttagca ataatactta gcaccatggc 600
ccccgcggtg gaattcatgg agtccccaag cgccgtcgtc cccggcacca cggcgccgct 660
gcttccttat gcgtacgcgc cgctgccgtc gtccgccgac gacgcccgtc aaaaccggag 720
tggcgggagg tggcgcgcgt gcgccgccgt gctggccgca tcggcgttgg cggtggtcgt 780
cgtggtcggg ctcctcgcgg gcggcagggt ggatcgggtc ccggccggcg gagacgtggc 840
gtcggccacg gtgccggccg tgccgatgga gttcccgagg agccggggca aggacttcgg 900
cgtgtcggag aagtcctccg gtgcctactc caccgacggc gggttcccgt ggagcaacgc 960
catgctgcag tggcagcgca ccgggttcca tttccagccg gagcagcact acatgaacga 1020
tcccaacggc cccgtgtact acggcggatg gtaccacctc ttctaccagc acaaccccaa 1080
gggcgacagc tggggcaaca tcgcgtgggc ccacgccgtc tccaaggaca tggtcaactg 1140
gcgccacctc cctctcgcca tggttcccga ccagtggtac gacagcaacg gcgtcctcac 1200
cggctccatc accgtgctcc ccgacggcca ggtcatcctg ctctacaccg gcaacaccga 1260
caccctagcc caggtccagt gcctcgccac gcccgccgac ccgtccgacc cgctcctccg 1320
cgagtgggtc aagcaccccg ccaaccccat cctctaccct ccccccggca tcggcctcaa 1380
ggacttccgc gacccctca ccgcctggtt cgaccactcc gaccacacct ggcgcaccgt 1440
catcggctcc aaggacgacg acggccacgc cggcatcatc ctcagctaca agaccaagga 1500
cttcgtcaac tacgagctca tgccggggaa catgcaccgc gggcccgacg gcaccggaat 1560
gtacgagtgc atcgacctct accccgtcgg cggcaactcg tccgagatgc tcggcggcga 1620
cgactcgccc ggcgtgctct tcgtgctcaa ggagagcagc gacgacgagc gccacgacta 1680
ctacgcgctc ggaaggttcg acgccgtcgc caacgtttgg acgcccatcg accgggagct 1740
ggaccttggg atcgggctca gatacgactg gggaaagtac tacgcctcca agtccttcta 1800
cgaccagaag aagaaccgcc gcatcgtatg ggcatacatc ggcgagaccg actccgagca 1860
ggccgacatc accaagggat gggccaatct catgacgatt ccaagaacgg tggagcttga 1920
caggaagacc cgcacaaacc tcatccaatg gccagtggag gaggtcgaca ccctccgcag 1980

```
gaactccacg gacctcggtc gcatcaccgt caacgccggc tccgtcattc gcctcccct   2040
ccaccagggc gctcaactcg acatcgaggc ctccttccaa ctcaactctt ccgacgtgga   2100
tgctatcaac gaggccgacg tcggctacaa ctgcagcacc agtggtgccg ccgtacgggg   2160
ggcgctcggc ccctttggcc tcctcgtcct tgccaacggc cgcaccgaac agacggctgt   2220
gtacttctac gtgtccaagg gcgtcgacgg tgccctccag acccacttct gccacgacga   2280
gtcacggtca acgcgggcaa aggatgtcgt gaataggatg attggcagca tcgtgccggt   2340
gcttgacggt gagacctttt cggtgagggt gctagtggac cactccatcg tgcagagctt   2400
cgcgatgggc gggaggatca cggcgacgtc gcgggcgtac ccgacggagg ccatctacgc   2460
ggccgcgggg gtctacctct tcaacaacgc cacgggcgcc accgtcaccg ccgagaggct   2520
cgtcgtgcac gagatggcct cagctgacaa ccatatcttc acgaacgacg acttgtagga   2580
attcaacaat aattttctga gcctagtatc catgatcatg atatagtaag ggaaaaatca   2640
tatctataag tttccgaact tagtgaaaaa aaacctgtaa aagatatgca gtcatataca   2700
catgtgaaat taggtaggaa aatatgataa tctcgtagat gaggaaaaaa tattgtacac   2760
caaactattg taagttacag taatgtaatg taaaaaaagt ttttaagtta cagaaggtac   2820
ataccgcaaa taatcatatt attttaccaa gatatttttt tctggagtat tcctttcaag   2880
tatcttttat ctctagaatc ttctccaatc atgagtggca accgaaatgg agctcctgtg   2940
ttgctccccg tgtctcaccc ctttcggccc cactgtcatt gggtggacct attctcacgg   3000
cggctgtcct gagaaacaaa aatagcagct gaaatgaaga cacggcgaca cgcaagccag   3060
catctctcat tgaacctgcg gagtgagata gctctcgtgg cgctgctcta cttgacgcgt   3120
ttgtctcata caacagcgca tggctccttc atgtcaggtc catgatccac agatggtatg   3180
attgggtttg gaacattttt tgggtttgtg atatgtcgta gatacaaagg gaaatgtctg   3240
aagcatgcat ggatgggttc cctgctcatg tactcaatgt                         3280
```

<210> SEQ ID NO 39
<211> LENGTH: 3641
<212> TYPE: DNA
<213> ORGANISM: Artificial Sequence
<220> FEATURE:
<223> OTHER INFORMATION: Expression construct

<400> SEQUENCE: 39

```
acccacatag gactaccagc ctggccgacc acctccgacg aagaagaagg ccgcctccac     60
cgtcgaaccc gaggctgctg ccccaggcgt cctcgtaccg cgggagaatc ccaaggtcac    120
cccctcgcac cggcgagaag cggaggggat ggcgccatcc caccaccagc cgccaccggt    180
gtgccgccgc cgggaggcag gggaggtcgc agcacagagg ccaccgtcgc ccctccatcc    240
tccgaccgcc gccgccccgc catcacacgg gaggccggaa gtccaccgcc gccgcccccc    300
catcgggagg caggaagccg ccgccgctgc atcgagggga ggacccagcc gccgtccccg    360
ccgcgccatg agggaagccc accgccgccg cggtggcggg aggagctagg gtttctgggg    420
tgcgggacgg gcgggaggag ctagggtttc tctatgatta agtgcatgta ttgcgaaatt    480
aatgtttcta cttttgtcat ggccttctag tccgtctaaa aaaagctgcc ttctagtggg    540
cgacatggaa ctcagcgaca ttcctccacc acacgcgcag cgatcgtcct ggccgatcca    600
gttgagctca acacccctgt gccctgtaca ggtgtccggc ccagggctcg ccacaccagc    660
cgccccatcc aggcacatcc accctccgag aacacgagag ccaatcgcaa cgcagatcgt    720
gatttgtgag ataaggacgt ggccccctcc cctcgcgcgc acggcatggt atttaagctc    780
```

-continued

```
catgcgctgc tcctctcttc cccacgcagc caccgatcaa tagaagcagc agcacatcag    840
cagcttgctc tattccgtcc aatagcagaa ttcgattatg gagtccagcg ccgtcgtcgc    900
ccaaggcacc acgtcgccgc tgctcccgta cgcctacgcg ccgctgccgt cctctgccga    960
cgacgcccgt gaaaaccaga gtagcggcgg cggtgtcagg tggcgcgcgt gcgcggcctc   1020
ggccctggtg gtgctgctgg tcgtcgtcgg cttcttcgcg ggtggcaggg tggatctggg   1080
tcaggacggc gaggtgtctg cgacttcttc ggttcctggg agcagcaggg gcaaggattc   1140
cggcgtgtcg gagaaggagt cgcccgccga cggcggcttc ccgtggagca acgccatgct   1200
gcagtggcag cacaccgggt tccatttcca gccactcaag cactacatga acgatcccaa   1260
cggtccggtc tactatggcg gatggtacca cctcttctac cagcacaacc cctatggcga   1320
ctcgtgggga aacgtatctt ggggacatgc cgtgtccaag gacctggtga actggcgcca   1380
cctcccggtc gccttggtgc ccgatcagtg gtacgacatc aacggcgtcc tgacgggctc   1440
tatcacagtg ctcccagacg ggcgtgtcat cctgctatat acggggaaca ccgacacctt   1500
ttcgcaggtc cagtgcctcg cagtgcccgc cgacccatct gacccgctcc tccgtagctg   1560
gatcaagcac cccgccaacc ccatcctctt cccgccacct gggatcgggc tcaaggactt   1620
ccgtgacccg ctcacagcct ggttcgaaca ttccgacaac acgtggcgca ccatcatcgg   1680
atccaaggat gacgacggcc acgccggcat cgtccttagc tacaagacca ccgactttgt   1740
gaattatgag ctcatgccag ggaacatgca tcgtggcccc gacggcaccg gcatgtacga   1800
gtgccttgac atctaccctg tgggcggcaa ctcatccgag atgttgggtg gcgactcctc   1860
acctgaggtg ttgttcgtgc tcaaggagag cgccaacgac gagtggcacg actactacgc   1920
gcttgggtgg tttgacgctg ccgccaacac gtggacgcca caggaccccg aggcggacct   1980
tgggatcggc ctcaggtacg actggggcaa gtactacgcg tccaagtcct tctacgaccc   2040
gatcaagaac cggcgtgtcg tttgggcttt cgtcggcgag accgactctg agcaggccga   2100
caaagccaag ggatgggcgt ccctcatgtc gattcccagg acggtggagc ttgacaagaa   2160
gacccggacg aacctgatcc aatggccagt ggaggagatc gagacccttc gcaggaacgt   2220
cacagacctc ggtggcatca ccgttgaagc cggctccgtc attcaccttc ccctccaaca   2280
aggcgggcag cttgacatcg aggcctcctt ccgtctcaac tcttcggaca tcgatgcact   2340
caacgaggcc gacgtcggct tcaactgcag tagcagcgat ggggcagccg tgcgtggtgc   2400
gctcggcccc tttggcctcc tcgtcttcgc cgacggtcgc cacgaacaga cggcggcgta   2460
cttctacgtg tccaagggcc tcgacggcag cctcctgacg cactactgcc acgacgagtc   2520
acggtcgacg cgagcaaagg acgtcgtgag ccgggtggtt ggcggcactg tgccagtgct   2580
tgacggtgaa accttttcag tgagggtgct agtggaccac tccatcgtgc agagcttcgt   2640
gatgggtggg aggaccacgg tgacatcgcg ggcatacccg acggaggcca tctacgccgc   2700
ggcaggggtg tacctgttca acaacgcaac gagcgccacc atcaccgccg aagggctcgt   2760
cgtgtacgag atggcctcgg ccgagagtcg ggccttcttg gctgacgaca tgtagatgaa   2820
aactagtcaa gaacatgtca atggcgatcg tcaagcttgc tggatgggga tcgtggtcac   2880
agagatcttc attcgcaagt tcgcgggtat gttgtagcta gggtggtgcc aaatcactag   2940
tgaattcaac aataattttc tgagcctagt atccatgatc atgatatagt aagggaaaaa   3000
tcatatctat aagtttccga acttagtgaa aaaaaacctg taaaagatat gcagtcatat   3060
acacatgtga aattaggtag gaaaatatga taatctcgta gatgaggaaa aaatattgta   3120
```

```
caccaaacta ttgtaagtta cagtaatgta atgtaaaaaa agtttttaag ttacagaagg   3180

tacataccgc aaataatcat attattttac caagatattt ttttctggag tattcctttc   3240

aagtatcttt tatctctaga atcttctcca atcatgagtg gcaaccgaaa tggagctcct   3300

gtgttgctcc ccgtgtctca cccctttcgg ccccactgtc attgggtgga cctattctca   3360

cggcggctgt cctgagaaac aaaaatagca gctgaaatga agacacggcg acacgcaagc   3420

cagcatctct cattgaacct gcggagtgag atagctctcg tggcgctgct ctacttgacg   3480

cgtttgtctc atacaacagc gcatggctcc ttcatgtcag gtccatgatc cacagatggt   3540

atgattgggt ttggaacatt ttttgggttt gtgatatgtc gtagatacaa agggaaatgt   3600

ctgaagcatg catggatggg ttccctgctc atgtactcaa t                       3641
```

```
<210> SEQ ID NO 40
<211> LENGTH: 5232
<212> TYPE: DNA
<213> ORGANISM: Artificial Sequence
<220> FEATURE:
<223> OTHER INFORMATION: Expression construct

<400> SEQUENCE: 40

tgttcatcta ccttactagt ctgcatgatt agtttattcg ttattttcgt agtcatgatt     60

tatcaattac tcgtacggat tatttcatat ggatatttgc ttatatttcc aacaatttac    120

actgtcgagt tttggcgcgg ctgctggagt tactcttaga gtagttggac ttgagacaaa    180

agctagaata tcaattatat ataggagtga ggagttattc tttcgaaaga actttaaacg    240

gtagctgcac ttagtcgtcg caatgaaata cttgtcgtac taccatgata attggtaata    300

tgagagggaa tattaattcc tcagtgattt gaattttgtg tgctcatgtg cagtcaccca    360

cgccatgcat ccgacgacgg gcggctatac caactcttgc actgatccgg agggataagg    420

cgccatgcaa ccagggaacg tcgtccaccc cttccacatc ctgtatcaaa ttaaggaacg    480

ggcgctgagc ctatgccgag acatatataa tgcggcgact cggacatgga ggggcctcag    540

gcatagccca gctagttatc tcattctctc cttagcaata atacttagca ccatggcccc    600

cgcggtgaat tcatggagtc cccaagcgcc gtcgtcccgg gcaccacggc gccgctgctt    660

ccttatgcgt acgcgccgct gccgtcgtcc gccgacgacg cccgtcaaaa ccggagtggc    720

gggaggtggc gcgcgtgcgc cgccgtgctg gccgcatcgg cgttgtcggt ggtcgtcgtg    780

gtcgggctcc tcgcgggcgg cagggtggat cgggtcccgg ccggcggaga cgtggcgtcg    840

gccacggtgc cggccgtgcc gatggagttc ccgaggagcc ggggcaagga cttcggcgtg    900

tcggagaagt cctccggtgc ctactccacc gacggcgggt tcccgtggag caacgccatg    960

ctgcagtggc agcgcaccgg gttccatttc cagccggagc agcactacat gaacgatccc   1020

aacggccccg tgtactacgg cggatggtac cacctcttct accagcacaa ccccaagggc   1080

gacagctggg gcaacatcgc gtgggcccac gccgtctcca aggacatggt caactggcgc   1140

cacctccctc tcgccatggt tcccgaccag tggtacgaca gcaacggcgt cctcaccggc   1200

tccatcaccg tgctccccga cggccaggtc atcctgctct acaccggcaa caccgacacc   1260

ctagcccagg tccagtgcct cgccacgccc gccgacccgt ccgacccgct cctccgcgag   1320

tgggtcaagc accccgccaa ccccatcctc taccctcccc ccggcatcgg cctcaaggac   1380

ttccgcgacc ccctcaccgc ctggttcgac cactccgacc acacctggcg caccgtcatc   1440

ggctccaagg acgacgacgg ccacgccggc atcatcctca gctacaagac caaggacttc   1500

gtcaactacg agctcatgcc ggggaacatg caccgcgggc ccgacggcac cggaatgtac   1560
```

-continued

```
gagtgcatcg acctctaccc cgtcggcggc aactcgtccg agatgctcgg cggcgacgac   1620
tcgcccggcg tgctcttcgt gctcaaggag agcagcgacg acgagcgcca cgactactac   1680
gcgctcggaa ggttcgatgc cgtcgccaac gtttggacgc ccatcgaccg ggagctggac   1740
cttgggatcg ggctcagata cgactgggga aagtactacg cctccaagtc cttctacgac   1800
cagaagaaga accgccgcat cgtatgggca tacatcggcg agaccgactc cgagcaggcc   1860
gacatcacca agggatgggc caatctcatg acgattccaa gaacggtgga gcttgacagg   1920
aagacccgca caaacctcat ccaatggcca gtggaggagg tcgacaccct ccgcaggaac   1980
tccacggacc tcggtcgcat caccgtcaac gccggctccg tcattcgcct ccccctccac   2040
cagggcgctc aactcgacat cgaggcctcc ttccaactca actcttccga cgtggatgct   2100
atcaacgagg ccgacgtcgg ctacaactgc agcaccagtg gtgccgccgt acggggggcg   2160
ctcggcccct ttggcctcct cgtccttgcc aacggccgca ccgaacagac ggctgtgtac   2220
ttctacgtgt ccaagggcgt cgacggtgcc ctccagaccc acttctgcca cgacgagtca   2280
cggtcaacgc gggcaaagga tgtcgtgaat aggatgattg gcagcatcgt gccggtgctt   2340
gacggtgaga ccttttcggt gagggtgcta gtggaccact ccatcgtgca gagcttcgcg   2400
atgggcggga ggatcacggc gacgtcgcgg gcgtacccga cggaggccat ctacgcggcc   2460
gcgggggtct acctcttcaa caacgccacg ggcgccaccg tcaccgccga gaggctcgtc   2520
gtgcacgaga tggcctcagc tgacaaccat atcttcacga acgacgactt gggaggagga   2580
aagcttggag gaggagagtc cagcgccgtc gtcgcccaag gcaccacgtc gccgctgctc   2640
ccgtacgcct acgcgccgct gccgtcctct gccgacgacg cccgtgaaaa ccagagtagc   2700
ggcggcggtg tcaggtggcg cgcgtgcgcg gcctcggccc tggtggtgct gctggtcgtc   2760
gtcggcttct tcgcgggtgg cagggtggat ctgggtcagg acggcgaggt gtctgcgact   2820
tcttcggttc ctgggagcag caggggcaag gattccggcg tgtcggagaa ggagtcgccc   2880
gccgacggcg gcttcccgtg gagcaacgcc atgctgcagt ggcagcacac cgggttccat   2940
ttccagccac tcaagcacta catgaacgat cccaacggtc cggtctacta tggcggatgg   3000
taccacctct tctaccagca caacccctat ggcgactcgt ggggaaacgt atcttgggga   3060
catgccgtgt ccaaggacct ggtgaactgg cgccacctcc cggtcgcctt ggtgcccgat   3120
cagtggtacg acatcaacgg cgtcctgacg ggctctatca cagtgctccc agacgggcgt   3180
gtcatcctgc tatatacggg gaacaccgac accttttcgc aggtccagtg cctcgcagtg   3240
cccgccgacc catctgaccc gctcctccgt agctggatca agcaccccgc caaccccatc   3300
ctcttcccgc cacctgggat cgggctcaag gacttccgtg acccgctcac agcctggttc   3360
gaacattccg acaacacgtg gcgcaccatc atcggatcca aggatgacga cggccacgcc   3420
ggcatcgtcc ttagctacaa gaccaccgac tttgtgaatt atgagctcat gccagggaac   3480
atgcatcgtg gccccgacgg caccggcatg tacgagtgcc ttgacatcta ccctgtgggc   3540
ggcaactcat ccgagatgtt gggtggcgac tcctcacatg aggtgttgtt cgtgctcaag   3600
gagagcgcca acgacgagtg gcacgactac tacgcgcttg ggtggtttga cgctgccgcc   3660
aacacgtgga cgccacagga ccccgaggcg gaccttggga tcggcctcag gtacgactgg   3720
ggcaagtact acgcgtccaa gtccttctac gacccgatca agaaccggcg tgtcgtttgg   3780
gctttcgtcg gcgagaccga ctctgagcag gccgacaaag ccaagggatg ggcgtccctc   3840
atgtcgattc ccaggacggt ggagcttgac aagaagaccc ggacgaacct gatccaatgg   3900
```

ccagtggagg agatcgagac ccttcgcagg aacgtcacag acctcggtgg catcaccgtt 3960
gaagccggct ccgtcattca ccttcccctc caacaaggcg ggcagcttga catcgaggcc 4020
tccttccgtc tcaactcttc ggacatcgat gcactcaacg aggccgacgt cggcttcaac 4080
tgcagtagca gcgatggggt agccgtgcgt ggtgcgctcg gcccctttgg cctcctcgtc 4140
ttcgccgacg gtcgccacga acagacggcg gcgtacttct acgtgtccaa gggcctcgac 4200
ggcagcctcc tgacgcacta ctgccacgac gagtcacggt cgacgcgagc aaaggacgtc 4260
gtgagccggg tggttggcgg cactgtgcca gtgcttgacg gtgaaacctt ttcagtgagg 4320
gtgctagtgg accactccat cgtgcagagc ttcgtgatgg gtgggaggac cacggtgaca 4380
tcgcgggcat acccgacgga ggccatctac gccgcggcag gggtgtacct gttcaacaac 4440
gcaacgagcg ccaccatcac cgccgaaggg ctcgtcgtgt acgagatggc ctcggccgag 4500
agtcgggcct tcttggctga cgacatgtag gaattcaaca ataattttct gagcctagta 4560
tccatgatca tgatatagta agggaaaaat catatctata agtttccgaa cttagtgaaa 4620
aaaaacctgt aaaagatatg cagtcatata cacatgtgaa attaggtagg aaaatatgat 4680
aatctcgtag atgaggaaaa aatattgtac accaaactat tgtaagttac agtaatgtaa 4740
tgtaaaaaaa gtttttaagt tacagaaggt acataccgca aataatcata ttattttacc 4800
aagatatttt tttctggagt attcctttca agtatctttt atctctagaa tcttctccaa 4860
tcatgagtgg caaccgaaat ggagctcctg tgttgctccc cgtgtctcac ccctttcggc 4920
cccactgtca ttgggtggac ctattctcac ggcggctgtc ctgagaaaca aaaatagcag 4980
ctgaaatgaa gacacggcga cacgcaagcc agcatctctc attgaacctg cggagtgaga 5040
tagctctcgt ggcgctgctc tacttgacgc gtttgtctca tacaacagcg catggctcct 5100
tcatgtcagg tccatgatcc acagatggta tgattgggtt tggaacattt tttgggtttg 5160
tgatatgtcg tagatacaaa gggaaatgtc tgaagcatgc atggatgggt tccctgctca 5220
tgtactcaat gt 5232

<210> SEQ ID NO 41
<211> LENGTH: 5226
<212> TYPE: DNA
<213> ORGANISM: Artificial Sequence
<220> FEATURE:
<223> OTHER INFORMATION: Expression construct

<400> SEQUENCE: 41
tgttcatcta ccttactagt ctgcatgatt agtttattcg ttattttcgt agtcatgatt 60
tatcaattac tcgtacggat tatttcatat ggatatttgc ttatatttcc aacaatttac 120
actgtcgagt tttggcgcgg ctgctggagt tactcttaga gtagttggac ttgagacaaa 180
agctagaata tcaattatat ataggagtga ggagttattc tttcgaaaga actttaaacg 240
gtagctgcac ttagtcgtcg caatgaaata cttgtcgtac taccatgata attggtaata 300
tgagagggaa tattaattcc tcagtgattt gaattttgtg tgctcatgtg cagtcaccca 360
cgccatgcat ccgacgacgg gcggctatac caactcttgc actgatccgg agggataagg 420
cgccatgcaa ccagggaacg tcgtccaccc cttccacatc ctgtatcaaa ttaaggaacg 480
ggcgctgagc ctatgccgag acatatataa tgcggcgact cggacatgga ggggcctcag 540
gcatagccca gctagttatc tcattctctc cttagcaata atacttagca ccatggcccc 600
cgcggtatgg agtccccaag cgccgtcgtc cccggcacca cggcgccgct gcttccttat 660
gcgtacgcgc cgctgccgtc gtccgccgac gacgcccgtc aaaaccggag tggcgggagg 720

-continued

```
tggcgcgcgt gcgccgccgt gctggccgca tcggcgttgg cggtggtcgt cgtggtcggg    780
ctcctcgcgg gcggcagggt ggatcgggtc ccagccggcg gagacgtggc gtcggccacg    840
gtgccggccg tgccgatgga gttcccgagg agccggggca aggacttcgg cgtgtcggag    900
aagtcctccg gtgcctactc caccgacggc gggttcccgt ggagcaacgc catgctgcag    960
tggcagcgca ccgggttcca tttccagccg gagcagcact acatgaacga tcccaacggc   1020
cccgtgtact acggcggatg gtaccacctc ttctaccagc acaaccccaa gggcgacagc   1080
tggggcaaca tcgcgtgggc ccacgccgtc tccaaggaca tggtcaactg gcgccacctc   1140
cctctcgcca tggttcccga ccagtggtac gacagcaacg gcgtcctcac cggctccatc   1200
accgtgctcc ccgacggcca ggtcatcctg ctctacaccg gcaacaccga caccctagcc   1260
caggtccagt gcctcgccac gcccgccgac ccgtccgacc cgctcctccg cgagtgggtc   1320
aagcaccccg ccaaccccat cctctaccct ccccccggca tcggcctcaa ggacttccgc   1380
gacccccctca ccgcctggtt cgaccactcc gaccacacct ggcgcaccgt catcggctcc   1440
aaggacgacg acggccacgc cggcatcatc ctcagctaca agaccaagga cttcgtcaac   1500
tacgagctca tgccggggaa catgcaccgc gggcccgacg gcaccggaat gtacgagtgc   1560
atcgacctct accccgtcgg cggcaactcg tccgagatgc tcggcggcga cgactcgccc   1620
ggcgtgctct tcgtgctcaa ggagagcagc gacgacgagc gccacgacta ctacgcgctc   1680
ggaaggttcg acgccgtcgc caacgtttgg acgcccatcg accgggagct ggaccttggg   1740
atcgggctca gatacgactg ggaaaagtac tacgcctcca agtccttcta cgaccagaag   1800
aagaaccgcc gcatcgtatg ggcatacatc ggcgagaccg actccgagca ggccgacatc   1860
accaagggat gggccaatct catgacgatt ccaagaacgg tggagcttga caggaagacc   1920
cgcacaaacc tcatccaatg gccagtggag gaggtcgaca ccctccgcag gaactccacg   1980
gacctcggtc gcatcaccgt caacgccggc tccgtcattc gcctccccct ccaccagggc   2040
gctcaactcg acatcgaggc ctccttccaa ctcaactctt ccgacgtgga tgctatcaac   2100
gaggccgacg tcggctacaa ctgcagcacc agtggtgccg ccgtacgggg ggcgctcggc   2160
ccctttggcc tcctcgtcct tgccaacggc cgcaccgaac agacggctgt gtacttctac   2220
gtgtccaagg gcgtcgacgg tgccctccag acccacttct gccacgacga gtcacggtca   2280
acgcgggcaa aggatgtcgt gaataggatg attggcagca tcgtgccggt gcttgacggt   2340
gagacctttt cggtgagggt gctagtggac cactccatcg tgcagagctt cgcgatgggc   2400
gggaggatca cggcgacgtc gcgggcgtac ccgacggagg ccatctacgc ggccgcgggg   2460
gtctacctct tcaacaacgc cacgggcgcc accgtcaccg ccgagaggct cgtcgtgcac   2520
gagatggcct cagctgacaa ccatatcttc acgaacgacg acttgggagg aggaaagctt   2580
aagcttggag gaggagagtc cagcgccgtc gtcgcccaag gcaccacgtc gccgctgctc   2640
ccgtacgcct acgcgccgct gccgtcctct gccgacgacg cccgtgaaaa ccagagtagc   2700
ggcggcggtg tcaggtggcg cgcgtgcgcg gcctcggccc tggtggtgct gctggtcgtc   2760
gtcggcttct tcgcgggtgg cagggtggat ctgggtcagg acggcgaggt gtctgcgact   2820
tcttcggttc ctgggagcag caggggcaag gattccggcg tgtcggagaa ggagtcgccc   2880
gccgacggcg gcttcccgtg gagcaacgcc atgctgcagt ggcagcacac cgggttccat   2940
ttccagccac tcaagcacta catgaacgat cccaacggtc cggtctacta tggcggatgg   3000
taccacctct tctaccagca caacccctat ggcgactcgt ggggaaacgt atcttggggga   3060
```

-continued catgccgtgt ccaaggacct ggtgaactgg cgccacctcc cggtcgcctt ggtgcccgat 3120
cagtggtacg acatcaacgg cgtcctgacg ggctctatca cagtgctccc agacgggcgt 3180
gtcatcctgc tatatacggg gaacaccgac accttttcgc aggtccagtg cctcgcagtg 3240
cccgccgacc catctgaccc gctcctccgt agctggatca agcaccccgc caaccccatc 3300
ctcttcccgc cacctgggat cgggctcaag gacttccgtg acccgctcac agcctggttc 3360
gaacattccg acaacacgtg gcgcaccatc atcggatcca aggatgacga cggccacgcc 3420
ggcatcgtcc ttagctacaa gaccaccgac tttgtgaatt atgagctcat gccagggaac 3480
atgcatcgtg gccccgacgg caccggcatg tacgagtgcc ttgacatcta ccctgtgggc 3540
ggcaactcat ccgagatgtt gggtggcgac tcctcacctg aggtgttgtt cgtgctcaag 3600
gagagcgcca acgacgagtg gcacgactac tacgcgcttg ggtggtttga cgctgccgcc 3660
aacacgtgga cgccacagga ccccgaggcg gaccttggga tcggcctcag gtacgactgg 3720
ggcaagtact acgcgtccaa gtccttctac gacccgatca agaaccggcg tgtcgtttgg 3780
gctttcgtcg gcgagaccga ctctgagcag gccgacaaag ccaagggatg ggcgtccctc 3840
atgtcgattc ccaggacggt ggagcttgac aagaagaccc ggacgaacct gatccaatgg 3900
ccagtggagg agatcgagac ccttcgcagg aacgtcacag acctcggtgg catcaccgtt 3960
gaagccggct ccgtcattca ccttcccctc caacaaggcg ggcagcttga catcgaggcc 4020
tccttccgtc tcaactcttc ggacatcgat gcactcaacg aggccgacgt cggcttcaac 4080
tgcagtagca gcgatggggc agccgtgcgt ggtgcgctcg gcccctttgg cctcctcgtc 4140
ttcgccgacg gtcgccacga acagacggcg gcgtacttct acgtgtccaa gggcctcgac 4200
ggcagcctcc tgacgcacta ctgccacgac gagtcacggt cgacgcgagc aaaggacgtc 4260
gtgagccggg tggttggcgg cactgtgcca gtgcttgacg gtgaaacctt ttcagtgagg 4320
gtgctagtgg accactccat cgtgcagagc ttcgtgatgg gtgggaggac cacggtgaca 4380
tcgcgggcat acccgacgga ggccatctac gccgcggcag gggtgtacct gttcaacaac 4440
gcaacgagcg ccaccatcac cgccgaaggg ctcgtcgtgt acgagatggc ctcggccgag 4500
agtcgggcct tcttggctga cgacatgtag aacaataatt ttctgagcct agtatccatg 4560
atcatgatat agtaagggaa aaatcatatc tataagtttc cgaacttagt gaaaaaaaac 4620
ctgtaaaaga tatgcagtca tatacacatg tgaaattagg taggaaaata tgataatctc 4680
gtagatgagg aaaaaatatt gtacaccaaa ctattgtaag ttacagtaat gtaatgtaaa 4740
aaaagttttt aagttacaga aggtacatac cgcaaataat catattattt taccaagata 4800
tttttttctg gagtattcct ttcaagtatc ttttatctct agaatcttct ccaatcatga 4860
gtggcaaccg aaatggagct cctgtgttgc tccccgtgtc tcaccccttt cggccccact 4920
gtcattgggt ggacctattc tcacggcggc tgtcctgaga aacaaaaata gcagctgaaa 4980
tgaagacacg gcgacacgca agccagcatc tctcattgaa cctgcggagt gagatagctc 5040
tcgtggcgct gctctacttg acgcgtttgt ctcatacaac agcgcatggc tccttcatgt 5100
caggtccatg atccacagat ggtatgattg ggtttggaac atttttttggg tttgtgatat 5160 gtcgtagata caaagggaaa tgtctgaagc atgcatggat gggttccctg ctcatgtact 5220
caatgt 5226

<210> SEQ ID NO 42
<211> LENGTH: 1307
<212> TYPE: PRT
<213> ORGANISM: Artificial Sequence
<220> FEATURE:
<223> OTHER INFORMATION: Expression construct

<400> SEQUENCE: 42

```
Met Glu Ser Pro Ser Ala Val Val Pro Gly Thr Thr Ala Pro Leu Leu
1               5                   10                  15

Pro Tyr Ala Tyr Ala Pro Leu Pro Ser Ser Ala Asp Asp Ala Arg Gln
            20                  25                  30

Asn Arg Ser Gly Gly Arg Trp Arg Ala Cys Ala Ala Val Leu Ala Ala
        35                  40                  45

Ser Ala Leu Ala Val Val Val Val Val Gly Leu Leu Ala Gly Gly Arg
    50                  55                  60

Val Asp Arg Val Pro Ala Gly Gly Asp Val Ala Ser Ala Thr Val Pro
65                  70                  75                  80

Ala Val Pro Met Glu Phe Pro Arg Ser Arg Gly Lys Asp Phe Gly Val
                85                  90                  95

Ser Glu Lys Ser Ser Gly Ala Tyr Ser Thr Asp Gly Gly Phe Pro Trp
            100                 105                 110

Ser Asn Ala Met Leu Gln Trp Gln Arg Thr Gly Phe His Phe Gln Pro
        115                 120                 125

Glu Gln His Tyr Met Asn Asp Pro Asn Gly Pro Val Tyr Tyr Gly Gly
    130                 135                 140

Trp Tyr His Leu Phe Tyr Gln His Asn Pro Lys Gly Asp Ser Trp Gly
145                 150                 155                 160

Asn Ile Ala Trp Ala His Ala Val Ser Lys Asp Met Val Asn Trp Arg
                165                 170                 175

His Leu Pro Leu Ala Met Val Pro Asp Gln Trp Tyr Asp Ser Asn Gly
            180                 185                 190

Val Leu Thr Gly Ser Ile Thr Val Leu Pro Asp Gly Gln Val Ile Leu
        195                 200                 205

Leu Tyr Thr Gly Asn Thr Asp Thr Leu Ala Gln Val Gln Cys Leu Ala
    210                 215                 220

Thr Pro Ala Asp Pro Ser Asp Pro Leu Leu Arg Glu Trp Val Lys His
225                 230                 235                 240

Pro Ala Asn Pro Ile Leu Tyr Pro Pro Pro Gly Ile Gly Leu Lys Asp
                245                 250                 255

Phe Arg Asp Pro Leu Thr Ala Trp Phe Asp His Ser Asp His Thr Trp
            260                 265                 270

Arg Thr Val Ile Gly Ser Lys Asp Asp Asp Gly His Ala Gly Ile Ile
        275                 280                 285

Leu Ser Tyr Lys Thr Lys Asp Phe Val Asn Tyr Glu Leu Met Pro Gly
    290                 295                 300

Asn Met His Arg Gly Pro Asp Gly Thr Gly Met Tyr Glu Cys Ile Asp
305                 310                 315                 320

Leu Tyr Pro Val Gly Gly Asn Ser Ser Glu Met Leu Gly Gly Asp Asp
                325                 330                 335

Ser Pro Gly Val Leu Phe Val Leu Lys Glu Ser Ser Asp Asp Glu Arg
            340                 345                 350

His Asp Tyr Tyr Ala Leu Gly Arg Phe Asp Ala Val Ala Asn Val Trp
        355                 360                 365

Thr Pro Ile Asp Arg Glu Leu Asp Leu Gly Ile Gly Leu Arg Tyr Asp
    370                 375                 380

Trp Gly Lys Tyr Tyr Ala Ser Lys Ser Phe Tyr Asp Gln Lys Lys Asn
385                 390                 395                 400
```

```
Arg Arg Ile Val Trp Ala Tyr Ile Gly Glu Thr Asp Ser Glu Gln Ala
                405                 410                 415

Asp Ile Thr Lys Gly Trp Ala Asn Leu Met Thr Ile Pro Arg Thr Val
            420                 425                 430

Glu Leu Asp Arg Lys Thr Arg Thr Asn Leu Ile Gln Trp Pro Val Glu
        435                 440                 445

Glu Val Asp Thr Leu Arg Arg Asn Ser Thr Asp Leu Gly Arg Ile Thr
    450                 455                 460

Val Asn Ala Gly Ser Val Ile Arg Leu Pro Leu His Gln Gly Ala Gln
465                 470                 475                 480

Leu Asp Ile Glu Ala Ser Phe Gln Leu Asn Ser Ser Asp Val Asp Ala
                485                 490                 495

Ile Asn Glu Ala Asp Val Gly Tyr Asn Cys Ser Thr Ser Gly Ala Ala
            500                 505                 510

Val Arg Gly Ala Leu Gly Pro Phe Gly Leu Leu Val Leu Ala Asn Gly
        515                 520                 525

Arg Thr Glu Gln Thr Ala Val Tyr Phe Tyr Val Ser Lys Gly Val Asp
    530                 535                 540

Gly Ala Leu Gln Thr His Phe Cys His Asp Glu Ser Arg Ser Thr Arg
545                 550                 555                 560

Ala Lys Asp Val Val Asn Arg Met Ile Gly Ser Ile Val Pro Val Leu
                565                 570                 575

Asp Gly Glu Thr Phe Ser Val Arg Val Leu Val Asp His Ser Ile Val
            580                 585                 590

Gln Ser Phe Ala Met Gly Gly Arg Ile Thr Ala Thr Ser Arg Ala Tyr
        595                 600                 605

Pro Thr Glu Ala Ile Tyr Ala Ala Ala Gly Val Tyr Leu Phe Asn Asn
    610                 615                 620

Ala Thr Gly Ala Thr Val Thr Ala Glu Arg Leu Val Val His Glu Met
625                 630                 635                 640

Ala Ser Ala Asp Asn His Ile Phe Thr Asn Asp Asp Leu Gly Gly Gly
                645                 650                 655

Lys Leu Lys Leu Gly Gly Gly Glu Ser Ser Ala Val Val Ala Gln Gly
            660                 665                 670

Thr Thr Ser Pro Leu Leu Pro Tyr Ala Tyr Ala Pro Leu Pro Ser Ser
        675                 680                 685

Ala Asp Asp Ala Arg Glu Asn Gln Ser Ser Gly Gly Gly Val Arg Trp
    690                 695                 700

Arg Ala Cys Ala Ala Ser Ala Leu Val Val Leu Leu Val Val Val Gly
705                 710                 715                 720

Phe Phe Ala Gly Gly Arg Val Asp Leu Gly Gln Asp Gly Glu Val Ser
                725                 730                 735

Ala Thr Ser Ser Val Pro Gly Ser Ser Arg Gly Lys Asp Ser Gly Val
            740                 745                 750

Ser Glu Lys Glu Ser Pro Ala Asp Gly Gly Phe Pro Trp Ser Asn Ala
        755                 760                 765

Met Leu Gln Trp Gln His Thr Gly Phe His Phe Gln Pro Leu Lys His
    770                 775                 780

Tyr Met Asn Asp Pro Asn Gly Pro Val Tyr Tyr Gly Gly Trp Tyr His
785                 790                 795                 800

Leu Phe Tyr Gln His Asn Pro Tyr Gly Asp Ser Trp Gly Asn Val Ser
                805                 810                 815
```

```
Trp Gly His Ala Val Ser Lys Asp Leu Val Asn Trp Arg His Leu Pro
            820                 825                 830

Val Ala Leu Val Pro Asp Gln Trp Tyr Asp Ile Asn Gly Val Leu Thr
        835                 840                 845

Gly Ser Ile Thr Val Leu Pro Asp Gly Arg Val Ile Leu Leu Tyr Thr
    850                 855                 860

Gly Asn Thr Asp Thr Phe Ser Gln Val Gln Cys Leu Ala Val Pro Ala
865                 870                 875                 880

Asp Pro Ser Asp Pro Leu Leu Arg Ser Trp Ile Lys His Pro Ala Asn
                885                 890                 895

Pro Ile Leu Phe Pro Pro Pro Gly Ile Gly Leu Lys Asp Phe Arg Asp
            900                 905                 910

Pro Leu Thr Ala Trp Phe Glu His Ser Asp Asn Thr Trp Arg Thr Ile
        915                 920                 925

Ile Gly Ser Lys Asp Asp Asp Gly His Ala Gly Ile Val Leu Ser Tyr
    930                 935                 940

Lys Thr Thr Asp Phe Val Asn Tyr Glu Leu Met Pro Gly Asn Met His
945                 950                 955                 960

Arg Gly Pro Asp Gly Thr Gly Met Tyr Glu Cys Leu Asp Ile Tyr Pro
                965                 970                 975

Val Gly Gly Asn Ser Ser Glu Met Leu Gly Gly Asp Ser Ser Pro Glu
            980                 985                 990

Val Leu Phe Val Leu Lys Glu Ser  Ala Asn Asp Glu Trp  His Asp Tyr
        995                 1000                1005

Tyr Ala  Leu Gly Trp Phe Asp  Ala Ala Ala Asn Thr  Trp Thr Pro
    1010                1015                1020

Gln Asp  Pro Glu Ala Asp Leu  Gly Ile Gly Leu Arg  Tyr Asp Trp
    1025                1030                1035

Gly Lys  Tyr Tyr Ala Ser Lys  Ser Phe Tyr Asp Pro  Ile Lys Asn
    1040                1045                1050

Arg Arg  Val Val Trp Ala Phe  Val Gly Glu Thr Asp  Ser Glu Gln
    1055                1060                1065

Ala Asp  Lys Ala Lys Gly Trp  Ala Ser Leu Met Ser  Ile Pro Arg
    1070                1075                1080

Thr Val  Glu Leu Asp Lys Lys  Thr Arg Thr Asn Leu  Ile Gln Trp
    1085                1090                1095

Pro Val  Glu Glu Ile Glu Thr  Leu Arg Arg Asn Val  Thr Asp Leu
    1100                1105                1110

Gly Gly  Ile Thr Val Glu Ala  Gly Ser Val Ile His  Leu Pro Leu
    1115                1120                1125

Gln Gln  Gly Gly Gln Leu Asp  Ile Glu Ala Ser Phe  Arg Leu Asn
    1130                1135                1140

Ser Ser  Asp Ile Asp Ala Leu  Asn Glu Ala Asp Val  Gly Phe Asn
    1145                1150                1155

Cys Ser  Ser Ser Asp Gly Ala  Ala Val Arg Gly Ala  Leu Gly Pro
    1160                1165                1170

Phe Gly  Leu Leu Val Phe Ala  Asp Gly Arg His Glu  Gln Thr Ala
    1175                1180                1185

Ala Tyr  Phe Tyr Val Ser Lys  Gly Leu Asp Gly Ser  Leu Leu Thr
    1190                1195                1200

His Tyr  Cys His Asp Glu Ser  Arg Ser Thr Arg Ala  Lys Asp Val
    1205                1210                1215

Val Ser  Arg Val Val Gly Gly  Thr Val Pro Val Leu  Asp Gly Glu
```

```
    1220                1225                1230

Thr Phe  Ser Val Arg Val Leu  Val Asp His Ser Ile  Val Gln Ser
    1235                1240                1245

Phe Val  Met Gly Gly Arg Thr  Thr Val Thr Ser Arg  Ala Tyr Pro
    1250                1255                1260

Thr Glu  Ala Ile Tyr Ala Ala  Ala Gly Val Tyr Leu  Phe Asn Asn
    1265                1270                1275

Ala Thr  Ser Ala Thr Ile Thr  Ala Glu Gly Leu Val  Val Tyr Glu
    1280                1285                1290

Met Ala  Ser Ala Glu Ser Arg  Ala Phe Leu Ala Asp  Asp Met
    1295                1300                1305


<210> SEQ ID NO 43
<211> LENGTH: 5929
<212> TYPE: DNA
<213> ORGANISM: Artificial Sequence
<220> FEATURE:
<223> OTHER INFORMATION: Expression construct

<400> SEQUENCE: 43

cgtggtcgag attgtgtatt attctttagt tattacaaga cttttagcta aaatttgaaa     60

gaatttactt taagaaaatc ttaacatctg agataatttc agcaatagat tatatttttc    120

attactctag cagtattttt gcagatcaat cgcaacatat atggttgtta gaaaaaatgc    180

actatatata tatatattat tttttcaatt aaaagtgcat gatatataat atatatatat    240

atatatatat gtgtgtgtgt atatggtcaa agaaattctt atacaaatat acacgaacac    300

atatatttga caaaatcaaa gtattacact aaacaatgag ttggtgcatg gccaaaacaa    360

atatgtagat taaaaattcc agcctccaaa aaaaaatcca agtgttgtaa agcattatat    420

atatatagta gatcccaaat ttttgtacaa ttccacactg atcgaatttt taaagttgaa    480

tatctgacgt aggatttttt taatgtctta cctgaccatt tactaataac attcatacgt    540

tttcatttga aatatcctct ataattatat tgaatttggc acataataag aaacctaatt    600

ggtgatttat tttactagta aatttctggt gatgggcttt ctactagaaa gctctcggaa    660

aatcttggac caaatccata ttccatgact tcgattgtta accctattag ttttcacaaa    720

catactatca atatcattgc aacggaaaag gtacaagtaa aacattcaat ccgataggga    780

agtgatgtag gaggttggga agacaggccc agaaagagat ttatctgact tgttttgtgt    840

atagttttca atgttcataa aggaagatgg agacttgaga agtttttttt ggactttgtt    900

tagctttgtt gggcgttttt tttttttgat caataacttt gttgggctta tgatttgtaa    960

tattttcgtg gactctttag tttatttaga cgtgctaact ttgttgggct tatgacttgt   1020

tgtaacatat tgtaacagat gacttgatgt gcgactaatc tttacacatt aaacatagtt   1080

ctgttttttg aaagttctta ttttcatttt tatttgaatg ttatatattt ttctatattt   1140

ataattctag taaaaggcaa attttgcttt taaatgaaaa aaatatatat tccacagttt   1200

cacctaatct tatgcattta gcagtacaaa ttcaaaaatt tcccattttt attcatgaat   1260

cataccatta tatattaact aaatccaagg taaaaaaaag gtatgaaagc tctatagtaa   1320

gtaaaatata aattccccat aaggaaaggg ccaagtccac caggcaagta aaatgagcaa   1380

gcaccactcc accatcacac aatttcactc atagataacg ataagattca tggaattatc   1440

ttccacgtgg cattattcca gcggttcaag ccgataaggg tctcaacacc tctccttagg   1500

cccttgtggc cgttaccaag taaaattaac ctcacacata tccacactca aatccaacg    1560
```

-continued

```
gtgtagatcc tagtccactt gaatctcatg tatcctagac cctccgatca ctccaaagct   1620
tgttctcatt gttgttatca ttatatatag atgaccaaag cactagacca aacctcagtc   1680
acacaaagag taaagaagaa cataagtttg tacaaaaaag caggcttcat ggagtcccca   1740
agcgccgtcg tccccggcac cacggcgccg ctgcttcctt atgcgtacgc gccgctgccg   1800
tcgtccgccg acgacgcccg tcaaaaccgg agtggcggga ggtggcgcgc gtgcgccgcc   1860
gtgctggccg catcggcgtt ggcggtggtc gtcgtggtcg ggctcctcgc gggcggcagg   1920
gtggatcggg tcccagccgg cggagacgtg gcgtcggcca cggtgccggc cgtgccgatg   1980
gagttcccga ggagccgggg caaggacttc ggcgtgtcgg agaagtcctc cggtgcctac   2040
tccaccgacg gcgggttccc gtggagcaac gccatgctgc agtggcagcg caccgggttc   2100
catttccagc cggagcagca ctacatgaac gatcccaacg gccccgtgta ctacggcgga   2160
tggtaccacc tcttctacca gcacaacccc aagggcgaca gctggggcaa catcgcgtgg   2220
gcccacgccg tctccaagga catggtcaac tggcgccacc tccctctcgc catggttccc   2280
gaccagtggt acgacagcaa cggcgtcctc accggctcca tcaccgtgct ccccgacggc   2340
caggtcatcc tgctctacac cggcaacacc gacaccctag cccaggtcca gtgcctcgcc   2400
acgcccgccg acccgtccga cccgctcctc cgcgagtggg tcaagcaccc cgccaacccc   2460
atcctctacc ctcccccggg catcggcctc aaggacttcc gcgacccccct caccgcctgg   2520
ttcgaccact ccgaccacac ctggcgcacc gtcatcggct ccaaggacga cgacggccac   2580
gccggcatca tcctcagcta caagaccaag gacttcgtca actacgagct catgccgggg   2640
aacatgcacc gcgggcccga cggcaccgga atgtacgagt gcatcgacct ctaccccgtc   2700
ggcggcaact cgtccgagat gctcggcggc gacgactcgc ccggcgtgct cttcgtgctc   2760
aaggagagca gcgacgacga gcgccacgac tactacgcgc tcggaaggtt cgacgccgtc   2820
gccaacgttt ggacgcccat cgaccgggag ctggaccttg ggatcgggct cagatacgac   2880
tggggaaagt actacgcctc caagtccttc tacgaccaga agaagaaccg ccgcatcgta   2940
tgggcataca tcggcgagac cgactccgag caggccgaca tcaccaaggg atgggccaat   3000
ctcatgacga ttccaagaac ggtggagctt gacaggaaga cccgcacaaa cctcatccaa   3060
tggccagtgg aggaggtcga caccctccgc aggaactcca cggacctcgg tcgcatcacc   3120
gtcaacgccg gctccgtcat tcgcctcccc ctccaccagg gcgctcaact cgacatcgag   3180
gcctccttcc aactcaactc ttccgacgtg gatgctatca acgaggccga cgtcggctac   3240
aactgcagca ccagtggtgc cgccgtacgg ggggcgctcg gccccctttgg cctcctcgtc   3300
cttgccaacg gccgcaccga acagacggct gtgtacttct acgtgtccaa gggcgtcgac   3360
ggtgccctcc agacccactt ctgccacgac gagtcacggt caacgcgggc aaaggatgtc   3420
gtgaatagga tgattggcag catcgtgccg gtgcttgacg gtgagacctt ttcggtgagg   3480
gtgctagtgg accactccat cgtgcagagc ttcgcgatgg gcgggaggat cacggcgacg   3540
tcgcgggcgt acccgacgga ggccatctac gcggccgcgg gggtctacct cttcaacaac   3600
gccacgggcg ccaccgtcac cgccgagagg ctcgtcgtgc acgagatggc ctcagctgac   3660
aaccatatct tcacgaacga cgacttggga ggaggaaagc ttaagcttgg aggaggagag   3720
tccagcgccg tcgtcgccca aggcaccacg tcgccgctgc tcccgtacgc ctacgcgccg   3780
ctgccgtcct ctgccgacga cgcccgtgaa aaccagagta gcggcggcgg tgtcaggtgg   3840
cgcgcgtgcg cggcctcggc cctggtggtg ctgctggtcg tcgtcggctt cttcgcgggt   3900
ggcagggtgg atctgggtca ggacggcgag gtgtctgcga cttcttcggt tcctgggagc   3960
```

agcaggggca aggattccgg cgtgtcggag aaggagtcgc ccgccgacgg cggcttcccg 4020
tggagcaacg ccatgctgca gtggcagcac accgggttcc atttccagcc actcaagcac 4080
tacatgaacg atcccaacgg tccggtctac tatggcggat ggtaccacct cttctaccag 4140
cacaacccct atggcgactc gtggggaaac gtatcttggg gacatgccgt gtccaaggac 4200
ctggtgaact ggcgccacct cccggtcgcc ttggtgcccg atcagtggta cgacatcaac 4260
ggcgtcctga cgggctctat cacagtgctc ccagacgggc gtgtcatcct gctatatacg 4320
gggaacaccg acaccttttc gcaggtccag tgcctcgcag tgcccgccga cccatctgac 4380
ccgctcctcc gtagctggat caagcacccc gccaacccca tcctcttccc gccacctggg 4440
atcgggctca aggacttccg tgacccgctc acagcctggt tcgaacattc cgacaacacg 4500
tggcgcacca tcatcggatc caaggatgac gacggccacg ccggcatcgt ccttagctac 4560
aagaccaccg actttgtgaa ttatgagctc atgccaggga acatgcatcg tggccccgac 4620
ggcaccggca tgtacgagtg ccttgacatc taccctgtgg gcggcaactc atccgagatg 4680
ttgggtggcg actcctcaca tgaggtgttg ttcgtgctca aggagagcgc caacgacgag 4740
tggcacgact actacgcgct tgggtggttt gacgctgccg ccaacacgtg gacgccacag 4800
gaccccgagg cggaccttgg gatcggcctc aggtacgact ggggcaagta ctacgcgtcc 4860
aagtccttct acgacccgat caagaaccgg cgtgtcgttt gggctttcgt cggcgagacc 4920
gactctgagc aggccgacaa agccaaggga tgggcgtccc tcatgtcgat tcccaggacg 4980
gtggagcttg acaagaagac ccggacgaac ctgatccaat ggccagtgga ggagatcgag 5040
acccttcgca ggaacgtcac agacctcggt ggcatcaccg ttgaagccgg ctccgtcatt 5100
caccttcccc tccaacaagg cgggcagctt gacatcgagg cctccttccg tctcaactct 5160
tcggacatcg atgcactcaa cgaggccgac gtcggcttca actgcagtag cagcgatggg 5220
gtagccgtgc gtggtgcgct cggccccttt ggcctcctcg tcttcgccga cggtcgccac 5280
gaacagacgg cggcgtactt ctacgtgtcc aagggcctcg acggcagcct cctgacgcac 5340
tactgccacg acgagtcacg gtcgacgcga gcaaaggacg tcgtgagccg ggtggttggc 5400
ggcactgtgc cagtgcttga cggtgaaacc ttttcagtga gggtgctagt ggaccactcc 5460
atcgtgcaga gcttcgtgat gggtgggagg accacggtga catcgcgggc atacccgacg 5520
gaggccatct acgccgcggc aggggtgtac ctgttcaaca acgcaacgag cgccaccatc 5580
accgccgaag ggctcgtcgt gtacgagatg gcctcggccg agagtcgggc cttcttggct 5640
gacgacatgt agacccagct ttcttgtaca aagtgggatc tagtaacata gatgacaccg 5700
cgcgcgataa tttatcctag tttgcgcgct atattttgtt ttctatcgcg tattaaatgt 5760
ataattgcgg gactctaatc ataaaaaccc atctcataaa taacgtcatg cattacatgt 5820
taattattac atgcttaacg taattcaaca gaaattatat gataatcatc gcaagaccgg 5880
caacaggatt caatcttaag aaactttatt gccaaatgtt tgaacgatc 5929

<210> SEQ ID NO 44
<211> LENGTH: 6614
<212> TYPE: DNA
<213> ORGANISM: Artificial Sequence
<220> FEATURE:
<223> OTHER INFORMATION: Expression construct

<400> SEQUENCE: 44
cctgcagaag taacaccaaa caacagggtg agcatcgaca aaagaaacag taccaagcaa 60

```
ataaatagcg tatgaaggca gggctaaaaa aatccacata tagctgctgc atatgccatc    120
atccaagtat atcaagatca aaataattat aaaacatact tgtttattat aatagatagg    180
tactcaaggt tagagcatat gaatagatgc tgcatatgcc atcatgtata tgcatcagta    240
aaacccacat caacatgtat acctatccta gatcgatatt tccatccatc ttaaactcgt    300
aactatgaag atgtatgaca cacacataca gttccaaaat taataaatac accaggtagt    360
ttgaaacagt attctactcc gatctagaac gaatgaacga ccgcccaacc acaccacatc    420
atcacaacca agcgaacaaa aagcatctct gtatatgcat cagtaaaacc cgcatcaaca    480
tgtataccta tcctagatcg atatttccat ccatcatttt caattcgtaa ctatgaatat    540
gtatggcaca cacatacaga tccaaaatta ataaatccac caggtagttt gaaacagaat    600
tctactccga tctagaacga ccgcccaacc agaccacatc atcacaacca agacaaaaaa    660
aagcatgaaa agatgacccg acaaacaagt gcacggcata tattgaaata aaggaaaagg    720
gcaaaccaaa ccctatgcaa cgaaacaaaa aaaatcatga aatcgatccc gtctgcggaa    780
cggctagagc catcccagga ttccccaaag agaaacactg gcaagttagc aatcagaacg    840
tgtctgacgt acaggtcgca tccgtgtacg aacgctagca gcacggatct aacacaaaca    900
cggatctaac acaaacatga acagaagtag aactaccggg ccctaaccat ggaccggaac    960
gccgatctag agaaggtaga gaggggggggg gggggaggac gagcggcgta ccttgaagcg   1020
gaggtgccga cgggtggatt tgggggagat ctggttgtgt gtgtgtgcgc tccgaacaac   1080
acgaggttgg ggaaagaggg tgtggagggg gtgtctattt attacggcgg gcgaggaagg   1140
gaaagcgaag gagcggtggg aaaggaatcc cccgtagctg ccggtgccgt gagaggagga   1200
ggaggccgcc tgccgtgccg gctcacgtct gccgctccgc cacgcaattt ctggatgccg   1260
acagcggagc aagtccaacg gtggagcgga actctcgaga ggggtccaga ggcagcgaca   1320
gagatgccgt gccgtctgct tcgcttggcc cgacgcgacg ctgctggttc gctggttggt   1380
gtccgttaga ctcgtcgacg gcgtttaaca ggctggcatt atctactcga aacaagaaaa   1440
atgtttcctt agttttttta atttcttaaa gggtatttgt ttaattttta gtcactttat   1500
tttattctat tttatatcta aattattaaa taaaaaaact aaaatagagt tttagttttc   1560
ttaatttaga ggctaaaata gaataaaata gatgtactaa aaaaattagt ctataaaaac   1620
cattaaccct aaaccctaaa tggatgtact aataaaatgg atgaagtatt atataggtga   1680
agctatttgc aaaaaaaaag gagaacacat gcacactaaa aagataaaac tgtagagtcc   1740
tgttgtcaaa atactcaatt gtcctttaga ccatgtctaa ctgttcattt atatgattct   1800
ctaaaacact gatattattg tagtactata gattatatta ttcgtagagt aaagtttaaa   1860
tatatgtata aagatagata aactgcactt caaacaagtg tgacaaaaaa aatatgtggt   1920
aatttttat aacttagaca tgcaatgctc attatctcta gagaggggca cgaccgggtc     1980
acgctgcact gcagatggag tccccaagcg ccgtcgtccc cggcaccacg gcgccgctgc   2040
ttccttatgc gtacgcgccg ctgccgtcgt ccgccgacga cgcccgtcaa aaccggagtg   2100
gcgggaggtg gcgcgcgtgc gccgccgtgc tggccgcatc ggcgttggcg gtggtcgtcg   2160
tggtcgggct cctcgcgggc ggcagggtgg atcgggtccc agccggcgga gacgtggcgt   2220
cggccacggt gccggccgtg ccgatggagt tcccgaggag ccggggcaag gacttcggcg   2280
tgtcggagaa gtcctccggt gcctactcca ccgacggcgg gttcccgtgg agcaacgcca   2340
tgctgcagtg gcagcgcacc gggttccatt tccagccgga gcagcactac atgaacgatc   2400
ccaacggccc cgtgtactac ggcggatggt accacctctt ctaccagcac aaccccaagg   2460
```

```
gcgacagctg gggcaacatc gcgtgggccc acgccgtctc caaggacatg gtcaactggc   2520
gccacctccc tctcgccatg gttcccgacc agtggtacga cagcaacggc gtcctcaccg   2580
gctccatcac cgtgctcccc gacggccagg tcatcctgct ctacaccggc aacaccgaca   2640
ccctagccca ggtccagtgc ctcgccacgc ccgccgaccc gtccgacccg ctcctccgcg   2700
agtgggtcaa gcaccccgcc aaccccatcc tctaccctcc ccccggcatc ggcctcaagg   2760
acttccgcga ccccctcacc gcctggttcg accactccga ccacacctgg cgcaccgtca   2820
tcggctccaa ggacgacgac ggccacgccg gcatcatcct cagctacaag accaaggact   2880
tcgtcaacta cgagctcatg ccggggaaca tgcaccgcgg gcccgacggc accggaatgt   2940
acgagtgcat cgacctctac cccgtcggcg gcaactcgtc cgagatgctc ggcggcgacg   3000
actcgcccgg cgtgctcttc gtgctcaagg agagcagcga cgacgagcgc cacgactact   3060
acgcgctcgg aaggttcgac gccgtcgcca acgtttggac gcccatcgac cgggagctgg   3120
accttgggat cgggctcaga tacgactggg gaaagtacta cgcctccaag tccttctacg   3180
accagaagaa gaaccgccgc atcgtatggg catacatcgg cgagaccgac tccgagcagg   3240
ccgacatcac caagggatgg gccaatctca tgacgattcc aagaacggtg gagcttgaca   3300
ggaagacccg cacaaacctc atccaatggc cagtggagga ggtcgacacc ctccgcagga   3360
actccacgga cctcggtcgc atcaccgtca acgccggctc cgtcattcgc ctcccccctcc  3420
accagggcgc tcaactcgac atcgaggcct ccttccaact caactcttcc gacgtggatg   3480
ctatcaacga ggccgacgtc ggctacaact gcagcaccag tggtgccgcc gtacgggggg   3540
cgctcggccc ctttggcctc ctcgtccttg ccaacggccg caccgaacag acggctgtgt   3600
acttctacgt gtccaagggc gtcgacggtg ccctccagac ccacttctgc cacgacgagt   3660
cacggtcaac gcgggcaaag gatgtcgtga ataggatgat tggcagcatc gtgccggtgc   3720
ttgacggtga gacctttttcg gtgagggtgc tagtggacca ctccatcgtg cagagcttcg  3780
cgatgggcgg gaggatcacg gcgacgtcgc gggcgtaccc gacggaggcc atctacgcgg   3840
ccgcgggggt ctacctcttc aacaacgcca cgggcgccac cgtcaccgcc gagaggctcg   3900
tcgtgcacga gatggcctca gctgacaacc atatcttcac gaacgacgac ttgggaggag   3960
gaaagcttaa gcttggagga ggagagtcca gcgccgtcgt cgcccaaggc accacgtcgc   4020
cgctgctccc gtacgcctac gcgccgctgc cgtcctctgc cgacgacgcc cgtgaaaacc   4080
agagtagcgg cggcggtgtc aggtggcgcg cgtgcgcggc ctcggccctg gtggtgctgc   4140
tggtcgtcgt cggcttcttc gcgggtggca gggtggatct gggtcaggac ggcgaggtgt   4200
ctgcgacttc ttcggttcct gggagcagca ggggcaagga ttccggcgtg tcggagaagg   4260
agtcgcccgc cgacggcggc ttcccgtgga gcaacgccat gctgcagtgg cagcacaccg   4320
ggttccattt ccagccactc aagcactaca tgaacgatcc caacggtccg gtctactatg   4380
gcggatggta ccacctcttc taccagcaca accccctatgg cgactcgtgg ggaaacgtat  4440
cttggggaca tgccgtgtcc aaggacctgg tgaactggcg ccacctcccg gtcgccttgg   4500
tgcccgatca gtggtacgac atcaacggcg tcctgacggg ctctatcaca gtgctcccag   4560
acgggcgtgt catcctgcta tatacgggga acaccgacac cttttcgcag gtccagtgcc   4620
tcgcagtgcc cgccgaccca tctgacccgc tcctccgtag ctggatcaag caccccgcca   4680
accccatcct cttcccgcca cctgggatcg ggctcaagga cttccgtgac ccgctcacag   4740
cctggttcga acattccgac aacacgtggc gcaccatcat cggatccaag gatgacgacg   4800
```

```
gccacgccgg catcgtcctt agctacaaga ccaccgactt tgtgaattat gagctcatgc   4860

cagggaacat gcatcgtggc cccgacggca ccggcatgta cgagtgcctt gacatctacc   4920

ctgtgggcgg caactcatcc gagatgttgg gtggcgactc ctcacctgag gtgttgttcg   4980

tgctcaagga gagcgccaac gacgagtggc acgactacta cgcgcttggg tggtttgacg   5040

ctgccgccaa cacgtggacg ccacaggacc ccgaggcgga ccttgggatc ggcctcaggt   5100

acgactgggg caagtactac gcgtccaagt ccttctacga cccgatcaag aaccggcgtg   5160

tcgtttgggc tttcgtcggc gagaccgact ctgagcaggc cgacaaagcc aagggatggg   5220

cgtccctcat gtcgattccc aggacggtgg agcttgacaa gaagacccgg acgaacctga   5280

tccaatggcc agtggaggag atcgagaccc ttcgcaggaa cgtcacagac ctcggtggca   5340

tcaccgttga agccggctcc gtcattcacc ttcccctcca acaaggcggg cagcttgaca   5400

tcgaggcctc cttccgtctc aactcttcgg acatcgatgc actcaacgag gccgacgtcg   5460

gcttcaactg cagtagcagc gatggggcag ccgtgcgtgg tgcgctcggc ccctttggcc   5520

tcctcgtctt cgccgacggt cgccacgaac agacggcggc gtacttctac gtgtccaagg   5580

gcctcgacgg cagcctcctg acgcactact gccacgacga gtcacggtcg acgcgagcaa   5640

aggacgtcgt gagccgggtg gttggcggca ctgtgccagt gcttgacggt gaaacctttt   5700

cagtgagggt gctagtggac cactccatcg tgcagagctt cgtgatgggt gggaggacca   5760

cggtgacatc gcgggcatac ccgacggagg ccatctacgc cgcggcaggg gtgtacctgt   5820

tcaacaacgc aacgagcgcc accatcaccg ccgaagggct cgtcgtgtac gagatggcct   5880

cggccgagag tcgggccttc ttggctgacg acatgtagaa caataatttt ctgagcctag   5940

tatccatgat catgatatag taagggaaaa atcatatcta taagtttccg aacttagtga   6000

aaaaaaacct gtaaaagata tgcagtcata tacacatgtg aaattaggta ggaaaatatg   6060

ataatctcgt agatgaggaa aaaatattgt acaccaaact attgtaagtt acagtaatgt   6120

aatgtaaaaa aagtttttaa gttacagaag gtacataccg caaataatca tattatttta   6180

ccaagatatt tttttctgga gtattccttt caagtatctt ttatctctag aatcttctcc   6240

aatcatgagt ggcaaccgaa atggagctcc tgtgttgctc cccgtgtctc accccttcg   6300

gccccactgt cattgggtgg acctattctc acggcggctg tcctgagaaa caaaaatagc   6360

agctgaaatg aagacacggc gacacgcaag ccagcatctc tcattgaacc tgcggagtga   6420

gatagctctc gtggcgctgc tctacttgac gcgtttgtct catacaacag cgcatggctc   6480

cttcatgtca ggtccatgat ccacagatgg tatgattggg tttggaacat tttttgggtt   6540

tgtgatatgt cgtagataca aagggaaatg tctgaagcat gcatggatgg gttccctgct   6600

catgtactca atgt                                                      6614
```

```
<210> SEQ ID NO 45
<211> LENGTH: 5908
<212> TYPE: DNA
<213> ORGANISM: Artificial Sequence
<220> FEATURE:
<223> OTHER INFORMATION: Expression construct

<400> SEQUENCE: 45

gatctccttt gccccagaga tcacaatgga cgacttcctc tatctctacg atctagtcag     60

gaagttcgac ggagaaggtg acgataccat gttcaccact gataatgaga agattagcct    120

tttcaatttc agaaagaatg ctaacccaca gatggttaga gaggcttacg cagcaggtct    180

catcaagacg atctacccga gcaataatct ccaggagatc aaataccttc ccaagaaggt    240
```

-continued

```
taaagatgca gtcaaaagat tcaggactaa ctgcatcaag aacacagaga aagatatatt    300
tctcaagatc agaagtacta ttccagtatg gacgattcaa ggcttgcttc acaaaccaag    360
gcaagtaata gagattggag tctctaaaaa ggtagttccc actgaatcaa aggccatgga    420
gtcaaagatt caaatagagg acctaacaga actcgccgta aagactggcg aacagttcat    480
acagagtctc ttacgactca atgacaagaa gaaaatcttc gtcaacatgg tggagcacga    540
cacacttgtc tactccaaaa atatcaaaga tacagtctca gaagaccaaa gggcaattga    600
gacttttcaa caaagggtaa tatccggaaa cctcctcgga ttccattgcc cagctatctg    660
tcactttatt gtgaagatag tggaaaagga aggtggctcc tacaaatgcc atcattgcga    720
taaaggaaag gccatcgttg aagatgcctc tgccgacagt ggtcccaaag atggaccccc    780
acccacgagg agcatcgtgg aaaaagaaga cgttccaacc acgtcttcaa agcaagtgga    840
ttgatgtgat aacatggtgg agcacgacac acttgtctac tccaaaaata tcaaagatac    900
agtctcagaa gaccaaaggg caattgagac ttttcaacaa agggtaatat ccggaaacct    960
cctcggattc cattgcccag ctatctgtca ctttattgtg aagatagtgg aaaaggaagg   1020
tggctcctac aaatgccatc attgcgataa aggaaaggcc atcgttgaag atgcctctgc   1080
cgacagtggt cccaaagatg gacccccacc cacgaggagc atcgtggaaa aagaagacgt   1140
tccaaccacg tcttcaaagc aagtggattg atgtgatatc tccactgacg taagggatga   1200
cgcacaatcc cactatcctt cgcaagaccc ttcctctata taaggaagtt catttcattt   1260
ggagaggaca cgctgaaatc accagtctat ggagtcccca agcgccgtcg tccccggcac   1320
cacggcgccg ctgcttcctt atgcgtacgc gccgctgccg tcgtccgccg acgacgcccg   1380
tcaaaaccgg agtggcggga ggtggcgcgc gtgcgccgcc gtgctggccg catcggcgtt   1440
ggcggtggtc gtcgtggtcg ggctcctcgc gggcggcagg gtggatcggg tcccagccgg   1500
cggagacgtg gcgtcggcca cggtgccggc cgtgccgatg gagttcccga ggagccgggg   1560
caaggacttc ggcgtgtcgg agaagtcctc cggtgcctac tccaccgacg gcgggttccc   1620
gtggagcaac gccatgctgc agtggcagcg caccgggttc catttccagc cggagcagca   1680
ctacatgaac gatcccaacg gccccgtgta ctacggcgga tggtaccacc tcttctacca   1740
gcacaacccc aagggcgaca gctggggcaa catcgcgtgg gcccacgccg tctccaagga   1800
catggtcaac tggcgccacc tccctctcgc catggttccc gaccagtggt acgacagcaa   1860
cggcgtcctc accggctcca tcaccgtgct ccccgacggc caggtcatcc tgctctacac   1920
cggcaacacc gacaccctag cccaggtcca gtgcctcgcc acgcccgccg acccgtccga   1980
cccgctcctc cgcgagtggg tcaagcaccc cgccaacccc atcctctacc ctccccccgg   2040
catcggcctc aaggacttcc gcgaccccct caccgcctgg ttcgaccact ccgaccacac   2100
ctggcgcacc gtcatcggct ccaaggacga cgacggccac gccggcatca tcctcagcta   2160
caagaccaag gacttcgtca actacgagct catgccgggg aacatgcacc gcgggcccga   2220
cggcaccgga atgtacgagt gcatcgacct ctaccccgtc ggcggcaact cgtccgagat   2280
gctcggcggc gacgactcgc ccggcgtgct cttcgtgctc aaggagagca gcgacgacga   2340
gcgccacgac tactacgcgc tcggaaggtt cgacgccgtc gccaacgttt ggacgcccat   2400
cgaccgggag ctggaccttg ggatcgggct cagatacgac tggggaaagt actacgcctc   2460
caagtccttc tacgaccaga agaagaaccg ccgcatcgta tgggcataca tcggcgagac   2520
cgactccgag caggccgaca tcaccaaggg atgggccaat ctcatgacga ttccaagaac   2580
```

-continued

```
ggtggagctt gacaggaaga cccgcacaaa cctcatccaa tggccagtgg aggaggtcga   2640
caccctccgc aggaactcca cggacctcgg tcgcatcacc gtcaacgccg gctccgtcat   2700
tcgcctcccc ctccaccagg gcgctcaact cgacatcgag gcctccttcc aactcaactc   2760
ttccgacgtg gatgctatca acgaggccga cgtcggctac aactgcagca ccagtggtgc   2820
cgccgtacgg ggggcgctcg gcccctttgg cctcctcgtc cttgccaacg gccgcaccga   2880
acagacggct gtgtacttct acgtgtccaa gggcgtcgac ggtgccctcc agacccactt   2940
ctgccacgac gagtcacggt caacgcgggc aaaggatgtc gtgaatagga tgattggcag   3000
catcgtgccg gtgcttgacg gtgagacctt ttcggtgagg gtgctagtgg accactccat   3060
cgtgcagagc ttcgcgatgg gcgggaggat cacggcgacg tcgcgggcgt acccgacgga   3120
ggccatctac gcggccgcgg gggtctacct cttcaacaac gccacgggcg ccaccgtcac   3180
cgccgagagg ctcgtcgtgc acgagatggc ctcagctgac aaccatatct tcacgaacga   3240
cgacttggga ggaggaaagc ttaagcttgg aggaggagag tccagcgccg tcgtcgccca   3300
aggcaccacg tcgccgctgc tcccgtacgc ctacgcgccg ctgccgtcct ctgccgacga   3360
cgcccgtgaa aaccagagta gcggcggcgg tgtcaggtgg cgcgcgtgcg cggcctcggc   3420
cctggtggtg ctgctggtcg tcgtcggctt cttcgcgggt ggcagggtgg atctgggtca   3480
ggacggcgag gtgtctgcga cttcttcggt tcctgggagc agcaggggca aggattccgg   3540
cgtgtcggag aaggagtcgc ccgccgacgg cggcttcccg tggagcaacg ccatgctgca   3600
gtggcagcac accgggttcc atttccagcc actcaagcac tacatgaacg atcccaacgg   3660
tccggtctac tatggcggat ggtaccacct cttctaccag cacaacccct atggcgactc   3720
gtggggaaac gtatcttggg gacatgccgt gtccaaggac ctggtgaact ggcgccacct   3780
cccggtcgcc ttggtgcccg atcagtggta cgacatcaac ggcgtcctga cgggctctat   3840
cacagtgctc ccagacgggc gtgtcatcct gctatatacg gggaacaccg acaccttttc   3900
gcaggtccag tgcctcgcag tgcccgccga cccatctgac ccgctcctcc gtagctggat   3960
caagcacccc gccaacccca tcctcttccc gccacctggg atcgggctca aggacttccg   4020
tgacccgctc acagcctggt tcgaacattc cgacaacacg tggcgcacca tcatcggatc   4080
caaggatgac gacggccacg ccggcatcgt ccttagctac aagaccaccg actttgtgaa   4140
ttatgagctc atgccaggga acatgcatcg tggccccgac ggcaccggca tgtacgagtg   4200
ccttgacatc taccctgtgg gcggcaactc atccgagatg ttgggtggcg actcctcacc   4260
tgaggtgttg ttcgtgctca aggagagcgc caacgacgag tggcacgact actacgcgct   4320
tgggtggttt gacgctgccg ccaacacgtg gacgccacag gaccccgagg cggaccttgg   4380
gatcggcctc aggtacgact ggggcaagta ctacgcgtcc aagtccttct acgacccgat   4440
caagaaccgg cgtgtcgttt gggctttcgt cggcgagacc gactctgagc aggccgacaa   4500
agccaaggga tgggcgtccc tcatgtcgat tcccaggacg gtggagcttg acaagaagac   4560
ccggacgaac ctgatccaat ggccagtgga ggagatcgag acccttcgca ggaacgtcac   4620
agacctcggt ggcatcaccg ttgaagccgg ctccgtcatt caccttcccc tccaacaagg   4680
cgggcagctt gacatcgagg cctccttccg tctcaactct tcggacatcg atgcactcaa   4740
cgaggccgac gtcggcttca actgcagtag cagcgatggg gcagccgtgc gtggtgcgct   4800
cggcccottt ggcctcctcg tcttcgccga cggtcgccac gaacagacgg cggcgtactt   4860
ctacgtgtcc aagggcctcg acggcagcct cctgacgcac tactgccacg acgagtcacg   4920
gtcgacgcga gcaaaggacg tcgtgagccg ggtggttggc ggcactgtgc cagtgcttga   4980
```

```
cggtgaaacc ttttcagtga gggtgctagt ggaccactcc atcgtgcaga gcttcgtgat   5040

gggtgggagg accacggtga catcgcgggc atacccgacg gaggccatct acgccgcggc   5100

aggggtgtac ctgttcaaca acgcaacgag cgccaccatc accgccgaag ggctcgtcgt   5160

gtacgagatg gcctcggccg agagtcgggc cttcttggct gacgacatgt agaacaataa   5220

ttttctgagc ctagtatcca tgatcatgat atagtaaggg aaaaatcata tctataagtt   5280

tccgaactta gtgaaaaaaa acctgtaaaa gatatgcagt catatacaca tgtgaaatta   5340

ggtaggaaaa tatgataatc tcgtagatga ggaaaaaata ttgtacacca aactattgta   5400

agttacagta atgtaatgta aaaaaagttt ttaagttaca gaaggtacat accgcaaata   5460

atcatattat tttaccaaga tattttttc tggagtattc ctttcaagta tcttttatct   5520

ctagaatctt ctccaatcat gagtggcaac cgaaatggag ctcctgtgtt gctccccgtg   5580

tctcacccct ttcggcccca ctgtcattgg gtggacctat tctcacggcg gctgtcctga   5640

gaaacaaaaa tagcagctga aatgaagaca cggcgacacg caagccagca tctctcattg   5700

aacctgcgga gtgagatagc tctcgtggcg ctgctctact tgacgcgttt gtctcataca   5760

acagcgcatg gctccttcat gtcaggtcca tgatccacag atggtatgat tgggtttgga   5820

acattttttg ggtttgtgat atgtcgtaga tacaaaggga aatgtctgaa gcatgcatgg   5880

atgggttccc tgctcatgta ctcaatgt                                       5908
```

<210> SEQ ID NO 46
<211> LENGTH: 5233
<212> TYPE: DNA
<213> ORGANISM: Artificial Sequence
<220> FEATURE:
<223> OTHER INFORMATION: Expression construct
<220> FEATURE:
<221> NAME/KEY: misc_feature
<222> LOCATION: (6)..(6)
<223> OTHER INFORMATION: n is a, c, g, or t

<400> SEQUENCE: 46

```
acgganggta aacaaattcg ggtcaaggcg gaagccagcg cgccacccca cgtcagcaaa     60

tacggaggcg cggggttgac ggcgtcaccc ggtcctaacg gcgaccaaca aaccagccag    120

aagaaattac agtaaaaaaa aagtaaattg cactttgatc caccttttat tacctaagtc    180

tcaatttgga tcacccttaa acctatcttt tcaatttggg ccgggttgtg gtttggacta    240

ccatgaacaa cttttcgtca tgtctaactt ccctttcagc aaacatatga accatatata    300

gaggagatcg gccgtatact agagctgatg tgtttaaggt cgttgattgc acgagaaaaa    360

aaaatccaaa tcgcaacaat agcaaattta tctggttcaa agtgaaaaga tatgtttaaa    420

ggtagtccaa agtaaaactt atagataata aaatgtggtc caaagcgtaa ttcactcaaa    480

aaaaatcaac gagacgtgta ccaaacggag acaaacggca tcttctcgaa atttccaacc    540

gtcgctcgcc gcctcgtctt cccggaaccg cggtggttta agcgtggcgg attcttcaag    600

cagacggaga cgtatggagt ccccaagcgc cgtcgtcccc ggcaccacgg cgccgctgct    660

tccttatgcg tacgcgccgc tgccgtcgtc cgccgacgac gcccgtcaaa accggagtgg    720

cgggaggtgg cgcgcgtgcg ccgccgtgct ggccgcatcg gcgttggcgg tggtcgtcgt    780

ggtcgggctc ctcgcgggcg gcagggtgga tcgggtccca gccggcggag acgtggcgtc    840

ggccacggtg ccggccgtgc cgatggagtt cccgaggagc cggggcaagg acttcggcgt    900

gtcggagaag tcctccggtg cctactccac cgacggcggg ttcccgtgga gcaacgccat    960
```

-continued

```
gctgcagtgg cagcgcaccg ggttccattt ccagccggag cagcactaca tgaacgatcc   1020
caacggcccc gtgtactacg gcggatggta ccacctcttc taccagcaca accccaaggg   1080
cgacagctgg ggcaacatcg cgtgggccca cgccgtctcc aaggacatgg tcaactggcg   1140
ccacctccct ctcgccatgg ttcccgacca gtggtacgac agcaacggcg tcctcaccgg   1200
ctccatcacc gtgctccccg acggccaggt catcctgctc tacaccggca acaccgacac   1260
cctagcccag gtccagtgcc tcgccacgcc cgccgacccg tccgacccgc tcctccgcga   1320
gtgggtcaag caccccgcca accccatcct ctaccctccc cccggcatcg gcctcaagga   1380
cttccgcgac cccctcaccg cctggttcga ccactccgac cacacctggc gcaccgtcat   1440
cggctccaag gacgacgacg gccacgccgg catcatcctc agctacaaga ccaaggactt   1500
cgtcaactac gagctcatgc cggggaacat gcaccgcggg cccgacggca ccggaatgta   1560
cgagtgcatc gacctctacc ccgtcggcgg caactcgtcc gagatgctcg gcggcgacga   1620
ctcgcccggc gtgctcttcg tgctcaagga gagcagcgac gacgagcgcc acgactacta   1680
cgcgctcgga aggttcgacg ccgtcgccaa cgtttggacg cccatcgacc gggagctgga   1740
ccttgggatc gggctcagat acgactgggg aaagtactac gcctccaagt ccttctacga   1800
ccagaagaag aaccgccgca tcgtatgggc atacatcggc gagaccgact ccgagcaggc   1860
cgacatcacc aagggatggg ccaatctcat gacgattcca agaacggtgg agcttgacag   1920
gaagacccgc acaaacctca tccaatggcc agtggaggag gtcgacaccc tccgcaggaa   1980
ctccacggac ctcggtcgca tcaccgtcaa cgccggctcc gtcattcgcc tccccctcca   2040
ccagggcgct caactcgaca tcgaggcctc cttccaactc aactcttccg acgtggatgc   2100
tatcaacgag gccgacgtcg gctacaactg cagcaccagt ggtgccgccg tacgggggc    2160
gctcggcccc tttggcctcc tcgtccttgc caacggccgc accgaacaga cggctgtgta   2220
cttctacgtg tccaagggcg tcgacggtgc cctccagacc cacttctgcc acgacgagtc   2280
acggtcaacg cgggcaaagg atgtcgtgaa taggatgatt ggcagcatcg tgccggtgct   2340
tgacggtgag accttttcgg tgagggtgct agtggaccac tccatcgtgc agagcttcgc   2400
gatgggcggg aggatcacgg cgacgtcgcg ggcgtacccg acggaggcca tctacgcggc   2460
cgcgggggtc tacctcttca acaacgccac gggcgccacc gtcaccgccg agaggctcgt   2520
cgtgcacgag atggcctcag ctgacaacca tatcttcacg aacgacgact tgggaggagg   2580
aaagcttaag cttggaggag gagagtccag cgccgtcgtc gcccaaggca ccacgtcgcc   2640
gctgctcccg tacgcctacg cgccgctgcc gtcctctgcc gacgacgccc gtgaaaacca   2700
gagtagcggc ggcggtgtca ggtggcgcgc gtgcgcggcc tcggccctgg tggtgctgct   2760
ggtcgtcgtc ggcttcttcg cgggtggcag ggtggatctg ggtcaggacg gcgaggtgtc   2820
tgcgacttct tcggttcctg ggagcagcag gggcaaggat tccggcgtgt cggagaagga   2880
gtcgcccgcc gacggcggct tcccgtggag caacgccatg ctgcagtggc agcacaccgg   2940
gttccatttc cagccactca agcactacat gaacgatccc aacggtccgg tctactatgg   3000
cggatggtac cacctcttct accagcacaa cccctatggc gactcgtggg gaaacgtatc   3060
ttggggacat gccgtgtcca aggacctggt gaactggcgc cacctcccgg tcgccttggt   3120
gcccgatcag tggtacgaca tcaacggcgt cctgacgggc tctatcacag tgctcccaga   3180
cgggcgtgtc atcctgctat atacggggaa caccgacacc ttttcgcagg tccagtgcct   3240
cgcagtgccc gccgacccat ctgacccgct cctccgtagc tggatcaagc accccgccaa   3300
ccccatcctc ttcccgccac ctgggatcgg gctcaaggac ttccgtgacc cgctcacagc   3360
```

-continued ctggttcgaa cattccgaca acacgtggcg caccatcatc ggatccaagg atgacgacgg 3420
ccacgccggc atcgtcctta gctacaagac caccgacttt gtgaattatg agctcatgcc 3480
agggaacatg catcgtggcc ccgacggcac cggcatgtac gagtgccttg acatctaccc 3540
tgtgggcggc aactcatccg agatgttggg tggcgactcc tcacctgagg tgttgttcgt 3600
gctcaaggag agcgccaacg acgagtggca cgactactac gcgcttgggt ggtttgacgc 3660
tgccgccaac acgtggacgc cacaggaccc cgaggcggac cttgggatcg gcctcaggta 3720
cgactggggc aagtactacg cgtccaagtc cttctacgac ccgatcaaga accggcgtgt 3780
cgtttgggct ttcgtcggcg agaccgactc tgagcaggcc gacaaagcca agggatgggc 3840
gtccctcatg tcgattccca ggacggtgga gcttgacaag aagacccgga cgaacctgat 3900
ccaatggcca gtggaggaga tcgagaccct tcgcaggaac gtcacagacc tcggtggcat 3960
caccgttgaa gccggctccg tcattcacct tcccctccaa caaggcgggc agcttgacat 4020
cgaggcctcc ttccgtctca actcttcgga catcgatgca ctcaacgagg ccgacgtcgg 4080
cttcaactgc agtagcagcg atggggcagc cgtgcgtggt gcgctcggcc cctttggcct 4140
cctcgtcttc gccgacggtc gccacgaaca gacggcggcg tacttctacg tgtccaaggg 4200
cctcgacggc agcctcctga cgcactactg ccacgacgag tcacggtcga cgcgagcaaa 4260
ggacgtcgtg agccgggtgg ttggcggcac tgtgccagtg cttgacggtg aaaccttttc 4320
agtgagggtg ctagtggacc actccatcgt gcagagcttc gtgatgggtg ggaggaccac 4380
ggtgacatcg cgggcatacc cgacggaggc catctacgcc gcggcagggg tgtacctgtt 4440
caacaacgca acgagcgcca ccatcaccgc cgaagggctc gtcgtgtacg agatggcctc 4500
ggccgagagt cgggccttct tggctgacga catgtagaac aataattttc tgagcctagt 4560
atccatgatc atgatatagt aagggaaaaa tcatatctat aagtttccga acttagtgaa 4620
aaaaaacctg taaaagatat gcagtcatat acacatgtga aattaggtag gaaaatatga 4680
taatctcgta gatgaggaaa aaatattgta caccaaacta ttgtaagtta cagtaatgta 4740
atgtaaaaaa agtttttaag ttacagaagg tacataccgc aaataatcat attattttac 4800
caagatattt ttttctggag tattcctttc aagtatcttt tatctctaga atcttctcca 4860
atcatgagtg gcaaccgaaa tggagctcct gtgttgctcc ccgtgtctca ccccttttcgg 4920 ccccactgtc attgggtgga cctattctca cggcggctgt cctgagaaac aaaaatagca 4980
gctgaaatga agacacggcg acacgcaagc cagcatctct cattgaacct gcggagtgag 5040
atagctctcg tggcgctgct ctacttgacg cgtttgtctc atacaacagc gcatggctcc 5100
ttcatgtcag gtccatgatc cacagatggt atgattgggt ttggaacatt ttttgggttt 5160
gtgatatgtc gtagatacaa agggaaatgt ctgaagcatg catggatggg ttccctgctc 5220
atgtactcaa tgt 5233

<210> SEQ ID NO 47
<211> LENGTH: 6024
<212> TYPE: DNA
<213> ORGANISM: Artificial Sequence
<220> FEATURE:
<223> OTHER INFORMATION: Expression construct

<400> SEQUENCE: 47
ctagcatact cgaggtcatt catatgcttg agaagagagt cgggatagtc caaaataaaa 60
caaaggtaag attacctggt caaaagtgaa aacatcagtt aaaaggtggt ataaagtaaa 120

-continued

```
atatcggtaa taaaaggtgg cccaaagtga aatttactct tttctactat tataaaaatt    180
gaggatgttt ttgtcggtac tttgatacgt catttttgta tgaattggtt tttaagttta    240
ttcgcttttg gaaatgcata tctgtatttg agtcgggttt taagttcgtt tgcttttgta    300
aatacagagg gatttgtata agaaatatct ttaaaaaaac ccatatgcta atttgacata    360
atttttgaga aaaatatata ttcaggcgaa ttctcacaat gaacaataat aagattaaaa    420
tagctttccc ccgttgcagc gcatgggtat tttttctagt aaaaataaaa gataaactta    480
gactcaaaac atttacaaaa acaacccta aagttcctaa agcccaaagt gctatccacg    540
atccatagca agcccagccc aacccaaccc aacccaaccc accccagtcc agccaactgg    600
acaatagtct ccacaccccc ccactatcac cgtgagttgt ccgcacgcac cgcacgtctc    660
gcagccaaaa aaaaaaaaaa gaaagaaaaa aaagaaaaag aaaaaacagc aggtgggtcc    720
gggtcgtggg ggccggaaac gcgaggagga tcgcgagcca gcgacgaggc cggccctccc    780
tccgcttcca aagaaacgcc ccccatcgcc actatataca tacccccccc tctcctccca    840
tccccccaac cctaccacca ccaccaccac cacctccacc tcctcccccc tcgctgccgg    900
acgacgagct cctcccccct ccccctccgc cgccgccgcg ccggtaacca ccccgcccct    960
ctcctctttc tttctccgtt ttttttccg tctcggtctc gatctttggc cttggtagtt   1020
tgggtgggcg agaggcggct tcgtgcgcgc ccagatcggt gcgcgggagg ggcgggatct   1080
cgcggctggg gctctcgccg gcgtggatcc ggcccggatc tcgcggggaa tggggctctc   1140
ggatgtagat ctgcgatccg ccgttgttgg gggagatgat ggggggttta aaatttccgc   1200
catgctaaac aagatcagga agaggggaaa agggcactat ggtttatatt tttatatatt   1260
tctgctgctt cgtcaggctt agatgtgcta gatctttctt tcttcttttt gtgggtagaa   1320
tttgaatccc tcagcattgt tcatcggtag tttttctttt catgatttgt gacaaatgca   1380
gcctcgtgcg gagctttttt gtagatggag tccccaagcg ccgtcgtccc cggcaccacg   1440
gcgccgctgc ttccttatgc gtacgcgccg ctgccgtcgt ccgccgacga cgcccgtcaa   1500
aaccggagtg gcgggaggtg gcgcgcgtgc gccgccgtgc tggccgcatc ggcgttggcg   1560
gtggtcgtcg tggtcgggct cctcgcgggc ggcagggtgg atcgggtccc agccggcgga   1620
gacgtggcgt cggccacggt gccggccgtg ccgatggagt tcccgaggag ccggggcaag   1680
gacttcggcg tgtcggagaa gtcctccggt gcctactcca ccgacggcgg gttcccgtgg   1740
agcaacgcca tgctgcagtg gcagcgcacc gggttccatt tccagccgga gcagcactac   1800
atgaacgatc ccaacggccc cgtgtactac ggcggatggt accacctctt ctaccagcac   1860
aaccccaagg gcgacagctg gggcaacatc gcgtgggccc acgccgtctc caaggacatg   1920
gtcaactggc gccacctccc tctcgccatg gttcccgacc agtggtacga cagcaacggc   1980
gtcctcaccg gctccatcac cgtgctcccc gacggccagg tcatcctgct ctacaccggc   2040
aacaccgaca ccctagccca ggtccagtgc ctcgccacgc ccgccgaccc gtccgacccg   2100
ctcctccgcg agtgggtcaa gcacccgcc aaccccatcc tctaccctcc ccccggcatc   2160
ggcctcaagg acttccgcga ccccctcacc gcctggttcg accactccga ccacacctgg   2220
cgcaccgtca tcggctccaa ggacgacgac ggccacgccg gcatcatcct cagctacaag   2280
accaaggact tcgtcaacta cgagctcatg ccggggaaca tgcaccgcgg gcccgacggc   2340
accggaatgt acgagtgcat cgacctctac cccgtcggcg gcaactcgtc cgagatgctc   2400
ggcggcgacg actcgcccgg cgtgctcttc gtgctcaagg agagcagcga cgacgagcgc   2460
cacgactact acgcgctcgg aaggttcgac gccgtcgcca acgtttggac gcccatcgac   2520
```

cgggagctgg accttgggat cgggctcaga tacgactggg gaaagtacta cgcctccaag 2580
tccttctacg accagaagaa gaaccgccgc atcgtatggg catacatcgg cgagaccgac 2640
tccgagcagg ccgacatcac caagggatgg gccaatctca tgacgattcc aagaacggtg 2700
gagcttgaca ggaagacccg cacaaacctc atccaatggc cagtggagga ggtcgacacc 2760
ctccgcagga actccacgga cctcggtcgc atcaccgtca acgccggctc cgtcattcgc 2820
ctccccctcc accagggcgc tcaactcgac atcgaggcct ccttccaact caactcttcc 2880
gacgtggatg ctatcaacga ggccgacgtc ggctacaact gcagcaccag tggtgccgcc 2940
gtacgggggg cgctcggccc ctttggcctc ctcgtccttg ccaacggccg caccgaacag 3000
acggctgtgt acttctacgt gtccaagggc gtcgacggtg ccctccagac ccacttctgc 3060
cacgacgagt cacggtcaac gcgggcaaag gatgtcgtga ataggatgat tggcagcatc 3120
gtgccggtgc ttgacggtga gacctttttcg gtgagggtgc tagtggacca ctccatcgtg 3180
cagagcttcg cgatgggcgg gaggatcacg gcgacgtcgc gggcgtaccc gacggaggcc 3240
atctacgcgg ccgcgggggt ctacctcttc aacaacgcca cgggcgccac cgtcaccgcc 3300
gagaggctcg tcgtgcacga gatggcctca gctgacaacc atatcttcac gaacgacgac 3360
ttgggaggag gaaagcttaa gcttggagga ggagagtcca gcgccgtcgt cgcccaaggc 3420
accacgtcgc cgctgctccc gtacgcctac gcgccgctgc cgtcctctgc cgacgacgcc 3480
cgtgaaaacc agagtagcgg cggcggtgtc aggtggcgcg cgtgcgcggc ctcggccctg 3540
gtggtgctgc tggtcgtcgt cggcttcttc gcgggtggca gggtggatct gggtcaggac 3600
ggcgaggtgt ctgcgacttc ttcggttcct gggagcagca ggggcaagga ttccggcgtg 3660
tcggagaagg agtcgcccgc cgacggcggc ttcccgtgga gcaacgccat gctgcagtgg 3720
cagcacaccg ggttccattt ccagccactc aagcactaca tgaacgatcc caacggtccg 3780
gtctactatg gcggatggta ccacctcttc taccagcaca accccctatgg cgactcgtgg 3840
ggaaacgtat cttggggaca tgccgtgtcc aaggacctgg tgaactggcg ccacctcccg 3900
gtcgccttgg tgcccgatca gtggtacgac atcaacggcg tcctgacggg ctctatcaca 3960
gtgctcccag acgggcgtgt catcctgcta tatacgggga acaccgacac cttttcgcag 4020
gtccagtgcc tcgcagtgcc cgccgaccca tctgacccgc tcctccgtag ctggatcaag 4080
caccccgcca accccatcct cttcccgcca cctgggatcg ggctcaagga cttccgtgac 4140
ccgctcacag cctggttcga acattccgac aacacgtggc gcaccatcat cggatccaag 4200
gatgacgacg gccacgccgg catcgtcctt agctacaaga ccaccgactt tgtgaattat 4260
gagctcatgc cagggaacat gcatcgtggc cccgacggca ccggcatgta cgagtgcctt 4320
gacatctacc ctgtgggcgg caactcatcc gagatgttgg gtggcgactc ctcacctgag 4380
gtgttgttcg tgctcaagga gagcgccaac gacgagtggc acgactacta cgcgcttggg 4440
tggtttgacg ctgccgccaa cacgtggacg ccacaggacc ccgaggcgga ccttgggatc 4500
ggcctcaggt acgactgggg caagtactac gcgtccaagt ccttctacga cccgatcaag 4560
aaccggcgtg tcgtttgggc tttcgtcggc gagaccgact ctgagcaggc cgacaaagcc 4620
aagggatggg cgtccctcat gtcgattccc aggacggtgg agcttgacaa gaagacccgg 4680
acgaacctga tccaatggcc agtggaggag atcgagaccc ttcgcaggaa cgtcacagac 4740
ctcggtggca tcaccgttga agccggctcc gtcattcacc ttcccctcca acaaggcggg 4800
cagcttgaca tcgaggcctc cttccgtctc aactcttcgg acatcgatgc actcaacgag 4860
gccgacgtcg gcttcaactg cagtagcagc gatggggcag ccgtgcgtgg tgcgctcggc 4920
ccctttggcc tcctcgtctt cgccgacggt cgccacgaac agacggcggc gtacttctac 4980
gtgtccaagg gcctcgacgg cagcctcctg acgcactact gccacgacga gtcacggtcg 5040
acgcgagcaa aggacgtcgt gagccgggtg gttggcggca ctgtgccagt gcttgacggt 5100
gaaacctttt cagtgagggt gctagtggac cactccatcg tgcagagctt cgtgatgggt 5160
gggaggacca cggtgacatc gcgggcatac ccgacggagg ccatctacgc cgcggcaggg 5220
gtgtacctgt tcaacaacgc aacgagcgcc accatcaccg ccgaagggct cgtcgtgtac 5280
gagatggcct cggccgagag tcgggccttc ttggctgacg acatgtagaa caataatttt 5340
ctgagcctag tatccatgat catgatatag taagggaaaa atcatatcta taagtttccg 5400
aacttagtga aaaaaaacct gtaaaagata tgcagtcata tacacatgtg aaattaggta 5460
ggaaaatatg ataatctcgt agatgaggaa aaaatattgt acaccaaact attgtaagtt 5520
acagtaatgt aatgtaaaaa aagtttttaa gttacagaag gtacataccg caaataatca 5580
tattatttta ccaagatatt tttttctgga gtattccttt caagtatctt ttatctctag 5640
aatcttctcc aatcatgagt ggcaaccgaa atggagctcc tgtgttgctc cccgtgtctc 5700 accccttcg gccccactgt cattgggtgg acctattctc acggcggctg tcctgagaaa 5760
caaaaatagc agctgaaatg aagacacggc gacacgcaag ccagcatctc tcattgaacc 5820
tgcggagtga gatagctctc gtggcgctgc tctacttgac gcgtttgtct catacaacag 5880
cgcatggctc cttcatgtca ggtccatgat ccacagatgg tatgattggg tttggaacat 5940
tttttgggtt tgtgatatgt cgtagataca aagggaaatg tctgaagcat gcatggatgg 6000
gttccctgct catgtactca atgt 6024

<210> SEQ ID NO 48
<211> LENGTH: 6214
<212> TYPE: DNA
<213> ORGANISM: Artificial Sequence
<220> FEATURE:
<223> OTHER INFORMATION: Expression construct

<400> SEQUENCE: 48
tttagcgaca cacatttagt gacgactgat tgacaaatta tttttcgtct cacaaaaatt 60
ttagtgacga aatatgattt ataaatgacg aaattatttg tccctgataa ttgaatttgt 120
tgtagtgagc cttaggagtt acatatgtta caaggtataa tggaggaata atgaatgaaa 180
ataaagggac acttaagcca ccaatggctt gggagttgct gcatgcacca agaaaattgt 240
aacatataca ccaactccat ttggagtaat gcagcaataa ttgttttcaa cggcaacaat 300
caactgccaa gtcatccatc attatgtaac atatatgaga agtgcaccaa cggccataaa 360
tcaacatcta tgtggccatg caaaaaatgt gaattcttaa attattaaaa tgccacacta 420
acaccataag aacaaatttc atctctgtca taaacatagc atatcagcaa aaaattacag 480
aacctaaata ttgtttcttt cctctctact tttagaatat aatgttgaat acattttatt 540
agagtaatta gtcataatta tcagagttat aactgttgct tatttattct actaagaaga 600
atctattgaa ttctagagat taaatacata tttatcaata aaatatcttt aaagataatg 660
ttcttaacac tcctcaaagc tggataacat tataattatt aaaagaagaa gaaattatga 720
aatgggaaaa agttattttc atagattttt tatttgggag atcttggaga gaatggtgta 780
tttttgggga aggggatttt ttttatttta aaaaactatt ttaattaatt ttcggatatt 840
tgccatccac aaatatgcta ccaataaaga aagaaagaag tacagaactc tcatgaggtg 900

```
gtttctttaa gtagatttag attgcactag ttattggaca agatatttct ttttataaag    960
aaaaagtcaa aaaaatatat gattcaaaac gagccttata aattgttggg taaagtttga   1020
gaggtaaaat tatttatctt taagataatt tttttgaaag aaaaggaggt gagttgaaag   1080
aaatcaaact taaaagggag atttatgtaa ttattgctgt atttttttta atctcttttc   1140
ttctagcata ttctaacttg gtaggtaaac tctgtgactt gacggatttt attgataaaa   1200
gaaaacatat ttcatcgggt ccaatctgag gaacagtttg tcggattttg agagtcaaat   1260
aatttaactt tgacagtaaa tttagacatg aaattttatt ttattttaaa aataaaaatat   1320
acatatttaa acaccatata aaaagtacat ttaagtcaca ataattaata attcaagata   1380
tatgaaaaag tttgcgataa aaaatatact tatttgaatt ctggaattgc cacaaagaaa   1440
ataaatattt tttggtaaag atttagagta ttataattga atgagtagct actcggacca   1500
ctacatgttt aaaacatggc aaggaatatg agtgtgttat cactctataa atagaaggct   1560
tcattagtct agagaactag tcacaagcaa tcaaatggag tccccaagcg ccgtcgtccc   1620
cggcaccacg gcgccgctgc ttccttatgc gtacgcgccg ctgccgtcgt ccgccgacga   1680
cgcccgtcaa aaccggagtg gcgggaggtg gcgcgcgtgc gccgccgtgc tggccgcatc   1740
ggcgttggcg gtggtcgtcg tggtcgggct cctcgcgggc ggcagggtgg atcgggtccc   1800
agccggcgga gacgtggcgt cggccacggt gccggccgtg ccgatggagt tcccgaggag   1860
ccggggcaag gacttcggcg tgtcggagaa gtcctccggt gcctactcca ccgacggcgg   1920
gttcccgtgg agcaacgcca tgctgcagtg gcagcgcacc gggttccatt tccagccgga   1980
gcagcactac atgaacgatc ccaacggccc cgtgtactac ggcggatggt accacctctt   2040
ctaccagcac aaccccaagg gcgacagctg gggcaacatc gcgtgggccc acgccgtctc   2100
caaggacatg gtcaactggc gccacctccc tctcgccatg gttcccgacc agtggtacga   2160
cagcaacggc gtcctcaccg gctccatcac cgtgctcccc gacggccagg tcatcctgct   2220
ctacaccggc aacaccgaca ccctagccca ggtccagtgc ctcgccacgc ccgccgaccc   2280
gtccgacccg ctcctccgcg agtgggtcaa gcaccccgcc aaccccatcc tctaccctcc   2340
ccccggcatc ggcctcaagg acttccgcga ccccctcacc gcctggttcg accactccga   2400
ccacacctgg cgcaccgtca tcggctccaa ggacgacgac ggccacgccg gcatcatcct   2460
cagctacaag accaaggact tcgtcaacta cgagctcatg ccggggaaca tgcaccgcgg   2520
gcccgacggc accggaatgt acgagtgcat cgacctctac cccgtcggcg gcaactcgtc   2580
cgagatgctc ggcggcgacg actcgcccgg cgtgctcttc gtgctcaagg agagcagcga   2640
cgacgagcgc cacgactact acgcgctcgg aaggttcgac gccgtcgcca acgtttggac   2700
gcccatcgac cgggagctgg accttgggat cgggctcaga tacgactggg gaaagtacta   2760
cgcctccaag tccttctacg accagaagaa gaaccgccgc atcgtatggg catacatcgg   2820
cgagaccgac tccgagcagg ccgacatcac caagggatgg gccaatctca tgacgattcc   2880
aagaacggtg gagcttgaca ggaagacccg cacaaacctc atccaatggc cagtggagga   2940
ggtcgacacc ctccgcagga actccacgga cctcggtcgc atcaccgtca acgccggctc   3000
cgtcattcgc ctcccccctcc accagggcgc tcaactcgac atcgaggcct ccttccaact   3060
caactcttcc gacgtggatg ctatcaacga ggccgacgtc ggctacaact gcagcaccag   3120
tggtgccgcc gtacgggggg cgctcggccc ctttggcctc ctcgtccttg ccaacggccg   3180
caccgaacag acggctgtgt acttctacgt gtccaagggc gtcgacggtg ccctccagac   3240
```

-continued

```
ccacttctgc cacgacgagt cacggtcaac gcgggcaaag gatgtcgtga ataggatgat   3300
tggcagcatc gtgccggtgc ttgacggtga gacctttttcg gtgagggtgc tagtggacca   3360
ctccatcgtg cagagcttcg cgatgggcgg gaggatcacg gcgacgtcgc gggcgtaccc   3420
gacggaggcc atctacgcgg ccgcgggggt ctacctcttc aacaacgcca cgggcgccac   3480
cgtcaccgcc gagaggctcg tcgtgcacga gatggcctca gctgacaacc atatcttcac   3540
gaacgacgac ttgggaggag gaaagcttaa gcttggagga ggagagtcca gcgccgtcgt   3600
cgcccaaggc accacgtcgc cgctgctccc gtacgcctac gcgccgctgc cgtcctctgc   3660
cgacgacgcc cgtgaaaacc agagtagcgg cggcggtgtc aggtggcgcg cgtgcgcggc   3720
ctcggccctg gtggtgctgc tggtcgtcgt cggcttcttc gcgggtggca gggtggatct   3780
gggtcaggac ggcgaggtgt ctgcgacttc ttcggttcct gggagcagca ggggcaagga   3840
ttccggcgtg tcggagaagg agtcgcccgc cgacggcggc ttcccgtgga gcaacgccat   3900
gctgcagtgg cagcacaccg ggttccattt ccagccactc aagcactaca tgaacgatcc   3960
caacggtccg gtctactatg gcggatggta ccacctcttc taccagcaca acccctatgg   4020
cgactcgtgg ggaaacgtat cttggggaca tgccgtgtcc aaggacctgg tgaactggcg   4080
ccacctcccg gtcgccttgg tgcccgatca gtggtacgac atcaacggcg tcctgacggg   4140
ctctatcaca gtgctcccag acgggcgtgt catcctgcta tatacgggga acaccgacac   4200
cttttcgcag gtccagtgcc tcgcagtgcc cgccgaccca tctgacccgc tcctccgtag   4260
ctggatcaag caccccgcca accccatcct cttcccgcca cctgggatcg ggctcaagga   4320
cttccgtgac ccgctcacag cctggttcga acattccgac aacacgtggc gcaccatcat   4380
cggatccaag gatgacgacg gccacgccgg catcgtcctt agctacaaga ccaccgactt   4440
tgtgaattat gagctcatgc cagggaacat gcatcgtggc cccgacggca ccggcatgta   4500
cgagtgcctt gacatctacc ctgtgggcgg caactcatcc gagatgttgg gtggcgactc   4560
ctcacctgag gtgttgttcg tgctcaagga gagcgccaac gacgagtggc acgactacta   4620
cgcgcttggg tggtttgacg ctgccgccaa cacgtggacg ccacaggacc ccgaggcgga   4680
ccttgggatc ggcctcaggt acgactgggg caagtactac gcgtccaagt ccttctacga   4740
cccgatcaag aaccggcgtg tcgtttgggc tttcgtcggc gagaccgact ctgagcaggc   4800
cgacaaagcc aagggatggg cgtccctcat gtcgattccc aggacggtgg agcttgacaa   4860
gaagacccgg acgaacctga tccaatggcc agtggaggag atcgagaccc ttcgcaggaa   4920
cgtcacagac ctcggtggca tcaccgttga agccggctcc gtcattcacc ttcccctcca   4980
acaaggcggg cagcttgaca tcgaggcctc cttccgtctc aactcttcgg acatcgatgc   5040
actcaacgag gccgacgtcg gcttcaactg cagtagcagc gatggggcag ccgtgcgtgg   5100
tgcgctcggc ccctttggcc tcctcgtctt cgccgacggt cgccacgaac agacggcggc   5160
gtacttctac gtgtccaagg gcctcgacgg cagcctcctg acgcactact gccacgacga   5220
gtcacggtcg acgcgagcaa aggacgtcgt gagccgggtg gttggcggca ctgtgccagt   5280
gcttgacggt gaaacctttt cagtgagggt gctagtggac cactccatcg tgcagagctt   5340
cgtgatgggt gggaggacca cggtgacatc gcgggcatac ccgacggagg ccatctacgc   5400
cgcggcaggg gtgtacctgt tcaacaacgc aacgagcgcc accatcaccg ccgaagggct   5460
cgtcgtgtac gagatggcct cggccgagag tcgggccttc ttggctgacg acatgtagaa   5520
caataatttt ctgagcctag tatccatgat catgatatag taagggaaaa atcatatcta   5580
taagtttccg aacttagtga aaaaaaacct gtaaaagata tgcagtcata tacacatgtg   5640
```

aaattaggta ggaaaatatg ataatctcgt agatgaggaa aaaatattgt acaccaaact 5700
attgtaagtt acagtaatgt aatgtaaaaa aagtttttaa gttacagaag gtacataccg 5760
caaataatca tattatttta ccaagatatt tttttctgga gtattccttt caagtatctt 5820
ttatctctag aatcttctcc aatcatgagt ggcaaccgaa atggagctcc tgtgttgctc 5880
cccgtgtctc accccctttcg gccccactgt cattgggtgg acctattctc acggcggctg 5940
tcctgagaaa caaaaatagc agctgaaatg aagacacggc gacacgcaag ccagcatctc 6000
tcattgaacc tgcggagtga gatagctctc gtggcgctgc tctacttgac gcgtttgtct 6060
catacaacag cgcatggctc cttcatgtca ggtccatgat ccacagatgg tatgattggg 6120
tttggaacat tttttgggtt tgtgatatgt cgtagataca aagggaaatg tctgaagcat 6180
gcatggatgg gttccctgct catgtactca atgt 6214

<210> SEQ ID NO 49
<211> LENGTH: 5455
<212> TYPE: DNA
<213> ORGANISM: Artificial Sequence
<220> FEATURE:
<223> OTHER INFORMATION: Expression construct

<400> SEQUENCE: 49
aagaatctca aacacggaga tcacaaagtt tgaaagaaaa tttatttctt cgactcaaaa 60
caaacttacg aaatttaggt agaacttata tacattatat tgtaattttt tgtaacaaaa 120
tgtttttatt attattatag aattttactg gttaaattaa aaatgaatag aaaaggtgaa 180
ttaagaggag agaggaggta aacattttct tctatttttt catattttca ggataaatta 240
ttgtaaaagt ttacaagatt tccatttgac tagtgtaaat gaggaatatt ctctagtaag 300
atcattattt catctacttc ttttatcttc taccagtaga ggaataaaca atatttagct 360
cctttgtaaa tacaaattaa ttttcgttct tgacatcatt caattttaat tttacgtata 420
aaataaaaga tcatacctat tagaacgatt aaggagaaat acaattcgaa tgagaaggat 480
gtgccgcttg ttataataaa cagccacacg acgtaaacgt aaaatgacca catgatgggc 540
caatagacat ggaccgacta ctaataatag taagttacat tttaggatgg aataaatatc 600
ataccgacat cagtttgaaa gaaaagggaa aaaaagaaaa aataaataaa agatatacta 660
ccgacatgag ttccaaaaag caaaaaaaaa gatcaagccg acacagacac gcgtagagag 720
caaaatgact ttgacgtcac accacgaaaa cagacgcttc atacgtgtcc ctttatctct 780
ctcagtctct ctataaactt agtgagaccc tcctctgttt tactcacaaa tttaaatgga 840
gtccccaagc gccgtcgtcc ccggcaccac ggcgccgctg cttccttatg cgtacgcgcc 900
gctgccgtcg tccgccgacg acgcccgtca aaaccggagt ggcgggaggt ggcgcgcgtg 960
cgccgccgtg ctggccgcat cggcgttggc ggtggtcgtc gtggtcgggc tcctcgcggg 1020
cggcagggtg gatcgggtcc cagccggcgg agacgtggcg tcggccacgg tgccggccgt 1080
gccgatggag ttcccgagga gccggggcaa ggacttcggc gtgtcggaga agtcctccgg 1140
tgcctactcc accgacggcg ggttcccgtg gagcaacgcc atgctgcagt ggcagcgcac 1200
cgggttccat ttccagccgg agcagcacta catgaacgat cccaacggcc ccgtgtacta 1260
cggcggatgg taccacctct tctaccagca caaccccaag ggcgacagct ggggcaacat 1320
cgcgtgggcc cacgccgtct ccaaggacat ggtcaactgg cgccacctcc ctctcgccat 1380
ggttcccgac cagtggtacg acagcaacgg cgtcctcacc ggctccatca ccgtgctccc 1440

```
cgacggccag gtcatcctgc tctacaccgg caacaccgac accctagccc aggtccagtg   1500
cctcgccacg cccgccgacc cgtccgaccc gctcctccgc gagtgggtca agcaccccgc   1560
caaccccatc ctctaccctc cccccggcat cggcctcaag gacttccgcg accccctcac   1620
cgcctggttc gaccactccg accacacctg gcgcaccgtc atcggctcca aggacgacga   1680
cggccacgcc ggcatcatcc tcagctacaa gaccaaggac ttcgtcaact acgagctcat   1740
gccggggaac atgcaccgcg ggcccgacgg caccggaatg tacgagtgca tcgacctcta   1800
ccccgtcggc ggcaactcgt ccgagatgct cggcggcgac gactcgcccg gcgtgctctt   1860
cgtgctcaag gagagcagcg acgacgagcg ccacgactac tacgcgctcg gaaggttcga   1920
cgccgtcgcc aacgtttgga cgcccatcga ccgggagctg gaccttggga tcgggctcag   1980
atacgactgg ggaaagtact acgcctccaa gtccttctac gaccagaaga agaaccgccg   2040
catcgtatgg gcatacatcg gcgagaccga ctccgagcag gccgacatca ccaagggatg   2100
ggccaatctc atgacgattc caagaacggt ggagcttgac aggaagaccc gcacaaacct   2160
catccaatgg ccagtggagg aggtcgacac cctccgcagg aactccacgg acctcggtcg   2220
catcaccgtc aacgccggct ccgtcattcg cctccccctc caccagggcg ctcaactcga   2280
catcgaggcc tccttccaac tcaactcttc cgacgtggat gctatcaacg aggccgacgt   2340
cggctacaac tgcagcacca gtggtgccgc cgtacggggg gcgctcggcc cctttggcct   2400
cctcgtcctt gccaacggcc gcaccgaaca gacggctgtg tacttctacg tgtccaaggg   2460
cgtcgacggt gccctccaga cccacttctg ccacgacgag tcacggtcaa cgcgggcaaa   2520
ggatgtcgtg aataggatga ttggcagcat cgtgccggtg cttgacggtg agaccttttc   2580
ggtgagggtg ctagtggacc actccatcgt gcagagcttc gcgatgggcg ggaggatcac   2640
ggcgacgtcg cgggcgtacc cgacggaggc catctacgcg gccgcggggg tctacctctt   2700
caacaacgcc acgggcgcca ccgtcaccgc cgagaggctc gtcgtgcacg agatggcctc   2760
agctgacaac catatcttca cgaacgacga cttgggagga ggaaagctta agcttggagg   2820
aggagagtcc agcgccgtcg tcgcccaagg caccacgtcg ccgctgctcc cgtacgccta   2880
cgcgccgctg ccgtcctctg ccgacgacgc ccgtgaaaac cagagtagcg gcggcggtgt   2940
caggtggcgc gcgtgcgcgg cctcggccct ggtggtgctg ctggtcgtcg tcggcttctt   3000
cgcgggtggc agggtggatc tgggtcagga cggcgaggtg tctgcgactt cttcggttcc   3060
tgggagcagc aggggcaagg attccggcgt gtcggagaag gagtcgcccg ccgacggcgg   3120
cttcccgtgg agcaacgcca tgctgcagtg gcagcacacc gggttccatt tccagccact   3180
caagcactac atgaacgatc ccaacggtcc ggtctactat ggcggatggt accacctctt   3240
ctaccagcac aacccctatg gcgactcgtg ggaaacgta tcttggggac atgccgtgtc   3300
caaggacctg gtgaactggc gccacctccc ggtcgccttg gtgcccgatc agtggtacga   3360
catcaacggc gtcctgacgg gctctatcac agtgctccca gacgggcgtg tcatcctgct   3420
atatacgggg aacaccgaca ccttttcgca ggtccagtgc ctcgcagtgc ccgccgaccc   3480
atctgacccg ctcctccgta gctggatcaa gcaccccgcc aaccccatcc tcttcccgcc   3540
acctgggatc gggctcaagg acttccgtga cccgctcaca gcctggttcg aacattccga   3600
caacacgtgg cgcaccatca tcggatccaa ggatgacgac ggccacgccg gcatcgtcct   3660
tagctacaag accaccgact ttgtgaatta tgagctcatg ccagggaaca tgcatcgtgg   3720
ccccgacggc accggcatgt acgagtgcct tgacatctac cctgtgggcg gcaactcatc   3780
cgagatgttg ggtggcgact cctcacctga ggtgttgttc gtgctcaagg agagcgccaa   3840
```

```
cgacgagtgg cacgactact acgcgcttgg gtggtttgac gctgccgcca acacgtggac   3900
gccacaggac cccgaggcgg accttgggat cggcctcagg tacgactggg gcaagtacta   3960
cgcgtccaag tccttctacg acccgatcaa gaaccggcgt gtcgtttggg ctttcgtcgg   4020
cgagaccgac tctgagcagg ccgacaaagc caagggatgg gcgtccctca tgtcgattcc   4080
caggacggtg gagcttgaca agaagacccg gacgaacctg atccaatggc cagtggagga   4140
gatcgagacc cttcgcagga acgtcacaga cctcggtggc atcaccgttg aagccggctc   4200
cgtcattcac cttcccctcc aacaaggcgg gcagcttgac atcgaggcct ccttccgtct   4260
caactcttcg gacatcgatg cactcaacga ggccgacgtc ggcttcaact gcagtagcag   4320
cgatggggca gccgtgcgtg gtgcgctcgg cccctttggc ctcctcgtct tcgccgacgg   4380
tcgccacgaa cagacggcgg cgtacttcta cgtgtccaag ggcctcgacg gcagcctcct   4440
gacgcactac tgccacgacg agtcacggtc gacgcgagca aaggacgtcg tgagccgggt   4500
ggttggcggc actgtgccag tgcttgacgg tgaaaccttt tcagtgaggg tgctagtgga   4560
ccactccatc gtgcagagct tcgtgatggg tgggaggacc acggtgacat cgcgggcata   4620
cccgacggag gccatctacg ccgcggcagg ggtgtacctg ttcaacaacg caacgagcgc   4680
caccatcacc gccgaagggc tcgtcgtgta cgagatggcc tcggccgaga gtcgggcctt   4740
cttggctgac gacatgtaga acaataattt tctgagccta gtatccatga tcatgatata   4800
gtaagggaaa aatcatatct ataagtttcc gaacttagtg aaaaaaaacc tgtaaaagat   4860
atgcagtcat atacacatgt gaaattaggt aggaaaatat gataatctcg tagatgagga   4920
aaaaatattg tacaccaaac tattgtaagt tacagtaatg taatgtaaaa aaagttttta   4980
agttacagaa ggtacatacc gcaaataatc atattatttt accaagatat ttttttctgg   5040
agtattcctt tcaagtatct tttatctcta gaatcttctc caatcatgag tggcaaccga   5100
aatggagctc ctgtgttgct ccccgtgtct cacccctttc ggccccactg tcattgggtg   5160
gacctattct cacggcggct gtcctgagaa acaaaaatag cagctgaaat gaagacacgg   5220
cgacacgcaa gccagcatct ctcattgaac ctgcggagtg agatagctct cgtggcgctg   5280
ctctacttga cgcgtttgtc tcatacaaca gcgcatggct ccttcatgtc aggtccatga   5340
tccacagatg gtatgattgg gtttggaaca tttttgggt ttgtgatatg tcgtagatac   5400
aaagggaaat gtctgaagca tgcatggatg ggttccctgc tcatgtactc aatgt        5455
```

<210> SEQ ID NO 50
<211> LENGTH: 5681
<212> TYPE: DNA
<213> ORGANISM: Artificial Sequence
<220> FEATURE:
<223> OTHER INFORMATION: Expression construct

<400> SEQUENCE: 50

```
aattgttgtc taatcttggt agtagtaatc actacattgg tgcttcacat accagagacc     60
tggattctca aggcagagcc atagtttgat attttggcgt ctccgataag catagattga    120
ctttggtcta gcggtaagag cacctcaagt gaggatctca tgagtcgtct ttctagttcc    180
agcacatggt agcgttttgc accaatggta tttgcaaatt tgttcttata acaatgtcat    240
aatgaaattt tttgaatagg ccccccatca agaaactagg gattgaaaga gagaattgga    300
tctctatttt tacacataag agatttggaa aggtctattg gtttttttcta ttcaatttgt    360
aaatgatcgt acatattgta acgattaaaa caattgaagc atagtttaaa gacttgccaa    420
```

```
aagttgtttc tcctcgagac accatttaga aaatgacaat tgttgtccat caaatatgaa    480
ttaagtttgc ttatgaagcg atttttggga tactttaatg tagtgtgctt tgtctctgct    540
aaaatttgta ccagagacct catgatttc aattgtttca ctgaacacat tacaattgga    600
acttatgctt gataggcaat aaataactga ggtcaaaatt tgaagaccac tttttatatg    660
caatttctta gttatttcac gttgatgtca tctagttcaa atatttttct cccgcgactc    720
tcttaatctt tgtattcaac aaatgaacat ttggacatag tcttacgggg agaagggtgg    780
agagagattg ttttcgaaaa gaaaaaaaaa attcatacgg aaggagcaat aattaaagga    840
aaaagaaaag tagtttgaaa agtgcaaaga aattgctgtg tcttattgga ccactactag    900
gcccacctaa ataaccaatc tataaaggaa acagcccact acccatttcg cacgcacaaa    960
aatcaaattg taggagaaag gaagagaatt ctaaaaaccg ctctcacttt ctctctctag   1020
aaaaacaaaa atctctctct ctctttctct ctctaacatc aatggagtcc ccaagcgccg   1080
tcgtccccgg caccacggcg ccgctgcttc cttatgcgta cgcgccgctg ccgtcgtccg   1140
ccgacgacgc ccgtcaaaac cggagtggcg ggaggtggcg cgcgtgcgcc gccgtgctgg   1200
ccgcatcggc gttggcggtg gtcgtcgtgg tcgggctcct cgcgggcggc agggtggatc   1260
gggtcccagc cggcggagac gtggcgtcgg ccacggtgcc ggccgtgccg atggagttcc   1320
cgaggagccg gggcaaggac ttcggcgtgt cggagaagtc ctccggtgcc tactccaccg   1380
acggcgggtt cccgtggagc aacgccatgc tgcagtggca gcgcaccggg ttccatttcc   1440
agccggagca gcactacatg aacgatccca acggccccgt gtactacggc ggatggtacc   1500
acctcttcta ccagcacaac cccaagggcg acagctgggg caacatcgcg tgggcccacg   1560
ccgtctccaa ggacatggtc aactggcgcc acctccctct cgccatggtt cccgaccagt   1620
ggtacgacag caacggcgtc ctcaccggct ccatcaccgt gctccccgac ggccaggtca   1680
tcctgctcta caccggcaac accgacaccc tagcccaggt ccagtgcctc gccacgcccg   1740
ccgacccgtc cgacccgctc ctccgcgagt gggtcaagca ccccgccaac cccatcctct   1800
accctccccc cggcatcggc ctcaaggact tccgcgaccc cctcaccgcc tggttcgacc   1860
actccgacca cacctggcgc accgtcatcg gctccaagga cgacgacggc cacgccggca   1920
tcatcctcag ctacaagacc aaggacttcg tcaactacga gctcatgccg ggaacatgc   1980
accgcgggcc cgacggcacc ggaatgtacg agtgcatcga cctctacccc gtcggcggca   2040
actcgtccga gatgctcggc ggcgacgact cgcccggcgt gctcttcgtg ctcaaggaga   2100
gcagcgacga cgagcgccac gactactacg cgctcggaag gttcgacgcc gtcgccaacg   2160
tttggacgcc catcgaccgg gagctggacc ttgggatcgg gctcagatac gactggggaa   2220
agtactacgc ctccaagtcc ttctacgacc agaagaagaa ccgccgcatc gtatgggcat   2280
acatcggcga gaccgactcc gagcaggccg acatcaccaa gggatgggcc aatctcatga   2340
cgattccaag aacggtggag cttgacagga agacccgcac aaacctcatc caatggccag   2400
tggaggaggt cgacaccctc cgcaggaact ccacggacct cggtcgcatc accgtcaacg   2460
ccggctccgt cattcgcctc cccctccacc agggcgctca actcgacatc gaggcctcct   2520
tccaactcaa ctcttccgac gtggatgcta tcaacgaggc cgacgtcggc tacaactgca   2580
gcaccagtgg tgccgccgta cggggggcgc tcggcccctt tggcctcctc gtccttgcca   2640
acggccgcac cgaacagacg gctgtgtact tctacgtgtc caagggcgtc gacggtgccc   2700
tccagaccca cttctgccac gacgagtcac ggtcaacgcg ggcaaaggat gtcgtgaata   2760
ggatgattgg cagcatcgtg ccggtgcttg acggtgagac cttttcggtg agggtgctag   2820
```

-continued

```
tggaccactc catcgtgcag agcttcgcga tgggcgggag gatcacggcg acgtcgcggg   2880
cgtacccgac ggaggccatc tacgcggccg cgggggtcta cctcttcaac aacgccacgg   2940
gcgccaccgt caccgccgag aggctcgtcg tgcacgagat ggcctcagct gacaaccata   3000
tcttcacgaa cgacgacttg ggaggaggaa agcttaagct tggaggagga gagtccagcg   3060
ccgtcgtcgc ccaaggcacc acgtcgccgc tgctcccgta cgcctacgcg ccgctgccgt   3120
cctctgccga cgacgcccgt gaaaaccaga gtagcggcgg cggtgtcagg tggcgcgcgt   3180
gcgcggcctc ggccctggtg gtgctgctgg tcgtcgtcgg cttcttcgcg ggtggcaggg   3240
tggatctggg tcaggacggc gaggtgtctg cgacttcttc ggttcctggg agcagcaggg   3300
gcaaggattc cggcgtgtcg gagaaggagt cgcccgccga cggcggcttc ccgtggagca   3360
acgccatgct gcagtggcag cacaccgggt tccatttcca gccactcaag cactacatga   3420
acgatcccaa cggtccggtc tactatggcg gatggtacca cctcttctac cagcacaacc   3480
cctatggcga ctcgtgggga aacgtatctt ggggacatgc cgtgtccaag gacctggtga   3540
actggcgcca cctcccggtc gccttggtgc ccgatcagtg gtacgacatc aacggcgtcc   3600
tgacgggctc tatcacagtg ctcccagacg ggcgtgtcat cctgctatat acggggaaca   3660
ccgacacctt ttcgcaggtc cagtgcctcg cagtgcccgc cgacccatct gacccgctcc   3720
tccgtagctg gatcaagcac cccgccaacc ccatcctctt cccgccacct gggatcgggc   3780
tcaaggactt ccgtgacccg ctcacagcct ggttcgaaca ttccgacaac acgtggcgca   3840
ccatcatcgg atccaaggat gacgacggcc acgccggcat cgtccttagc tacaagacca   3900
ccgactttgt gaattatgag ctcatgccag ggaacatgca tcgtggcccc gacggcaccg   3960
gcatgtacga gtgccttgac atctaccctg tgggcggcaa ctcatccgag atgttgggtg   4020
gcgactcctc acctgaggtg ttgttcgtgc tcaaggagag cgccaacgac gagtggcacg   4080
actactacgc gcttgggtgg tttgacgctg ccgccaacac gtggacgcca caggaccccg   4140
aggcggacct tgggatcggc ctcaggtacg actggggcaa gtactacgcg tccaagtcct   4200
tctacgaccc gatcaagaac cggcgtgtcg tttgggcttt cgtcggcgag accgactctg   4260
agcaggccga caaagccaag ggatgggcgt ccctcatgtc gattcccagg acggtggagc   4320
ttgacaagaa gacccggacg aacctgatcc aatggccagt ggaggagatc gagacccttc   4380
gcaggaacgt cacagacctc ggtggcatca ccgttgaagc cggctccgtc attcaccttc   4440
ccctccaaca aggcgggcag cttgacatcg aggcctcctt ccgtctcaac tcttcggaca   4500
tcgatgcact caacgaggcc gacgtcggct tcaactgcag tagcagcgat ggggcagccg   4560
tgcgtggtgc gctcggcccc tttggcctcc tcgtcttcgc cgacggtcgc cacgaacaga   4620
cggcggcgta cttctacgtg tccaagggcc tcgacggcag cctcctgacg cactactgcc   4680
acgacgagtc acggtcgacg cgagcaaagg acgtcgtgag ccgggtggtt ggcggcactg   4740
tgccagtgct tgacggtgaa acctttttcag tgagggtgct agtggaccac tccatcgtgc   4800
agagcttcgt gatgggtggg aggaccacgg tgacatcgcg ggcataccccg acggaggcca   4860
tctacgccgc ggcaggggtg tacctgttca acaacgcaac gagcgccacc atcaccgccg   4920
aagggctcgt cgtgtacgag atggcctcgg ccgagagtcg ggccttcttg gctgacgaca   4980
tgtagaacaa taattttctg agcctagtat ccatgatcat gatatagtaa gggaaaaatc   5040
atatctataa gtttccgaac ttagtgaaaa aaaacctgta aaagatatgc agtcatatac   5100
acatgtgaaa ttaggtagga aaatatgata atctcgtaga tgaggaaaaa atattgtaca   5160
```

-continued

```
ccaaactatt gtaagttaca gtaatgtaat gtaaaaaaag tttttaagtt acagaaggta   5220

cataccgcaa ataatcatat tattttacca agatattttt ttctggagta ttcctttcaa   5280

gtatctttta tctctagaat cttctccaat catgagtggc aaccgaaatg gagctcctgt   5340

gttgctcccc gtgtctcacc cctttcggcc ccactgtcat tgggtggacc tattctcacg   5400

gcggctgtcc tgagaaacaa aaatagcagc tgaaatgaag acacggcgac acgcaagcca   5460

gcatctctca ttgaacctgc ggagtgagat agctctcgtg gcgctgctct acttgacgcg   5520

tttgtctcat acaacagcgc atggctcctt catgtcaggt ccatgatcca cagatggtat   5580

gattgggttt ggaacatttt ttgggtttgt gatatgtcgt agatacaaag ggaaatgtct   5640

gaagcatgca tggatgggtt ccctgctcat gtactcaatg t                       5681
```

<210> SEQ ID NO 51
<211> LENGTH: 52
<212> TYPE: DNA
<213> ORGANISM: Artificial Sequence
<220> FEATURE:
<223> OTHER INFORMATION: Primer sequence

<400> SEQUENCE: 51

```
ggggacaagt ttgtacaaaa aagcaggctt catggagtcc ccaagcgccg tc             52
```

<210> SEQ ID NO 52
<211> LENGTH: 35
<212> TYPE: DNA
<213> ORGANISM: Artificial Sequence
<220> FEATURE:
<223> OTHER INFORMATION: Primer sequence

<400> SEQUENCE: 52

```
tctaagcctt tcctcctccc aagtcgtcgt tcgtg                                35
```

<210> SEQ ID NO 53
<211> LENGTH: 31
<212> TYPE: DNA
<213> ORGANISM: Artificial Sequence
<220> FEATURE:
<223> OTHER INFORMATION: Primer sequence

<400> SEQUENCE: 53

```
actaagcttg gaggaggaga gtccagcgcc g                                    31
```

<210> SEQ ID NO 54
<211> LENGTH: 55
<212> TYPE: DNA
<213> ORGANISM: Artificial Sequence
<220> FEATURE:
<223> OTHER INFORMATION: Primer sequence

<400> SEQUENCE: 54

```
ggggaccact ttgtacaaga aagctgggtc ctacatgtcg tcagccaaga aggcc          55
```

<210> SEQ ID NO 55
<211> LENGTH: 44
<212> TYPE: DNA

<213> ORGANISM: Artificial Sequence
<220> FEATURE:
<223> OTHER INFORMATION: Primer sequence

<400> SEQUENCE: 55
ggggacaagt ttgtacaaaa aagcaggctt cgagtccagc gccg 44

<210> SEQ ID NO 56
<211> LENGTH: 44
<212> TYPE: DNA
<213> ORGANISM: Artificial Sequence
<220> FEATURE:
<223> OTHER INFORMATION: Primer sequence

<400> SEQUENCE: 56
tctaagcctt tcctcctccc tacatgtcgt cagccaagaa ggcc 44

<210> SEQ ID NO 57
<211> LENGTH: 39
<212> TYPE: DNA
<213> ORGANISM: Artificial Sequence
<220> FEATURE:
<223> OTHER INFORMATION: Primer sequence

<400> SEQUENCE: 57
actaagcttg gaggaggaat ggagtcccca agcgccgtc 39

<210> SEQ ID NO 58
<211> LENGTH: 46
<212> TYPE: DNA
<213> ORGANISM: Artificial Sequence
<220> FEATURE:
<223> OTHER INFORMATION: Primer sequence

<400> SEQUENCE: 58
ggggaccact ttgtacaaga aagctgggtc caagtcgtcg ttcgtg 46

<210> SEQ ID NO 59
<211> LENGTH: 23
<212> TYPE: PRT
<213> ORGANISM: Artificial Sequence
<220> FEATURE:
<223> OTHER INFORMATION: Transmembrane sequence

<400> SEQUENCE: 59

Pro Ser Ala Val Val Pro Gly Thr Thr Ala Pro Leu Leu Pro Tyr Ala
1 5 10 15

Tyr Ala Pro Leu Pro Ser Ser
20

<210> SEQ ID NO 60
<211> LENGTH: 23
<212> TYPE: PRT
<213> ORGANISM: Artificial Sequence
<220> FEATURE:
<223> OTHER INFORMATION: Transmembrane sequence

<400> SEQUENCE: 60

Ala Cys Ala Ala Val Leu Ala Ala Ser Ala Leu Ser Val Val Val Val
1 5 10 15

Val Gly Leu Leu Ala Gly Gly
20

<210> SEQ ID NO 61
<211> LENGTH: 23

-continued

```
<212> TYPE: PRT
<213> ORGANISM: Artificial Sequence
<220> FEATURE:
<223> OTHER INFORMATION: Transmembrane sequence

<400> SEQUENCE: 61

Ala Cys Ala Ala Ser Ala Leu Val Val Leu Leu Val Val Val Gly Phe
1               5                   10                  15

Phe Ala Gly Gly Arg Val Asp
            20
```

MODIFICATION OF FRUCTAN BIOSYNTHESIS, INCREASING PLANT BIOMASS, AND ENHANCING PRODUCTIVITY OF BIOCHEMICAL PATHWAYS IN A PLANT

FIELD OF THE INVENTION

The present invention relates to the modification of fructan biosynthesis in plants and, more particularly, to methods of manipulating fructan biosynthesis in photosynthetic cells, and to related nucleic acids and constructs.

The present invention also relates to increasing plant biomass and, more particularly, to methods of enhancing biomass yield and/or yield stability, including shoot and/or root growth in a plant, and to related nucleic acids and constructs.

The present invention also relates to methods of enhancing the productivity of biochemical pathways and, more particularly, to fusion proteins in plants, and to related nucleic acids and constructs.

BACKGROUND OF THE INVENTION

Fructans are a type of water-soluble carbohydrate whose primary function is to provide a readily accessible energy reserve for plant growth. Fructans are associated with various advantageous characters in grasses, such as cold and drought tolerance, increased tiller survival, enhanced persistence, good regrowth after cutting or grazing, improved recovery from stress, early spring growth and increased nutritional quality.

Figure 6:
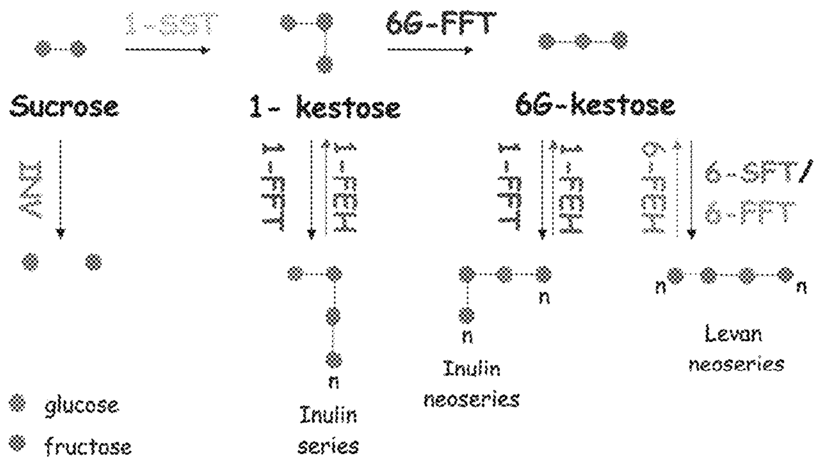

Fructan synthesis and metabolism in grasses and cereals is complex. Fructans consist of linear or branched fructose chains attached to sucrose. The chain length of plant fructans ranges from three up to a few hundred fructose units. Different types of fructans can be distinguished based on the linkage types present. In perennial ryegrass three types of fructans have been identified: inulins, inulin neoseries and levan neoseries, with four fructosyltransferse (FT) enzymes involved in this fructan profile (FIG. 6). The enzyme 1-SST (sucrose: sucrose 1-fructosyltransferase) catalyses the first step in fructan biosynthesis while the remaining enzymes elongate the growing fructose chain (1-FFT: fructan: fructan 1-fructosyltransferase, 6G-FFT: 6-glucose fructosyltransferase, and 6-SFT: sucrose: fructose 6-fructosyltransferase). The enzymes 1-FEH or 6-FEH (fructoexohydrolase) reduce fructan chain length by releasing fructose molecules.

Fructans represent the major non-structural carbohydrate in 15% of plant species and play a key role in forage quality. Ruminant livestock grazing on high fructan diets show improved animal performance.

In grasses the level and composition of fructans has been increased in stems and leaf sheaths through the engineered expression of fructosyltransferase (FT) genes.

However, manipulating biochemical pathways by manipulating the activity of enzymes in the pathways may be difficult because of the ways in which the various enzymes and their substrates may interact.

Thus, it would be desirable to have improved methods of manipulating biochemical pathways, particularly in plants. For example, it would be desirable to have methods of manipulating fructan biosynthesis in plants, including grass species such as *Lolium* and *Festuca* and cereals such as wheat and maize, thereby facilitating the production of eg. forage grasses with improved herbage quality, leading to improved pasture production, improved animal production and reduced environmental pollution, bioenergy grasses with enhanced biomass yield e.g. for bioethanol production, and eg. cereals with increased grain and biomass yield.

Nucleic acid sequences encoding some of the enzymes involved in the fructan biosynthetic pathway have been isolated for certain species of plants. For example, PCT/AU01/00705 to the present applicants, describes fructosyltransferase homologues from *Lolium* and *Festuca*. However, there remains a need for materials useful in the modification of fructan biosynthesis in plants, and also to engineer fructan accumulation in different parts of the plant.

It is an object of the present invention to overcome, or at least alleviate, one or more of the difficulties or deficiencies associated with the prior art.

SUMMARY OF THE INVENTION

Applicants have found that it is possible to nutritionally enhance plants eg. forage grasses and/or to increase plant biomass by spatial reprogramming of the fructan-biosynthesis pathway in photosynthetic cells. Using this process it is possible to drive fructan accumulation in leaf blades, the plant organs that are primarily grazed by livestock, and which may not normally accumulate fructans. Thus, accumulation of fructans, especially those exhibiting a high degree of polymerization ('high DP fructans'), provides more accessible nutrition for grazing animals. Fructans accumulate in the stems and leaf sheaths, with leaf fructans only forming during periods where $CO_2$ assimilation outperforms growth. Forage grasses may be nutritionally enhanced by expressing fructan genes in photosynthetic cells where sucrose is synthesised, thus driving fructan accumulation preferentially in leaf blades and providing more energy to grazing livestock.

Fructans in forage grasses contribute significantly to the readily available energy in the feed for grazing ruminant animals. The fermentation processes in the rumen require considerable readily available energy. The improvement of the readily available energy in the rumen can increase the efficiency of rumen digestion. An increased efficiency in rumen digestion leads to an improved conversion of the forage protein fed to the ruminant animal into milk or meat, and to a reduction in nitrogenous waste.

Applicants have also found that reprogramming photosynthetic cells for extended life, for example by delaying leaf senescence, helps increase plant biomass.

Applicants have also found that it is possible to enhance the productivity of a biochemical pathway by co-ordinating enzymatic activity in the pathway by means of a genetic construct encoding a fusion, more preferably a translational fusion, of two or more enzymes from the pathway.

While applicant does not wish to be restricted by theory, it is thought that by bringing two enzymes in a pathway into close proximity, for example by expressing a translational fusion, expression of the individual enzymes may be coordinated thereby improving the efficiency of the pathway.

For example, by expressing a translational fusion of two or more FT genes (e.g. Lp1-SST and Lp6G-FFT), problems associated with differences in the expression patterns of these genes independently integrated into the plant genome may be alleviated, resulting in conversion of the sucrose molecules directly to fructans, those exhibiting a low degree of polymerisation ('low DP fructans') and a high degree of polymerization ('high DP fructans'). Furthermore, the FT proteins may physically associate with each other to form a metabolic channel for the efficient biosynthesis of fructans.

Furthermore, expression of FT genes in photosynthetic cells leading to the accumulation of low and high DP fructans in photosynthetic cells may lead to a release from inhibition mechanisms of photosynthesis, facilitating solar energy capture and increased $CO_2$ fixation.

Thus, applicants have found that reprogramming photosynthetic cells for extended life and enhanced fructan biosynthesis facilitates solar energy capture and increases plant biomass production including shoot and/or root growth.

Furthermore, since accumulation of low and high DP fructans has been associated with plants' tolerance to abiotic stress such as cold and drought; and since enhanced root growth and/or delayed leaf senescence has also been implicated in plants' tolerance of drought stress, reprogramming photosynthetic cells for extended life and/or enhanced fructan biosynthesis may facilitate yield stability and/or plants' tolerance of abiotic stresses.

Accordingly, in one aspect, the present invention provides a method of manipulating fructan biosynthesis in photosynthetic cells of a plant, said method including introducing into said plant an effective amount of a genetic construct including a promoter, or a functionally active fragment or variant thereof, operatively linked to nucleic acids encoding one or more fructan biosynthetic enzymes, or functionally active fragments or variants thereof.

By 'manipulating fructan biosynthesis' is generally meant increasing fructan biosynthesis in a transformed plant relative to an untransformed control plant. However, for some applications it may be desirable to reduce or otherwise modify fructan biosynthesis in the transformed plant relative to the untransformed control plant. For example, it may be desirable to increase or decrease the activity of certain enzymes in the fructan biosynthetic pathway, in the transformed plant relative to the untransformed control plant.

By 'photosynthetic cells' is meant those cells of a plant in which photosynthesis takes place. Such cells generally contain the pigment chlorophyll and are otherwise known as green cells. Most photosynthetic cells are contained in the leaves of plants. Preferably, the genetic construct of the present invention is expressed in bundle sheath cells, more preferably in mesophyll and/or parenchymatous bundle sheath cells.

By 'an effective amount' is meant an amount sufficient to result in an identifiable phenotypic trait in said plant, or in a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor, the entire disclosure of which is incorporated herein by reference.

By 'genetic construct' is meant a recombinant nucleic acid molecule.

By a 'promoter' is meant a nucleic acid sequence sufficient to direct transcription of an operatively linked nucleic acid sequence.

By 'operatively linked' is meant that the nucleic acid(s) and a regulatory sequence, such as a promoter, are linked in such a way as to permit expression of said nucleic acid under appropriate conditions, for example when appropriate molecules such as transcriptional activator proteins are bound to the regulatory sequence. Preferably an operatively linked promoter is upstream of the associated nucleic acid.

By 'upstream' is meant in the 3' to 5' direction along the nucleic acid.

By 'nucleic acid' is meant a chain of nucleotides capable of carrying genetic information. The term generally refers to genes or functionally active fragments or variants thereof and/or other sequences in the genome of the organism that influence its phenotype. The term 'nucleic acid' includes DNA (such as cDNA or genomic DNA) and RNA (such as mRNA or microRNA) that is single- or double-stranded, optionally containing synthetic, non-natural or altered nucleotide bases, synthetic nucleic acids and combinations thereof.

By a 'nucleic acid encoding a fructan biosynthetic enzyme' is meant a nucleic acid encoding an enzyme of the fructan biosynthetic pathway in plants, for example fructosyltransferases such as sucrose:sucrose 1-fructosyltransferase (1-SST); fructan:fructan 1-fructosyltransferase (1-FFT); sucrose:fructan 6-fructosyltransferase (6-SFT); and fructan: fructan 6G-fructosyl transferase (6G-FFT); and fructoexohydrolases such as 1-fructoexohydrolase (1-FEH) and 6-fructoexohydrolase (6-FEH).

By 'functionally active fragment or variant' in relation to a promoter is meant that the fragment or variant (such as an analogue, derivative or mutant) is capable of directing transcription of an operatively linked nucleic acid. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence to which the fragment or variant corresponds, more preferably at least approximately 90% identity, even more preferably at least approximately 95% identity, most preferably at least approximately 98% identity. Preferably the fragment has a size of at least 20 nucleotides, more preferably at least 50 nucleotides, more preferably at least 100 nucleotides, more preferably at least 200 nucleotides, more preferably at least 300 nucleotides.

By 'functionally active' in relation to the nucleic acid encoding a fructan biosynthetic enzyme is meant that the fragment or variant (such as an analogue, derivative or mutant) is capable of manipulating fructan biosynthesis in a plant by the method of the present invention, for example by being translated into an enzyme that is able to participate in the fructan biosynthetic pathway. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence to which the fragment or variant corresponds, more preferably at least approximately 90% identity, even more preferably at least approximately 95% identity, most preferably at least approximately 98% identity. Such functionally active variants and fragments include, for example, those having conservative nucleic acid changes.

By 'conservative nucleic acid changes' is meant nucleic acid substitutions that result in conservation of the amino acid in the encoded protein, due to the degeneracy of the genetic code. Such functionally active variants and fragments also include, for example, those having nucleic acid changes which result in conservative amino acid substitutions of one or more residues in the corresponding amino acid sequence.

By 'conservative amino acid substitutions' is meant the substitution of an amino acid by another one of the same class, the classes being as follows:

Nonpolar: Ala, Val, Leu, Ile, Pro, Met Phe, Trp
Uncharged polar: Gly, Ser, Thr, Cys, Tyr, Asn, Gln
Acidic: Asp, Glu
Basic: Lys, Arg, His Other conservative amino acid substitutions may also be made as follows:

Aromatic: Phe, Tyr, His
Proton Donor Asn, Gln, Lys, Arg, His, Trp
Proton Acceptor: Glu, Asp, Thr, Ser, Tyr, Asn, Gln Particularly preferred fragments and variants include one or more conserved sucrose binding/hydrolysis domains. Examples of such domains are shown in FIGS. 17, 18 and 36 hereto, for example (N/S)DP(N)G, FRDP and EC(I)D.

Figure 17A:
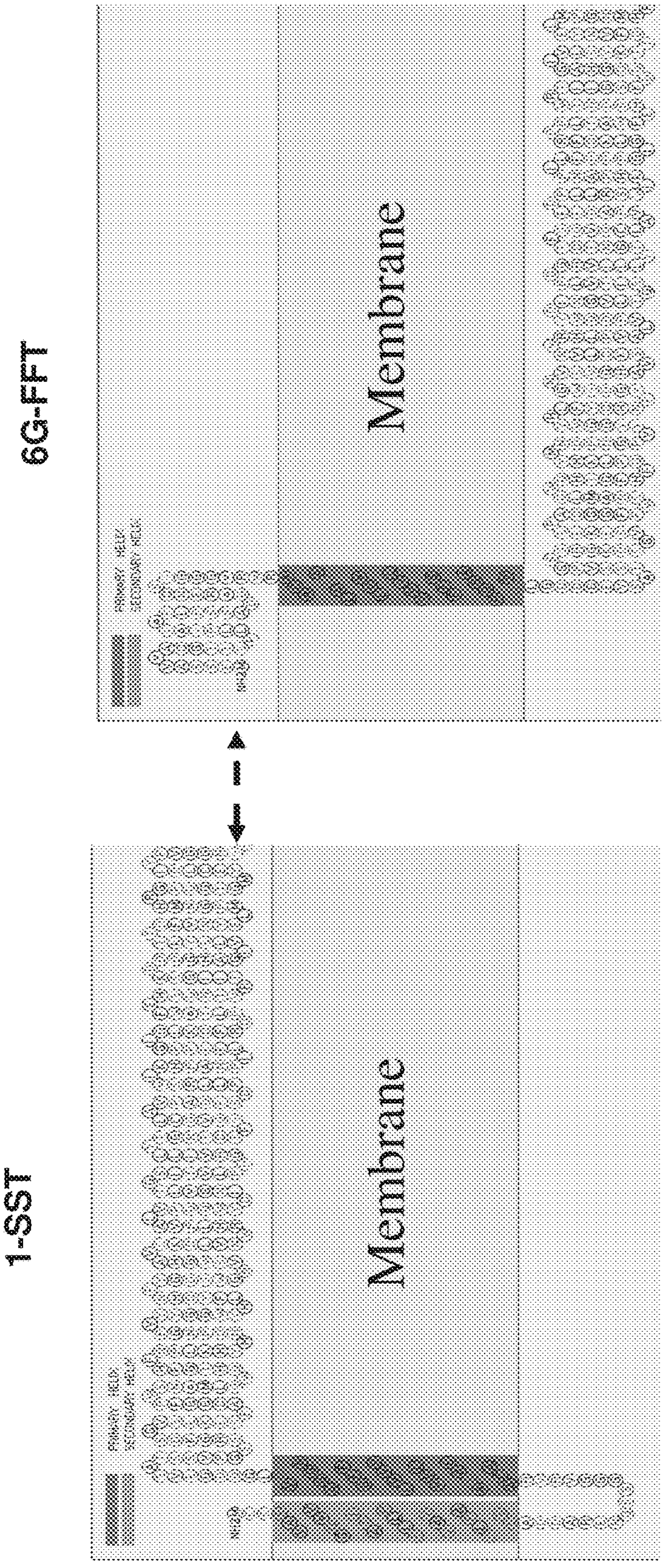
Figure 17B:
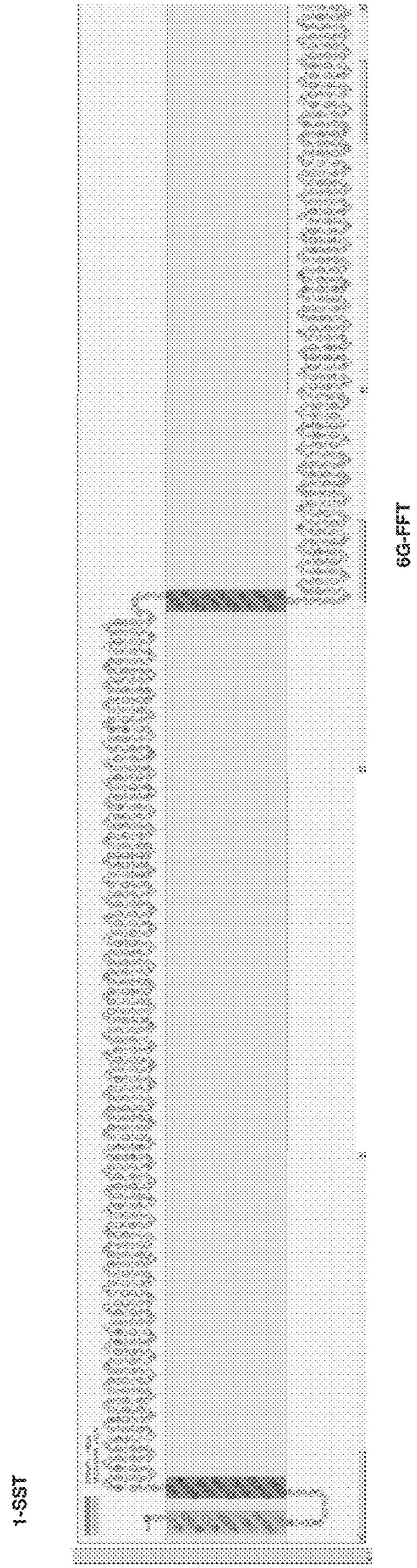
Figure 17C:
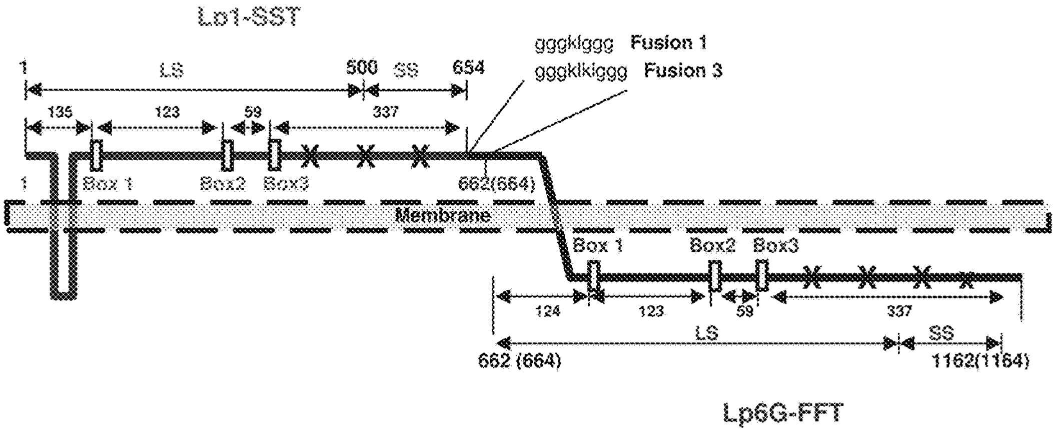
Figure 18:
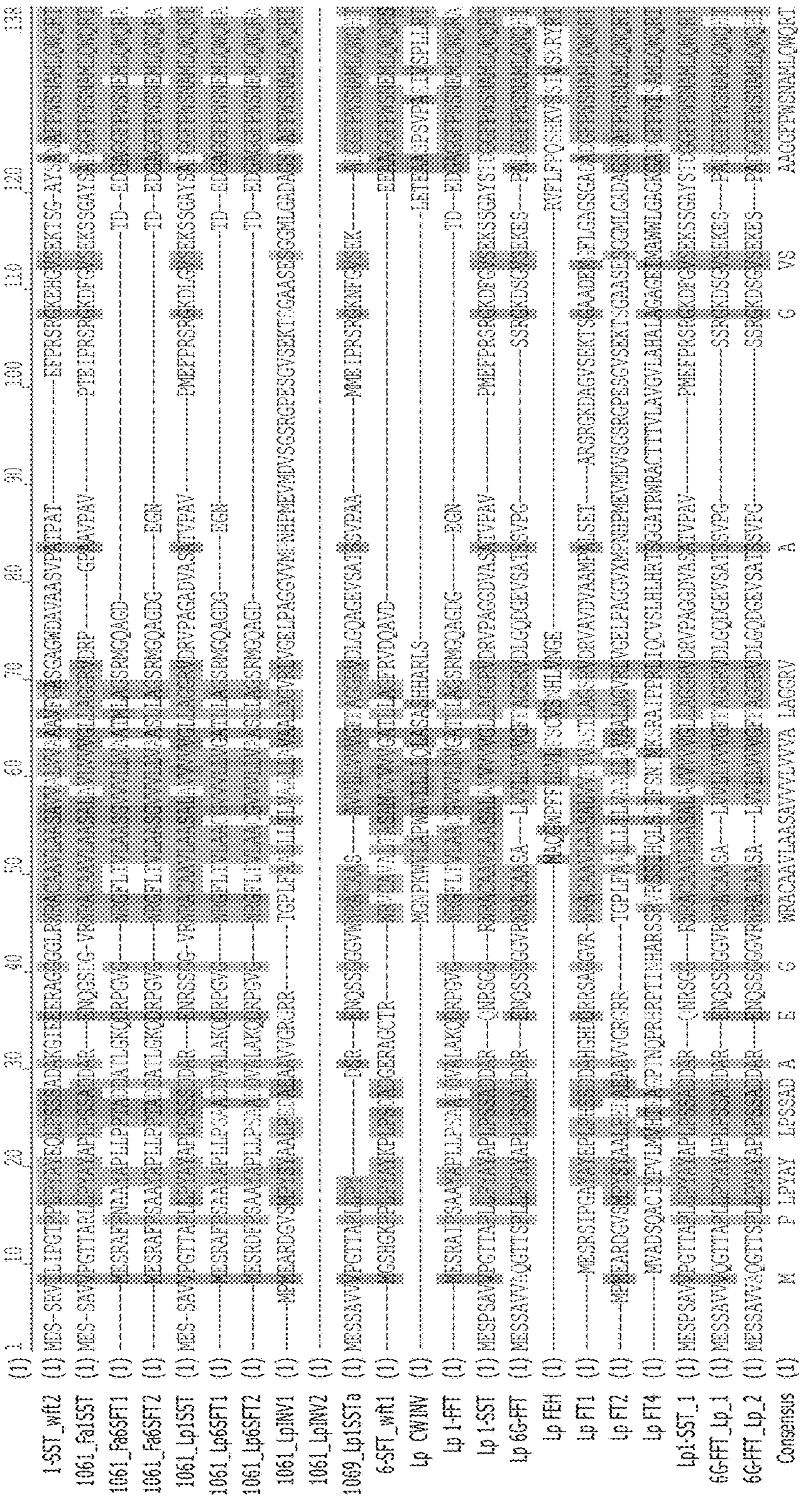
Figure 18:
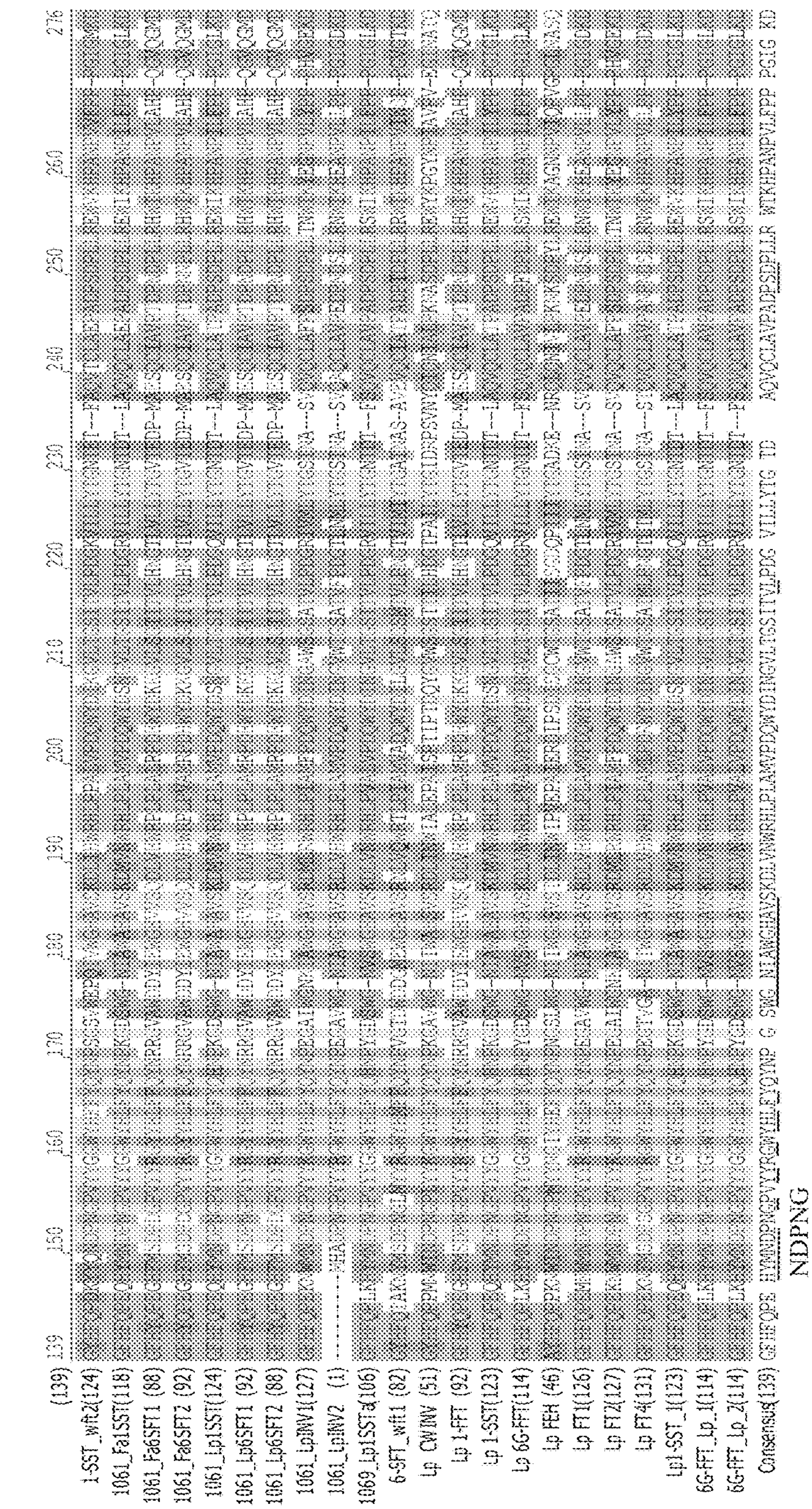
Figure 18:
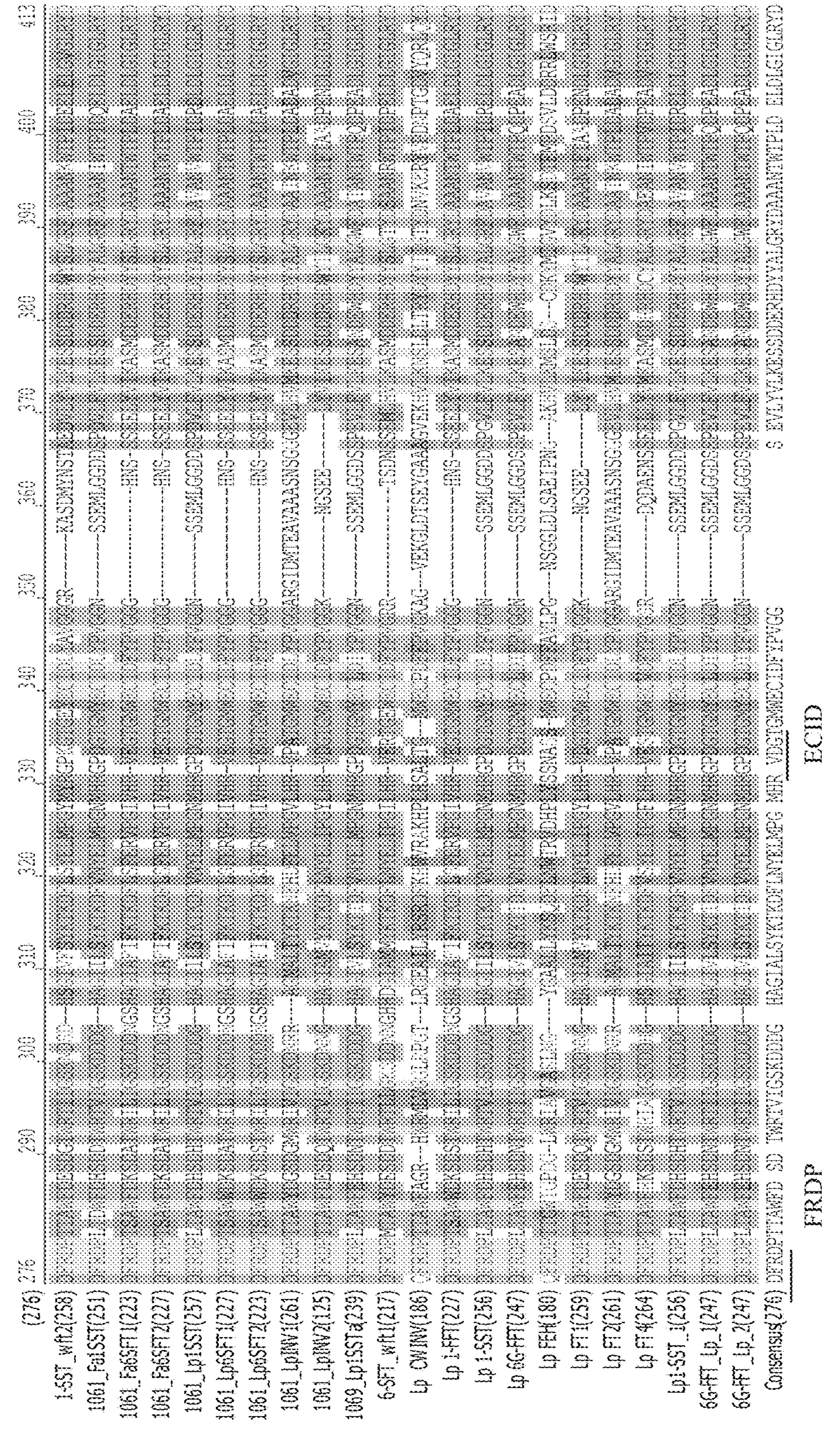
Figure 18:
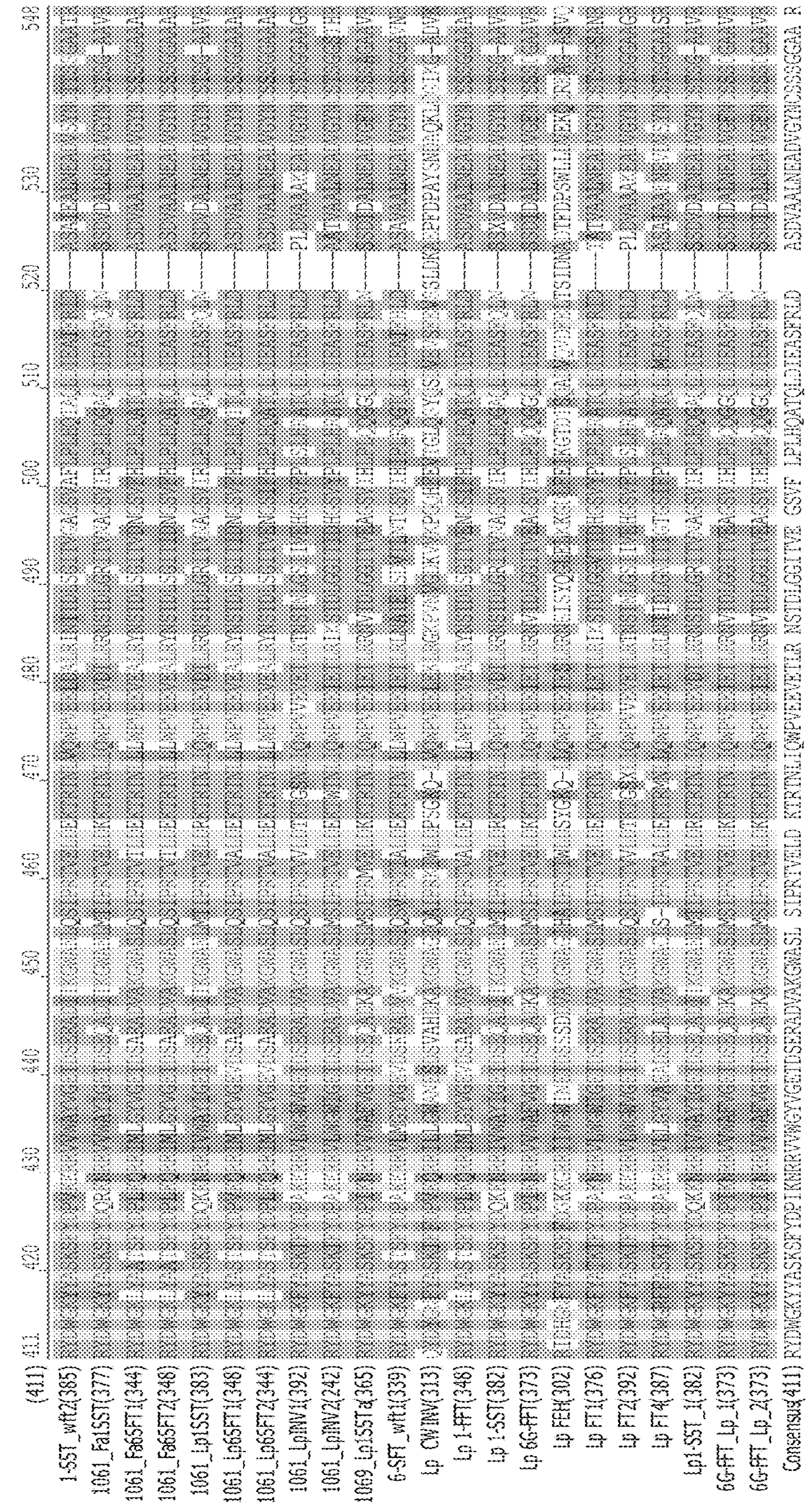
Figure 18:
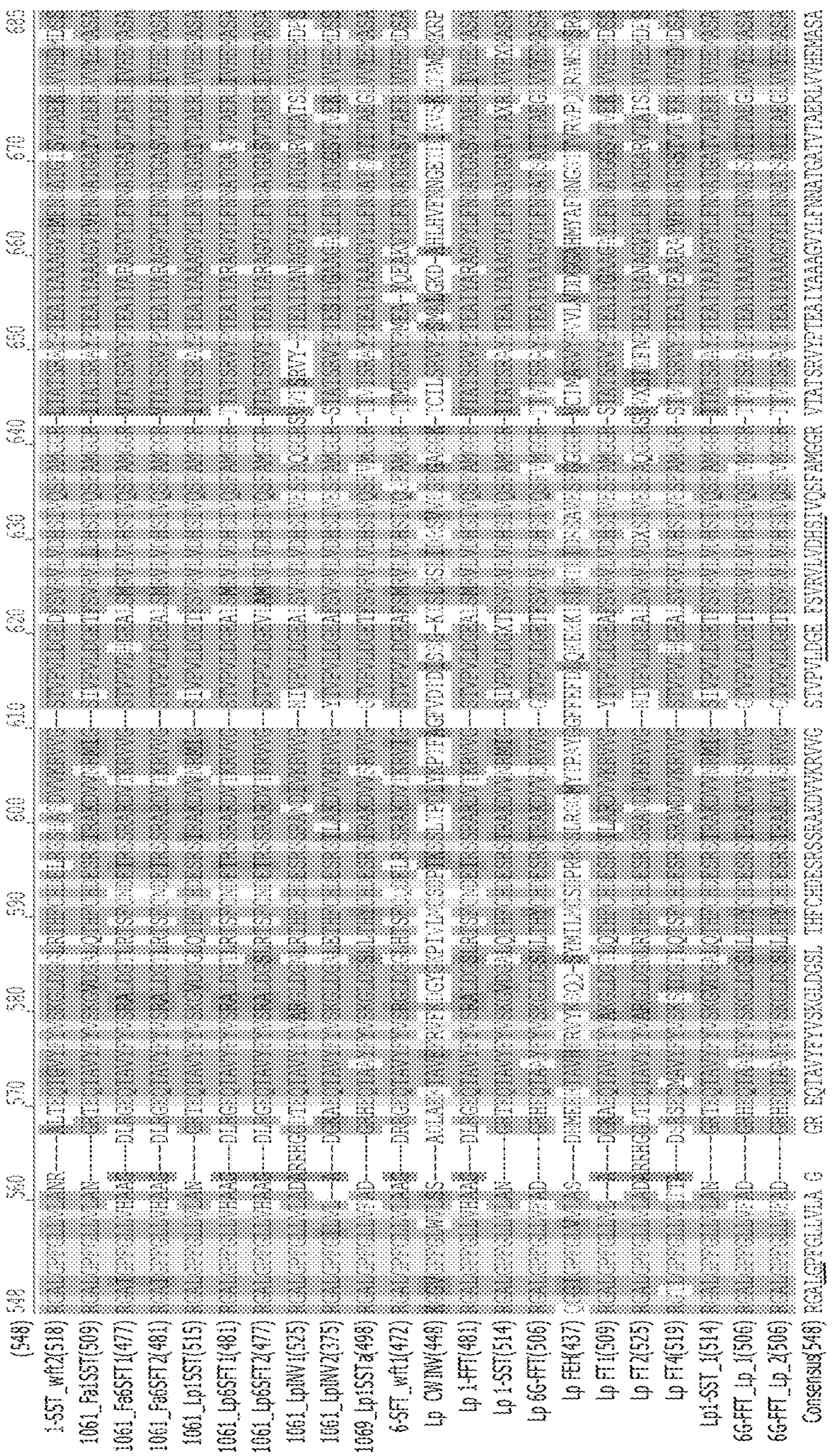

Particularly preferred fragments and variants may also include one or more conserved amino acid domains found in *Lolium* FT, invertase and FEH sequences, for example as shown in FIGS. 17, 18 and 36 hereto.

Preferably the fragment has a size of at least 20 nucleotides, more preferably at least 50 nucleotides, more preferably at least 100 nucleotides, more preferably at least 200 nucleotides, more preferably at least 500 nucleotides.

Preferably, the nucleic acid encoding one or more fructan biosynthetic enzymes is selected from the group consisting of genes encoding 1-SST, 1-FFT, 6-SFT and 6G-FFT, combinations thereof, and functionally active fragments and variants thereof. Preferably, the nucleic acid encodes a FT fusion protein of two or more of these fructan biosynthetic enzymes.

Even more preferably the nucleic acid encoding one or more fructan biosynthetic enzymes encodes 1-SST and/or 6G-FFT, even more preferably a FT fusion protein of 1-SST and 6G-FFT, or functionally active fragments or variants thereof.

Preferably, the nucleic acid encoding one or more fructan biosynthetib enzymes is isolated from or corresponds to a gene or genes from a species of interest. More preferably the gene or genes are from a ryegrass, fescue or wheat species, including Italian or annual ryegrass, perennial ryegrass, tall fescue, meadow fescue, red fescue, bread wheat and durum wheat. Even more preferably, the nucleic acid encoding one or more fructan biosynthetic enzymes is isolated from or corresponds to a gene from a *Lolium* species such as *Lolium perenne* or *Lolium arundinaceum.*

Suitable nucleic acids encoding fructan biosynthetic enzymes are described in PCT/AU01/00705 and PCT/AU01/01275, the entire disclosures of which are incorporated herein by reference.

In a particularly preferred embodiment the nucleic acid encoding 1-SST includes a sequence selected from the group consisting of the sequence shown in SEQ ID NO: 11 of PCT/AU01/00705; and the nucleotide sequences encoding the polypeptide sequence shown in SEQ ID NO: 12 of PCT/AU01/00705; and functionally active fragments and variants thereof.

In a particularly preferred embodiment the nucleic acid encoding the 6G-FFT includes a sequence selected from the group consisting of the sequences shown in SEQ ID NO: 110 of PCT/AU01/01275, and FIG. 7 hereto; and the nucleic acid sequences encoding the polypeptide sequences shown in SEQ ID NO: 111 of PCT/AU01/01275; and FIG. 8 hereto; and functionally active fragments and variants thereof.

In a particularly preferred embodiment, the nucleic acid encoding the 1-FFT includes a sequence selected from the group consisting of the sequences shown in SEQ ID NO: 3 of PCT/AU01/00705, SEQ ID NOS: 103 and 105-109 of PCT/AU01/01275 and FIG. 9 hereto; and the nucleotide sequences encoding the polypeptide sequences shown in SEQ ID No: 4 of PCT/AU01/00705, SEQ ID NO: 104 of PCT/AU01/01275 and FIG. 10 hereto; and functionally active fragments and variants thereof.

Applicants have found that by generating a translational fusion of two FT genes as a single open reading frame, for example sucrose-sucrose 1-fructosyltransferase (Lp1-SST) and fructan-fructan 6G-fructosyltransferase (Lp6G-FFT) from *Lolium perenne*, a single mRNA transcript is produced which is translated as a single protein, with combined enzyme activities. By expressing a translational fusion of two FT genes (e.g. Lp1-SST and Lp6G-FFT), problems associated with differences in the expression patterns of these two genes independently integrated in to the plant genome may be alleviated, resulting in the conversion of sucrose to low and high DP fructans.

In a particularly preferred embodiment the nucleic acid encoding the FT fusion protein of 1-SST and 6G-FFT includes a sequence selected from the group consisting of the sequences shown in FIGS. 12 and 14 hereto and the nucleic acid sequences encoding the polypeptide sequences shown in FIGS. 13 and 15 hereto; and functionally active fragments and variants thereof.

In a particularly preferred embodiment, the genetic construct includes a sequence selected from the group consisting of the sequences shown in FIGS. 24 to 27, 31, 32, 35, 36, 38 and 41 to 47 hereto; and functionally active fragments and variants thereof.

In a further aspect, the present invention provides a method of enhancing productivity of a biochemical pathway in a plant, said method including introducing into said plant an effective amount of a genetic construct including nucleic acids encoding two or more enzymes from said pathway, or functionally active fragments or variants thereof.

Preferably, said nucleic acids are linked to form a fusion gene encoding a fusion protein of said two or more enzymes.

By a 'biochemical pathway' is meant a plurality of chemical reactions occurring within a cell which are catalysed by more than one enzyme or enzyme subunit and result in the conversion of a substrate into a product. This includes, for example, a situation in which two or more enzyme subunits (each being a discrete protein coded by a separate gene) combine to form a processing unit that converts a substrate into a product. A 'biochemical pathway' is not constrained by temporal or spatial sequentiality.

By 'enhancing productivity' is generally meant that the amount of product of the biochemical pathway, or the rate of production of the product, is increased in a transformed plant relative to an untransformed control plant. However, for some applications it may be desirable to reduce or otherwise modify the amount of product of the biochemical pathway or the rate of production of the product in the transformed plant relative to the untransformed control plant. For example, it may be desirable to increase or decrease the amount of an intermediate of the pathway, or its rate of production, in a transformed plant relative to an untransformed control plant.

By a 'fusion protein' is meant a hybrid or chimeric protein produced recombinantly by expressing a fusion gene including two or more linked nucleic acids which originally encoded separate proteins, or functionally active fragments or variants thereof.

By a 'fusion', 'translational fusion' or 'fusion gene' is meant that two or more nucleic acids are linked in such a way as to permit expression of the fusion protein, preferably as a translational fusion. This typically involves removing the stop codon from a nucleic acid sequence coding for a first protein, then appending the nucleic acid sequence of a second protein in a frame. The FT fusion gene is then expressed by a cell as a single protein. The protein may be engineered to include the full sequence of both original proteins, or a functionally active fragment or variant of either or both.

The genetic construct may also include a nucleic acid sequence encoding a linker between the two linked nucleic acids. A 'linker' is any chemical, synthetic, carbohydrate, lipid, polypeptide molecule (or combination thereof) positioned between and joined to two adjacent active fragments in a fusion protein. A preferred linker of the invention is a flexible linker, such as a polypeptide chain consisting of one or more amino acid residues joined by amino acid bonds to the two active fragments. For example, a $(Gly_4 Ser)_3$ linker may be positioned between the two active fragments in the fusion protein.

By 'functionally active' in relation to the nucleic acids encoding two or more enzymes from a biochemical pathway is meant that the fragment or variant (such as an analogue, derivative or mutant) is capable of enhancing productivity of the biochemical pathway in a plant by the method of the present invention. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence to which the fragment or, variant corresponds more preferably at least approximately 90% identity, even more preferably at least approximately 95% identity, most preferably at least approximately 98% identity. Such functionally active variants and fragments include, for example, those having conservative nucleic acid changes. By 'conservative nucleic acid changes' is meant nucleic acid substitutions that result in conservation of the same amino acid in the encoded protein, due to the degeneracy of the genetic code. Such functionally active variants and fragments also include, for example, those having nucleic acid changes which result in conservative amino acid substitutions of one or more residues in the corresponding amino acid sequence. By 'conservative amino acid substitutions' is meant the substitution of an amino acid by another one of the same class, the classes being as follows:

Nonpolar: Ala, Val, Leu, Ile, Pro, Met Phe, Trp

Uncharged polar: Gly, Ser, Thr, Cys, Tyr, Asn, Gln

Acidic: Asp, Glu

Basic: Lys, Arg, His

Other conservative amino acid substitutions may also be made as follows:

Aromatic: Phe, Tyr, His

Proton Donor Asn, Gln, Lys, Arg, His, Trp

Proton Acceptor Glu, Asp, Thr, Ser, Tyr, Asn, Gln

Particularly preferred fragments and variants include one or more conserved sucrose binding/hydrolysis domains. Examples of such domains are shown in FIGS. 17, 18 and 36 hereto, for example (N/S)DP(N)G, FRDP and EC(I)D.

Particularly preferred fragments and variants may also include one or more conserved amino acid domains found in *Lolium* FT, invertase and FEH sequences, for example as shown in FIGS. 17, 18 and 36 hereto.

Preferably the fragment has a size of at least 20 nucleotides, more preferably at least 50 nucleotides, more preferably at least 100 nucleotides, more preferably at least 200 nucleotides, more preferably at least 500 nucleotides.

Preferably, the biochemical pathway is a fructan biosynthetic pathway.

Preferably, the two or more enzymes from said pathway are selected from the group consisting of enzymes of the fructan biosynthetic pathway in plants, for example fructosyltransferases such as sucrose:sucrose 1-fructosyltransferase (1-SST); fructan:fructan 1-fructosyltransferase (1-FFT); sucrose:fructan 6-fructosyltransferase (6-SFT); and fructan: fructan 6G-fructosyl transferase (6G-FFT); and fructoexohydrolases such as 1-fructoexohydrolase (1-FEH) and 6-fructoexohydrolase (6-FEH).

Even more preferably, the nucleic acids encoding a FT fusion protein include two or more nucleic acids selected from the group consisting of genes encoding 1-SST, 1-FFT, 6-SFT and 6G-FFT, and functionally active fragments and variants thereof, linked to form a FT fusion gene. The nucleic acids are optionally connected by a linker such as a flexible linker.

Even more preferably, the nucleic acids encoding a FT fusion protein include two or more nucleic acids linked to form a FT fusion protein of 1-SST and 6G-FFT, or functionally active fragments or variants thereof, optionally connected by a linker such as a flexible linker.

Preferably, the genes encoding enzymes of the fructan biosynthetic pathway are isolated from or correspond to genes from a ryegrass or fescue species, including Italian or annual ryegrass, perennial ryegrass, tall fescue, meadow fescue and red fescue. Even more preferably, the genes encoding enzymes of the fructan biosynthetic pathway are isolated from or correspond to genes from a *Lolium* species such as *Lolium perenne* or *Lolium arundinaceum.*

Suitable nucleic acids encoding fructan biosynthetic enzymes are described in PCT/AU01/00705 and PCT/AU01/01275, the entire disclosures of which are incorporated herein by reference.

In a particularly preferred embodiment the nucleic acid encoding 1-SST includes a sequence selected from the group consisting of the sequence shown in SEQ ID NO: 11 of PCT/AU01/00705; and the nucleotide sequences encoding the polypeptide sequence shown in SEQ ID NO: 12 of PCT/AU01/00705; and functionally active fragments and variants thereof.

In a particularly preferred embodiment the nucleic acid encoding the 6G-FFT includes a sequence selected from the group consisting of the sequences shown in SEQ ID NO: 110 of PCT/AU01/01275, and FIG. 7 hereto; and the nucleic acid sequences encoding the polypeptide sequences shown in SEQ ID NO: 111 of PCT/AU01/01275; and FIG. 8 hereto; and functionally active fragments and variants thereof.

In a particularly preferred embodiment, the nucleic acid encoding the 1-FFT includes a sequence selected from the group consisting of the sequences shown in SEQ ID NO: 3 of PCT/AU01/00705, SEQ ID NOS: 103 and 105-109 of PCT/AU01/01275 and FIG. 9 hereto; and the nucleotide sequences encoding the polypeptide sequences shown in SEQ ID No: 4 of PCT/AU01/00705, SEQ ID NO: 104 of PCT/AU01/01275 and FIG. 10 hereto; and functionally active fragments and variants thereof.

In a particularly preferred embodiment the nucleic acid encoding the of 1-SST and 6G-FFT includes a sequence selected from the group consisting of the sequences shown in FIGS. 12 and 14 hereto and the nucleic acid sequences encoding the polypeptide sequences shown in FIGS. 13 and 15 hereto; and functionally active fragments and variants thereof.

In a particularly preferred embodiment, the genetic construct includes a sequence selected from the group consisting of the sequences shown in FIGS. 24 to 27, 31, 32, 35, 36, 38 and 41 to 475 hereto, and functionally active fragments and variants thereof.

The promoter used in the constructs and methods of the present invention may be a constitutive, tissue specific or inducible promoter. In a preferred embodiment, the promoter is a light-regulated promoter, more preferably a photosynthetic promoter. By a 'light regulated promoter' is meant a promoter capable of mediating gene expression in response to light stimulus. By a 'photosynthetic promoter' is meant a promoter capable of mediating expression of a gene encoding a protein involved in a photosynthetic pathway in plants.

Less fructans accumulate in mature leaf blades than in leaf sheaths and stems. In order to specifically increase the level of fructans in leaf blades, a strategic approach has been devised that co-ordinately expresses fructan biosynthesis genes in photosynthetic cells (FIG. 1). The use of light-regulated or photosynthetic promoters may provide the following advantages:

- Photosynthetic promoters are active in a large group of cells including leaf blades, the upper and outer stem (>55% cells);
- They are active in sucrose producing cells (mesophyll and parenchymatous bundle sheath cells);
- Their expression pattern temporally and spatially overlaps with sucrose accumulation;
- Frutosyltransferase activity will remove sucrose from the source thereby preventing feedback suppression on photosynthesis, and may facilitate increases in $CO_2$ fixation;

Particularly preferred light-regulated promoters include a ribulose-1,5-bisphosphate carboxylase/oxygtenase small subunit (RbcS) promoter and a chlorophyll a/b binding protein (CAB) promoter, and functionally active fragments and variants thereof.

The light-regulated promoter may be from any suitable plant species including monocotyledonous plants [such as maize, rice, wheat, barley, sorghum, sugarcane, forage grasses, bioenergy grasses], dicotyledonous plants (such as *Arabidopsis*, soybean, canola, cotton, alfalfa and tobacco) and gymnosperms.

Preferably, the light-regulated promoter is isolated from or corresponds to a promoter from a ryegrass or fescue species, including Italian or annual ryegrass, perennial ryegrass, tall fescue, meadow fescue and red fescue. Even more preferably, the light regulated promoter is isolated from or corresponds to a promoter from a *Lolium* species such as *Lolium perenne* or *Lolium arundinaceum.*

In another embodiment, preferably the light-regulated promoter is isolated from or corresponds to a promoter from *Arabidopsis*, even more preferably *Arabidopsis thaliana.*

In a particularly preferred embodiment, the RbcS promoter includes a sequence selected from the group consisting of the sequence shown in FIG. 5 hereto, and functionally active fragments and variants thereof.

In a particularly preferred embodiment, the RbcS promoter includes a sequence selected from the group consisting of the sequence shown in FIG. 38 hereto, and functionally active fragments and variants thereof.

In another particularly preferred embodiment, the CAB promoter includes a sequence selected from the group consisting of the sequence shown in FIG. 4 hereto, and functionally active fragments and variants thereof.

In another preferred embodiment, the promoter may be a constitutive promoter, such as a ubiquitin (Ubi) promoter.

In a particularly preferred embodiment, the Ubi promoter includes a sequence selected from the group consisting of the sequence shown in FIG. 41 hereto, and functionally active fragments and variants thereof.

The genetic constructs of the present invention may be introduced into the plants by any suitable technique. Techniques for incorporating the genetic constructs of the present invention into plant cells (for example by transduction, transfection, transformation or gene targeting) are well known to those skilled in the art. Such techniques include *Agrobacterium*-mediated introduction, *Rhizobium*-mediated introduction, electroporation to tissues, cells and protoplasts, protoplast fusion, injection into reproductive organs, injection into immature embryos and high velocity projectile introduction to cells, tissues, calli, immature and mature embryos, biolistic transformation, Whiskers transformation, and combinations thereof. The choice of technique will depend largely on the type of plant to be transformed, and may be readily determined by an appropriately skilled person.

Cells incorporating the genetic constructs of the present invention may be selected, as described below, and then cultured in an appropriate medium to regeneratetransformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

The methods of the present invention may be applied to a variety of plants, including monocotyledons [such as grasses (e.g. forage, turf and bioenergy grasses including perennial ryegrass, tall fescue, Italian ryegrass, red fescue, reed canarygrass, big bluestem, cordgrass, napiergrass, wildrye, wild sugarcane, *Miscanthus*, switchgrass), corn or maize, rice, wheat, barley, sorghum, sugarcane, rye, oat)], dicotyledons [such as *Arabidopsis*, tobacco, soybean, canola, alfalfa, potato, cassava, clovers (e.g. white clover, red clover, subterranean clover), vegetable brassicas, lettuce, spinach] and gymnosperms.

In a further aspect of the present invention, there is provided a genetic construct capable of manipulating fructan biosynthesis in photosynthetic cells of a plant, said genetic construct including a light-regulated promoter, or functionally active fragment or variant thereof, operatively linked to nucleic acids encoding one or more fructan biosynthetic enzymes, or functionally active fragments or variants thereof.

In a still further aspect of the present invention there is provided a genetic construct capable of enhancing productivity of a biochemical pathway in a plant said genetic construct including nucleic acids encoding two or more enzymes from said pathway, or functionally active fragments or variants thereof.

Preferably, said nucleic acids are linked to form a fusion gene encoding a fusion protein of said two or more enzymes.

In preferred embodiments, the genetic constructs according to the various aspects of the present invention may be vectors.

By a 'vector' is meant a genetic construct used to transfer genetic material to a target cell.

The vector may be of any suitable type and may be viral or non-viral. The vector may be an expression vector. Such vectors include chromosomal, non-chromosomal and synthetic nucleic acid sequences, eg. derivatives of plant viruses; bacterial plasmids; derivatives of the Ti plasmid from *Agrobacterium tumefaciens*; derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable or integrative or viable in the plant cell.

In a preferred embodiment of this aspect of the invention, the genetic construct may further include a terminator; said promoter, gene and terminator being operably linked.

The promoter, gene and terminator may be of any suitable type and may be endogenous to the target plant cell or may be exogenous, provided that they are functional in the target plant cell.

A variety of terminators which may be employed in the genetic constructs of the present invention are also well known to those skilled in the art. The terminator may be from the same gene as the promoter sequence or a different gene. Particularly suitable terminators are polyadenylation signals, such as the (CaMV)35S polyA and other terminators from the nopaline synthase (nos) and the octopine synthase (ocs) genes.

The genetic construct, in addition to the promoter, the gene and the terminator, may include further elements necessary for expression of the nucleic acid, in different combinations, for example vector backbone, origin of replication (ori), multiple cloning sites, spacer sequences, enhancers, introns (such as the maize Ubiquitin Ubi intron), antibiotic resistance genes and other selectable marker genes [such as the neomycin phosphotransferase (nptII) gene, the hygromycin phosphotransferase (hph) gene, the phosphinothricin acetyltransferase (bar or pat) gene], and reporter genes (such as beta-glucuronidase (GUS) gene (gusA)]. The genetic construct may also contain a ribosome binding site for translation initiation. The genetic construct may also include appropriate sequences for amplifying expression.

In particular, the genetic construct may further include a nucleic acid sequence. encoding a linker between the two linked nucleic acids, as hereinbefore described.

Those skilled in the art will appreciate that the various components of the genetic construct are operably linked, so as to result in expression of said nucleic acid. Techniques for operably linking the components of the genetic construct of the present invention are well known to those skilled in the art. Such techniques include the use of linkers, such as synthetic linkers, for example including one or more restriction enzyme sites.

Preferably, the genetic construct is substantially purified or isolated. By 'substantially purified' is meant that the genetic construct is free of the genes, which, in the naturally-occurring genome of the organism from which the nucleic acid or promoter of the invention is derived, flank the nucleic acid or promoter. The term therefore includes, for example, a genetic construct which is incorporated into a vector; into an autonomously replicating plasmid or virus; or into the genomic DNA of a prokaryote or eukaryote; or which exists as a separate molecule (eg. a cDNA or a genomic or cDNA fragment produced by PCR or restriction endonuclease digestion) independent of other sequences. It also includes a genetic construct which is part of a hybrid gene encoding additional polypeptide sequence. Preferably, the substantially purified genetic construct is at least approximately 90% pure, more preferably at least approximately 95% pure, even more preferably at least approximately 98% pure.

The term "isolated" means that the material is removed from its original environment (eg. the natural environment if it is naturally occurring). For example, a naturally occurring nucleic acid present in a living plant is not isolated, but the same nucleic acid separated from some or all of the coexisting materials in the natural system, is isolated. Such nucleic acids could be part of a vector and/or such nucleic acids could be part of a composition, and still be isolated in that such a vector or composition is not part of its natural environment.

As an alternative to use of a selectable marker gene to provide a phenotypic trait for selection of transformed host cells, the presence of the genetic construct in transformed cells may be determined by other techniques well known in the art, such as PCR (polymerase chain reaction), Southern blot hybridisation analysis, histochemical assays (e.g. GUS assays), thin layer chromatography (TLC), northern and western blot hybridisation analyses.

Applicant has also found that the methods of the present invention may result in enhanced biomass in the transformed plant relative to an untransformed control plant. This enhanced biomass may in turn be used as a selection tool for identifying transformed plants. This has the advantage that in some circumstances there may be no need to include an antibiotic resistance or other marker to select for transformants, where subsequent removal of such markers (and for the creation of marker-free plants) may present difficulties.

By 'enhancing biomass' or 'enhanced biomass' is meant enhancement of, increase in, or increased stability of biomass yield, including shoot and/or root growth, in a transformed plant relative to an untransformed control plant. For example, one or more growth characteristics selected from the group consisting of plant height, herbage dry weight, total leaf area, cumulative leaf area, leaf growth dynamics (ie. number of leaves over time), number of shoots, number of tillers, number of roots, root mass or weight, shoot mass or weight, root length, shoot length, stolon length, number of tubers, tuber weight, number of flowers, number of fruits, number of seeds, seed weight, fruit weight, percentage of flowering plants and seed yield per flower or per area sown; may be enhanced, increased or more stable in a transformed plant relative to an untransformed control plant.

This technique is particularly applicable to plants that are substantially genetically uniform or genetically identical or exhibit small phenotype differences in biomass prior to transformation.

Accordingly, in a further aspect of the present invention, there is provided a method of enhancing biomass in a plant, said method including introducing into said plant an effective amount of a genetic construct including a promoter, or a functionally active fragment or variant thereof, operatively liked to nucleic acids encoding one or more fructan biosynthetic enzymes, or functionally active fragments or variants thereof. Preferably, the promoter is a light regulated promoter.

In a still further aspect of the present invention there is provided a method of enhancing biomass in a plant, said method including introducing into said plant an effective amount of a genetic construct including nucleic acids encoding two or more enzymes from a biochemical pathway in said plant, or functionally active fragments or variants thereof.

In a still further aspect of the present invention, there is provided a method of enhancing biomass in a plant, said method including introducing into said plant effective amounts of genetic construct capable of manipulating fructan biosynthesis in photosynthetic cells of the plant and a genetic construct capable of manipulating senescence in the plant.

The genetic constructs may be introduced into the plant by any suitable technique, as hereinbefore described, and may be introduced concurrently, sequentially or separately.

Preferably the genetic construct capable of manipulating fructan biosynthesis includes a promoter, or a functionally active fragment or variant thereof, operatively linked to nucleic acids encoding one or more fructan biosynthetic enzymes, or functionally active fragments or variants thereof. Preferably the promoter is a light regulated promoter.

Preferably the genetic construct capable of manipulating senescence in the plant is capable of manipulating senescence in photosynthetic cells of the plant.

Preferably the genetic construct capable of manipulating senescence includes a MYB gene promoter or modified MYB gene promoter, or a functionally active fragment or variant thereof, operatively linked to a gene encoding an enzyme involved in biosynthesis of a cytokinin, or a functionally active fragment or variant thereof.

Suitable genetic constructs or vectors are described in International patent application PCT/AU01/01092 and U.S. patent application Ser. No. 11/789,526, the entire disclosures of which are incorporated herein by reference.

"Manipulating senescence" generally relates to delaying senescence in the transformed plant or cells or organs of the transformed plant, eg photosynthetic cells, relative to an untransformed control plant. However, for some applications it may be desirable to promote or otherwise modify senescence in the plant. Senescence may be promoted or otherwise modified for example, by utilizing an antisense gene.

The MYB gene promoter may be of any suitable type. Preferably the MYB gene promoter is a MYB32 gene promoter. Preferably the MYB gene promoter is from *Arabidopsis*, more preferably *Arabidopsis thaliana*. Most preferably the MYB gene promoter includes a nucleotide sequence selected from the group consisting of the sequence shown in Sequence ID No: 1 of PCT/AU01/01092 and functionally active fragments and variants thereof.

A suitable promoter is described in Li et al., Cloning of three MYB-like genes from *Arabidopsis* (PGR 99-138) Plant Physiology 121:313 (1999), the entire disclosure of which is incorporated herein by reference.

By a "modified MYB gene promoter" is meant a promoter normally associated with a MYB gene, which promoter is modified to delete or inactivate one or more root specific motifs and/or pollen specific motifs in said promoter.

Preferably the modified MYB gene promoter is a modified MYB32 gene promoter. Preferably the modified MYB gene promoter is modified from the MYB gene promoter from *Arabidopsis*, or more preferably *Arabidopsis thaliana*.

A suitable promoter which may be modified according to the present invention is described in Li et al., Cloning of three MYB-like genes from *Arabidopsis* (PGR 99-138) Plant Physiology 121:313 (1999), the entire disclosure of which is incorporated herein by reference.

By a "root specific motif" is meant a sequence of 3-7 nucleotides, preferably 4-6 nucleotides, more preferably 5 nucleotides, which directs expression of any associated gene in the roots of a plant.

Preferably the root specific motif includes a consensus sequence ATATT or AATAT.

By a "pollen specific motif" is meant a sequence of 3-7 nucleotides, preferably 4-6 nucleotides, more preferably 4 or 5 nucleotides, which directs expression of an associated gene in the pollen of a plant.

Preferably the pollen specific motif includes a consensus sequence selected from the group consisting of TTTCT, AGAAA, TTCT and AGAA.

A root or pollen specific motif may be inactivated by adding, deleting, substituting or derivatizing one or more nucleotides within the motif, so that it no longer has the preferred consensus sequence.

Preferably the modified MYB gene promoter includes a nucleotide sequence selected from the group consisting of the sequences show in SEQ ID NOS: 2, 3 and 4 of U.S. Ser. No. 11/789,526 and functionally active fragments and variants thereof.

By a "gene encoding an enzyme involved in biosynthesis of a cytokinin" is meant a gene encoding an enzyme involved in the synthesis of cytokinins such kinetin, zeatin and benzyl adenine, for example a gene encoding isopentyl transferase (IPT), or IPT-like gene such as the sho gene (eg. from *petunia*). Preferably the gene is an isopentenyl transferase (IPT) gene or sho gene. In a preferred embodiment, the gene is from a species selected from the group consisting of *Agrobacterium*, more preferably *Agrobacterium tumefaciens; Lotus*, more preferably *Lotus japonicus*; and *Petunia*, more preferably *Petunia hybrida*.

Most preferably the gene includes a nucleotide sequence selected from the group consisting of the sequences shown in SEQ ID NOS: 5, 7 and 9 of U.S. Ser. No. 11/789,526, sequences encoding the polypeptides shown in SEQ ID NOS: 6, 8 and 10 of U.S. Ser. No. 11/789,526, and functionally active fragments and variants thereof.

The present invention also provides a method of selecting for transformed plants, said method including introducing into said plants an effective amount of a genetic construct including a promoter, or a functionally active fragment or variant thereof, operatively liked to nucleic acids encoding one or more fructan biosynthetic enzymes, or functionally active fragments or variants thereof and selecting plants with enhanced biomass. Preferably the promoter is a light regulated promoter.

In a further aspect of the present invention there is provided a transgenic plant cell, plant, plant seed or other plant part with modified fructan biosynthetic characteristics or enhanced biomass relative to an untransformed control plant.

By "modified fructan biosynthetic characteristics" is meant that the transformed plant exhibits increased fructan biosynthesis and/or contains increased levels of soluble carbohydrate relative to an untransformed control plant.

In a preferred embodiment the a transgenic plant cell, plant, plant seed or other plant part with enhanced biomass has an increase in biomass of at least approximately 10%, more preferably at least approximately 20%, more preferably at least approximately 30%, more preferably at least approximately 40% relative to an untransformed control plant.

For example, biomass may be increased by between approximately 10% and 300%, more preferably between approximately 20% and 200%, more preferably between approximately 30% and 100%, more preferably between approximately 40% and 80% relative to an untransformed control plant.

For example, plant height may be increased by between approximately 10% and 300%, more preferably between approximately 20% and 200%, more preferably between approximately 30% and 100%, more preferably between approximately 40% and 80% relative to an untransformed control plant.

For example, herbage dry weight may be increased by between approximately 10% and 600%, more preferably between approximately 20% and 400%, more preferably between approximately 30% and 300%, more preferably between approximately 40% and 200% relative to an untransformed control plant.

In a preferred embodiment, the transgenic plant cell, plant, plant seed or other plant part with modified fructan biosynthetic characteristics has an increase in soluble carbohydrate of least approximately 10%, more preferably at least approximately 20%, more preferably at least approximately 30%, more preferably at least approximately 40% relative to an untransformed control plant.

For example, soluble carbohydrates may be increased by between approximately 10% and 300%, more preferably between approximately 20% and 200%, more preferably between approximately 30% and 100%, more preferably between approximately 40% and 80% relative to an untransformed control plant.

For example, fructan concentration may be increased between approximately 10% and 600%, more preferably between approximately 20% and 400%, more preferably between approximately 30% and 200%, more preferably between approximately 40% and 150% relative to an untransformed control plant.

Preferably said plant cell, plant, plant seed or other plant part includes a genetic construct or vector according to the present invention. Preferably the transgenic plant cell, plant, plant seed or other plant part is produced by a method according to the present invention.

The present invention also provides a transgenic plant, plant seed or other plant part derived from a plant cell of the present invention and including a genetic construct or vector of the present invention.

The present invention also provides a transgenic plant, plant seed or other plant part derived from a plant of the present invention and including a genetic construct or vector of the present invention.

Preferably, the transgenic plant cell, plant, plant seed or other plant part is a *Lolium* species, more preferably *Lolium perenne* or *Lolium arundinaceum.*

Preferably, the transgenic plant cell, plant, plant seed or other plant part is a cereal grain, more preferably a *Triticum* species, more preferably wheat (*Triticum aestivum*).

For example, the present invention enables the production of transgenic perennial ryegrass plants with increased fructans in leaf blades, vigorous growth and/or greater tolerance to abiotic stress, for improved nutrition for grazing animals.

The present invention also enables the production of transgenic wheat plants with increased fructans, vigorous growth, and/or tolerance to abiotic stress, for increased mass of usable carbohydrates, eg. for bio-fuel production or animal feed.

By 'plant cell' is meant any self-propagating cell bounded by a semi-permeable membrane and containing a plastid. Such a cell also requires a cell wall if further propagation is desired. Plant cell, as used herein includes, without limitation, algae, cyanobacteria, seeds suspension cultures, embryos, meristematic regions, callus tissue, leaves, roots, shoots, gametophytes, sporophytes, pollen and microspores.

By 'transgenic' is meant any cell which includes a DNA sequence which is inserted by artifice into a cell and becomes part of the genome of the organism which develops from that cell. As used herein, the transgenic organisms are generally transgenic plants and the DNA (transgene) is inserted by artifice into either the nuclear or plastidic genome.

In a further aspect of the present invention there is provided a fusion protein comprising two or more enzymes of a biochemical pathway in a plant, or functionally active fragments or variants thereof.

By 'functionally active' in this context is meant that the fragment or variant has one or more of the biological properties of the corresponding protein from which the fragment or variant is derived. Additions, deletions, substitutions and derivatizations of one or more of the amino acids are contemplated so long as the modifications do not result in loss of functional activity of the fragment or variant. Preferably the fragment or variant has at least approximately 80% identity to the relevant part of the above mentioned sequence to which the fragment or variant corresponds, more preferably at least approximately 90% identity, more preferably at least approximately 95% identity, most preferably at least approximately 98% identity. Such functionally active variants and fragments include, for example, those having conservative amino acid substitutions of one or more residues in the corresponding amino acid sequence.

Preferably the fragment has a size of at least 10 amino acids, more preferably at least 20 amino acids, more preferably at least 50 amino acids, more preferably at least 100 amino acids, more preferably at least 200 amino acids.

Preferably, the biochemical pathway is in the fructan biosynthetic pathway.

Preferably, the two or more enzymes from said pathway are selected from the group consisting of enzymes of the fructan biosynthetic pathway in plants, for example fructosyltransferases such as sucrose:sucrose 1-fructosyltransferase (1-SST); fructan:fructan 1-fructosyltransferase (1-FFT); sucrose:fructan 6-fructosyltransferase (6-SFT); and fructan: fructan 6G-fructosyl transferase (6G-FFT); and fructoexohydrolases such as 1-fructoexohydrolase (1-FEH) and 6-fructoexohydrolase (6-FEH).

Even more preferably, the fusion protein is a FT fusion protein of 1-SST and 6G-FFT, or functionally active fragments or variants thereof.

Preferably, the two or more enzymes from said pathway correspond to enzymes from a ryegrass or fescue species, including Italian or annual ryegrass, perennial ryegrass, tall fescue, meadow fescue and red fescue. Even more preferably, the two or more enzymes from said pathway correspond to enzymes from a *Lolium* species such as *Lolium perenne* or *Lolium arundinaceum.*

Suitable fructan biosynthetic enzymes are described in PCT/AU01/00705 and PCT/AU01/01275, the entire disclosures of which are incorporated herein by reference.

In a particularly preferred embodiment the 1-SST includes an amino acid sequence shown in SEQ ID NO: 12 of PCT/AU01/00705, or a functionally active fragment or variant thereof.

In a particularly preferred embodiment the 6G-FFT includes an amino acid sequence shown in SEQ ID NO: 111 of PCT/AU01/01275 or FIG. 8 hereto, or functionally active fragments or variants thereof.

In a particularly preferred embodiment the 1-SST_6G-FFT FT fusion protein includes an amino acid sequence shown in FIG. 13 or 15 hereto, or functionally active fragments or variants thereof.

DETAILED DESCRIPTION OF THE EMBODIMENTS

The present invention will now be more fully described with reference to the accompanying examples and drawings.

It should be understood, however, that the description following is illustrative only and should not be taken in any way as a restriction on the generality of the invention described above.

In the Figures:

FIG. 1. Model for targeted expression of fructan biosynthesis genes in photosynthetic cells in leaf blades. Expression of fructosyl transferase (FT) genes is driven by photosynthetic promoters. Fructan biosynthesis then occurs in sucrose producing, photosynthetic cells. Pyramiding with modification of cytokinin biosynthesis to delay leaf senescence, thus extending life of photosynthetic cells that are engineered to synthesise fructans and leading to increased biomass production.

Figure 2:
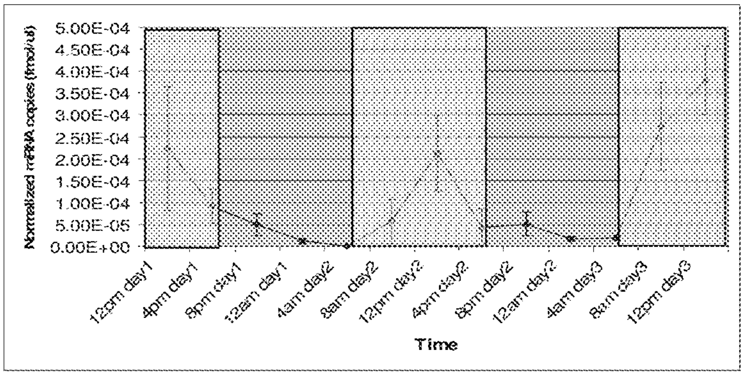

FIG. 2. The expression of the RuBisCO Small subunit gene in perennial ryegrass is light regulated as shown by quantitative real-time RT-PCR. Tissue sampling occurred every four hours. Boxes represent periods of daylight.

Figure 3:
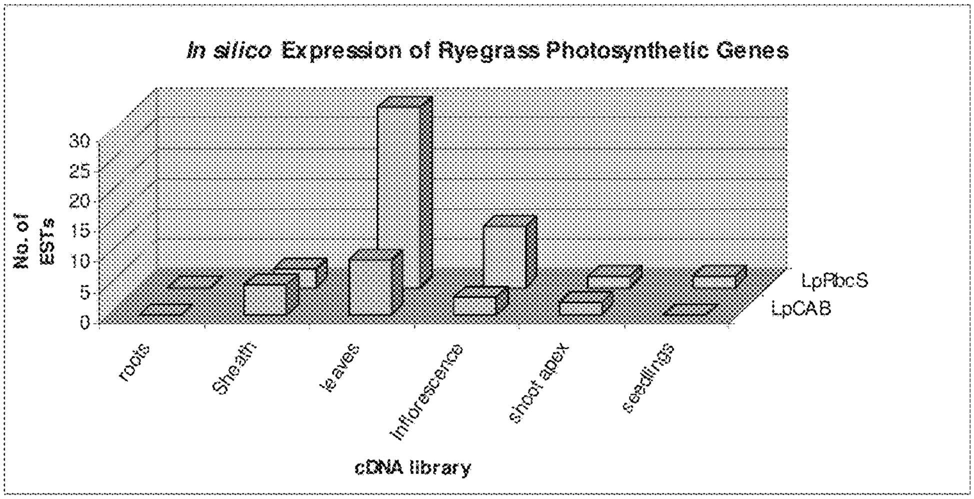

FIG. 3. In silico expression patterns of the Ribulose-1,5-bisphosphate carboxylase/oxygenase Small subunit (LpRbcS) and Chlorophyll a/b Binding Protein (LpCAB) in perennial ryegrass shows that it is most abundant in vegetative tissues. LpRbcS (contig LPCL9_C359) is represented by the 47 ESTs and LpRbcS (contig LPCL1112_C12) is represented by 19 ESTs.

FIG. 4. Nucleotide sequences of LpCAB promoter (SEQ ID No: 1).

FIG. 5. Nucleotide sequences of LpRbcS promoter (SEQ ID No: 2).

FIG. 6. Schematic representation of the fructan biosynthetic pathway in some grasses.

FIG. 7. Nucleotide sequence of Lp6G-FFT open reading frame (SEQ ID No: 3).

FIG. 8. Deduced amino acid sequence of Lp6G-FFT (SEQ ID No: 4).

FIG. 9. Nucleotide sequence of Lp1-FFT open reading frame (SEQ ID No: 5).

FIG. 10. Deduced amino acid sequence of Lp1-FFT (SEQ ID No: 6).

Figure 11:
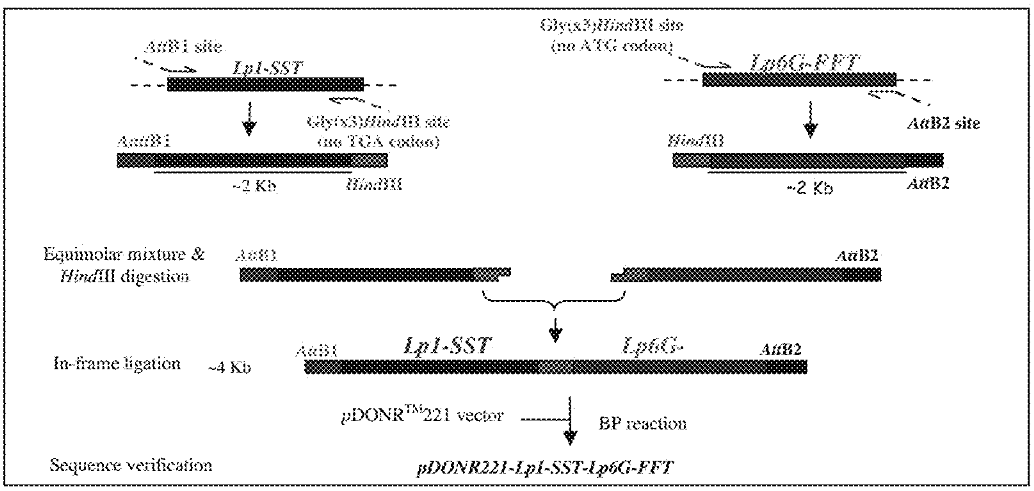

FIG. 11. Diagrammatic representation of the strategy used to generate the translational FT fusion of the Lp1-SST and Lp6G-FFT fructosyl transferase genes (Lp1-SST_Lp6G-FFT).

FIG. 12. Nucleotide sequence of Lp1-SST_Lp6G-FFT FT fusion 1 open reading frame (SEQ ID No: 7).

FIG. 13. Deduced amino acid sequence of Lp1-SST_Lp6G-FFT FT fusion 1 (SEQ ID No: 8).

FIG. 14. Nucleotide sequence of Lp1-SST_Lp6G-FFT FT fusion 3 open reading frame (SEQ ID No: 9).

FIG. 15. Deduced amino acid sequence of Lp1-SST_Lp6G-FFT FT fusion 3 (SEQ ID No: 10).

Figure 16:
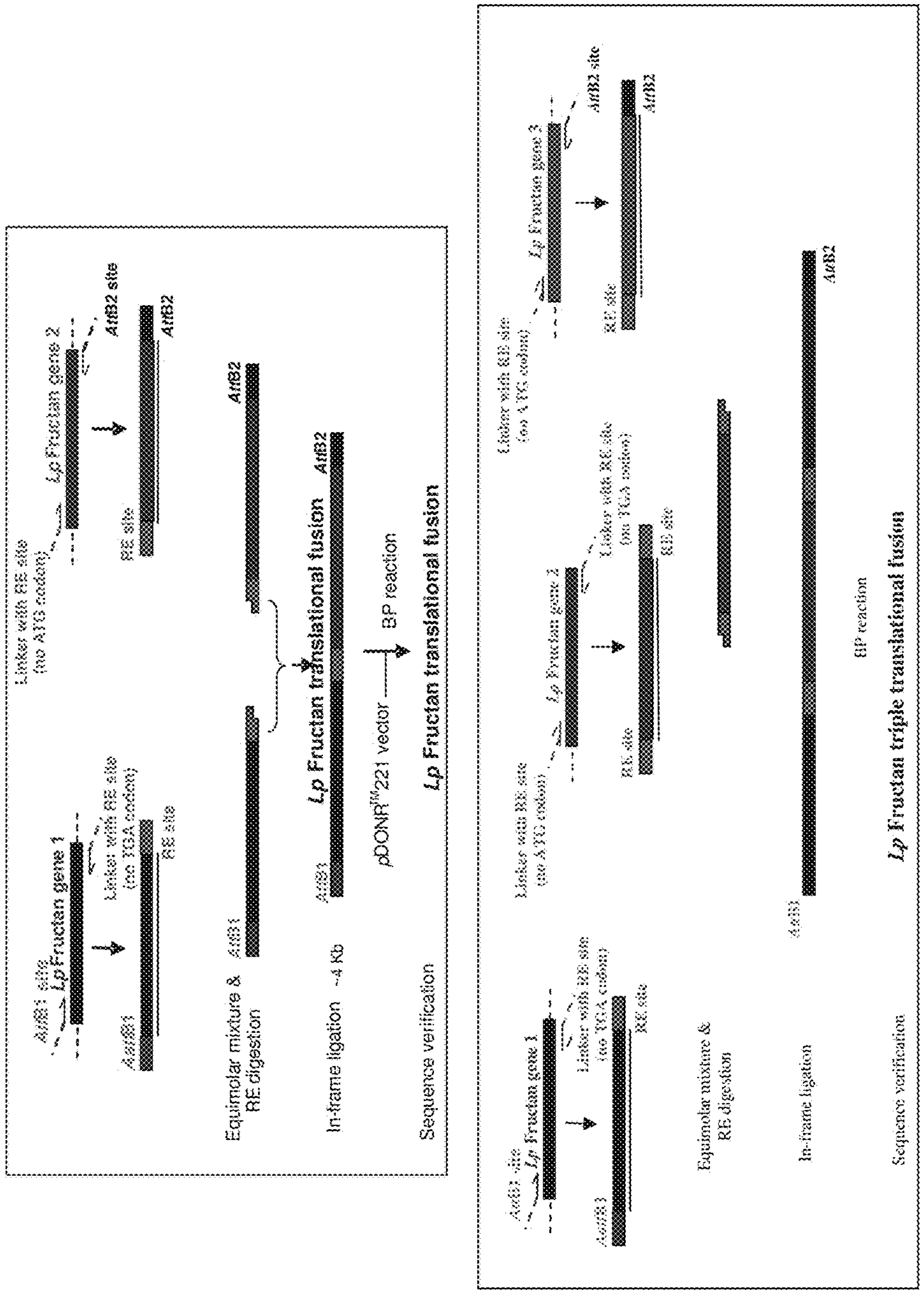

FIG. 16. Diagrammatic representation of the strategy to be used to generate the different translational FT fusions of the Lp1-SST, Lp6G-FFT and Lp1-FFT fructosyl transferase genes.

FIG. 17. (A) and (B) Hypothetical model of the interaction of FT proteins to form a transmembrane protein. (C) Representation of the key protein domains in Lp1-SST-6G-FFT proteins. Box1: (N/S)DPNG; Box2: RDP and Box3: EC represent the highly conserved domains involved in substrate (sucrose) binding and hydrolysis. Crosses (X) represent the highly conserved amino acid sequences (domains) found among the FT, invertase and FEH sequences from *Lolium* species. LS-large subunit, SU-Small subunit. Representation of the active domains within the amino acid sequence of the Lp1-SST_Lp6G-FFT FT fusion 3 protein can be found in FIG. 36.

FIG. 18. Amino acid alignment of FT, INV and FEH from *Lolium perenne* (SEQ ID Nos: 11-33). The key protein domains found among the FT, invertase and FEH sequences, such as (N/S)DPNG, RDP and EC, which represent the highly conserved domains involved in substrate (sucrose) binding and hydrolysis, are bold underlined and labelled. Highly conserved amino acid domains found among the FT, invertase and FEH sequences from *Lolium* species are underlined. Representation of the active domains within the amino acid sequence of the Lp1-SST_Lp6G-FFT FT fusion 3 protein can be found in FIG. 36.

Figure 19:
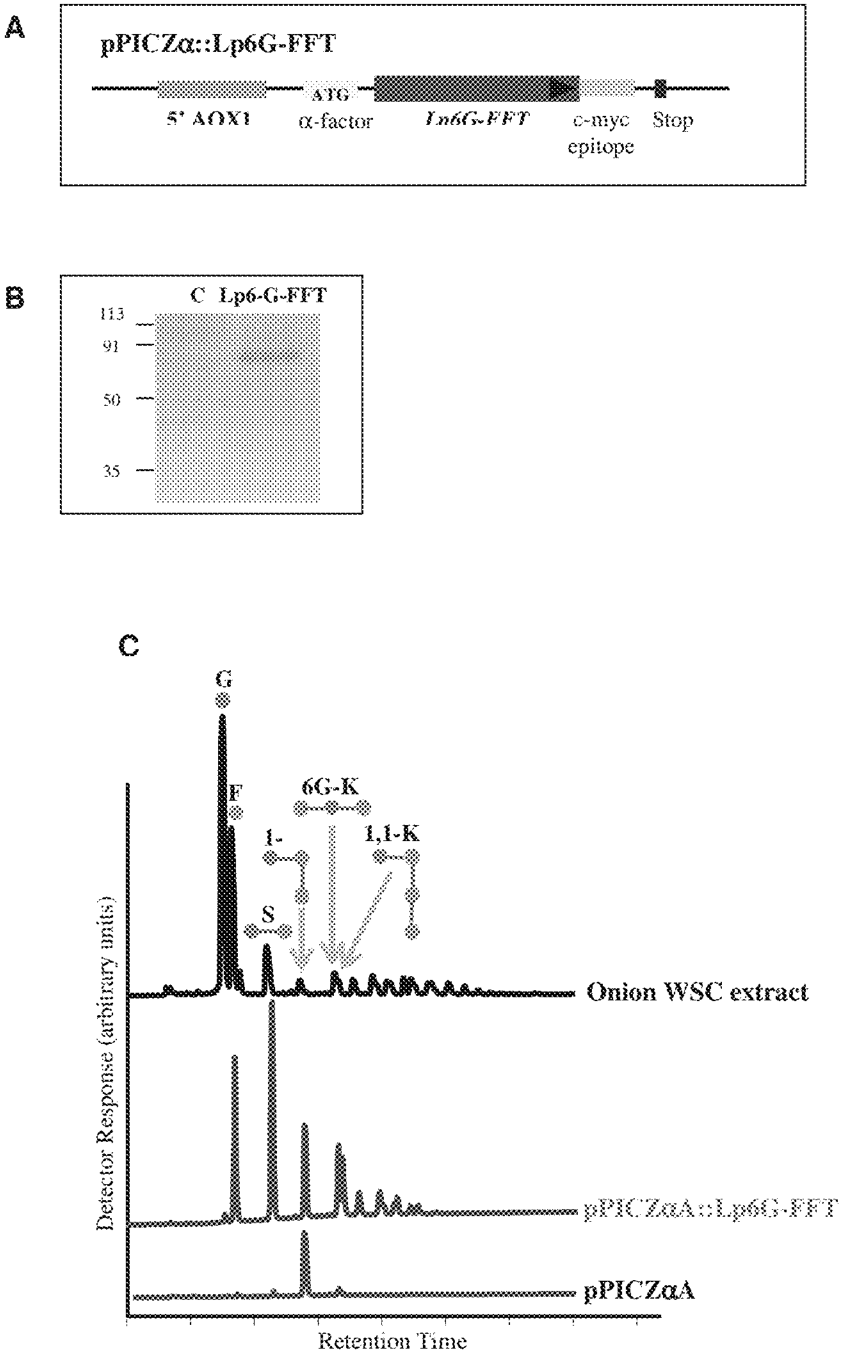

FIG. 19. Functional analysis of fructan:fructan 6G-fructosyltransferase (Lp6G-FFT). A. Plasmid map of Lp6G-FFT in the yeast expression vector. B. Excreted protein from yeast containing either pPICZαA::Lp6G-FFT or pPICZαA vector only separated by polyacrylamide gel electrophoresis. C. Water soluble carbohydrate (WSC) traces after high pressure anion exchange chromatography (HPAEC). WSC were isolated from onion, or solution of 1-kestose incubated with either Lp6G-FFT purified protein (pPICZαA::Lp6G-FFT) or vector only control (pPICZαA).

Figure 20:
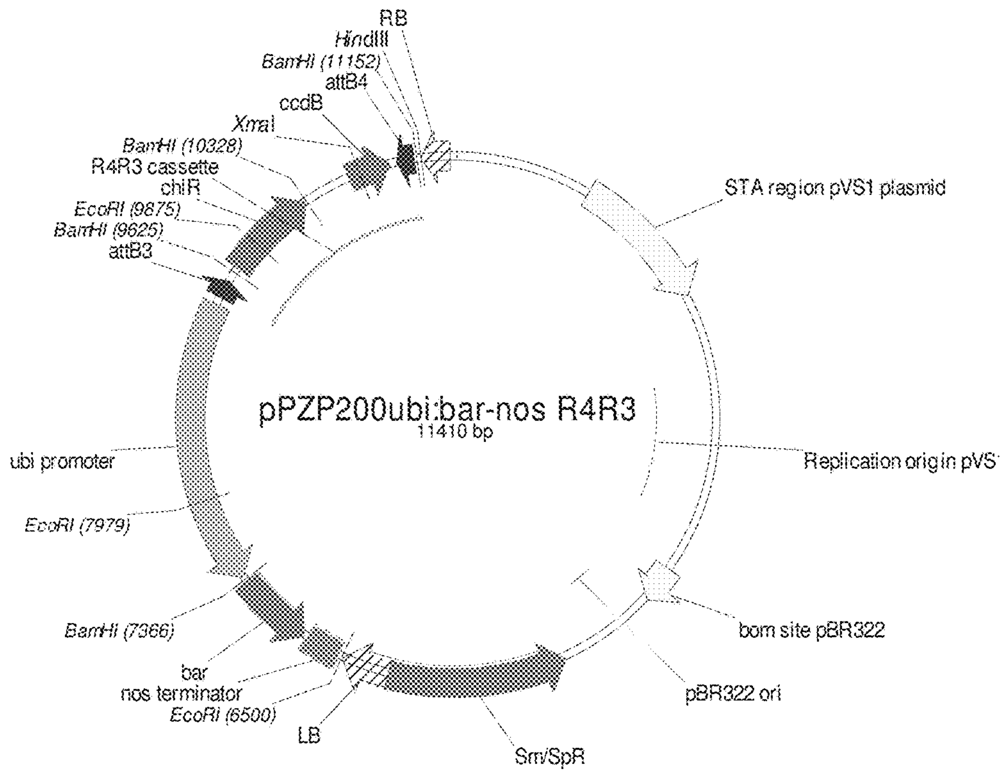

FIG. 20. Base destination vector, pPZP200-ubi:bar-nos R4 R3, used in Multisite Gateway recombinational cloning.

Figure 21:
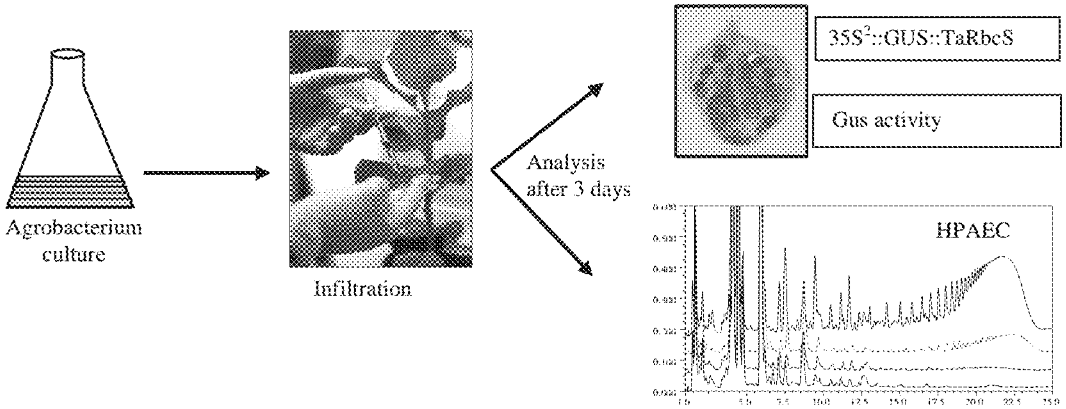

FIG. 21. Outline of the procedure for the in planta transient expression system. *Agrobacterium* cultures are prepared that harbour the expression constructs. These are injected into tobacco leaves. After three days post filtration expression of the proteins are tested. Upper right panel shows GUS activity, lower right panel shows example of water soluble carbohydrate separation by HPAEC.

Figure 22:
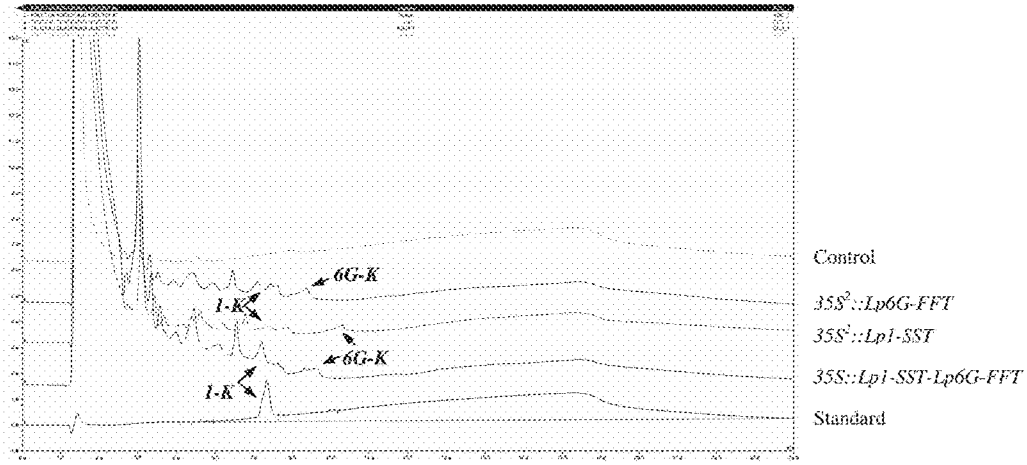

FIG. 22. High performance anion exchange chromatography (HPAEC) is used to separate and quantify carbohydrates using standards (1-kestose), and to quantify the amount of total fructans extracted from a control plant (35S::GUS) and transgenic plants transiently over-expressing Lp1-SST (355::1-SST), Lp6G-FFT (35S::6G-FFT) and the FT fusion (35S::Lp1-SST_Lp6G-FFT).

FIG. 23. Destination vectors of wheat RuBisCO promoter driving expression of (A) Lp1-SST, (B) Lp6G-FFT, (C) Lp1SST_Lp6GFFT FT fusion 1, (D) Lp1SST_Lp6GFFT FT fusion 3, and (E) the GUS marker gene.

FIG. 24. Sequence of TaRbcS::Lp1-SST::TaRbcS expression cassette (SEQ ID No: 34). The regulatory sequences, TaRbcS promoter and terminator are indicated in italics and underlined italics, respectively. The ORF sequence is indicated in regular font and the start (ATG) and stop (TAG) codons are shaded.

FIG. 25. Sequence of TaRbcS::Lp6GFFT::TaRbcS expression cassette (SEQ ID No: 35). The regulatory sequences, TaRbcS promoter and terminator are indicated in italics and underlined italics, respectively. The ORF sequence is indicated in regular font and the start (ATG) and stop (TAG) codons are shaded.

FIG. 26. Sequence of TaRbcS::Lp1-SST_Lp6G-FFT::TaRbcS FT fusion 1 expression cassette (SEQ ID No: 36). The regulatory sequences, TaRbcS promoter and terminator are indicated in italics and underlined italics, respectively. The ORF sequence is indicated in regular font and the start (ATG) and stop (TAG) codons are shaded.

FIG. 27. Sequence of TaRbcS::Lp1-SST_Lp6G-FFT::TaRbcS FT fusion 3 expression cassette (SEQ ID No: 37). The regulatory sequences, TaRbcS promoter and terminator are indicated in italics and underlined italics, respectively. The ORF sequence is indicated in regular font and the start (ATG) and stop (TAG) codons are shaded.

Figure 28:
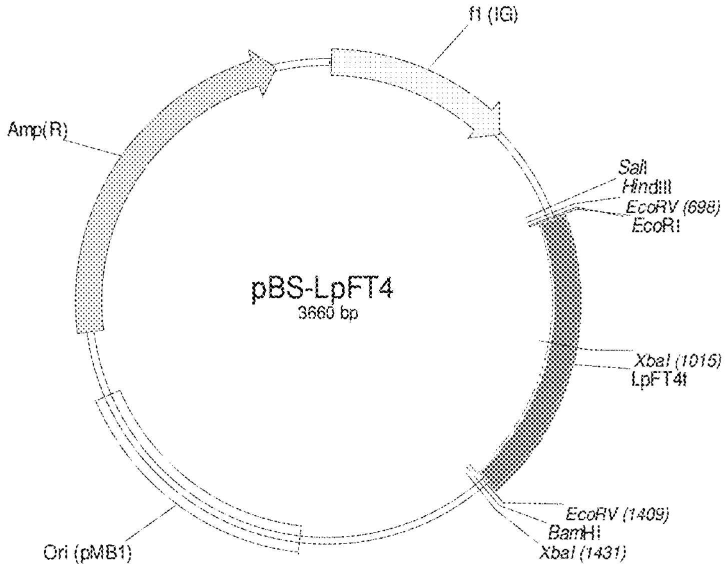

FIG. 28. Vector pBlueScript SK harbouring the LpFT4 3' terminator sequence, pBS-LpFT4.

FIG. 29. (A) The plasmid pBS-Lp1-SST::FT4 and (B) the plasmid pBS-LpRbcS::Lp1-SST::LpFT4.

FIG. 30. (A) The plasmid pBS-LpCAB::LpFT4 and (B) the plasmid pBS-LpCAB::Lp6G-FFT::LpFT4.

FIG. 31. Sequence of LpRbcS::Lp1-SST::LpFT4 expression cassette (SEQ ID No: 38). The regulatory sequences, LpRbcS promoter and LpFT4 terminator are indicated in italics and underlined italics, respectively. The ORF sequence is indicated in regular font and the start (ATG) and stop (TAG) codons are shaded.

FIG. 32. Sequence of LpCAB::Lp6G-FFT::LpFT4 expression cassette (SEQ ID No: 39). The regulatory sequences, LpRbcS promoter and LpFT4 terminator are indicated in italics and underlined italics, respectively. The ORF sequence is indicated in regular font and the start (ATG) and stop (TAG) codons are shaded.

Figure 33:
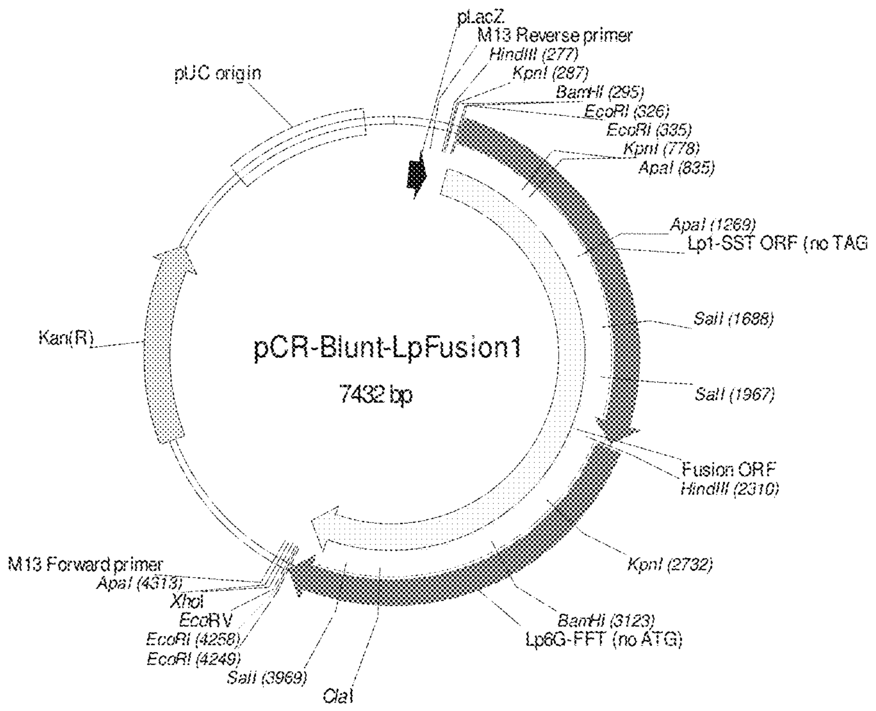

FIG. 33. The plasmid PCR Blunt-Lp1-SST_Lp6G-FFT FT fusion.

FIG. 34. Destination vectors containing the ryegrass RuBisCO (LpRbcs) promoter driving FT fusions 1 and 3. (A) pBS-LpRbcS::Lp1-SST_Lp6G-FFT::LpFT4 FT fusion1 and (B) pBS-LpRbcS::Lp1-SST-Lp6G-FFT::LpFT4 FT fusion 3.

FIG. 35. Sequence of LpRbcS::Lp1-SST_Lp6G-FFT::LpFT4 FT fusion 1 expression cassette (SEQ ID No: 40). The regulatory sequences, LpRbcS promoter and LpFT4 terminator are indicated in italics and underlined italics, respectively. The ORF sequence is indicated in regular font and the start (ATG) and stop (TAG) codons are shaded.

FIG. 36. Sequence of LpRbcS::Lp1-SST_Lp6G-FFT::LpFT4 FT fusion 3 expression cassette (SEQ ID No: 41). The regulatory sequences, LpRbcS promoter and LpFT4 terminator are indicated in italics and underlined italics, respectively. The ORF sequence is indicated in regular font and the start (ATG) and stop (TAG) codons are shaded. The amino acid sequence is indicated in bold (SEQ ID No: 42). Domains are highlighted as follows: the boxes indicate the highly conserved motifs in the family of the 32 glycoside hydrolases including invertases, fructosyltransferases and fructan exohydrolases which are involved in substrate binding and hydrolysis: double underlines show trans-membrane domains; and shaded boxes represent conservative domains among 32 glycoside hydrolases.

Figure 37:
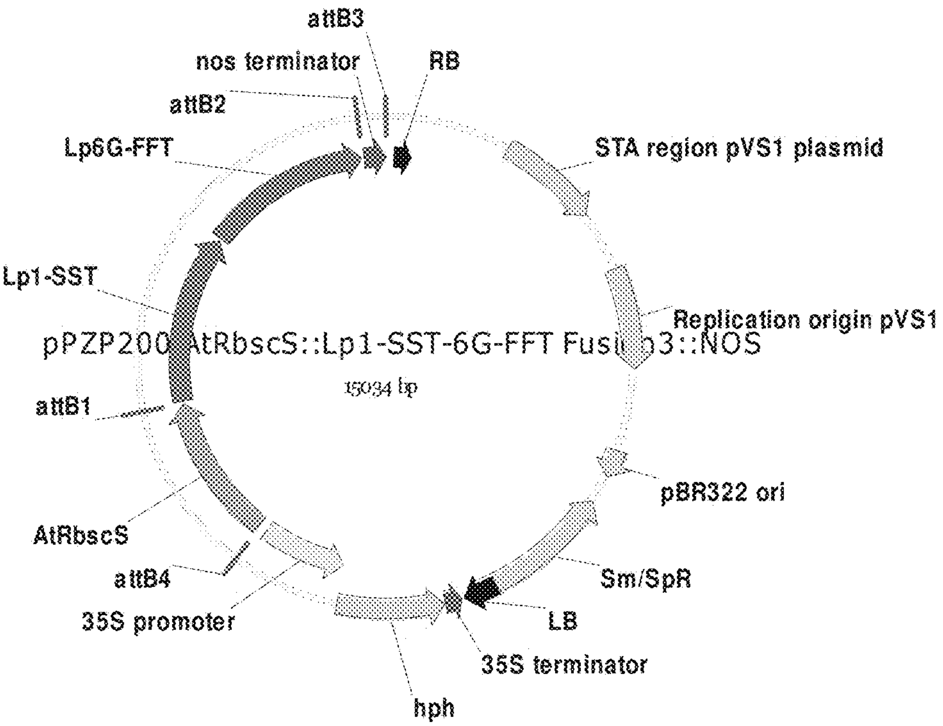

FIG. 37. Destination vector containing the *Arabidopsis* RuBisCO (AtRbcS) promoter driving FT fusion 3, pPZP200_AtRbcS::Lp1-SST_6G-FFT::nos FT fusion 3.

FIG. 38. Sequence of the AtRbcS::Lp1-SST-6G-FFT::nos FT fusion 3 expression construct (SEQ ID No: 43).

Figure 39:
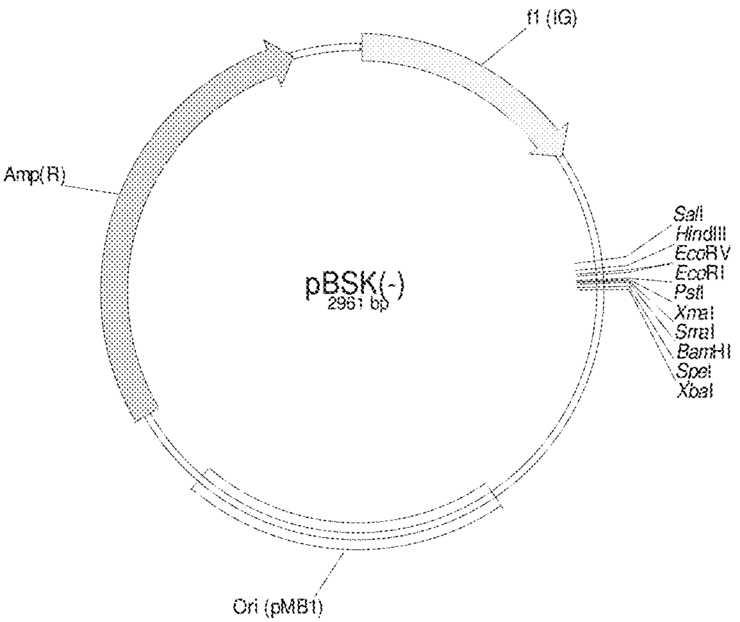

FIG. 39. Details of the base vector pBlueScript SK(−) from Promega, with the positions of the restriction endonuclease sites for cloning indicated.

Figure 40:
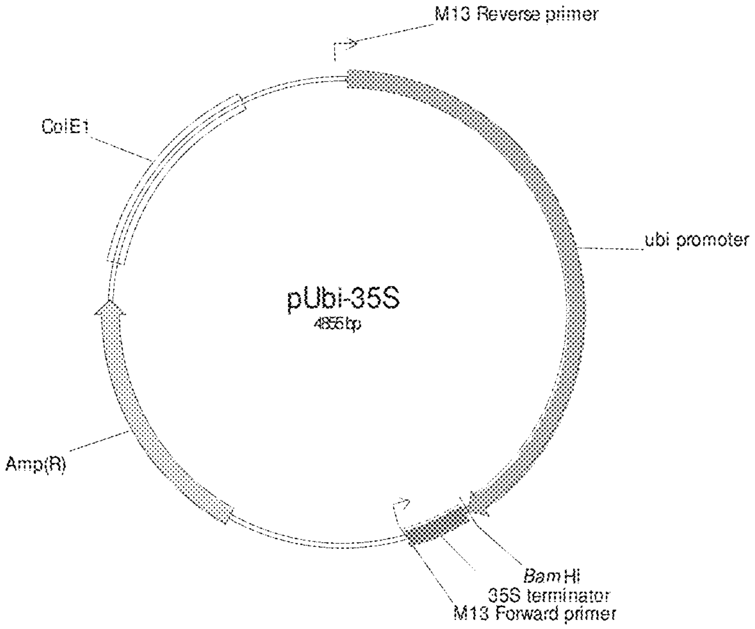

FIG. 40. Vector backbone used for construction of p-Ubi::Lp1-SST::35S and p-Ubi::Lp6G-FFT::35S (Ye et al., 2001).

FIG. 41. Representative sequence of a constitutive (Ubi) promoter combined with a FT fusion protein and a terminator sequence (SEQ ID No: 44). The regulatory sequences, Ubi promoter and LpFT4 terminator are indicated in italics and underlined italics, respectively. The ORF sequence is indicated in regular font and the start (ATG) and stop (TAG) codons are shaded.

FIG. 42. Representative sequence of a constitutive ((CAMV)35S$^2$) promoter combined with a FT fusion protein and a terminator sequence (SEQ ID No: 45). The regulatory sequences, (CAMV)35S$^2$ promoter and LpFT4 terminator are indicated in italics and underlined italics, respectively. The ORF sequence is indicated in regular font and the start (ATG) and stop (TAG) codons are shaded.

FIG. 43. Representative sequence of a constitutive (RUBQ2) promoter combined with a FT fusion protein and a terminator sequence (SEQ ID No: 46). The regulatory sequences, RUBQ2i promoter and LpFT4 terminator are indicated in italics and underlined italics, respectively. The ORF sequence is indicated in regular font and the start (ATG) and stop (TAG) codons are shaded.

FIG. 44. Representative sequence of a constitutive (OsAct1) promoter combined with a FT fusion protein and a terminator sequence (SEQ ID No: 47). The regulatory sequences, OsAct1 promoter and LpFT4 terminator are indicated in italics and underlined italics, respectively. The ORF sequence is indicated in regular font and the start (ATG) and stop (TAG) codons are shaded.

FIG. 45. Representative sequence of a tissue specific (tuber) promoter (Cathlnh) combined with a FT fusion protein and a terminator sequence (SEQ ID No: 48). The regulatory sequences, Cathlnh promoter and LpFT4 terminator are indicated in italics and underlined italics, respectively. The ORF sequence is indicated in regular font and the start (ATG) and stop (TAG) codons are shaded.

FIG. 46. Representative sequence of a stress regulated (Atrd29a) promoter combined with a FT fusion protein and a terminator sequence (SEQ ID No: 49). The regulatory sequences, Atrd29a promoter and LpFT4 terminator are indicated in italics and underlined italics, respectively. The ORF sequence is indicated in regular font and the start (ATG) and stop (TAG) codons are shaded.

FIG. 47. Representative sequence of a sucrose regulated (16R) promoter combined with a FT fusion protein and a terminator sequence (SEQ ID No: 50). The regulatory sequences, 16R promoter and LpFT4 terminator are indicated in italics and underlined italics, respectively. The ORF sequence is indicated in regular font and the start (ATG) and stop (TAG) codons are shaded.

Figure 48:
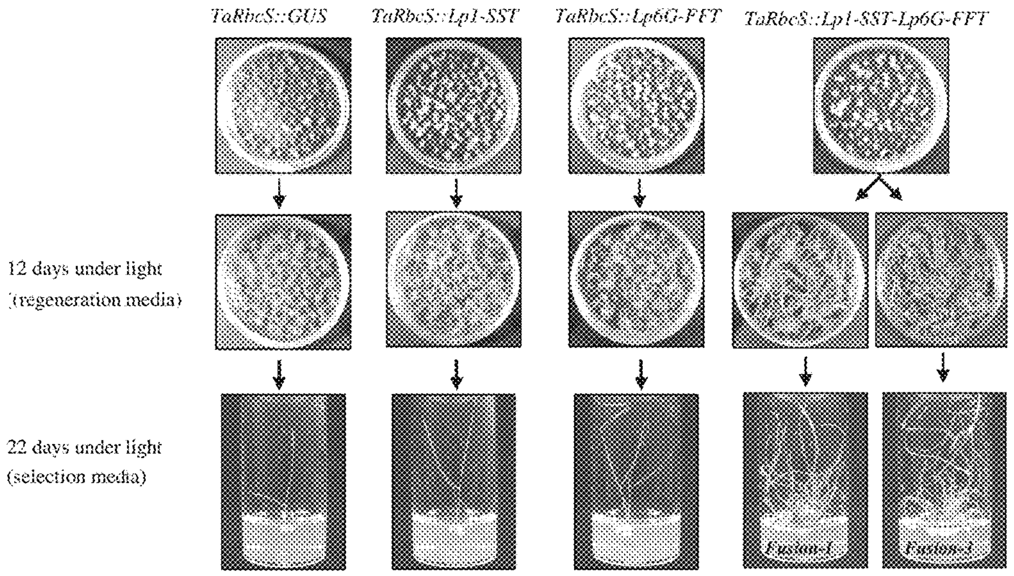

FIG. 48. Plant regeneration phenotypes of transgenic perennial ryegrass after co-transformation with the TaRbcS promoter light-regulated gene constructs (Table 1) and the pACH1 vector, with selection on hygromycin. The plants that contain either of the TaRbcS::Lp1-SST_Lp6G-FFT::TaRbcS FT fusion constructs show growth advantage under in vitro culture conditions thus allowing for their early identification and screening (far right column).

FIG. 49. Plant regeneration phenotypes of transgenic perennial ryegrass after co-transformation with the LpRbcS promoter light-regulated gene constructs with selection on hygromycin. The plants contain either the LpRbcS::Lp1-SST::LpFT4 or the LpRbcS::Lp1-SST_Lp6G-FFT::LPFT4 FT fusion 1/3 constructs. The plants that contain the FT fusion constructs show growth advantage under in vitro culture conditions FIG. 50. Mature plant phenotypes under glasshouse conditions. Representative samples of transgenic perennial ryegrass plants at the vegetative stage. The TaRbcS::Lp1-SST_Lp6G-FFT::LpFT4 FT fusion transgenic perennial ryegrass plants show enhanced growth performance with larger leaves, enhanced tillers, increased root growth compared to control, non-transgenic perennial ryegrass plants. The plants were trimmed equally three weeks earlier. Close up micrographs of the leaf blades indicate and increase leaf diameter in FT fusion transgenics.

Figure 51:
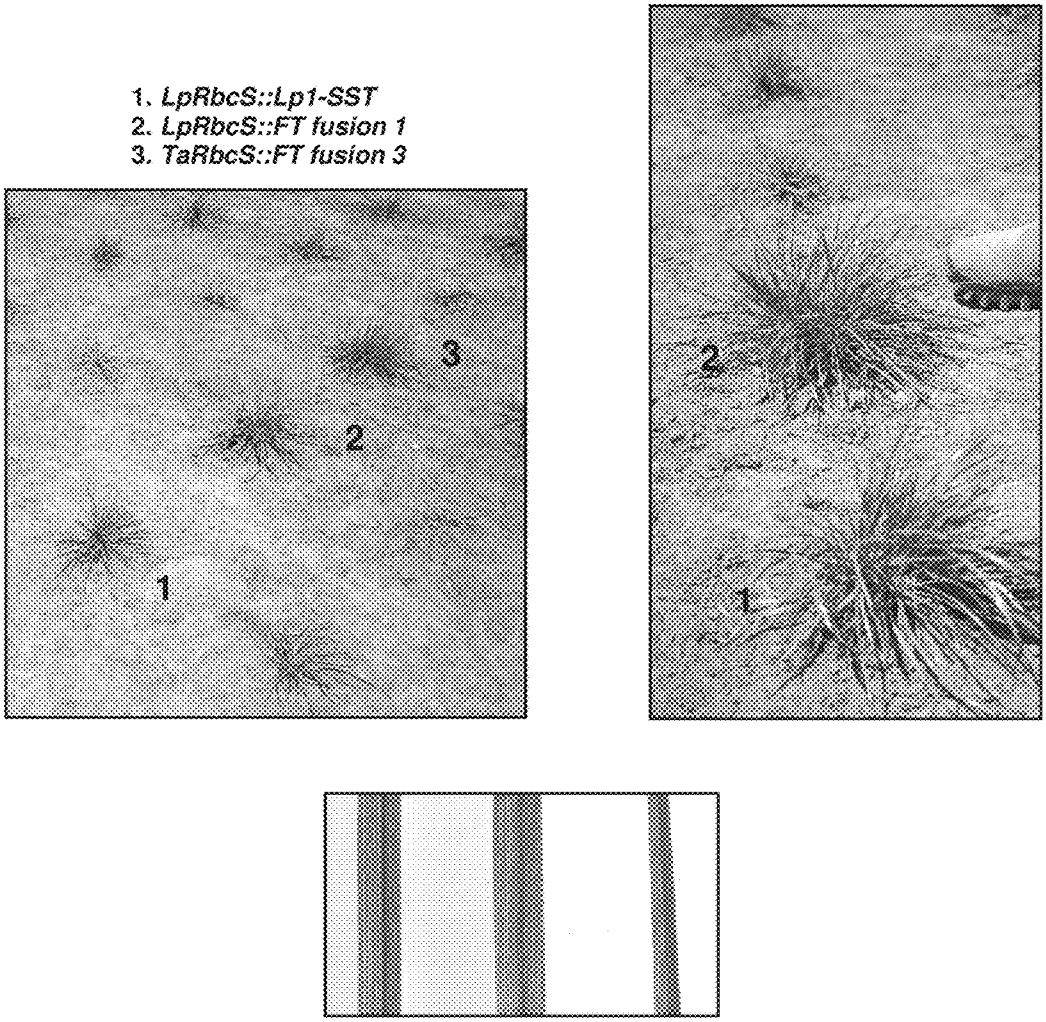

FIG. 51. Representative samples of transgenic perennial ryegrass mature plant phenotypes (4 weeks) under field conditions. The FT fusion transgenic perennial ryegrass plants show enhanced growth performance with larger leaves, enhanced tillers, increased root growth compared to control Lp1-SST transgenic perennial ryegrass plants.

Figure 52:
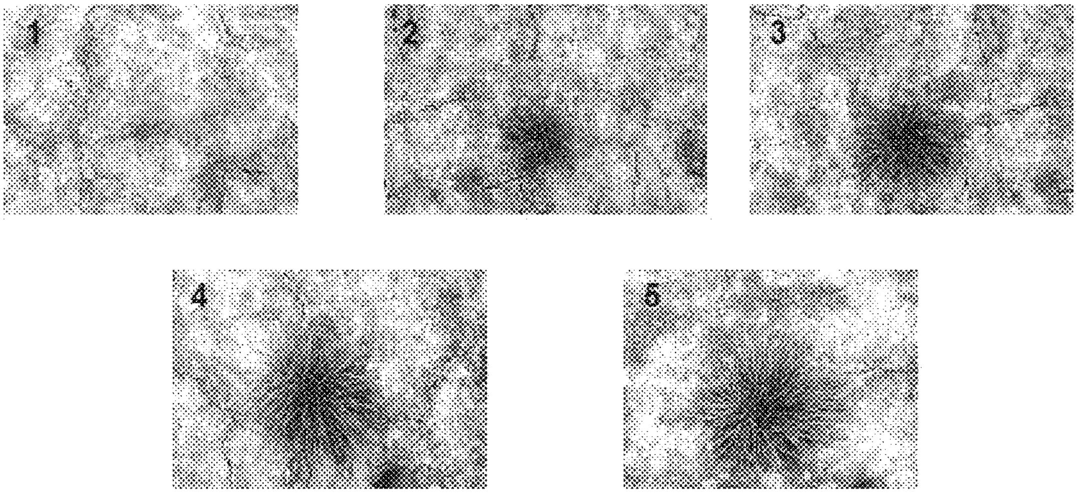

FIG. 52. Representative examples of phenotypic biomass scores (1—least biomass to 5—most biomass) of transgenic perennial ryegrass plants expressing FT fusion transgenes under field conditions.

Figure 53:
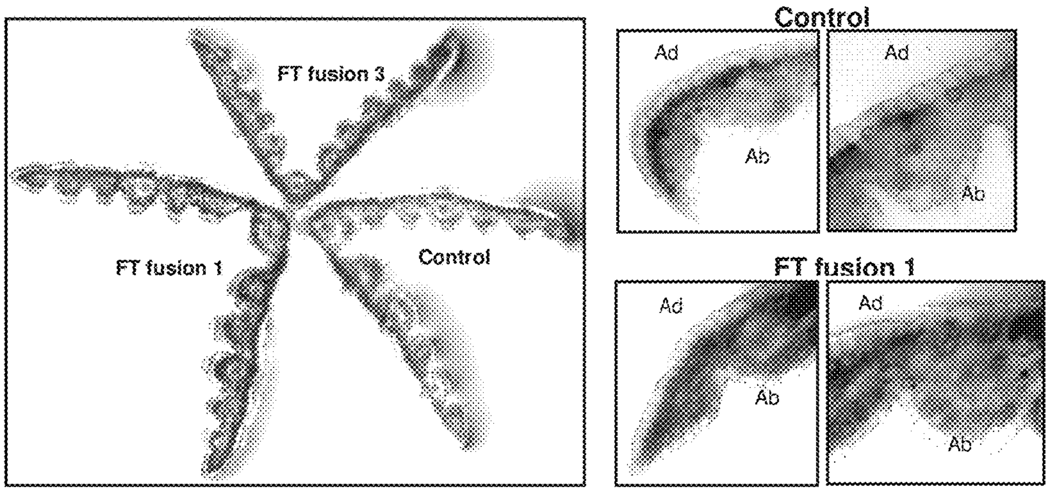

FIG. 53. Leaf phenotypes of transgenic perennial ryegrass. Representative samples of hand sections of leaf blades at vegetative stage. Left shows comparison of whole leaf sections, right magnified areas of leaf sections. Ad-Adaxial, Ab-abaxial.

Figure 54:
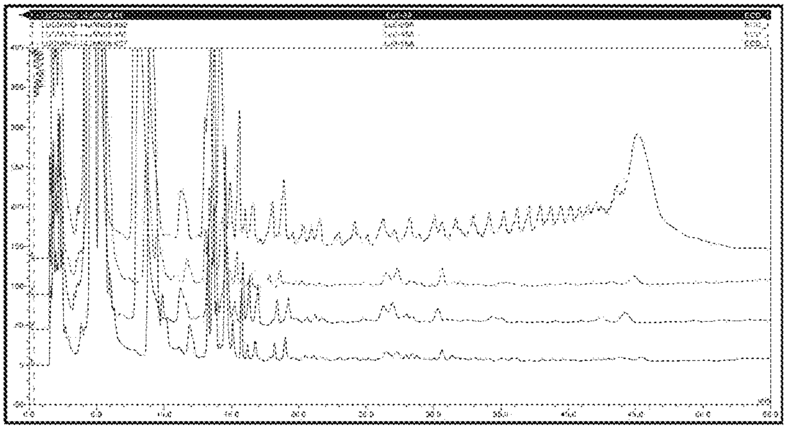

FIG. 54. Biochemical analysis (HPAEC) of fructan level and composition present in stable transgenic TaRbcS::Lp1-SST_Lp6G-FFT::TaRbcS FT fusion 3, TaRbcS::Lp1-SST::TaRbcS, TaRbcS::Lp6G-FFT::TaRbcS perennial ryegrass plants and control perennial ryegrass plants harbouring only the selectable marker (hph gene).

Figure 55:
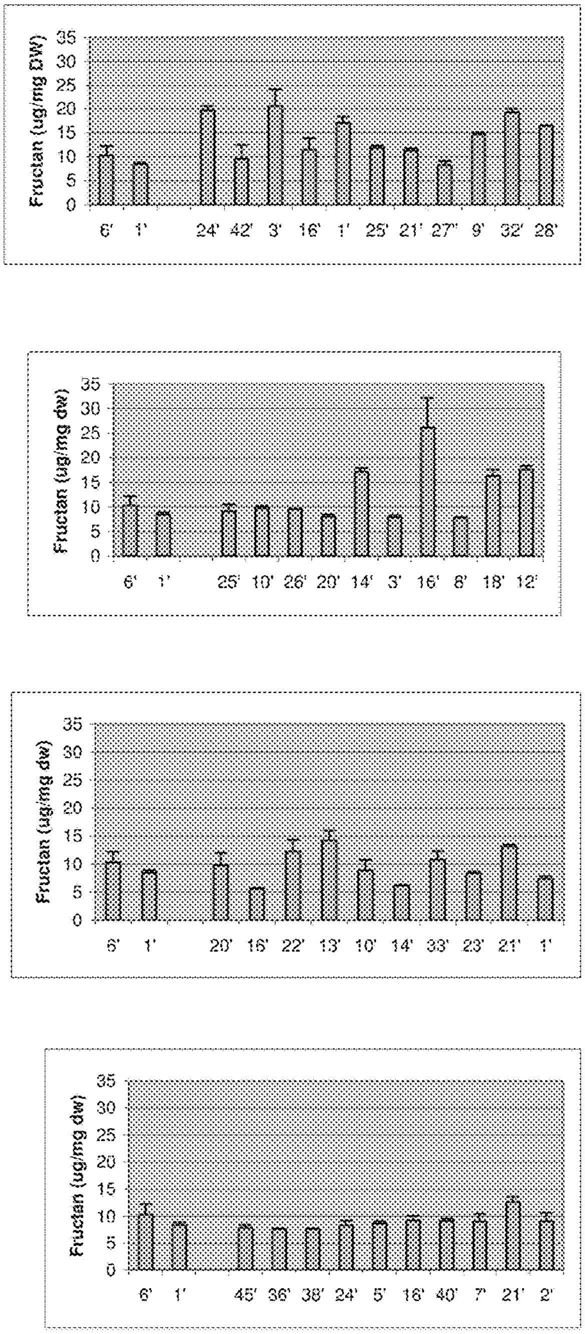

FIG. 55. Biochemical analysis (HPAEC) of total fructans present in whole tillers of (A) TaRbcS::Lp1-SST_Lp6G-FFT::TaRbcS FT fusion 1, (B) TaRbcS::Lp1-SST_Lp6G-FFT::TaRbcS FT fusion 3, (C) TaRbcS::Lp1-SST::TaRbcS, and (D) TaRbcS::6G-FFT::TaRbcS transgenic perennial ryegrass plants compared to control perennial ryegrass plants (lanes 6' and 1'), harbouring only the selectable marker (hph gene).

Figure 56:
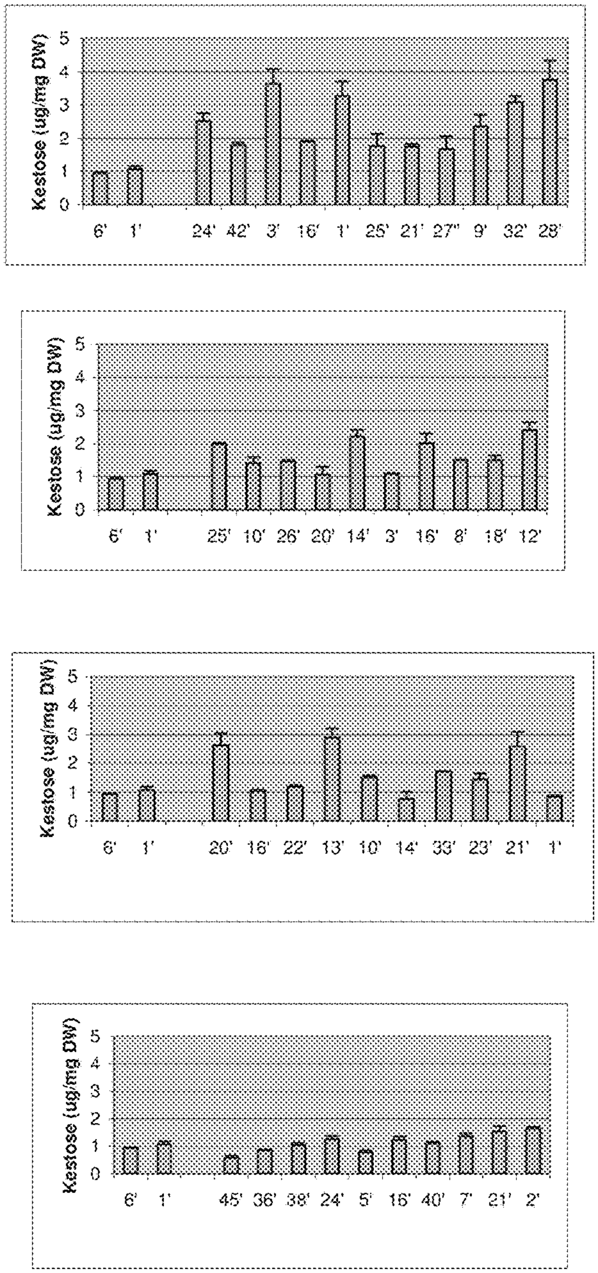

FIG. 56. Biochemical analysis (HPAEC) of 1-kestose present in whole tillers of (A) TaRbcS::Lp1-SST_Lp6G-FFT::TaRbcS FT fusion 1, (B) TaRbcS::Lp1-SST_Lp6G-FFT::TaRbcS FT fusion 3, (C) TaRbcS::Lp1-SST::TaRbcS, and (D) TaRbcS::6G-FFT::TaRbcS transgenic perennial ryegrass plants compared to control perennial ryegrass plants (lanes 6' and 1'), harbouring only the selectable marker (hph gene).

Figure 57:
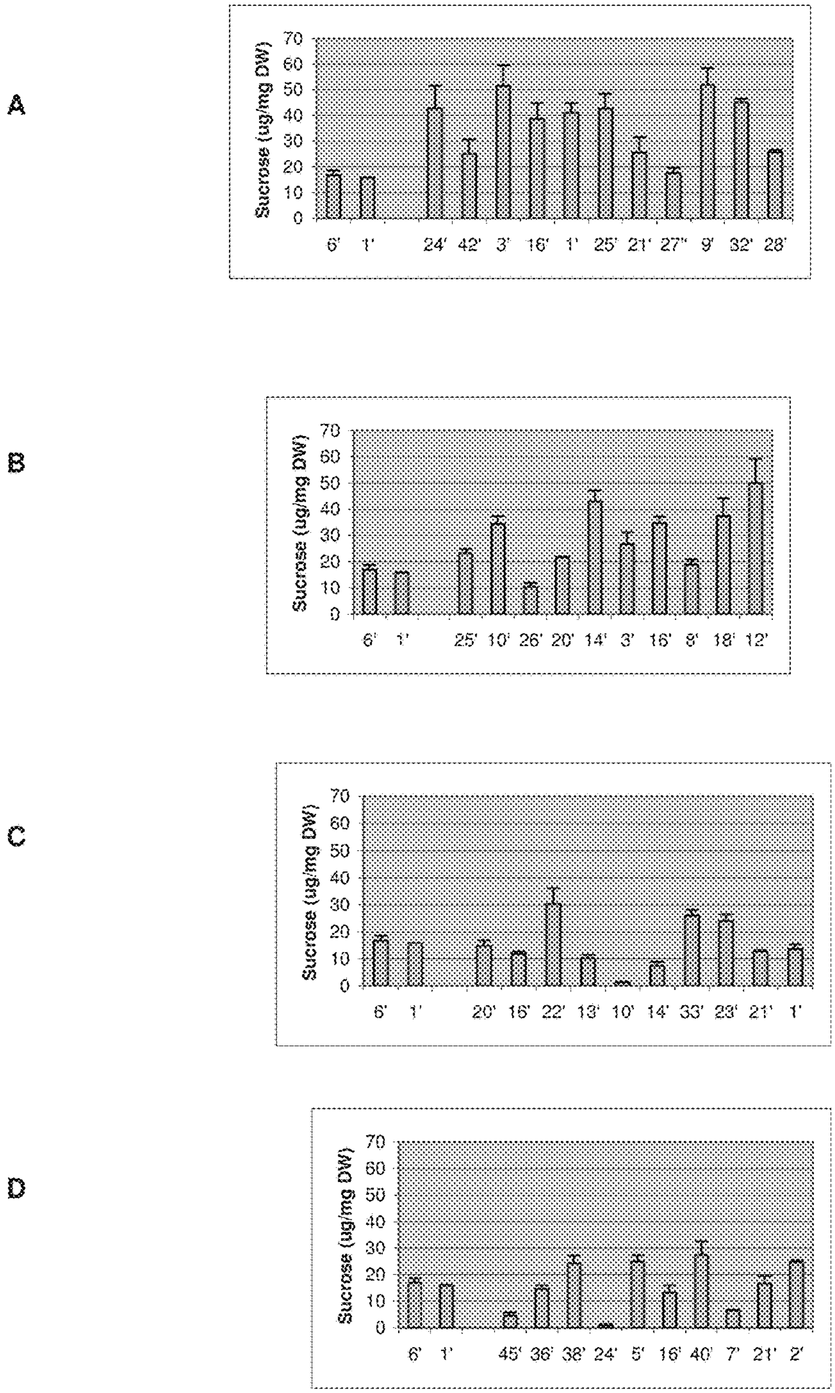

FIG. 57. Biochemical analysis (HPAEC) of sucrose present in whole tillers of (A) TaRbcS::Lp1-SST_Lp6G-FFT::TaRbcS FT fusion 1, (B) TaRbcS::Lp1-SST_Lp6G-FFT::TaRbcS FT fusion 3, (C) TaRbcS::Lp1-SST::TaRbcS, and (D) TaRbcS::6G-FFT::TaRbcS transgenic perennial ryegrass plants compared to a control perennial ryegrass plants (lanes 6' and 1'), harbouring only the selectable marker (hph gene).

Figure 58:
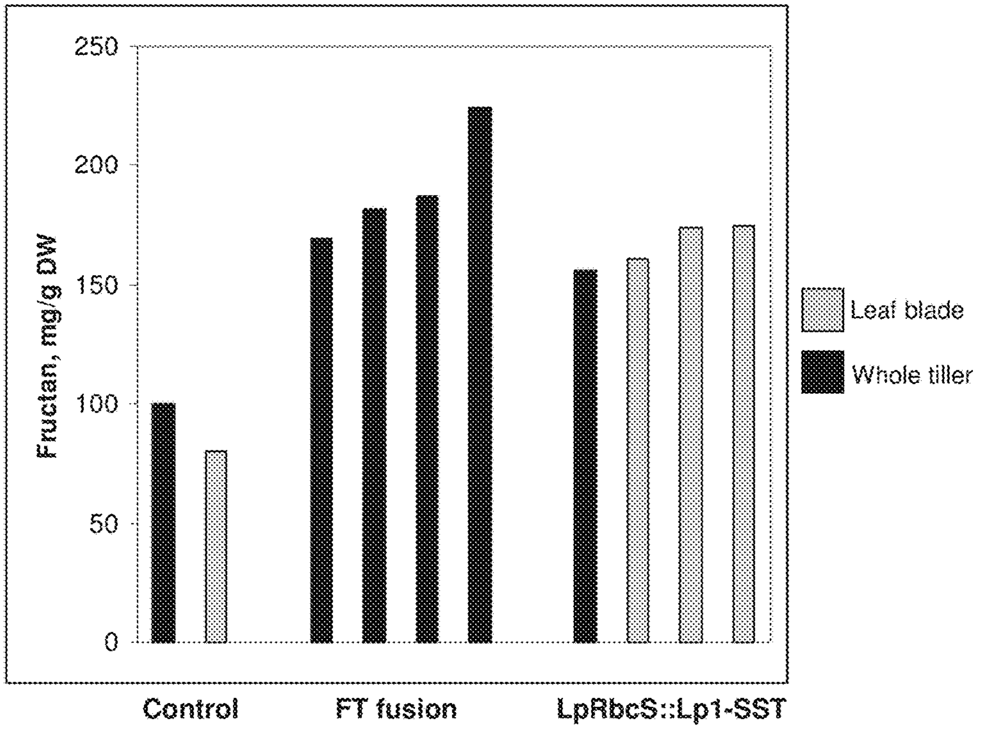

FIG. 58. Fructan levels in whole tillers and leaf blades in wild-type (control) and FT fusion and LpRbcS::Lp1-SST transgenic perennial ryegrass plants grown under field conditions and harvested in December 2009.

Figure 59:
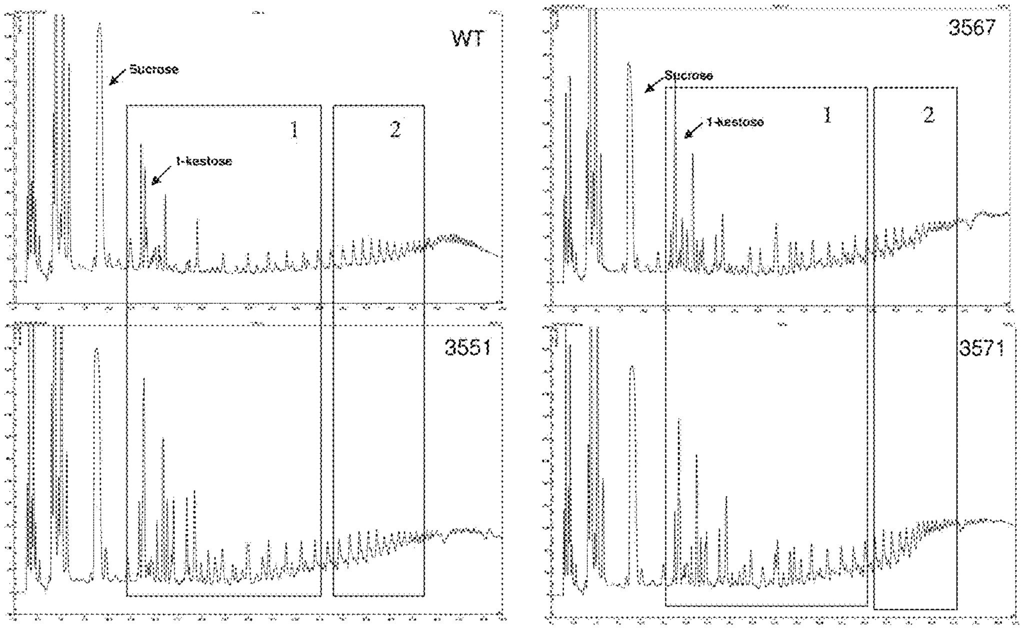

FIG. 59. Fructan composition in leaf blades of wild-type and LpRbcS::Lp1-SST transgenic perennial ryegrass plants grown under field conditions. Box 1 represents low DP fructan (DP up to 10-15). Box 2 represents high DP fructan (DP higher than 10-15).

Figure 60:
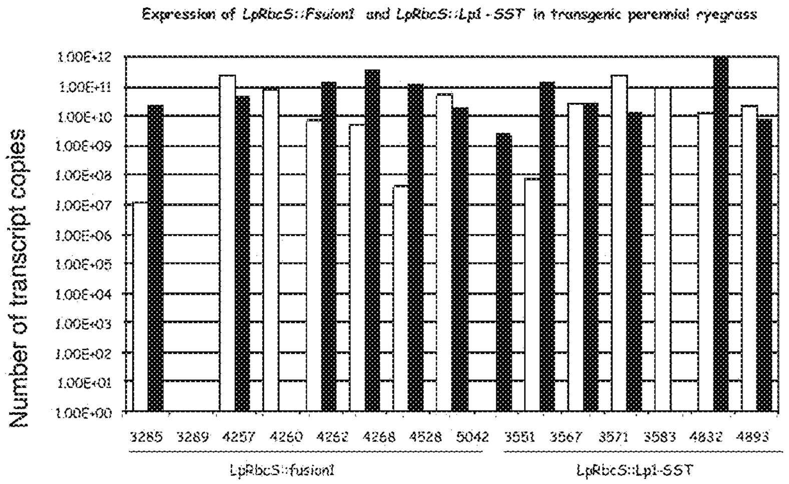

FIG. 60. Transgene expression in whole tillers of LpRbcS FT fusion and LpRbcS::Lp1-SST transgenic perennial ryegrass plants grown under field conditions. Samples were collected in November (white bars) and December (black bars) 2009. Samples were normalised against endogenous histone expression and are presented as number of transcript copies per 35 ng of RNA.

Figure 61:
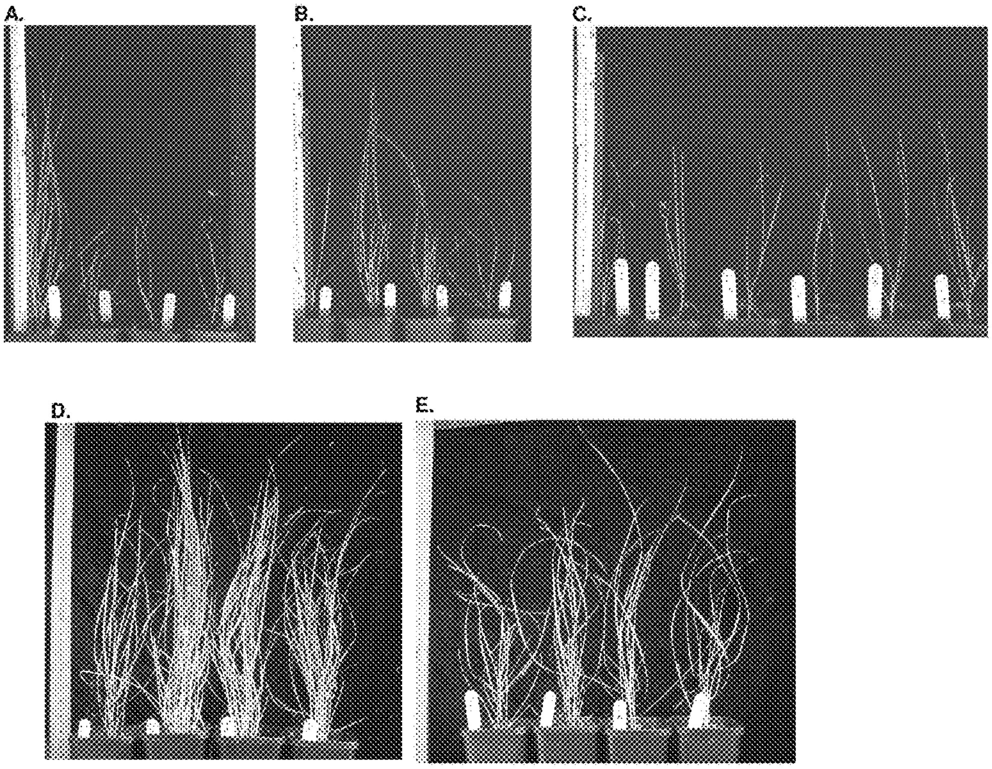

FIG. 61. Phenotypic analysis of the transgenic perennial ryegrass after 7 weeks (A-C) and 12 weeks (D-E) propagation in potting mix from a single tiller. TarbcS::Lp1-SST_Lp6G-FFT::Tarbcs FT fusion 1 (A, D) and TarbcS::Lp1-SST_Lp6G-FFT::Tarbcs FT fusion 3 (B) plants, show greater leaf length and number of tillers in fusion plants compared to the control plants expressing only the hph gene (C, E)

Figure 62:
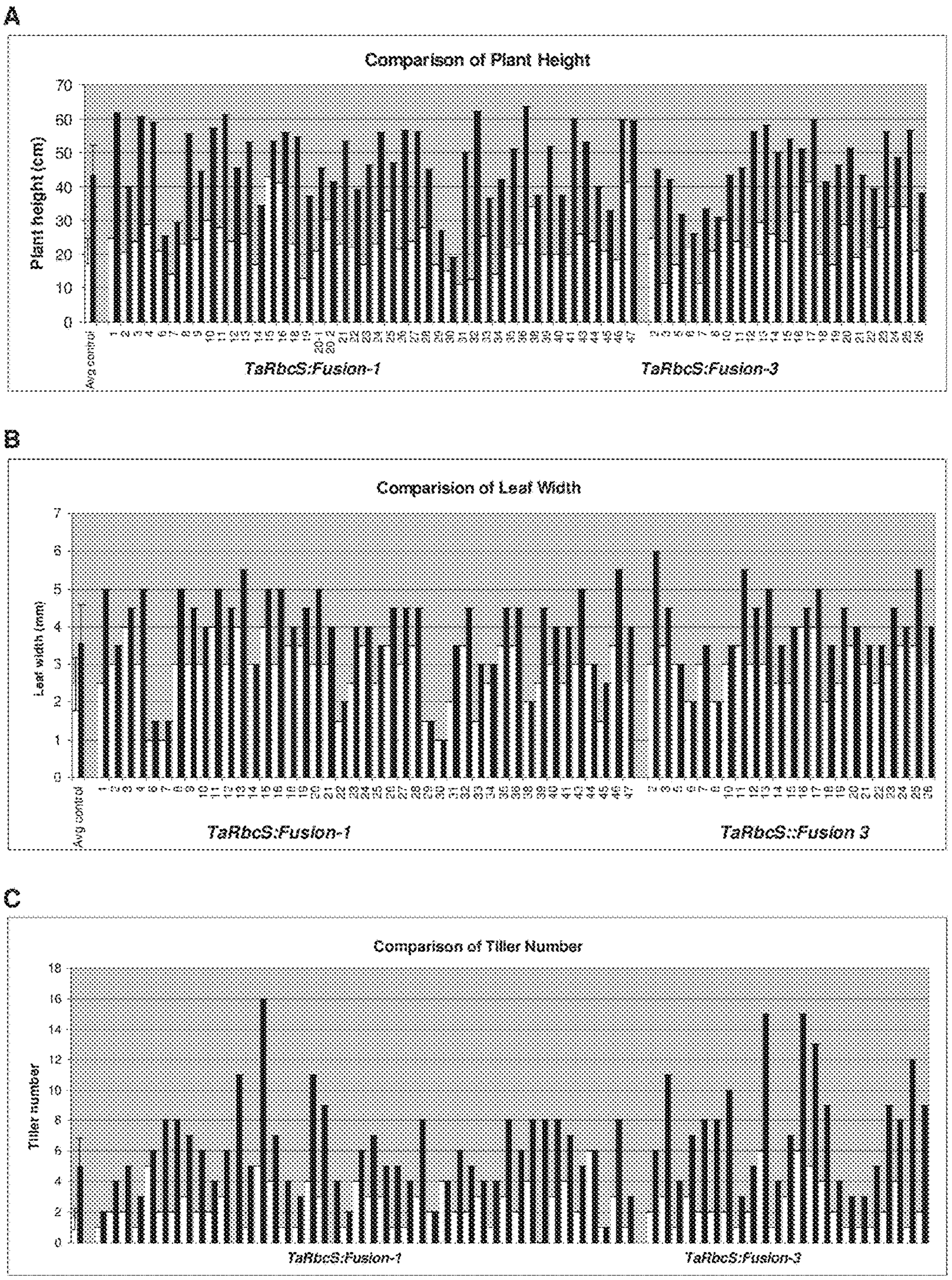

FIG. 62. Quantitative phenotypic analysis of the transgenic TarbcS::Lp1-SST_Lp6G-FFT::Tarbcs FT fusion 1 and TarbcS::Lp1-SST_Lp6G-FFT::Tarbcs FT fusion 3 plants after 7 weeks (white bars) and 12 weeks (black bars) growth. Measurements were conducted for plant height (A), leaf width (B) and tiller number (C) compared to the average of 8 control plants expressing only the hph gene.

Figure 63:
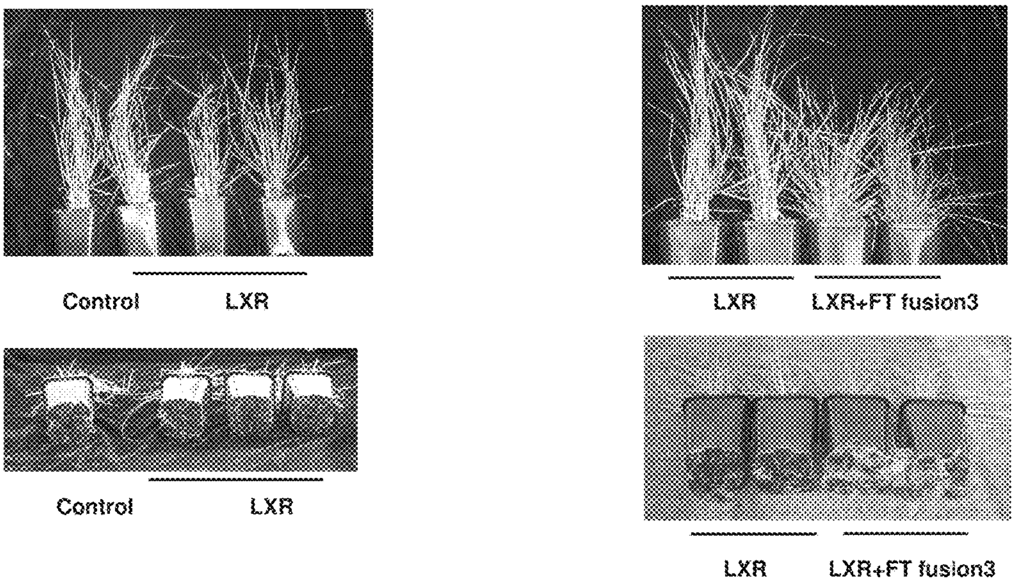

FIG. 63. Transgenic perennial ryegrass plants expressing LXR® technology alone (AtMYB32::IPT), LpRbcS::Lp1-SST_Lp6G-FFT::LpFT4 FT fusion 3 alone, as well as LXR® and LpRbcS::Lp1-SST_Lp6G-FFT::LpFT4 FT fusion 3 together under glasshouse conditions.

Figure 64:
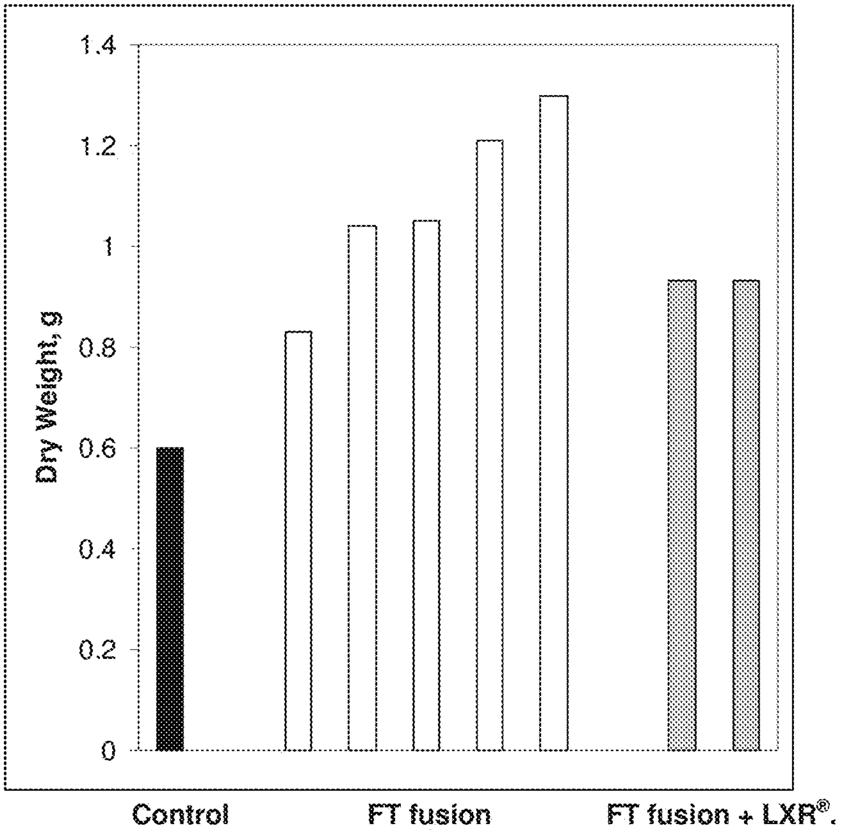

FIG. 64. Herbage dry weight analysis of GOI-ve control (average of five lines) and independent FT fusion alone or the FT fusion plus LXR® transgenic perennial ryegrass plants, grown under glasshouse conditions and collected 6 weeks post-trim.

Figure 65:
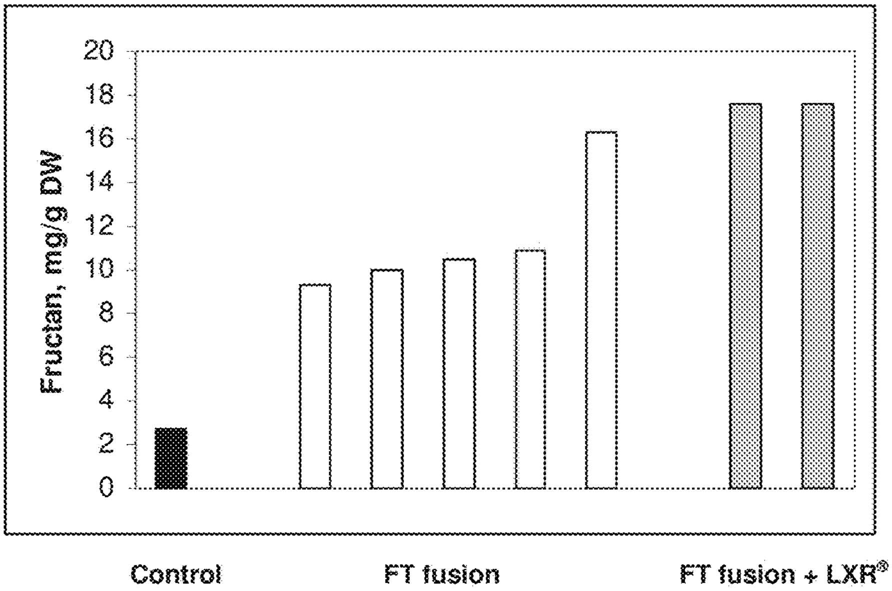

FIG. 65. Fructan levels in leaf blades of GOI-ve control (average of five lines) and independent FT fusion alone or FT fusion plus LXR® transgenic perennial ryegrass plants, grown under glasshouse conditions.

FIG. 66. Transgenic tall fescue plants expressing LpRbcS::Lp1-SST_Lp6G-FFT::LpFT4 FT fusion 3 under glasshouse conditions.

Figure 67:
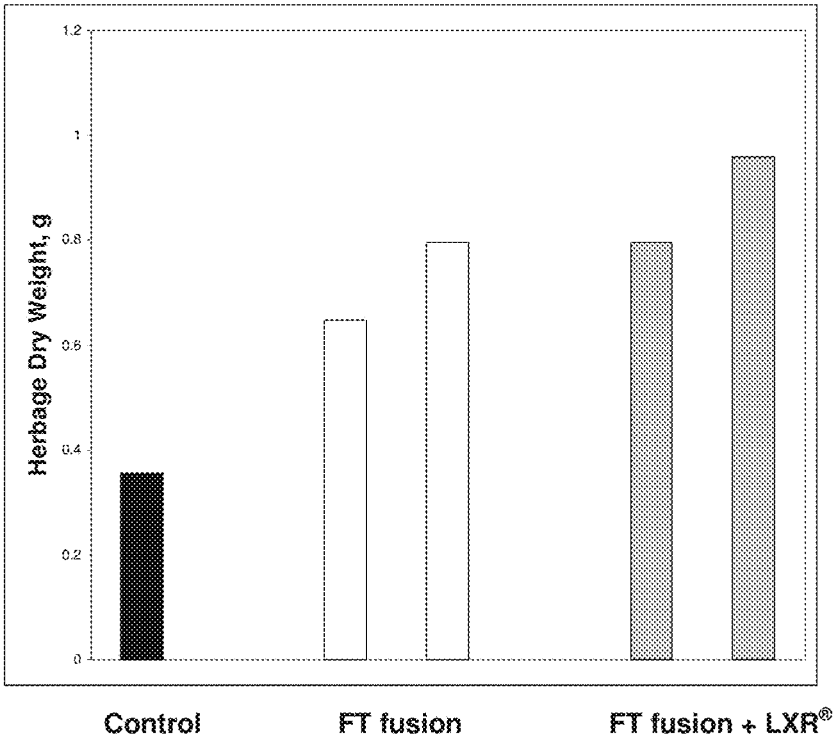

FIG. 67. Herbage dry weight analysis of glass house grown GOI-ve control (average of five lines) and independent FT fusion alone or FT fusion plus LXR® transgenic tall fescue plants.

Figure 68:
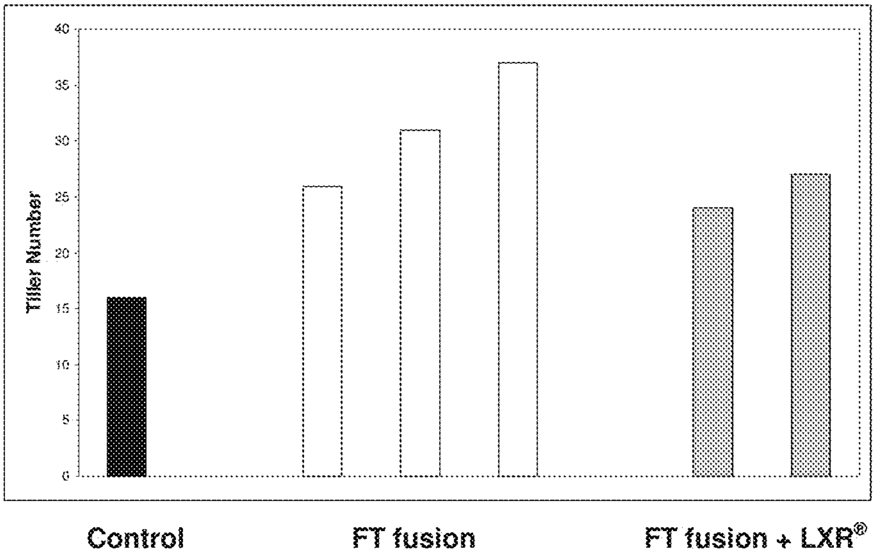

FIG. 68. Tiller number of glass house grown GOI-ve control (average of five lines) and independent FT fusion alone or FT fusion plus LXR® transgenic tall fescue plants.

Figure 69:
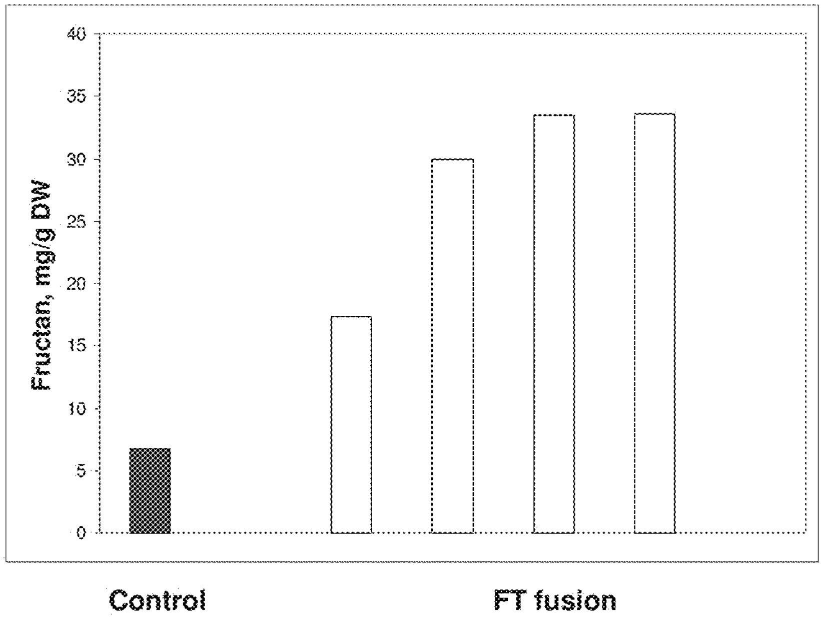

FIG. 69. Fructan accumulation in leaf blades of glass house grown GOI-ve control (average of five lines) and independent transgenic tall fescue lines expressing the FT fusion.

FIG. 70. Plant regeneration phenotypes of transgenic wheat plants after transformation with the light-regulated gene constructs. The transgenic wheat plants growing in vitro that contain the Lp1-SST_Lp6G-FFT FT fusion construct show growth advantage under in vitro culture conditions thus allowing for their early identification and screening. The superior growth phenotype of the transgenic wheat FT fusion lines was observed during the early stages of in vitro plant regeneration conducted on tissue culture plates. Six weeks after incubation under light conditions the calli showed further developed in vitro growing tillers/shoots (panel A) and more specifically further developed in vitro growing roots (panel B) in the transgenic wheat plants growing in vitro that contain the Lp1-SST_Lp6G-FFT FT fusion construct compared to the control plants.

Figure 71:
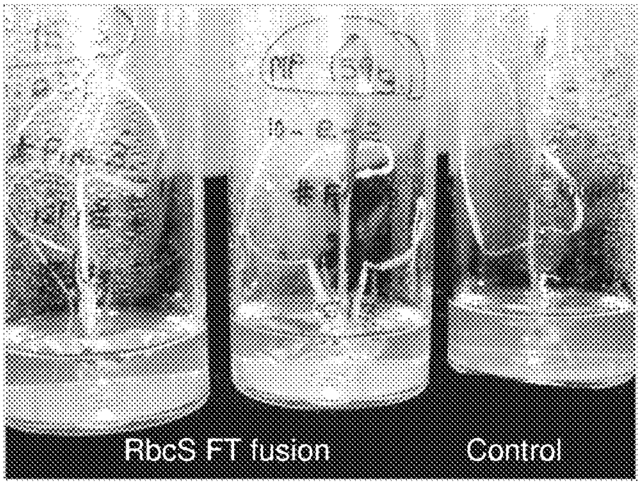

FIG. 71. The transgenic wheat plants that contain the TaRbcS::Lp1-SST_Lp6G-FFT::TaRbcS FT fusion construct showed an obvious early increase in tiller number as compared to control plants growing under (A) 2 months in in vitro conditions.

FIG. 72. Transgenic wheat plants that contain FT fusion constructs showed an obvious early increase in tiller number as compared to control plants growing under glasshouse conditions.

Figure 73:
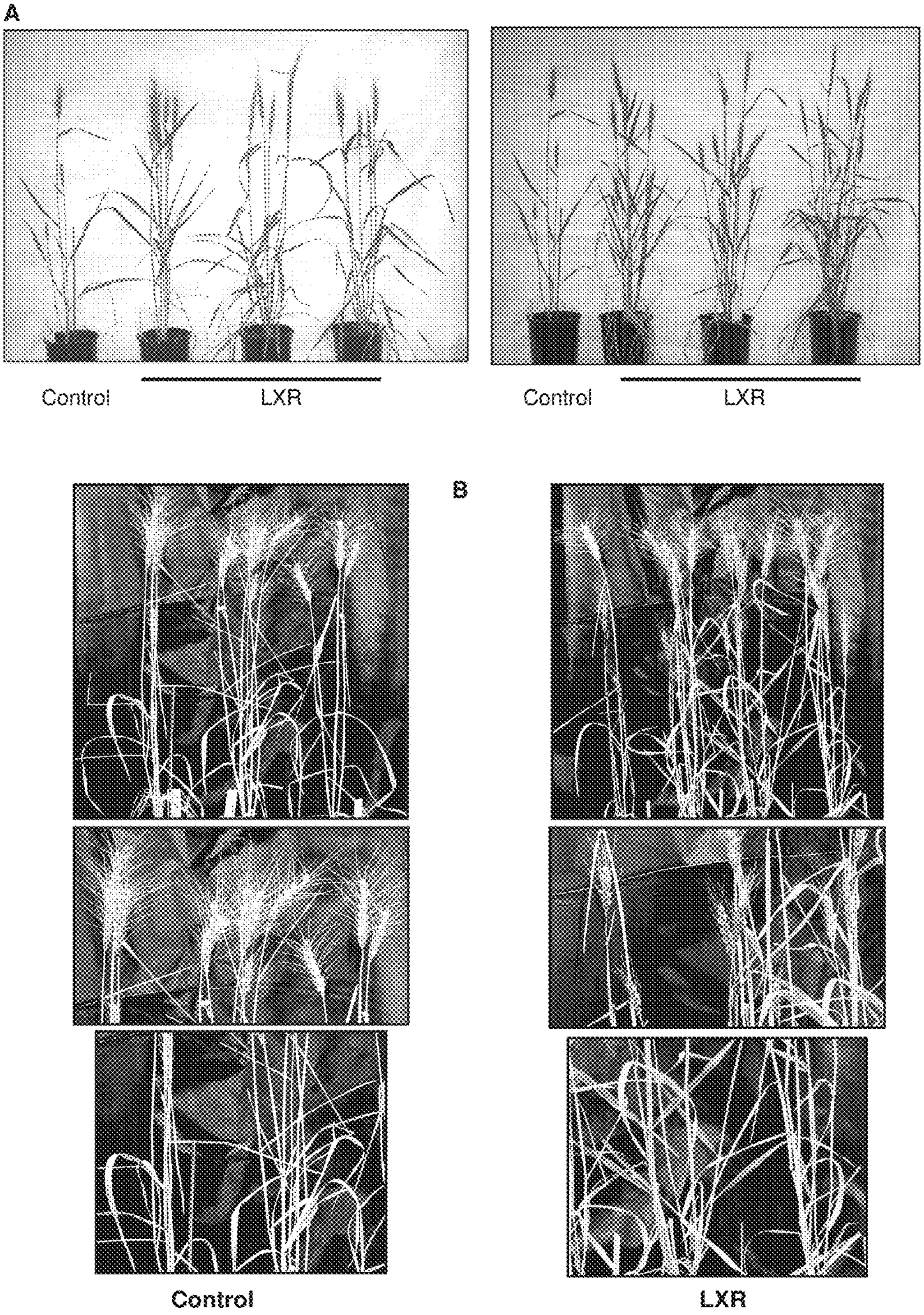

FIG. 73. The transgenic wheat plants that contain LXR® technology showed an obvious early increase in tiller number as compared to control plants under glasshouse conditions (A). They also showed and increase of photosynthetic tissue after 35 days under glasshouse conditions (B).

Figure 74:
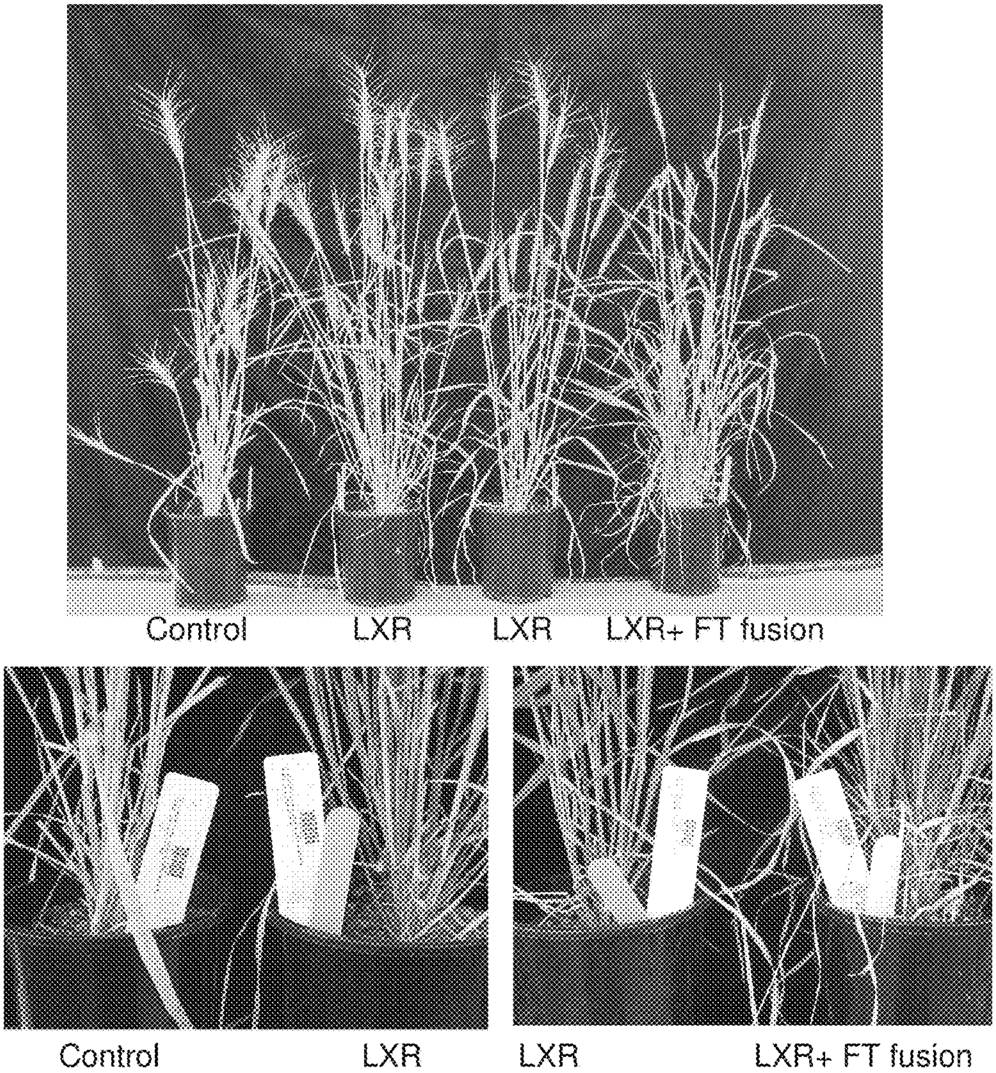

FIG. 74. Phenotypic analysis of transgenic wheat plants expressing LXR® technology alone (AtMYB3::IPT::35S), TaRbcS::Lp1-SST_Lp6G-FFT::TaRbcS FT fusion 3 alone, as well as LXR® and TaRbcS::Lp1-SST_Lp6G-FFT::TaRbcS FT fusion 3 together under glasshouse conditions.

Figure 75:
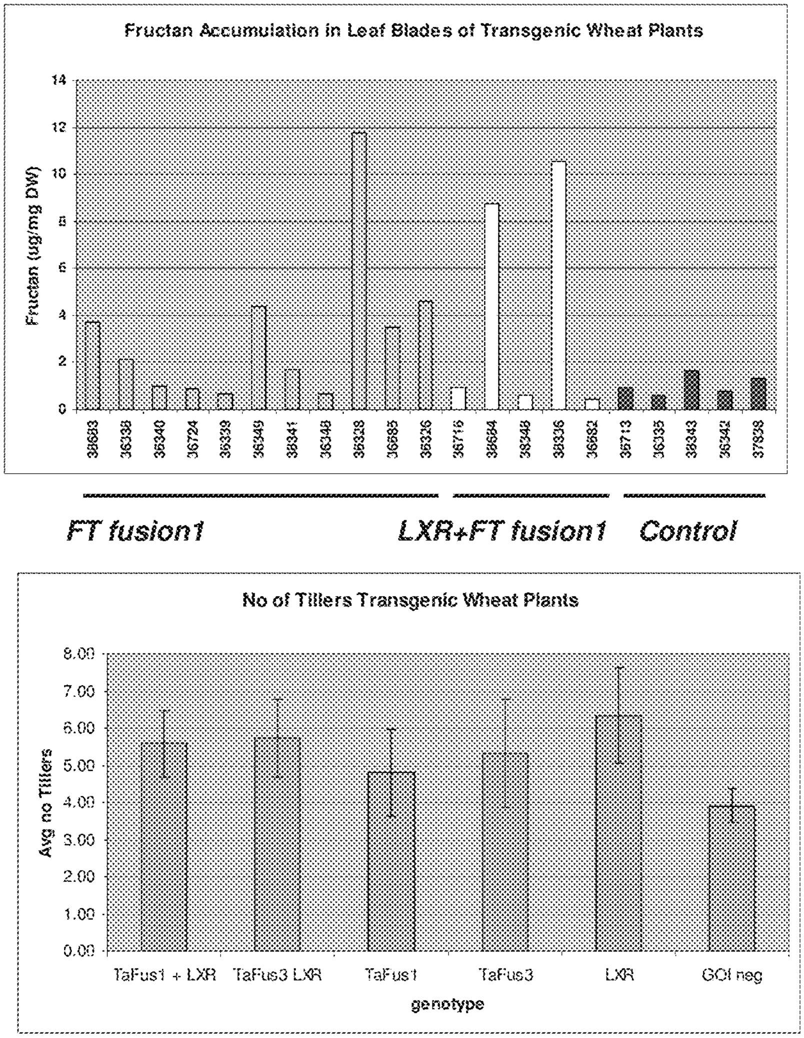

FIG. 75. Fructan accumulation and tiller number in transgenic wheat plants containing either FT fusion constructs alone or LXR® plus FT fusion constructs, as compared to transformed gene of interest minus (GOI−) controls.

Figure 76:
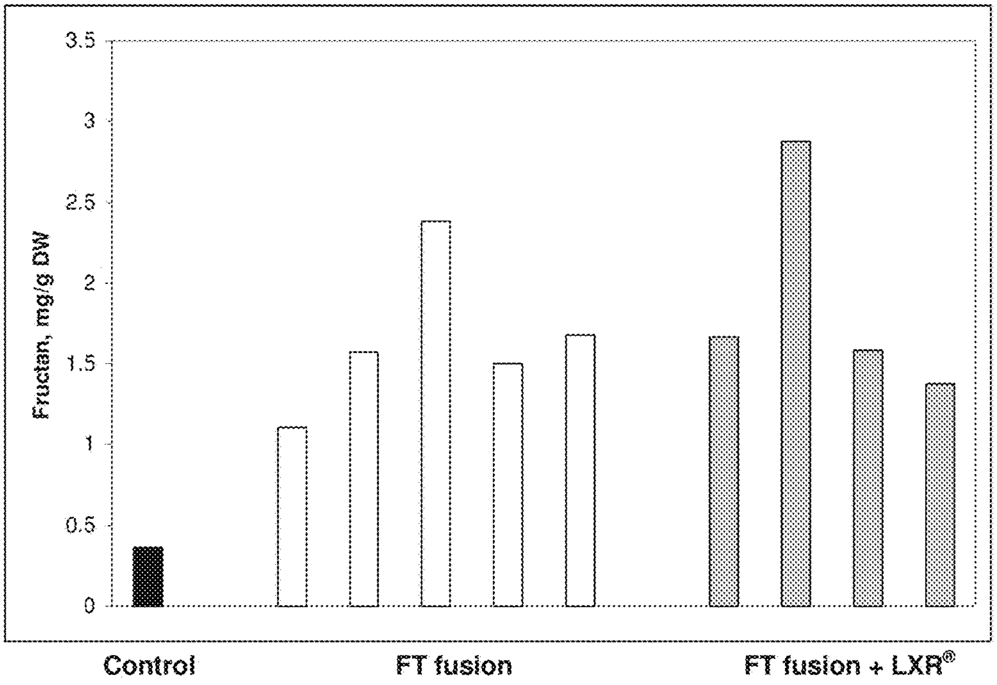

FIG. 76. Fructan accumulation in $T_1$ GOI-ve control, FT fusion alone and LXR® plus FT fusion transgenic wheat plants nine weeks after sowing. The fructan level in the control represents the data average obtained from six GOI-ve plants.

Figure 77:
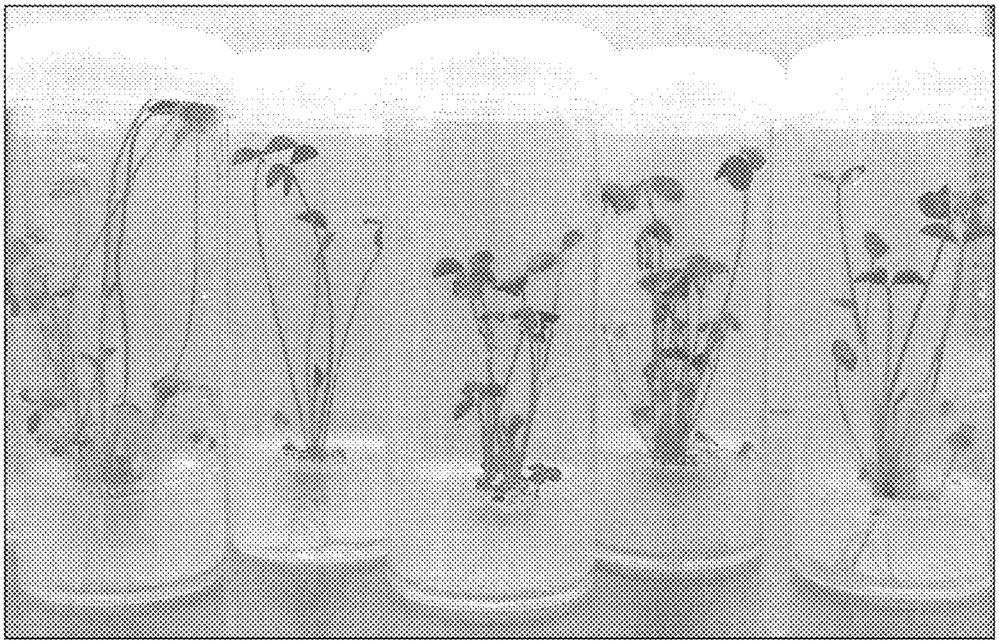

FIG. 77. Phenotype of transgenic white clover plants expressing LXR®, AtRbcS::Lp1-SST-6G_FF::nos FT fusion or LXR® plus AtRbcS::Lp1-SST-6G_FF::nos FT fusion constructs as compared to transformed GOI minus controls.

Figure 78:
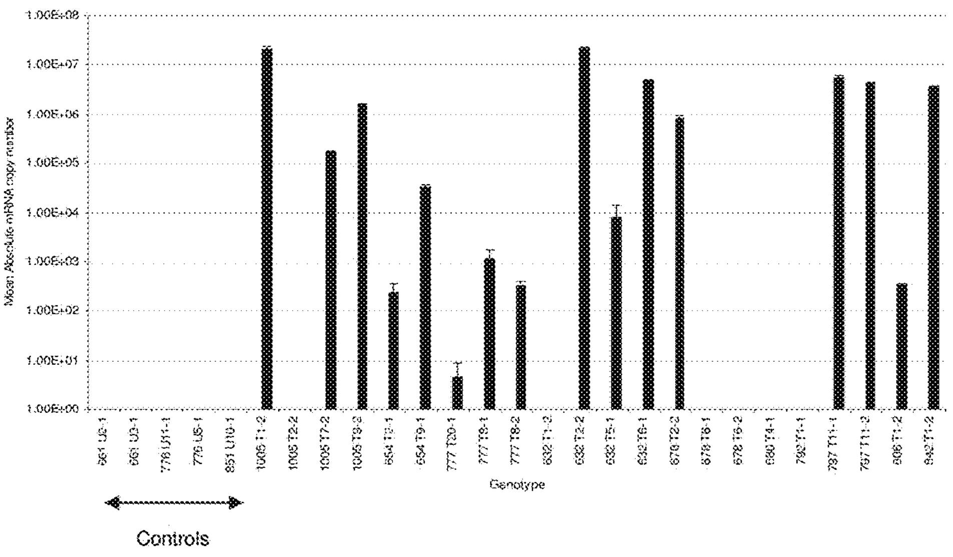

FIG. 78. Transgene expression levels of the FT fusion transgene driven by the AtRbcS promoter in white clover plants. Controls were wild type plants. Samples were normalised against endogenous histone expression and are presented as number of transcript copies per 35 ng of RNA.

Figure 79:
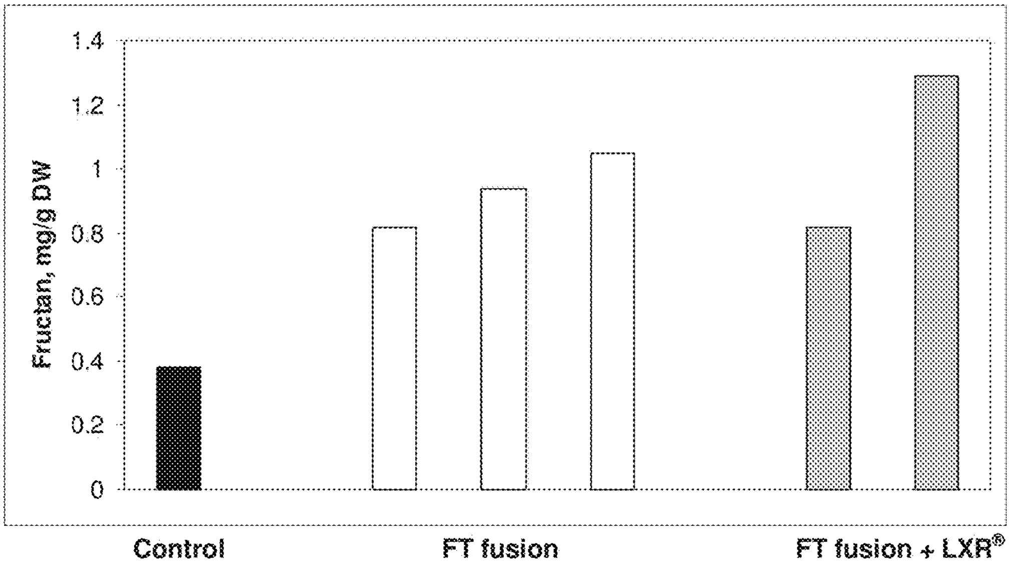

FIG. 79. Fructan accumulation in wild-type control, AtRbcS FT fusion and AtRbcS FT fusion plus LXR® transgenic white clover lines.

Figure 80:
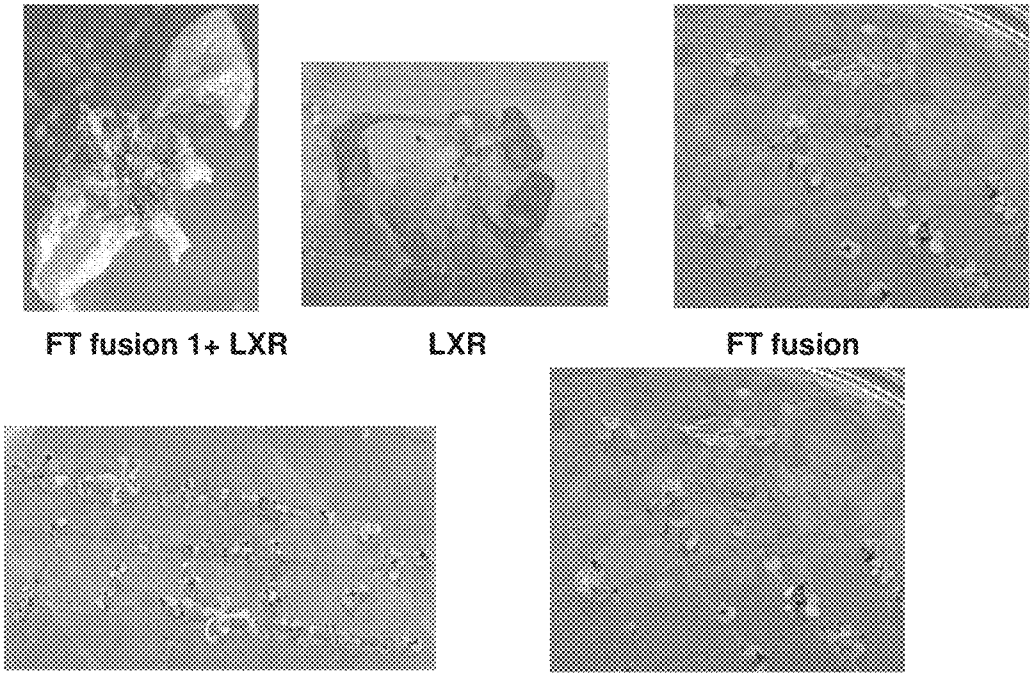

FIG. 80. Phenotype of transgenic *Arabidopsis* plants expressing LXR®, AtRbcS::Lp1-SST-6G_FF::nos FT fusion or LXR® plus AtRbcS::Lp1-SST-6G_FF::nos FT fusion constructs as compared to transformed GOI minus controls.

Figure 81:
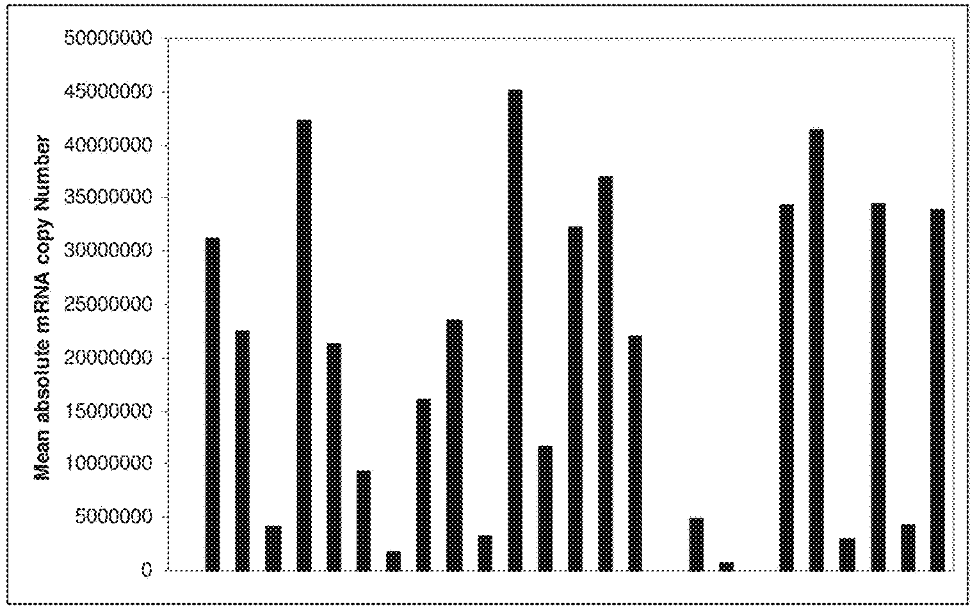

FIG. 81. Transgene expression levels of the FT fusion transgene driven by the AtRbcS promoter in *Arabidopsis* plants. Controls were wild type plants. Samples were normalised against endogenous histone expression and are presented as number of transcript copies per 35 ng of RNA.

Figure 82:
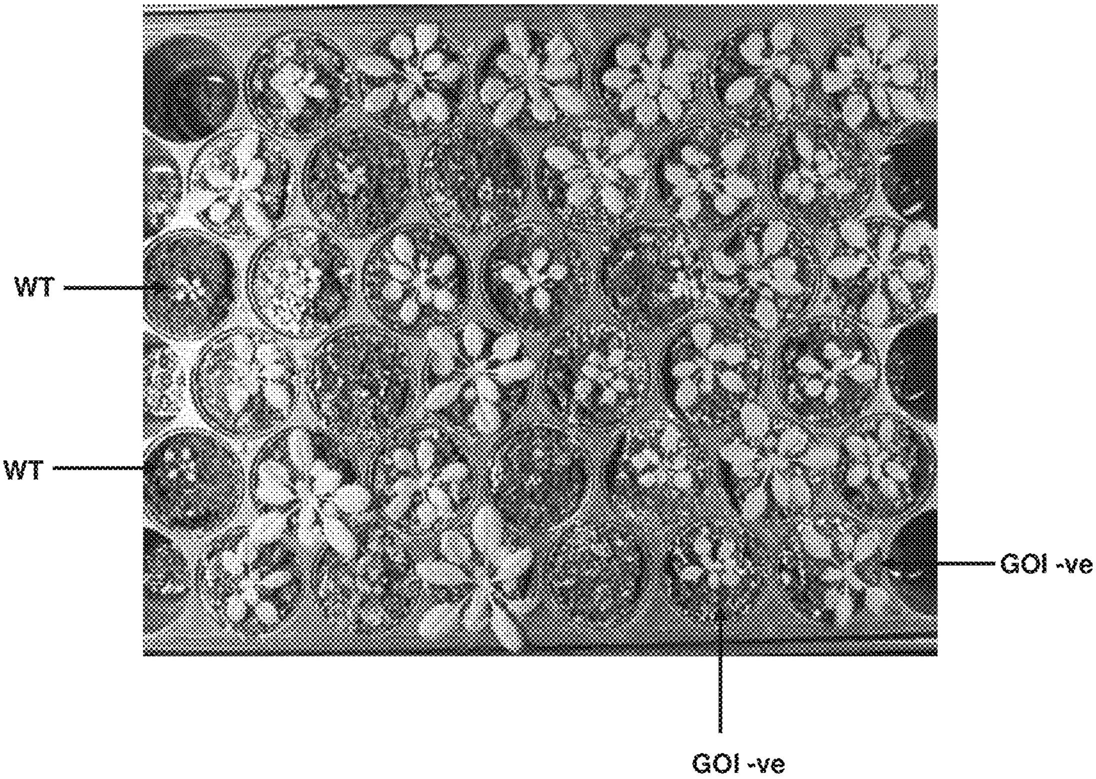

FIG. 82. Transgenic $T_2$ FT fusion *Arabidopsis* plants grown in soil.

Figure 83:
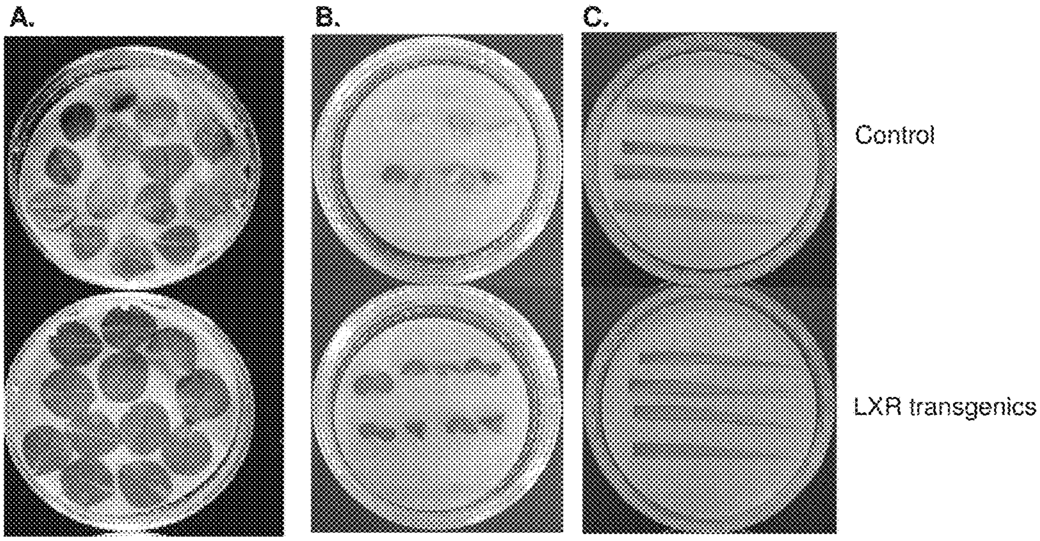

FIG. 83. Leaves from A. white clover, B. canola and C. wheat plants displaying delayed leaf senescence (leaves from LXR® transgenic plants, lower images) as compared to negative control plants (leaves from control plants, upper images) 7-20 days following detachment of leaves from plants.

Figure 84:
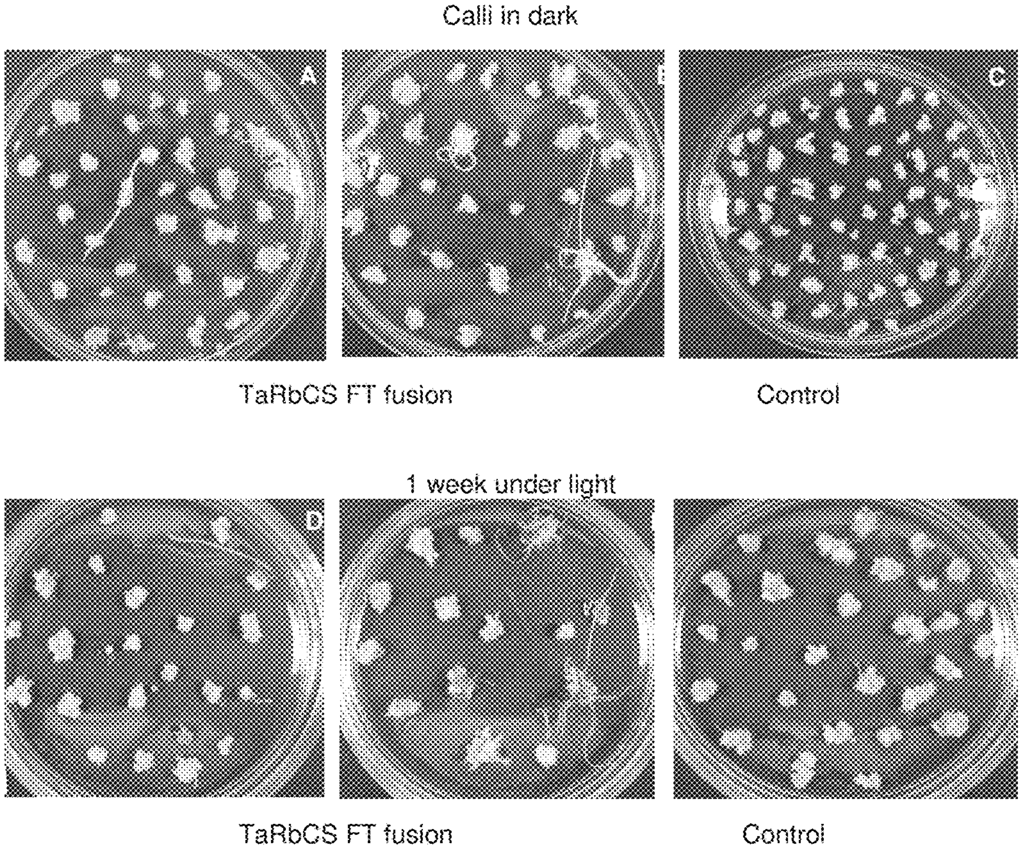

FIG. 84. Positive selection of perennial ryegrass transgenic plants by screening of in vitro growth phenotype on plates without antibiotic selection. A-C. Calli in dark for 8 weeks after transformation; D-F. 1 week after transfer to light.

Figure 85:
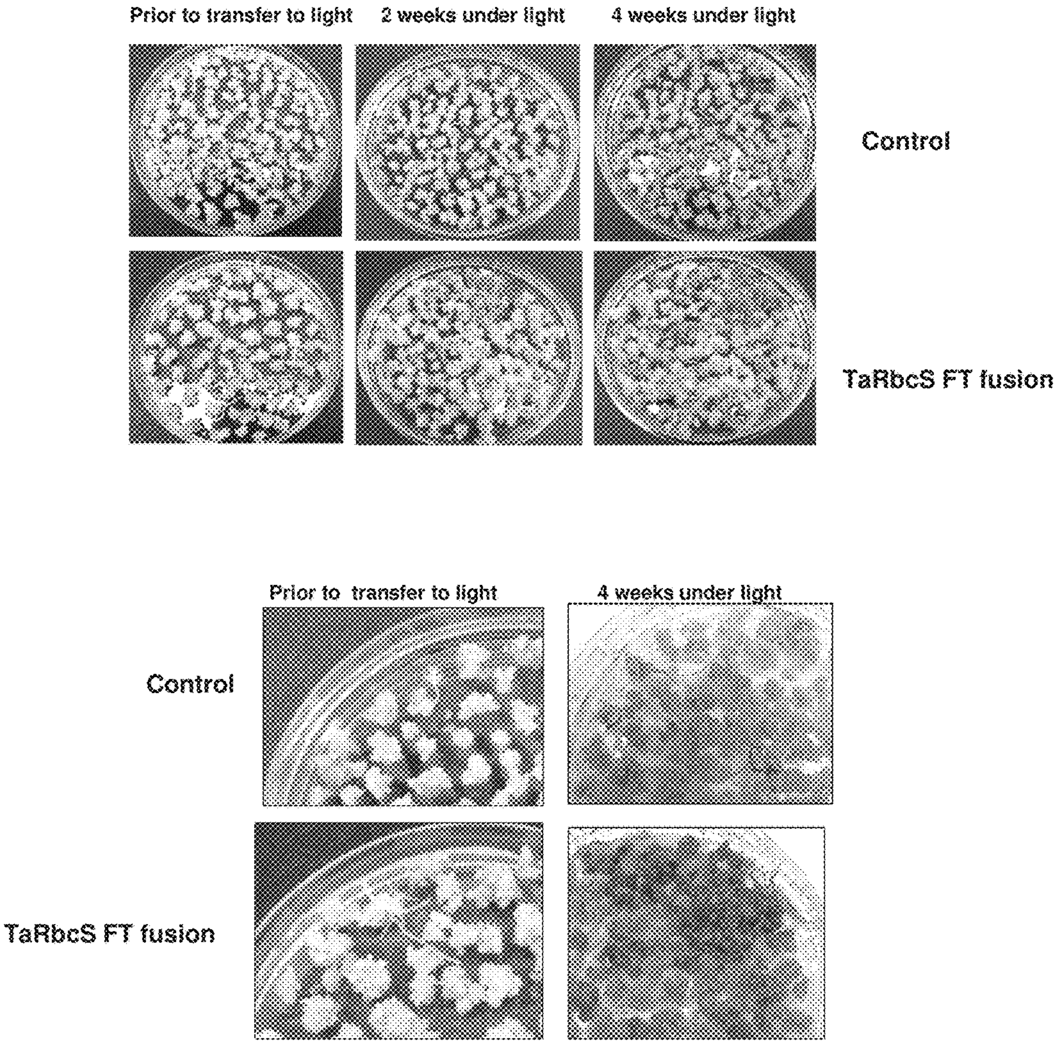

FIG. 85. Embryogenic perennial ryegrass calli bombarded with gold particles alone (control) and gold particles covered with TaRbcS FT fusion vector prior to, and four weeks post, transfer to light.

FIG. 86. Embryogenic perennial ryegrass calli bombarded with gold particles alone (control) and gold particles covered with TaRbcS FT fusion 1 alone, TaRbcS FT fusion 3 alone, LXR alone, as well as TaRbcS FT fusion plus LXR vectors five weeks after transfer to light. Molecular analysis positive lines: TaRbcS FT fusion 1 #1, 2, 3, 4, 7, 6, 12, 13, 14, 16, 17; TaRbcS FT fusion 3 #1, 2, 3, 5, 8, 10, 11, 12, 13; TaRbcS FT fusion 1 plus LXR #1, 2, 7, 12 (TaRbcS FT fusion 1 alone); #8, 14 (TaRbcS FT fusion 1 plus LXR).

EXAMPLE 1

Isolation of Photosynthetic Promoters

Cloning of a Photosynthetic Promoter from Bread Wheat

The Ribulose-1,5-bisphosphate carboxylase/oxygenase Small subunit (RbcS) is a well-characterised light-regulated gene in higher plants. The bread wheat (*Triticum aestivum*), TaRbcS regulatory sequences (promoter and terminator) have previously been cloned (Zeng, et al., 1995; Sasanuma, 2001). A 695 bp promoter fragment from sequence previously published containing the TATA signal from the TaRbcS gene (NCBI accession number AB042069) was PCR-amplified.

Cloning of a Photosynthetic Promoter from *Arabidopsis*

A 1700 bp fragment of the *Arabidopsis thaliana* Ribulose-1,5-bisphosphate carboxylase/oxygenase Small subunit (AtRbcS) promoter sequence has previously been cloned. Primers will be designed to amplify a smaller fragment containing the TATA signal from the AtRbcS promoter for use in expression vectors.

Discovery and Cloning of Photosynthetic Promoters from Perennial Ryegrass

The expression of RbcS and Chlorophyll a/b Binding Protein (CAB) are well characterised light-regulated genes in higher plants. The abundance of LpRbcS mRNA transcripts in perennial ryegrass by quantitative real time PCR is illustrated in FIG. 2.

Both LpRbcS and LpCAB genes were chosen for promoter discovery and isolation in perennial ryegrass. Publicly available cDNA sequences (LpRbcS, EC778430 and LpCAB, EC778438) were used as query sequences in a BLAST search of the perennial ryegrass EST database in our in-house database. As both genes are members of multigene families, several contigs (each contig represents an individual gene) were identified in our perennial ryegrass EST collection. Nine contigs were identified to be homologous to the published LpRbcS cDNA sequence and thirteen contigs were found to be homologous to the LpCAB cDNA sequence. Two contigs, LPCL9_C359 (LpRbcS) and LpCL1112_C12 (LpCAB), representing the genes of the promoters to be isolated, contained (47) and (19) EST sequences, respectively. These sequences came from a variety of libraries representing a range of different tissues. This data was used for in silico expression analysis and indicated that both genes are only expressed in photosynthetic tissues (FIG. 3).

DNA sequence alignments for each of the gene family members were performed, and gene-specific primers were designed for contigs LpRbcS_C359 and LpCAB_C12 and used to screen perennial ryegrass BAC DNA pools by PCR. The BAC clones were identified and sequenced. Primers were designed and the *Lolium perenne* specific promoter regulatory sequences were cloned, sequenced (FIGS. 4 and 5) and the cis-regulatory sequences specific for photosynthetic promoters were identified by PLACE (www.dna.affrc.go.jp/PLACE/) (Table 1). The sequences included the I-Box motif and the GT1 box for RbcS (Terzaghi, et al., 1995; Martinez-Hernandez, et al., 2002). In addition 16/19 nucleotides of the LpRbcS sequence shared homology with the monocot RbcS Consensus sequence (Schaffner, et al., 1991). The 1-Core box and SORL1Ps cis-regulatory sequences were present in the CAB promoter. SORL1Ps were found to be over-represented in light-induced promoters in *Arabidopsis* (Hudson, et al., 2003).

TABLE 1

The position of the cis-regulatory sequences identified by the PLACE database. Common cis-acting regulatory sequences are listed (Schaffner, et al., 1991; Terzaghi, et al., 1995; Martinez-Hernandez, et al., 2002; Hudson, et al., 2003). Positions noted are the first nucleotide in the sequence relative to the ATG.

| cis-acting regulatory seq. | Accession# | position LpRbcS | position LpCAB |
|---|---|---|---|
| I-Box Core | S000199 | −184 | −137 |
| I-Box | S000124 | −311 | −137 |

TABLE 1-continued

The position of the cis-regulatory sequences identified by the PLACE database. Common cis-acting regulatory sequences are listed (Schaffner, et al., 1991; Terzaghi, et al., 1995; Martinez-Hernandez, et al., 2002; Hudson, et al., 2003). Positions noted are the first nucleotide in the sequence relative to the ATG.

| cis-acting regulatory seq. | Accession# | position LpRbcS | position LpCAB |
|---|---|---|---|
| GT1 consensus | S000198 | −304 | n.p. |
| RbcS monocot seq | Schaffner et al, 1991 | −173 to −151 | n.p. |
| SORLIPs | S000482 | n.p. | −58, −217, −647, −695 |

(n.p.—not present).

These *L. perenne* specific promoter regulatory sequences were subsequently used in the construction of backbone-free expression cassettes with fructan biosynthesis genes.

EXAMPLE 2

Isolation of Fructan Biosynthesis Genes

Isolation of Fructan Biosynthesis Genes from *Lolium perenne*

The *Lolium perenne* cDNA clones encoding sequences for Lp1-SST and Lp6G-FFT have previously been isolated from a perennial ryegrass cDNA library (Chalmers, et al., 2003; Chalmers, et al., 2005). The complete gene sequences of the isolated perennial ryegrass fructosyltransferase homologues are available, and nucleotide and protein sequences for Lp1-SST are disclosed in International patent application PCT AU01/00705 (SEQ ID NOS 11 and 12).

Partial sequence for Lp6G-FFT is disclosed in International patent PCT/AU/01/01275 SEQ IDs 109 and 110, for nucleotide and amino acid sequences respectively. The full-length clone was PCR amplified from a cDNA, cloned and sequenced (FIG. 7). When the Lp6G-FFT ORF was compared with the published Lp6G-FFT from *L. perenne* 23 nucleotide changes were noted. Comparison of the predicted protein sequences revealed only two changes between the two amino acid sequences (FIG. 8).

Other FT genes that may be used and, either transformed singly or co-transformed with Lp1-SST and Lp6G-FFT include Lp1-FFT, Lp6-SFT and Lp6-SST. The cDNA sequence for Lp1-FFT has been isolated from perennial ryegrass (FIG. 9) and the amino acid sequence is represented in FIG. 10. As an example, primers based on this sequence could be used to amplify the full-length cDNA by PCR for cloning and use in the present invention as described below.

Other homologous proteins can be found by screening databases such as EMBL (vvvvvv.ebi.ac.uk/Tools/index.htm) or the National Center for Biotechnology Information (NCBI, www.ncbi.nlm.nih.gov/blast/Blast.cgi#). In such a database search, for example the sequences described in FIGS. 7-10 are set as a query, using default parameter settings set for the database. For example, for protein sequence alignments (Blastp) with NCBI these settings are as follows: limit entrez=not activated; filter=low complexity activated; expect value=10; word size=3; matrix=BLOSUM; gapcostsexistence-11, extension=1. Such database searches can be used for finding proteins with domains contained in FTs (using default parameters).

EXAMPLE 3

Creation of Translational FT Fusion Proteins

Cloning of FT Translational FT Fusion

A genetic FT fusion was created between the open reading frames for Lp1-SST and Lp6G-FFT, following the procedure depicted in FIG. 11. The Lp1-SST gene was PCR-amplified with a GATEWAY recombination site incorporated in the forward primer. A sequence that codes for three glycine residues followed by a Hind III site was incorporated into the reverse primer, with the stop codon removed. The Lp6G-FFT gene was PCR-amplified with a Hind III site followed by sequence that codes for three glycine residues and the gene specific sequence without the ATG. The reverse primer for the Lp6G-FFT gene was flanked by a second GATEWAY recombination site. The primer sequences are provided in Table 2. The purified fragments were digested with Hind III and the ligated product was cloned into the Invitrogen GATEWAY pDONR221 Entry vector. When the resultant pENTRY1-Lp1-SST-Lp6G-FFT-2 entry clones were sequenced, one sequence (FT fusion 1) was confirmed to be the predicted product, with eight amino acids in the linker joining the two genes (FIGS. 12 and 13). Whereas, another sequence (FT fusion 3) contained two consecutive Hind III sites, which would result in the addition of another two amino acids, giving a total of ten amino acids between the two FT genes upon translation (FIGS. 14 and 15).

TABLE 2

Primer sequences used to amplify the PCR fragments used to generate the translational FT fusion of the Lp1-SST and Lp6G-FFT fructosyltransferase genes (FT Lp1-SST_Lp6G-FFT). Shaded sequences are gene-specific, bold and underlined (Hind III RE site) sequences are nucleotides introduced to generate the linker region, and italic nucleotides represent the recombination-specific sequences.

| Gene | Forward primer | Reverse Primer |
|---|---|---|
| Lp1-SST | GGGG*ACAAGTTTGTACAAAAAAGCAG GCTTC*ATGGAGTCCCCAAGCGCCGTC (SEQ ID No: 51) | TCT**AAGCTTTCCTCCTCC**CAAGTC GTCGTTCGTG (SEQ ID No: 52) |
| Lp6G-FFT | ACT**AAGCTTGGAGGAGGA**GAGTCCAG CGCCG (SEQ ID No: 53) | GGGG*ACCACTTTGTACAAGAAAGCTGG GTCC*TACATGTCGTCAGCCAAGAAGGC C (SEQ ID No: 54) |

By using the primer sequences outlined in Table 3 it is possible to create a new FT fusion reversing the order to Lp6G-FFT-Lp1SST using the same method as illustrated above.

TABLE 3

Primer sequences used to amplify the PCR fragments used to generate the translational FT fusion of the Lp1-SST and Lp6G-FFT fructosyl transferase genes (Lp6G-FFT-Lp1-SST). Shaded sequences are gene-specific, bold and underlined (Hind III RE site) sequences are nucleotides introduced to generate the linker region, and italic nucleotides represent the recombination-specific sequences.

| Gene | Forward primer | Reverse Primer |
|---|---|---|
| Lp6G-FFT | GGGGA*CAAGTTTGTACAAAAAAGCAG GCTTC*GAGTCCAGCGCCG (SEQ ID No: 55) | TCT**AAGCCTTTCCTCCTCC**CTACAT GTCGTCAGCCAAGAAGGCC (SEQ ID No: 56) |
| Lp1-SST | ACT**AAGCTTGGAGGAGGA** ATGGAGTCCCCAAGCGCCGTC (SEQ ID No: 57) | GGGGA*CCACTTTGTACAAGAAAGCT GGGTC*CAAGTCGTCGTTCGTG (SEQ ID No: 58) |

In Lp1-SST_Lp6G-FFT the FT proteins physically associate with each other to form a FT fusion protein which contains three transmembrane domains as designated by SOSUI, a classification and secondary structure prediction of membrane proteins database (Table 4, FIGS. 17 and 18).

TABLE 4

FT fusion 1/3 transmembrane domains as indicated by SOSUI, a Classification and Secondary Structure Prediction of Membrane Proteins database (http://bp.nuap.nagoya-u.ac.jp/sosui/sosui_submit.html)

| No. | N terminal | transmembrane region | C. terminal | type | Length |
|---|---|---|---|---|---|
| 1 | 4 | PSAVVPGTTAPLLP YAYAPLPSS (SEQ ID No: 59) | 26 | SECONDARY | 23 |
| 2 | 41 | ACAAVLAASALSVVV VVGLLAGG (SEQ ID No: 60) | 63 | PRIMARY | 23 |
| 3 | 704 | ACAASALVVLLVVVG FFAGGRVD (SEQ ID No: 61) | 726 | PRIMARY | 23 |

Structural Features of Plant Fructosyltransferases

Plant FTs have a high degree of amino acid homology to the vacuolar, acid invertases (b-fructosidases) which are the members of the glycoside hydrolase family 32. (GH32) and share three highly conserved regions characterised by the motifs (N/S)DPNG (also called b-fructosidase motif), RDP, and EC (Altenbach et al., 2005) (FIGS. 17, 18 and 36). Another common feature of plant FTs and vacuolar invertases is that they usually are composed of a large and a small subunit due to posttranslational processing. The large subunit, which harbours all three conserved motifs mentioned above, determines the catalytic specificity (Altenbach et al., 2004).

The other FT genes Lp1-FFT, Lp6-SFT and Lp6-SST may also be used in combination with Lp1-SST or Lp6G-FFT to produce a selection of translational FT fusions, by the scheme outlined in FIG. 16A, as indicated below.

Lp6G-FFT::Lp1-SST

Lp1-SST::(Lp1-FFT/Lp6-SFT/Lp-SST)

(Lp1-FFT/Lp6-SFT/Lp-SST)::Lp1-SST

A triplicate FT fusion could also be created using a similar methodology (FIG. 16B). It is proposed that the triplicate fusion would be constructed to incorporate the genes Lp1-SST, Lp6G-FFT and Lp1-FFT, Lp6-SFT or Lp6-SST. By altering the primer sequences used to join the two FT genes together it is possible to change the linker size and potentially add up to approximately 30 amino acids. FT proteins could physically associate with each other to form a metabolic channel, therefore the distance separating the FT genes within the translational fusion may affect protein function. FT fusion proteins preferably contain the sequences which represent the domains which are highly conserved among the FT, INV and FEH proteins from *Lolium perenne* plants indicated in FIGS. 17, 18 and 36.

EXAMPLE 4

Transient Assays of Fructan Biosynthesis Gene Function

Function of Lp1-SST, Lp6G-FFT and FT Fusion Protein

The cDNA sequence encoding the Lp1-SST mature protein has been previously expressed in *Pichia pastoris* for functional characterisation (Chalmers, et al., 2003) and the conversion of sucrose to 1-kestose by expression of this protein was demonstrated. Similarly, the Lp6G-FFT cDNA was cloned into the expression vector pPICZαA (Invitrogen) that contains a methanol-inducible promoter and the *Saccharomyces cerevisiae* α-factor sequence to enable secretion of the recombinant protein for isolation for functional characterisation. The recombinant Lp6G-FFT enzyme was produced from single colonies of transformed *P. pastoris* inoculated into a pre-culture medium and induced by the addition of methanol for a 45 hr duration. The supernatant was concentrated and samples were incubated with 100 mM sucrose overnight. The carbohydrates produced were analysed by HPAEC according to Chalmers et al., 2003, using fructan extracts from onion as a control (FIG. 19).

Generation of Vectors for Transient Gene Expression Assays

A number of vectors were constructed using Invitrogen Multisite Gateway™ technology (see www.Invitogen.com for product manual) based on recombinational cloning. This methodology relies on the generation of individual Entry plasmids containing, either the promoter, gene of interest (GOI), or terminator sequences flanked by recombination sites. The recombination sites facilitate the directional triple insertion of each of the Entry plasmids into a Gateway-enabled destination vector, by recombination. The final vector is then sequenced and used directly for plant co-transformation with a plasmid, or expression cassette, for expression of a plant selectable marker.

In order to test the function of the FT fusion protein, the FT fusion 1 and 3 ORFs were cloned under the control of the enhanced cauliflower mosaic virus (CAMV)35S$^2$ promoter (Kay, et al., 1987), using the Multisite Gateway™ Technology recombination system (see www.Invitrogen.com for product manual) into *Agrobacterium* binary vector (FIG. 21) (Hajdukiewicz, et al., 1994).

Gateway Entry vectors were constructed for the (CAMV) 35S$^2$ promoter, the TaRbcS terminator sequence, as well as FT fusion 1 and 3 ORFs. The cloned fragments were sequence-verified and used for three-way recombination cloning with the cloned GOI cDNA sequences into the pPZP200-ubi:bar-nos R4 R3 destination vector. In addition, constructs also included the Lp6G-FFT and Lp1-SST single ORF driven by the (CAMV)35S$^2$ promoter as controls. As an example, the Lp1-FFT (or Lp6-SFT, Lp6-SST) single ORF is also cloned in the same manner. As a control the GUS ORF was used for confirmation of expression. The following constructs were made.

pPZP200-35S$^2$::Lp6G-FFT::TaRbcS
pPZP200-35S$^2$::Lp1-SST::TaRbcS
pPZP200-35S$^2$::(Lp1-FFT/Lp6-SFT/Lp-SST)::TaRbcS
pPZP200-35S$^2$::Lp1-SST::6G-FFT::TaRbcS (FT fusion 1 and 3)
pPZP200-35S$^2$::GUS::TaRbcS Utilising Invitrogen Multisite Gateway™ Technology the following vectors are created containing the Atrbcs photosynthetic promoter and the (CAMV)35S terminator for use in transient assays.

pPZP200-AtrbcS::Lp1-SST::35S
pPZP200-AtrbcS:: Lp6G-FFT::35S
pPZP200-AtrbcS::(Lp1-FFT/Lp6-SFT/Lp-SST)::35S
pPZP200-AtrbcS::Lp1-SST::6G-FFT::35S (FT fusion 1 and 3)

Function of Lp1-SST, Lp6G-FFT and FT Fusion Protein in Transient Transgene Expression Assays For proof-of-function transient expression of the constructs containing chimeric Lp1-SST, Lp6G-FFT and FT fusion protein genes driven by the (CaMV)35S promoter was conducted in tobacco plants, as they do not naturally produce fructans. The method involved Agro-infiltration of the individual constructs into *N. benthamiana* leaves (Kapila, et al., 1997; Wydro, et al., 2006) followed by biochemical analysis by anion exchange chromatography. A diagram of the transient expression procedure is illustrated in FIG. 21. Three days after the injection the plant material was harvested and the water-soluble carbohydrates were extracted using a hot water extraction method. The extracts were separated using high performance anion exchange chromatography (HPAEC). The results show production of fructans, with the increased production of both 1-kestose and 6G-kestose by the FT fusion protein (FIG. 22). An equivalent experiment is used to assess the function constructs containing chimeric Lp1-SST, Lp6G-FFT and FT fusion protein genes driven by the AtRbcS promoter.

Agro-Infiltration Using a Combination of Vectors for Transcriptional Co-Transformation To assess the function of the fructan biosynthesis when transcriptionally co-ordinated together in a cell, triple agro-infiltration experiments are conducted using the groups of vectors outlined below. The transient expression procedure as illustrated in FIG. 21 is used to insert three vectors together in the same plant tissue. Three days after the injection, the plant material is harvested and the water-soluble carbohydrates extracted using a hot water extraction method. The extracts are separated using high performance anion exchange chromatography (HPAEC). The results indicate the differences resulting from the independent expression of three fructan biosynthesis genes in the plant genome.

pPZP200-35S$^2$::Lp6G-FFT::TaRbcS+
pPZP200-35S$^2$::Lp1-SST::TaRbcS+
pPZP200-35S$^2$::(Lp1-FFT/Lp6-SFT/Lp-SST)::TaRbcS
pPZP200-AtRbcS::Lp1-SST::35S+
pPZP200-AtRbcS:: Lp6G-FFT::35S+
pPZP200-AtRbcS::(Lp1-FFT/Lp6-SFT/Lp-SST)::35S

Agro-Infiltration Using a FT Fusion Vectors for Translational Co-Transformation

By comparison to the transcriptional co-transformation experiments are conducted to compare translational co-transformation by conducting transient assays with the vectors that have previously been discussed and are indicated below.

pPZP200-35S2::Lp1-SST_6G-FFT::TaRbcS (FT fusion 1 and 3)
pPZP200-AtRbcS::Lp1-SST_6G-FFT::35S (FT fusion 1 and 3)

EXAMPLE 5

Generation of Vectors for Stable Transformation and Production of Transgenic Plants Production of LXR® Vector for Biolistic and *Agrobacterium*-Mediated Transformation LXR® technology is based on vectors containing one cytokinin biosynthesis gene encoding isopentenyl transferase (IPT) for delayed leaf senescence under the control of the AtMYB32 gene promoter. The LXR® vector for biolistic transformation was constructed utilising Gateway™ Multisite technology. Details of the binary vector pBS-ubi::bar::nos_AtMYB32_IPT_35S are described in International patent application PCT/AU01/01092.

The production of the LXR® vectors for *Agrobacterium*-mediated transformation is disclosed in International patent application PCT/AU01/01092. The candidate gene constructs were fully sequenced and the vectors were generated for *Agrobacterium* mediated transformation following strict quality assurance protocols.

Constructs Containing a Wheat Photosynthetic Promoter

A 695 kb promoter fragment from sequence previously published containing the TATA signal from the TaRbcS gene (NCBI accession number AB042069) was PCR-amplified with Gateway™ (Invitrogen) recombination sites at the primer flanks. The fragment was cloned into the Invitrogen pDONRP4-P1R Entry vector using Gateway™ recombination technology. The 696 bp TaRbcS gene termination signal sequence (Sasanuma, 2001) was also PCR-amplified using primers with recombination sites and cloned into the Invitrogen pDONRP2-P3R Entry vector. The cloned fragments were sequence-verified and used for three-way recombination cloning with the cloned GOI cDNA sequences into the pDEST-R4R3 destination vector: pDESTR1-R2R-Lp1-SST, pDESTR1-R2-Lp6G-FFT, and pDESTP1-P2R-Lp1-SST_Lp6G-FFT gene FT fusion expression vectors. The following constructs for photosynthetic-regulation of expression of fructosyltransferases by the TaRbcS promoter to be used are outlined below and graphically depicted in FIG. 23. Expression cassette sequences for pDEST-TaRbcS::Lp1-SST::TaRbcS, pDEST-TaRbcS::Lp6G-FFT::

TaRbcS and pDEST-TaRbcS::Lp1-SST_Lp6G-FFT::TaRbcS FT fusion1 and 3 are provided in FIGS. 24-27.

pDEST-TaRbcS::Lp1-SST::TaRbcS
pDEST-TaRbcS::Lp6G-FFT::TaRbcS
pDEST-TaRbcS::Lp1-SST_Lp6G-FFT::TaRbcS FT fusion 1 and 3
pDEST-TaRbcS::GUS::TaRbcS Constructs Containing a Ryegrass Photosynthetic Promoter Constructs containing a ryegrass photosynthetic promoter were produced by conventional cloning methods. The 693 base pair (bp) fructosyltransferase 4 gene (LpFT4) termination sequence (Lidgett, et al., 2002) was amplified by PCR using gene specific primers containing the restriction endonuclease (RE) site EcoR I at the 5' end of the forward PCR primer. EcoR V and Xma I endonuclease restriction sites were incorporated at the 3' end of the reverse PCR primer. The PCR product was cloned into the EcoR I and Xma I restriction endonuclease sites of the pBlueScript SK(−) vector DNA (Short, et al., 1988), resulting in the plasmid pBS-LpFT4 (FIG. 28).

The LpRbcS promoter was amplified using gene specific primers containing the endonuclease restriction sites Xho I and EcoR V at the 5' end of the forward primer and an EcoR I restriction site was incorporated in the 3' end of the reverse primer. The 610 bp PCR product was cloned into the pBS-LpFT4 plasmid digested with EcoR I and Xho I, resulting in the plasmid pBS-LpRbcS::LpFT4 (FIG. 29A). The Lp1-SST coding region was amplified from a cDNA template (Chalmers et al., 2003) with EcoR I sites flanking both forward and reverse PCR primers, and cloned into the EcoR I site of pBS-LpRbcS::LpFT4 vector, generating the final construct pBS-LpRbcS::Lp1-SST::LpFT4 (FIG. 29B). Sequence of the expression cassette, indicating promoter and terminator, as well as ORF is provided in FIG. 31. The expression cassette containing the *L. perenne* sequences may be excised from the plasmid vector DNA using the EcoR V restriction endonuclease. Following agarose gel electrophoresis, the resulting DNA fragment is purified from the agarose matrix prior to being used for plant transformation to produce DNA with out vector backbone sequences.

The plasmid pBS-LpFT4 (FIG. 28) containing the 693 base pair LpFT4 terminator sequence was prepared as outlined above. The LpCAB promoter fragment of 870 base pairs was amplified with a forward PCR primer containing the Xho I and EcoR V sites and a reverse PCR primer containing the EcoR I restriction site. This fragment was cloned in the Xho I and EcoR I sites of pBS-LpFT4, generating the pBS-LpCAB::LpFT4 plasmid (FIG. 30A). The Lp6G-FFT coding region was amplified from a cDNA template (Chalmers, et al., 2005) with EcoR I sites flanking both forward and reverse PCR primers, and cloned into the EcoR I site of pBS-LpCAB::LpFT4 vector, generating the final construct pBS-LpCAB::Lp6G-FFT::LpFT4 (FIG. 30B). Sequence of the expression cassette, indicating promoter and terminator, as well as ORF is provided in FIG. 32. The DNA expression cassette may be excised from the plasmid vector DNA using the EcoR V restriction endonuclease. Following agarose gel electrophoresis, the resulting DNA fragment is purified from the agarose matrix prior to being used for plant transformation to produce DNA without vector backbone sequences.

To generate an expression construct, the translational FT fusion between the genes Lp1-SST and Lp6G-FFT was amplified from pDEST-TaRbcS::Lp1-SST_Lp6G-FFT::TaRbcS FT fusion 1 and 3 plasmids (FIG. 23C-D) using primers specific for a region just outside the ORF, with EcoR I restriction sites engineered in the 3' region on both the forward and reverse primers. The 3920 bp ORF was PCR amplified and cloned into pCR®-Blunt vector (Invitrogen) to produce PCR Blunt-Lp1-SST-Lp6G-FFT FT fusion (FIG. 33). It was then excised using EcoR I restriction enzymes to remove the vector-specific sequences, and cloned into the pBS-LpRbcS::LpFT4 plasmid (FIG. 29A) at the EcoR I restriction site, generating the pBS-LpRbcS::Lp1-SST_Lp6G-FFT::LpFT4 (FIG. 34). Sequence of the expression cassette of FT fusion 1 and 3, indicating relevant domains (FT fusion 3), is provided in FIGS. 35 and 36, respectively. The DNA expression cassette may be excised from the plasmid vector DNA using the EcoR V restriction endonuclease. Following agarose gel electrophoresis, the resulting DNA fragment is purified from the agarose matrix prior to being used for plant transformation to produce DNA without vector backbone sequences.

The constructs for photosynthetic-regulation of expression of fructosyltransferases by *L perenne* promoter sequences are outlined below.

pBS-LpRbcS::Lp1-SST::LpFT4
pBS-LpCAB::Lp6G-FFT::LpFT4
pBS-LpRbcS::Lp1-SST_Lp6G-FFT::LpFT4 FT fusion 1 and 3

Constructs Containing an *Arabidopsis* Photosynthetic Promoter

A construct containing an *Arabidopsis* photosynthetic promoter driving expression of FT fusion 3 was produced using Multisite Gateway cloning methods -pPZP200_AtRbcS:: Lp1-SST_6G-FFT::35S FT fusion 3 (FIG. 37). The sequence of the AtRbcS::Lp1-SST 6G-FFT::nos FT fusion 3 expression cassette is provided in FIG. 38.

Constructs Containing a Constitutive Ubiquitin Promoter

Constructs containing the promoter and first intron of the maize (*Zea mays*) ubiquitin (Ubi) gene (Christensen et al., 1992) were produced by conventional cloning methods.

The Ubi promoter is considered a constitutive promoter, but expression is highest in young actively growing grass tissues (Rooke et al., 2000).

A cDNA copy of the candidate genes Lp1-SST and Lp6G-FFT was amplified by PCR as described by Chalmers et. al. (2003) and cloned into the pBlueScript SK(−) vector (FIG. 39). The cDNA fragments were excised using the restriction endonucleases Xho I and Xba I, and then blunt-end cloned into the BamH I site of p-Ubi-35S vector (FIG. 40). The p-Ubi-35S binary plant expression vector has been previously described in other transformation experiments of *L. multiflorum* (Ye et al., 2001). The p-Ubi::Lp1-SST::35S and p-Ubi::Lp6G-FFT::35S clones containing the DNA insert in the required 5' to 3' orientation were confirmed by DNA sequencing. A representative sequence of the constitutive (Ubi) promoter combined with a FT fusion protein and a terminator sequence is provided in FIG. 41. A similar method is used to construct p-Ubi::Lp1-FFT::35S clones.

The constructs for photosynthetic-regulation of expression of fructosyltransferases by the Ubi promoter sequences are outlined below.

p-Ubi::Lp1-SST::35S
p-Ubi::Lp6G-FFT::35S
p-Ubi::(Lp1-FFT/Lp6-SFT/Lp-SST)::35S

Constructs Containing the Cauliflower Mosaic Virus 35S Promoter

The constructs for regulation of expression of fructosyltransferases under the control of the enhanced cauliflower mosaic virus (CAMV)35$S^2$ promoter (Kay, et al., 1987), are described in a previous section and are outlined below.

pPZP200-35$S^2$::Lp6G-FFT::TaRbcS
pPZP200-35$S^2$::Lp1-SST::TaRbcS pPZP200-35S$^2$::(Lp1-FFT/Lp6-SFT/Lp-SST)::TaRbcS pPZP200-35S$^2$::Lp1-SST_6G-FFT::TaRbcS FT fusion1 and 3

Constructs Containing Tissue Specific or Regulated Promoters

Promoters with tissue-specificity are desirable to drive expression of transgenes in crops to target accumulation in particular tissues/organs and to avoid unwanted expression elsewhere. Examples of different promoters to drive transgene expression for different objectives are presented in Table 5. Representative examples of promoters for constitutive (Ubi, (CAMV)35S$^2$, RUBQ2, OsAct1), tuber and stolon specific (Cathlnh), stress regulated (Atrd29a) and sucrose responsive (14-3-3 protein family 16R) linked to FT fusions are presented in FIGS. 42-48, respectively.

TABLE 5

Examples of different promoters to drive transgene expression.

| Specificity/ Tissue | Gene promoter | Ogranism | Reference |
|---|---|---|---|
| Constitutive | | | |
| Constitutive/all | Ubiquitin, Ubi | *Zea mays* (maize) | Christensen et al. (1992) |
| | (CAMV)35S$^2$ | Cauliflower mosaic virus | Kay et al. (1987) |
| | Polyubiquitin, RUBQ2 | *Oryza sativa* (rice) | Liu et al. (2003) |
| | Actin 1, OsAct1 | *Oryza sativa* (rice) | McElroy et al. (1990) |
| Tissue Specific | | | |
| Tuber and stolon specific | Sucrose synthetase, Sus4 | *Solanum tuberosum* (potato) | Lin et al. (2008) |
| | Cathepsin D inhibitor gene, Cathinh | *Solanum tuberosum* (potato) | Herbers et al. (1994) |
| Root and shoot of sugar beet | Helicase-like genes, helA, helB and helC | *Pseudomonas* plasmid | Zhang et al. (2004) |
| Seed | β-conglycinin, a soybean seed storage protein | *Glycine max* (soybean) | Chen et al. (1988) |
| Phloem | Sucrose synthase, Suc2 | *Zea mays* (maize) | Yang and Russell (1990) |
| Xylem | phenylalanine ammonialyase gene 2, PAL2 | *Nicotiana. benthamiana* (tobacco) | Keller and Baumgartner (1991) |
| | 4-coumarate:coenzyme A ligase. 4CL | *Nicotiana. benthamiana* (tobacco) | Hauffe et al. (1993) |
| Inducible | | | |
| Cold, dehydration and salt stress responsive | Calcium dependent protein kinases, OsCPK6, OsCPK13, OsCPK25 | *Oryza sativa* (rice) | Wan et al. (2007) |
| Dehydration stress | early responsive to dehydration stress, ERD1 | *Arabidopsis thaliana* | Tran et al. (2004) |
| Stress responsive | rd29a | *Arabidopsis thaliana* | Yamaguchi-Shinozaki and Shinozaki (1993) |
| Sucrose responsive | ADP-glucose pyrophosphorylase, IbAGP1 | *Ipomoea batatas* (sweet potato) | Kwak et al. (2005) |
| | ADP-glucose pyrophosphorylase, LeAgp S1 | *Lycopersicon esculentum* (tomato) | Li et al. (2001) |
| | 14-3-3 protein family, 16R | *Solanum tuberosum* (potato) | Szopa et al. (2003) |
| Ethylene responsive | ethelyene responsive binding elements, GhERF4 | *Gossypium hirsutum* (cotton) | Jin and Lui (2008) |
| Cold responsive | wcs120 | *Triticum aestivum* (wheat) | Ouellet et al. (1998) |
| Dessication responsive in leaves, organ specific in flowers and green fruit | StDS2 | *Solanum tuberosum* (potato) | Doczi et al. (2005) |
| | LeDS2 | *Lycopersicon esculentum* (tomato) | Doczi et al. (2005) |
| Oxidative stress induced by high light and ozone | Peptide methionine sulfoxide reductase A, PMRSA | *Arabidopsis thaliana* | Romero et al. (2006) |
| Wound | Wun1, proteinase inhibitor II genes of potato | *Solanum tuberosum* (potato) | Siebertz et al. (1989) |
| Starch | ADP Glucose Pyrophosphorylase, ADPGlc | *Arabidopsis thaliana* | Stark et al. 1992 |

TABLE 5-continued

Examples of different promoters to drive transgene expression.

| Specificity/ Tissue | Gene promoter | Ogranism | Reference |
|---|---|---|---|
| Light regulated | Ribulose-1,5-bisphosphate carboxylase/oxygenase Small subunit, TaRbcS, AtRbcS, and LpRbcS respectively<br>Chlorophyll a/b Binding Protein, LpCAB | *Triticum aestivum* (wheat), *Arabidopsis thaliana*, and *Lolium perenne* respectively<br>*Lolium perenne* (ryegrass) | Zeng, et al., (1995), Sasanuma, (2001) |

Several photosynthetic promoters have been shown to be strong regulators of expression of transgenes in light-responsive tissues. Advantages of photosynthetic promoters for expressing fructan biosynthesis genes include that they are active in the large group of cells of the leaves and upper part of the stems which accounts the majority of the plants biomass. They are not constitutively expressed, however their expression pattern temporally and spatially overlaps with sucrose accumulation.

Using a Combination of Vectors for Transcriptional Co-Transformation

The following vectors are transformed singly or in groups (double and triple) to assess synergistic responses of co-expression required for the generation of low and high DP fructans.

pDEST-TaRbcS::Lp1-SST::TaRbcS
pBS-LpRbcS::Lp1-SST::LpFT4
p-Ubi::Lp1-SST::35S
pPZP200-35S$^2$::Lp1-SST::TaRbcS
pDEST-TaRbcS::Lp6G-FFT::TaRbcS
pBS-LpCAB::Lp6G-FFT::LpFT4
p-Ubi::Lp6G-FFT::35S
pPZP200-35S$^2$::Lp6G-FFT::TaRbcS
pDEST-TaRbcS::(Lp1-FFT/Lp6-SFT/Lp-SST)::TaRbcS
p-Ubi::(Lp1-FFT/Lp6-SFT/Lp-SST)::35S
pPZP200-35S$^2$::(Lp1-FFT/Lp6-SFT/Lp-SST)::TaRbcS

Using FT Fusion Vectors for Translational Co-Transformation

To make comparisons with the transcriptional co-transformations as indicated above, translational co-transformation experiments are also conducted with the FT fusion vectors that have previously been discussed and are indicated below.

pDEST-TaRbcS::Lp1-SST_Lp6G-FFT::TaRbcS FT fusion1 and 3
pBS-LpRbcS::Lp1-SST_Lp6G-FFT::LpFT4 FT fusion1 and 3
pPZP200-35S$^2$::Lp1-SST_6G-FFT::TaRbcS FT fusion1 and 3

EXAMPLE 6

Production of Stable Transgenic Plants by Transformation

Transformation of Plants

The genetic constructs of the present invention may be introduced into plant cells by transduction, transfection, transformation or gene targeting. Such techniques include *Agrobacterium*-mediated introduction, electroporation of tissues, cells and protoplasts, protoplast fusion, injection into reproductive organs, injection into immature embryos and high velocity projectile introduction to cells, tissues, calli, immature and mature embryos, microinjection into cells and protoplasts, polyethylene glycol mediated direct gene transfer into protoplasts, biolistic transformation, Whiskers transformation and combinations thereof. The choice of technique depends largely on the type of plant to be transformed and the appropriate vector for the method chosen are used.

Cells incorporating the genetic constructs of the present invention may be selected, as directed by the vectors used, and then cultured in an appropriate medium to regenerate transformed plants, using techniques well established. The resulting plants may be reproduced, either sexually or asexually, to produce successive generations of transformed plants.

The present invention may be applied to a variety of plants, including monocotyledons [such as wheat, corn or maize, rice, barley, sorghum, sugarcane, oats, rye, grasses (e.g. forage, turf and bioenergy grasses including perennial ryegrass, tall fescue, Italian ryegrass, red fescue, reed canary-grass, big bluestem, cordgrass, napiergrass, switchgrass, wildrye, wild sugarcane, *Miscanthus, Paspalum*)], dicotyledons [such as *Arabidopsis*, tobacco, soybean, canola, alfalfa, cotton, potato, tomato, tobacco, clovers (e.g. white clover, red clover, subterranean clover), vegetable brassicas, lettuce, spinach] and gymnosperms. In particular, invention may be applied to cereals such as *Triticum aestivum* (wheat), C3 grasses containing native fructans such as *Lolium perenne* (ryegrass) and *Lolium arundinaceum* (tall fescue), as well as *Paspalum dilatatum* (*paspalum*) a C4 perennial apomitic grass with no native fructans. The invention may also be applied to dicots such as *Arabidopsis thaliana, Brassica napus* (canola), *Nicotiana benthamiana* (tobacco) and *Trifolium repens* (white clover).

Biolistic Transformation of Monocots Eg Wheat, Perennial Ryegrass, Tall Fescue and *Paspalum*

The candidate genes are inserted into the plant genome by particle bombardment using whole plasmids so vector backbone sequences may also be incorporated into the genome. Transgenic plant tissues are recovered by survival on tissue culture media containing a selective agent.

*Agrobacterium*-Mediated Transformation of Dicots Eg *Arabidopsis*, Tobacco, Canola and White Clover

*Agrobacterium*-mediated transformation takes advantage of the natural pathogenic activity of the soil bacterium *Agrobacterium tumefaciens. A. tumefaciens* infects the roots & stems of dicotyledonous plants resulting in infection directed by the tumor inducing (Ti) plasmid by the insertion of specific genes (T-DNA) into the genome of infected plant cells. The candidate genes were inserted into the plant genome by *Agrobacterium*-mediated transformation using binary vectors based on the Ti plasmids.

EXAMPLE 7

Production of Transgenic Perennial Grasses

Use of Constructs Containing Photosynthetic Promoters

Biolistic co-transformation of perennial ryegrass with the vectors containing the TaRbcS and LpRbcS regulatory sequences, driving the expression of individual fructan genes or as a FT translational fusion, and the pACH1 vector for hygromycin resistance was conducted on embryogenic calli for perennial ryegrass. The pACH1 vector was previously constructed and has been used successfully in plant transformation experiments (Bilang, et al., 1991; Spangenberg, et al., 1995a; Spangenberg, et al., 1995b; Ye, et al., 1997; Bai, et al., 2001). The GUS marker gene was also cloned as a positive control. Table 6 summarises the transformation and molecular analysis for the generation of these lines.

TABLE 6

Summary of production of transgenic perennial ryegrass plants for expression of Lp1-SST and Lp6G-FFT and FT fusion ORFs under control of photosynthetic promoter from wheat.

| Plant Species | Transforming DNA | Number of calli bombarded | Number of putative transgenic plants | Number of plants analysed | Number of hph positive plants | Number of FT positive plants |
|---|---|---|---|---|---|---|
| *L. perenne* | TaRbcS::Lp1-SST::TaRbcS + pACH1 | 500 | 46 | 46 | 37 | 32 |
| *L. perenne* | TaRbcS::Lp6G-FFT::TaRbcS + pACH1 | 500 | 50 | 50 | 48 | 38 |
| *L. perenne* | TaRbcS::Lp1-SST_Lp6G-FFT::TaRbcS FT fusion 1 + pACH1 | 500 | 47 | 47 | 47 | 44 |
| *L. perenne* | TaRbcS::Lp1-SST_Lp6G-FFT::TaRbcS FT fusion 3 + pACH1 | 500 | 26 | 26 | 26 | 23 |
| *L. perenne* | TaRbcS::GUS::TaRbcS + pACH1 | 500 | 13 | 13 | 11 | 9 |

"Cassette DNA" containing *L. perenne* sequences was excised from the plasmid vectors pBS-LpRbcS::Lp1-SST::LpFT4, pBS-LpCAB::Lp6G-FFT::LpFT4 and pBS-LpRbcS::Lp1-SST_Lp6G-FFT::LpFT4 (FIGS. 29, 30 and 34 respectively) using the EcoR V restriction endonuclease. Following agarose gel electrophoresis, the resulting DNA fragment was purified from the agarose gel prior to being used for plant transformation to produce DNA without vector backbone sequences. The pACH1 vector previously constructed and used successfully in plant transformation experiments was also digested with restriction enzymes to produce a DNA fragment for the expression of the selectable marker only.

Biolistic co-transformation of perennial ryegrass with the vectors containing the *L. perenne* regulatory sequences, driving the expression of individual fructan genes or as a translational FT fusion, and the pACH1 expression cassette for hygromycin resistance was conducted on embryogenic calli for perennial ryegrass. Table 7 summarises the transformation and molecular analysis for the generation of these lines.

TABLE 7

Summary of transformation progress for production of transgenic perennial ryegrass plants for expression of Lp1-SST and Lp6G-FFT and FT fusion ORFs under control of ryegrass photosynthetic promoters.

| Plant Species | Transforming DNA | Number of calli bombarded |
|---|---|---|
| *L. perenne* | LpRbcS::Lp1-SST::LpFT4 + pACH1 | 2500 |
| *L. perenne* | LpCAB::Lp6G-FFT:: LpFT4 + pACH1 | 500 |
| *L. perenne* | LpRbcS::Lp1-SST-Lp6G-FFT::LpFT4 FT fusion 1 + pACH1 | 1000 |
| *L. perenne* | LpRbcS::Lp1-SST-Lp6G-FFT::LpFT4 FT fusion 3 + pACH1 | 1000 |
| *L. perenne* | LpCAB::Lp6G-FFT::LpFT4 + LpRbcS::Lp1-SST::LpFT4 + pACH1 | 1000 |

EXAMPLE 8

Characterisation of Transgenic Perennial Grasses

Characterisation of Transgenic FT and FT Fusion Perennial Ryegrass Plants

During the regeneration of the transgenic perennial ryegrass plants differences in growth phenotypes were noticed between the lines. Both the tissue culture regenerants and corresponding soil grown plants from both of the FT fusion 1 and FT fusion 3 transgenic plants showed a superior growth performance phenotype compared to the transgenic plants containing either a single fructan biosynthesis gene or control plants containing only the selectable marker, hph. Phenotypic examples of transgenic perennial ryegrass plants in tissue culture are displayed for the TaRbcS promoter and LpRbcS FT fusion transgenics in FIGS. 48-51.

The plants showing the superior growth performance phenotype were confirmed to contain the FT gene of interest. The superior growth performance phenotype of the transgenic FT fusion 1 and FT fusion 3 plants was first observed during the early stages of plant regeneration conducted on plates. Specifically just 12 days after incubation under lights the transgenic calli showed further developed green shoots. The fast growth rate of the FT fusion transgenic plants became more evident 22 days after transferring to rooting media. Transgenic plants containing either FT fusion 1 or FT fusion 3 constructs showed clearly greater numbers of tillers. In addition, the FT fusion transgenic plants consistently showed a higher tiller density per plant compared to control plants in vitro (FIGS. 48-49).

Figure 50:
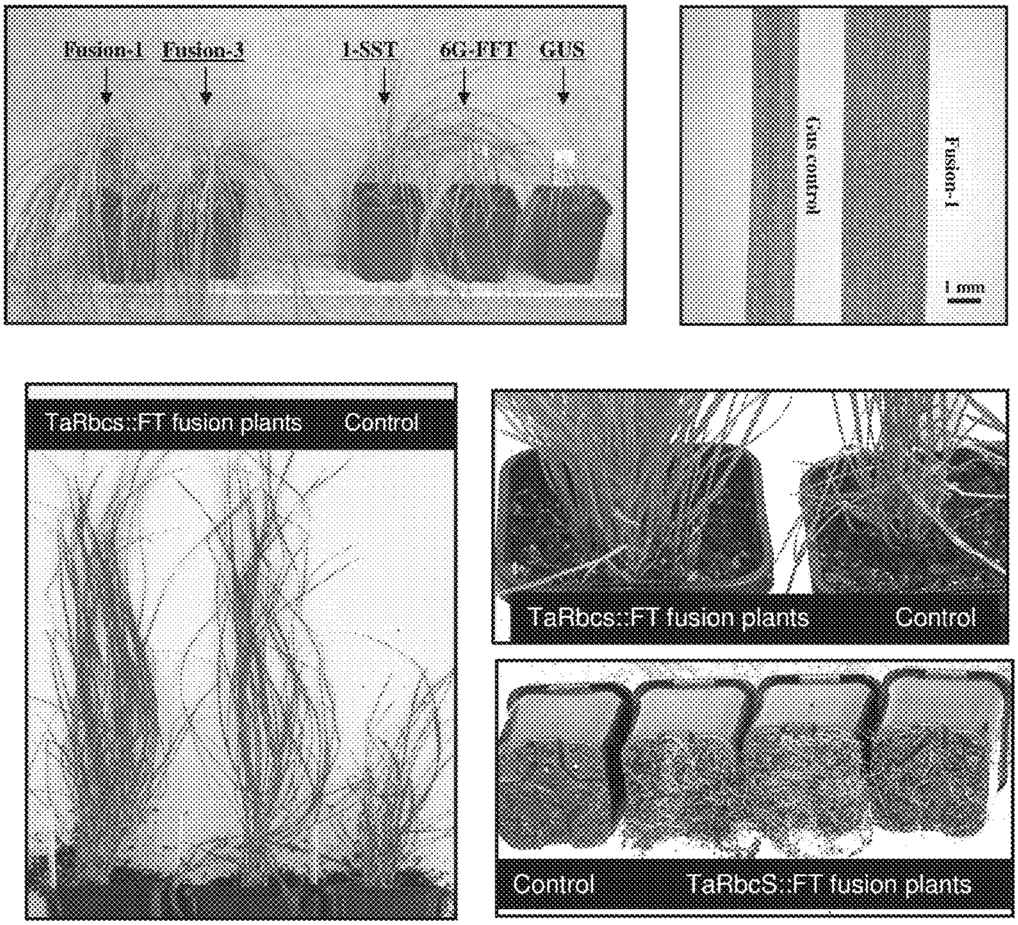

Following transfer to soil and propagation under glasshouse conditions more specific differences were observed between the FT fusion 1 and FT fusion 3 lines. Even though both FT fusion plants displayed enhanced growth performance, FT fusion 1 plants had longer, thicker and a slightly darker green leaf blades. Also the plants were physically more robust with thicker leaf sheaths and leaf blades. FT fusion 3 lines continued to grow faster than the other control plants with longer leaf blades and more vigorous tiller growth, but the leaf morphology was more similar to wild-type. An increase in root biomass was also observed in both FT fusion 1 and FT fusion 3 soil grown transgenic perennial ryegrass plants (FIG. 50). The control transgenic plants harbouring either the Lp1-SST or Lp6G-FFT as single genes did not show the level of increased growth rate that was observed in the FT fusion 1 and 3 transgenic plants. Their appearance is similar to each other, although some developed more vigorously than the transgenic plants containing either GUS or hph (FIG. 50).

A similar phenotype to that observed in the glasshouse was also observed in the field. The FT fusion transgenic plants showed a more vigorous growth phenotype with increased number of tillers and longer leaf blades (FIG. 51). The field trial transgenic plants were analysed for biomass production (Table 8). Biomass was assessed, as outlined in FIG. 52, ranging from a score of 1 having the least biomass to 5 having the most.

TABLE 8

Percent of plants indicating the range of biomass scores per genotype observed under field trial growth conditions.

| | Biomass score | | | | |
|---|---|---|---|---|---|
| | 1 | 2 | 3 | 4 | 5 |
| Wild-type | | 6% | 79% | 15% | |
| LpRbcS::1-SST | 11% | 28% | 39% | 22% | |
| LpRbcS FT fusion | | 4% | 54% | 38% | 4% |

Leaf blades from individual plants were cut and hand sectioned (FIG. 53). Obvious differences seen were in the amount of chloroplasts in each cell, and the number of cells with chloroplasts: being more in both of the transgenic FT fusion plants than in the control plants. In addition, chloroplasts were present in cells located on the abaxial side (lower part of the leaf) of transgenic plants, despite that both plants were grown under the same light conditions in the growth room. Sometimes it was observed that control plants produced more chloroplasts in mesophyll cells located on the adaxial side (upper side which face the light source) than on the abaxial side, whereas the transgenic plants most often produced near-equal number of chloroplasts on both sides.

Biochemical analysis by HPAEC of water soluble carbohydrates extracted from independent transformants harbouring the TaRbcS::Lp1-SST_Lp6G-FFT::TaRbcS FT fusion 1, TaRbcS::Lp1-SST_Lp6G-FFT::TaRbcS FT fusion 3, TaRbcS::Lp1-SST::TaRbcS, TaRbcS:: Lp6G-FFT::TaRbcS, and two control lines (hph only) showed that the FT fusion 1 and FT fusion 3 transgenic plants contained significantly higher levels of total fructans (FIG. 54), showing up to 2.5 fold increase over the control lines (FIG. 54). In addition, the levels of 1-kestose were up to 4 times higher in FT fusion 1 lines (up to 3.7 μg/mg of DW, total fructans: 20.5 μg/mg of DW and sucrose 51.2 μg/mg of DW.), and 3 times higher in FT fusion 3 lines (2.4 μg/mg of DW, total fructans: 26.0 μg/mg of DW and sucrose 49.8 μg/mg of DW) compared to the hph controls (FIG. 55A-B). In the TaRbcS::Lp1-SST:: TaRbcS plants 1-Kestose has increased up to 2.9 μg/mg of DW (a 3-fold increase) whereas total fructan content only increased 0.5 fold to 14 μg/mg of DW. In contrast 1-kestose levels in the TaRbcS::Lp6G-FFT::TaRbcS transgenic plant lines showed marginal increases up to 1.6 μg/mg of DW for 1-kestose (up to 0.5 fold) and only one line showed a small increase in total fructans to 10 μg/mg of DW (FIGS. 55C-D and 56C-D). Analysis of sucrose contents of all the lines revealed that some of the high fructan lines also showed an increase in total sucrose content (FIG. 57).

The transgenic perennial ryegrass was also evaluated under field conditions for total fructan level and composition (FIGS. 58 & 59) and transgene expression (FIG. 60C). The control and transgenic perennial ryegrass plants were sampled repeatedly throughout the field trial growing season. Biochemical analysis of wild-type controls and independent transformants was conducted to show the level of total fructan per plant. FIG. 58 illustrates fructan levels in milligrams (mg) per gram (g) of dry weight (DW) transgenic and wild-type field grown whole tillers and leaf blades. Multiple individual FT fusion and LpRbcS::Lp1-SST transgenic plants were identified with fructan concentrations between 80 to 120 percent higher than the corresponding the wild-type (WT) control plants in both whole tiller and leaf blade samples (FIG. 58).

Representative results on the composition of fructans in leaf blades of three LpRbcS::Lp1-SST transgenic perennial ryegrass plants as compared to wild-type controls are shown in FIG. 59. The results indicate an increased level of low DP fructans in transgenic plants expressing LpRbcS::Lp1-SST (Box 1, FIG. 59).

Transgene expression was detected in representative LpRbcS FT fusion and LpRbcS::Lp1SST transgenic perennial ryegrass plants analysed by quantitative reverse transcription PCR (qRT-PCR) (FIG. 60).

In order to quantify the increase in biomass single tillers were separated from each of the $T_0$ transgenic lines and control lines, and propagated in potting mix under glasshouse conditions. After 7 weeks and 12 weeks each plant was analysed for plant height, leaf blade width and total tiller number (FIGS. 61 and 62). After 7 weeks the control plants showed an average height of 24 cm, the average leaf width was 2.5 mm, and each plant had an average of two tillers. The transgenic FT fusion 1 and fusion 3 lines, however, showed up to an 80% increase in plant height (43 cm), up to 60% increase in leaf width (4 mm), and up to 3 fold increase in tiller number (6 tillers). After 12 weeks the control plants were, on average, 43 cm tall, leaf blades width was 3.5 mm, with 5 tillers per plant produced. Over the same period of time the transgenic FT fusion 1 and fusion 3 plants had grown up to 62 cm tall (43% increase compared to controls). The leaf width was up to 6 mm (70% increase) and the maximum number of tillers observed was 16 per plant (220% increase) (FIG. 62).

Characterisation of Transgenic LXR® and Transgenic FT Fusion Plus LXR® Perennial Ryegrass Plants Co-transformation of the FT fusion and LXR® technology produced an enhanced growth phenotype. Plants grown under glasshouse conditions showed an increased number of tillers and an enhanced root biomass compared to control and LXR® alone transgenic plants (FIG. 65).

Dry weight experiments of plant tissue were conducted to establish the biomass of individual FT fusion and LXR® transgenic plants. Transgenic perennial ryegrass plants grown under glasshouse conditions were trimmed 5 mm below the lowest leaf sheath at the 10 tiller stage. After 6 weeks all plant biomass from a height of 5 cm above the soil level was harvested into paper bags, oven-dried and weighed on a precision balance.

The control was calculated as the average of five independent 'gene of interest' negative (GOI-ve) plants. Both FT fusion and FT fusion plus LXR® transgenic plants produced plants with a dry weight higher (up to two fold) than the average level for the control (FIG. 64).

Biochemical analysis of GOI-ve controls and independent transformants was also conducted to show levels of total fructan per plant. Fructan levels in the leaf blades of FT fusion alone, as well as FT fusion plus LXR® transgenic plants showed up to a six fold increase compared to the average value of the control plants (FIG. 65).

Characterisation of Transgenic FT Fusion Tall Fescue Plants

Transformation of tall fescue grass with the vectors containing the *L. perenne* regulatory sequences, driving the FT translational fusion, and the pACH1 expression cassette for hygromycin resistance was conducted. Transgenic tall fescue plants grown under glasshouse conditions showed an increased number of tillers and an enhanced root biomass compared to control transgenic plants (FIG. 66).

Characterisation of Transgenic LXR® and Transgenic FT Fusion Plus LXR® Tall Fescue Plants Transgenic tall fescue (*Lolium arundinaceum* cv Jesup S3) plants expressing LpRbcS FT fusion 3 alone, TaRbcS FT fusion 3 alone, as well as TaRbcS FT fusion 3 plus LXR® technology (AtMYB32::IPT) together have been produced. Table 9 summarises the transformation and molecular analysis for the generation of these lines.

TABLE 9

Summary of transformation progress for tall fescue with photosynthetic-regulated expression of FT fusion 3 and/or LXR ®.

| Species | Transforming DNA | # putative transgenics | FT f3 +ve plants | LXR +ve plants | FT f3 & LXR +ve plants |
|---|---|---|---|---|---|
| *L arundinaceum* | LpRbcS FT fusion 3 | 10 | 6 | | |
| *L arundinaceum* | TaRbcS FT fusion 3 | 15 | 11 | | |
| *L arundinaceum* | LXR: | 10 | | 4 | |
| *L arundinaceum* | TaRbcS FT fusion 3 + LXR | 15 | | | 5 |

Dry weight experiments of plant tissue were conducted to establish the biomass of individual transgenic plants. Transgenic tall fescue plants grown under glasshouse conditions were trimmed 5 mm below the lowest leaf sheath at the 5 tiller stage. After 6 weeks all plant biomass from a height of 5 cm above the soil level was harvested into paper bags, oven-dried and weighed on a precision balance.

The control was calculated as the average of five independent GOI-ve plants. Transgenic FT fusion alone and FT fusion plus LXR® tall fescue plants both showed a two fold increase in herbage dry weight as compared to the average value of the control plants (FIG. 67).

Tiller number experiments were also conducted to establish the growth vigour of individual transgenic plants. Both tall fescue transgenic and GOI-ve control plants, at the 5 tiller stage, were trimmed as mentioned above and left growing under glasshouse conditions for 6 weeks before tiller numbers were counted. The tiller number in the control represents the average tiller number obtained from five independent GOI-ve plants. Transgenic lines of FT fusion alone and FT fusion plus LXR® tall fescue plants showed up to a two fold increase in tiller number compared to the average value of the control plants (FIG. 68).

Transgenic tall fescue plants (5 tillers) were trimmed (as indicated above) and grown under glasshouse conditions for 6 weeks when leaf blades were collected and freeze-dried for fructan analysis. The average fructan level in controls represents data obtained from five independent GOI-ve plants. Transgenic lines of FT fusion tall fescue plants show a dramatic increase (between three to five fold) in fructan accumulation in leaf blades compared to the average fructan level in GOI-ve control plants (FIG. 69).

EXAMPLE 9

Production of Transgenic Wheat Plants

Transformation of Light-Regulated Promoter Expressing Single Fructan Genes or the FT Translational Fusion Biolistic co-transformation of wheat with the vectors containing the photosynthetic promoter regulatory sequences, driving the expression of individual fructan genes or as a translational FT fusion, and a vector containing a chimeric Ubi::bar::nos selectable marker gene for glufosinate resistance (pACH25) was conducted on wheat embryogenic calli.

Transformation of AtMYB32 Promoter and IPT Gene for Delayed Senescence

A transformation vector has been constructed for biolistic transformation of wheat containing the chimeric AtMYB32::IPT::35S with a chimeric Ubi::bar::nos selectable marker gene for glufosinate resistance. Genetic transformation of wheat with LXR® vector was based on biolistic transformation of embryogenic calli from *Triticum aestivum* L Bobwhite 26 wheat line as described in International patent application PCT/AU01/01092. The candidate gene was inserted into the wheat genome by particle bombardment using whole plasmids so vector backbone sequences may also be incorporated into the genome. Transgenic plant tissues were recovered by survival on tissue culture media containing a selective agent.

Production of Transgenic Plants for Re-Programmed Fructan Biosynthesis in Photosynthetic Cells and Extended Life of Photosynthetic Cells Using the methods outlined above transgenic plants were generated that contain both fructan biosynthetic genes driven by light-regulated promoters and the LXR® technology for re-programmed fructan biosynthesis in photosynthetic cells and extended life of photosynthetic cells. Table 8 summarises the transformation and molecular analysis for the generation of these transgenic plants.

TABLE 10

Summary of transformation progress for production of transgenic wheat plants for expression of Lp1-SST and Lp6G-FFT and FT fusion ORFs under control of photosynthetic promoters of wheat and in combination with LXR ® technology for re-programmed fructan biosynthesis in photosynthetic cells and extended life of photosynthetic cells.

| Plant Species | Transforming DNA | Number of embryos bombarded |
|---|---|---|
| *T aestivum* | TaRbcS::Lp1-SST_Lp6G-FFT::TaRbcS FT fusion 1 + pAcH25 | 2000 |
| *T aestivum* | TaRbcS::Lp1-SST_Lp6G-FFT::TaRbcS FT fusion 3 + pAcH25 | 2000 |

TABLE 10-continued

Summary of transformation progress for production of transgenic wheat plants for expression of Lp1-SST and Lp6G-FFT and FT fusion ORFs under control of photosynthetic promoters of wheat and in combination with LXR ® technology for re-programmed fructan biosynthesis in photosynthetic cells and extended life of photosynthetic cells.

| Plant Species | Transforming DNA | Number of embryos bombarded |
|---|---|---|
| *T aestivum* | TaRbcS::Lp1-SST_Lp6G-FFT::TaRbcS FT fusion 1 + LXR ® + pAcH25 | 2000 |
| *T aestivum* | TaRbcS::Lp1-SST_Lp6G-FFT::TaRbcS (FT fusion 3 + LXR ® + pAcH25 | 2000 |
| *T aestivum* | LXR ® + pAcH25 | 2000 |
| *T aestivum* | pAHc25 (Control) | 2000 |

EXAMPLE 10

Characterisation of Transgenic Wheat Plants

Characterisation of Transgenic FT Fusion Wheat Plants

During the regeneration of the transgenic wheat plants differences in in vitro growth phenotypes were noticed. The tissue culture regenerants from both of the FT fusion 1 and FT fusion 3 transgenic plants showed a superior vigour phenotype compared to control plants.

The superior growth phenotype of the transgenic FT fusion 1 and FT fusion 3 plants was first observed during the early stages of in vitro plant regeneration conducted on tissue culture plates. Following biolistic transformation calli were kept for two weeks on tissue culture plates in the dark and then transferred to light conditions. Approximately 6 weeks after incubation under light conditions the transformed calli showed more fully developed green shoots and the roots of the FT fusion transgenic regenerants grew at an extremely advanced rate (FIG. 70).

The fast growth rate of the FT fusion transgenic plants became more evident after transferring to rooting media. FT fusion transgenic plants showed an obvious early increase in tiller number at around 2 months as compared to null controls (up to 5 tillers compare to one tiller observed in control plants). The width of the leaves of the some of the plants was 4-5 mm compare to control plants 2-3 mm. In addition, the FT fusion transgenics consistently showed a higher tiller density per plant compared to control lines (FIG. 71).

Following transfer to soil and propagation under glasshouse conditions the transgenic wheat plants that contain the FT fusion constructs continued to show an increase in tiller number as compared to control plants (FIG. 72).

Characterisation of Transgenic LXR® and FT Fusion Plus LXR® Wheat Plants

The transgenic wheat plants that contain the LXR® technology construct showed an increase in tiller number as compared to control plants under glasshouse conditions (FIG. 73A). They also showed and increase of photosynthetic tissue after 35 days under glasshouse conditions (FIG. 73B).

Co-transformation of the FT fusion construct and LXR® technology produced an enhanced growth phenotype of glasshouse grown plants. Some of the plants also showed an obvious late senescence (at 40 days) under glasshouse conditions (FIG. 74). Transgenic wheat plants expressing the FT fusion construct and the FT fusion construct plus LXR® also showed an enhanced level of fructans in leaves and an increased number of tillers as compared to control plants under glasshouse conditions (FIG. 75).

Biochemical analysis of GOI-ve controls, FT fusion, as well as FT fusion plus LXR® independent $T_1$ wheat transformants, grown under glass house conditions, was conducted to show levels of total fructan per plant. A dramatic increase in fructan level (up to five fold) was detected for both transgenic lines (FIG. 76).

EXAMPLE 11

Production of Transgenic *Paspalum dilatatum* Plants

Transformation of IPT Gene Under Control of AtMYB32 Promoter for Delayed Leaf Senescence Genetic transformation of *Paspalum dilatatum* (apomictic dallisgrass) was based on biolistic transformation as described in International patent application PCT/AU01/01092.

The candidate gene expression construct was inserted into the *Paspalum dilatatum* genome by particle bombardment using whole plasmids so vector backbone sequences may also be incorporated into the genome. Transgenic plant tissues were recovered by survival on tissue culture media containing a selective agent.

Transformation of FT Translational Fusion Under Control of Light-Regulated Promoter for Engineering Fructan Biosynthesis in Photosynthetic Cells Genetic transformation of *Paspalum dilatatum* with photosynthetic regulated fructan biosynthesis genes is conducted using the same method as was used to produce the LXR® transgenic *Paspalum dilatatum* plants.

EXAMPLE 12

Characterisation of Transgenic *Paspalum dilatatum* Plants

LXR® Transgenic Plants Display a Superior Growth Phenotype.

Transgenic *Paspalum dilatatum* plants expressing the IPT gene under control of the AtMYB32 promoter revealed an enhanced biomass accumulation. During the regeneration of the putative transgenic *P. dilatatum* plants differences in growth phenotypes were noticed showing a superior growth phenotype compared to control plants. The distinctive growth phenotype may be used as a selection tool for identifying transformed plants in combination with co-transformed vectors.

EXAMPLE 13

Production of Transgenic Dicotyledonous Plants

Transformation of LXR® and FT Fusion Plus LXR® Dicot Plants

Binary vectors containing the FT fusion and LXR® technology have been generated for *Agrobacterium*-mediated transformation of dicot plants. Transformation vectors also contained a chimeric 35S::nptII::35 S or 35S::hph::35S as selectable marker genes.

Production of Transgenic Dicot Plants

Transgenic white clover (*Trifolium repens*) and *Arabidopsis thaliana* plants expressing LXR® technology alone (AtMYB3::IPT), AtRbcS::Lp1-SST_Lp6G-FFT::35S FT fusion alone, as well as LXR® technology and the AtRbcS::Lp1-SST_Lp6G-FFT::35S FT fusion together have been produced (FIGS. 77 and 80). Tables 11 and 12 summarise the transformation and molecular analysis for the generation of these lines, respectively.

TABLE 11

Summary of transformation progress for white clover with *Arabidopsis* photosynthetic-regulated expression of FT fusion and/or LXR ®

| Species | | Transforming DNA | No putative transgenics | hph +ve plants | FT fusion +ve plants | LXR +ve plants | FT fusion & LXR +ve |
|---|---|---|---|---|---|---|---|
| *T repens* | Mink | AtRbcS FT fusion | 177 | 158 | ND | — | |
| *T repens* | Mink | AtRbcS FT fusion + LXR | 146 | ND | 85 | 33 | 13 |

TABLE 12

Summary of transformation progress for *Arabidopsis* with *Arabidopsis* photosynthetic-regulated expression of FT fusion and/or LXR ®

| Species | Transforming DNA | No putative transgenics | hph +ve plants | FT fusion +ve plants | LXR +ve plants | FT fusion & LXR +ve |
|---|---|---|---|---|---|---|
| *A thaliana* | AtRbcS FT fusion + LXR | 50 | 30 | 15 | 10 | 2 |

Characterisation of Transgenic White Clover Plants

Quantitative RT-PCR was used to confirm transformants and detect expression levels of the AtRbcS FT fusion in selected lines (FIG. 78). These lines, showing expression of the transgene also demonstrated an increased level of fructans (FIG. 68B). No expression was detected in control lines (FIG. 78).

Biochemical analysis by HPAEC of water soluble carbohydrates extracted from independent transformants expressing AtRbcS FT fusion alone, AtRbcS FT fusion plus LXR® and GOI-ve control lines was conducted to show levels of total fructans per plant. AtRbcS FT fusion and AtRbcS FT fusion plus LXR® transgenic lines showed a two fold increase of fructan accumulation in leaves higher than that observed in the controls (FIG. 79).

Characterisation of Transgenic *Arabidopsis* Plants

Quantitative RT-PCR was used to confirm transformants and detect expression levels of the AtRbcS FT fusion in selected lines (FIG. 81). Transgenic $T_2$ FT fusion *Arabidopsis* plants grown in soil are shown in FIG. 82. Gene of interest negative plants (GOI-ve) are also presented and show no phenotypic difference to FT fusion transgenic plants shown to express the transgene.

Binary vectors were also used for *Agrobacterium*-mediated transformation of *Brassica napus* (canola) hypocotyl segments (Patent PCT/AU01/01092).

EXAMPLE 14

Characterisation of Transgenic Dicotyledonous Plants

Characterisation of Transgenic LXR® Dicot Plants

A functionally active fragment of the AtMYB32 promoter was used to drive IPT expression in transgenic white clover and canola plants as described in International patent application PCT/AU01/01092. Outcomes observed from the LXR® technology in dicot plants have been delayed leaf senescence; enhanced leaf growth dynamics; reduced stolon death; enhanced biomass production; increased cumulative green leaf area; increased seed yield; enhanced drought tolerance; increased shading tolerance; enhanced herbage quality reflected by enhanced ruminal fermentation kinetics and higher dry matter digestibility.

Transgenic Plants Display a Delayed Leaf Senescence Phenotype.

The regulation of developmental senescence may be assessed by simulating and initiating artificial aging of detached leaves in vitro on moist filter paper. Incubation of detached leaves in darkness is highly effective in inducing Senescence Associated Genes (SAGS), leaf yellowing and chlorophyll loss (Weaver and Amasino, 2001). FIG. 83 demonstrates detached senescence assay data associated with expression of the IPT gene under control of one of two functionally active fragments of the AtMYB32 promoter in white clover and canola. The transgenic plants displayed a significant delay of leaf senescence as compared to leaves from control plants 7-20 days following detachment.

EXAMPLE 15

Production of Transgenic Plants for Re-Programming Fructan Biosynthesis in Photosynthetic Cells and for Extended Life of these Photosynthetic Cells Using the methods outlined above transgenic plants have been generated that contain both, fructan biosynthetic genes (FT including FT fusion genes) under control of light-regulated, photosynthetic promoters for re-programming fructan biosynthesis in photosynthetic cells and LXR® technology through co-expression of IPT gene driven by the AtMYB32 promoter for extending life of the photosynthetic cells.

EXAMPLE 16

Use of the Distinctive Growth Phenotype as a Selection Tool to Identify Transgenic Plants In Vitro The superior growth phenotype of the transgenic FT fusion 1 or FT fusion 3 plants was observed in all plant types to which it was transformed (eg perennial ryegrass and wheat). In both ryegrass and wheat it was first observed during the early stages of plant regeneration conducted in plates. In the experiments conducted without antibiotic selection, strong shoot induction has been observed at the stage when after bombardment the calli have been kept in dark conditions for 8 weeks. (FIG. 84 A-C). After transferring the plates to light conditions (7 days after transfer) strong shoot induction was observed in the transgenic plants and much lower level of shoot regeneration was detected in control plants (FIG. 84 D-F).

Expression of the FT fusion under control of TaRbcS or other photosynthetic, sucrose-regulated or constitutive promoters could be used as a selection tool for the identification of transformed plants at the tissue culture stage. Expression of the FT fusion protein may be also driven by a set of promoters, which are active due to the high concentration of sucrose that exists in tissue culture medium, and much less active at the low sucrose levels present in soil-grown plants. This transgene may subsequently be segregated away from the transgenic plants in successive generations. The increased biomass of the transformed plants to be used as the selective agent should not require an antibiotic resistance marker for the selection process, enabling the production of a market ready product.

Analysis was carried out to assess the use of the distinctive growth phenotype to detect a positive transformation result in perennial ryegrass. Embryogenic perennial ryegrass calli FLP410-20 were bombarded with gold particles covered in TaRbcS FT fusion 1 alone, TaRbcS FT fusion 3 alone, AtMYB32::IPT (LXR®) alone, as well as TaRbcS FT fusion 1 plus LXR® vectors without any selectable marker. Control calli were bombarded just with golden particles.

Plants were regenerated without antibiotic selection and kept 2 weeks under dark conditions and then transferred to light conditions (16/8 hr light/dark photo-period). The plant's growth was examined prior to transfer to light and weekly for five weeks under light conditions. Calli were kept under progressively starving conditions on the same plate for five weeks (Callus induction medium: MS full strength+250 mg/L L-asparagine+2.5 mg/L 2,4-D+6% sucrose+0.7% agar).

Control plant growth was initiated during the first two to three weeks under light conditions but slowed significantly four and five weeks later (FIG. 85). Some calli bombarded with TaRbcS FT fusion vectors showed more vigorous growth during the first two to three weeks and continued growing (with reduced rate) at weeks four and five (FIG. 85). No obvious differences were observed for LXR® alone bombarded calli. Co-transformation with TaRbcS FT fusion 1 plus LXR® vectors showed an intermediate phenotype between the control and the TaRbcS FT fusion 1 vector alone (FIG. 86).

Molecular analysis was undertaken to detect the presence of the TaRbcS FT fusion transgenes using qRT-PCR in putative transgenic lines. FT fusion transgenics showed between 60% and 70% transformation and selection efficiency without antibiotics. No LXR alone transgenic plants showed presence of the transgene. Co-transformation of TaRbcS FT fusion and LXR showed an 11% efficiency of co-transformation and selection (FIG. 86).

A method of co-transformation of FT fusions and LXR® for positive selection to determine the co-transformation efficiency has been developed and is outlined below.

Initially, the co-transformation efficiency is determined for a variety of transformation events which include a vector containing an antibiotic selectable marker. These co-transformation events include:

1. FT fusion regulated by a photosynthetic promoter+hph selectable marker
2. LXR® plus hph selectable marker
3. FT fusion regulated by a photosynthetic promoter plus LXR® plus hph selectable marker Selection on antibiotic media for transgenics takes place and the presence of the transgene for each double or triple co-transformation event is determined, generating a co-transformation efficiency number for each event.

A second round of co-transformation events also takes place without an antibiotic selectable marker on selection free media. These co-transformation events include:

1. FT fusion regulated by a photosynthetic promoter+dsRED marker
2. LXR® plus dsRED marker
3. FT fusion regulated by a photosynthetic promoter plus LXR® plus dsRED marker Selection for increased growth rate of shoots and/or roots takes place and the presence of the transgene for each double or triple co-transformation event is determined. The presence of the dsRED marker gene is easily determined by visualisation of fluorescence and helps determine the co-transformation efficiency for each of the transformation events. Comparison of the co-transformation efficiencies determined with and without selectable marker aids in establishing the efficacy of using a superior phenotype as a selection tool.

REFERENCES

Documents cited in this specification are for reference purposes only and their inclusion is not acknowledgment that they form part of the common general knowledge in the relevant art.

Altenbach, D., et al. (2004) "The large subunit determines catalytic specificity of barley sucrose:fructan 6-fructosyltransferase and fescue sucrose:sucrose 1-fructosyltransferase." *FEBS Lett.* 567: 214-218.

Altenbach, D., et al. (2005) "Mutational analysis of the active center of plant fructosyltransferases: *Festuca* 1-SST and barley 6-SFT." *FEBS Lett.* 579: 4647-53.

Bai, Y., et al. (2001). "Genetic transformation of elite turf-type cultivars of Tall Fescue." *International Turfgrass Society Research Journal* 9: 129-136.

Barry, G., et al. (1984). "Identification of a cloned cytokinin biosynthetic gene." *Proc Nat Acad Sci* 81: 4776-4780.

Biggs, D., et al. (1998). "In vitro digestion of bacterial and plant fructans and effects on ammonia accumulation in cow and sheep rumen fluids." *J Gen Appl Microbiol* 44: 167-171.

Bilang, R., et al. (1991). "The 3'-terminal region of the hygromycin-B-resistance gene is important for its activity in *Escherichia coli* and *Nicotiana tabacum.*" *Gene* 100: 247-250.

Brenner W. G., et al. (2005). "Immediate-early and delayed cytokinin response genes of *Arabidopsis thaliana* identified by genome-wide expression profiling reveal novel cytokinin-sensitive processes and suggest cytokinin action through transcriptional cascades." *Plant J* 44: 314-333.

Chalmers, J., et al. (2003). "Isolation and characterisation of a sucrose:sucrose 1-fructosyltransferase gene from perennial ryegrass (*Lolium perenne*)." *J Plant Physiol* 160(11): 1385-1391.

Chalmers, J., et al. (2005). "Functional genomics of fructan metabolism in temperate grasses." *Plant Biotech J* 3(5): 459-474.

Chandlee, J. (2001). "Current molecular understanding of the genetically programmed process of leaf senescence." *Physiologia Plantarum* 93: 113.

Chen, Z. et al. (1988) "A DNA sequence element that confers seed-specific enhancement to a constitutive promoter." *EMBO J.* 7: 297-302.

Christensen, A. H., et al. (1992). "Maize polyubiquitin genes: structure, thermal perturbation of expression and transcript splicing, and promoter activity following transfer to protoplasts by electroporation." *Plant Mol Biol* 18: 675-689.

Doczi, R., et al. (2005) "Conservation of the drought-inducible DS2 genes and divergences from their ARS paralogues in solanaceous species." *Plant Phys. Biochem.* 43: 269-276.

Faiss, M. et al. (1997) "Conditional transgenic expression of the IPT gene indicates a function for cytokinins in paracrine signalling." *The Plant Journal* 12: 401-415.

Gadegaard, G., et al. (2007). "Improved fructan accumulation in perennial ryegrass transformed with the onion fructosyltransferase genes 1-SST and 6G-FFT." *J Plant Physiol* published on-line (doi:10.1016/j.jplph.2007.06.019).

Gan, S. S., et al. (1999). "Developmental targeting of gene expression by the use of a senescence-specific promoter." *Inducible Gene Expression in Plants*. R. P. New York, CAB International: 169-186.

Guerrand, D., et al. (1996). "Fructan metabolism in expanding leaves, mature leaf sheaths and mature leaf blades of *Lolium perenne*. Fructan synthesis, fructosyltransferase and invertase activities." *New Phytol* 134: 205-214.

Hajdukiewicz, P., et al. (1994). "The small, versatile pPZP family of *Agrobacterium* binary vectors RT for plant transformation." *Plant Mol Biol* 25: 989-994.

Hauffe, K. et al. (1993) "Combinatorial interactions between positive and negative cis-acting elements control spatial patterns of 4CL-1 expression in transgenic tobacco." *Plant J.* 4:235-53.

Heazlewood, J. (2000) "AtMYB32: a MYB related gene from *Arabidopsis thaliana* expressed in developing anthers and roots" PhD thesis (Botany Department of La Trobe University).

Hendry, G., et al. (1993). "The origin, distribution and evolutionary significance of fructans." *Science and Technology of Fructans*. Suzuki M and Chatterton N J. Florida, CRC Press: 119-139.

Herbers, K., et al. (1994) "Cloning and characterization of a cathepsin D inhibitor gene from *Solanum tuberosum* L." *Plant Mol. Biol.* 26:73-83.

Hewelt, A., et al. (1994) "Promoter tagging with a promoterless IPT gene leads to cytokinin-induced phenotypic variability in transgenic tobacco plants: implications of gene dosage effects." *The Plant Journal* 6: 879-891

Hisano, H., et al. (2004). "Transgenic perennial ryegrass plants expressing wheat fructosyltransferase genes accumulate increased amounts of fructan and acquire increased tolerance on a cellular level to freezing." *Plant Sci* 167: 861-868.

Hudson, M. E., et al. (2003). "Identification of promoter motifs involved in the network of phytochrome A-regulated gene expression by combined analysis of genomic sequence and microarray data." *Plant Physiol* 133: 1605-1616.

Huynh, L. N., et al. (2005) "Regulation of flooding tolerance of SAG12:IPT *Arabidopsis* plants by cytokinin." *Journal of experimental botany* 56: 1397-1407.

Jin, L. and Lui, J. (2008) Molecular cloning, expression profile and promoter analysis of the novel ethylene responsive transcription factor gene GhERF4 from cotton. "*Plant Phys Biochem.* 46: 46-53.

Kapila, J., et al. (1997). "An *Agrobacterium*-mediated transient gene expression system for intact leaves." *Plant Sci* 124(2): 227-227.

Kay, R., et al. (1987). "Duplication of (CAMV)35S promoter sequences creates a strong enhancer for plant genes." *Science* 236: 1299-1302.

Khodakovskyaya, et al. (2004) "Distinct isoprenoid origins of cis- and trans-zeatin biosynthesis in *Arabidopsis*. Journal of biological" *Chemistry* 279: 14049-14054.

Kwak, M., et al. (2005) "Two sweet potato ADP-glucose phosphorylase isoforms are regulated antagonistically in response to sucrose content in storage roots." *Gene* 366: 87-96.

Li, X., et al. (2001) Sucrose regulation of ADP-glucose pyrophosphorylase subunit genes transcript levels in leaves and fruit. *Plant Science* 162: 239-244.

Lidgett, A., et al. (2002). "Isolation and characterisation of a fructosyltransferase gene from perennial ryegrass (*Lolium perenne*)." *J Plant Physiol* 159(9): 1037-1043.

Lin, K., et al. (2008) "Generation and analysis of the transgenic potatoes expressing heterologous Thermostable B-amylase" *Plant science* 174: 649-657.

Liu, D., et al. (2003) "High transgene expression levels in sugarcane (*Saccharum officinarum* L.) driven by the rice ubiquitin promoter RUBQ2." *Plant Science* 165: 743-750.

Martinez-Hernandez, A., et al. (2002). "Functional properties and regulatory complexity of a minimal RBCS light-responsive unit activated by phytochrome, cryptochrome, and plastid signals." *Plant Physiol* 128: 1223-1233.

Mcabe, M., et al. (2001) "Effects of PSAG12-IPT gene expression on development and senesence in transgenic lettuce." *Plant Physiology* 127: 505-516.

McElroy, D., et al. (1990). "Isolation of an efficient actin promoter for use in rice transformation." *Plant Cell* 2: 163-171.

Medford, J. I, et al. (1989) "Alterations of endogenous cytokinins in transgenic plants using chimeric isopentenyl transferase gene." *The Plant Cell.* 1: 403-413.

Nocek, J., et al. (1988). "Protein and energy as in integrated system. Relationship of ruminal protein and carbohydrate availability to microbial synthesis and milk production." *J Dairy Sci* 70: 2070-2107.

Pollock, C., et al. (1979). "Seasonal patterns of fructan metabolism in forage grasses." *New Phytol* 83: 9-15.

Preston, J., et al. (2004) "AtMYB32 is required for normal pollen development in *Arabidopsis thaliana." The Plant Journal,* 40: 979-995.

Ouellet, F., et al. (1998) "The wheat wcs120 promoter is cold-inducible in both monocottyledeonous and dicotelydonous species." *FEBS Letters* 423: 324-328.

RIRDC. (2007). "Biofuels in Australia—an overview of issues and prospects." from www.rirdc.gov.au.

Romero, H., et al. (2006) Expression profile analysis and biochemical properties of the peptide methionine sulfoxide reductase A (PMSRA) gene family in *Arabidopsis. "Plant Science* 170:705-714.

Rooke, L., D. et al (2000). "Marker gene expression driven by the maize ubiquitin promoter in transgenic wheat." *Ann Appl Bio* 136: 167-172.

Sasanuma, (2001). "Characterization of the rbcS multigene family in wheat: subfamily classification, determination of chromosomal location and evolutionary analysis." *Mol Genetics Genomics* 265(1): 161-171.

Schaffner, A. R., et al. (1991). "Maize RbcS Promoter Activity Depends on Sequence Elements Not Found in Dicot rbcS Promoters." *Plant Cell* 3: 997-1012.

Siebertz, B., et al. (1989) "cis-Analysis of the wound inducible promoter wun-1 in transgenic tobacco plants and histochemical localisation of its expression." *The Plant Cell* 1: 960-968.

Short, J., et al. (1988). "Lambda ZAP: a bacteriophage lambda expression vector with in vivo excision properties." *Nucleic Acids Res* 16(15): 7583-7600.
Smart, C. (1994). "Gene expression during leaf senescence." *New Phytol* 126: 419-448.
Spangenberg, G., et al. (1995a). "Transgenic tall fescue and red fescue plants from microprojectile bombardment of embryogenic suspension cells." *J Plant Physiol* 145: 693-701.
Spangenberg, G., et al. (1995b). "Transgenic perennial ryegrass (*Lolium perenne*) plants from microprojectile bombardment of embryogenic suspension cells." *Plant Sci* 108(2): 209-217.
Stark, D. et al. 1992 "Regulation of the Amount of Starch in Plant Tissues by ADP Glucose Pyrophosphorylase" Science 258: 287-292.
Szopa, J., et al. (2003) "Structural organisation, expression, and promoter analysis of a 16R isoform of 14-3-3 protein gene from potato." *Plant Phys Biochem.* 41: 417-423.
Taweel, H. Z., et al. (2005). "Effects of feeding perennial ryegrass with an elevated concentration of water-soluble carbohydrates on intake, rumen function and performance of dairy cows." *Ani Feed Sci Tech* 121: 243-256.
Terzaghi, W. B., et al. (1995). "Light-regulated transcription." *Annu Rev Plant Physiol Plant Mol Biol* 46: 445-474.
Thomas, H., et al. (1999). "Partitioning of sugars in *Lolium perenne* (perennial ryegrass) during drought and on rewatering." *New Phytol* 142: 295-305.
Tran, L. et al. (2004) "Isolation and functional analysis of *Arabidopsis* stress-inducible NAC transcription factors that bind to a drought-responsive cis-element in the early responsive to dehydration stress 1 promoter." *Plant Cell* 16: 2481-98.
Wan, B., et al. (2007) "Expression of rice $Ca^{2+}$-dependent protein kinases (CDPKs) genes under different environmental stresses." *FEBS Letters* 581: 1179-1189.
Weaver L. M. and Amasino, R. M. (2001) "Senescence is induced in individually darkened *Arabidopsis* leaves but inhibited in whole darkened plants." *Plant Physiology* 127: 876-886.
Weaver, L. M., et al. (1998). "A comparison of the expression patterns of several senescence-associated genes in response to stress and hormone treatment." *Plant Mol Biol* 37: 455-469.
Wydro, M., et al. (2006). "Optimization of transient *Agrobacterium*-mediated gene expression system in leaves of *Nicotiana benthamiana.*" *Acta biochim Pol* 53(2): 289-298.
Yamaguchi-Shinozaki K. and Shinozaki K. (1993). Characterisation of the expression of a desiccation-responsive rd29 gene of *Arabidopsis thaliana* and analysis of its promoter in transgenic plants. *Mol. Gen. Genet.* 236: 331-340.
Ye, X., et al. (1997). "Transgenic Italian ryegrass (*Lolium multiflorum*) plants from microprojectile bombardment of embryogenic suspension cells." *Plant Cell Rep* 16(6): 379-384.
Ye, X., et al. (2001). "Altered fructan accumulation in transgenic *Lolium multiflorum* plants expressing a *Bacillus subtilis* sacB gene." *Plant Cell Rep* 20: 205-212.
Zeng, W. K., et al. (1995). "PCR Amplification and Sequencing of a Wheat rbcS Gene Promoter." *Acta Bot Sinica* 37(6): 496-500.
Zhang, X., et al. (2004) "The indigenous plasmid pQBR103 encodes plant-inducible genes, including three putative helicases." *FEMS Micro. Ecol.* 51: 9-17.

The invention claimed is:

1. A method selected from the group consisting of (a) enhancing productivity of a fructan biochemical pathway in a plant, (b) manipulating fructan biosynthesis in photosynthetic cells of a plant, (c) enhancing biomass in a plant, and (d) selecting for transformed plants, said method comprising the step of:

introducing into said plant an effective amount of a genetic construct comprising nucleic acids encoding two fructan biosynthetic enzymes operatively linked to a light-regulated promoter, wherein said nucleic acids are linked to form a fusion gene encoding a fusion protein of said two fructan biosynthetic enzymes, and wherein when said method is selecting for transformed plants, said method further includes selecting plants with enhanced biomass.

2. The method according to claim 1 wherein said fructan biosynthetic enzymes are selected from the group consisting of 1-SST, 1-FFT, 6-SFT and 6G-FFT.

3. The method according to claim 1 wherein said fructan biosynthetic enzymes are 1-SST and 6G-FFT.

4. The method according to claim 1 wherein said fructan biosynthetic enzymes are 1-SST and 6-SFT.

5. A genetic construct, said genetic construct comprising nucleic acids encoding two fructan biosynthetic enzymes operatively linked to a light-regulated promoter, wherein said nucleic acids are linked to form a fusion gene encoding a fusion protein of said two fructan biosynthetic enzymes.

6. The genetic construct according to claim 5 wherein said fructan biosynthetic enzymes are selected from the group consisting of 1-SST, 1-FFT, 6-SFT and 6G-FFT.

7. A method of enhancing biomass in a plant, said method including introducing into said plant effective amounts of the genetic construct according to claim 5 and a genetic construct capable of manipulating senescence in the plant.

8. The method according to claim 7 wherein the genetic construct capable of manipulating senescence includes a MYB gene promoter or modified MYB gene promoter, operatively linked to a gene encoding an enzyme involved in biosynthesis of a cytokinin.

9. A transgenic plant cell, plant, plant seed or other plant part with modified fructan biosynthetic characteristics or enhanced biomass relative to an untransformed control plant, wherein the transgenic plant cell, plant, plant seed or other plant part has an increase in biomass of at least 10%, relative to an untransformed control plant, and wherein said plant cell, plant, plant seed or other plant part includes the genetic construct according to claim 5.

10. The transgenic plant cell, plant, plant seed or other plant part according to claim 9 having an increase in soluble carbohydrate of least 10%, relative to an untransformed control plant.

11. The genetic construct according to claim 5 wherein said fructan biosynthetic enzymes are 1-SST and 6G-FFT.

12. The genetic construct according to claim 5 wherein said fructan biosynthetic enzymes are 1-SST and 6-SFT.

* * * * *

UNITED STATES PATENT AND TRADEMARK OFFICE

CERTIFICATE OF CORRECTION

PATENT NO. : 9,890,387 B2
APPLICATION NO. : 13/063992
DATED : February 13, 2018
INVENTOR(S) : Spangenberg et al.

It is certified that error appears in the above-identified patent and that said Letters Patent is hereby corrected as shown below:

Column 24, Line 56 - Column 25, Line 15, should read:

Table 1. The position of the cis-regulatory sequences identified by the PLACE database. Common cis-acting regulatory sequences are listed (Schaffner, et al., 1991; Terzaghi, et al., 1995; Martinez-Hernandez, et al., 2002; Hudson, et al., 2003). Positions noted are the first nucleotide in the sequence relative to the ATG. (n.p. - not present).

| **cis-acting regulatory seq.** | **Accession #** | **position *LpRbcS*** | **position *LpCAB*** |
|---|---|---|---|
| I-Box Core | S000199 | -184 | -137 |
| I-Box | S000124 | -311 | -137 |
| GT1 consensus | S000198 | -304 | n.p. |
| RbcS moncot seq | Schaffner et al, 1991 | -173 to -151 | n.p. |
| SORLIPs | S000482 | n.p. | -58, -217, -647, -695 |

Signed and Sealed this
Twentieth Day of March, 2018

Andrei Iancu
*Director of the United States Patent and Trademark Office*

Column 33 and 34, Line 10 thru Column 35 and 36, Line 11 approximately, should read:

Table 5. Examples of different promoters to drive transgene expression.

| **Specificity/Tissue** | **Gene Promoter** | **Organism** | **Reference** |
|---|---|---|---|
| **Constitutive** | | | |
| Constitutive / all | Ubiquitin, *Ubi* | *Zea mays* (maize) | Christensen et al. (1992) |
| | (CAMV) *35S*[2] | Cauliflower mosaic virus | Kay et al. (1987) |
| | Polyubiquitin, *RUBQ2* | *Oryza sativa* (rice) | Liu et al. (2003) |
| | Actin 1, Os*Act1* | *Oryza sativa (rice)* | McElroy et al. (1990) |
| **Tissue Specific** | | | |
| Tuber and stolon specific | Sucrose synthetase, *Sus4* | *Solanum tuberosum* (potato) | Lin et al. (2008) |
| | Cathepsin D inhibitor gene, *Cathinh* | *Solanum tuberosum* (potato) | Herbers et al. (1994) |
| | | | |
| Root and shoot of sugar beet | Helicase-like genes, *helA*, *helB* and *helC* | *Pseudomonas* plasmid | Zhang et al. (2004) |
| | | | |
| Seed | β-conglycinin, a soybean seed storage protein | *Glycine max* (soybean) | Chen et al. (1988) |
| | | | |
| Phloem | Sucrose synthase, *Suc2* | *Zea mays* (maize) | Yang and Russell (1990) |
| | | | |
| Xylem | phenylalanine ammonialyase gene 2, *PAL2* | *Nicotiana. benthamiana* (tobacco) | Keller and Baumgartner (1991) |
| | 4-coumarate: coenzyme A ligase. *4CL* | *Nicotiana. benthamiana* (tobacco) | Hauffe et al. (1993) |

| | | | |
|---|---|---|---|
| **Inducible** | | | |
| Cold, dehydration and salt stress responsive | Calcium dependent protein kinases, Os*CPK6*, Os*CPK13*, Os*CPK25* | *Oryza sativa* (rice) | Wan et al. (2007) |
| | | | |
| Dehydration stress | early responsive to dehydration stress, *ERD1* | *Arabidopsis thaliana* | Tran et al. (2004) |
| | | | |
| Stress responsive | *rd29a* | *Arabidopsis thalina* | Yamaguchi-Shinozaki and Shinozaki (1993) |
| | | | |
| Sucrose responsive | ADP-glucose pyrophosphorylase, *IbAGP1* | *Ipomoea batatas* (sweet potato) | Kwak et al. (2005) |
| | ADP-glucose pyrophosphorylase, *LeAgp S1* | *Lycopersicon esculentum* (tomato) | Li et al. (2001) |
| | 14-3-3 protein family, *16R* | *Solanum tuberosum* (potato) | Szopa et al. (2003) |
| | | | |
| Ethylene responsive | ethylene responsive binding elements Gh*ERF4* | *Gossypium hirsutum* (cotton) | Jin and Lui (2008) |
| | | | |
| Cold responsive | *wcs120* | *Triticum aestivum* (wheat) | Ouellet et al. (1998) |
| | | | |
| Dessication responsive in leaves, organ specific in flowers and green fruit | *StDS2* | *Solanum tuberosum* (potato) | Doczi et al. (2005) |

| | | | |
|---|---|---|---|
| | Le*DS2* | *Lycopersicon esculentum* (tomato) | Doczi et al. (2005) |
| | | | |
| Oxidative stress induced by high light and ozone | Peptide methionine sulfoxide reductase A, *PMRSA* | *Arabidopsis thaliana* | Romero et al. (2006) |
| | | | |
| Wound | *Wun1*, proteinase inhibitor II genes of potato | *Solanum tuberosum* (potato) | Siebertz et al. (1989) |
| | | | |
| Starch | ADP Glucose Pyrophosphorylase, *ADPGlc* | *Arabidopsis thaliana* | Stark et al. (1992) |

| | | | |
|---|---|---|---|
| | | | |
| Light regulated | Ribulose-1, 5-bisphosphate carboxylase/oxygenase Small subunit, *TaRbcS*, *AtRbcS*, and Lp*RbcS* respectively | *Triticum, aestivum* (wheat), *Arabidopsis thaliana*, and *Lolium perenne* respectively | Zeng et al., (1995),<br><br>Sasanuma, (2001) |
| | Chlorophyll a/b Binding Protein, Lp*CAB* | *Lolium perenne* (ryegrass) | |